US 6,677,368 B2

(12) United States Patent
Cui et al.

(10) Patent No.: US 6,677,368 B2
(45) Date of Patent: Jan. 13, 2004

(54) 4-ARYL SUBSTITUTED INDOLINONES

(75) Inventors: Jingrong Cui, Foster City, CA (US);
Ruofei Zhang, Foster City, CA (US);
Hong Shen, San Francisco, GA (US);
Ji Yu Chu, Fremont, CA (US);
Fang-Jie Zhang, San Jose, CA (US);
Marcel Koenig, Burlingame, CA (US);
Steven Huy Do, San Jose, CA (US);
Xiaoyuan Li, Los Altos, CA (US);
Chung Chen Wei, Foster City, CA (US); Peng Cho Tang, Moraga, CA (US)

(73) Assignee: Sugen, Inc., South San Francisco, CA (US)

( * ) Notice: Subject to any disclaimer, the term of this patent is extended or adjusted under 35 U.S.C. 154(b) by 0 days.

(21) Appl. No.: 10/023,488

(22) Filed: Dec. 20, 2001

(65) Prior Publication Data

US 2003/0069297 A1 Apr. 10, 2003

Related U.S. Application Data

(60) Provisional application No. 60/256,479, filed on Dec. 20, 2000.

(51) Int. Cl.$^7$ .................. A61K 31/40; A61K 31/33; C07D 209/04; C07D 207/30
(52) U.S. Cl. .................. 514/427; 514/183; 514/254.09; 514/408; 514/415; 514/418; 514/422; 514/423; 548/452; 548/459; 548/489; 548/560; 548/564
(58) Field of Search .................. 514/183, 427, 514/254.09, 408, 415, 418, 422, 423; 548/452, 459, 484, 560, 564

(56) References Cited

U.S. PATENT DOCUMENTS 5,792,783 A * 8/1998 Tang et al. .................. 514/397

FOREIGN PATENT DOCUMENTS

| WO | 9403427 | * | 2/1994 |
| WO | 9640116 | * | 12/1996 |
| WO | 2000035909 | * | 6/2000 |
| WO | 2001037820 | * | 5/2001 |
| WO | 2001060814 | * | 8/2001 |

OTHER PUBLICATIONS

Chem Abstract DN 135:195497, pp. 121–130 of Search for US Sr. No. 10023488.12 = WO2001060814.*

Chem. Abstract DN 2001037820, pp. 131–139 of search forUS Sr. No. 10023488.12 = WO 2001037820.*

Chemical Abstract DN 133:43433, also cited as WO 2000035909.*

* cited by examiner

Primary Examiner—Mukund J. Shah
Assistant Examiner—Sudhaker B. Patel
(74) Attorney, Agent, or Firm—Beth A. Burrous; Foley & Lardner

(57) ABSTRACT

The present invention relates to 4-arylindolinones, as well as pharmaceutical compositions thereof, capable of modulating protein kinase signal transduction in order to regulate, modulate and/or inhibit abnormal cell proliferation. The present invention also relates to methods for treating protein kinase related disorders.

20 Claims, No Drawings

4-ARYL SUBSTITUTED INDOLINONES

This application relates to provisional application serial No. 60/256,479, filed on Dec. 20, 2000 the entire contents of which are hereby incorporated by reference.

BACKGROUND OF THE INVENTION

The following is offered as background information only and is not admitted to be prior art to the present invention.

Protein kinases ("PKs") are enzymes that catalyze the phosphorylation of hydroxy groups on tyrosine, serine and threonine residues of proteins. The consequences of this seemingly simple activity are staggering; cell growth, differentiation and proliferation, i.e., virtually all aspects of cell life in one way or another depend on PK activity. Furthermore, abnormal PK activity has been related to a host of disorders, ranging from relatively non-life threatening diseases such as psoriasis to extremely virulent diseases such as glioblastoma (brain cancer).

The PKs can be conveniently broken down into two classes, the protein tyrosine kinases (PTKs) and the serine-threonine kinases (STKs).

One of the prime aspects of PTK activity is their involvement with growth factor receptors. Growth factor receptors are cell-surface proteins. When bound by a growth factor ligand, growth factor receptors are converted to an active form which interacts with proteins on the inner surface of a cell membrane. This leads to phosphorylation on tyrosine residues of the receptor and other proteins and to the formation inside the cell of complexes with a variety of cytoplasmic signaling molecules that, in turn, effect numerous cellular responses such as cell division (proliferation), cell differentiation, cell growth, expression of metabolic effects to the extracellular microenvironment, etc. For a more complete discussion, see Schlessinger and Ullrich, Neuron 9:303–391 (1992), which is incorporated by reference, including any drawings, as if fully set forth herein.

Growth factor receptors with PTK activity are known as receptor tyrosine kinases ("RTKs"). They comprise a large family of transmembrane receptors with diverse biological activity. At present, at least nineteen (19) distinct subfamilies of RTKs have been identified. An example of these is the subfamily designated the "HER" RTKs, which include EGFR (epithelial growth factor receptor), HER2, HER3 and HER4. These RTKs consist of an extracellular glycosylated ligand binding domain, a transmembrane domain and an intracellular cytoplasmic catalytic domain that can phosphorylate tyrosine residues on proteins.

Another RTK subfamily consists of insulin receptor (IR), insulin-like growth factor I receptor (IGF-1R) and insulin receptor related receptor (IRR). IR and IGF-1R interact with insulin, IGF-I and IGF-II to form a heterotetramer of two entirely extracellular glycosylated α subunits and two β subunits which cross the cell membrane and which contain the tyrosine kinase domain.

A third RTK subfamily is referred to as the platelet derived growth factor receptor ("PDGFR") group, which includes PDGFRα, PDGFRβ, CSFIR, c-kit and c-fms. These receptors consist of glycosylated extracellular domains composed of variable numbers of immunoglobin-like loops and an intracellular domain wherein the tyrosine kinase domain is interrupted by unrelated amino acid sequences.

Another group which, because of its similarity to the PDGFR subfamily, is sometimes subsumed into the later group is the fetus liver kinase ("flk") receptor subfamily. This group is believed to be made of up of kinase insert domain-receptor fetal liver kinase-1 (KDR/FLK-1), flk-1R, flk-4 and fms-like tyrosine kinase 1 (flt-1).

A further member of the tyrosine kinase growth factor receptor family is the fibroblast growth factor ("FGF") receptor subgroup. This group consists of four receptors, FGFR1–4, and seven ligands, FGF1–7. While not yet well defined, it appears that the receptors consist of a glycosylated extracellular domain containing a variable number of immunoglobin-like loops and an intracellular domain in which the tyrosine kinase sequence is interrupted by regions of unrelated amino acid sequences.

Still another member of the tyrosine kinase growth factor receptor family is the vascular endothelial growth factor ("VEGF") receptor subgroup. VEGF is a dimeric glycoprotein similar to PDGF but has different biological functions and target cell specificity in vivo. In particular, VEGF is presently thought to play an essential role is vasculogenesis and angiogenesis.

Still another member of the tyrosine kinase growth factor receptor family is MET, often referred to as c-Met. c-Met is thought to play a role in priimary tumor growth and metastasis.

A more complete listing of the known RTK subfamilies is described in Plowman et al., DN&P, 7(6):334–339 (1994), which is incorporated by reference, including any drawings, as if fully set forth herein.

In addition to the RTKs, there also exists a family of entirely intracellular PTKs called "non-receptor tyrosine kinases" or "cellular tyrosine kinases." This latter designation, abbreviated "CTK," will be used herein. CTKs do not contain extracellular and transmembrane domains. At present, over 24 CTKs in 11 subfamilies (Src, Frk, Btk, Csk, Abl, Zap70, Fes, Fps, Fak, Jak and Ack) have been identified. The Src subfamily appear so far to be the largest group of CTKs and includes Src, Yes, Fyn, Lyn, Lck, Blk, Hck, Fgr and Yrk. For a more detailed discussion of CTKs, see Bolen, Oncogene, 8:2025–2031 (1993), which is incorporated by reference, including any drawings, as if fully set forth herein.

The serine/threonine kinases, STKs, like the CTKs, are predominantly intracellular although there are a few receptor kinases of the STK type. STKs are the most common of the cytosolic kinases; i.e., kinases that perform their function in that part of the cytoplasm other than the cytoplasmic organelles and cytoskelton. The cytosol is the region within the cell where much of the cell's intermediary metabolic and biosynthetic activity occurs; e.g., it is in the cytosol that proteins are synthesized on ribosomes.

RTKs, CTKs and STKs have all been implicated in a host of pathogenic conditions including, significantly, cancer. Other pathogenic conditions which have been associated with PTKs include, without limitation, psoriasis, hepatic cirrhosis, diabetes, angiogenesis, restenosis, ocular diseases, rheumatoid arthritis and other inflammatory disorders, immunological disorders such as autoimmune disease, cardiovascular disease such as atherosclerosis and a variety of renal disorders.

With regard to cancer, two of the major hypotheses advanced to explain the excessive cellular proliferation that drives tumor development relate to functions known to be PK regulated. That is, it has been suggested that malignant cell growth results from a breakdown in the mechanisms that control cell division and/or differentiation. It has been shown that the protein products of a number of proto-oncogenes are involved in the signal transduction pathways that regulate cell growth and differentiation. These protein products of proto-oncogenes include the extracellular growth factors, transmembrane growth factor PTK receptors (RTKs), cytoplasmic PTKs (CTKs) and cytosolic STKs, discussed above.

In view of the apparent link between PK-related cellular activities and wide variety of human disorders, it is no surprise that a great deal of effort is being expended in an attempt to identify ways to modulate PK activity. Some of these have involved biomimetic approaches using large molecules patterned on those involved in the actual cellular processes (e.g., mutant ligands (U.S. application Ser. No. 4,966,849); soluble receptors and antibodies (Application No. WO 94/10202, Kendall and Thomas, *Proc. Nat'l Acad. Sci.*, 90:10705–10709 (1994), Kim, et al., *Nature*, 362:841–844 (1993)); RNA ligands (Jelinek, et al., *Biochemistry*, 33:10450–56); Takano, et al., *Mol. Bio. Cell*, 4:358A (1993); Kinsella, et al., *Exp. Cell Res.*, 199:56–62 (1992); Wright, et al., *J. Cellular Phys.*, 152:448–57) and tyrosine kinase inhibitors (WO 94/03427; WO 92/21660; WO 91/15495; WO 94/14808; U.S. Pat. No. 5,330,992; Mariani, et al., *Proc. Am. Assoc. Cancer Res.*, 35:2268 (1994)).

In addition to the above, attempts have been made to identify small molecules which act as PK inhibitors. For example, bis-monocylic, bicyclic and heterocyclic aryl compounds (PCT WO 92/20642), vinylene-azaindole derivatives (PCT WO 94/14808) and 1-cyclopropyl-4-pyridylquinolones (U.S. Pat. No. 5,330,992) have been described as tyrosine kinase inhibitors. Styryl compounds (U.S. Pat. No. 5,217,999), styryl-substituted pyridyl compounds (U.S. Pat. No. 5,302,606), quinazoline derivatives (EP Application No. 0 566 266 A1), selenaindoles and selenides (PCT WO 94/03427), tricyclic polyhydroxylic compounds (PCT WO 92/21660) and benzylphosphonic acid compounds (PCT WO 91/15495) have all been described as PTK inhibitors useful in the treatment of cancer.

SUMMARY OF THE INVENTION

A family of novel pyrrole-substituted 2-indolinone compounds have been discovered which exhibit PK modulating ability and have a salutary effect against disorders related to abnormal PK activity (U.S. Pat. No. 5,792,783; U.S. application Ser. No. 09/322,297). It has been demonstrated that this family of compounds modulates the catalytic activity of receptor tyrosine kinases (RTKs), non-receptor protein tyrosine kinases (CTKs) and serine/threonine protein kinases (STKs).

For example, the catalytic activity of RTKs such as, without limitation, EGF, MET, HER2, HER3, HER4, IR, IGF-1R, IRR, PDGFRα, PDGFRβ, CSFIR, C-Kit, C-fms, Flk-1R, Flk4, KDR/Flk-1, Flt-1, FGFR-1R, FGFR-2R, FGFR-3R and FGFR-4R may be modulated with pyrrole-substituted 2-indolinone compounds, in particular Met may be modulated. By affecting the catalytic activity of RTKs, CTKs and/or STKs, such compounds can interfere with the signals transduced by such proteins. This application also encompasses affecting the catalytic activity of protein kinases disclosed in U.S. application Ser. Nos. 09/233,857; 09/291,417; 60/149,005 and 60/136,503, and PCT Application No. PCT/US99/13533, the entire disclosures of which are hereby incorporated by reference.

1. CHEMISTRY

In one aspect, the present invention relates to compounds having the following chemical structure (Formula I).

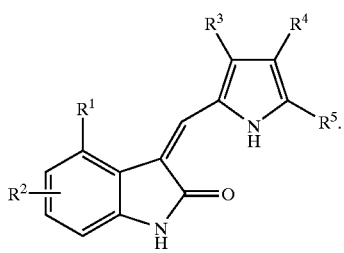

wherein:
R$^1$ is an aryl or heteroaryl substituent, optionally substituted by one or more substituent selected from the group consisting of halogen, —OR$^6$, —COR$^6$, —COOR$^6$, —OCOR$^6$, —CONR$^6$R$^7$, —R$^6$NCOR$^7$, —NR$^6$R$^7$, —CN, —NO$_2$, —CX$_3$, —SR$^6$, SOR$^6$, —SO$_2$R$^6$, —SO$_2$OR$^6$, —SO$_2$NR$^6$R$^7$, —R$^6$NSO$_2$R$^7$, perfluoroalkyl, lower alkyl, lower alkyl further substituted by one or more of R$^2$, lower alkenyl, lower alkenyl further substituted by one or more of R$^2$, lower alkenyl, lower alkenyl, lower alkenyl further substituted by one or more of R$^2$, cycloalkyl, cycloalkyl further substituted by one or more of R$^2$, a heterocyclic ring, a heterocyclic ring further substituted by one or more of R$^2$, aryl and aryl further substituted by one or more of R$^2$;

R$^2$ is selected from the group consisting of hydrogen, halogen, —OR$^6$, —COR$^6$, —COOR$^6$, —OCOR$^6$, CONR$^6$R$^7$, —RNCOR$^7$, —NR$^6$R$^7$, —CN, —NO$_2$, —CX$_3$, —SR$^6$, —SOR$^6$, —SO$_2$R$^6$, —SO$_2$OR$^6$, —SO$_2$NR$^6$R$^7$, —R$^6$NSO$_2$R$^7$, perfluoroalkyl, lower alkyl, lower alkenyl, lower alkenyl, cycloalkyl, a heterocyclic ring and aryl;

R$^3$ is selected from the group consisting of hydrogen, halogen, —OR$^6$, —COR$^6$, —COOR$^6$, —OCOR$^6$, —CONR$^6$R$^7$, —R$^6$NCOR$^7$, —NR$^6$R$^7$, —CN, —NO$_2$, —CX$_3$, —SR$^6$, —SOR$^6$, —SO$_2$R$^6$, —SO$_2$OR$^6$, —SO$_2$NR$^6$R$^7$, —R$^6$NSO$_2$R$^7$, perfluoroalkyl, lower alkyl, lower alkenyl, lower alkenyl, cycloalkyl, a heterocyclic ring, a heterocyclic ring further substituted by one or more of R$^2$, and aryl, wherein said lower alkyl is further substituted by —CONR$^6$R$^7$, NR$^6$R$^7$, —SO$_2$R$^6$, —R$^6$NSO$_2$R, or —SO$_2$NR$^6$R$^7$;

R$^4$ is selected from the group consisting of hydrogen, halogen, —OR$^6$, —COR$^6$, —COOR$^6$, —OCOR$^6$, —CONR$^6$R$^7$, —R$^6$NCOR$^7$, —NR$^6$R$^7$, —CN, —NO$_2$, —CX$_3$, —SR$^6$, —SOR$^6$, —SO$_2$R$^6$, —SO$_2$OR$^6$, —SO$_2$NR$^6$R$^7$, —R$^6$NSO$_2$R$^7$, perfluoroalkyl, lower alkyl, lower alkenyl, lower alkenyl, cycloalkyl, a heterocyclic ring and aryl, wherein said lower alkyl is further substituted by —CONR$^6$R$^7$, NR$^6$R$^7$, —SO$_2$R$^6$, —R$^6$NSO$_2$R, or SO$_2$NR$^6$R$^7$;

R$^5$ is selected from the group consisting of hydrogen, halogen, —OR$^6$, —COR$^6$, —COOR$^6$, —OCOR$^6$, —CONR$^6$R$^7$, —R$^6$NCOR$^7$, —NR$^6$R$^7$, —CN, —NO$_2$, —CX$_3$, —SR, —SOR$^6$, —SO$_2$R$^6$, —SO$_2$OR$^6$, —SO$_2$NR$^6$R$^7$, —R$^6$NSO$_2$R$^7$, perfluoroalkyl, lower alkyl, lower alkenyl, lower alkenyl, cycloalkyl, a heterocyclic ring and aryl;

provided that no more than one of R$^3$, R$^4$, or R$^5$ is hydrogen;

R$^3$ and R$^4$ or R$^4$ and R$^5$ may be linked together to form a 4-, 5-, 6- or 7-membered ring optionally containing one or more hetero atoms selected from the group consisting of O, N, S, SO and SO$_2$, which may contain 1 or 2 double bonds and may be further substituted by one or more of —(CH$_2$)$_n$—NR$^6$R$^7$, —(CH$_2$)$_n$—CR$^6$R$^7$, —(CH$_2$)$_n$—C(O)—(CH$_2$)$_n$—NR$^6$R$^7$, —(CH$_2$)$_n$SO$_2$R$^6$R$^7$, —(CH$_2$)$_n$NSO$_2$R$^6$R$^7$ or —(CH$_2$)$_n$—C(O)—R$^6$, wherein n is 0–4;

R$^6$ and R$^7$ are independently selected from the group consisting of hydrogen, —CX$_3$, perfluoroalkyl, lower alkyl, lower alkenyl, lower alkenyl, cycloalkyl, a heterocyclic ring and aryl;

wherein lower alkyl, lower alkenyl, lower alkenyl, cycloalkyl, the heteocyclic ring or aryl may be further substituted by one or more of (i) —NR$^{12}$R$^{13}$, (ii) hydroxy, (iii) halo, (iv) a heterocyclic ring, (v) lower alkyl, (vi) —C(O)—NR$^{12}$R$^{13}$, (vii) —OR$^{12}$, (viii) —SO$_2$R$^{12}$R$^{13}$, or (ix) —COR$^6$;

wherein said heterocyclic ring (iv) may be further substituted by one or more of lower alkyl, —COR$^{12}$, —NR$^{12}$COR$^{13}$, halogen, —OR$^{12}$, CX$_3$, —C(O)NR$^{12}$R$^{13}$, —SO$_2$R$^{12}$R$^{13}$, or —SO$_2$NR$^{12}$R$^{13}$, or R$^6$ and R$^7$ may be linked together to form a 4, 5- or 6-membered ring, optionally containing a hetero atom selected from the group consisting of N, O, S and SO$_2$, which may be further substituted by —CONR$^{12}$R$^{13}$, lower alkyl, hydroxy, —(CH$_2$)$_n$—NR$^{12}$R$^{13}$, —(CH$_2$)$_n$-heterocycle, —(CH$_2$)$_n$—C(O)—N$^{12}$R$^{13}$, —(CH$_2$)$_n$SO$_2$R$^{12}$R$^{13}$, or —(CH$_2$)$_n$NSO$_2$R$^{12}$R$^{13}$, wherein said heterocycle may be further substituted by halo, lower alkyl, —COR$^{12}$, hydroxy, —C(O)—NR$^{12}$R$^{13}$, —OR$^{12}$, —SO$_2$R$^{12}$R$^{13}$, or —SO$_2$NR$^{12}$R$^{13}$;

X is fluorine, chlorine, bromine or iodine;

R$^{12}$ is selected from the group consisting of hydrogen, —CX$_3$, perfluoroalkyl, lower alkyl, lower alkenyl, lower alkenyl, —(CH$_2$)$_n$-cycloalkyl, —(CH$_2$)$_n$-heterocycle, and aryl;

R$^{13}$ is selected from the group consisting of hydrogen, —CX$_3$, perfluoroalkyl, lower alkyl, lower alkenyl, lower alkenyl, —(CH$_2$)$_n$-cycloalkyl, —(CH$_2$)$_n$-heterocycle, and aryl;

or R$^{12}$ and R$^{13}$ may be linked together to form a 4-, 5- or 6-membered ring optionally containing one or more hetero atoms selected from the group consisting of O, N, S, SO and SO$_2$, which may contain 1 or 2 double bonds;

or a pharmaceutically acceptable salt thereof.

Compounds—Preferred Structural Features

In a preferred aspect, R$^3$ and R$^4$ or R$^4$ and R$^5$ may be linked together to form a ring.

In a particularly preferred aspect, R$^3$ and R$^4$ or R$^4$ and R$^5$ are linked together to form a ring, the ring together with pyrrole is selected from the group consisting of:

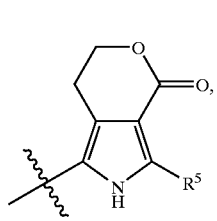
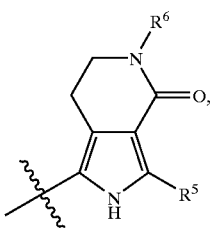

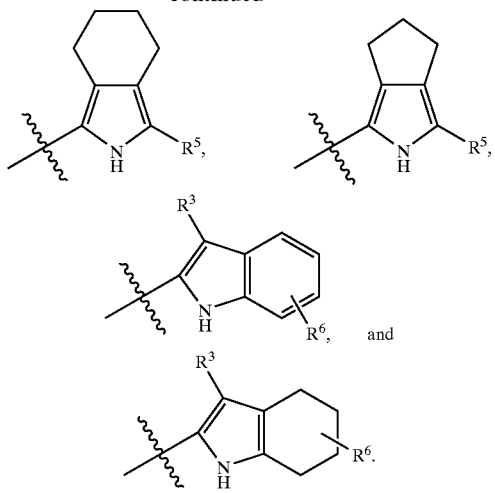

In another preferred aspect, R$^3$ may be excluded when both R$^4$ and R$^5$ are hydrogen. In still a further preferred aspect, R$^1$ is aryl.

A preferred aspect of the invention relates to compounds of Formula II

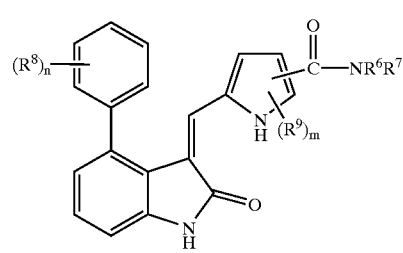

II wherein each R$^8$ is independently halogen, —OR$^6$, —COR$^6$, —COOR$^6$, OCOR$^6$, —CONR$^6$R$^7$, —RNCOR$^7$, —NR$^6$R$^7$, —CN, —NO$_2$, —CX$_3$, —SR$^6$, SOR$^6$, —SO$_2$R$^6$, —SO$_2$OR$^6$, —SO$_2$NR$^6$R$^7$, —R$^6$NSO$_2$R$^7$, perfluoroalkyl, lower alkyl, lower alkyl further substituted by one or more of R$^2$, lower alkenyl, lower alkenyl further substituted by one or more of R$^2$, lower alkenyl, lower alkenyl further substituted by one or more of R$^2$, cycloalkyl, cycloalkyl further substituted by one or more of R$^2$, a heterocyclic ring, a heterocyclic ring further substituted by one or more of R$^2$, aryl and aryl further substituted by one or more of R$^2$;

R$^2$ is selected from the group consisting of hydrogen, halogen, —OR$^6$, —COR$^6$, —COOR$^6$, OCOR$^6$, —CONR$^6$R$^7$, —R$^{12}$NCOR$^{13}$, —NR$^6$R$^7$, —RNC(O)R$^7$, —CN, —NO$_2$, —CX$_3$, —SR$^6$, —SOR$^6$, —SO$_2$R$^6$, —SO$_2$OR$^6$, —SO$_2$NR$^6$R$^7$, —R$^6$NSO$_2$R$^7$, perfluoroalkyl, lower alkyl, lower alkenyl, lower alkenyl, cycloalkyl, a heterocyclic ring and aryl;

R$^6$ and R$^7$ are independently selected from the group consisting of hydrogen, —CX$_3$, perfluoroalkyl, lower alkyl, lower alkenyl, lower alkenyl, cycloalkyl, a heterocyclic ring and aryl;

wherein lower alkyl, lower alkenyl, lower alkenyl, cycloalkyl, the heteocyclic ring or aryl may be further substituted by one or more of (i) —NR$^{12}$R$^{13}$, (ii) hydroxy, (iii) halo, (iv) a heterocyclic ring, (v)

lower alkyl, (vi) —C(O)—NR$^{12}$R$^{13}$, (vii) —OR$^{12}$, (viii) —SO$_2$R$^{12}$R$^{13}$, or (ix) —COR$^6$;
  wherein said heterocyclic ring (iv) may be further substituted by one or more of lower alkyl, —COR$^{12}$, —NR$^{12}$COR$^{13}$, halogen, —OR$^{12}$, CX$_3$, —C(O)NR$^{12}$R$^{13}$, —SO$_2$R$^{12}$R$^{13}$, or —SO$_2$NR$^{12}$R$^{13}$, or R$^6$ and R$^7$ may be linked together to form a 4, 5- or 6-membered ring, optionally containing a hetero atom selected from the group consisting of N, O, S and SO$_2$, which may be further substituted by —CONR$^{12}$R$^{13}$, lower alkyl, hydroxy, —(CH$_2$)$_n$—NR$^{12}$R$^{13}$, —(CH$_2$)$_n$-heterocycle, —(CH$_2$)$_n$—C(O)—NR$^{12}$R$^{13}$, —(CH$_2$)$_n$SO$_2$R$^{12}$R$^{13}$, or —(CH$_2$)$_n$NSO$_2$R$^{12}$R$^{13}$, wherein said heterocycle may be further substituted by halo, lower alkyl, —COR$^{12}$, hydroxy, —C(O)—NR$^{12}$R$^{13}$, —OR$^{12}$, —SO$_2$R$^{12}$R$^{13}$, or —SO$_2$NR$^{12}$R$^{13}$;

X is fluorine, chlorine, bromine or iodine;

R$^{12}$ is selected from the group consisting of hydrogen, —CX$_3$, perfluoroalkyl, lower alkyl, lower alkenyl, lower alkenyl, —(CH$_2$)$_n$-cycloalkyl, —(CH$_2$)$_n$-heterocycle, and aryl;

R$^{13}$ is selected from the group consisting of hydrogen, —CX$_3$, perfluoroalkyl, lower alkyl, lower alkenyl, lower alkenyl, —(CH$_2$)$_n$-cycloalkyl, —(CH$_2$)$_n$-heterocycle, and aryl;

or R$^{12}$ and R$^{13}$ may be linked together to form a 4-, 5- or 6-membered ring optionally containing one or more hetero atoms selected from the group consisting of O, N, S, SO and SO$_2$, which may contain 1 or 2 double bonds and may be further substituted by halogen, —OR$^6$, —COR$^6$, —COOR$^6$, OCOR$^6$, —CONR$^6$R$^7$, —R$^{12}$NCOR$^{13}$, —NR$^6$R$^7$, —R$^6$NC(O)R$^7$, —CN, —NO$_2$, —CX$_3$, —SR$^6$, SOR$^6$, —SO$_2$R$^6$, —SO$_2$OR$^6$, —SO$_2$NR$^6$R$^7$, —RNSO$_2$R$^7$, perfluoroalkyl, lower alkyl, lower alkenyl, lower alkenyl, cycloalkyl, a heterocyclic ring and aryl;

R$^9$ is selected from the group consisting of halogen, —CX$_3$, lower alkyl, cycloalkyl, a heterocyclic ring and aryl, each of which may be further substituted by halogen, —OR$^6$, —COOR$^6$, —OCOR$^6$, —CONR$^6$R$^7$, —R$^6$NCOR$^7$, —NR$^6$R$^7$, —CX$_3$, —SR$^6$, SOR$^6$, SO$_2$R$^6$, —SO$_2$OR$^6$, SO$_2$NR$^6$R$^7$, or —R$^6$NSO$_2$R$^7$; and m is 1 or 2, or a pharmaceutically acceptable salt thereof.

Another preferred aspect of the invention relates to compounds of Formula III,

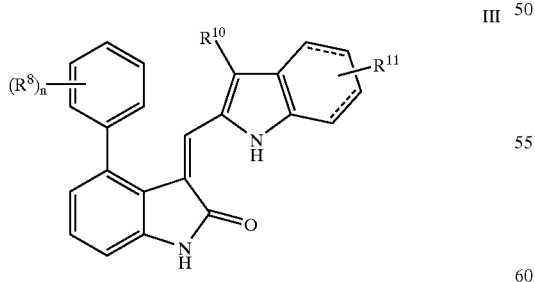

III wherein each R$^8$ is independently halogen, —OR$^6$, —COR$^6$, —COOR$^6$, OCOR$^6$, —CONR$^6$R$^7$, —RNCOR$^7$, —NR$^6$R$^7$, —CN, —NO$_2$, —CX$_3$, —SR$^6$, —SO$_2$R$^6$, —SO$_2$OR$^6$, —SO$_2$NR$^6$R$^7$, —R$^6$NSO$_2$R$^7$, perfluoroalkyl, lower alkyl, lower alkyl further substituted by one or more of R$^2$, lower alkenyl, lower alkenyl further substituted by one or more of R$^2$, lower alkynyl, lower alkynyl further substituted by one or more of R$^2$, cycloalkyl, cycloalkyl further substituted by one or more of R$^2$, a heterocyclic ring, a heterocyclic ring further substituted by one or more of R$^2$, aryl and aryl further substituted by one or more of R$^2$;

R$^2$ is selected from the group consisting of hydrogen, halogen, —OR$^6$, —COR$^6$, —COOR$^6$, OCOR$^6$, —CONR R$^7$, —R$^6$COR$^7$, —NR$^6$R$^7$, —CN, —NO$_2$, —CX$_3$, —SO$_2$R$^6$, —SO$_2$OR$^6$, —SO$_2$NR$^6$R$^7$, —R$^6$NSO$_2$R$^7$, perfluoroalkyl, lower alkyl, lower alkenyl, lower alkynyl, cycloalkyl, a heterocyclic ring and aryl;

R$^6$ and R$^7$ are independently selected from the group consisting of hydrogen, —CX$_3$, perfluoroalkyl, lower alkyl, lower alkenyl, lower alkynyl, cycloalkyl, a heterocyclic ring and aryl;
  wherein lower alkyl, lower alkenyl, lower alkynyl, cycloalkyl, the heteocyclic ring or aryl may be further substituted by one or more of (i) —NR$^{12}$R$^{13}$, (ii) hydroxy, (iii) halo, (iv) a heterocyclic ring, (v) lower alkyl, (vi) —C(O)—NR$^{12}$R$^{13}$, (vii) —OR$^{12}$, (viii) —SO$_2$R$^{12}$R$^{13}$, or (ix) —COR$^6$;
    wherein said heterocyclic ring (iv) may be further substituted by one or more of lower alkyl, —COR$^{12}$, —NR$^{12}$COR$^{13}$, halogen, OR$^{12}$, CX$_3$, —C(O)NR$^{12}$R$^{13}$, —SO$_2$R$^{12}$R$^{13}$, or —SO$_2$NR$^{12}$R$^{13}$, or R$^6$ and R$^7$ may be linked together to form a 4, 5- or 6-membered ring, optionally containing a hetero atom selected from the group consisting of N, O, S and SO$_2$, which may be further substituted by —CONR$^{12}$R$^{13}$, lower alkyl, hydroxy, —(CH$_2$)$_n$—NR$^{12}$R$^{13}$, —(CH$_2$)$_n$-heterocycle, —(CH$_2$)$_n$—C(O)—NR$^{12}$R$^{13}$, —(CH$_2$)$_n$SO$_2$R$^{12}$R$^{13}$, or —(CH$_2$)$_n$NSO$_2$R$^{12}$R$^{13}$, wherein said heterocycle may be further substituted by halo, lower alkyl, —COR$^{12}$, hydroxy, —C(O)—NR$^{12}$R$^{13}$, —OR$^{12}$, —SO$_2$R$^{12}$R$^{13}$, or —SO$_2$NR$^{12}$R$^{13}$;

X is fluorine, chlorine, bromine or iodine;

R$^{10}$ is H, lower alkyl, lower alkyl substituted with one or more of R$^2$, —(CH$_2$)$_n$NR$^6$R$^7$, —CONR$^6$R$^7$, —SO$_2$NR$^6$R$^7$, —(CH$_2$)$_n$—SR$^6$, —(CH$_2$)$_n$—SOR$^6$, —(CH$_2$)$_n$—SO$_2$NR$^6$R$^7$, or —(CH$_2$)$_n$—OR$^6$;

R$^{11}$ is H, lower alkyl, lower alkyl substituted with one or more of R$^2$, —(CH$_2$)$_n$NR$^6$R$^7$, —CONR$^6$R$^7$, —SO$_2$NR$^6$R$^7$, —(CH$_2$)$_n$—SR$^6$, —(CH$_2$)$_n$—SOR$^6$, —(CH$_2$)$_n$—SO$_2$NR$^6$R$^7$, or —(CH$_2$)$_n$—OR$^6$;

R$^{12}$ is selected from the group consisting of hydrogen, —CX$_3$, perfluoroalkyl, lower alkyl, lower alkenyl, lower alkynyl, —(CH$_2$)$_n$-cycloalkyl, —(CH$_2$)$_n$-heterocycle, and aryl;

R$^{13}$ is selected from the group consisting of hydrogen, —CX$_3$, perfluoroalkyl, lower alkyl, lower alkenyl, lower alkynyl, —(CH$_2$)$_n$-cycloalkyl, —(CH$_2$)$_n$-heterocycle, and aryl;

or R$^{12}$ and R$^{13}$ may be linked together to form a 4-, 5- or 6-membered ring optionally containing one or more hetero atoms selected from the group consisting of O, N, S, SO and SO$_2$, which may contain 1 or 2 double bonds; and wherein ==== is a single or double bond; and n is 0–4, or a pharmaceutically acceptable salt thereof.

The compounds presented herein are exemplary only and are not to be construed as limiting the scope of this invention in any manner.

The chemical formulae referred to herein may exhibit the phenomena of tautomerism and structural isomerism. For example, the compounds described herein may adopt an E or a Z configuration about the double bond connecting the 2-indolinone moiety to the pyrrole moiety or they may be a mixture of E and Z. This invention encompasses any tautomeric or structural isomeric form and mixtures thereof which possess the ability to modulate RTK, CTK and/or STK activity and is not limited to any one tautomeric or structural isomeric form.

In addition, the formulae referred to herein may also exhibit stereoisomerism, in which such compounds may adopt an R or S configuration at chiral centers. Thus, this invention also encompasses any stereoisomeric form, their corresponding enantiomers (d- and l- or (+) and (−) isomers) and diastereomers thereof, and mixtures thereof, which possess the ability to modulate RTK, CTK and/or STK activity and is not limited to any one stereoisomeric form.

Table 1 shows the chemical structures of the preferred compounds of the invention.

TABLE 1

Preferred 4-Aryl Substituted Indolinones

| Example | Structure | Name |
|---------|-----------|------|
| 1 | 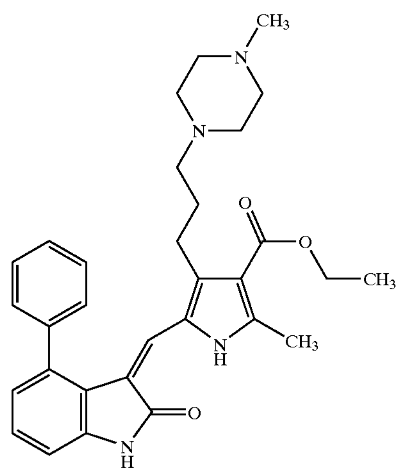 | 2-Methyl-4-[3-(4-methyl-piperazin-1-yl)-propyl]-5-(2-oxo-4-phenyl-1,2-dihydro-indol-3-ylidenemethyl)-1H-pyrrole-3-carboxylic acid ethyl ester |
| 2 | 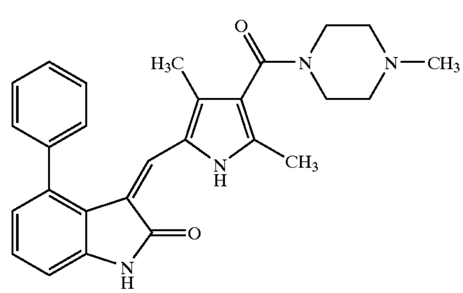 | 3-[3,5-Dimethyl-4-(4-methyl-piperazine-1-carbonyl)-1H-pyrrol-2-ylmethylene]-4-phenyl-1,3-dihydro-indol-2-one |
| 3 | 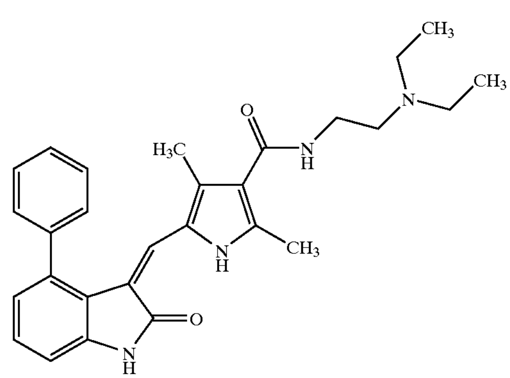 | 2,4-Dimethyl-5-(2-oxo-4-phenyl-1,2-dihydro-indol-3-ylidenemethyl)-1H-pyrrole-3-carboxylic acid (2-diethylamino-ethyl)-amide |

TABLE 1-continued

Preferred 4-Aryl Substituted Indolinones

| Example | Structure | Name |
|---|---|---|
| 4 | 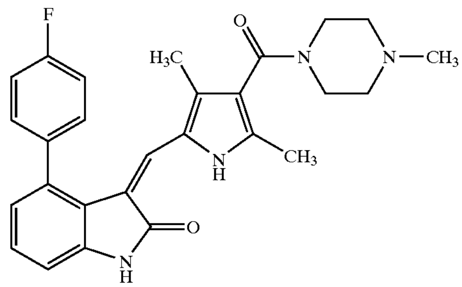 | 3-[3,5-Dimethyl-4-(4-methyl-piperazine-1-carbonyl)-1H-pyrrol-2-ylmethylene]-4-(4-fluoro-phenyl)-1,3-dihydro-indol-2-one |
| 5 | 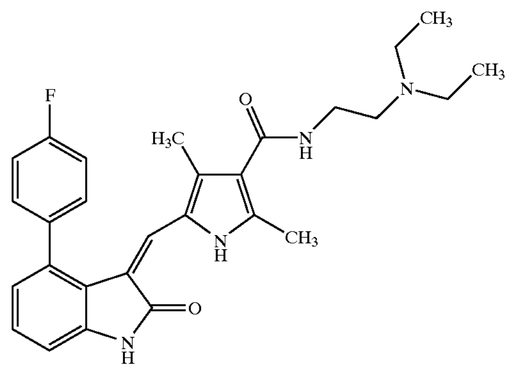 | 5-[4-(4-Fluoro-phenyl)-2-oxo-1,2-dihydro-indol-3-ylidenemethyl]-2,4-dimethyl-1H-pyrrole-3-carboxylic acid (2-diethylamino-ethyl)-amide |
| 6 | 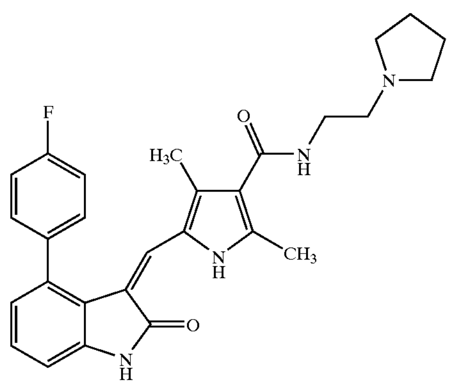 | 5-[4-(4-Fluoro-phenyl)-2-oxo-1,2-dihydro-indol-3-ylidenemethyl]-2,4-dimethyl-1H-pyrrole-3-carboxylic acid (2-pyrrolidin-1-yl-ethyl)-amide |
| 7 | 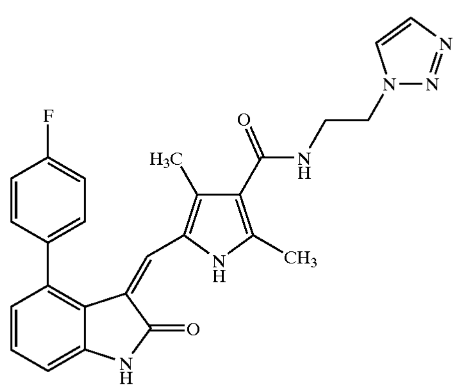 | 5-[4-(4-Fluoro-phenyl)-2-oxo-1,2-dihydro-indol-3-ylidenemethyl]-2,4-dimethyl-1H-pyrrole-3-carboxylic acid (2-[1,2,3]triazol-1-yl-ethyl)-amide |

TABLE 1-continued

Preferred 4-Aryl Substituted Indolinones

| Example | Structure | Name |
|---|---|---|
| 8 | 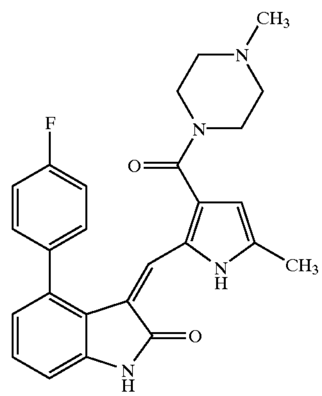 | 4-(4-Fluoro-phenyl)-3-[5-methyl-3-(4-methyl piperazine-1-carbonyl)-1H-pyrrol-2-ylmethylene]-1,3-dihydro-indol-2-one |
| 9 | 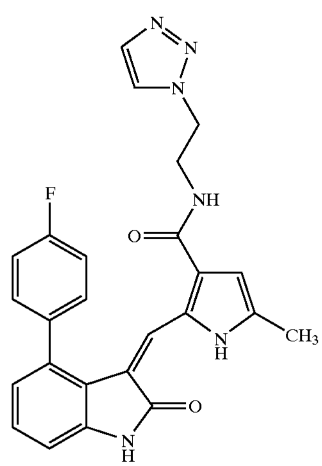 | 2-[4-(4-Fluoro-phenyl)-2-oxo-1,2-dihydro-indol-3-ylidenemethyl]-5-methyl-1H-pyrrole-3-carboxylic acid (2-[1,2,3]triazol-1-yl-ethyl) amide |
| 10 | 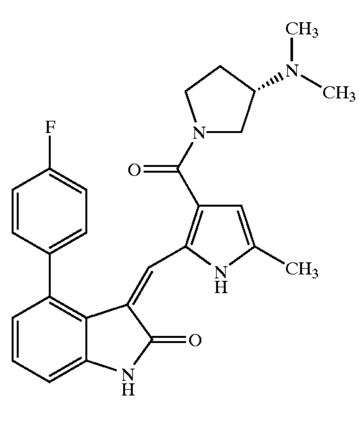 | 3-[3-((S)-3-Dimethylamino-pyrrolidine-1-carbonyl)-5-methyl-1H-pyrrol-2-yhnethylene]-4-(4-fluoro-phenyl)-1,3-dihydro indol-2-one |

TABLE 1-continued

Preferred 4-Aryl Substituted Indolinones

| Example | Structure | Name |
|---|---|---|
| 11 | 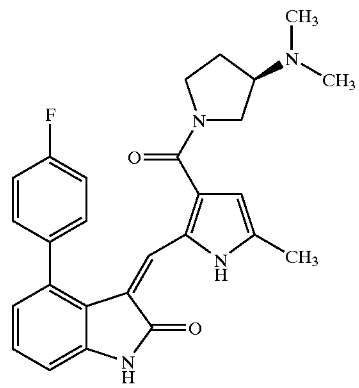 | 3-[3-((R)-3-Dimethylamino-pyrrolidine-1-carbonyl)-5-methyl-1H-pyrrol-2-ylmethylene]-4-(4-fluoro-phenyl)-1,3-dihydro indol-2-one |
| 12 | 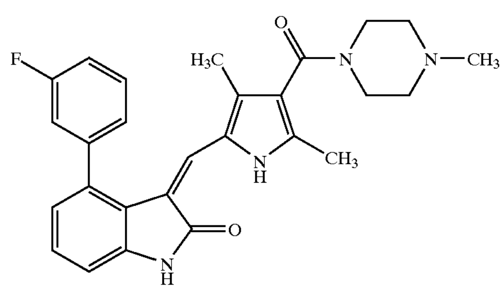 | 3-[3,5-Dimethyl-4-(4-methyl-piperazine-1-carbonyl)-1H-pyrrol-2-ylmethylene]-4-(3-fluoro-phenyl)-1,3-dihydro-indol-2-one |
| 13 | 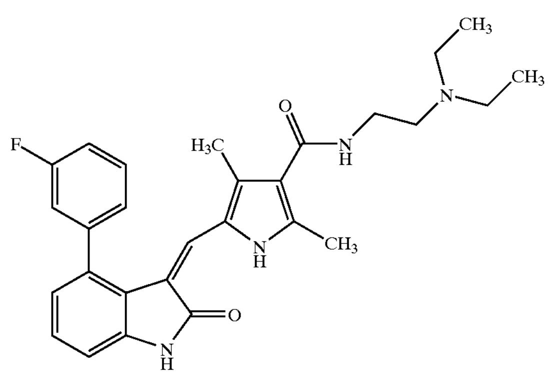 | 5-[4-(3-Fluoro-phenyl)-2-oxo-1,2-dihydro-indol-3-ylidenemethyl]-2,4-dimethyl-1H-pyrrole-3-carboxylic acid (2-diethylamino-ethyl)-amide |
| 14 | 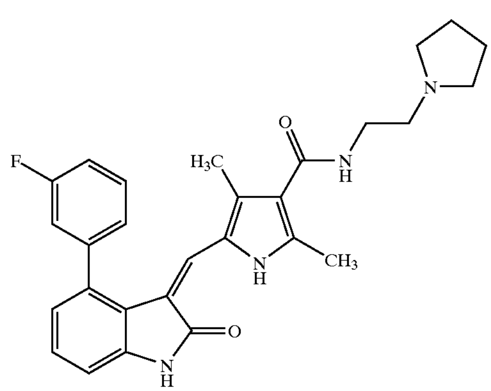 | 5-[4-(3-Fluoro-phenyl)-2-oxo-1,2-dihydro-indol-3-ylidenemethyl]-2,4-dimethyl-1H-pyrrole-3-carboxylic acid (2-pyrrolidin-1-yl-ethyl)-amide |

TABLE 1-continued

Preferred 4-Aryl Substituted Indolinones

| Example | Structure | Name |
|---------|-----------|------|
| 15 | 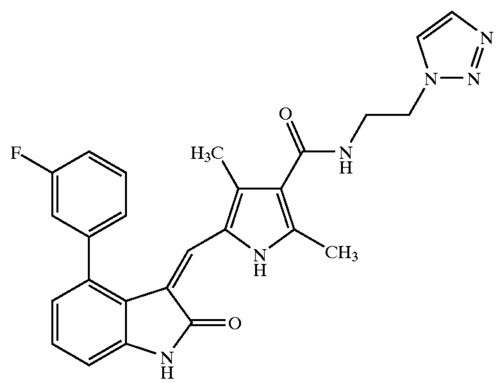 | 5-[4-(3-Fluoro-phenyl)-2-oxo-1,2-dihydro-indol-3-ylidenemethyl]-2,4-dimethyl-1H-pyrrole-3-carboxylic acid (2-[1,2,3]triazol-1-yl-ethyl)-amide |
| 16 | 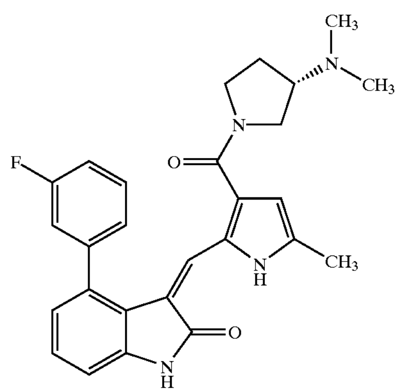 | 3-[3-((S)-3-Dimethylamino-pyrrolidine-1-carbonyl)-5-methyl-1H-pyrrol-2-ylmethylene]-4-(3-fluoro-phenyl)-1,3-dihydro indol-2-one |
| 17 | 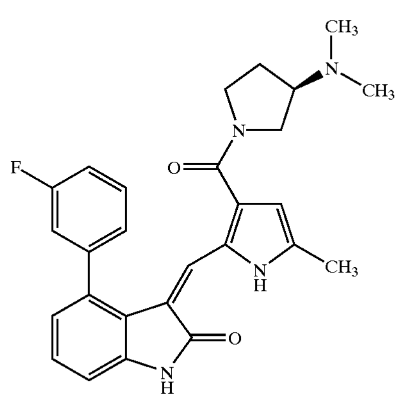 | 3-[3-((R)-3-Dimethylamino-pyrrolidine-1-carbonyl)-5-methyl-1H-pyrrol-2-ylmethylene]-4-(3-fluoro-phenyl)-1,3-dihydro indol-2-one |

TABLE 1-continued

Preferred 4-Aryl Substituted Indolinones

| Example | Structure | Name |
|---|---|---|
| 18 | 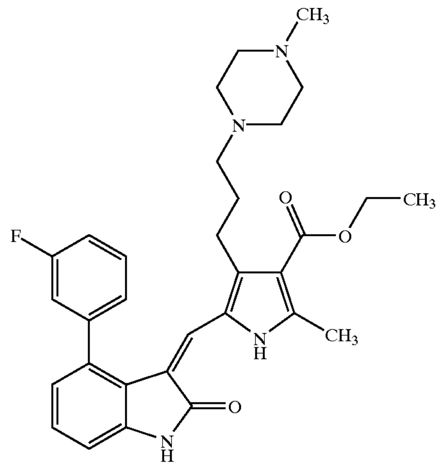 | 5-[4-(3-Fluoro-phenyl])-2-oxo-1,2-dihydro-indol-3-ylidenemethyl]-2-methyl-4-[3-(4-methyl-piperazin-1-yl)-propyl]-1H-pyrrole-3-carboxylic acid ethyl ester |
| 19 | 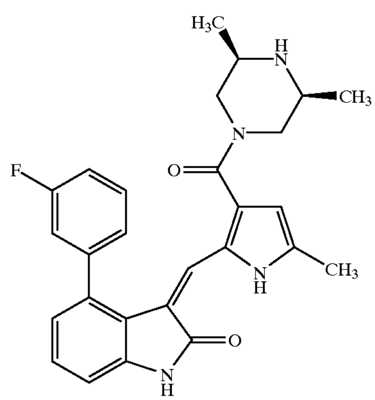 | 3-[3-(cis-3,5-Dimethyl-piperazine-1-carbonyl)-5-methyl-1H-pyrrol-2-ylmethylene]-4-(3-fluoro-phenyl)-1,3-dihydro indol-2-one |
| 20 | 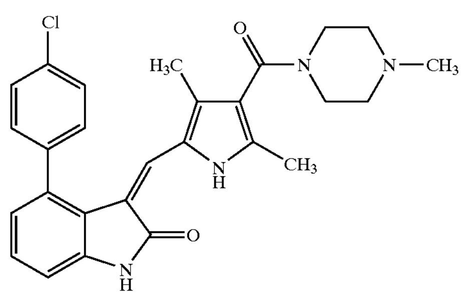 | 4-(4-Chloro-phenyl)-3-[3,5-dimethyl-4-(4-methyl-piperazine-1-carbonyl)-1H-pyrrol-2-ylmethylene]-1,3-dihydro-indol-2-one |
| 21 | 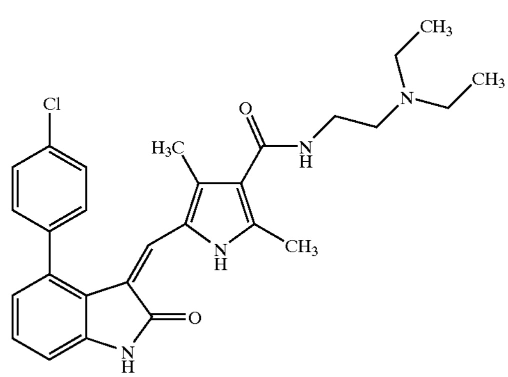 | 5-[4-(4-Chloro-phenyl)-2-oxo-1,2-dihydro-indol-3-ylidenemethyl]-2,4-dimethyl-1H-pyrrole-3-carboxylic acid (2-diethylamino-ethyl)-amide |

TABLE 1-continued

Preferred 4-Aryl Substituted Indolinones

| Example | Structure | Name |
|---|---|---|
| 22 | 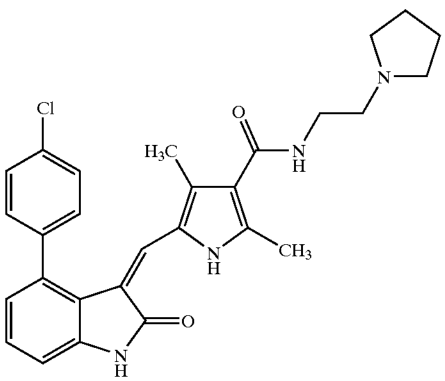 | 5-[4-(4-Chloro-phenyl)-2-oxo-1,2-dihydro-indol-3-ylidenemethyl]-2,4-dimethyl-1H-pyrrole-3-carboxylic acid (2-pyrrolidin-1-yl-ethyl)-amide |
| 23 | 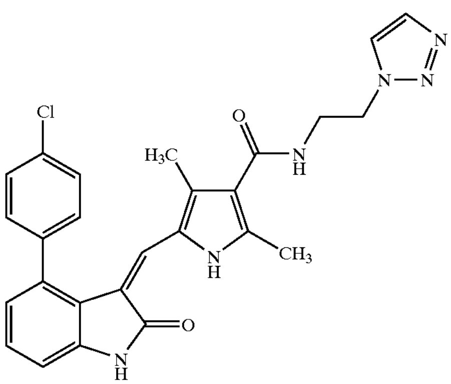 | 5-[4-(4-Chloro-phenyl)-2-oxo-1,2-dihydro-indol-3-ylidenemethyl]-2,4-dimethyl-1H-pyrrole-3-carboxylic acid (2-[1,2,3]triazol-1-yl-ethyl)-amide |
| 24 | 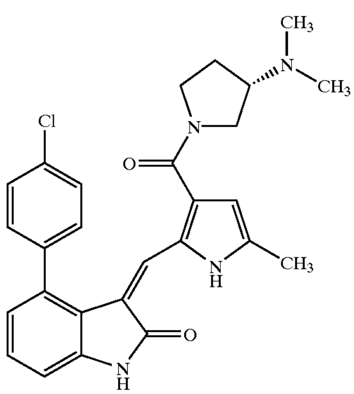 | 4-(4-Chloro-phenyl)-3-[3-((S)-3-dimethylamino-pyrrolidine-1-carbonyl)-5-methyl-1H-pyrrol-2-ylmethylene]-1,3-dihydro-indol-2-one |
| 25 | 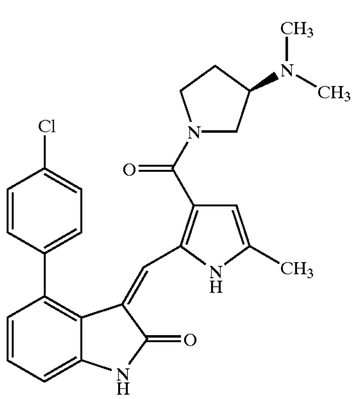 | 4-(4-Chloro-phenyl)-3-[3-((R)-3-dimethylamino-pyrrolidine-1-carbonyl)-5-methyl-1H-pyrrol-2-ylmethylene]-1,3-dihydro-indol-2-one |

TABLE 1-continued

Preferred 4-Aryl Substituted Indolinones

| Example | Structure | Name |
|---|---|---|
| 26 | 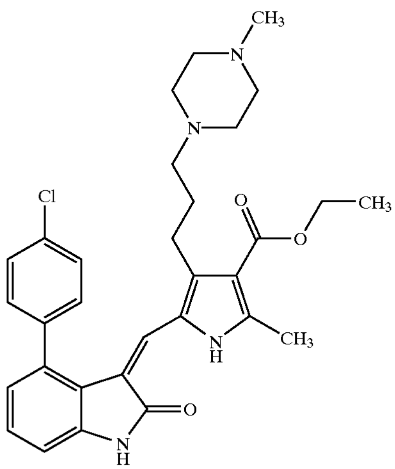 | 5-[4-(4-Chloro-phenyl)-2-oxo-1,2-dihydro-indol-3-ylidenemethyl]-2-methyl-4-[3-(4-methyl-piperazin-1-yl)-propyl]-1H-pyrrole-3-carboxylic acid ethyl ester |
| 27 | 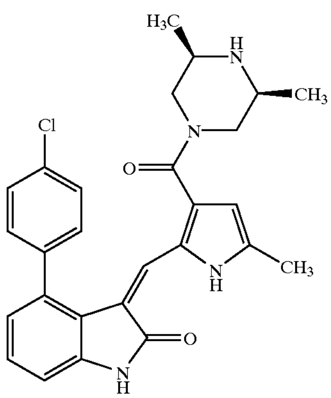 | 4-(4-Chloro-phenyl)-3-[3-(cis-3,5-dimethyl-piperazine-1-carbonyl)-5-methyl-1H-pyrrol-2-ylmethylene]-1,3-dihydro-indol-2-one |
| 28 | 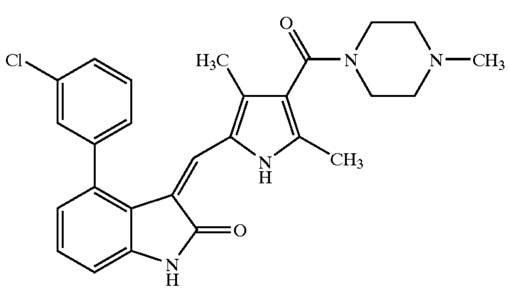 | 4-(3-Chloro-phenyl)-3-[3,5-dimethyl-4-(4-methyl-piperazine-1-carbonyl)-1H-pyrrol-2-ylmethylene]-1,3-dihydro-indol-2-one |
| 29 | 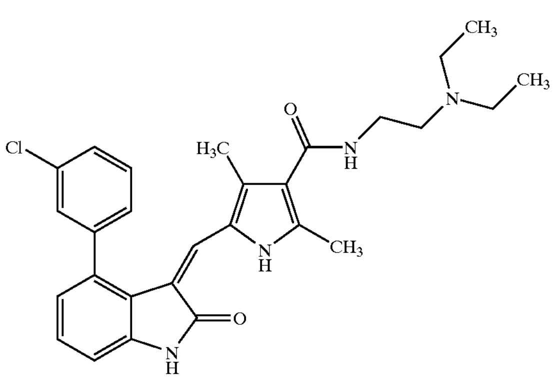 | 5-[4-(3-Chloro-phenyl)-2-oxo-1,2-dihydro-indol-3-ylidenemethyl]-2,4-dimethyl-1H-pyrrole-3-carboxylic acid (2-diethylamino-ethyl)-amide |

TABLE 1-continued

Preferred 4-Aryl Substituted Indolinones

| Example | Structure | Name |
|---|---|---|
| 30 | 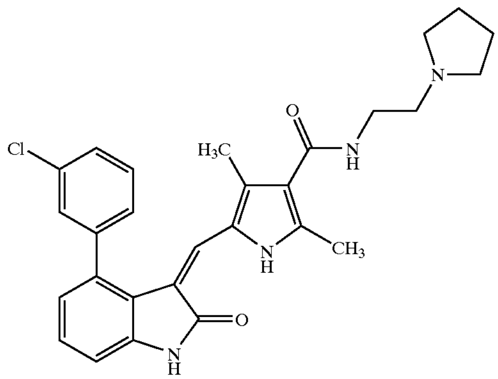 | 5-[4-(3-Chloro-phenyl)-2-oxo-1,2-dihydro-indol-3-ylidenemethyl]-2,4-dimethyl-1H-pyrrole-3-carboxylic acid (2-pyrrolidin-1-yl-ethyl)-amide |
| 31 | 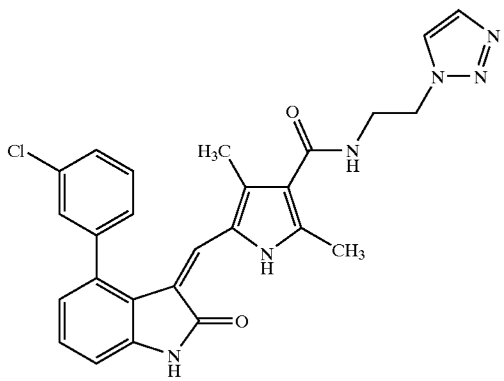 | 5-[4-(3-Chloro-phenyl)-2-oxo-1,2-dihydro-indol-3-ylidenemethyl]-2,4-dimethyl-1H-pyrrole-3-carboxylic acid (2-[1,2,3]triazol-1-yl-ethyl)-amide |
| 32 | 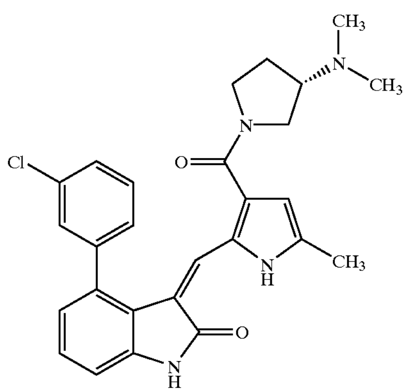 | 4-(3-Chloro-phenyl)-3-[3-((S)-3-dimethylamino-pyrrolidine-1-carbonyl)-5-methyl-1H-pyrrol-2-ylmethylene]-1,3-dihydro-indol-2-one |
| 33 | 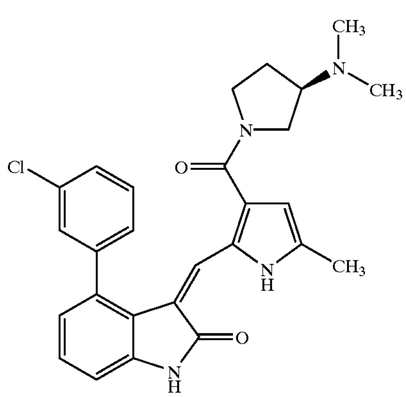 | 4-(3-Chloro-phenyl)-3-[3-((R)-3-dimethylamino-pyrrolidine-1-carbonyl)-5-methyl-1H-pyrrol-2-ylmethylene]-1,3-dihydro-indol-2-one |

TABLE 1-continued

Preferred 4-Aryl Substituted Indolinones

| Example | Structure | Name |
|---|---|---|
| 34 | 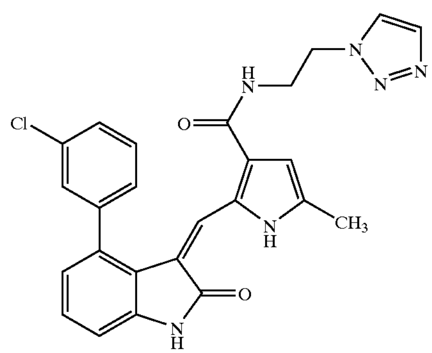 | 2-[4-(3-Chloro-phenyl)-2-oxo-1,2-dihydro-indol-3-ylidenemethyl]-5-methyl-1H-pyrrole-3-carboxylic acid (2-[1,2,3]triazol-1-yl-ethyl)-amide |
| 35 | 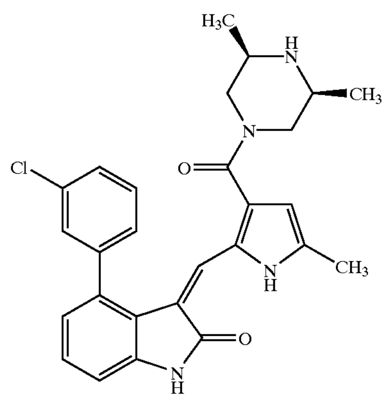 | 4-(3-Chloro-phenyl)-3-[3-(cis-3,5-dimethyl-piperazine-1-carbonyl)-5-methyl-1H-pyrrol-2 ylmethylene]-1,3-dihydro-indol-2-one |
| 36 | 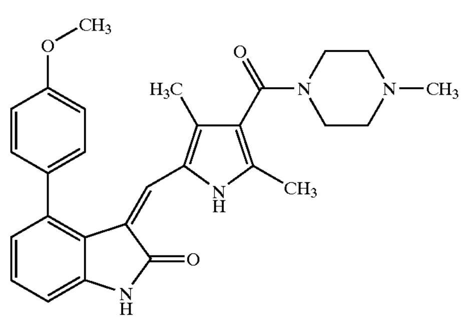 | 3-[3,5-Dimethyl-4-(4-methyl-piperazine-1-carbonyl)-1H-pyrrol-2-ylmethylene]-4-(4-methoxy-phenyl)-1,3-dihydro-indol-2-one |
| 37 | 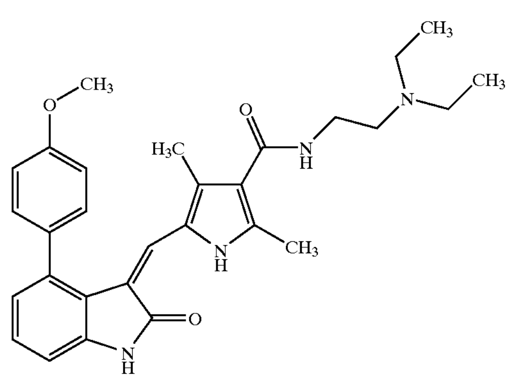 | 5-[4-(4-Methoxy-phenyl)-2-oxo-1,2-dihydro-indol-3-ylidenemethyl]-2,4-dimethyl-1H-pyrrole-3-carboxylic acid (2-diethylamino-ethyl)-amide |

TABLE 1-continued

Preferred 4-Aryl Substituted Indolinones

| Example | Structure | Name |
|---|---|---|
| 38 | 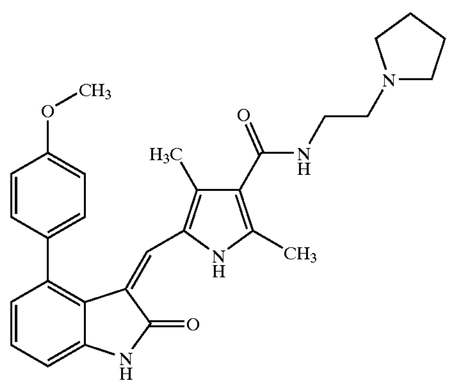 | 5-[4-(4-Methoxy-phenyl)-2-oxo-1,2-dihydro-indol-3-ylidenemethyl]-2,4-dimethyl-1H-pyrrole-3-carboxylic acid (2-pyrrolidin-1-yl-ethyl)-amide |
| 39 | 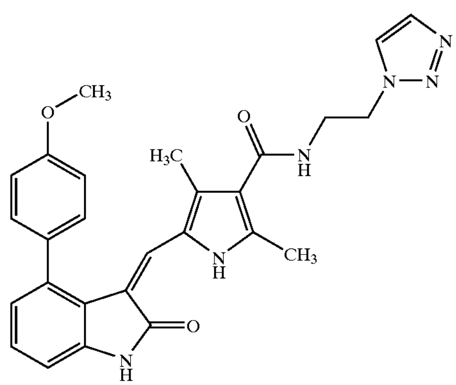 | 5-[4-(4-Methoxy-phenyl)-2-oxo-1,2-dihydro-indol-3-ylidenemethyl]-2,4-dimethyl-1H-pyrrole-3-carboxylic acid (2-[1,2,3]triazol-1-yl-ethyl)-amide |
| 40 | 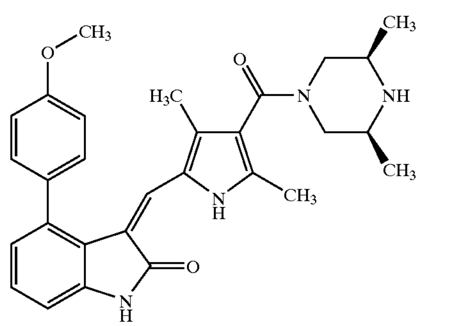 | 3-[4-(cis-3,5-Dimethyl-piperazine-1-carbonyl)-3,5-dimethyl-1H-pyrrol-2-ylmethylene]-4-(4-methoxy-phenyl)-1,3-dihydro-indol-2-one |
| 41 | 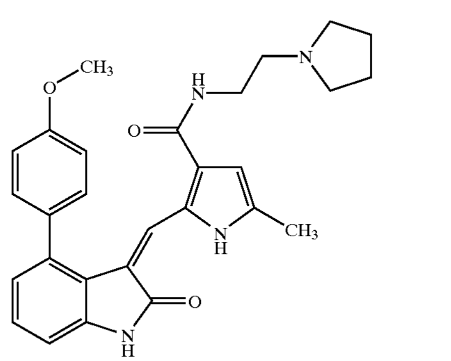 | 2-[4-(4-Methoxy-phenyl)-2-oxo-1,2-dihydro-indol-3-ylidenemethyl]-5-methyl-1H-pyrrole-3-carboxylic acid (2-pyrrolidin-1-yl-ethyl)-amide |

TABLE 1-continued

Preferred 4-Aryl Substituted Indolinones

| Example | Structure | Name |
|---|---|---|
| 42 | 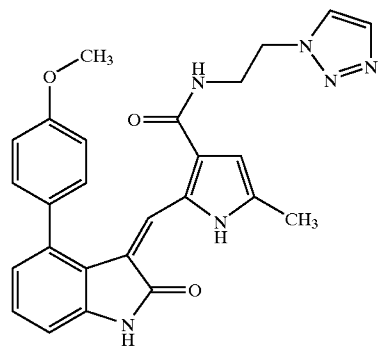 | 2-[4-(4-Methoxy-phenyl)-2-oxo-1,2-dihydro-indol-3-ylidenemethyl]-5-methyl-1H-pyrrole-3-carboxylic acid (2-[1,2,3]triazol-1-yl-ethyl)-amide |
| 43 | 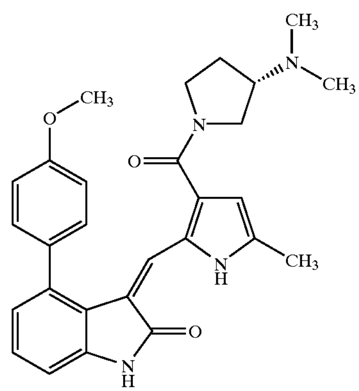 | 3-[3-((S)-3-Dimethylamino-pyrrolidine-1-carbonyl)-5-methyl-1H-pyrrol-2-ylmethylene]-4-(4-methoxy-phenyl)-1,3-dihydro-indol-2-one |
| 44 | 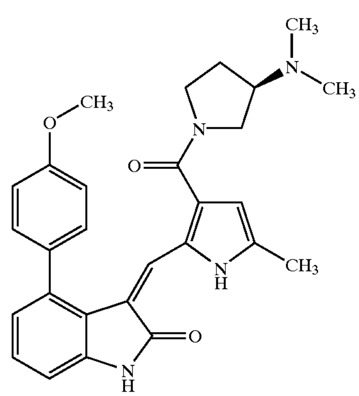 | 3-[3-((R)-3-Dimethylamino-pyrrolidine-1-carbonyl)-5-methyl-1H-pyrrol-2-ylmethylene]-4-(4-methoxy-phenyl)-1,3-dihydro-indol-2-one |
| 45 | 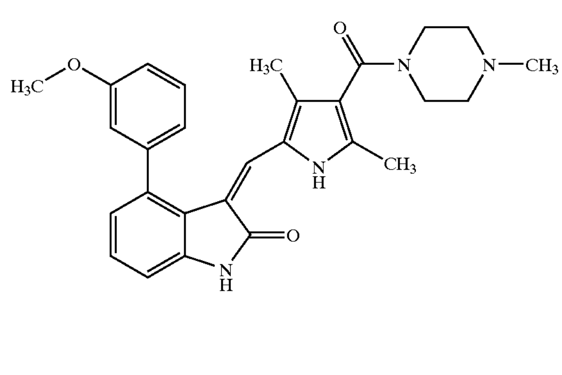 | 3-[3,5-Dimethyl-4-(4-methyl-piperazine-1-carbonyl)-1H-pyrrol-2-ylmethylene]-4-(3-methoxy-phenyl)-1,3-dihydro-indol-2-one |

TABLE 1-continued

Preferred 4-Aryl Substituted Indolinones

| Example | Structure | Name |
|---|---|---|
| 46 | 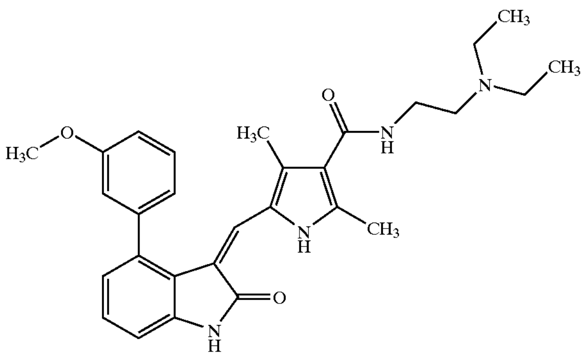 | 5-[4-(3-Methoxy-phenyl)-2-oxo-1,2-dihydro-indol-3-ylidenemethyl]-2,4-dimethyl-1H-pyrrole-3-carboxylic acid (2-diethylamino-ethyl)-amide |
| 47 | 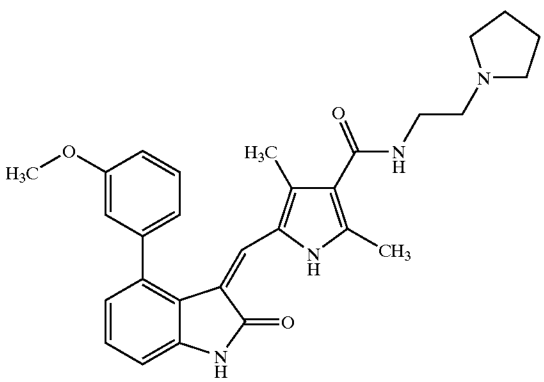 | 5-[4-(3-Methoxy-phenyl)-2-oxo-1,2-dihydro-indol-3-ylidenemethyl]-2,4-dimethyl-1H-pyrrole-3-carboxylic acid (2-pyrrolidin-1-yl-ethyl)-amide |
| 48 | 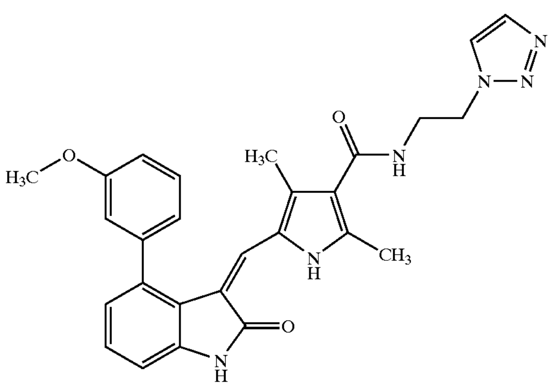 | 5-[4-(3-Methoxy-phenyl)-2-oxo-1,2-dihydro-indol-3-ylidenemethyl]-2,4-dimethyl-1H-pyrrole-3-carboxylic acid (2-[1,2,3]triazol-1-yl-ethyl)-amide |
| 49 | 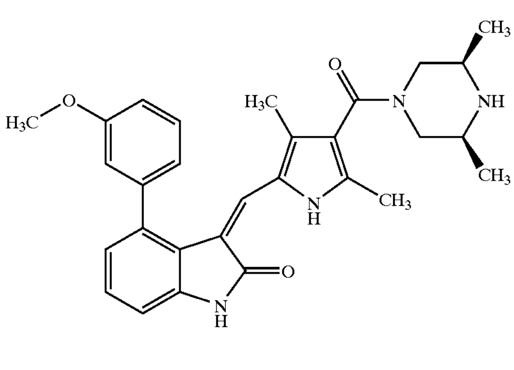 | 3-[4-(cis-3,5-Dimethyl-piperazine-1-carbonyl)-3,5-dimethyl-1H-pyrrol-2-ylmethylene]-4-(3-methoxy-phenyl)-1,3-dihydro-indol-2-one |

TABLE 1-continued

Preferred 4-Aryl Substituted Indolinones

| Example | Structure | Name |
|---|---|---|
| 50 | 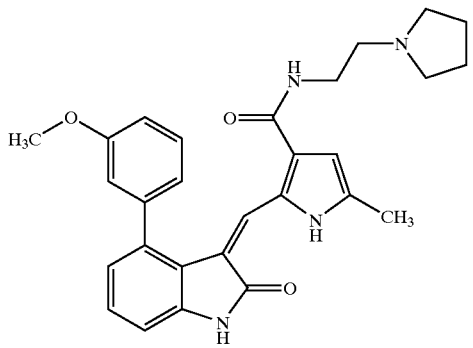 | 2-[4-(3-Methoxy-phenyl)-2-oxo-1,2-dihydro-indol-3-ylidenemethyl]-5-methyl-1H-pyrrole-3-carboxylic acid (2-pyrrolidin-1-yl-ethyl)-amide |
| 51 | 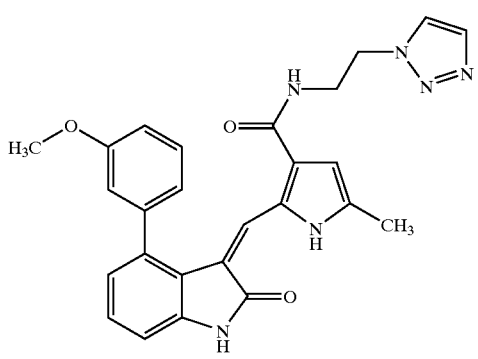 | 2-[4-(3-Methoxy-phenyl)-2-oxo-1,2-dihydro-indol-3-ylidenemethyl]-5-methyl-1H-pyrrole-3-carboxylic acid (2-[1,2,3]triazol-1-yl-ethyl)-amide |
| 52 | 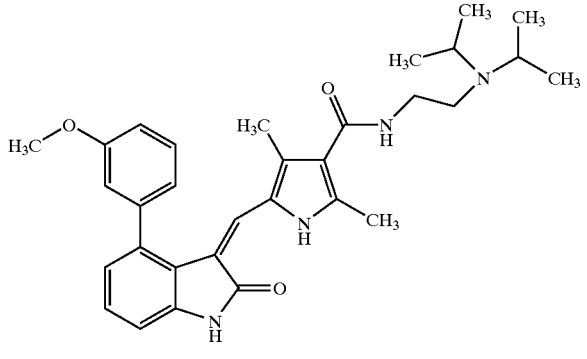 | 5-[4-(3-Methoxy-phenyl)-2-oxo-1,2-dihydro-indol-3-ylidenemethyl]-2,4-dimethyl-1H-pyrrole-3-carboxylic acid (2-diisopropylamino-ethyl)-amide |
| 53 | 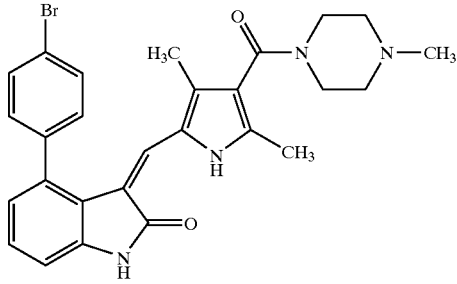 | 4-(4-Bromo-phenyl)-3-[3,5-dimethyl-4-(4-methyl-piperazine-1-carbonyl)-1H-pyrrol-2-ylmethylene]-1,3-dihydro-indol-2-one |

TABLE 1-continued

Preferred 4-Aryl Substituted Indolinones

| Example | Structure | Name |
|---|---|---|
| 54 | 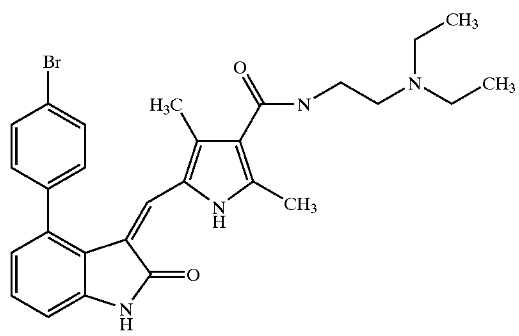 | 5-[4-(4-Bromo-phenyl)-2-oxo-1,2-dihydro-indol-3-ylidenemethyl]-2,4-dimethyl-1H-pyrrole-3-carboxylic acid (2-diethylamino-ethyl)-amide |
| 55 | 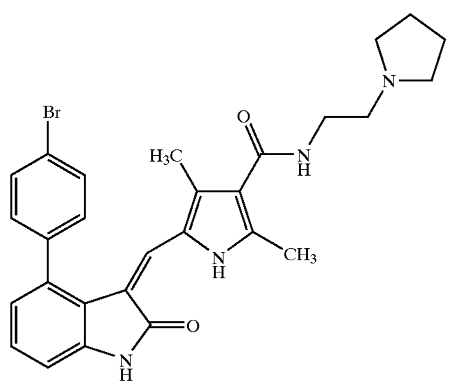 | 5-[4-(4-Bromo-phenyl)-2-oxo-1,2-dihydro-indol-3-ylidenemethyl]-2,4-dimethyl-1H-pyrrole-3-carboxylic acid (2-pyrrolidin-I-yl-ethyl)-amide |
| 56 | 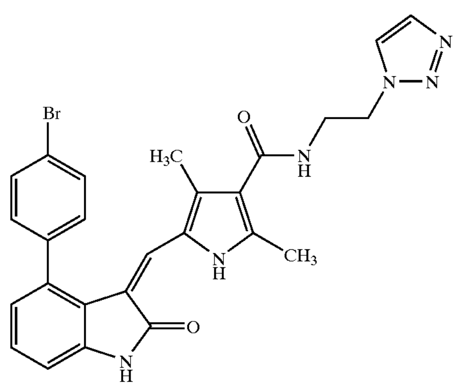 | 5-[4-(4-Bromo-phenyl)-2-oxo-1,2-dihydro-indol-3-ylidenemethyl]-2,4-dimethyl-1H-pyrrole-3-carboxylic acid (2-[1,2,3]triazol-1-yl-ethyl)-amide |
| 57 | 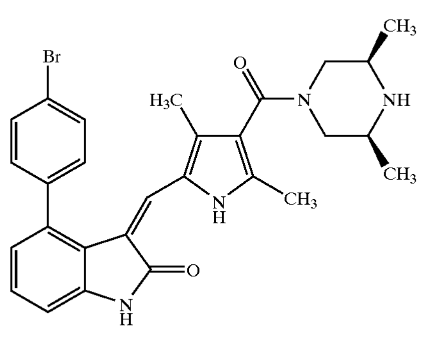 | 4-(4-Bromo-phenyl)-3-[4-[cis-3,5-dimethyl-piperazine-1-carbonyl)-3,5-dimethyl-1H-pyrrol-2-ylmethylene]-1,3-dihydro-indol-2-one |

TABLE 1-continued

Preferred 4-Aryl Substituted Indolinones

| Example | Structure | Name |
|---|---|---|
| 58 | 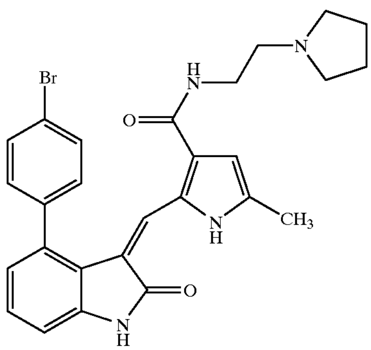 | 2-[4-(4-Bromo-phenyl)-2-oxo-1,2-dihydro-indol-3-ylidenemethyl]-5-methyl-1H-pyrrole-3-carboxylic acid (2-pyrrolidin-1-yl-ethyl)-amide |
| 59 | 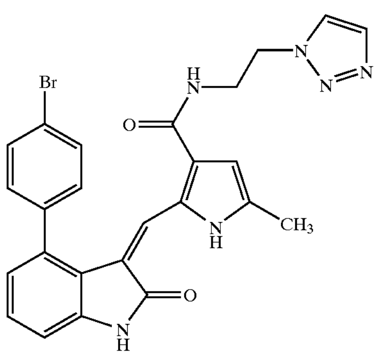 | 2-[4-(4-Bromo-phenyl)-2-oxo-1,2-dihydro-indol-3-ylidenemethyl]-5-methyl-1H-pyrrole-3-carboxylic acid (2-E1,2,3]triazol-1-yl-ethyl)-amide |
| 60 | 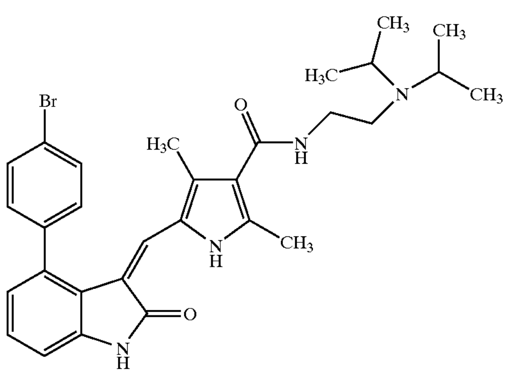 | 5-[4-(4-Bromo-phenyl)-2-oxo-1,2-dihydro-indol-3-ylidenemethyl]-2,4-dimethyl-1H-pyrrole-3-carboxylic acid (2-diisopropylamino-ethyl)-amide |
| 61 | 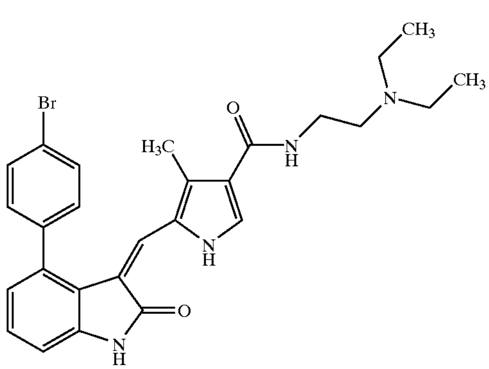 | 5-[4-(4-Bromo-phenyl)-2-oxo-1,2-dihydro-indol-3-ylidenemethyl]-4-methyl-1H-pyrrole-3-carboxylic acid (2-diethylamino-ethyl)-amide |

TABLE 1-continued

Preferred 4-Aryl Substituted Indolinones

| Example | Structure | Name |
|---|---|---|
| 62 | 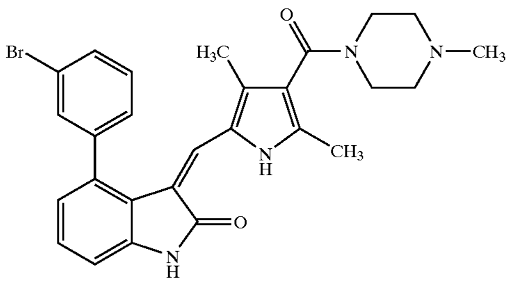 | 3-[3,5-Dimethyl-4-(4-methyl-piperazine-1-carbonyl)-1H-pyrrol-2-ylmethylene]-4-(3-bromo-phenyl)-1,3-dihydro-indol-2-one |
| 63 | 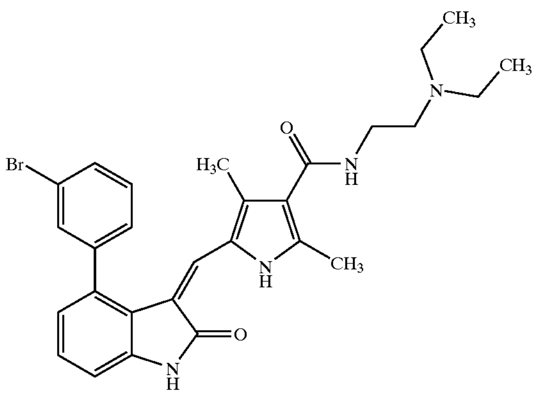 | 5-[4-(3-Bromo-phenyl)-2-oxo-1,2-dihydro-indol-3-ylidenemethyl]-2,4-dimethyl-1H-pyrrole-3-carboxylic acid (2-diethylamino-ethyl)-amide |
| 64 | 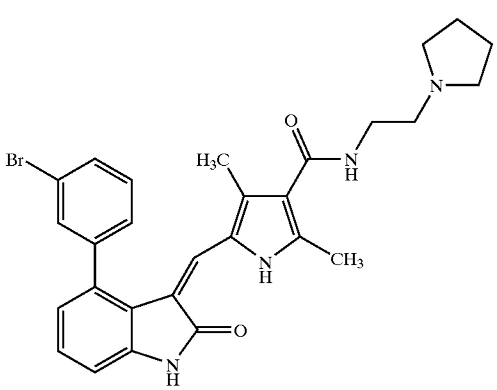 | 5-[4-(3-Bromo-phenyl)-2-oxo-1,2-dihydro-indol-3-ylidenemethyl]-2,4-dimethyl-1H-pyrrole-3-carboxylic acid (2-pyrrolidin-1-yl-ethyl)-amide |
| 65 | 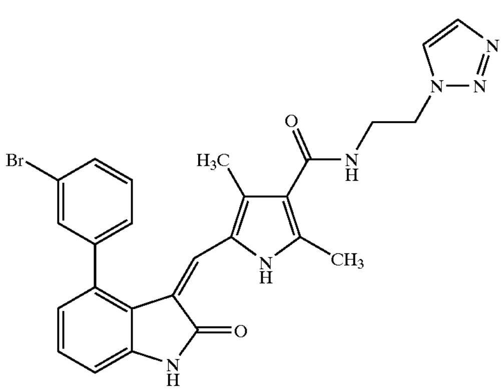 | 5-[4-(3-Bromo-phenyl)-2-oxo-1,2-dihydro-indol-3-ylidenemethyl]-2,4-dimethyl-1H-pyrrole-3-carboxylic acid (2-[1,2,3]triazol-1-yl-ethyl)-amide |

TABLE 1-continued

Preferred 4-Aryl Substituted Indolinones

| Example | Structure | Name |
|---|---|---|
| 66 | 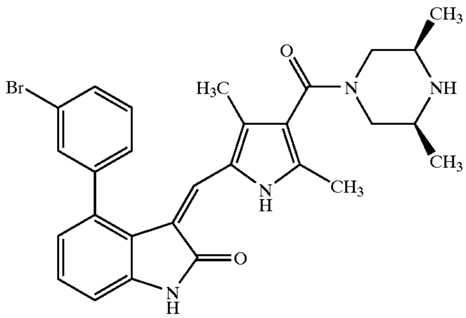 | 3-[4-(cis-3,5-Dimethyl-piperazine-1-carbonyl)-3,5-dimethyl-1H-pyrrol-2-ylmethylene]-4-(3-bromo-phenyl)-1,3-dihydro-indol-2-one |
| 67 | 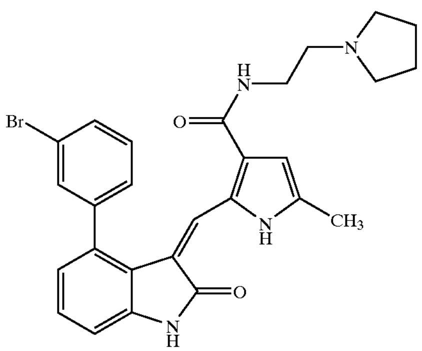 | 2-[4-(3-Bromo-phenyl)-2-oxo-1,2-dihydro-indol-3-ylidenemethyl]-5-methyl-1H-pyrrole-3-carboxylic acid (2-pyrrolidin-1-yl-ethyl)-amide |
| 68 | 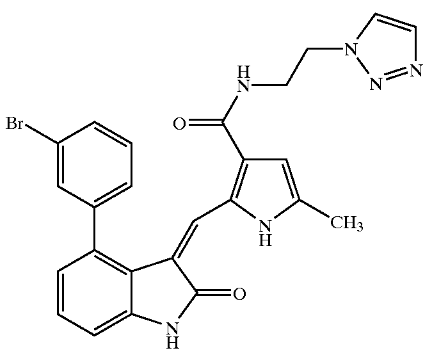 | 2-[4-(3-Bromo-phenyl)-2-oxo-1,2-dihydro-indol-3-ylidenemethyl]-5-methyl-1H-pyrrole-3-carboxylic acid (2-[1,2,3]triazole-1-yl-ethyl)-amide |
| 69 | 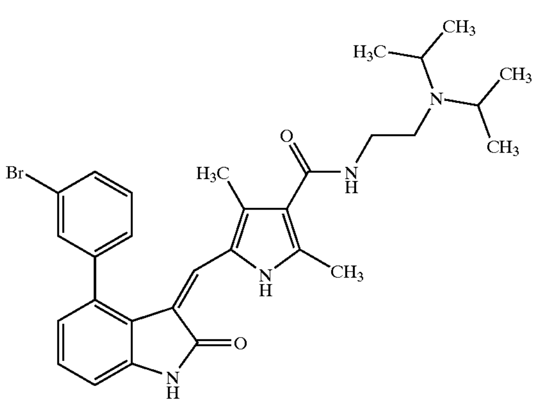 | 5-[4-(3-Bromo-phenyl)-2-oxo-1,2-dihydro-indol-3-ylidenemethyl]-2,4-dimethyl-1H-pyrrole-3-carboxylic acid (2-diisopropylamino-ethyl)-amide |

TABLE 1-continued

Preferred 4-Aryl Substituted Indolinones

| Example | Structure | Name |
|---|---|---|
| 70 | 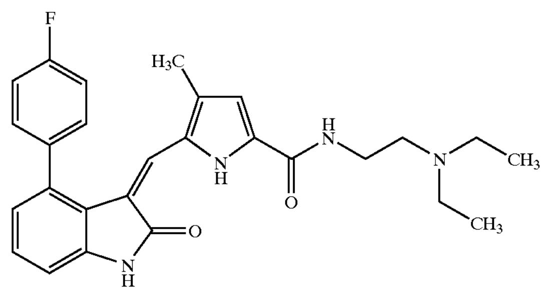 | 5-[4-(4-Fluoro-phenyl)-2-oxo-1,2-dihydro-indol-3-ylidenemethyl]-4-methyl-1H-pyrrole-2-carboxylic acid (2-diethylamino-ethyl)-amide |
| 71 | 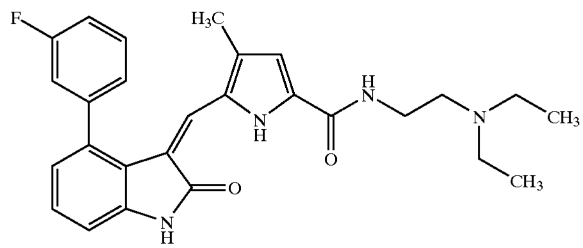 | 5-[4-(3-Fluoro-phenyl)-2-oxo-1,2-dihydro-indol-3-ylidenemethyl]-4-methyl-1H-pyrrole-2-carboxylic acid (2-diethylamino-ethyl)-amide |
| 72 | 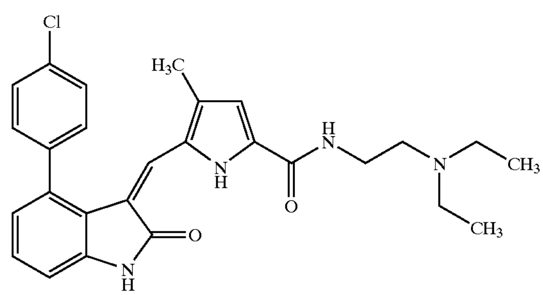 | 5-[4-(4-Chloro-phenyl)-2-oxo-1,2-dihydro-indol-3-ylidenemethyl]-4-methyl-1H-pyrrole-2-carboxylic acid (2-diethylamino-ethyl)-amide |
| 73 | 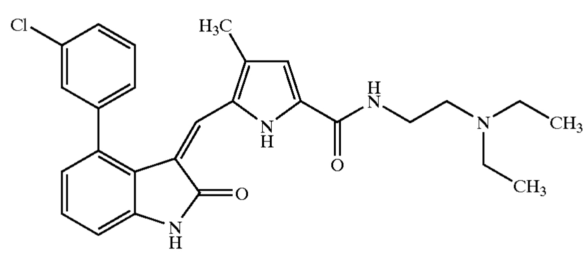 | 5-[4-(3-Chloro-phenyl)-2-oxo-1,2-dihydro-indol-3-ylidenemethyl]-4-methyl-1H-pyrrole-2-carboxylic acid (2-diethylamino-ethyl)-amide |
| 74 | 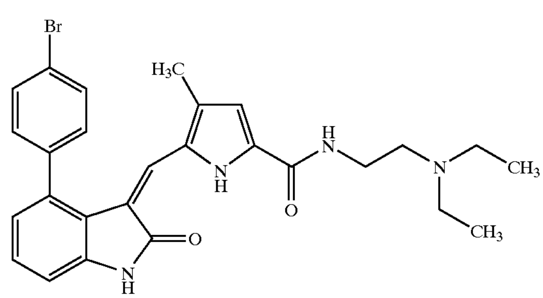 | 5-[4-(4-Bromo-phenyl)-2-oxo-1,2-dihydro-indol-3-ylidenemethyl]-4-methyl-1H-pyrrole-2-carboxylic acid (2-diethylamino-ethyl)-amide |

TABLE 1-continued

Preferred 4-Aryl Substituted Indolinones

| Example | Structure | Name |
|---|---|---|
| 75 | 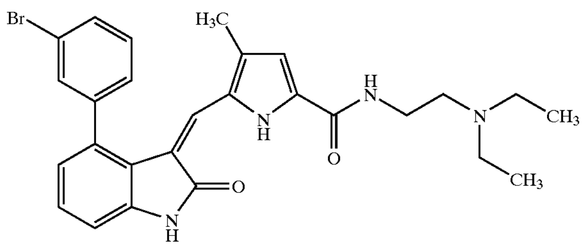 | 5-[4-(3-Bromo-phenyl)-2-oxo-1,2-dihydro-indol-3-ylidenemethyl]-4-methyl-1H-pyrrole-2-carboxylic acid (2-diethylamino-ethyl)-amide |
| 76 | 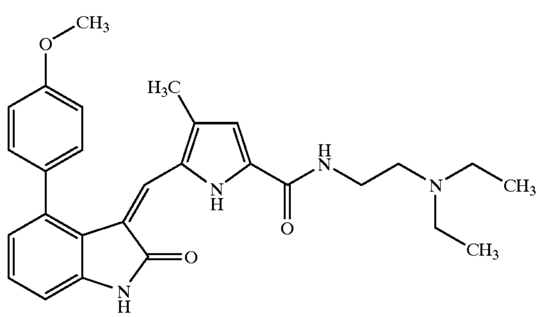 | 5-[4-(4-Methoxy-phenyl)-2-oxo-1,2-dihydro-indol-3-ylidenemethyl]-4-methyl-1H-pyrrole-2-carboxylic acid (2-diethylamino-ethyl)-amide |
| 77 | 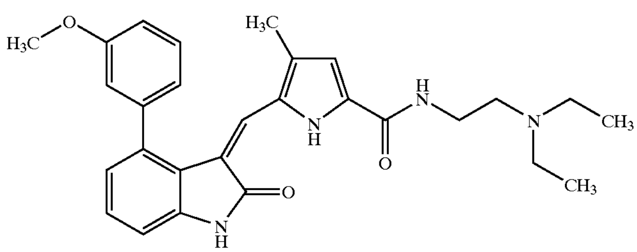 | 5-[4-(3-Methoxy-phenyl)-2-oxo-1,2-dihydro-indol-3-ylidenemethyl]-4-methyl-1H-pyrrol-2-carboxylic acid (2-diethylamino-ethyl)-amide |
| 78 | 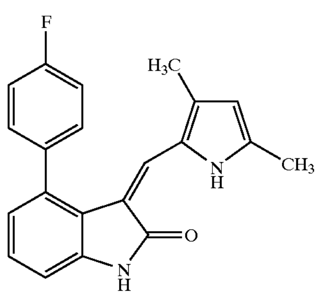 | 3-(3,5-Dimethyl-1H-pyrrol-2-ylmethylene)-4 (4-fluoro-phenyl)-1,3-dihydro-indol-2-one |
| 79 | 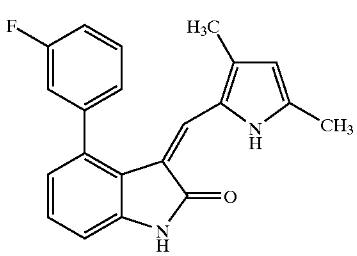 | 3-(3,5-Dimethyl-1H-pyrrol-2-ylmethylene)-4 (3-fluoro-phenyl)-1,3-dihydro-indol-2-one |

TABLE 1-continued

Preferred 4-Aryl Substituted Indolinones

| Example | Structure | Name |
|---|---|---|
| 80 | 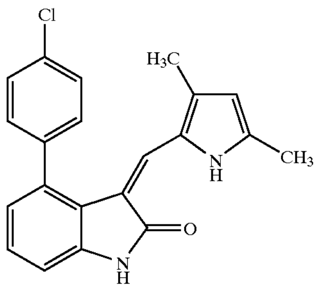 | 3-(3,5-Dimethyl-1H-pyrrol-2-ylmethylene)-4 (4-chloro-phenyl)-1,3-dihydro-indol-2-one |
| 81 | 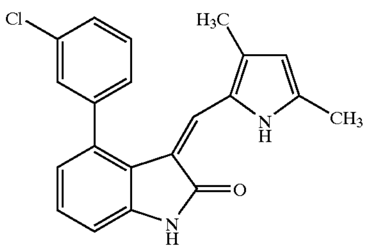 | 3-(3,5-Dimethyl-1H-pyrrol-2-ylmethylene)-4 (3-chloro-phenyl)-1,3-dihydro-indol-2-one |
| 82 | 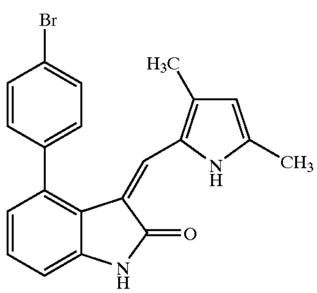 | 3-(3,5-Dimethyl-1H-pyrrol-2-ylmethylene)-4 (4-bromo-phenyl)-1,3-dihydro-indol-2-one |
| 83 | 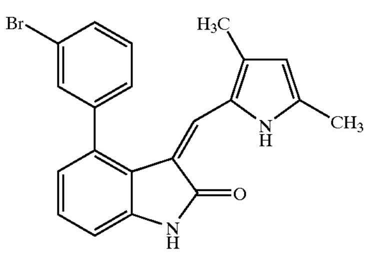 | 3-(3,5-Dimethyl-1H-pyrrol-2-ylmethylene)-4 (3-bromo-phenyl)-1,3-dihydro-indol-2-one |
| 84 | 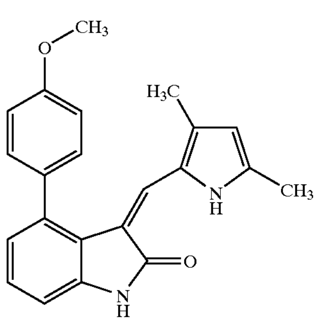 | 3-(3,5-Dimethyl-1H-pyrrol-2-ylmethylene)-4 (4-methoxy-phenyl)-l,3-dihydro-indol-2-one |

TABLE 1-continued

Preferred 4-Aryl Substituted Indolinones

| Example | Structure | Name |
|---|---|---|
| 85 | 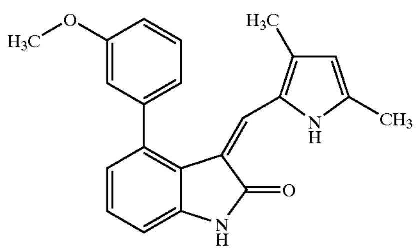 | 3-(3,5-Dimethyl-1H-pyrrol-2-ylmethylene)-4 (3-methoxy-phenyl)-1,3-dihydro-indol-2-one |
| 86 | 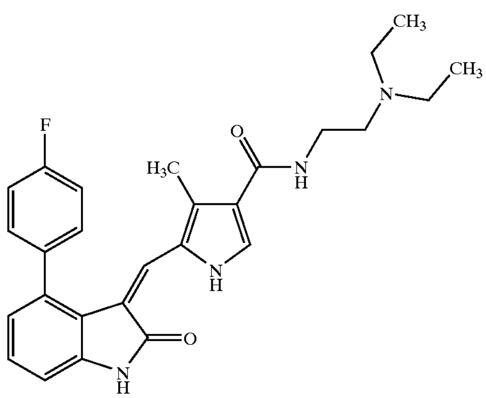 | 5-[4-(4-Fluoro-phenyl)-2-oxo-1,2-dihydro-indol-3-ylidenemethyl]-4-methyl-1H-pyrrole-3-carboxylic acid (2-diethylamino-ethyl)-amide |
| 87 | 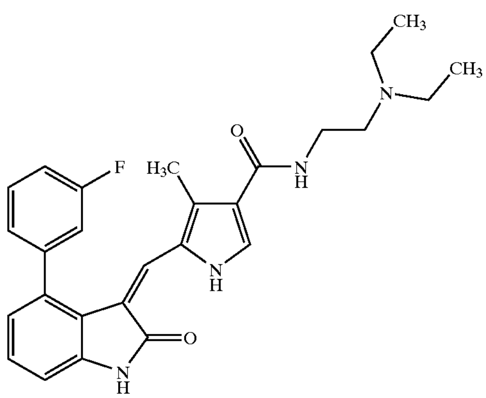 | 5-[4-(3-Fluoro-phenyl)-2-oxo-1,2-dihydro-indol-3-ylidenemethyl]-4-methyl-1H-pyrrole-3-carboxylic acid (2-diethylamino-ethyl)-amide |
| 88 | 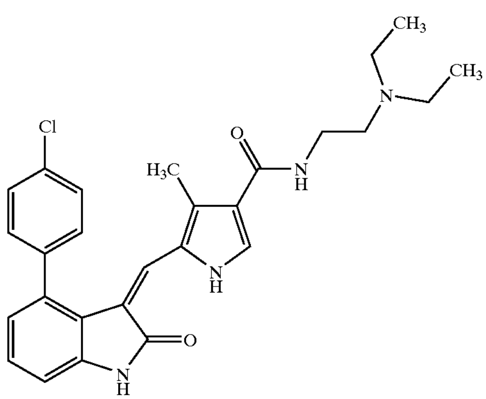 | 5-[4-(4-Chloro-phenyl)-2-oxo-1,2-dihydro-indol-3-ylidenemethyl]-4-methyl-1H-pyrrole-3-carboxylic acid (2-diethylamino-ethyl)-amide |

TABLE 1-continued

Preferred 4-Aryl Substituted Indolinones

| Example | Structure | Name |
|---|---|---|
| 89 | 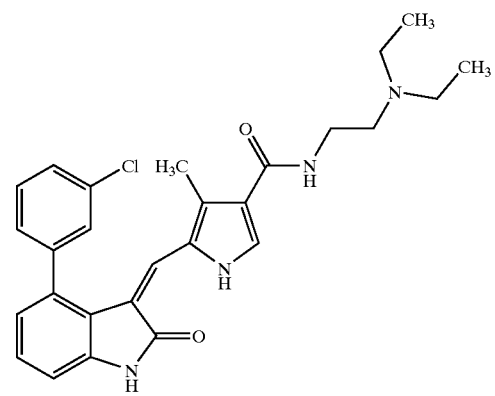 | 5-[4-(3-Chloro-phenyl)-2-oxo-1,2-dihydro-indol-3-ylidenemethyl]-4-methyl-1H-pyrrole-3-carboxylic acid (2-diethylamino-ethyl)-amide |
| 90 | 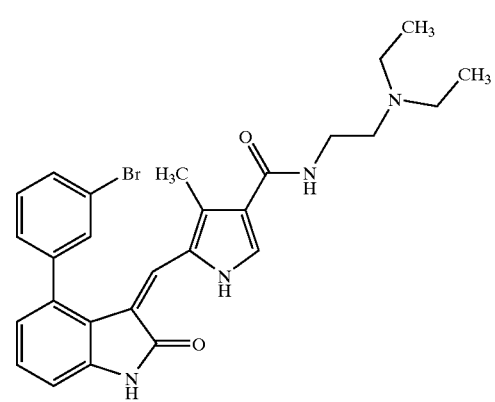 | 5-[4-(3-bromo-phenyl)-2-oxo-1,2-dihydro-indol-3-ylidenemethyl]-4-methyl-1H-pyrrole-3-carboxylic acid (2-diethylamino-ethyl)-amide |
| 91 | 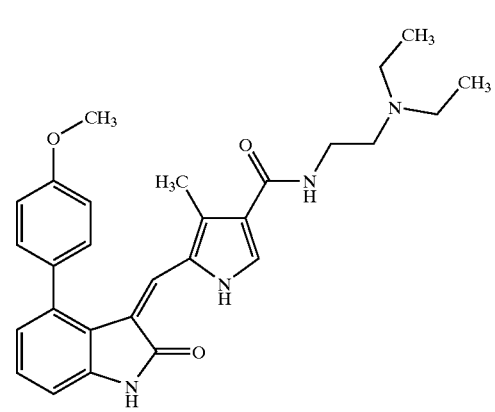 | 5-[4-(4-Methoxy-phenyl)-2-oxo-1,2-dihydro-indol-3-ylidenemethyl]-4-methyl-1H-pyrrole-3-carboxylic acid (2-diethylamino-ethyl)-amide |

TABLE 1-continued

Preferred 4-Aryl Substituted Indolinones

| Example | Structure | Name |
|---------|-----------|------|
| 92 | 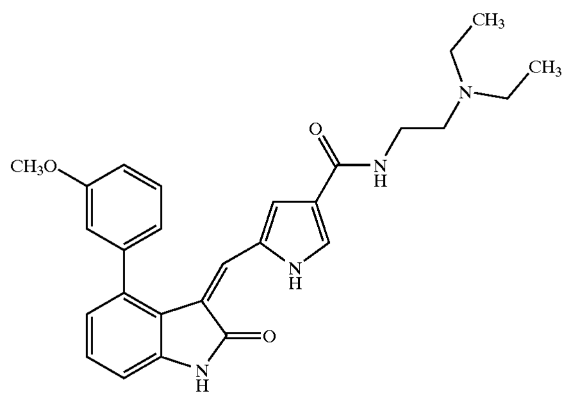 | 5-[4-(3-Methoxy-phenyl)-2-oxo-1,2-dihydro-indol-3-ylidenemethyl]-4-methyl-1H-pyrrole-3-carboxylic acid (2-diethylamino-ethyl)-amide |
| 93 | 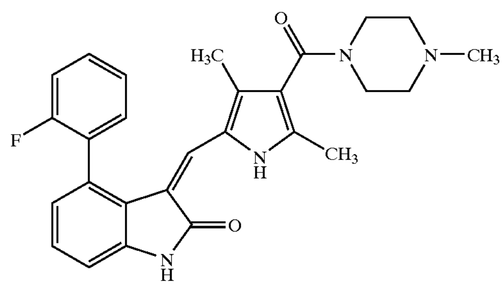 | 3-[3,5-Dimethyl-4-(4-methyl-piperazine-1-carbonyl)-1H-pyrrol-2-ylmethylene]-4-(2-fluoro-phenyl)-1,3-dihydro-indol-2-one |
| 94 | 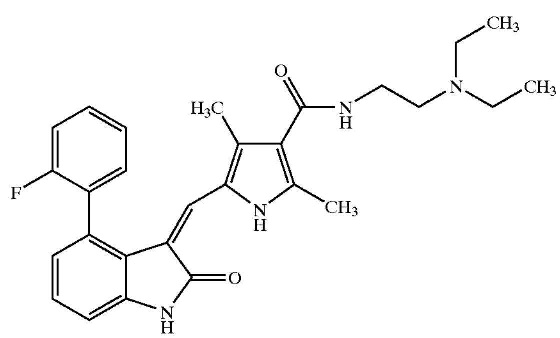 | 5-[4-(2-Fluoro-phenyl)-2-oxo-1,2-dihydro-indol-3-ylidenemethyl]-2,4-dimethyl-1H-pyrrole-3-carboxylic acid (2-diethylamino-ethyl)-amide |
| 95 | 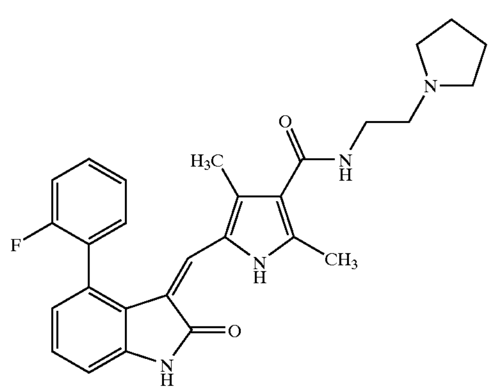 | 5-[4-(2-Fluoro-phenyl)-2-oxo-1,2-dihydro-indol-3-ylidenemethyl]-2,4-dimethyl-1H-pyrrole-3-carboxylic acid (2-pyrrolidin-1-yl-ethyl)-amide |

TABLE 1-continued

Preferred 4-Aryl Substituted Indolinones

| Example | Structure | Name |
|---|---|---|
| 96 | 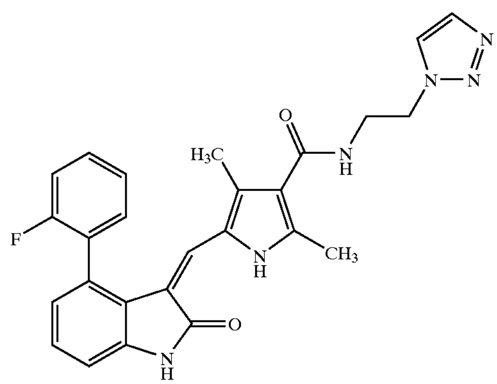 | 5-[4-(2-Fluoro-phenyl)-2-oxo-1,2-dihydro-indol-3-ylidenemethyl]-2,4-dimethyl-1H-pyrrole-3-carboxylic acid (2-[1,2,3]triazol-1-yl-ethyl)-amide |
| 97 | 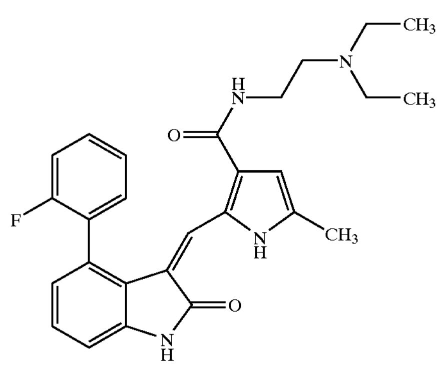 | 2-[4-(2-fluoro-phenyl)-2-oxo-1,2-dihydro-indol-3-ylidenemethyl]-5-methyl-1H-pyrrole-3-carboxylic acid (2-diethylamino-ethyl)-amide |
| 98 | 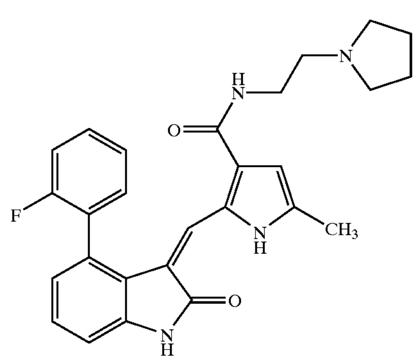 | 2-[4-(2-fluoro-phenyl)-2-oxo-1,2-dihydro-indol-3-ylidenemethyl]-5-methyl-1H-pyrrole-3-carboxylic acid (2-pyrrolidin-1-yl-ethyl)-amide |

TABLE 1-continued

Preferred 4-Aryl Substituted Indolinones

| Example | Structure | Name |
|---|---|---|
| 99 | 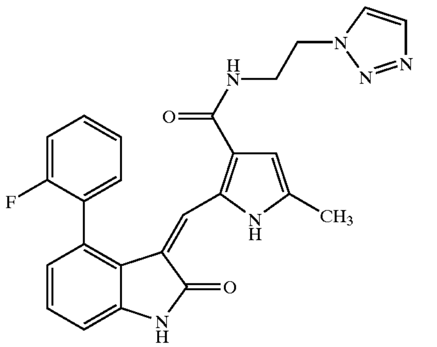 | 2-[4-(2-fluoro-phenyl)-2-oxo-1,2-dihydro-indol-3-ylidenemethyl]-5-methyl-1H-pyrrole-3-carboxylic acid (2-[1,2,3]triazol-1-yl-ethyl)-amide |
| 100 | 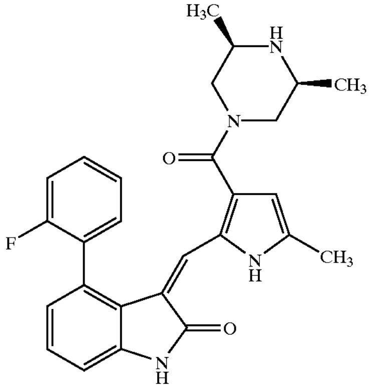 | 3-[3-(cis-3,5-dimethyl-piperazine-1-carbonyl)-5-methyl-1H-pyrrol-2-ylmethylene]-4-(2-fluoro-phenyl)-1,3-dihydro-indol-2-one |
| 101 | 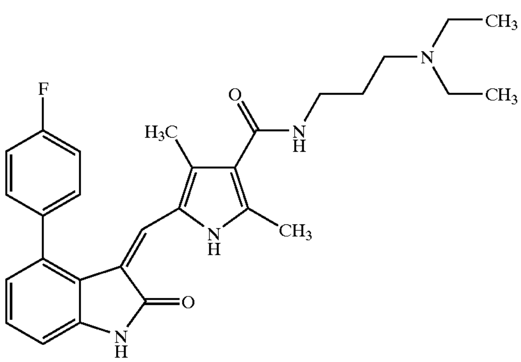 | 5-[4-(4-Fluoro-phenyl)-2-oxo-1,2-dihydro-indol-3-ylidenemethyl]-2,4-dimethyl-1H-pyrrole-3-carboxylic acid (3-diethylamino-propyl)-amide |
| 102 | 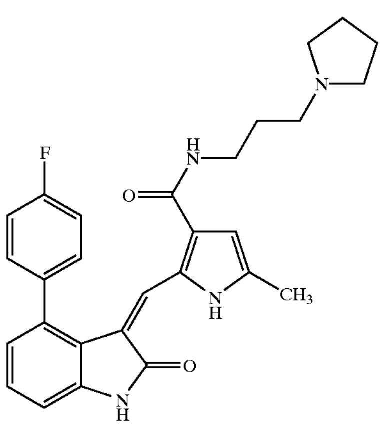 | 2-[4-(4-fluoro-phenyl)-2-oxo-1,2-dihydro-indol-3-ylidenemethyl]-5-methyl-1H-pyrrole-3-carboxylic acid (3-pyrrolidin-1-yl-propyl)-amide |

TABLE 1-continued

Preferred 4-Aryl Substituted Indolinones

| Example | Structure | Name |
|---|---|---|
| 103 | 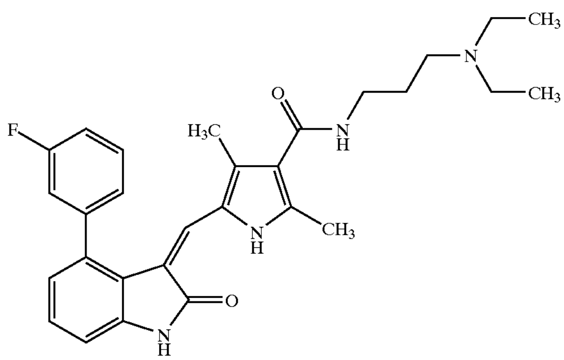 | 5-[4-(3-Fluoro-phenyl)-2-oxo-1,2-dihydro-indol-3-ylidenemethyl]-2,4-dimethyl-1H-pyrrole-3-carboxylic acid (3-diethylamino-propyl)-amide |
| 104 | 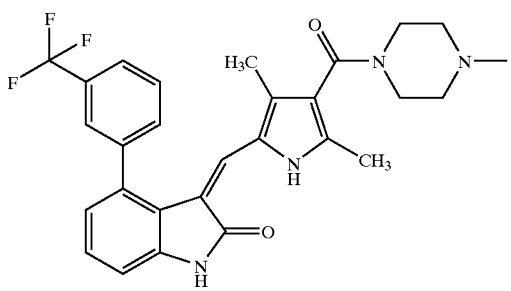 | 3-[3,5-Dimethyl-4-(4-methyl-piperazine-1-carbonyl)-1H-pyrrol-2-ylmethylene]-4-(3-trifluoromethyl-phenyl)-1,3-dihydro-indol-2-one |
| 105 | 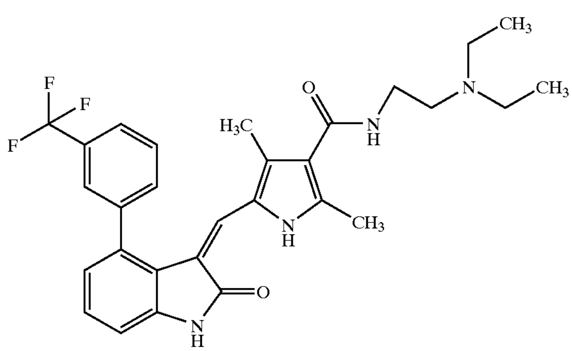 | 2,4-Dimethyl-5-[2-oxo-4-(3-trifluoromethyl-phenyl)-1,2-dihydro-indol-3-ylidenemethyl]-1H-pyrrole-3-carboxylic acid (2-diethylamino-ethyl)-amide |
| 106 | 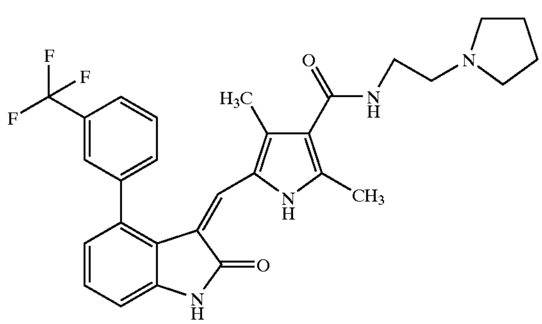 | 2,4-Dimethyl-5-[2-oxo-4-(3-trifluoromethyl-phenyl)-1,2-dihydro-indol-3-ylidenemethyl]-1H-pyrrole-3-carboxylic acid (2-pyrrolidin-1-yl-ethyl)-amide |

TABLE 1-continued

Preferred 4-Aryl Substituted Indolinones

| Example | Structure | Name |
|---|---|---|
| 107 | 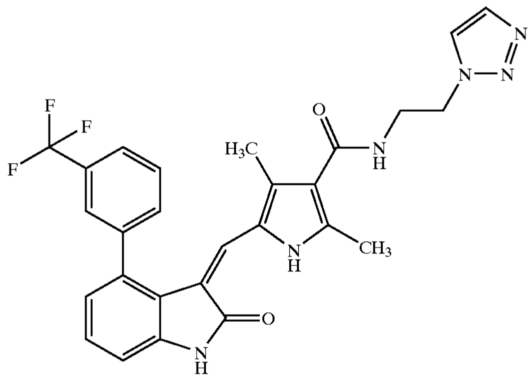 | 2,4-Dimethyl-5-[2-oxo-4-(3-trifluoromethyl-phenyl)-1,2-dihydro-indol-3-ylidenemethyl]-1H-pyrrole-3-carboxylic acid (2-[1,2,3]triazol-1-yl-ethyl)-amide |
| 108 | 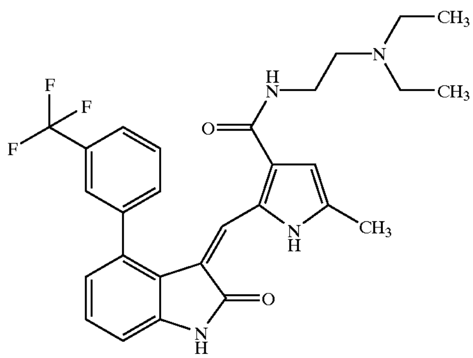 | 5-methyl-2-[2-oxo-4-(3-trifluoromethyl-phenyl)-1,2-dihydro-indol-3-ylidenemethyl]-1H-pyrrole-3-carboxylic acid (2-diethylamino-ethyl)-amide |
| 109 | 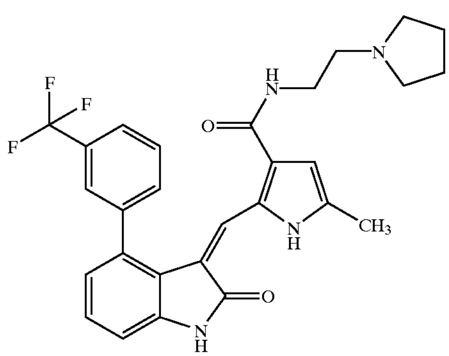 | 5-methyl-2-[2-oxo-4-(3-trifluoromethyl-phenyl)-1,2-dihydro-indol-3-ylidenemethyl]-1H-pyrrole-3-carboxylic acid (2-pyrrolidin-1-yl-ethyl)-amide |
| 110 | 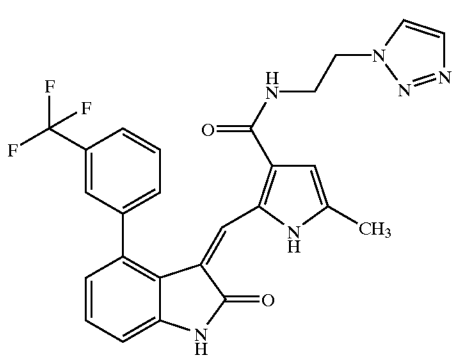 | 5-methyl-2-[2-oxo-4-(3-trifluoromethyl-phenyl)-1,2-dihydro-indol-3-ylidenemethyl]-1H-pyrrole-3-carboxylic acid (2-[1,2,3]triazol-1-yl-ethyl)-amide |

TABLE 1-continued

Preferred 4-Aryl Substituted Indolinones

| Example | Structure | Name |
|---|---|---|
| 111 | 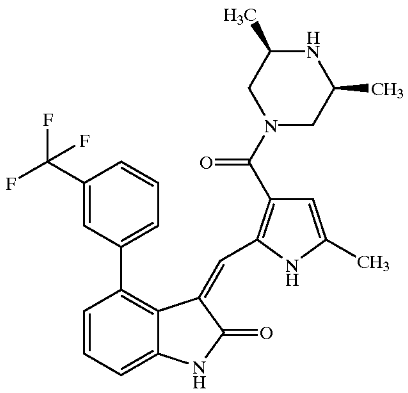 | 3-[3-(cis-3,5-dimethyl-piperazine-1-carbonyl)-5-methyl-1H-pyrrol-2-ylmethylene]-4-(2-trifluoromethyl-phenyl)-1,3-dihydro-indol-2-one |
| 112 | 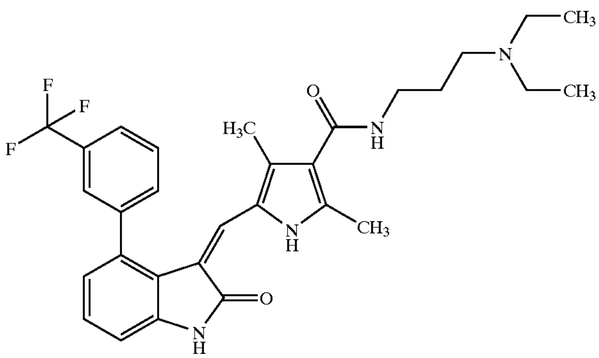 | 2,4-Dimethyl-5-[2-oxo-4-(3-trifluoromethyl-phenyl)-1,2-dihydro-indol-3-ylidenemethyl]-1H-pyrrole-3-carboxylic acid (3-diethylamino-propyl)-amide |
| 113 | 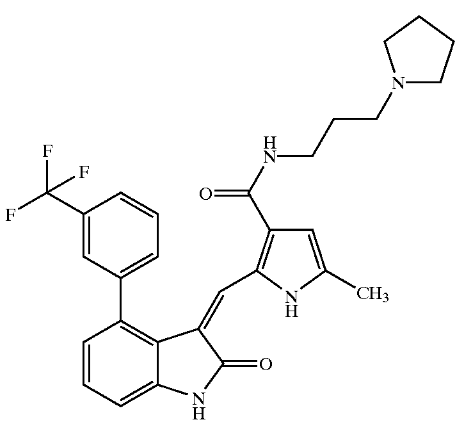 | 5-methyl-2-[2-oxo-4-(3-trifluoromethyl-phenyl)-1,2-dihydro-indol-3-ylidenemethyl]-1H-pyrrole-3-carboxylic acid (3-pyrrolidin-1-yl-propyl)-amide |
| 114 | 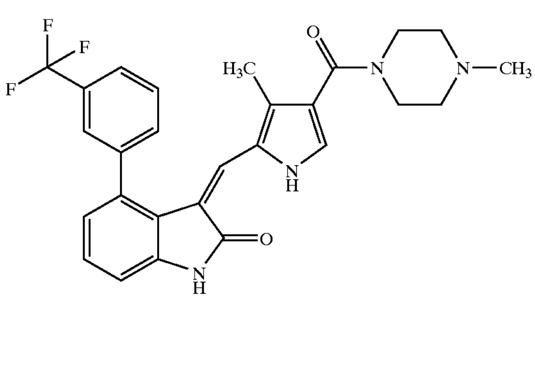 | 3-[3-methyl-4-(4-methyl-piperazine-1-carbonyl)-1H-pyrrol-2-ylmethylene]-4-(3-trifluoromethyl-phenyl)-1,3-dihydro indol-2-one |

TABLE 1-continued

Preferred 4-Aryl Substituted Indolinones

| Example | Structure | Name |
|---|---|---|
| 115 | 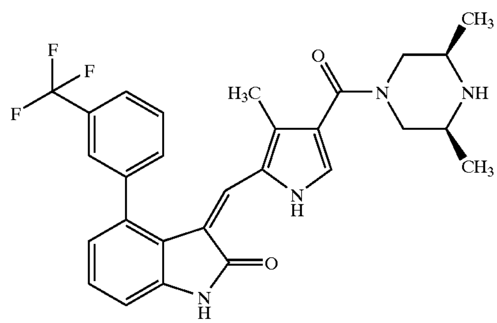 | 3-[3-Methyl-4-(cis-3,5-dimethyl-piperazine-1-carbonyl)-1H-pyrrol-2-ylmethylene]-4-(3-trifluoromethyl-phenyl)-1,3-dihydro-indol-2-one |
| 116 | 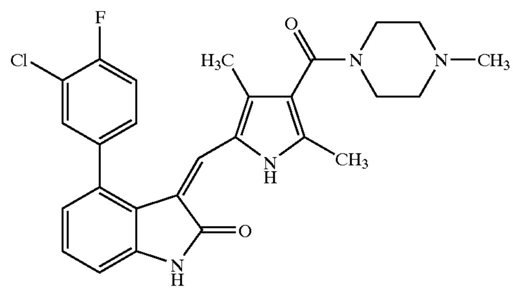 | 4-(3-chloro-4-fluoro-phenyl)-3-[3,5-dimethyl-4-(4-methyl-piperazine-1-carbonyl)-1H-pyrrol-2-ylmethylene]-1,3-dihydro-indol-2-one |
| 117 | 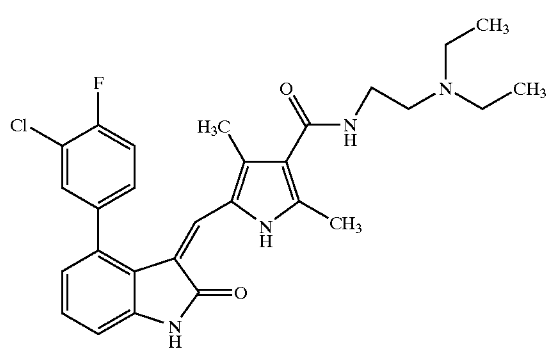 | 5-[4-(3-chloro-4-fluoro-phenyl)-2-oxo-1,2-dihydro-indol-3-ylidenemethyl]-2,4-dimethyl-1H-pyrrole-3-carboxylic acid (2-diethylamino-ethyl)-amide |
| 118 | 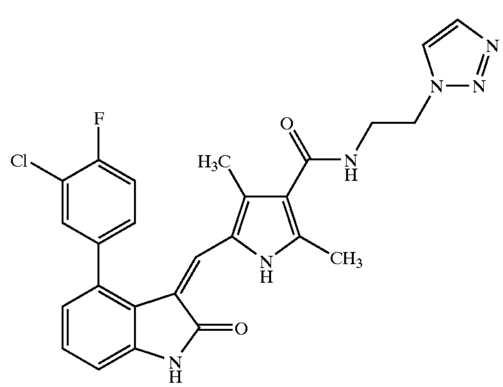 | 5-[4-(3-chloro-4-fluoro-phenyl)-2-oxo-1,2-dihydro-indol-3-ylidenemethyl]-2,4-dimethyl-1H-pyrrole-3-carboxylic acid (2-[1,2,3]triazol-1-yl-ethyl)-amide |

TABLE 1-continued

Preferred 4-Aryl Substituted Indolinones

| Example | Structure | Name |
|---|---|---|
| 119 | 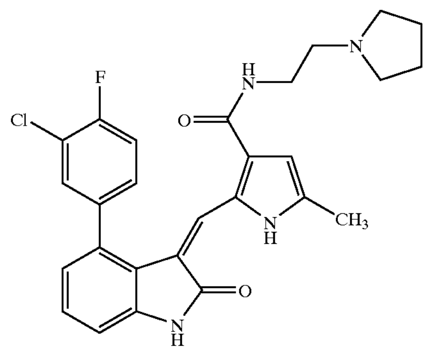 | 2-[4-(3-chloro-4-fluoro-phenyl)-2-oxo-1,2-dihydro-indol-3-ylidenemethyl]-5-methyl-1H-pyrrole-3-carboxylic acid(2-pyrrolidin-1-yl-ethyl)-amide |
| 120 | 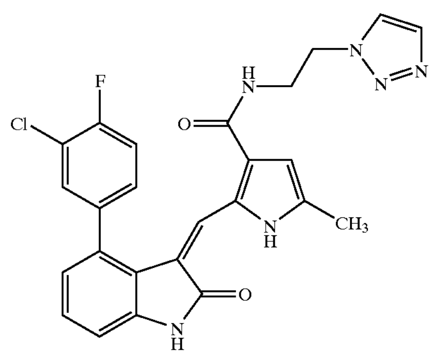 | 2-[4-(3-chloro-4-fluoro-phenyl)-2-oxo-1,2-dihydro-indol-3-ylidenemethyl]-5-methyl-1H pyrrole-3-carboxylic acid (2-[1,2,3]triazol-1-yl-ethyl)-amide |
| 121 | 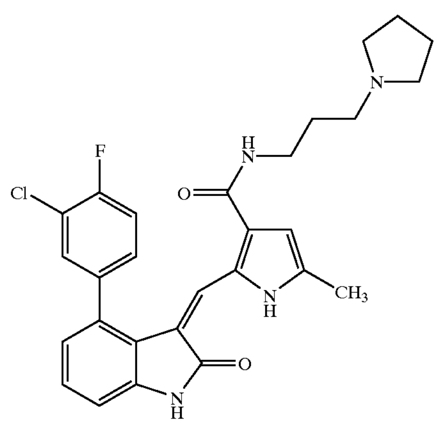 | 2-[4-(3-chloro-4-fluoro-phenyl)-2-oxo-1,2-dihydro-indol-3-ylidenemethyl]-5-methyl-1H pyrrole-3-carboxylic acid (3-pyrrolidin-1-yl-propyl)-amide |
| 122 | 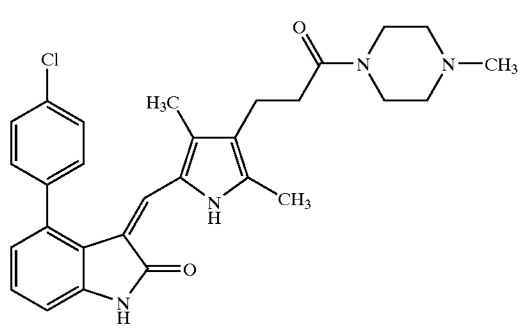 | 4-(4-chloro-phenyl)-3-[3,5-dimethyl-4-[3-(4-methyl-piperazin-1-yl)-3-oxo-propyl]-1H-pyrrol-2-ylmethylene]-1,3-dihydro-indol-2-one |

TABLE 1-continued

Preferred 4-Aryl Substituted Indolinones

| Example | Structure | Name |
|---|---|---|
| 123 | 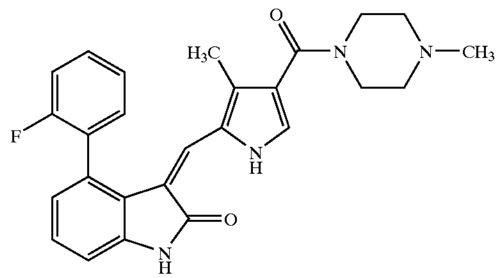 | 4-(2-fluoro-phenyl)-3-[3-methyl-4-(4-methyl-piperazine-1-carbonyl)-1H-pyrrol-2-ylmethylene]-1,3-dihydro-indol-2-one |
| 124 | 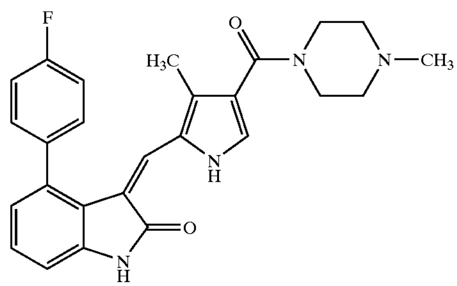 | 4-(4-fluoro-phenyl)-3-[3-methyl-4-(4-methyl-piperazine-1-carbonyl)-1H-pyrrol-2-ylmethylene]-1,3-dihydro-indol-2-one |
| 125 | 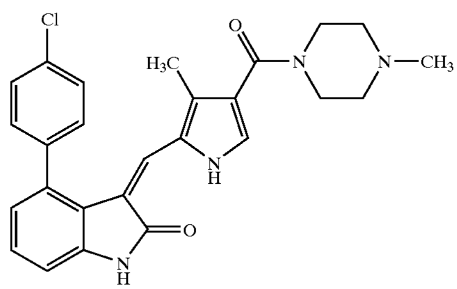 | 4-(4-chloro-phenyl)-3-[3-methyl-4-(4-methyl-piperazine-1-carbonyl)-1H-pyrrol-2-ylmethylene]-1,3-dihydro-indol-2-one |
| 126 | 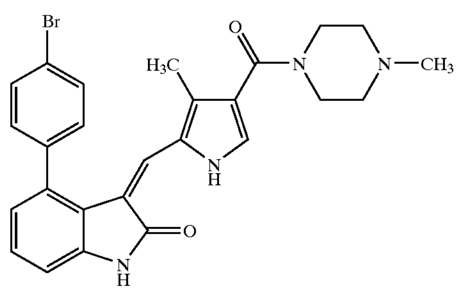 | 4-(4-bromo-phenyl)-3-[3-methyl-4-(4-methyl-piperazine-1-carbonyl)-1H-pyrrol-2-ylmethylene]-1,3-dihydro-indol-2-one |
| 127 | 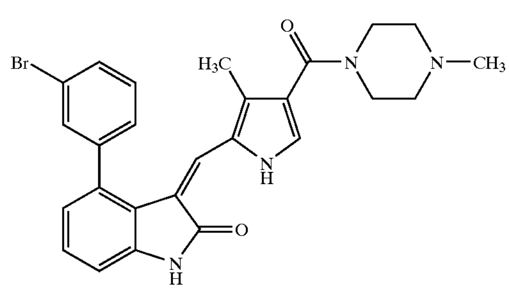 | 4-(3-bromo-phenyl)-3-[3-methyl-4-(4-methyl-piperazine-1-carbonyl)-1H-pyrrol-2-ylmethylene]-1,3-dihydro-indol-2-one |

TABLE 1-continued

Preferred 4-Aryl Substituted Indolinones

| Example | Structure | Name |
|---|---|---|
| 128 | 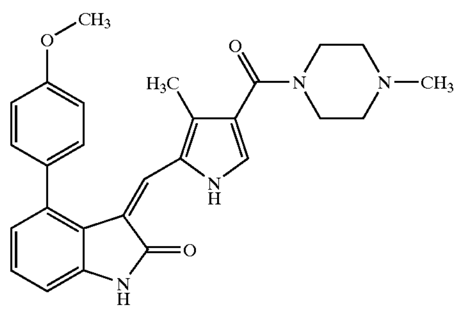 | 4-(4-methoxy-phenyl)-3-[3-methyl-4-(4-methyl-piperazine-1-carbonyl)-1H-pyrrol-2-ylmethylene]-1,3-dihydro-indol-2-one |
| 129 | 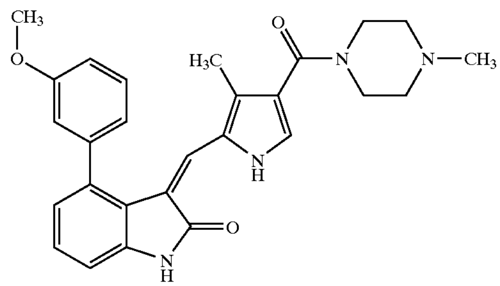 | 4-(3-methoxy-phenyl)-3-[3-methyl-4-(4-methyl-piperazine-1-carbonyl)-1H-pyrrol-2-ylmethylene]-1,3-dihydro-indol-2-one |
| 130 | 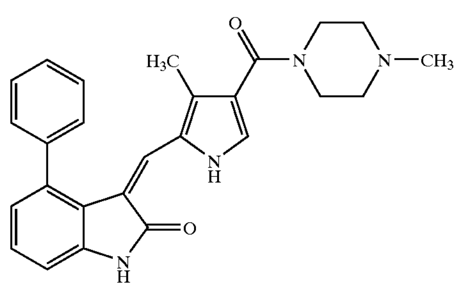 | 3-[3-methyl-4-(4-methyl-piperazine-1-carbonyl)-1H-pyrrol-2-ylmethylene]-4-phenyl-1,3-dihydro-indol-2-one |
| 131 | 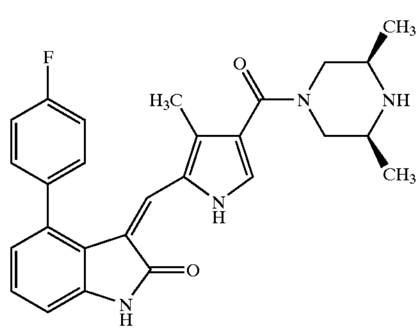 | 3-[4-(cis-3,5-dimethyl-piperazine-1-carbonyl)-3-methyl-1H-pyrrol-2-ylmethylene]-4-(4-fluoro-phenyl)-1,3-dihydro indol-2-one |
| 132 | 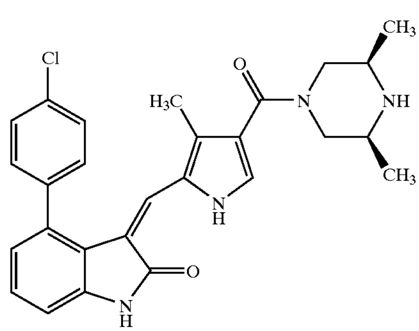 | 4-(4-Chloro-phenyl)-3-[4-[cis-3,5-dimethyl-piperazine-1-carbonyl)-3-methyl-1H-pyrrol-2 ylmethylene]-1,3-dihydro-indol-2-one |

TABLE 1-continued

Preferred 4-Aryl Substituted Indolinones

| Example | Structure | Name |
|---|---|---|
| 133 | 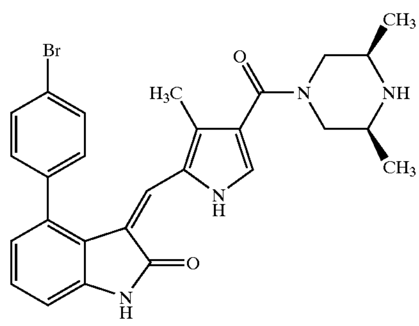 | 4-(4-Bromo-phenyl)-3-[4-(cis-3,5-dimethyl-piperazine-1-carbonyl)-3-methyl-1H-pyrrol-2-ylmethylene]-1,3-dihydro-indol-2-one |
| 134 | 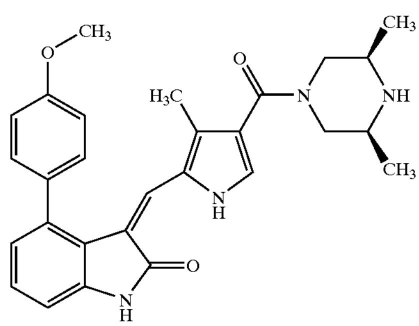 | 3-[4-(cis-3,5-dimethyl-piperazine-1-carbonyl)-3-methyl-1H-pyrrol-2-ylmethylene-4-(4-methoxy-phenyl)-1,3-dihydro-indol-2-one |
| 135 | 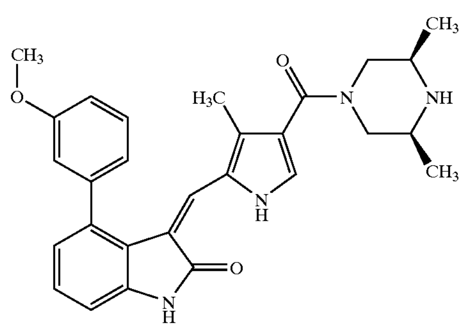 | 3-[4-(cis-3,5-dimethyl-piperazine-1-carbonyl)-3-methyl-1H-pyrrol-2-ylmethylene]-4-(3-methoxy-phenyl)-1,3-dihydro-indol-2-one |
| 136 | 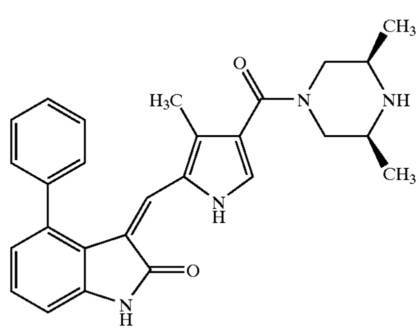 | 3-[4-(cis-3,5-dimethyl-piperazine-1-carbonyl)-3-methyl-1H-pyrrol-2-ylmethylene]-4-phenyl-1,3-dihydro-indol-2-one |

TABLE 1-continued

Preferred 4-Aryl Substituted Indolinones

| Example | Structure | Name |
|---|---|---|
| 137 | 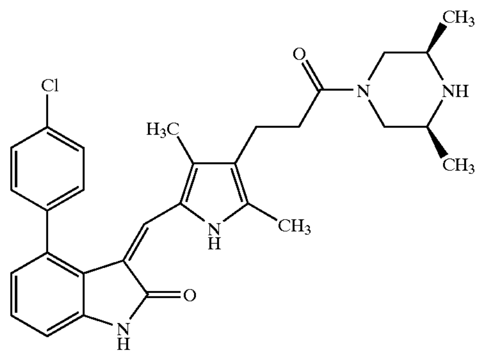 | 4-(4-chloro-phenyl)-3-[4-[3-(cis-3,5-dimethyl-piperazin-1-yl)-3-oxo-propyl]-3,5-dimethyl-1H-pyrrol-2-ylmethylene]-1,3-dihydro-indol-2-one |
| 138 | 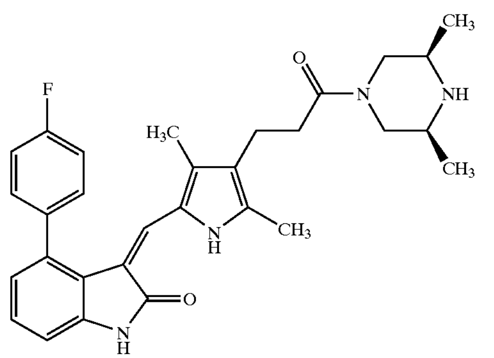 | 3-{4-[3-(cis-3,5-Dimethyl-piperazin-1-yl)-3-oxo-propyl]-3,5-dimethyl-1H-pyrrol-2-ylmethylene}-4-(4-fluoro-phenyl)-1,3-dihydro-indol-2-one |
| 139 | 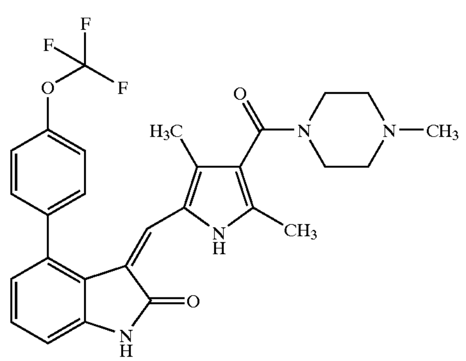 | 3-[3,5-Dimethyl-4-(4-methyl-piperazine-1-carbonyl)-1H-pyrrol-2-ylmethylene]-4-(4-trifluoromethoxy-phenyl)-1,3-dihydro-indol-2-one |
| 140 | 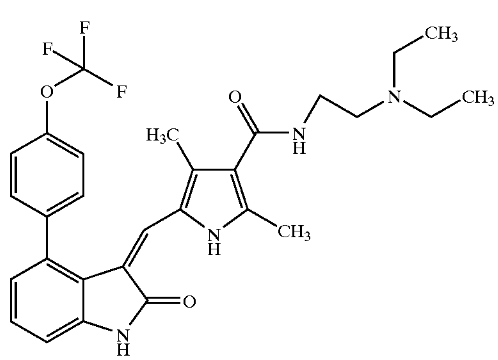 | 2,4-Dimethyl-5-[2-oxo-4-(4-trifluoromethoxyphenyl)-1,2-dihydro-indol-3-ylidenemethyl]-1H-pyrrole-3-carboxylic acid (2-diethylamino-ethyl)-amide |

TABLE 1-continued

Preferred 4-Aryl Substituted Indolinones

| Example | Structure | Name |
|---|---|---|
| 141 | 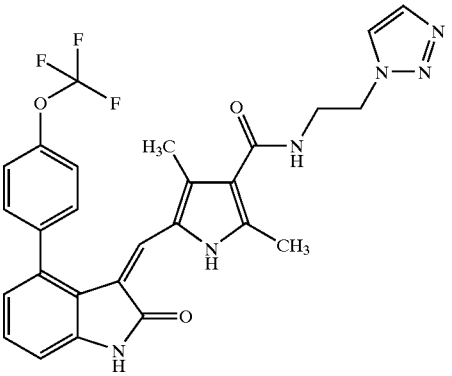 | 2,4-Dimethyl-5-[2-oxo-4-(4-trifluoromethoxy phenyl)-1,2-dihydro-indol-3-ylidenemethyl]-1H-pyrrole-3-carboxylic acid (2-[1,2,3]triazol 1-yl-ethyl)-amide |
| 142 | 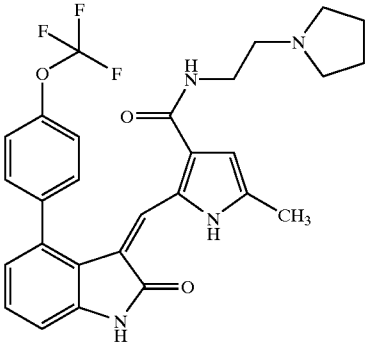 | 5-methyl-2-[2-oxo-4-(4-trifluoromethoxy-phenyl)-1,2-dihydro-indol-3-ylidenemethyl]-1H-pyrrole-3-carboxylic acid (2-pyrrolidin-1-yl-ethyl)-amide |
| 143 | 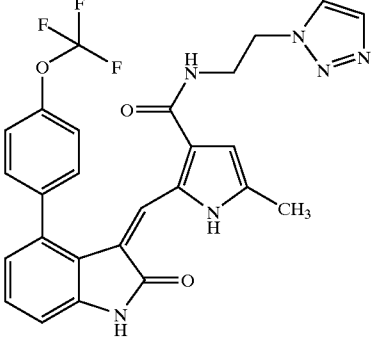 | 5-methyl-2-[2-oxo-4-(4-trifluoromethoxy-phenyl)-1,2-dihydro-indol-3-ylidenemethyl]-1H-pyrrole-3-carboxylic acid (2-[1,2,3]triazol 1-yl-ethyl)-amide |
| 144 | 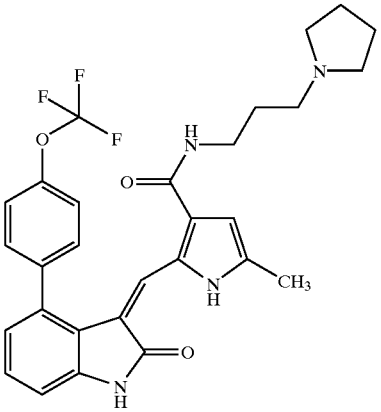 | 5-methyl-2-[2-oxo-4-(4-trifluoromethyl-phenyl)-1,2-dihydro-indol-3-ylidenemethyl]-1H-pyrrole-3-carboxylic acid (3-pyrrolidin-1-yl-propyl)-amide |

TABLE 1-continued

Preferred 4-Aryl Substituted Indolinones

| Example | Structure | Name |
|---|---|---|
| 145 | 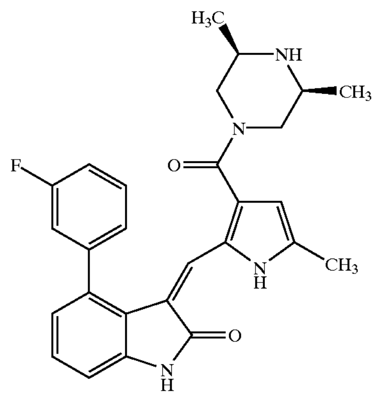 | 3-[3-(trans-3,5-Dimethyl-piperazine-1-carbonyl)-5-methyl-1H-pyrrol-2-ylmethylene]-4-(3-fluoro-phenyl)-1,3-dihydro-indol-2-one |
| 146 | 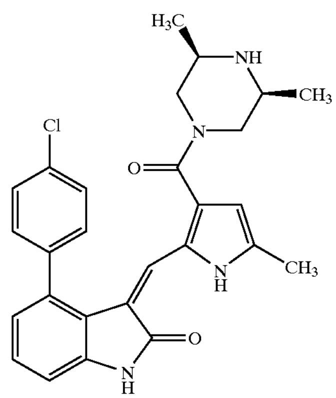 | 4-(4-Chloro-phenyl)-3-[3-(trans-3,5-dimethyl piperazine-1-carbonyl)-5-methyl-1H-pyrrol-2 ylmethylene]-1,3-dihydro-indol-2-one |
| 147 | 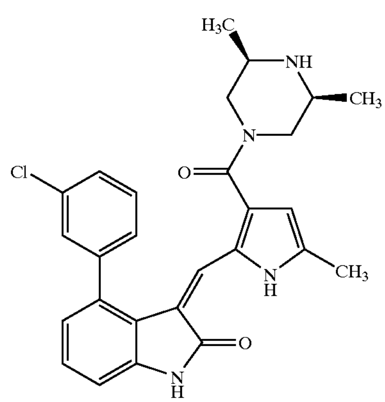 | 4-(3-Chloro-phenyl)-3-[3-(trans-3,5-dimethyl piperazine-1-carbonyl)-5-methyl-1H-pyrrol-2 ylmethylene]-1,3-dihydro-indol-2-one |

TABLE 1-continued

Preferred 4-Aryl Substituted Indolinones

| Example | Structure | Name |
|---|---|---|
| 148 | 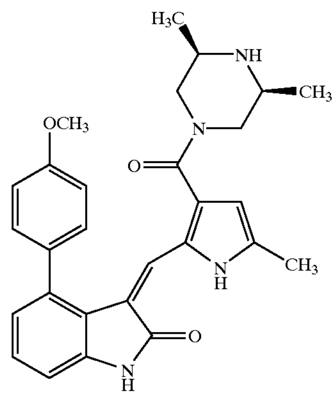 | 3-[4-(trans-3,5-Dimethyl-piperazine-1-carbonyl)-3,5-dimethyl-1H-pyrrol-2-ylmethylene]-4-(4-methoxy-phenyl)-1,3-dihydro-indol-2-one |
| 149 | 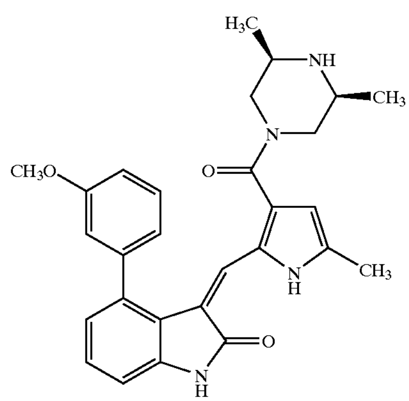 | 3-[4-(trans-3,5-Dimethyl-piperazine-1-carbonyl)-3,5-dimethyl-1H-pyrrol-2-ylmethylene]-4-(3-methoxy-phenyl)-1,3-dihydro-indol-2-one |
| 150 | 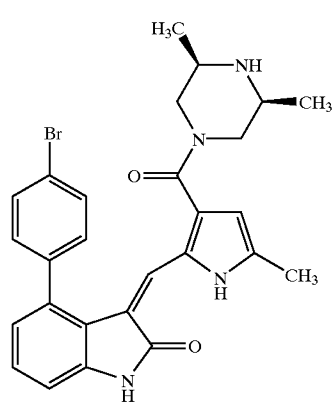 | 4-(4-Bromo-phenyl)-3-[4-[trans-3,5-dimethyl piperazine-1-carbonyl)-3,5-dimethyl-1H-pyrrol-2-ylmethylene]-1,3-dihydro-indol-2-one |

TABLE 1-continued

Preferred 4-Aryl Substituted Indolinones

| Example | Structure | Name |
|---|---|---|
| 151 | 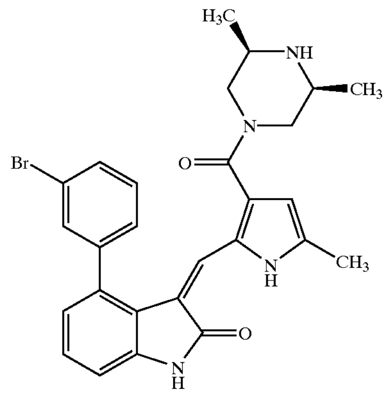 | 3-[4-(trans-3,5-Dimethyl-piperazine-1-carbonyl)-3,5-dimethyl-1H-pyrrol-2-ylmethylene]-4-(3-bromo-phenyl)-1,3-dihydro-indol-2-one |
| 152 | 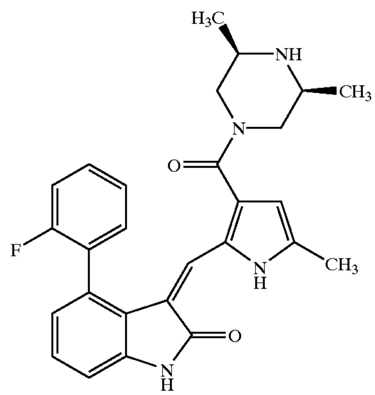 | 3-[3-[trans-3,5-dimethyl-piperazine-1-carbonyl]-5-methyl-1H-pyrrol-2-ylmethylene]-4-(2-fluoro-phenyl)-1,3-dihydro-indol-2-one |
| 153 | 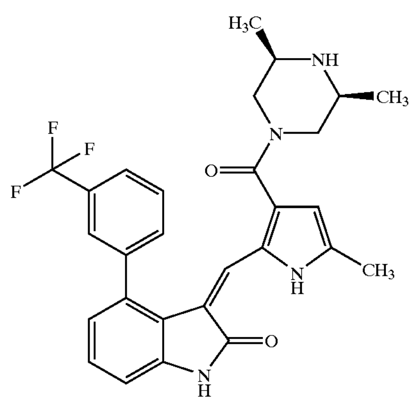 | 3-{3-[trans-3,5-dimethyl-piperazine-1-carbonyl]-5-methyl-1H-pyrrol-2-ylmethylene}-4-(2-trifluoromethyl-phenyl)-1,3-dihydro-indol-2-one |
| 154 | 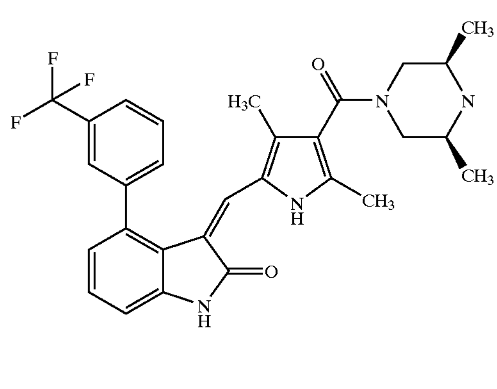 | 3-[3-Methyl-4-[trans-3,5-dimethyl-piperazine-1-carbonyl]-1H-pyrrol-2-ylmethylene]-4-(3-trifluoromethyl-phenyl)-1,3-dihydro-indol-2-one |

TABLE 1-continued

Preferred 4-Aryl Substituted Indolinones

| Example | Structure | Name |
|---|---|---|
| 155 | 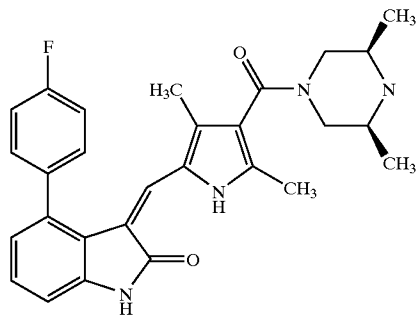 | 3-{4-[trans-3,5-dimethyl-piperazine-1-carbonyl]-3-methyl-1N-pyrrol-2-ylmethylene}-4-(4-fluoro-phenyl)-1,3-dihydro-indol-2-one |
| 156 | 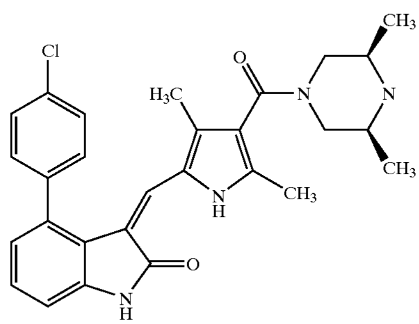 | 4-(4-Chloro-phenyl)-3-[4-[trans-3,5-dimethyl-piperazine-1-carbonyl]-3-methyl-1H-pyrrol-2-ylmethylene]-1,3-dihydro-indol-2-one |
| 157 | 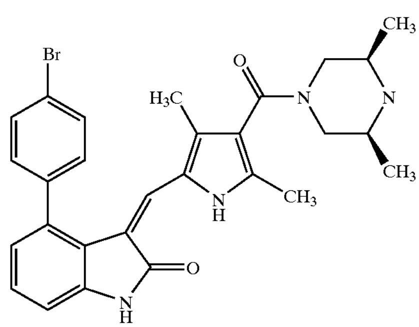 | 4-(4-Bromo-phenyl)-3-[4-[trans-3,5-dimethyl-piperazine-1-carbonyl]-3-methyl-1H-pyrrol-2-ylmethylene]-1,3-dihydro-indol-2-one |
| 158 | 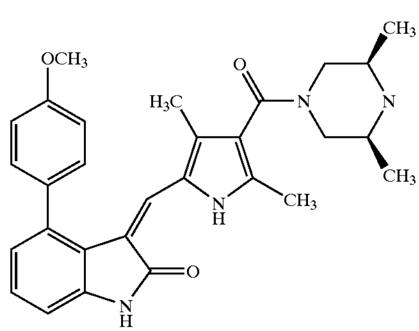 | 3-{4-[trans-3,5-dimethyl-piperazine-1-carbonyl]-3-methyl-1H-pyrrol-2-ylmethylene}-4-(4-methoxy-phenyl)-1,3-dihydro-indol-2-one |

TABLE 1-continued

Preferred 4-Aryl Substituted Indolinones

| Example | Structure | Name |
|---|---|---|
| 159 | 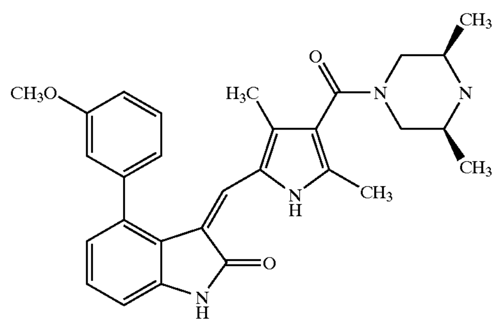 | 3-{4-[trans-3,5-dimethyl-piperazine-1-carbonyl]-3-methyl-1H-pyrrol-2-ylmethylene}-4-(3-methoxy-phenyl)-1,3-dihydro-indol-2-one |
| 160 | 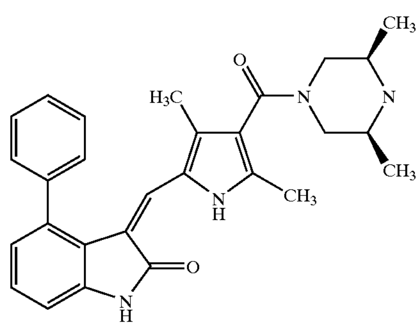 | 3-{4-[trans-3,5-dimethyl-piperazine-1-carbonyl]-3-methyl-1H-pyrrol-2-ylmethylene}-4-phenyl-1,3-dihydro-indol-2-one |
| 161 | 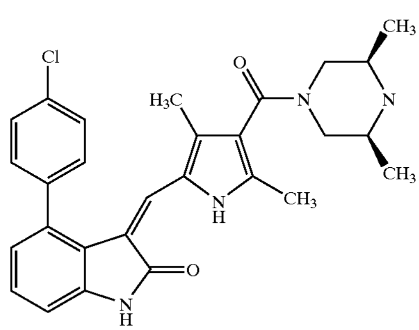 | 4-(4-chloro-phenyl)-3-{4-{3-[trans-3,5-dimethyl-piperazin-1-yl]-3-oxo-propyl}-3,5-dimethyl-1H-pyrrol-2-ylmethylene}-1,3-dihydro-indol-2-one |
| 162 | 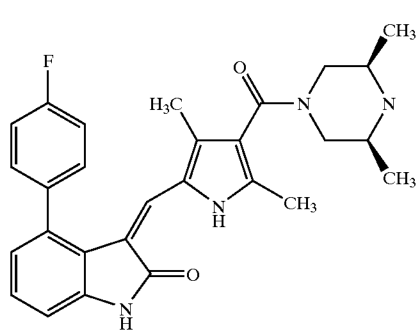 | 3-{4-{3-[trans-3,5-Dimethyl-piperazin-1-yl]-3-oxo-propyl}-3,5-dimethyl-1H-pyrrol-2-ylmethylene}-4-(4-fluoro-phenyl)-1,3-dihydro-indol-2-one |

TABLE 1-continued

Preferred 4-Aryl Substituted Indolinones

| Example | Structure | Name |
|---|---|---|
| 163 | 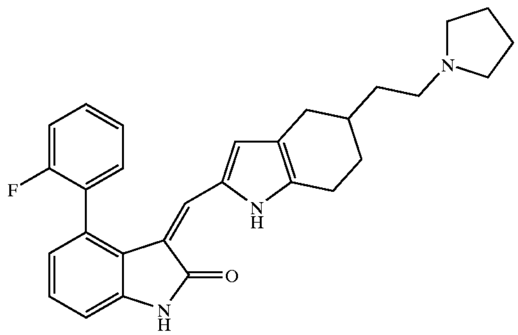 | 4-(2-Fluoro-phenyl)-3-[1-[5-(2-pyrrolidin-1-yl-ethyl)-4,5,6,7-tetrahydro-1H-indol-2-yl]-meth-(Z)-ylidene]-1,3-dihydro-indol-2-one |
| 164 | 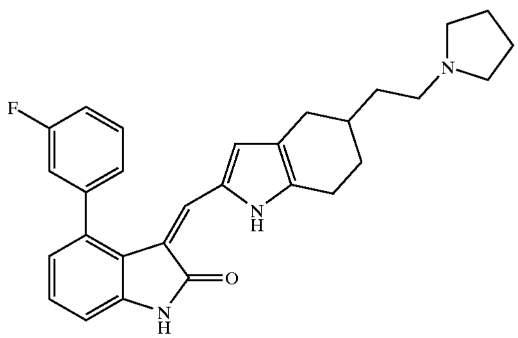 | 4-(3-Fluoro-phenyl)-3-[1-[5-(2-pyrrolidin-1-yl-ethyl)-4,5,6,7-tetrahydro-1H-indol-2-yl]-meth-(Z)-ylidene]-1,3-dihydro-indol-2-one |
| 165 | 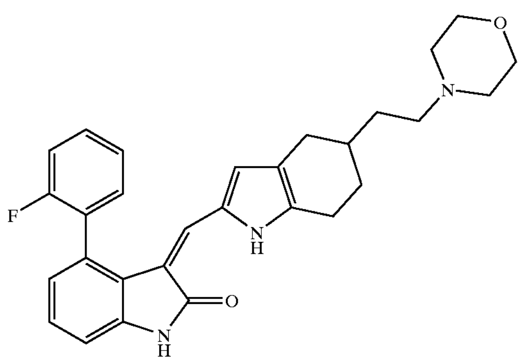 | 4-(2-Fluoro-phenyl)-3-[1-[5-(2-morpholin-4-yl-ethyl)-4,5,6,7-tetrahydro-1H-indol-2-yl]-meth-(Z)-ylidene]-1,3-dihydro-indol-2-one |
| 166 | 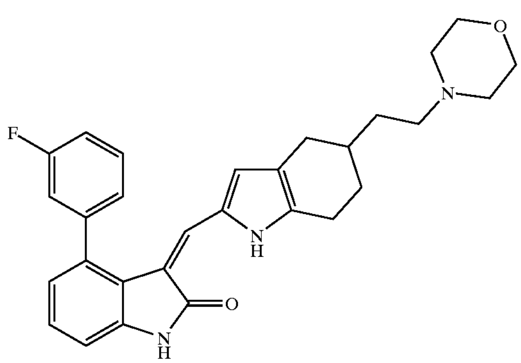 | 4-(3-Fluoro-phenyl)-3-[1-[5-(2-morpholin-4-yl-ethyl)-4,5,6,7-tetrahydro-1H-indol-2-yl]-meth-(Z)-ylidene]-1,3-dihydro-indol-2-one |

TABLE 1-continued

Preferred 4-Aryl Substituted Indolinones

| Example | Structure | Name |
|---|---|---|
| 167 | 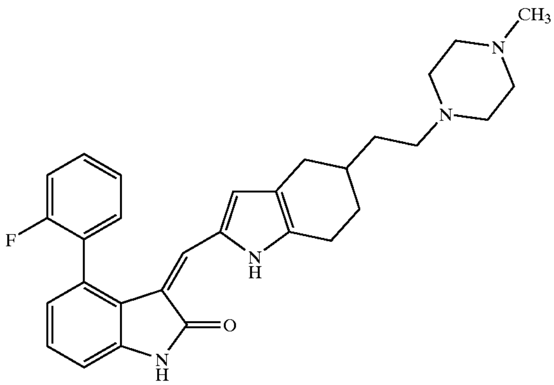 | 4-(2-Fluoro-phenyl)-3-[1-{5-[2-(4-methyl-piperazin-1-yl)-ethyl]-4,5,6,7-tetrahydro-1H-indol-2-yl}-meth-(Z)-ylidene]-1,3-dihydro-indol-2-one |
| 168 | 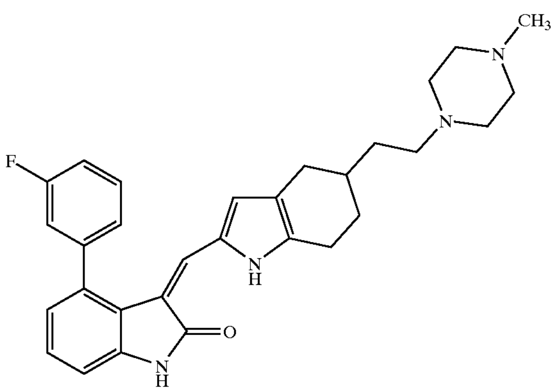 | 4-(3-Fluoro-phenyl)-3-[1-{5-[2-(4-methyl-piperazin-1-yl)-ethyl]-4,5,6,7-tetrahydro-1H-indol-2-yl}-meth-(Z)-ylidene]-1,3-dihydro-indol-2-one |
| 169 | 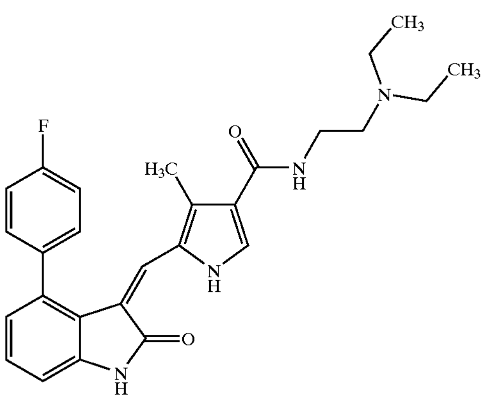 | 5-[4-(4-Fluoro-phenyl)-2-oxo-1,2-dihydro-indol-(3Z)-ylidenemethyl]-4-methyl-1H-pyrrole-3-carboxylic acid (2-diethylamino-ethyl)-amide |

US 6,677,368 B2

TABLE 1-continued

Preferred 4-Aryl Substituted Indolinones

| Example | Structure | Name |
|---------|-----------|------|
| 170 | 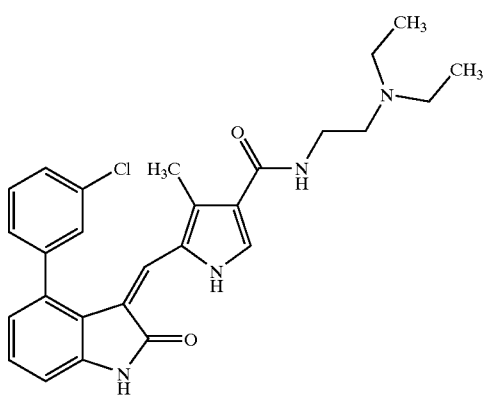 | 5-[4-(3-Chloro-phenyl)-2-oxo-1,2-dihydro-indol-(3Z)-ylidenemethyl]-4-methyl-1H-pyrrole-3-carboxylic acid (2-diethylamino-ethyl)-amide |
| 171 | 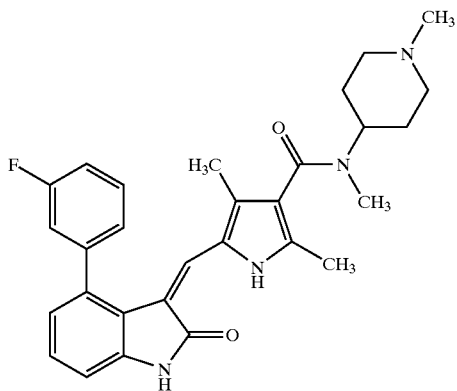 | 5-[4-(3-Fluoro-phenyl)-2-oxo-1,2-dihydro-indol-(3Z)-ylidenemethyl]-2,4-dimethyl-1H-pyrrole-3-carboxylic acid methyl-(1-methyl-piperidin-4-yl)-amide |
| 172 | 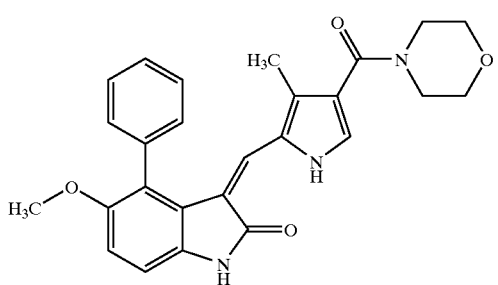 | 5-Methoxy-3-[1-[3-methyl-4-(morpholine-4-carbonyl)-1H-pyrrol-2-yl]-meth-(Z)-ylidene]-4-phenyl-1,3-dihydro-indol-2-one |
| 173 | 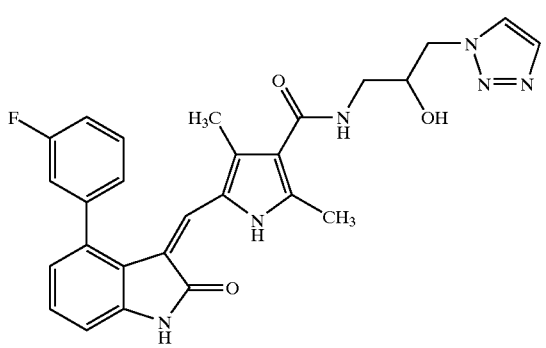 | 5-[4-(3-Fluoro-phenyl)-2-oxo-1,2-dihydro-indol-(3Z)-ylidenemethyl]-2,4-dimethyl-1H-pyrrol-3-carboxylic acid (2-hydroxy-3-[1,2,3]triazol-1-yl-propyl)-amide |

TABLE 1-continued

Preferred 4-Aryl Substituted Indolinones

| Example | Structure | Name |
|---------|-----------|------|
| 174 | 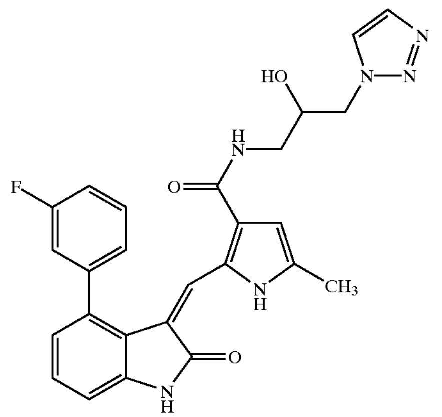 | 2-[4-(3-Fluoro-phenyl)-2-oxo-1,2-dihydro-indol-(3Z)-ylidenemethyl]-5-methyl-1H-pyrrole-3-carboxylic acid (2-hydroxy-3-[1,2,3]triazol-1-yl-propyl)-amide |
| 175 | 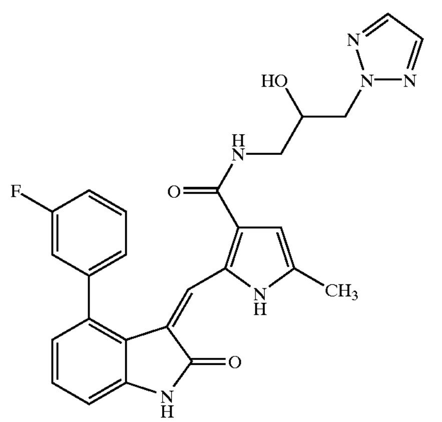 | 2-[4-(3-Fluoro-phenyl)-2-oxo-1,2-dihydro-indol-(3Z)-ylidenemethyl]-5-methyl-1H-pyrrole-3-carboxylic acid (2-hydroxy-3-[1,2,3]triazol-2-yl-propyl)-amide |
| 176 | 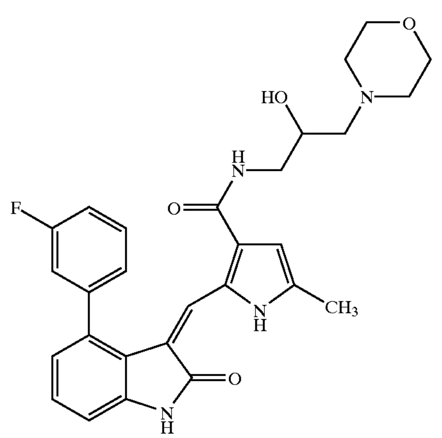 | 2-[4-(3-Fluoro-phenyl)-2-oxo-1,2-dihydro-indol-(3Z)-ylidenemethyl]-5-methyl-1H-pyrrole-3-carboxylic acid (2-hydroxy-3-morpholin-4-yl-propyl)-amide |

TABLE 1-continued

Preferred 4-Aryl Substituted Indolinones

| Example | Structure | Name |
|---------|-----------|------|
| 177 | 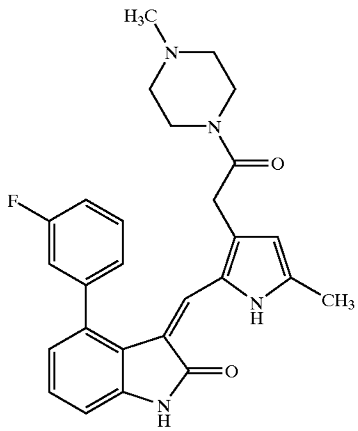 | 4-(3-Fluoro-phenyl)-3-[1-{5-methyl-3-[2-(4-methyl-piperazin-1-yl)-2-oxo-ethyl]-1H-pyrrol-2-yl}-meth-(Z)-ylidene]-1,3-dihydro-indol-2-one |
| 178 | 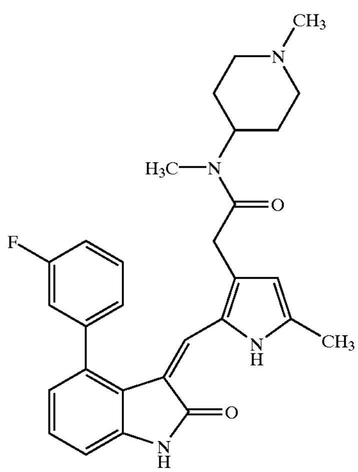 | 2-{2-[4-(3-Fluoro-phenyl)-2-oxo-1,2-dihydro-indol-(3Z)-ylidenemethyl]-5-methyl-1H-pyrrol-3-yl}-N-methyl-N-(1-methyl-piperidin-4-yl)-acetamide |
| 179 | 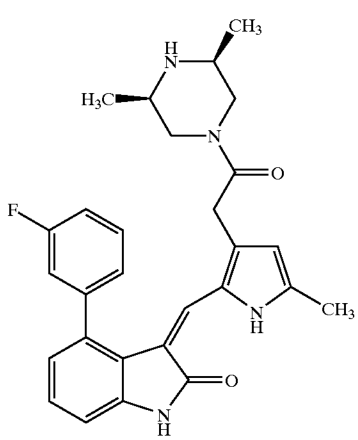 | 3-[1-{3-[2-((3R,5S)-3,5-Dimethyl-piperazin-1-yl)-2-oxo-ethyl]-5-methyl-1H-pyrrol-2-yl}-meth-(Z)-ylidene]-4-(3-fluoro-phenyl)-1,3-dihydro-indol-2-one |

TABLE 1-continued

Preferred 4-Aryl Substituted Indolinones

| Example | Structure | Name |
|---|---|---|
| 180 | 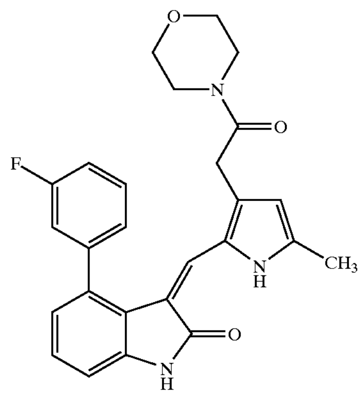 | 4-(3-Fluoro-phenyl)-3-[1-[5-methyl-3-(2-morpholin-4-yl-2-oxo-ethyl)-1H-pyrrol-2-yl]-meth-(Z)-ylidene]-1,3-dihydro-indol-2-one |
| 181 | 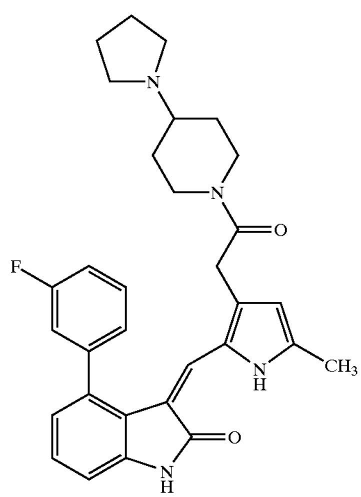 | 4-(3-Fluoro-phenyl)-3-[1-{5-methyl-3-[2-oxo-2-(4-pyrrolidin-1-yl-piperidin-1-yl)-ethyl]-1H-pyrrol-2-yl}-meth-(Z)-ylidene]-1,3-dihydro-indol-2-one |
| 182 | Chiral | 4-(3-Fluoro-phenyl)-3-[1-{5-methyl-3-[2-oxo-2-((S)-2-pyrrolidin-1-ylmethyl-pyrrolidin-1-yl)-ethyl]-1H-pyrrol-2-yl}-meth-(Z)-ylidene]-1,3-dihydro-indol-2-one |

TABLE 1-continued

Preferred 4-Aryl Substituted Indolinones

| Example | Structure | Name |
|---|---|---|
| 183 | 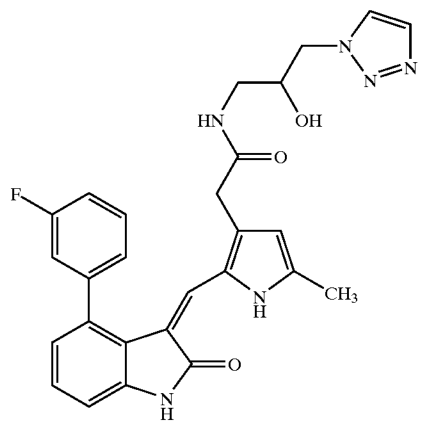 | 2-{2-[4-(3-Fluoro-phenyl)-2-oxo-1,2-dihydro-indol-(3Z)-ylidenemethyl]-5-methyl-1H-pyrrol-3-yl}-N-(2-hydroxy-3-[1,2,3]triazol-1-yl-propyl)-acetamide |
| 184 | 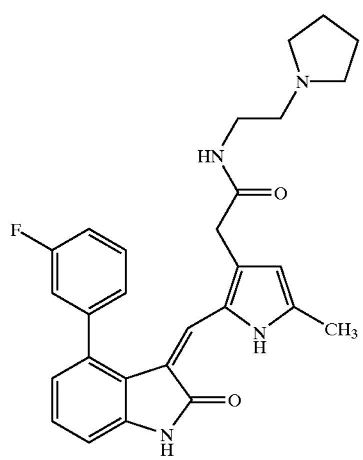 | 2-{2-[4-(3-Fluoro-phenyl)-2-oxo-1,2-dihydro-indol-(3Z)-ylidenemethyl]-5-methyl-1H-pyrrol-3-yl}-N-(2-pyrrolidin-1-yl-ethyl)-acetamide |
| 185 | 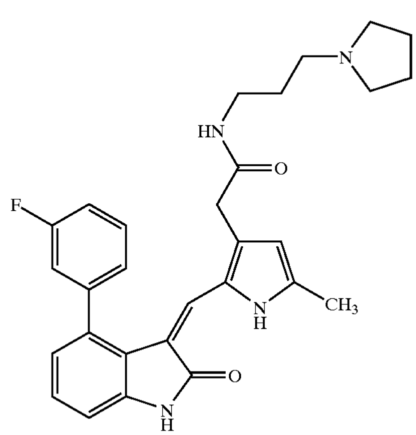 | 2-{2-[4-(3-Fluoro-phenyl)-2-oxo-1,2-dihydro-indol-(3Z)-ylidenemethyl]-5-methyl-1H-pyrrol-3-yl}-N-(3-pyrrolidin-1-yl-propyl)-acetamide |

TABLE 1-continued

Preferred 4-Aryl Substituted Indolinones

| Example | Structure | Name |
|---|---|---|
| 186 | 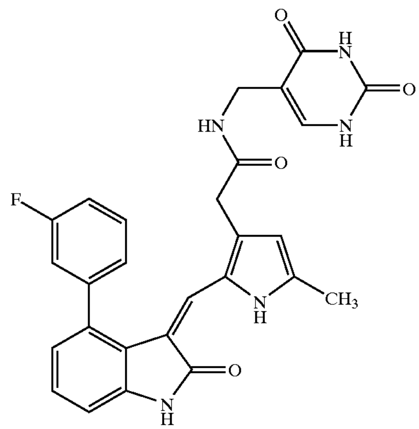 | N-(2,4-Dioxo-1,2,3,4-tetrahydro-pyrimidin-5-ylmethyl)-2-{2-[4-(3-fluoro-phenyl)-2-oxo-1,2-dihydro-indol-(3Z)-ylidenemethyl]-5-methyl-1H-pyrrol-3-yl}-acetamide |
| 187 | 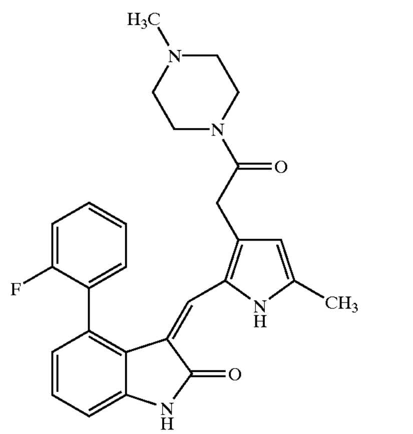 | 4-(2-Fluoro-phenyl)-3-[1-{5-methyl-3-[2-(4-methyl-piperazin-1-yl)-2-oxo-ethyl]-1H-pyrrol-2-yl}-meth-(Z)-ylidene]-1,3-dihydro-indol-2-one |
| 188 | 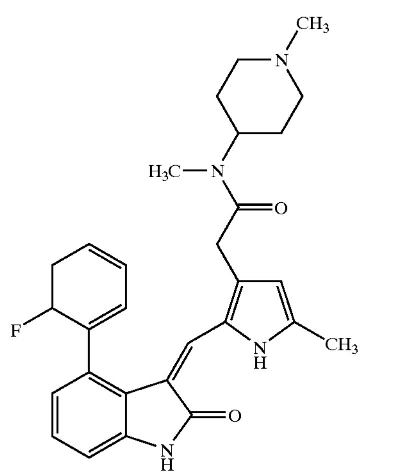 | 2-{2-[4-(2-Fluoro-phenyl)-2-oxo-1,2-dihydro-indol-(3Z)-ylidenemethyl]-5-methyl-1H-pyrrol-3-yl}-N-methyl-N-(1-methyl-pyridin-4-yl)-acetamide |

TABLE 1-continued

Preferred 4-Aryl Substituted Indolinones

| Example | Structure | Name |
|---|---|---|
| 189 | 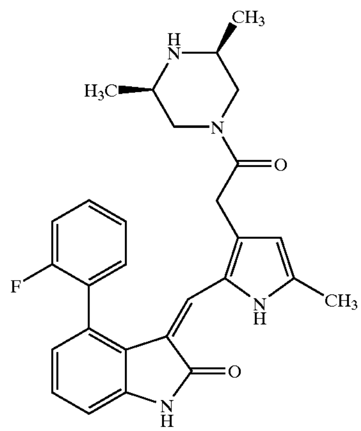 | 3-[1-{3-[2-((3R,5S)-3,5-Dimethyl-piperazin-1-yl)-2-oxo-ethyl]-5-methyl-1H-pyrrol-2-yl}-meth-(Z)-ylidene]-4-(2-fluoro-phenyl)-1,3-dihydro-indol-2-one |
| 190 | 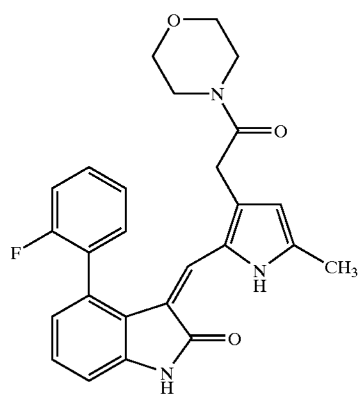 | 4-(2-Fluoro-phenyl)-3-[1-[5-methyl-3-(2-morpholin-4-yl-2-oxo-ethyl)-1H-pyrrol-2-yl]-meth-(Z)-ylidene]-1,3-dihydro-indol-2-one |
| 191 | 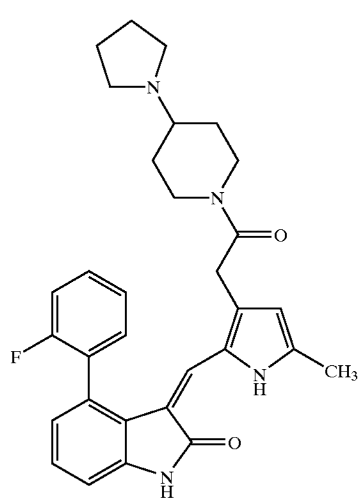 | 4-(2-Fluoro-phenyl)-3-[1-{5-methyl-3-[2-oxo-2-(4-pyrrolidin-1-yl-piperidin-1-yl)-ethyl]-1H-pyrrol-2-yl}-meth-(Z)-ylidene]-1,3-dihydro-indol-2-one |

TABLE 1-continued

Preferred 4-Aryl Substituted Indolinones

| Example | Structure | Name |
|---|---|---|
| 192 | 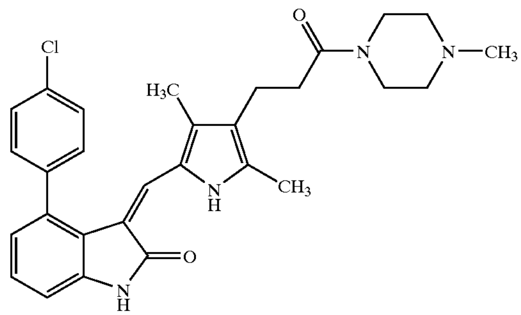 | 4-(4-Chloro-phenyl)-3-[1-{3,5-dimethyl-4-[3-(4-methyl-piperazin-1-yl)-3-oxo-propyl]-1H-pyrrol-2-yl}-meth-(Z)-ylidene]-1,3-dihydro-indol-2-one |
| 193 | 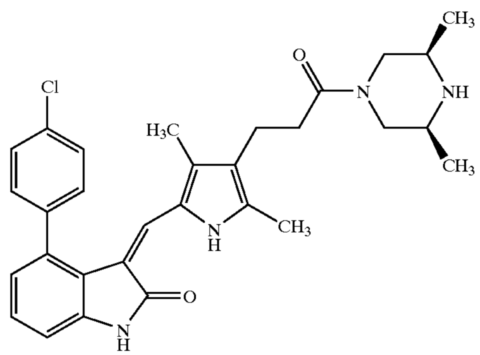 | 4-(4-Chloro-phenyl)-3-[1-{4-[3-((3R,5S)-3,5-dimethyl-piperazin-1-yl)-3-oxo-propyl]-3,5-dimethyl-1H-pyrrol-2-yl}-meth-(Z)-ylidene]-1,3-dihydro-indol-2-one |
| 194 | 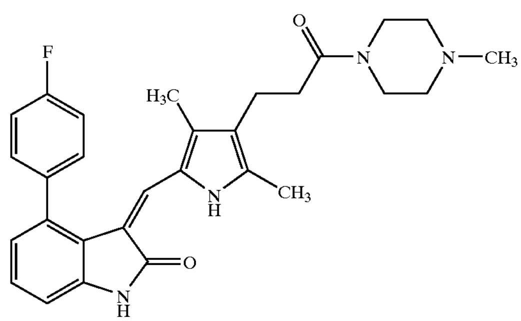 | 3-[1-{3,5-Dimethyl-4-[3-(4-methyl-piperazin-1-yl)-3-oxo-propyl]-1H-pyrrol-2-yl}-meth-(Z)-ylidene]-4-(4-fluoro-phenyl)-1,3-dihydro-indol-2-one |
| 195 | 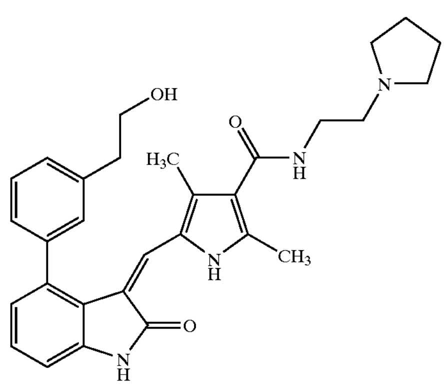 | 5-[4-[3-(2-Hydroxy-ethyl)-phenyl]-2-oxo-1,2-dihydro-indol-(3Z)-ylidenemethyl]-2,4-dimethyl-1H-pyrrole-3-carboxylic acid (2-pyrrolidin-1-yl-ethyl)-amide |

TABLE 1-continued

Preferred 4-Aryl Substituted Indolinones

| Example | Structure | Name |
|---|---|---|
| 196 | 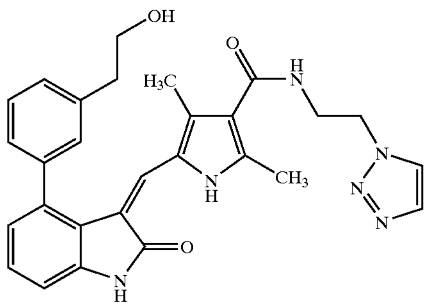 | 5-[4-[3-(2-Hydroxy-ethyl)-phenyl]-2-oxo-1,2-dihydro-indol-(3Z)-ylidenemethyl]-2,4-dimethyl-1H-pyrrole-3-carboxylic acid (2-[1,2,3]triazol-1-yl-ethyl)-amide |
| 197 | 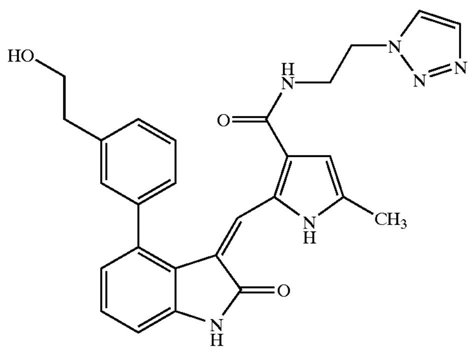 | 2-[4-[3-(2-Hydroxy-ethyl)-phenyl]-2-oxo-1,2-dihydro-indol-(3Z)-ylidenemethyl]-5-methyl-1H-pyrrole-3-carboxylic acid (2-[1,2,3]triazol-1-yl-ethyl)-amide |
| 198 | 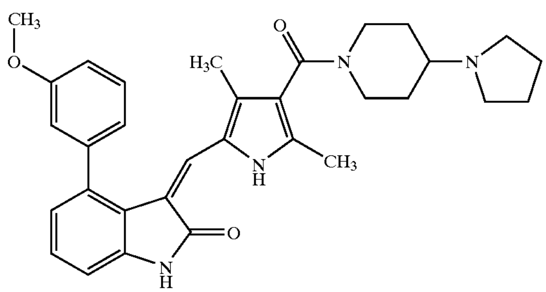 | 3-[1-[3,5-Dimethyl-4-(4-pyrrolidin-1-yl-piperidine-1-carbonyl)-1H-pyrrol-2-yl]-meth-(Z)-ylidene]-4-(3-methoxy-phenyl)-1,3-dihydro-indol-2-one |
| 199 | 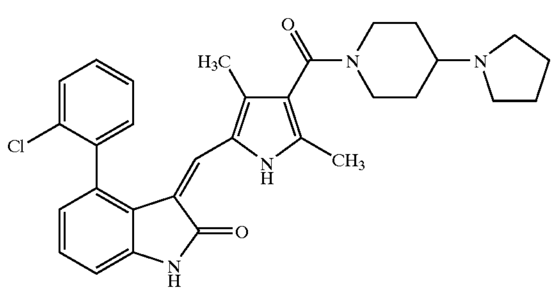 | 4-(2-Chloro-phenyl)-3-[1-[3,5-dimethyl-4-(4-pyrrolidin-1-yl-piperidine-1-carbonyl)-1H-pyrrol-2-yl]-meth-(Z)-ylidene]-1,3-dihydro-indol-2-one |
| 200 | 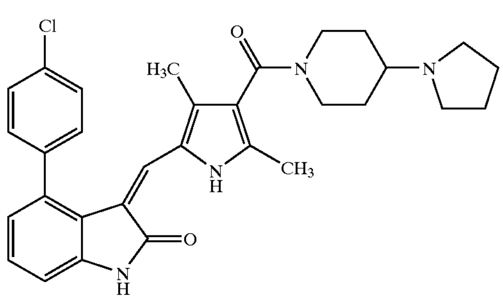 | 4-(4-Chloro-phenyl)-3-[1-[3,5-dimethyl-4-(4-pyrrolidin-1-yl-piperidine-1-carbonyl)-1H-pyrrol-2-yl]-meth-(Z)-ylidene]-1,3-dihydro-indol-2-one |

TABLE 1-continued

Preferred 4-Aryl Substituted Indolinones

| Example | Structure | Name |
|---|---|---|
| 201 | 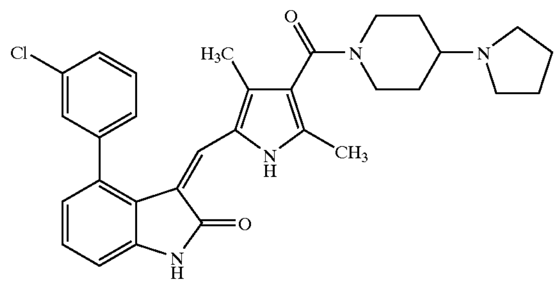 | 4-(3-Chloro-phenyl)-3-[1-[3,5-dimethyl-4-(4-pyrrolidin-1-yl-piperidine-1-carbonyl)-1H-pyrrol-2-yl]-meth-(Z)-ylidene]-1,3-dihydro-indol-2-one |
| 202 | 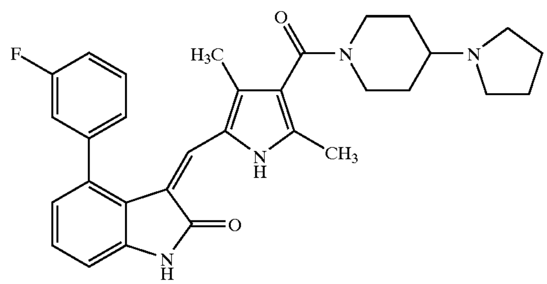 | 3-[1-[3,5-Dimethyl-4-(4-pyrrolidin-1-yl-piperidine-1-carbonyl)-1H-pyrrol-2-yl]-meth-(Z)-ylidene]-4-(3-fluoro-phenyl)-1,3-dihydro-indol-2-one |
| 203 | 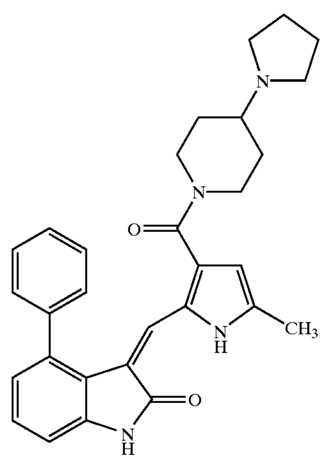 | 3-[1-[5-Methyl-3-(4-pyrrolidin-1-yl-piperidine-1-carbonyl)-1H-pyrrol-2-yl]-meth-(Z)-ylidene]-4-phenyl-1,3-dihydro-indol-2-one |
| 204 | 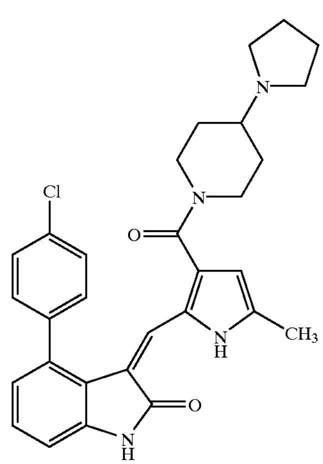 | 4-(4-Chloro-phenyl)-3-[1-[5-methyl-3-(4-pyrrolidin-1-yl-piperidine-1-carbonyl)-1H-pyrrol-2-yl]-meth-(Z)-ylidene]-1,3-dihydro-indol-2-one |

TABLE 1-continued

Preferred 4-Aryl Substituted Indolinones

| Example | Structure | Name |
|---|---|---|
| 205 | 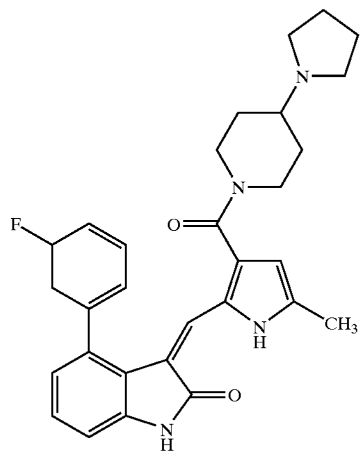 | 4-(3-Fluoro-phenyl)-3-[1-[5-methyl-3-(4-pyrrolidin-1-yl-piperidine-1-carbonyl)-1H-pyrrol-2-yl]-meth-(Z)-ylidene]-1,3-dihydro-indol-2-one |
| 206 | 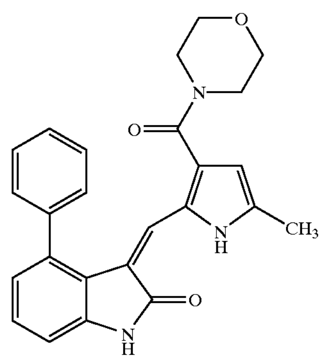 | 3-[1-[5-Methyl-3-(morpholine-4-carbonyl)-1H-pyrrol-2-yl]-meth-(Z)-ylidene]-4-phenyl-1,3-dihydro-indol-2-one |
| 207 | 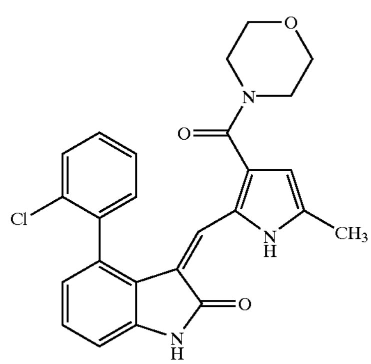 | 4-(2-Chloro-phenyl)-3-[1-[5-methyl-3-(morpholine-4-carbonyl)-1H-pyrrol-2-yl]-meth-(Z)-ylidene]-1,3-dihydro-indol-2-one |
| 208 | 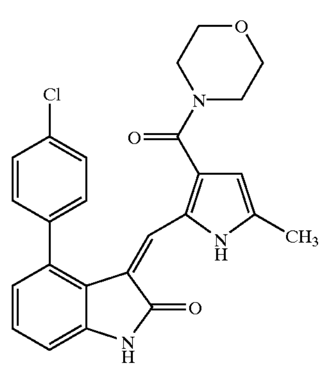 | 4-(4-Chloro-phenyl)-3-[1-[5-methyl-3-(morpholine-4-carbonyl)-1H-pyrrol-2-yl]-meth-(Z)-ylidene]-1,3-dihydro-indol-2-one |

TABLE 1-continued

Preferred 4-Aryl Substituted Indolinones

| Example | Structure | Name |
|---|---|---|
| 209 | 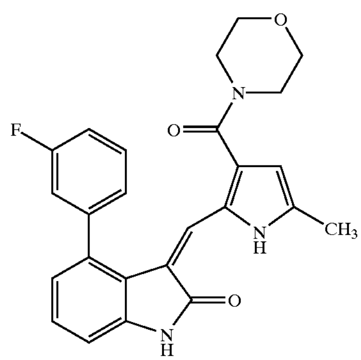 | 4-(3-Fluoro-phenyl)-3-[1-[5-methyl-3-(morpholine-4-carbonyl)-1H-pyrrol-2-yl]-meth-(Z)-ylidene]-1,3-dihydro-indol-2-one |
| 210 | 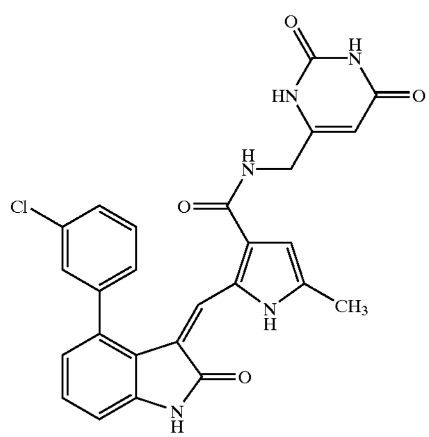 | 2-[4-(3-Chloro-phenyl)-2-oxo-1,2-dihydro-indol-(3Z)-ylidenemethyl]-5-methyl-1H-pyrrole-3-carboxylic acid (2,6-dioxo-1,2,3,6-tetrahydro-pyrimidin-4-ylmethyl)-amide |
| 211 | 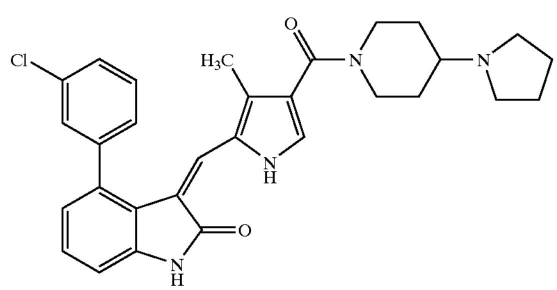 | 4-(3-Chloro-phenyl)-3-[1-[3-methyl-4-(4-pyrrolidin-1-yl-piperidine-1-carbonyl]-1H-pyrrol-2-yl]-meth-(Z)-ylidene]-1,3-dihydro-indol-2-one |
| 212 | 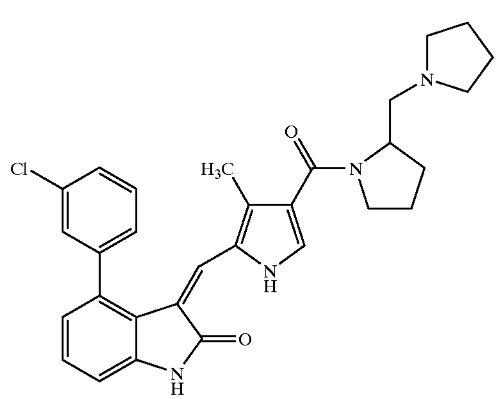 | 4-(3-Chloro-phenyl)-3-[1-[3-methyl-4-(2-pyrrolidin-1-ylmethyl-pyrrolidine-1-carbonyl)-1H-pyrrol-2-yl]-meth-(Z)-ylidene]-1,3-dihydro-indol-2-one |

TABLE 1-continued

Preferred 4-Aryl Substituted Indolinones

| Example | Structure | Name |
|---|---|---|
| 213 | 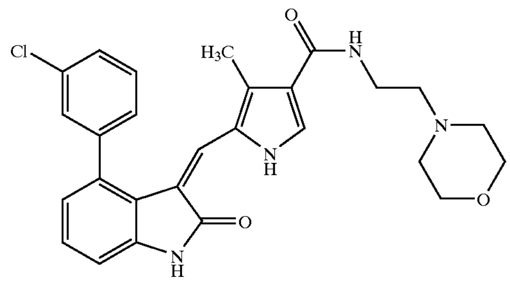 | 5-[4-(3-Chloro-phenyl)-2-oxo-1,2-dihydro-indol-(3Z)-ylidenemethyl]-4-methyl-1H-pyrrole-3-carboxylic acid (2-morpholin-4-yl-ethyl)-amide |
| 214 | 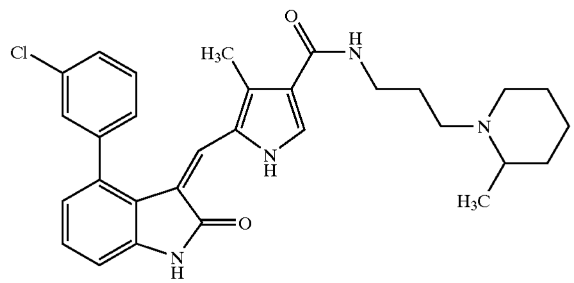 | 5-[4-(3-Chloro-phenyl)-2-oxo-1,2-dihydro-indol-(3Z)-ylidenemethyl]-4-methyl-1H-pyrrole-3-carboxylic acid [3-(2-methyl-piperidin-1-yl)-propyl]-amide |
| 215 | 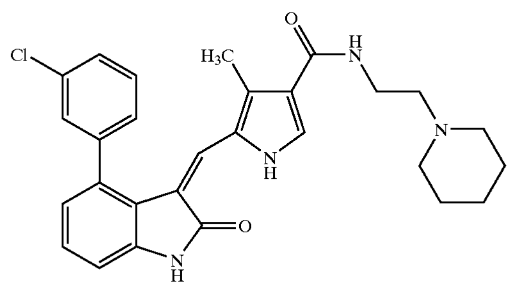 | 5-[4-(3-Chloro-phenyl)-2-oxo-1,2-dihydro-indol-(3Z)-ylidenemethyl]-4-methyl-1H-pyrrole-3-carboxylic acid (2-piperidin-1-yl-ethyl)-amide |
| 216 | 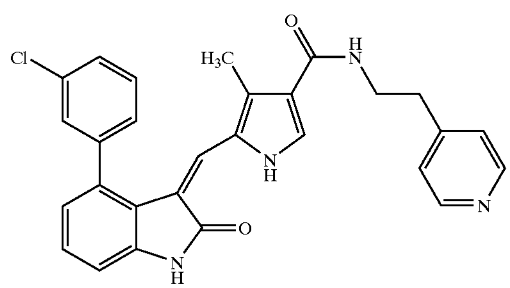 | 5-[4-(3-Chloro-phenyl)-2-oxo-1,2-dihydro-indol-(3Z)-ylidenemethyl]-4-methyl-1H-pyrrole-3-carboxylic acid (2-pyridin-4-yl-ethyl)-amide |
| 217 | 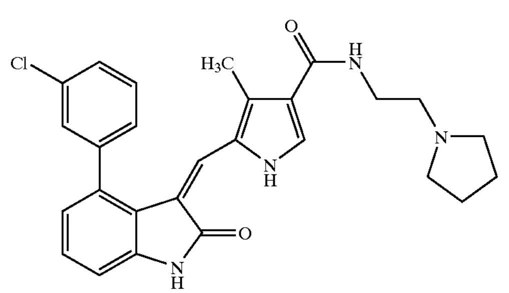 | 5-[4-(3-Chloro-phenyl)-2-oxo-1,2-dihydro-indol-(3Z)-ylidenemethyl]-4-methyl-1H-pyrrole-3-carboxylic acid (2-pyrrolidin-1-yl-ethyl)-amide |

TABLE 1-continued

Preferred 4-Aryl Substituted Indolinones

| Example | Structure | Name |
|---|---|---|
| 218 | 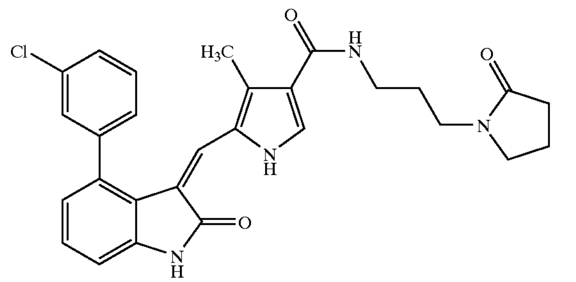 | 5-[4-(3-Chloro-phenyl)-2-oxo-1,2-dihydro-indol-(3Z)-ylidenemethyl]-4-methyl-1H-pyrrole-3-carboxylic acid [3-(2-oxo-pyrrolidin-1-yl)-propyl]-amide |
| 219 | 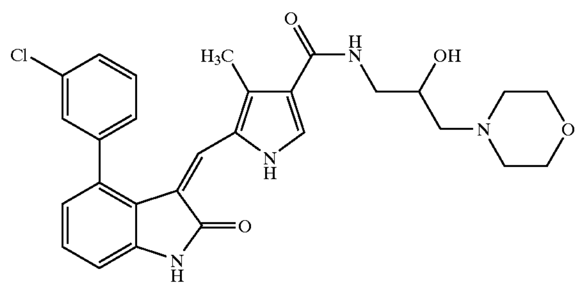 | 5-[4-(3-Chloro-phenyl)-2-oxo-1,2-dihydro-indol-(3Z)-ylidenemethyl]-4-methyl-1H-pyrrole-3-carboxylic acid (2-hydroxy-3-morpholin-4-yl-propyl)-amide |
| 220 | 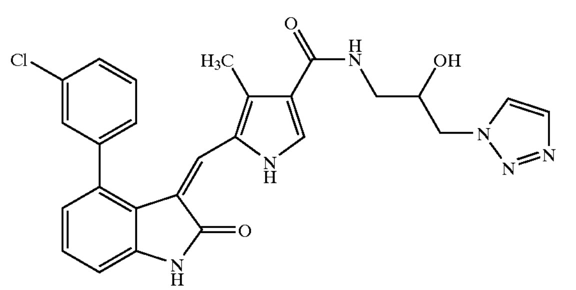 | 5-[4-(3-Chloro-phenyl)-2-oxo-1,2-dihydro-indol-(3Z)-ylidenemethyl]-4-methyl-1H-pyrrole-3-carboxylic acid (2-hydroxy-3-[1,2,3]triazol-1-yl-propyl)-amide |
| 221 | 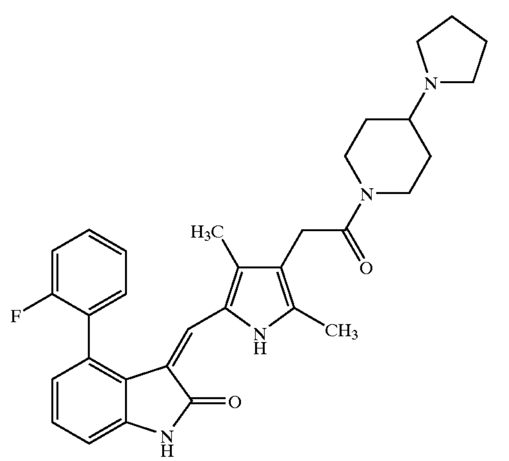 | 3-[1-{3,5-Dimethyl-4-[2-oxo-2-(4-pyrrolidin-1-yl-piperidin-1-yl)-ethyl]-1H-pyrrol-2-yl}-meth-(Z)-ylidene]-4-(2-fluoro-phenyl)-1,3-dihydro-indol-2-one |

TABLE 1-continued

Preferred 4-Aryl Substituted Indolinones

| Example | Structure | Name |
|---------|-----------|------|
| 222 | 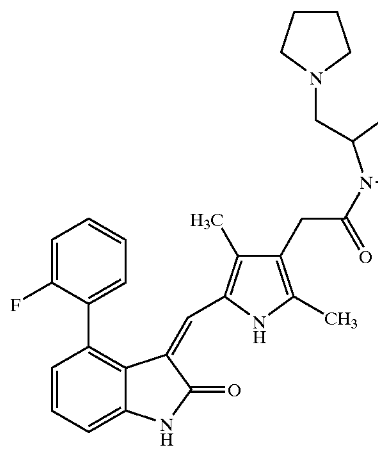 | 3-[1-{3,5-Dimethyl-4-[2-oxo-2-((S)-2-pyrrolidin-1-ylmethyl-pyrrolidin-1-yl)-ethyl]-1H-pyrrol-2-yl}-meth-(Z)-ylidene]-4-(2-fluoro-phenyl)-1,3-dihydro-indol-2-one |
| 223 | 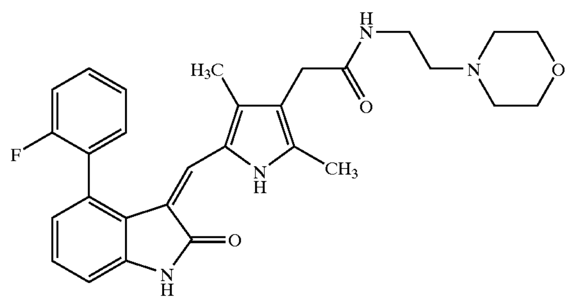 | 2-{5-[4-(2-Fluoro-phenyl)-2-oxo-1,2-dihydro-indol-(3Z)-ylidenemethyl]-2,4-dimethyl-1H-pyrrol-3-yl}-N-(2-morpholin-4-yl-ethyl)-acetamide |
| 224 | 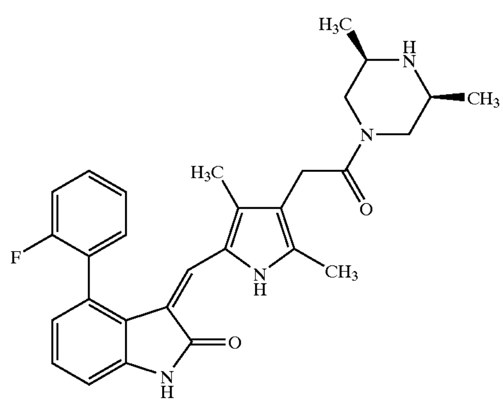 | 3-[1-{4-[2-((3R,5S)-3,5-Dimethyl-piperazin-1-yl)-2-oxo-ethyl]-3,5-dimethyl-1H-pyrrol-2-yl}-meth-(Z)-ylidene]-4-(2-fluoro-phenyl)-1,3-dihydro-indol-2-one |
| 225 | 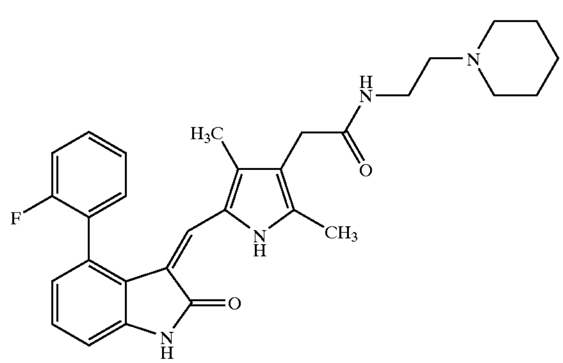 | 2-{5-[4-(2-Fluoro-phenyl)-2-oxo-1,2-dihydro-indol-(3Z)-ylidenemethyl]-2,4-dimethyl-1H-pyrrol-3-yl}-N-(2-piperidin-1-yl-ethyl)-acetamide |

TABLE 1-continued

Preferred 4-Aryl Substituted Indolinones

| Example | Structure | Name |
|---------|-----------|------|
| 226 | 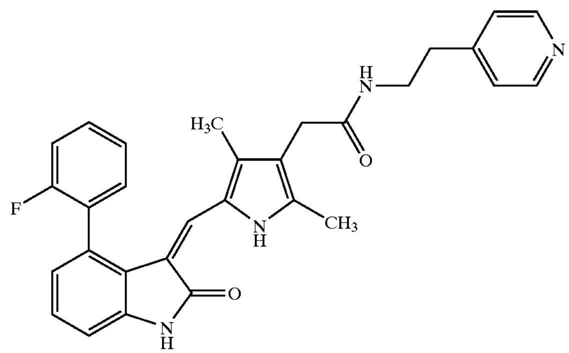 | 2-{5-[4-(2-Fluoro-phenyl)-2-oxo-1,2-dihydro-indol-(3Z)-ylidenemethyl]-2,4-dimethyl-1H-pyrrol-3-yl}-N-(2-pyridin-4-yl-ethyl)-acetamide |
| 227 | 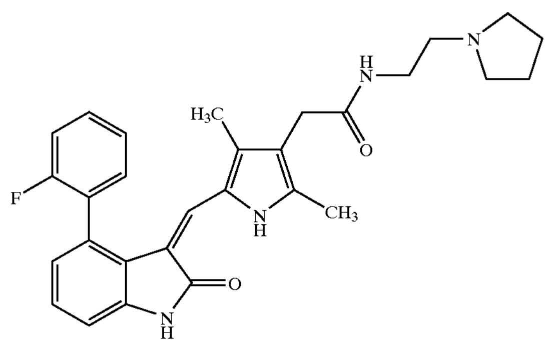 | 2-{5-[4-(2-Fluoro-phenyl)-2-oxo-1,2-dihydro-indol-(3Z)-ylidenemethyl]-2,4-dimethyl-1H-pyrrol-3-yl}-N-(2-pyrrolidin-1-yl-ethyl)-acetamide |
| 228 | 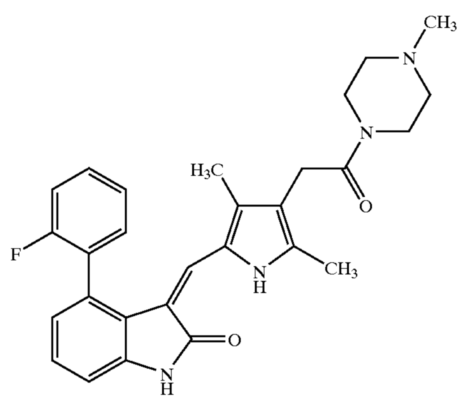 | 3-[1-{3,5-Dimethyl-4-[2-(4-methyl-piperazin-1-yl)-2-oxo-ethyl]-1H-pyrrol-2-yl}-meth-(Z)-ylidene]-4-(2-fluoro-phenyl)-1,3-dihydro-indol-2-one |
| 229 | 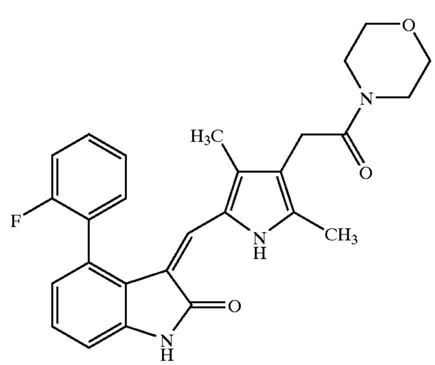 | 3-[1-[3,5-Dimethyl-4-(2-morpholin-4-yl-2-oxo-ethyl)-1H-pyrrol-2-yl]-meth-(Z)-ylidene]-4-(2-fluoro-phenyl)-1,3-dihydro-indol-2-one |

TABLE 1-continued

Preferred 4-Aryl Substituted Indolinones

| Example | Structure | Name |
| --- | --- | --- |
| 230 | 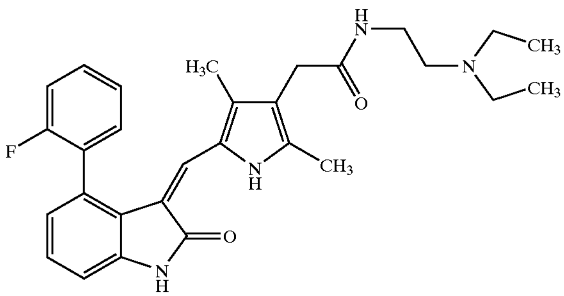 | N-(2-Diethylamino-ethyl)-2-{5-[4-(2-fluoro-phenyl)-2-oxo-1,2-dihydro-indol-(3Z)-ylidenemethyl]-2,4-dimethyl-1H-pyrrol-3-yl}-acetamide |
| 231 | 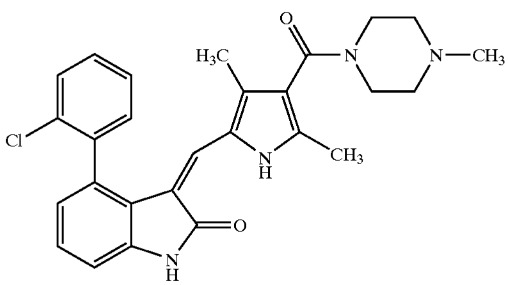 | 4-(2-Chloro-phenyl)-3-[1-[3,5-dimethyl-4-(4-methyl-piperazine-1-carbonyl)-1H-pyrrol-2-yl]-meth-(Z)-ylidene]-1,3-dihydro-indol-2-one |
| 232 | 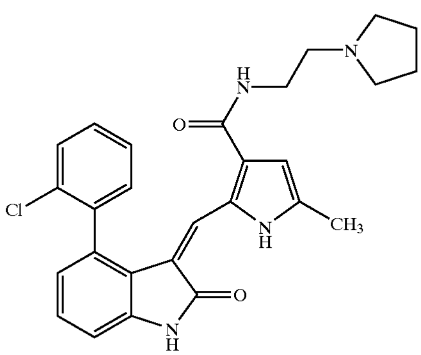 | 2-[4-(2-Chloro-phenyl)-2-oxo-1,2-dihydro-indol-(3Z)-ylidenemethyl]-5-methyl-1H-pyrrole-3-carboxylic acid (2-pyrrolidin-1-yl-ethyl)-amide |
| 233 | 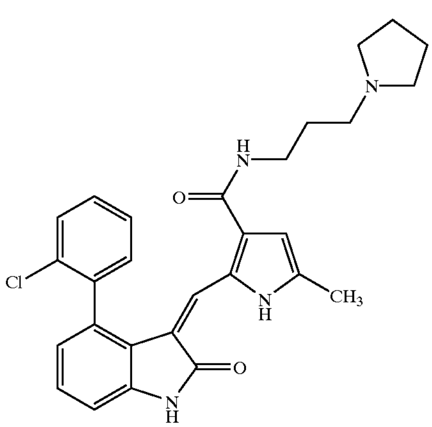 | 2-[4-(2-Chloro-phenyl)-2-oxo-1,2-dihydro-indol-(3Z)-ylidenemethyl]-5-methyl-1H-pyrrole-3-carboxylic acid (3-pyrrolidin-1-yl-propyl)-amide |

TABLE 1-continued

Preferred 4-Aryl Substituted Indolinones

| Example | Structure | Name |
| --- | --- | --- |
| 234 | 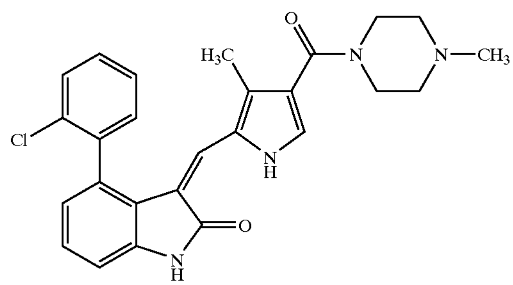 | 4-(2-Chloro-phenyl)-3-[1-[3-methyl-4-(4-methyl-piperazine-1-carbonyl)-1H-pyrrol-2-yl]-meth-(Z)-ylidene]-1,3-dihydro-indol-2-one |
| 235 | 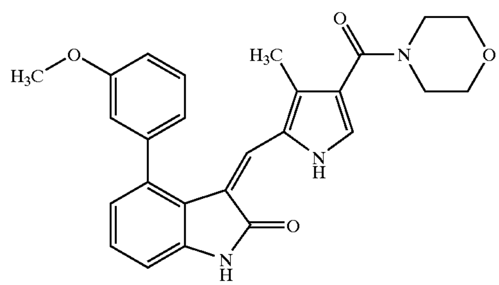 | 4-(3-Methoxy-phenyl)-3-[1-[3-methyl-4-(morpholine-4-carbonyl)-1H-pyrrol-2-yl]-meth-(Z)-ylidene]-1,3-dihydro-indol-2-one |
| 236 | 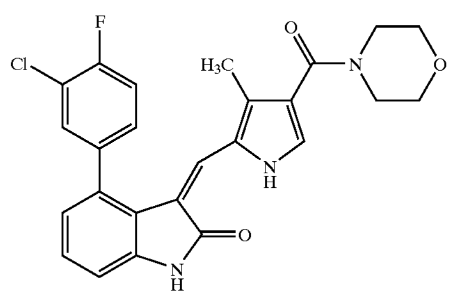 | 4-(3-Chloro-4-fluoro-phenyl)-3-[1-[3-methyl-4-(morpholine-4-carbonyl)-1H-pyrrol-2-yl]-meth-(Z)-ylidene]-1,3-dihydro-indol-2-one |
| 237 | 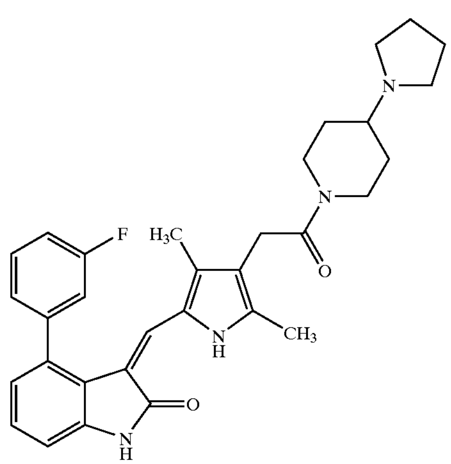 | 3-[1-{3,5-Dimethyl-4-[2-oxo-2-(4-pyrrolidin-1-yl-piperidin-1-yl)-ethyl]-1H-pyrrol-2-yl}-meth-(Z)-ylidene]-4-(3-fluoro-phenyl)-1,3-dihydro-indol-2-one |

TABLE 1-continued

Preferred 4-Aryl Substituted Indolinones

| Example | Structure | Name |
|---|---|---|
| 238 | 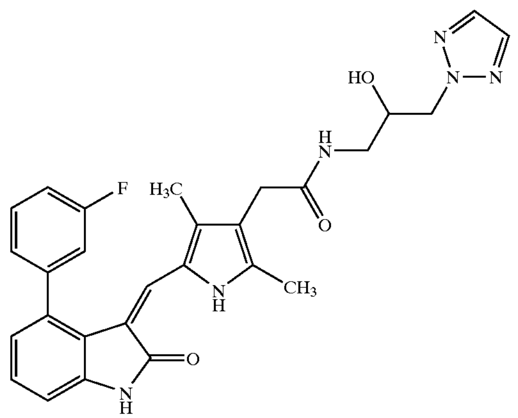 | 2-{5-[4-(3-Fluoro-phenyl)-2-oxo-1,2-dihydro-indol-(3Z)-ylidenemethyl]-2,4-dimethyl-1H-pyrrol-3-yl}-N-(2-hydroxy-3-[1,2,3]triazol-2-yl-propyl)-acetamide |
| 239 | 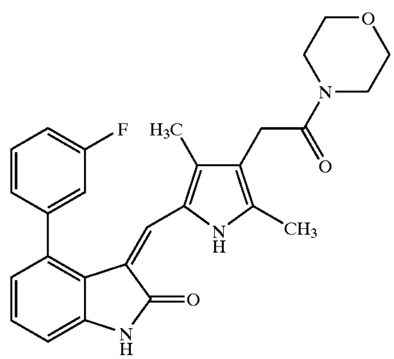 | 3-[1-[3,5-Dimethyl-4-(2-morpholin-4-yl-2-oxo-ethyl)-1H-pyrrol-2-yl]-meth-(Z)-ylidene]-4-(3-fluoro-phenyl)-1,3-dihydro-indol-2-one |
| 240 | 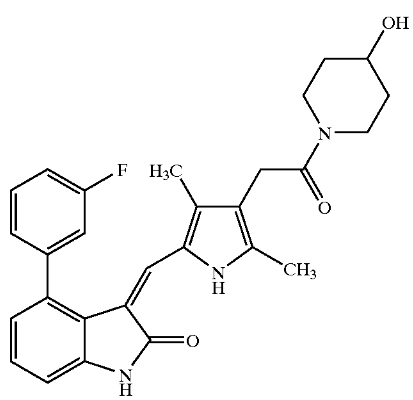 | 4-(3-Fluoro-phenyl)-3-[1-{4-[2-(4-hydroxy-piperidin-1-yl)-2-oxo-ethyl]-3,5-dimethyl-1H-pyrrol-2-yl}-meth-(Z)-ylidene]-1,3-dihydro-indol-2-one |
| 241 | 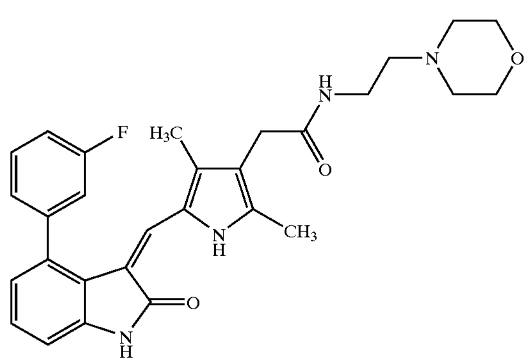 | 2-{5-[4-(3-Fluoro-phenyl)-2-oxo-1,2-dihydro-indol-(3Z)-ylidenemethyl]-2,4-dimethyl-1H-pyrrol-3-yl}-N-(2-morpholin-4-yl-ethyl)-acetamide |

TABLE 1-continued

Preferred 4-Aryl Substituted Indolinones

| Example | Structure | Name |
|---|---|---|
| 242 | 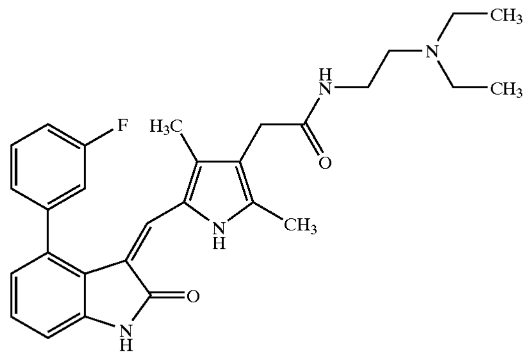 | N-(2-Diethylamino-ethyl)-2-{5-[4-(3-fluoro-phenyl)-2-oxo-1,2-dihydro-indol-(3Z)-ylidenemethyl]-2,4-dimethyl-1H-pyrrol-3-yl}-acetamide |
| 243 | 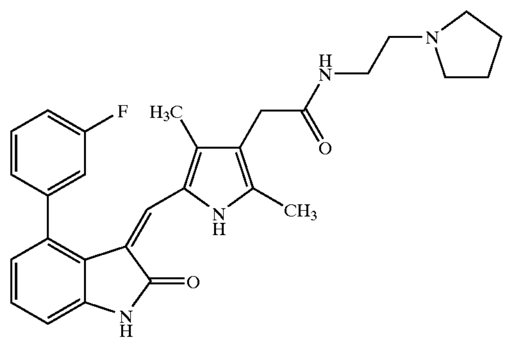 | 2-{5-[4-(3-Fluoro-phenyl)-2-oxo-1,2-dihydro-indol-(3Z)-ylidenemethyl]-2,4-dimethyl-1H-pyrrol-3-yl}-N-(2-pyrrolidin-1-yl-ethyl)-acetamide |
| 244 | 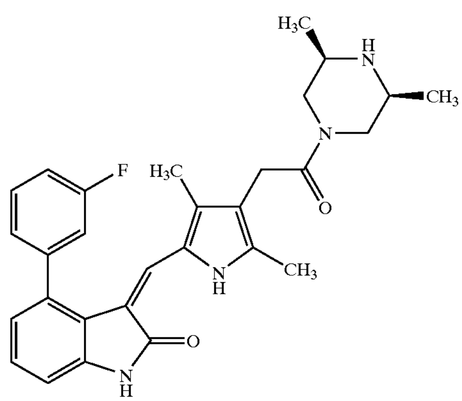 | 3-[1-{4-[2-((3R,5S)-3,5-Dimethyl-piperazin-1-yl)-2-oxo-ethyl]-3,5-dimethyl-1H-pyrrol-2-yl}-meth-(Z)-ylidene]-4-(3-fluoro-phenyl)-1,3-dihydro-indol-2-one |
| 245 | 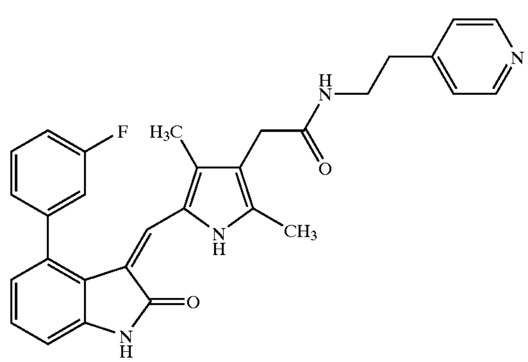 | 2-{5-[4-(3-Fluoro-phenyl)-2-oxo-1,2-dihydro-indol-(3Z)-ylidenemethyl]-2,4-dimethyl-1H-pyrrol-3-yl}-N-(2-pyridin-4-yl-ethyl)-acetamide |

TABLE 1-continued

Preferred 4-Aryl Substituted Indolinones

| Example | Structure | Name |
|---|---|---|
| 246 | 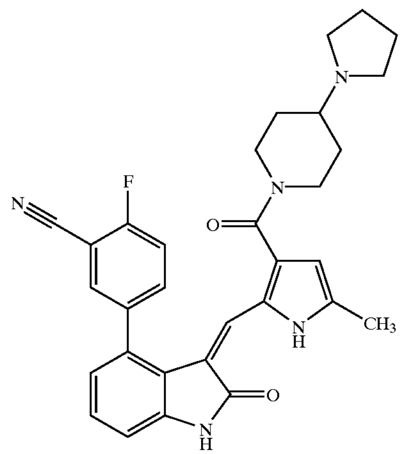 | 2-Fluoro-5-{3-[1-[5-methyl-3-(4-pyrrolidin-1-yl-piperidine-1-carbonyl)-1H-pyrrol-2-yl]-meth-(Z)-ylidene]-2-oxo-2,3-dihydro-1H-indol-4-yl}-benzonitrile |
| 247 | 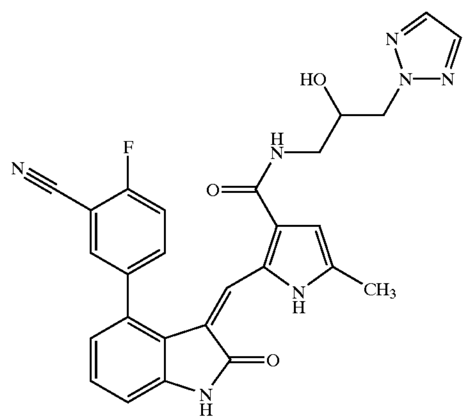 | 2-[4-(3-Cyano-4-fluoro-phenyl)-2-oxo-1,2-dihydro-indol-(3Z)-ylidenemethyl]-5-methyl-1H-pyrrole-3-carboxylic acid (2-hydroxy-3-[1,2,3]triazol-2-yl-propyl)-amide |
| 248 | 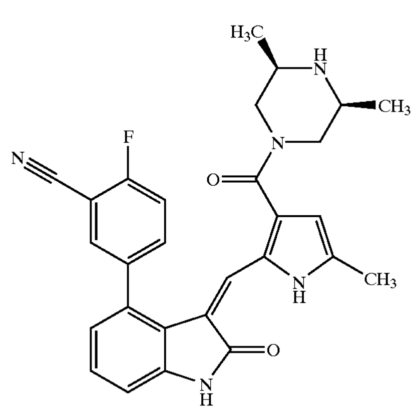 | 5-{3-[1-[3-((3R,5S)-3,5-Dimethyl-piperazine-1-carbonyl)-5-methyl-1H-pyrrol-2-yl]-meth-(Z)-ylidene]-2-oxo-2,3-dihydro-1H-indol-4-yl}-2-fluoro-benzonitrile |

TABLE 1-continued
Preferred 4-Aryl Substituted Indolinones
| Example | Structure | Name |
|---------|-----------|------|
| 249 | 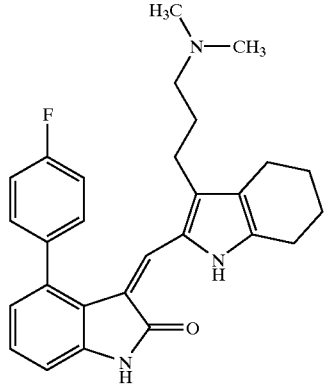 | 3-[1-[3-(3-Dimethylamino-propyl)-4,5,6,7-tetrahydro-1H-indol-2-yl]-meth-(Z)-ylidene]-4-(4-fluoro-phenyl)-1,3-dihydro-indol-2-one |
| 250 | 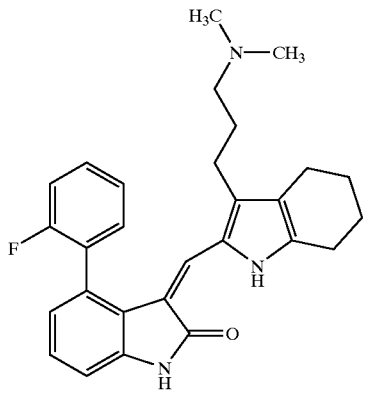 | 3-[1-[3-(3-Dimethylamino-propyl)-4,5,6,7-tetrahydro-1H-indol-2-yl]-meth-(Z)-ylidene]-4-(2-fluoro-phenyl)-1,3-dihydro-indol-2-one |
| 251 | 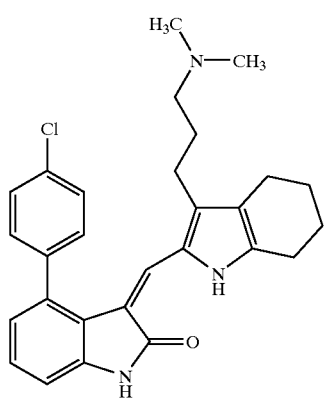 | 4-(4-Chloro-phenyl)-3-[1-[3-(3-dimethylamino-propyl)-4,5,6,7-tetrahydro-1H-indol-2-yl]-meth-(Z)-ylidene]-1,3-dihydro-indol-2-one |

TABLE 1-continued

Preferred 4-Aryl Substituted Indolinones

| Example | Structure | Name |
| --- | --- | --- |
| 252 | 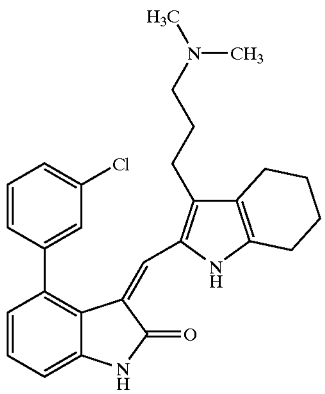 | 4-(3-Chloro-phenyl)-3-[1-[3-(3-dimethylamino-propyl)-4,5,6,7-tetrahydro-1H-indol-2-yl]-meth-(Z)-ylidene]-1,3-dihydro-indol-2-one |
| 253 | 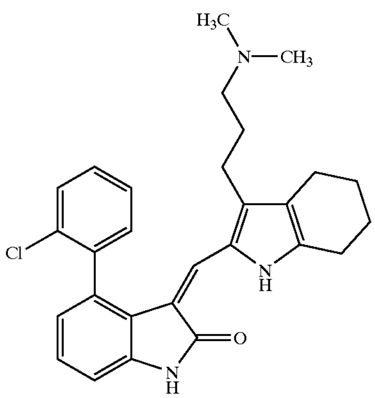 | 4-(2-Chloro-phenyl)-3-[1-[3-(3-dimethylamino-propyl)-4,5,6,7-tetrahydro-1H-indol-2-yl]-meth-(Z)-ylidene]-1,3-dihydro-indol-2-one |
| 254 | 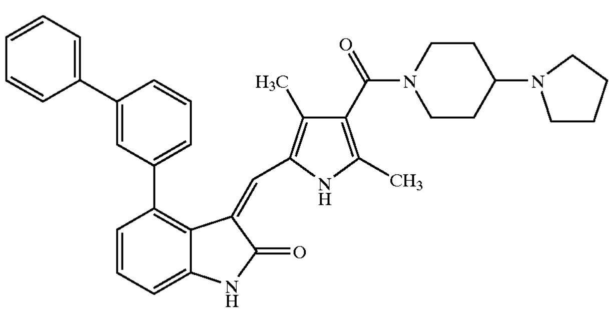 | 4-Biphenyl-3-yl-3-[1-[3,5-dimethyl-4-(4-pyrrolidin-1-yl-piperidine-1-carbonyl)-1H-pyrrol-2-yl]-meth-(Z)-ylidene]-1,3-dihydro-indol-2-one |
| 255 | 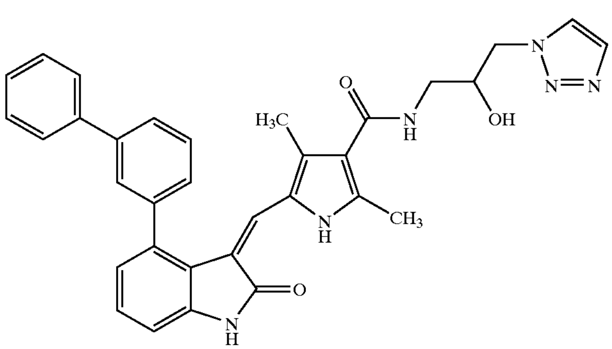 | 5-[4-Biphenyl-3-yl-2-oxo-1,2-dihydro-indol-(3Z)-ylidenemethyl]-2,4-dimethyl-1H-pyrrole-3-carboxylic acid (2-hydroxy-3-[1,2,3]triazol-1-yl-propyl)-amide |

TABLE 1-continued

Preferred 4-Aryl Substituted Indolinones

| Example | Structure | Name |
|---|---|---|
| 256 | 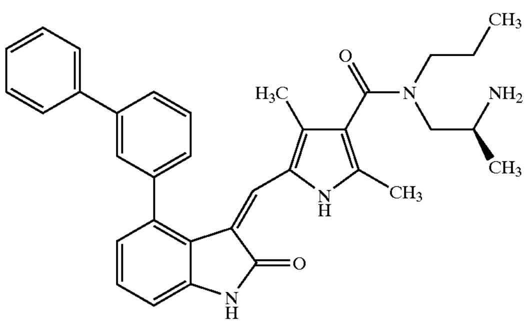 | 4-Biphenyl-3-yl-3-[1-[4-((3R,5S)-3,5-dimethyl-piperazine-1-carbonyl)-3,5-dimethyl-1H-pyrrol-2-yl]-meth-(Z)-ylidene]-1,3-dihydro-indol-2-one |
| 257 | 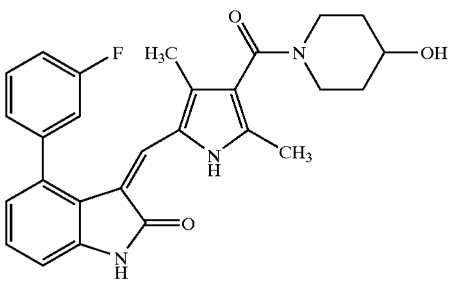 | 4-(3-Fluoro-phenyl)-3-[1-[4-(4-hydroxy-piperidine-1-carbonyl)-3,5-dimethyl-1H-pyrrol-2-yl]-meth-(Z)-ylidene]-1,3-dihydro-indol-2-one |
| 258 | 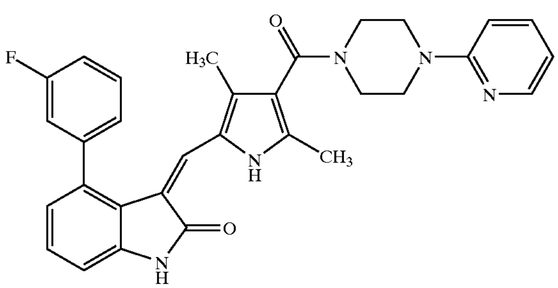 | 3-[1-[3,5-Dimethyl-4-(4-pyridin-2-yl-piperazine-1-carbonyl)-1H-pyrrol-2-yl]-meth-(Z)-ylidene]-4-(3-fluoro-phenyl)-1,3-dihydro-indol-2-one |
| 259 | 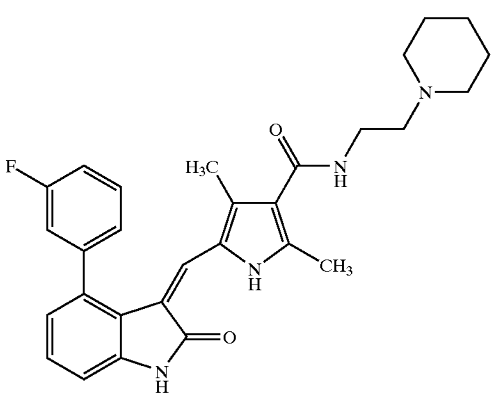 | 5-[4-(3-Fluoro-phenyl)-2-oxo-1,2-dihydro-indol-(3Z)-ylidenemethyl]-2,4-dimethyl-1H-pyrrole-3-carboxylic acid (2-piperidine-1-yl-ethyl)-amide |

TABLE 1-continued

Preferred 4-Aryl Substituted Indolinones

| Example | Structure | Name |
|---------|-----------|------|
| 260 | 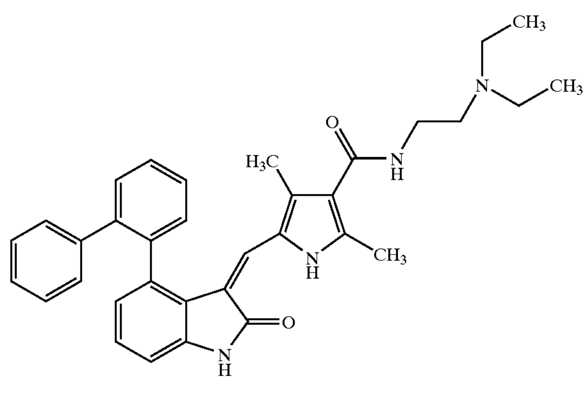 | 5-[4-Biphenyl-2-yl-2-oxo-1,2-dihydro-indol-(3Z)-ylidenemethyl]-2,4-dimethyl-1H-pyrrole-3-carboxylic acid (2-diethylamino-ethyl)-amide |
| 261 | 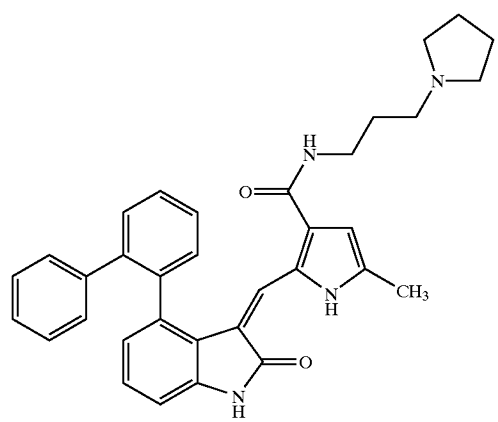 | 2-[4-Biphenyl-2-yl-2-oxo-1,2-dihydro-indol-(3Z)-ylidenemethyl]-5-methyl-1H-pyrrole-3-carboxylic acid (3-pyrrolidin-1-yl-propyl)-amide |
| 262 | 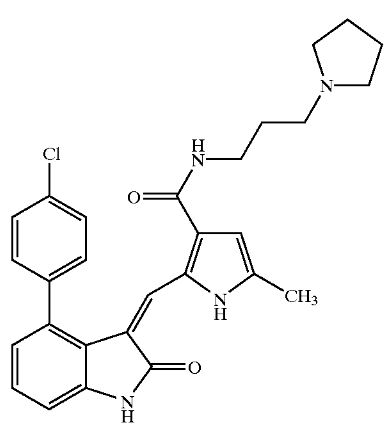 | 2-[4-(4-Chloro-phenyl)-2-oxo-1,2-dihydro-indol-(3Z)-ylidenemethyl]-5-methyl-1H-pyrrole-3-carboxylic acid (3-pyrrolidin-1-yl-propyl)-amide |

TABLE 1-continued

Preferred 4-Aryl Substituted Indolinones

| Example | Structure | Name |
|---|---|---|
| 263 | 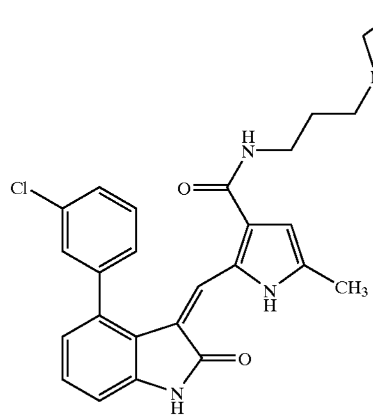 | 2-[4-(3-Chloro-phenyl)-2-oxo-1,2-dihydro-indol-(3Z)-ylidenemethyl]-5-methyl-1H-pyrrole-3-carboxylic acid (3-pyrrolidin-1-yl-propyl)-amide |
| 264 | 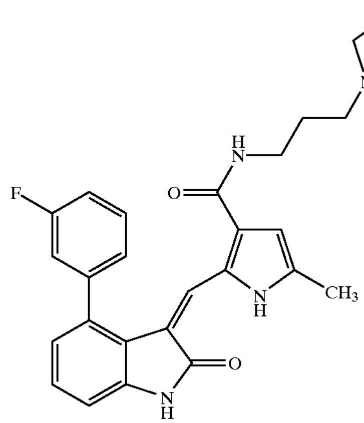 | 2-[4-(3-Fluoro-phenyl)-2-oxo-1,2-dihydro-indol-(3Z)-ylidenemethyl]-5-methyl-1H-pyrrole-3-carboxylic acid (3-pyrrolidin-1-yl-propyl)-amide |
| 265 | 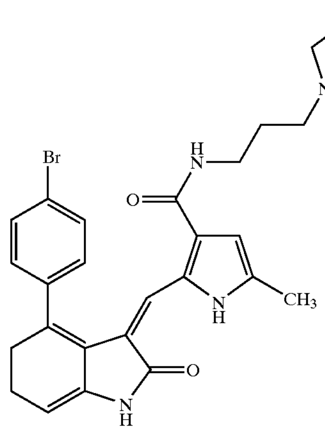 | 2-[4-(4-Bromo-phenyl)-2-oxo-1,2-dihydro-indol-(3Z)-ylidenemethyl]-5-methyl-1H-pyrrole-3-carboxylic acid (3-pyrrolidin-1-yl-propyl)-amide |

TABLE 1-continued

Preferred 4-Aryl Substituted Indolinones

| Example | Structure | Name |
|---|---|---|
| 266 | 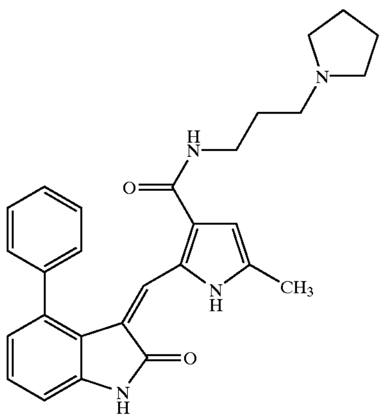 | 5-Methyl-2-[2-oxo-4-phenyl-1,2-dihydro-indol-(3Z)-ylidenemethyl]-1H-pyrrole-3-carboxylic acid (3-pyrrolidin-1-yl-propyl)-amide |
| 267 | 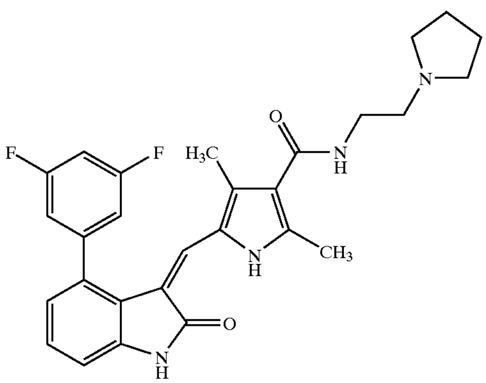 | 5-[4-(3,5-Difluoro-phenyl)-2-oxo-1,2-dihydro-indol-(3Z)-ylidenemethyl]-2,4-dimethyl-1H-pyrrole-3-carboxylic acid (2-pyrrolidin-1-yl-ethyl)-amide |
| 268 | 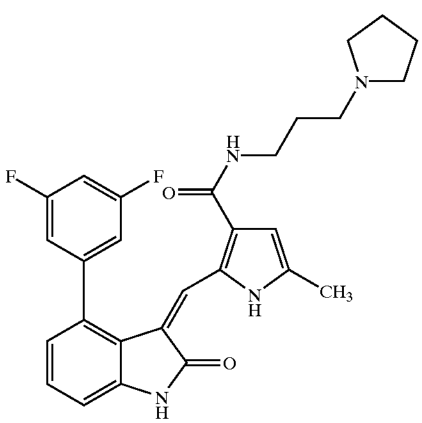 | 2-[4-(3,5-Difluoro-phenyl)-2-oxo-1,2-dihydro-indol-(3Z)-ylidenemethyl]-5-methyl-1H-pyrrole-3-carboxylic acid (3-pyrrolidin-1-yl-propyl)-amide |
| 269 | 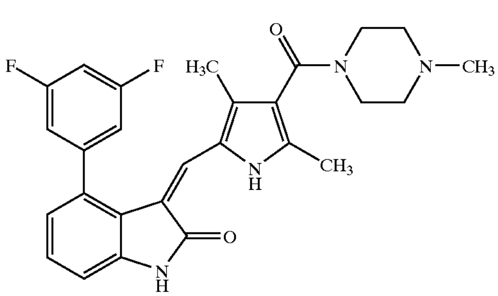 | 4-(3,5-Difluoro-phenyl)-3-[1-[3,5-dimethyl-4-(4-methyl-piperazine-1-carbonyl)-1H-pyrrol-2-yl]-meth-(Z)-ylidene]-1,3-dihydro-indol-2-one |

TABLE 1-continued

Preferred 4-Aryl Substituted Indolinones

| Example | Structure | Name |
|---|---|---|
| 270 | 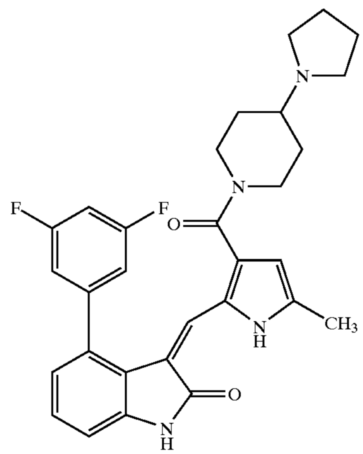 | 4-(3,5-Difluoro-phenyl)-3-[1-[5-methyl-3-(4-pyrrolidin-1-yl-piperidine-1-carbonyl)-1H-pyrrol-2-yl]-meth-(Z)-ylidene]-1,3-dihydro-indol-2-one |
| 271 | 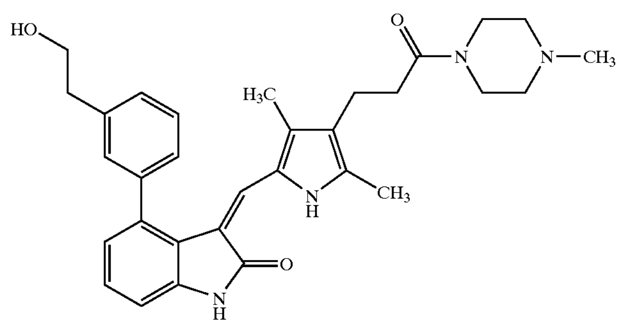 | 3-[1-{3,5-Dimethyl-4-[3-(4-methyl-piperazin-1-yl)-3-oxo-propyl]-1H-pyrrol-2-yl}-meth-(Z)-ylidene]-4-[3-(2-hydroxy-ethyl)-phenyl]-1,3-dihydro-indol-2-one |
| 272 | 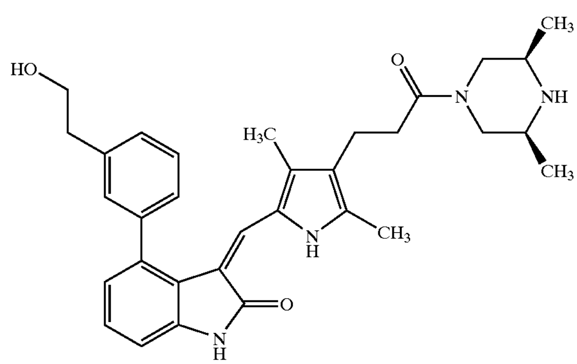 | 3-[1-{4-[3-((3R,5S)-3,5-Dimethyl-piperazin-1-yl)-3-oxo-propyl]-3,5-dimethyl-1H-pyrrol-2-yl}-meth-(Z)-ylidene]-4-[3-(2-hydroxy-ethyl)-phenyl]-1,3-dihydro-indol-2-one |
| 273 | 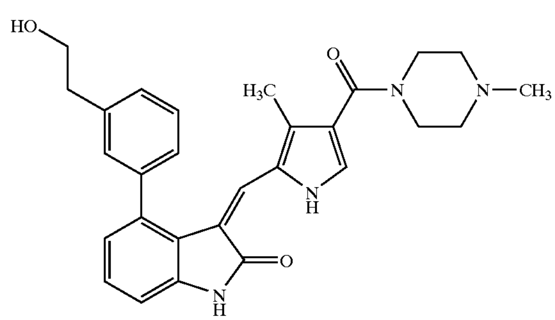 | 4-[3-(2-Hydroxy-ethyl)-phenyl]-3-[1-[3-methyl-4-(4-methyl-piperazine-1-carbonyl)-1H-pyrrol-2-yl]-meth-(Z)-ylidene]-1,3-dihydro-indol-2-one |

TABLE 1-continued

Preferred 4-Aryl Substituted Indolinones

| Example | Structure | Name |
|---|---|---|
| 274 | 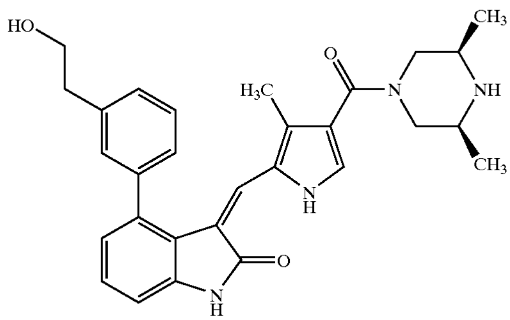 | 3-[1-[4-((3R,5S)-3,5-Dimethyl-piperazine-1-carbonyl)-3-methyl-1H-pyrrol-2-yl]-meth-(Z)-ylidene]-4-[3-(2-hydroxy-ethyl)-phenyl]-1,3-dihydro-indol-2-one |
| 275 | 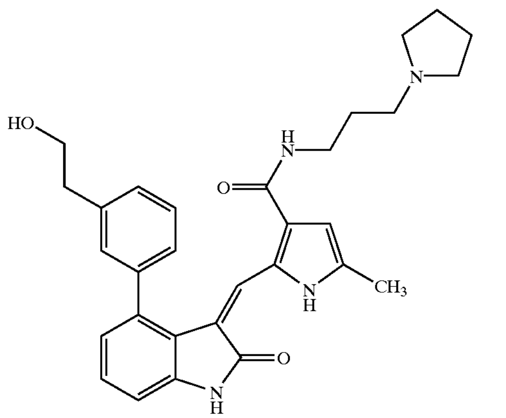 | 2-[4-[3-(2-Hydroxy-ethyl)-phenyl]-2-oxo-1,2-dihydro-indol-(3Z)-ylidenemethyl]-5-methyl-1H-pyrrole-3-carboxylic acid (3-pyrrolidin-1-yl-propyl)-amide |
| 276 | 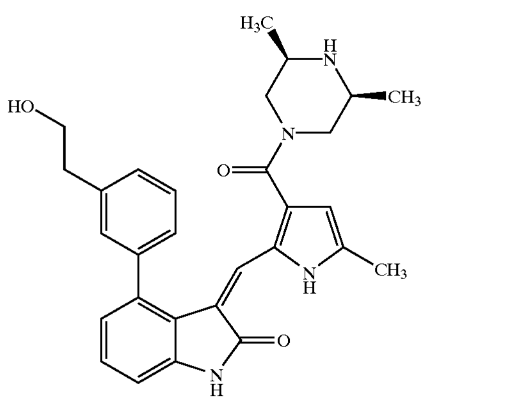 | 3-[1-[3-((3R,5S)-3,5-Dimethyl-piperazine-1-carbonyl)-5-methyl-1H-pyrrol-2-yl]-meth-(Z)-ylidene]-4-[3-(2-hydroxy-ethyl)-phenyl]-1,3-dihydro-indol-2-one |
| 277 | 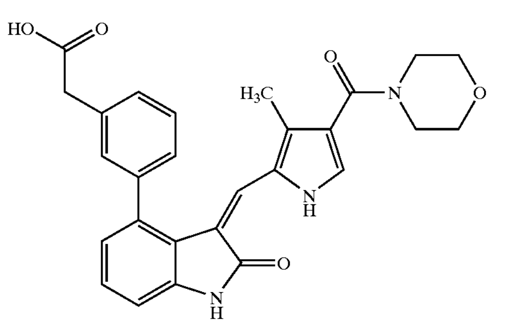 | (3-{3-[1-[3-Methyl-4-(morpholine-4-carbonyl)-1H-pyrrol-2-yl]-meth-(Z)-ylidene]-2-oxo-2,3-dihydro-1H-indol-4-yl}-phenyl)-acetic acid |

TABLE 1-continued

_Preferred 4-Aryl Substituted Indolinones_

| Example | Structure | Name |
| --- | --- | --- |
| 278 | 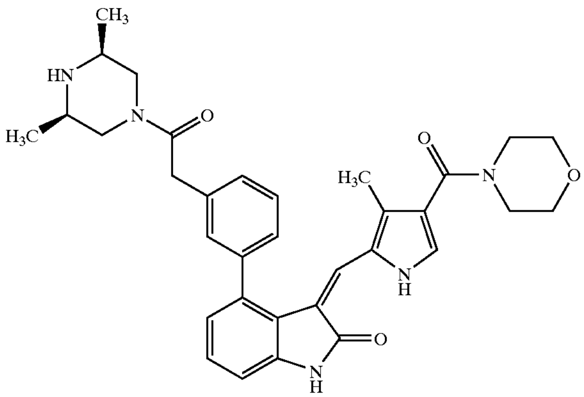 | 4-{3-[2-((3R,5S)-3,5-Dimethyl-piperazin-1-yl)-2-oxo-ethyl]-phenyl}-3-[1-[3-methyl-4-(morpholine-4-carbonyl)-1H-pyrrol-2-yl]-meth-(Z)-ylidene]-1,3-dihydro-indol-2-one |
| 279 | 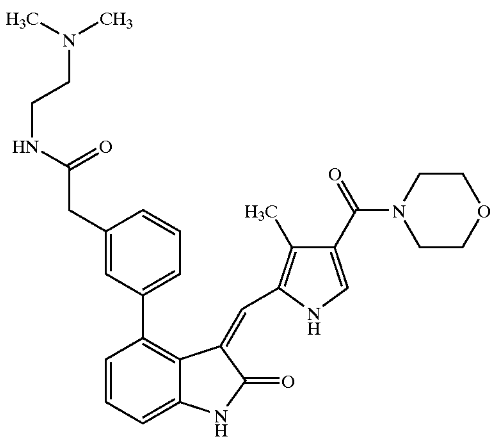 | N-(2-Dimethylamino-ethyl)-2-(3-{3-[1-[3-methyl-4-(morpholine-4-carbonyl)-1H-pyrrol-2-yl]-meth-(Z)-ylidene]-2-oxo-2,3-dihydro-1H-indol-4-yl}-phenyl)-acetamide |
| 280 | 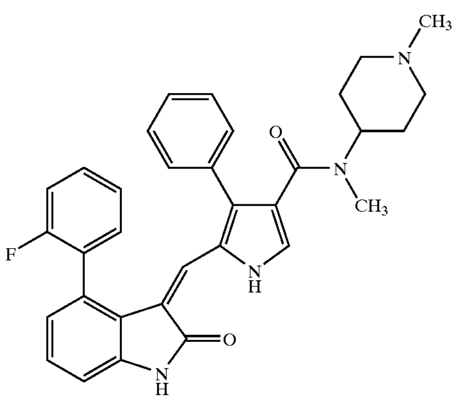 | 5-[4-(2-Fluoro-phenyl)-2-oxo-1,2-dihydro-indol-(3Z)-ylidenemethyl]-4-phenyl-1H-pyrrole-3-carboxylic acid methyl-(1-methyl-piperidin-4-yl)-amide |
| 281 | 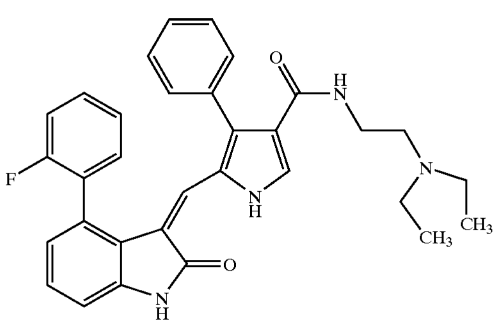 | 5-[4-(2-Fluoro-phenyl)-2-oxo-1,2-dihydro-indol-(3Z)-ylidenemethyl]-4-phenyl-1H-pyrrole-3-carboxylic acid (2-diethylamino-ethyl)-amide |

TABLE 1-continued

Preferred 4-Aryl Substituted Indolinones

| Example | Structure | Name |
|---|---|---|
| 282 | 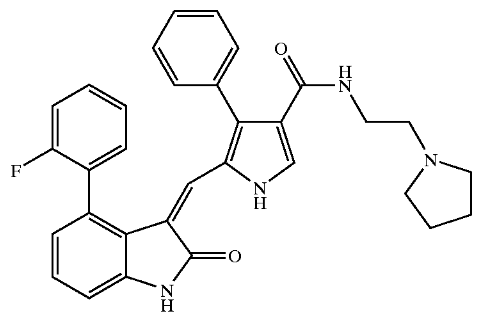 | 5-[4-(2-Fluoro-phenyl)-2-oxo-1,2-dihydro-indol-(3Z)-ylidenemethyl]-4-phenyl-1H-pyrrole-3-carboxylic acid (2-pyrrolidin-1-yl-ethyl)-amide |
| 283 | 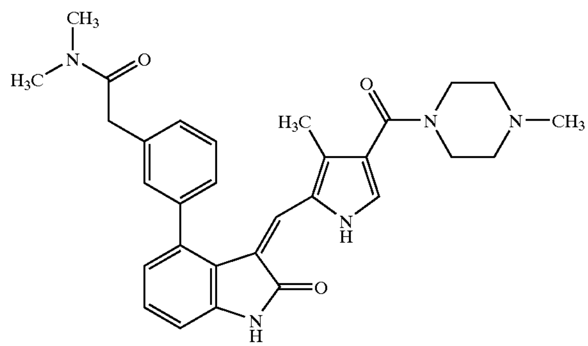 | N,N-Dimethyl-2-(3-{3-[1-[3-methyl-4-(4-methyl-piperazine-1-carbonyl)-1H-pyrrol-2-yl]-meth-(Z)-ylidene]-2-oxo-2,3-dihydro-1H-indol-4-yl}-phenyl)-acetamide |
| 284 | 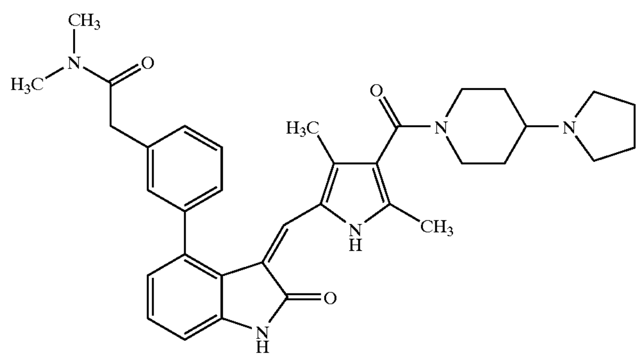 | 2-(3-{3-[1-[3,5-Dimethyl-4-(4-pyrrolidin-1-yl-piperidine-1-carbonyl)-1H-pyrrol-2-yl]-meth-(Z)-ylidene]-2-oxo-2,3-dihydro-1H-indol-4-yl}-phenyl)-N,N-dimethyl-acetamide |
| 285 | 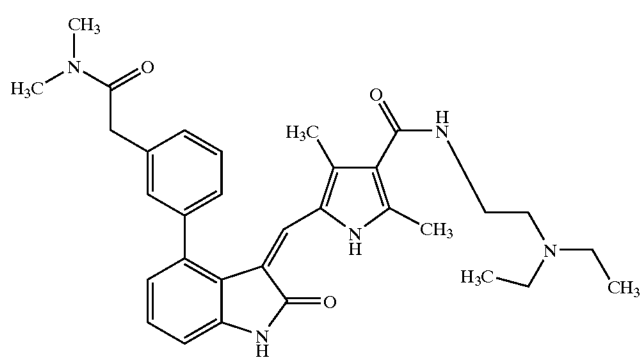 | 5-[4-(3-Dimethylcarbamoylmethyl-phenyl)-2-oxo-1,2-dihydro-indol-(3Z)-ylidenemethyl]-2,4-dimethyl-1H-pyrrole-3-carboxylic acid (2-diethylamino-ethyl)-amide |

TABLE 1-continued

Preferred 4-Aryl Substituted Indolinones

| Example | Structure | Name |
|---|---|---|
| 286 | 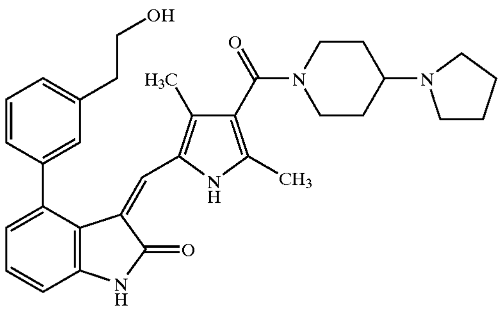 | 3-[1-[3,5-Dimethyl-4-(4-pyrrolidin-1-yl-piperidine-1-carbonyl)-1H-pyrrol-2-yl]-meth-(Z)-ylidene]-4-[3-(2-hydroxy-ethyl)-phenyl]-1,3-dihydro-indol-2-one |
| 287 | 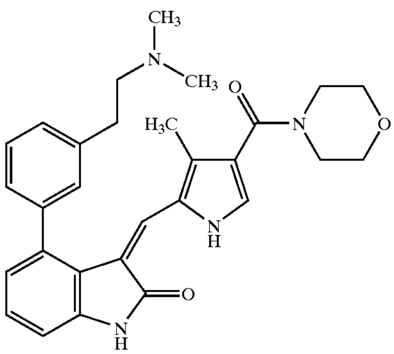 | 4-[3-(2-Dimethylamino-ethyl)-phenyl]-3-[1-[3-methyl-4-(morpholine-4-carbonyl)-1H-pyrrol-2-yl]-meth-(Z)-ylidene]-1,3-dihydro-indol-2-one |
| 288 | 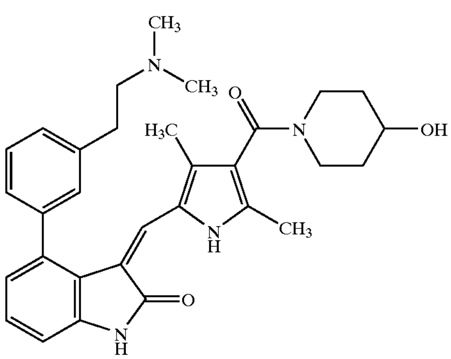 | 4-[3-(2-Dimethylamino-ethyl)-phenyl]-3-[1-[4-(4-hydroxy-piperidine-1-carbonyl)-3,5-dimethyl-1H-pyrrol-2-yl]-meth-(Z)-ylidene]-1,3-dihydro-indol-2-one |
| 289 | 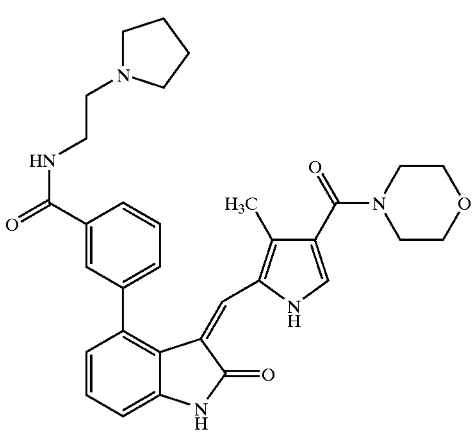 | 3-{3-[1-[3-Methyl-4-(morpholine-4-carbonyl)-1H-pyrrol-2-yl]-meth-(Z)-ylidene]-2-oxo-2,3-dihydro-1H-indol-4-yl}-N-(2-pyrrolidin-1-yl-ethyl)-benzamide |

TABLE 1-continued

Preferred 4-Aryl Substituted Indolinones

| Example | Structure | Name |
|---|---|---|
| 290 | 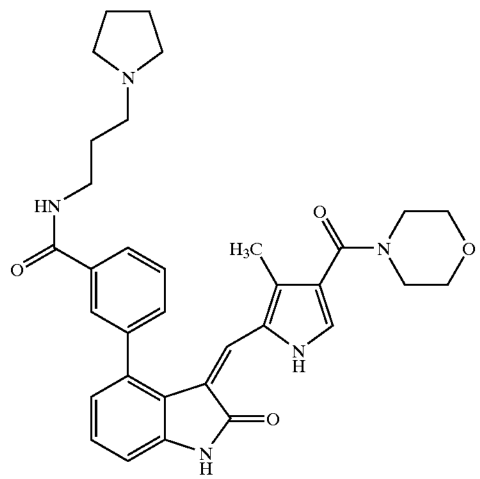 | 3-{3-[1-[3-Methyl-4-(morpholine-4-carbonyl)-1H-pyrrol-2-yl]-meth-(Z)-ylidene]-2-oxo-2,3-dihydro-1H-indol-4-yl}-N-(3-pyrrolidin-1-yl-propyl)-benzamide |
| 291 | 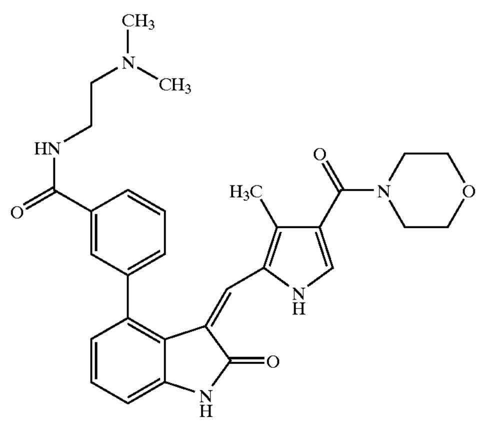 | N-(2-Dimethylamino-ethyl)-3-{3-[1-[3-methyl-4-(morpholine-4-carbonyl)-1H-pyrrol-2-yl]-meth-(Z)-ylidene]-2-oxo-2,3-dihydro-1H-indol-4-yl}-benzamide |
| 292 | 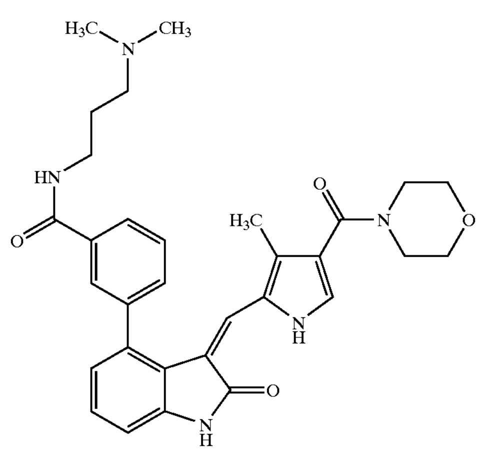 | N-(3-Dimethylamino-propyl)-3-{3-[1-[3-methyl-4-(morpholine-4-carbonyl)-1H-pyrrol-2-yl]-meth-(Z)-ylidene]-2-oxo-2,3-dihydro-1H-indol-4-yl}-benzamide |

TABLE 1-continued

Preferred 4-Aryl Substituted Indolinones

| Example | Structure | Name |
|---------|-----------|------|
| 293 | 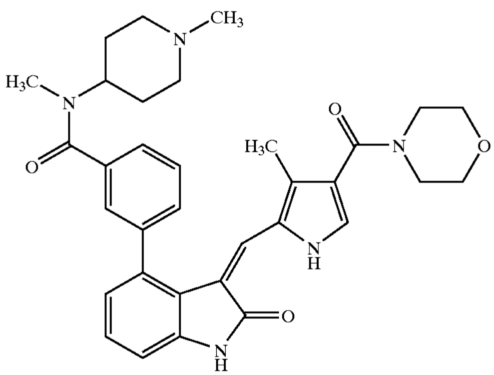 | N-Methyl-3-{3-[1-[3-methyl-4-(morpholine-4-carbonyl)-1H-pyrrol-2-yl]-meth-(Z)-ylidene]-2-oxo-2,3-dihydro-1H-indol-4-yl}-N-(1-methyl-piperidin-4-yl)-benzamide |
| 294 | 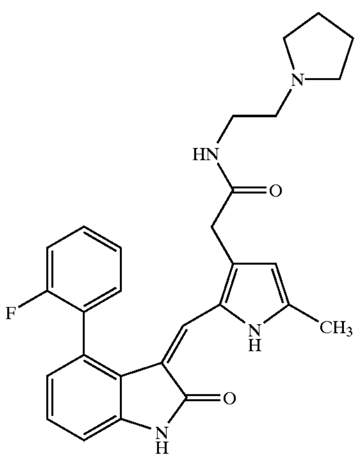 | 2-{2-[4-(2-Fluoro-phenyl)-2-oxo-1,2-dihydro-indol-(3Z)-ylidenemethyl]-5-methyl-1H-pyrrol-3-yl}-N-(2-pyrrolidin-1-yl-ethyl)-acetamide |
| 295 | 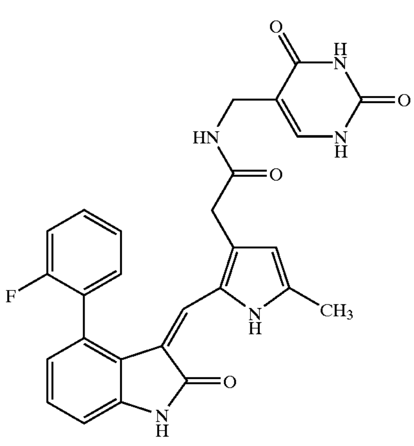 | N-(2,4-Dioxo-1,2,3,4-tetrahydro-pyrimidin-5-ylmethyl)-2-{2-[4-(2-fluoro-phenyl)-2-oxo-1,2-dihydro-indol-(3Z)-ylidenemethyl]-5-methyl-1H-pyrrol-3-yl}-acetamide |

TABLE 1-continued

Preferred 4-Aryl Substituted Indolinones

| Example | Structure | Name |
|---|---|---|
| 296 | 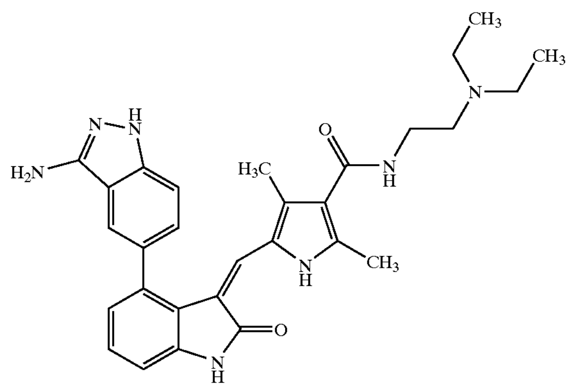 | 5-[4-(3-Amino-1H-indazol-5-yl)-2-oxo-1,2-dihydro-indol-(3Z)-ylidenemethyl]-2,4-dimethyl-1H-pyrrole-3-carboxylic acid (2-diethylamino-ethyl)-amide |
| 297 | 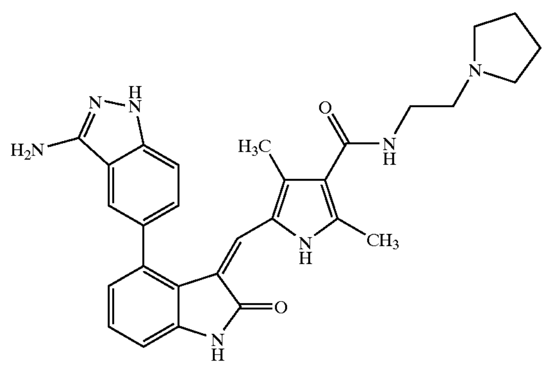 | 5-[4-(3-Amino-1H-indazol-5-yl)-2-oxo-1,2-dihydro-indol-(3Z)-ylidenemethyl]-2,4-dimethyl-1H-pyrrole-3-carboxylic acid (2-pyrrolidin-1-yl-ethyl)-amide |
| 298 | 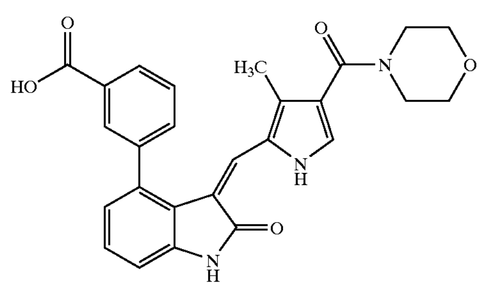 | 3-{3-[1-[3-Methyl-4-(morpholine-4-carbonyl)-1H-pyrrol-2-yl]-meth-(Z)-ylidene]-2-oxo-2,3-dihydro-1H-indol-4-yl}-benzoic acid |
| 299 | 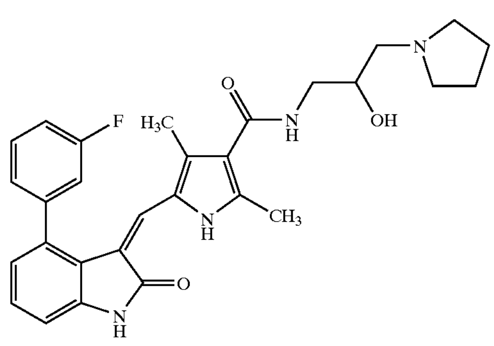 | 5-[4-(3-Fluoro-phenyl)-2-oxo-1,2-dihydro-indol-(3Z)-ylidenemethyl]-2,4-dimethyl-1H-pyrrole-3-carboxylic acid (2-hydroxy-3-pyrrolidin-1-yl-propyl)-amide |

TABLE 1-continued

Preferred 4-Aryl Substituted Indolinones

| Example | Structure | Name |
|---|---|---|
| 300 | 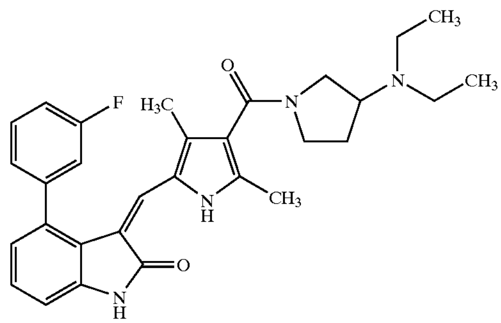 | 3-[1-[4-(3-Diethylamino-pyrrolidin-1-carbonyl)-3,5-dimethyl-1H-pyrrol-2-yl]-meth-(Z)-ylidene]-4-(3-fluoro-phenyl)-1,3-dihydro-indol-2-one |
| 301 | 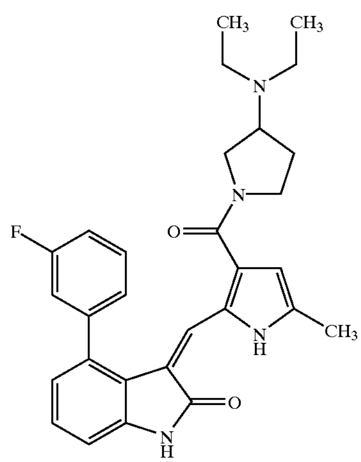 | 3-[1-[3-(3-Diethylamino-pyrrolidine-1-carbonyl)-5-methyl-1H-pyrrol-2-yl]-meth-(Z)-ylidene]-4-(3-fluoro-phenyl)-1,3-dihydro-indol-2-one |
| 302 | 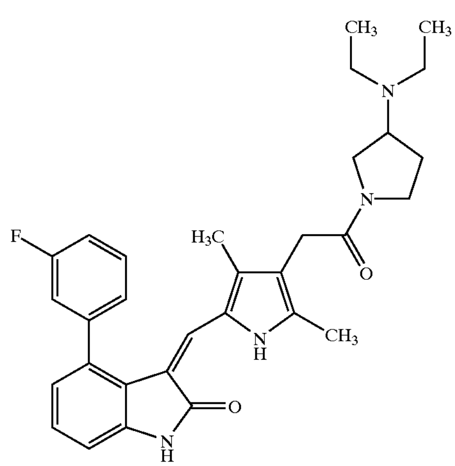 | 3-[1-{4-[2-(3-Diethylamino-pyrrolidin-1-yl)-2-oxo-ethyl]-3,5-dimethyl-1H-pyrrol-2-yl}-meth-(Z)-ylidene]-4-(3-fluoro-phenyl)-1,3-dihydro-indol-2-one |

TABLE 1-continued

Preferred 4-Aryl Substituted Indolinones

| Example | Structure | Name |
| --- | --- | --- |
| 303 | 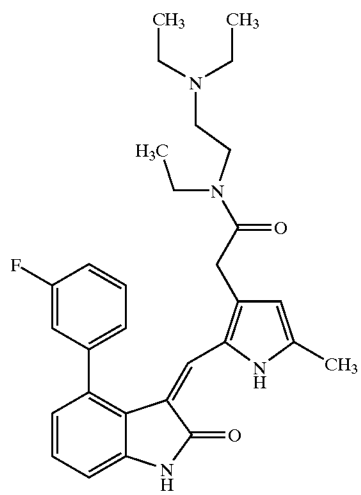 | 3-[1-{3-[2-(3-Diethylamino-pyrrolidin-1-yl)-2-oxo-ethyl]-5-methyl-1H-pyrrol-2-yl}-meth-(Z)-ylidene]-4-(3-fluoro-phenyl)-1,3-dihydro-indol-2-one |
| 304 | 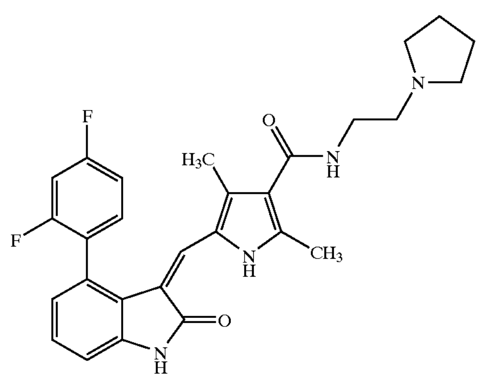 | 5-[4-(2,4-Difluoro-phenyl)-2-oxo-1,2-dihydro-indol-(3Z)-ylidenemethyl]-2,4-dimethyl-1H-pyrrole-3-carboxylic acid (2-pyrrolidin-1-yl-ethyl)-amide |
| 305 | 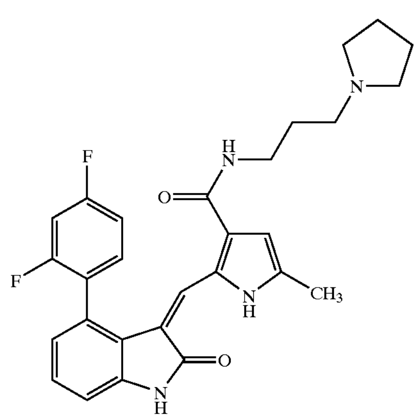 | 2-[4-(2,4-Difluoro-phenyl)-2-oxo-1,2-dihydro-indol-(3Z)-ylidenemethyl]-5-methyl-1H-pyrrole-3-carboxylic acid (3-pyrrolidin-1-yl-propyl)-amide |

TABLE 1-continued

Preferred 4-Aryl Substituted Indolinones

| Example | Structure | Name |
|---|---|---|
| 306 | 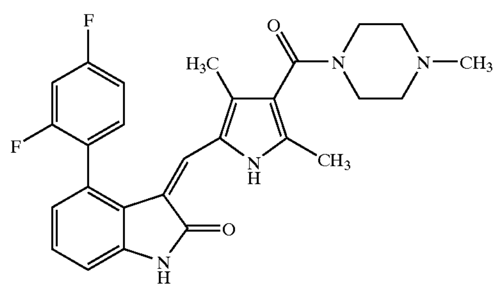 | 4-(2,4-Difluoro-phenyl)-3-[1-[3,5-dimethyl-4-(4-methyl-piperazine-1-carbonyl)-1H-pyrrol-2-yl]-meth-(Z)-ylidene]-1,3-dihydro-indol-2-one |
| 307 | 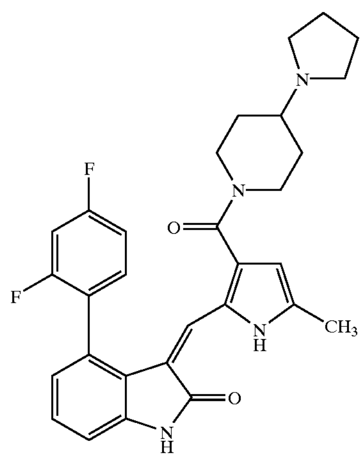 | 4-(2,4-Difluoro-phenyl)-3-[1-[3-methyl-4-(morpholine-4-carbonyl)-1H-pyrrol-2-yl]-meth-(Z)-ylidene]-1,3-dihydro-indol-2-one |
| 308 | 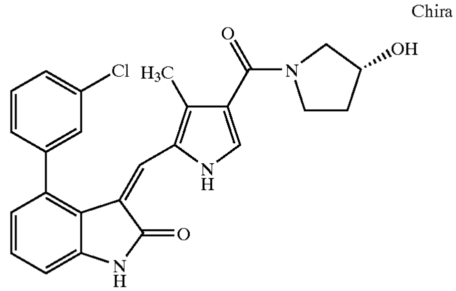 | 4-(3-Chloro-phenyl)-3-[1-[4-((R)-3-hydroxy-pyrrolidine-1-carbonyl)-3-methyl-1H-pyrrol-2-yl]-meth-(Z)-ylidene]-1,3-dihydro-indol-2-one |
| 309 | 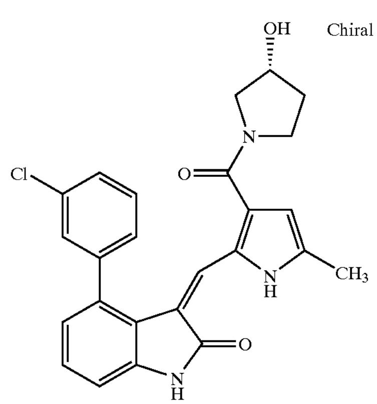 | 4-(3-Chloro-phenyl)-3-[1-[3-((R)-3-hydroxy-pyrrolidine-1-carbonyl)-5-methyl-1H-pyrrol-2-yl]-meth-(Z)-ylidene]-1,3-dihydro-indol-2-one |

TABLE 1-continued

Preferred 4-Aryl Substituted Indolinones

| Example | Structure | Name |
|---|---|---|
| 310 | Chiral | 4-(2-Fluoro-phenyl)-3-[1-[4-((R)-3-hydroxy-pyrrolidine-1-carbonyl)-3-methyl-1H-pyrrol-2-yl]-meth-(Z)-ylidene]-1,3-dihydro-indol-2-one |
| 311 | Chira | 4-(3-Fluoro-phenyl)-3-[1-[4-((R)-3-hydroxy-pyrrolidine-1-carbonyl)-3,5-dimethyl-1H-pyrrol-2-yl]-meth-(Z)-ylidene]-1,3-dihydro-indol-2-one |
| 312 | Chiral | 4-(3-Fluoro-phenyl)-3-[1-{4-[2-((R)-3-hydroxy-pyrrolidin-1-yl)-2-oxo-ethyl]-3,5-dimethyl-1H-pyrrol-2-yl}-meth-(Z)-ylidene]-1,3-dihydro-indol-2-one |
| 313 | 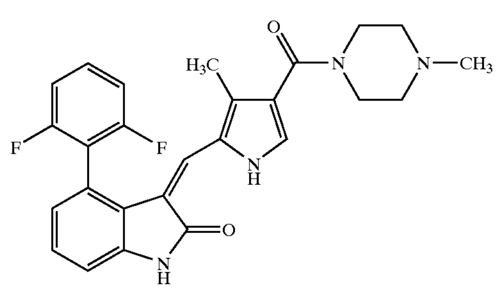 | 4-(2,6-Difluoro-phenyl)-3-[1-[3-methyl-4-(4-methyl-piperazine-1-carbonyl)-1H-pyrrol-2-yl]-meth-(Z)-ylidene]-1,3-dihydro-indol-2-one |

TABLE 1-continued

Preferred 4-Aryl Substituted Indolinones

| Example | Structure | Name |
|---|---|---|
| 314 | 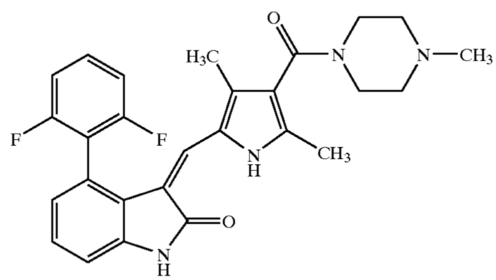 | 4-(2,6-Difluoro-phenyl)-3-[1-[3,5-dimethyl-4-(4-methyl-piperazine-1-carbonyl)-1H-pyrrol-2-yl]-meth-(Z)-ylidene]-1,3-dihydro-indol-2-one |
| 315 | 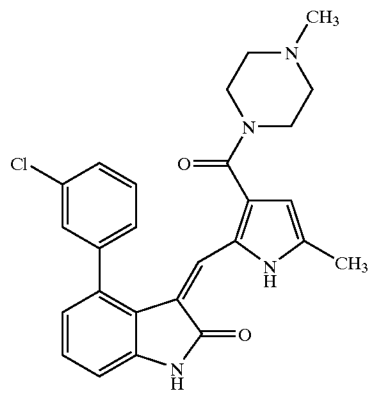 | 4-(3-Chloro-phenyl)-3-[1-[5-methyl-3-(4-methyl-piperazine-1-carbonyl)-1H-pyrrol-2-yl]-meth-(Z)-ylidene]-1,3-dihydro-indol-2-one |
| 316 | 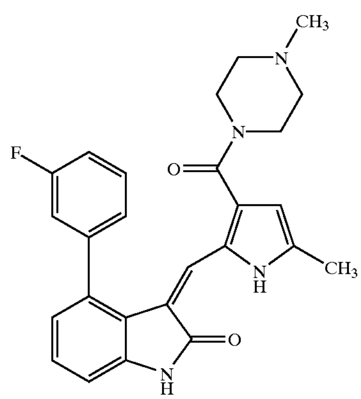 | 4-(3-Fluoro-phenyl)-3-[1-[5-methyl-3-(4-methyl-piperazine-1-carbonyl)-1H-pyrrol-2-yl]-meth-(Z)-ylidene]-1,3-dihydro-indol-2-one |
| 317 | 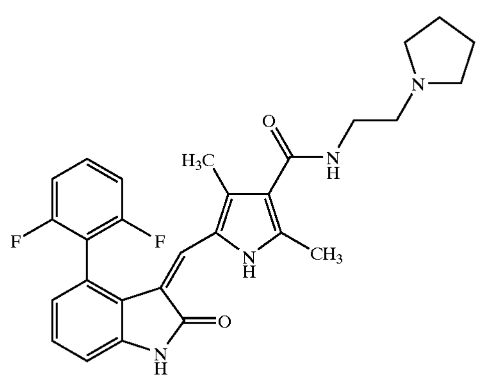 | 5-[4-(2,6-Difluoro-phenyl)-2-oxo-1,2-dihydro-indol-(3Z)-ylidenemethyl]-2,4-dimethyl-1H-pyrrole-3-carboxylic acid (2-pyrrolidin-1-yl-ethyl)-amide |

TABLE 1-continued

Preferred 4-Aryl Substituted Indolinones

| Example | Structure | Name |
|---|---|---|
| 318 | 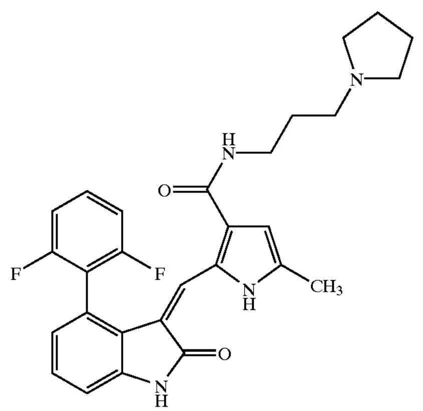 | 2-[4-(2,6-Difluoro-phenyl)-2-oxo-1,2-dihydro-indol-(3Z)-ylidenemethyl]-5-methyl-1H-pyrrole-3-carboxylic acid (3-pyrrolidin-1-yl-propyl)-amide |
| 319 | 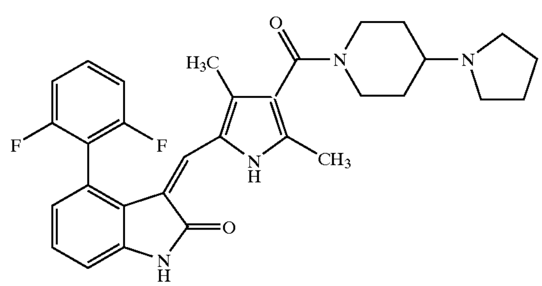 | 4-(2,6-Difluoro-phenyl)-3-[1-[3,5-dimethyl-4-(4-pyrrolidin-1-yl-piperidine-1-carbonyl)-1H-pyrrol-2-yl]-meth-(Z)-ylidene]-1,3-dihydro-indol-2-one |
| 320 | 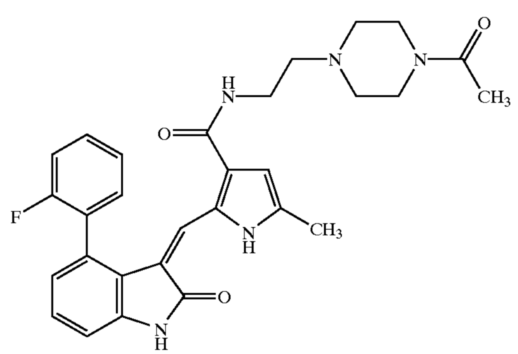 | 2-[4-(2-Fluoro-phenyl)-2-oxo-1,2-dihydro-indol-(3Z)-ylidenemethyl]-5-methyl-1H-pyrrole-3-carboxylic acid [2-(4-acetyl-piperazin-1-yl)-ethyl]-amide |
| 321 | 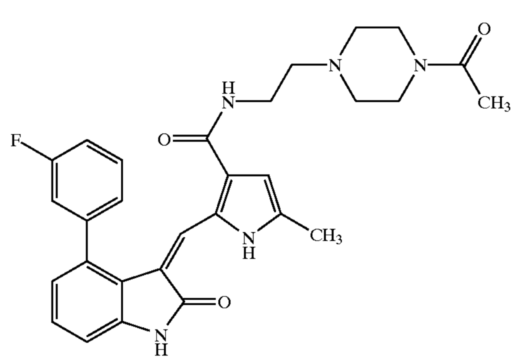 | 2-[4-(3-Fluoro-phenyl)-2-oxo-1,2-dihydro-indol-(3Z)-ylidenemethyl]-5-methyl-1H-pyrrole-3-carboxylic acid [2-(4-acetyl-piperazin-1-yl)-ethyl]-amide |

TABLE 1-continued

Preferred 4-Aryl Substituted Indolinones

| Example | Structure | Name |
| --- | --- | --- |
| 322 | 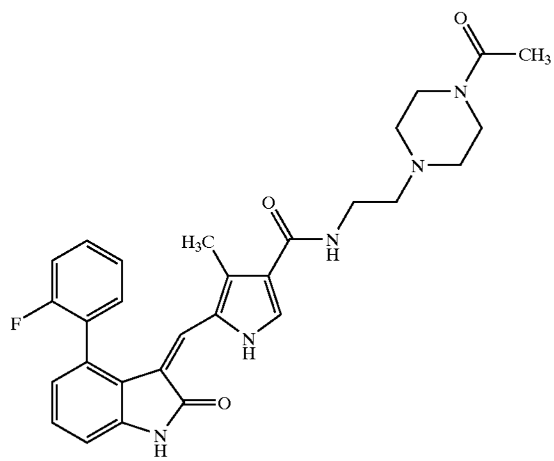 | 5-[4-(2-Fluoro-phenyl)-2-oxo-1,2-dihydro-indol-(3Z)-ylidenemethyl]-4-methyl-1H-pyrrole-3-carboxylic acid [2-(4-acetyl-piperazin-1-yl)-ethyl]-amide |
| 323 | 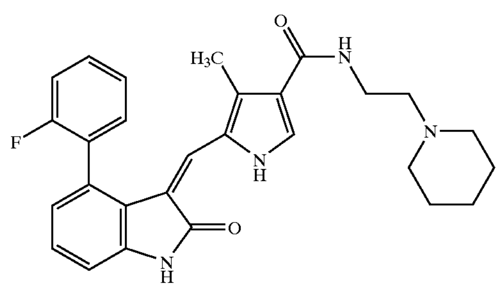 | 5-[4-(2-Fluoro-phenyl)-2-oxo-1,2-dihydro-indol-(3Z)-ylidenemethyl]-4-methyl-1H-pyrrole-3-carboxylic acid (2-piperidin-1-yl-ethyl)-amide |
| 324 | 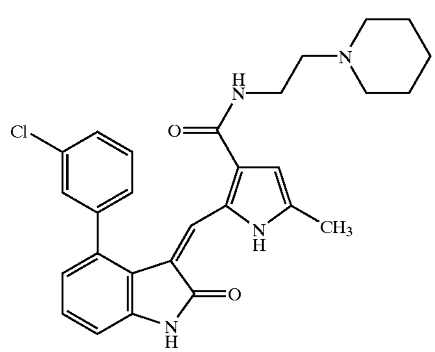 | 2-[4-(3-Chloro-phenyl)-2-oxo-1,2-dihydro-indol-(3Z)-ylidenemethyl]-5-methyl-1H-pyrrole-3-carboxylic acid (2-piperidin-1-yl-ethyl)-amide |
| 325 | 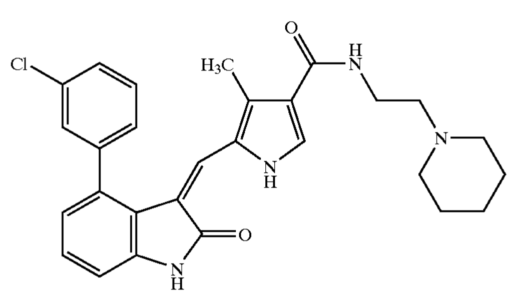 | 5-[4-(3-Chloro-phenyl)-2-oxo-1,2-dihydro-indol-(3Z)-ylidenemethyl]-4-methyl-1H-pyrrole-3-carboxylic acid (2-piperidin-1-yl-ethyl)-amide |

TABLE 1-continued

Preferred 4-Aryl Substituted Indolinones

| Example | Structure | Name |
|---|---|---|
| 326 | 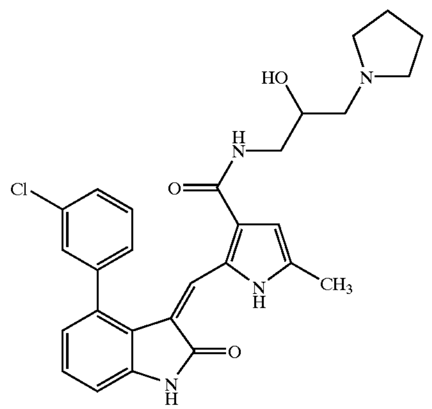 | 2-[4-(3-Chloro-phenyl)-2-oxo-1,2-dihydro-indol-(3Z)-ylidenemethyl]-5-methyl-1H-pyrrole-3-carboxylic acid (2-hydroxy-3-pyrrolidin-1-yl-propyl)-amide |
| 327 | 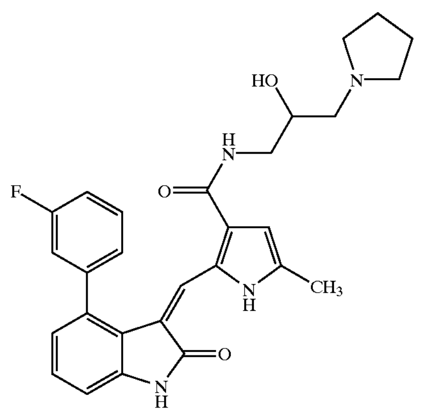 | 2-[4-(3-Fluoro-phenyl)-2-oxo-1,2-dihydro-indol-(3Z)-ylidenemethyl]-5-methyl-1H-pyrrole-3-carboxylic acid (2-hydroxy-3-pyrrolidin-1-yl-propyl)-amide |
| 328 | 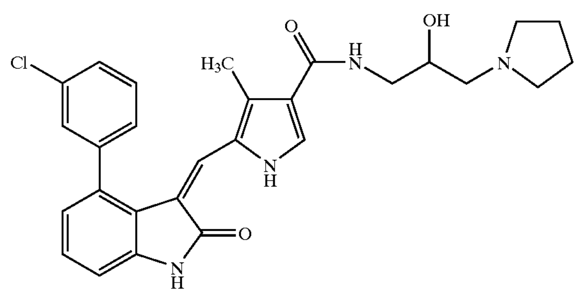 | 5-[4-(3-Chloro-phenyl)-2-oxo-1,2-dihydro-indol-(3Z)-ylidenemethyl]-4-methyl-1H-pyrrole-3-carboxylic acid (2-hydroxy-3-pyrrolidin-1-yl-propyl)-amide |
| 329 | 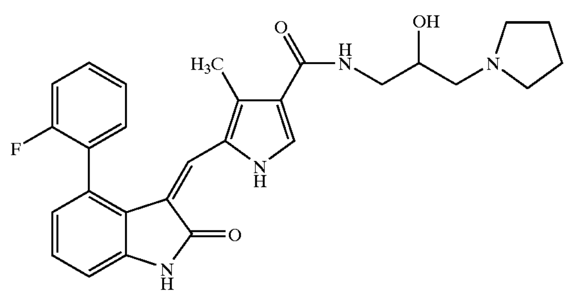 | 5-[4-(2-Fluoro-phenyl)-2-oxo-1,2-dihydro-indol-(3Z)-ylidenemethyl]-4-methyl-1H-pyrrole-3-carboxylic acid (2-hydroxy-3-pyrrolidin-1-yl-propyl)-amide |

TABLE 1-continued

Preferred 4-Aryl Substituted Indolinones

| Example | Structure | Name |
|---------|-----------|------|
| 330 | 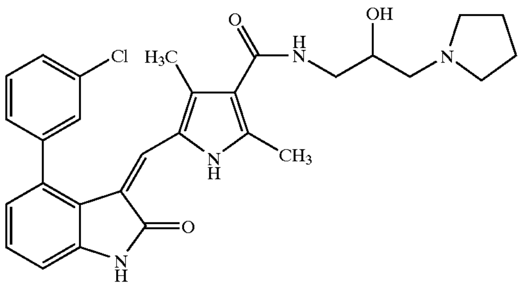 | 5-[4-(3-Chloro-phenyl)-2-oxo-1,2-dihydro-indol-(3Z)-ylidenemethyl]-2,4-dimethyl-1H-pyrrole-3-carboxylic acid (2-hydroxy-3-pyrrolidin-1-yl-propyl)-amide |
| 331 | Chiral | 4-(3-Chloro-phenyl)-3-[1-[4-((S)-3-hydroxy-pyrrolidine-1-carbonyl)-3,5-dimethyl-1H-pyrrol-2-yl]-meth-(Z)-ylidene]-1,3-dihydro-indol-2-one |
| 332 | Chiral | 4-(3-Chloro-phenyl)-3-[1-[4-((S)-3-hydroxy-pyrrolidine-1-carbonyl)-3-methyl-1H-pyrrol-2-yl]-meth-(Z)-ylidene]-1,3-dihydro-indol-2-one |
| 333 | Chiral | 4-(3-Chloro-phenyl)-3-[1-[3-((S)-3-hydroxy-pyrrolidine-1-carbonyl)-5-methyl-1H-pyrrol-2-yl]-meth-(Z)-ylidene]-1,3-dihydro-indol-2-one |

TABLE 1-continued

Preferred 4-Aryl Substituted Indolinones

| Example | Structure | Name |
|---|---|---|
| 334 | Chiral | 4-(2-Fluoro-phenyl)-3-[1-[4-((S)-3-hydroxy-pyrrolidine-1-carbonyl)-3-methyl-1H-pyrrol-2-yl]-meth-(Z)-ylidene]-1,3-dihydro-indol-2-one |
| 335 | Chiral | 4-(3-Fluoro-phenyl)-3-[1-[4-((S)-3-hydroxy-pyrrolidine-1-carbonyl)-3,5-dimethyl-1H-pyrrol-2-yl]-meth-(Z)-ylidene]-1,3-dihydro-indol-2-one |
| 336 | Chiral | 4-(3-Fluoro-phenyl)-3-[1-{4-[2-((S)-3-hydroxy-pyrrolidin-1-yl)-2-oxo-ethyl]-3,5-dimethyl-1H-pyrrol-2-yl}-meth-(Z)-ylidene]-1,3-dihydro-indol-2-one |
| 337 | 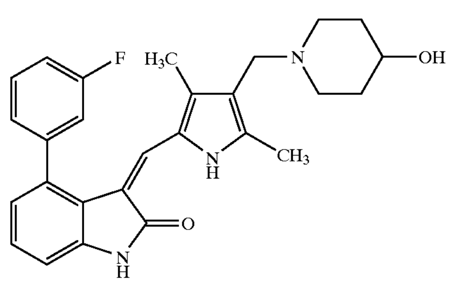 | 4-(3-Fluoro-phenyl)-3-[1-[4-(4-hydroxy-piperidin-1-ylmethyl)-3,5-dimethyl-1H-pyrrol-2-yl]-meth-(Z)-ylidene]-1,3-dihydro-indol-2-one |

TABLE 1-continued

Preferred 4-Aryl Substituted Indolinones

| Example | Structure | Name |
|---|---|---|
| 338 | 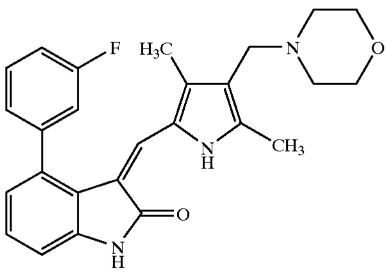 | 3-[1-(3,5-Dimethyl-4-morpholin-4-ylmethyl-1H-pyrrol-2-yl)-meth-(Z)-ylidene]-4-(3-fluoro-phenyl)-1,3-dihydro-indol-2-one |
| 339 | 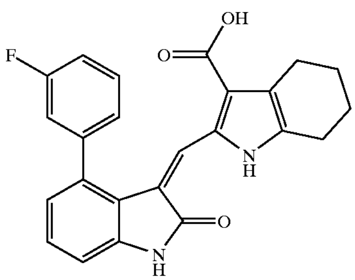 | 2-[4-(3-Fluoro-phenyl)-2-oxo-1,2-dihydro-indol-(3Z)-ylidenemethyl]-4,5,6,7-tetrahydro-1H-indole-3-carboxylic acid |
| 340 | 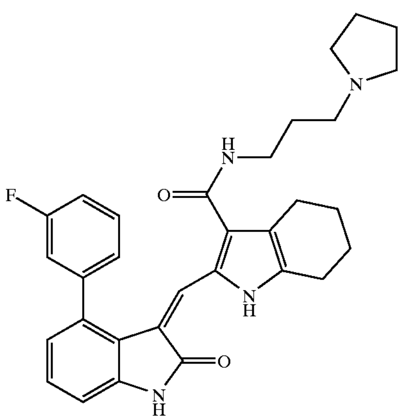 | 2-[4-(3-Fluoro-phenyl)-2-oxo-1,2-dihydro-indol-(3Z)-ylidenemethyl]-4,5,6,7-tetrahydro-1H-indole-3-carboxylic acid (3-pyrrolidin-1-yl-propyl)-amide |
| 341 | Chiral | 4-(3-Fluoro-phenyl)-3-[1-[3-(3-hydroxy-pyrrolidine-1-carbonyl)-4,5,6,7-tetrahydro-1H-indol-2-yl]-meth-(Z)-ylidene]-1,3-dihydro-indol-2-one |

TABLE 1-continued

Preferred 4-Aryl Substituted Indolinones

| Example | Structure | Name |
|---|---|---|
| 342 | 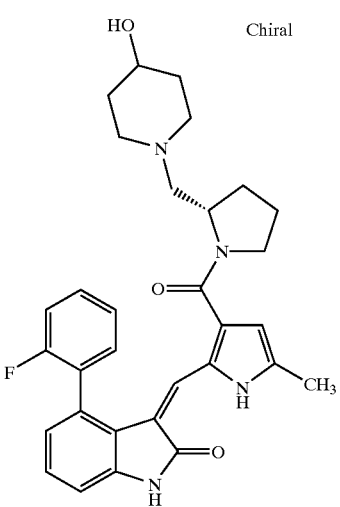 | 4-(2-Fluoro-phenyl)-3-[1-{3-[(S)-2-(4-hydroxy-piperidin-1-ylmethyl)-pyrrolidine-1-carbonyl]-5-methyl-1H-pyrrol-2-yl}-meth-(Z)-ylidene]-1,3-dihydro-indol-2-one |
| 343 | 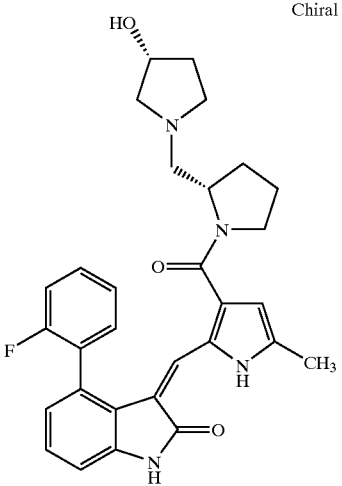 | 4-(2-Fluoro-phenyl)-3-[1-{3-[(S)-2-((R)-3-hydroxy-pyrrolidin-1-ylmethyl)-pyrrolidine-carbonyl]-5-methyl-1H-pyrrol-2-yl}-meth-(Z)-ylidene]-1,3-dihydro-indol-2-one |
| 344 | 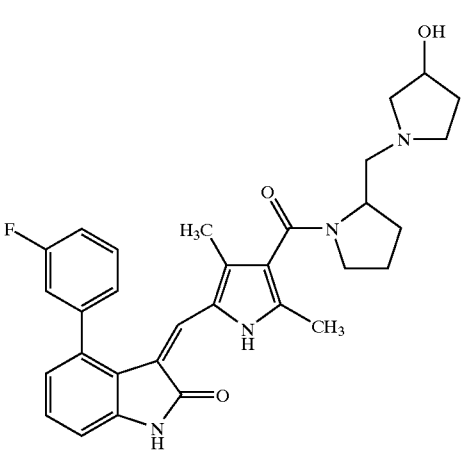 | 4-(3-Fluoro-phenyl)-3-[1-{4-[(S)-2-((R)-3-hydroxy-pyrrolidin-1-ylmethyl)-pyrrolidine-1-carbonyl]-3,5-dimethyl-1H-pyrrol-2-yl}-meth-(Z)-ylidene]-1,3-dihydro-indol-2-one |

TABLE 1-continued

Preferred 4-Aryl Substituted Indolinones

| Example | Structure | Name |
|---|---|---|
| 345 | 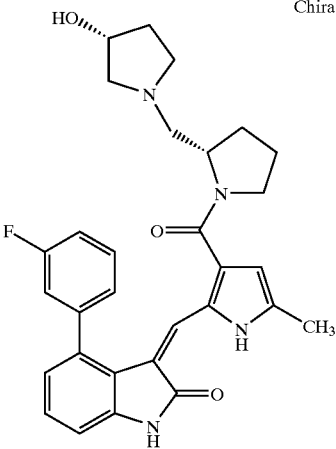 Chiral | 4-(3-Fluoro-phenyl)-3-[1-{3-[(S)-2-((R)-3-hydroxy-pyrrolidin-1-ylmethyl)-pyrrolidine-1-carbonyl]-5-methyl-1H-pyrrol-2-yl}-meth-(Z)-ylidene]-1,3-dihydro-indol-2-one |
| 346 | 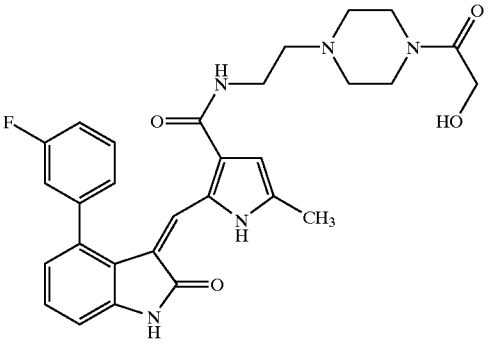 | 2-[4-(3-Fluoro-phenyl)-2-oxo-1,2-dihydro-indol-(3Z)-ylidenemethyl]-5-methyl-1H-pyrrole-3-carboxylic acid {2-[4-(2-hydroxy-acetyl)-piperazin-1-yl]-ethyl}-amide |
| 347 | 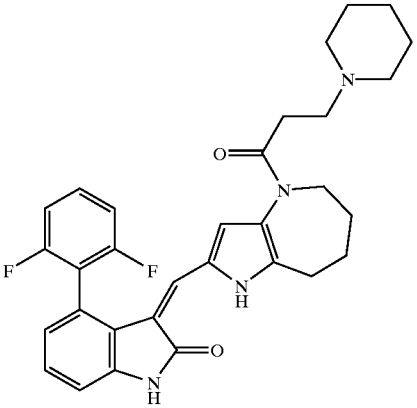 | 4-(2,6-Difluoro-phenyl)-3-[1-[4-(3-piperidin-1-yl-propionyl)-1,4,5,6,7,8-hexahydro-pyrrolo[3,2-b]azepin-2-yl]-meth-(Z)-ylidene]-1,3-dihydro-indol-2-one |

TABLE 1-continued

Preferred 4-Aryl Substituted Indolinones

| Example | Structure | Name |
|---------|-----------|------|
| 348 | 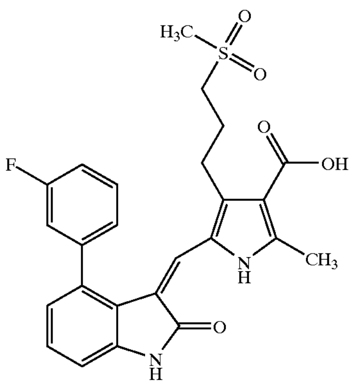 | 5-[4-(3-Fluoro-phenyl)-2-oxo-1,2-dihydro-indol-(3Z)-ylidenemethyl]-4-(3-methanesulfonyl-propyl)-2-methyl-1H-pyrrole-3-carboxylic acid |
| 349 | 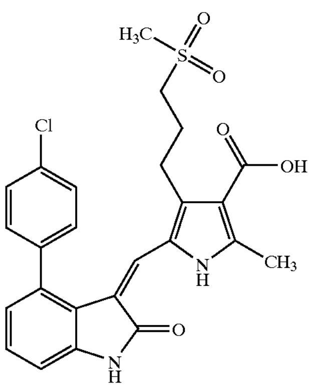 | 5-[4-(4-Chloro-phenyl)-2-oxo-1,2-dihydro-indol-(3Z)-ylidenemethyl]-4-(3-methanesulfonyl-propyl)-2-methyl-1H-pyrrole-3-carboxylic acid |
| 350 | Chiral | 4-(3-Fluoro-phenyl)-3-[1-[4-((R)-3-hydroxy-pyrrolidine-1-carbonyl)-3-(3-methanesulfonyl-propyl)-5-methyl-1H-pyrrol-2-yl]-meth-(Z)-ylidene]-1,3-dihydro-indol-2-one |
| 351 | 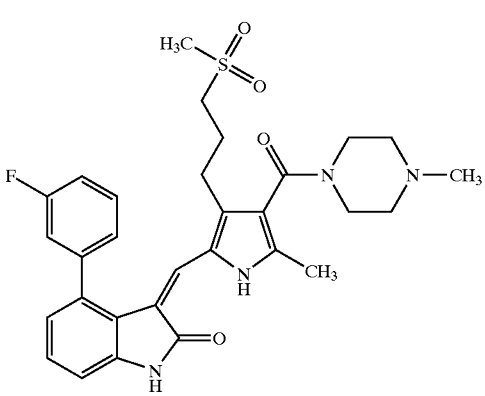 | 4-(3-Fluoro-phenyl)-3-[1-[3-(3-methanesulfonyl-propyl)-5-methyl-4-(4-methyl-piperazine-1-carbonyl)-1H-pyrrol-2-yl]-meth-(Z)-ylidene]-1,3-dihydro-indol-2-one |

TABLE 1-continued

Preferred 4-Aryl Substituted Indolinones

| Example | Structure | Name |
|---|---|---|
| 352 | 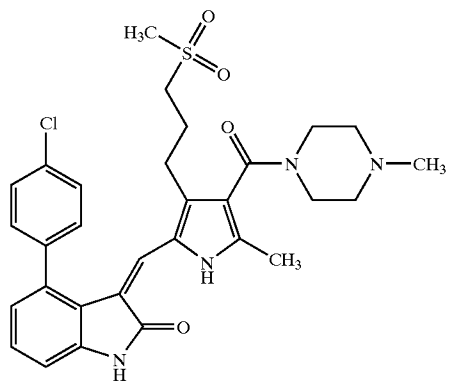 | 4-(4-Chloro-phenyl)-3-[1-[3-(3-methanesulfonyl-propyl)-5-methyl-4-(4-methyl-piperazine-1-carbonyl)-1H-pyrrol-2-yl]-meth-(Z)-ylidene]-1,3-dihydro-indol-2-one |
| 353 | 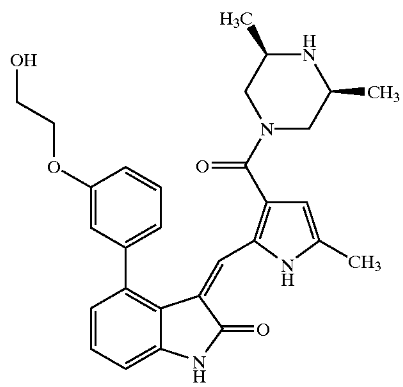 | 3-[1-[3-((3R,5S)-3,5-Dimethyl-piperazine-1-carbonyl)-5-methyl-1H-pyrrol-2-yl]-meth-(Z)-ylidene]-4-[3-(2-hydroxy-ethoxy)-phenyl]-1,3-dihydro-indol-2-one |
| 354 | 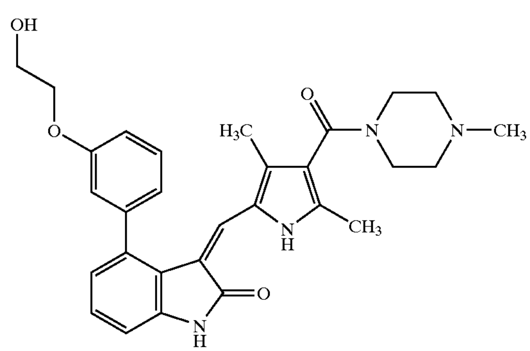 | 3-[1-[3,5-Dimethyl-4-(4-methyl-piperazine-1-carbonyl)-1H-pyrrol-2-yl]-meth-(Z)-ylidene]-4-[3-(2-hydroxy-ethoxy)-phenyl]-1,3-dihydro-indol-2-one |
| 355 | 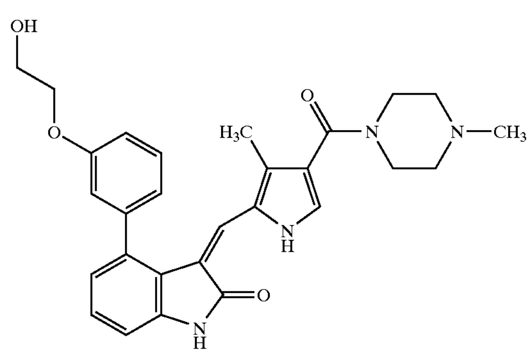 | 4-[3-(2-Hydroxy-ethoxy)-phenyl]-3-[1-[3-methyl-4-(4-methyl-piperazine-1-carbonyl)-1H-pyrrol-2-yl]-meth-(Z)-ylidene]-1,3-dihydro-indol-2-one |

TABLE 1-continued

Preferred 4-Aryl Substituted Indolinones

| Example | Structure | Name |
|---|---|---|
| 356 | 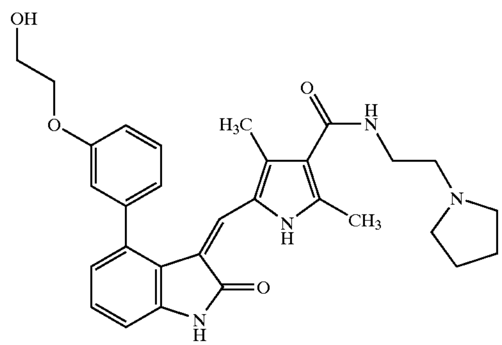 | 5-[4-[3-(2-Hydroxy-ethoxy)-phenyl]-2-oxo-1,2-dihydro-indol-(3Z)-ylidenemethyl]-2,4-dimethyl-1H-pyrrole-3-carboxylic acid (2-pyrrolidin-1-yl-ethyl)-amide |
| 357 | 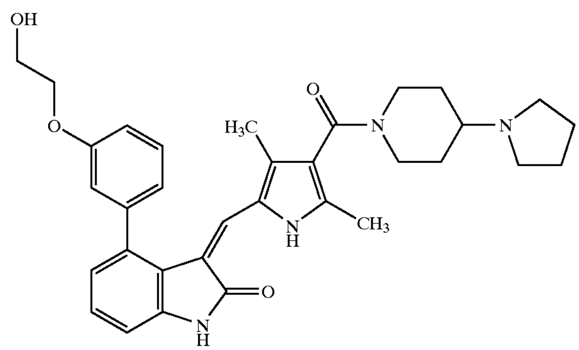 | 3-[1-[3,5-Dimethyl-4-(4-pyrrolidin-1-yl-piperidine-1-carbonyl)-1H-pyrrol-2-yl]-meth-(Z)-ylidene]-4-[3-(2-hydroxy-ethoxy)-phenyl]-1,3-dihydro-indol-2-one |
| 358 | 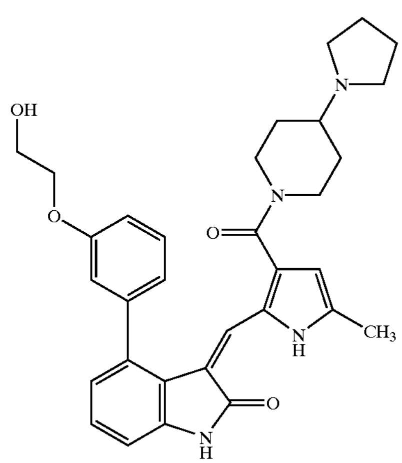 | 4-[3-(2-Hydroxy-ethoxy)-phenyl]-3-[1-[5-methyl-3-(4-pyrrolidin-1-yl-piperidine-1-carbonyl)-1H-pyrrol-2-yl]-meth-(Z)-ylidene]-1,3-dihydro-indol-2-one |
| 359 | Chiral | 4-[3-(2-Hydroxy-ethoxy)-phenyl]-3-[1-[4-((R)-3-hydroxy-pyrrolidine-1-carbonyl)-3,5-dimethyl-1H-pyrrol-2-yl]-meth-(Z)-ylidene]-1,3-dihydro-indol-2-one |

TABLE 1-continued

| Preferred 4-Aryl Substituted Indolinones | | |
|---|---|---|
| Example | Structure | Name |
| 360 | | 5-[4-(4-Chloro-phenyl)-2-oxo-1,2-dihydro-indol-(3Z)-ylidenemethyl]-2,4-dimethyl-1H-pyrrole-3-carboxylic acid |
| 361 | | 2-[4-(4-Chloro-phenyl)-2-oxo-1,2-dihydro-indol-(3Z)-ylidenemethyl]-5-methyl-1H-pyrrole-3-carboxylic acid |
| 362 | | 3-[1-[3,5-Dimethyl-4-(4-morpholin-4-yl-piperidine-1-carbonyl)-1H-pyrrol-2-yl]-meth-(Z)-ylidene]-4-(3-fluoro-phenyl)-1,3-dihydro-indol-2-one |
| 363 | | 4-(3,4-Dimethoxy-phenyl)-3-[1-[3-methyl-4-(4-methyl-piperazine-1-carbonyl)-1H-pyrrol-2-yl]-meth-(Z)-ylidene]-1,3-dihydro-indol-2-one |

TABLE 1-continued

Preferred 4-Aryl Substituted Indolinones

| Example | Structure | Name |
|---|---|---|
| 364 | 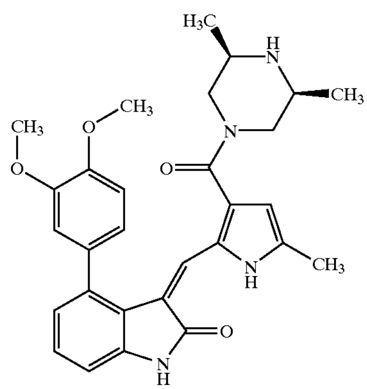 | 4-(3,4-Dimethoxy-phenyl)-3-[1-[3-((3R,5S)-3,5-dimethyl-piperazine-1-carbonyl)-5-methyl-1H-pyrrol-2-yl]-meth-(Z)-ylidene]-1,3-dihydro-indol-2-one |
| 365 | 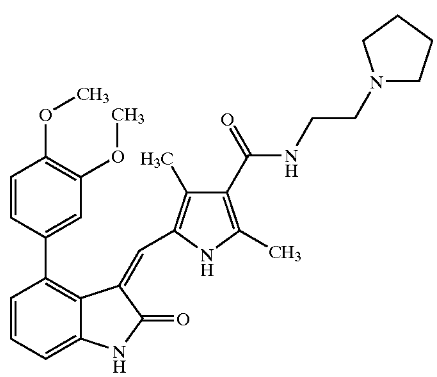 | 5-[4-(3,4-Dimethoxy-phenyl)-2-oxo-1,2-dihydro-indol-(3Z)-ylidenemethyl]-2,4-dimethyl-1H-pyrrole-3-carboxylic acid (2-pyrrolidin-1-yl-ethyl)-amide |
| 366 | 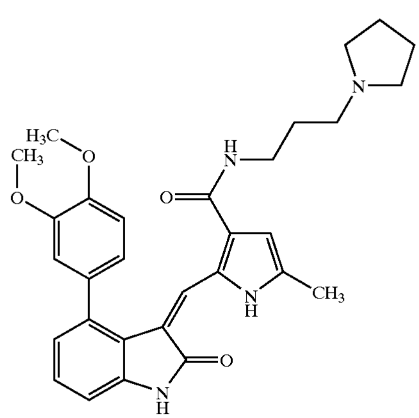 | 2-[4-(3,4-Dimethoxy-phenyl)-2-oxo-1,2-dihydro-indol-(3Z)-ylidenemethyl]-5-methyl-1H-pyrrole-3-carboxylic acid (3-pyrrolidin-1-yl-propyl)-amide |

TABLE 1-continued

Preferred 4-Aryl Substituted Indolinones

| Example | Structure | Name |
|---|---|---|
| 367 | 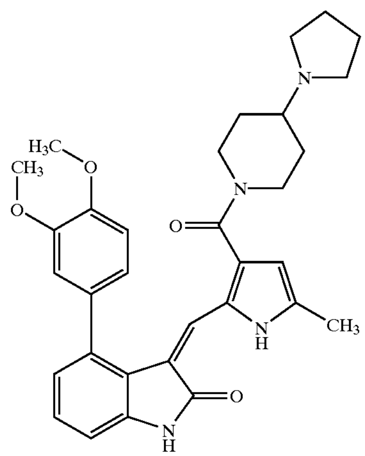 | 4-(3,4-Dimethoxy-phenyl)-3-[1-[5-methyl-3-(4-pyrrolidin-1-yl-piperidine-1-carbonyl)-1H-pyrrol-2-yl]-meth-(Z)-ylidene]-1,3-dihydro-indol-2-one |
| 368 | Chiral | 4-(3,4-Dimethoxy-phenyl)-3-[1-[4-((R)-3-hydroxy-pyrrolidine-1-carbonyl)-3,5-dimethyl-1H-pyrrol-2-yl]-meth-(Z)-ylidene]-1,3-dihydro-indol-2-one |
| 369 | 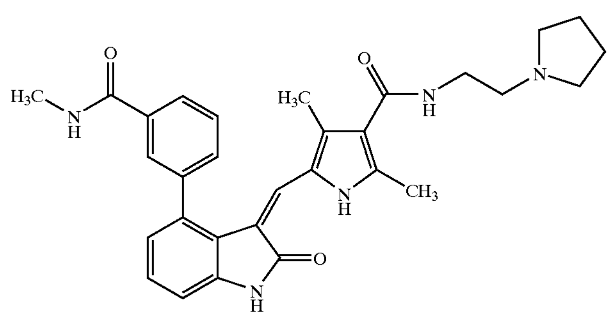 | 2,4-Dimethyl-5-[4-(3-methylcarbamoyl-phenyl)-2-oxo-1,2-dihydro-indol-(3Z)-ylidenemethyl]-1H-pyrrole-3-carboxylic acid (2-pyrrolidin-1-yl-ethyl)-amide |
| 370 | 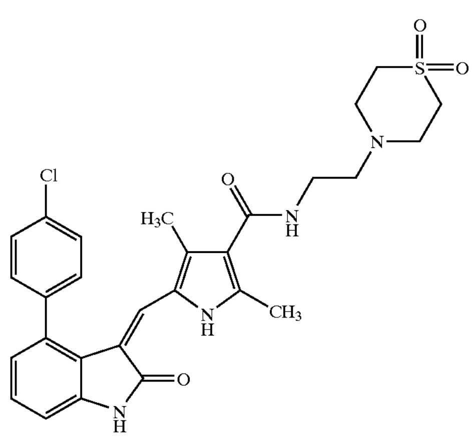 | 5-[4-(4-Chloro-phenyl)-2-oxo-1,2-dihydro-indol-(3Z)-ylidenemethyl]-2,4-dimethyl-1H-pyrrole-3-carboxylic acid [2-(1,1-dioxo-1□-thiomorpholin-4-yl)-ethyl]-amide |

TABLE 1-continued

Preferred 4-Aryl Substituted Indolinones

| Example | Structure | Name |
|---|---|---|
| 371 | 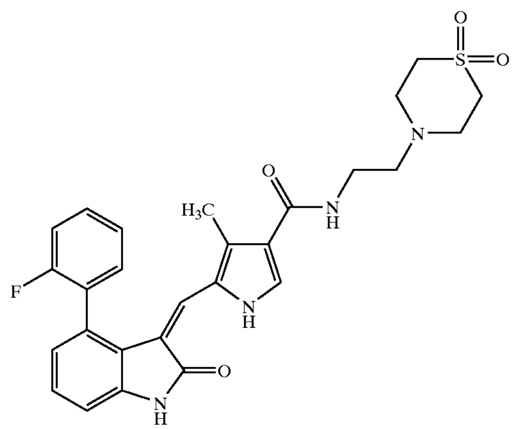 | 5-[4-(2-Fluoro-phenyl)-2-oxo-1,2-dihydro-indol-(3Z)-ylidenemethyl]-4-methyl-1H-pyrrole-3-carboxylic acid [2-(1,1-dioxo-1□-thiomorpholin-4-yl)-ethyl]-amide |
| 372 | 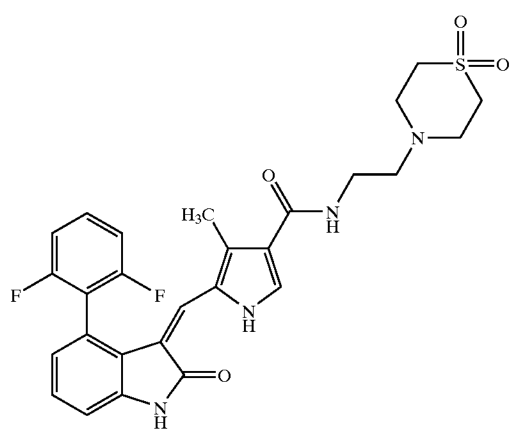 | 5-[4-(2,6-Difluoro-phenyl)-2-oxo-1,2-dihydro-indol-(3Z)-ylidenemethyl]-4-methyl-1H-pyrrole-3-carboxylic acid [2-(1,1-dioxo-1□-thiomorpholin-4-yl)-ethyl]-amide |
| 373 | 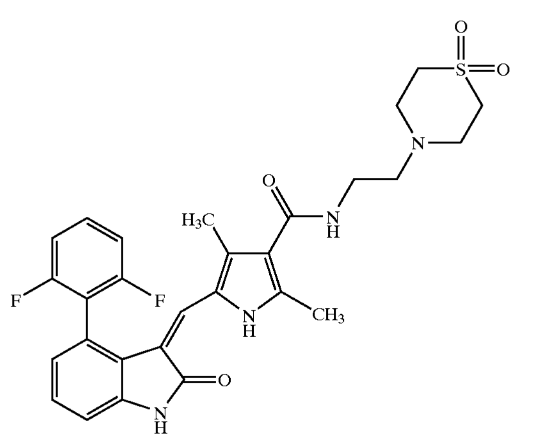 | 5-[4-(2,6-Difluoro-phenyl)-2-oxo-1,2-dihydro-indol-(3Z)-ylidenemethyl]-2,4-dimethyl-1H-pyrrole-3-carboxylic acid [2-(1,1-dioxo-1□-thiomorpholin-4-yl)-ethyl]-amide |

TABLE 1-continued

Preferred 4-Aryl Substituted Indolinones

| Example | Structure | Name |
|---|---|---|
| 374 | 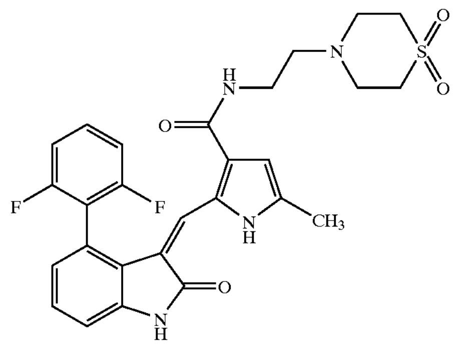 | 2-[4-(2,6-Difluoro-phenyl)-2-oxo-1,2-dihydro-indol-(3Z)-ylidenemethyl]-5-methyl-1H-pyrrole-3-carboxylic acid [2-(1,1-dioxo-1□-thiomorpholin-4-yl)-ethyl]-amide |
| 375 | 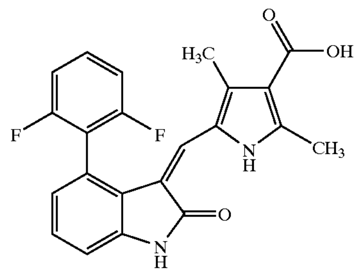 | 5-[4-(2,6-Difluoro-phenyl)-2-oxo-1,2-dihydro-indol-(3Z)-ylidenemethyl]-2,4-dimethyl-1H-pyrrole-3-carboxylic acid |
| 376 | 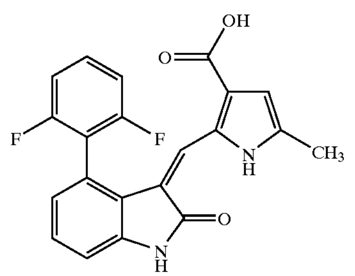 | 2-[4-(2,6-Difluoro-phenyl)-2-oxo-1,2-dihydro-indol-(3Z)-ylidenemethyl]-5-methyl-1H-pyrrole-3-carboxylic acid |
| 377 | 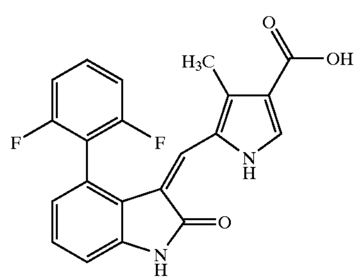 | 5-[4-(2,6-Difluoro-phenyl)-2-oxo-1,2-dihydro-indol-(3Z)-ylidenemethyl]-4-methyl-1H-pyrrole-3-carboxylic acid |
| 378 | 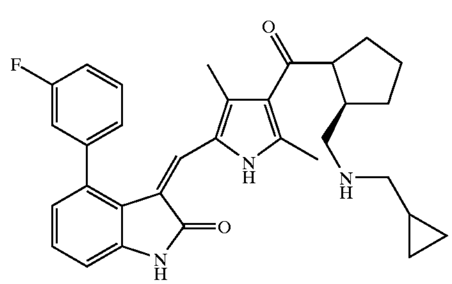 | 3-[1-(4-{(S)-2-[(Cyclopropylmethyl-amino)-methyl]-pyrrolidine-1-carbonyl}-3,5-dimethyl-1H-pyrrol-2-yl)-meth-(Z)-ylidene]-4-(3-fluoro-phenyl)-1,3-dihydro-indol-2-one |

TABLE 1-continued

Preferred 4-Aryl Substituted Indolinones

| Example | Structure | | Name |
|---|---|---|---|
| 379 | 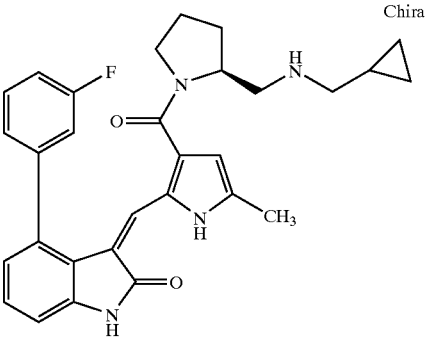 | Chiral | 3-[1-(3-{(S)-2-[(Cyclopropylmethyl-amino)-methyl]-pyrrolidine-1-carbonyl}-5-methyl-1H-pyrrol-2-yl)-meth-(Z)-ylidene]-4-(3-fluoro-phenyl)-1,3-dihydro-indol-2-one |
| 380 | 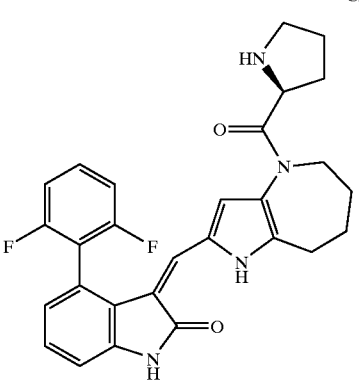 | Chiral | 4-(2,6-Difluoro-phenyl)-3-[1-[4-((S)-pyrrolidine-2-carbonyl)-1,4,5,6,7,8-hexahydro-pyrrolo[3,2-b]azepin-2-yl]-meth-(Z)-ylidene]-1,3-dihydro-indol-2-one |
| 381 | 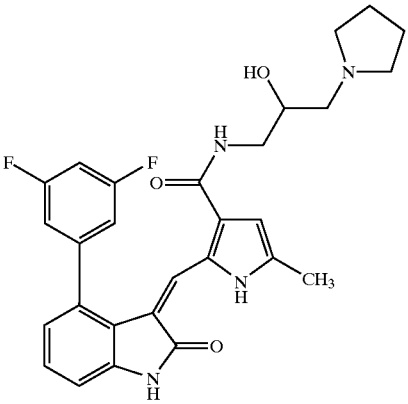 | | 2-[4-(3,5-Difluoro-phenyl)-2-oxo-1,2-dihydro-indol-(3Z)-ylidenemethyl]-5-methyl-1H-pyrrole-3-carboxylic acid (2-hydroxy-3-pyrrolidin-1-yl-propyl)-amide |

TABLE 1-continued

Preferred 4-Aryl Substituted Indolinones

| Example | Structure | Name |
|---|---|---|
| 382 | 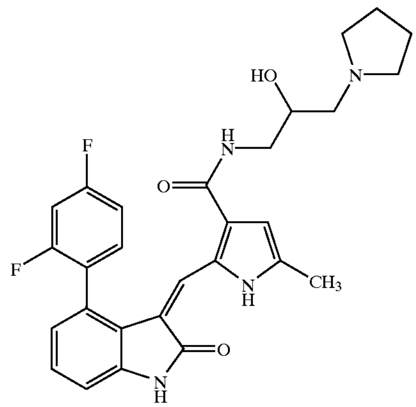 | 2-[4-(2,4-Difluoro-phenyl)-2-oxo-1,2-dihydro-indol-(3Z)-ylidenemethyl]-5-methyl-1H-pyrrole-3-carboxylic acid (2-hydroxy-3-pyrrolidin-1-yl-propyl)-amide |
| 383 | 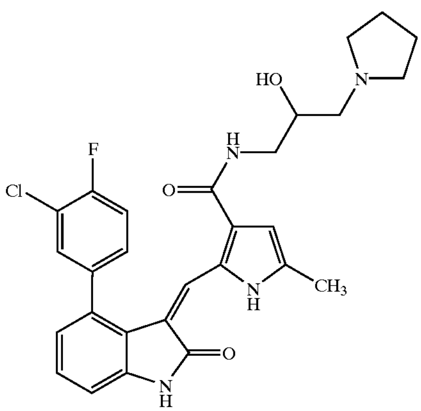 | 2-[4-(3-Chloro-4-fluoro-phenyl)-2-oxo-1,2-dihydro-indol-(3Z)-ylidenemethyl]-5-methyl-1H-pyrrole-3-carboxylic acid (2-hydroxy-3-pyrrolidin-1-yl-propyl)-amide |
| 384 | 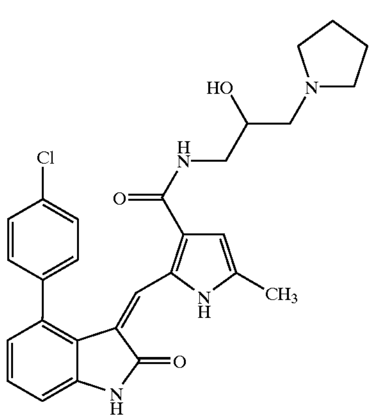 | 2-[4-(4-Chloro-phenyl)-2-oxo-1,2-dihydro-indol-(3Z)-ylidenemethyl]-5-methyl-1H-pyrrole-3-carboxylic acid (2-hydroxy-3-pyrrolidin-1-yl-propyl)-amide |

TABLE 1-continued

Preferred 4-Aryl Substituted Indolinones

| Example | Structure | Name |
|---------|-----------|------|
| 385 | 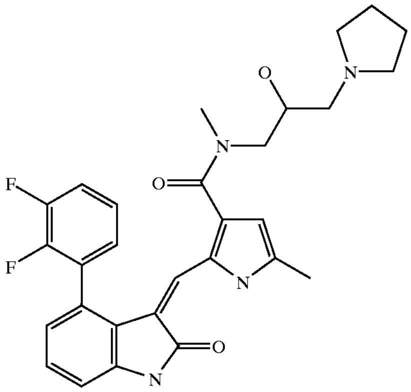 | 2-[4-(2,3-Difluoro-phenyl)-2-oxo-1,2-dihydro-indol-(3Z)-ylidenemethyl]-5-methyl-1H-pyrrole-3-carboxylic acid (2-hydroxy-3-pyrrolidin-1-yl-propyl)-methyl-amide |
| 386 | Chiral | 4-(3-Fluoro-phenyl)-3-[1-[4-((R)-3-hydroxy-pyrrolidin-1-ylmethyl)-3,5-dimethyl-1H-pyrrol-2-yl]-meth-(Z)-ylidene]-1,3-dihydro-indol-2-one |
| 387 | 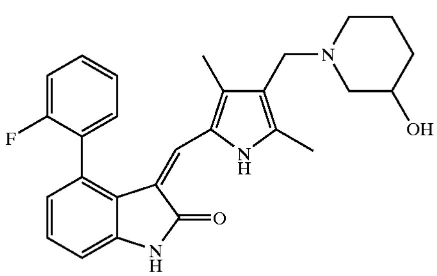 | 4-(2-Fluoro-phenyl)-3-[1-[4-(3-hydroxy-piperidin-1-ylmethyl)-3,5-dimethyl-1H-pyrrol-2-yl]-meth-(Z)-ylidene]-1,3-dihydro-indol-2-one |
| 388 | 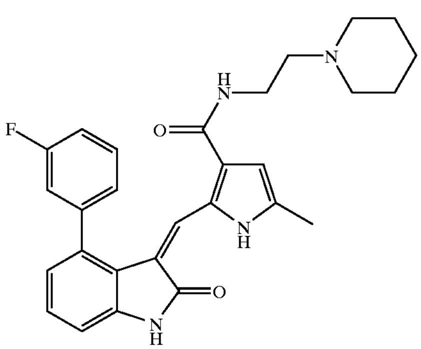 | 2-[4-(3-Fluoro-phenyl)-2-oxo-1,2-dihydro-indol-(3Z)-ylidenemethyl]-5-methyl-1H-pyrrole-3-carboxylic acid (2-piperidin-1-yl-ethyl)-amide |

TABLE 1-continued

Preferred 4-Aryl Substituted Indolinones

| Example | Structure | Name |
|---|---|---|
| 389 | 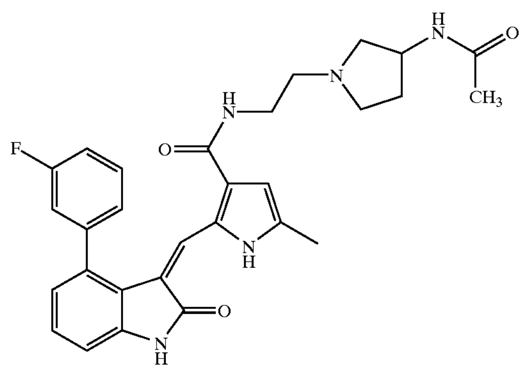 | 2-[4-(3-Fluoro-phenyl)-2-oxo-1,2-dihydro-indol-(3Z)-ylidenemethyl]-5-methyl-1H-pyrrole-3-carboxylic acid [2-(3-acetylamino-pyrrolidin-1-yl)-ethyl]-amide |
| 390 | 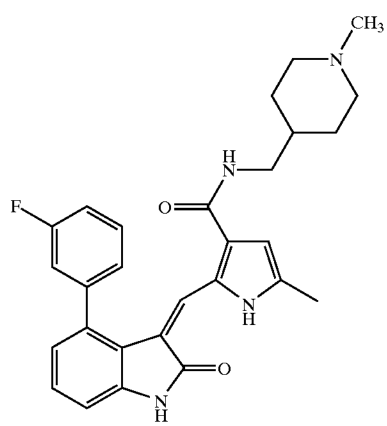 | 2-[4-(3-Fluoro-phenyl)-2-oxo-1,2-dihydro-indol-(3Z)-ylidenemethyl]-5-methyl-1H-pyrrole-3-carboxylic acid (1-methyl-piperidin-4-ylmethyl)-amide |
| 391 | 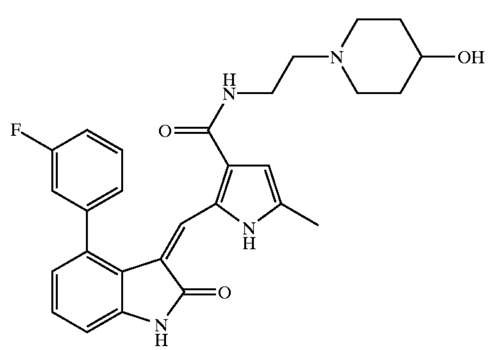 | 2-[4-(3-Fluoro-phenyl)-2-oxo-1,2-dihydro-indol-(3Z)-ylidenemethyl]-5-methyl-1H-pyrrole-3-carboxylic acid [2-(4-hydroxy-piperidin-1-yl)-ethyl]-amide |

TABLE 1-continued

Preferred 4-Aryl Substituted Indolinones

| Example | Structure | Name |
|---|---|---|
| 392 | 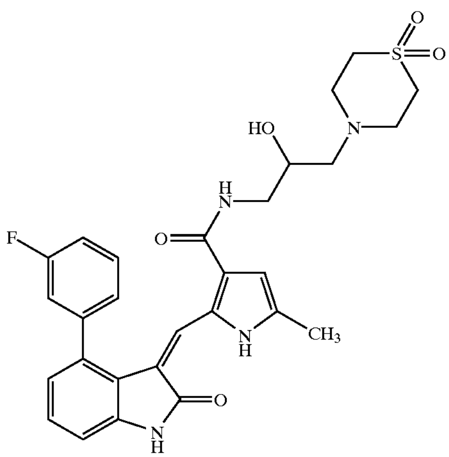 | 2-[4-(3-Fluoro-phenyl)-2-oxo-1,2-dihydro-indol-(3Z)-ylidenemethyl]-5-methyl-1H-pyrrole-3-carboxylic acid [3-(1,1-dioxo-1□-thiomorpholin-4-yl)-2-hydroxy-propyl]-amide |
| 393 | 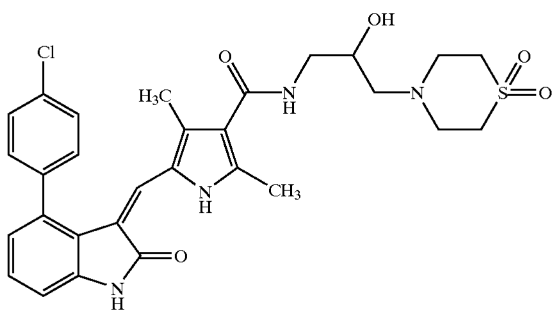 | 5-[4-(4-Chloro-phenyl)-2-oxo-1,2-dihydro-indol-(3Z)-ylidenemethyl]-2,4-dimethyl-1H-pyrrole-3-carboxylic acid [3-(1,1-dioxo-1□-thiomorpholin-4-yl)-2-hydroxy-propyl]-amide |
| 394 | 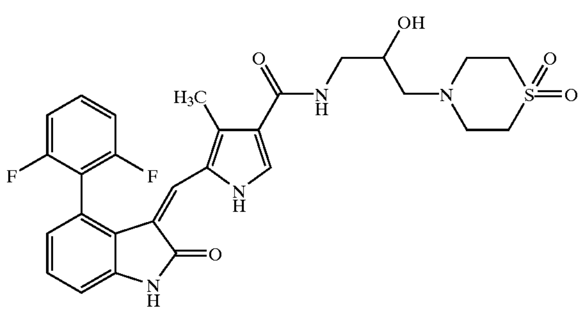 | 5-[4-(2,6-Difluoro-phenyl)-2-oxo-1,2-dihydro-indol-(3Z)-ylidenemethyl]-4-methyl-1H-pyrrole-3-carboxylic acid [3-(1,1-dioxo-1□-thiomorpholin-4-yl)-2-hydroxy-propyl]-amide |
| 395 | 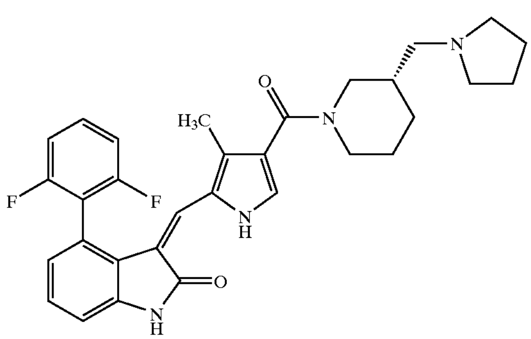 | 4-(2,6-Difluoro-phenyl)-3-[1-[3-methyl-4-((S)-3-pyrrolidin-1-ylmethyl-piperidine-1-carbonyl)-1H-pyrrol-2-yl]-meth-(Z)-ylidene]-1,3-dihydro-indol-2-one |

TABLE 1-continued

Preferred 4-Aryl Substituted Indolinones

| Example | Structure | Name |
|---|---|---|
| 396 | 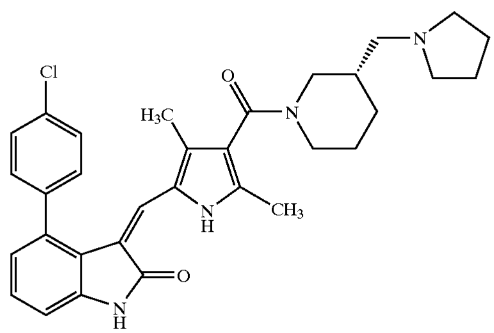 | 4-(4-Chloro-phenyl)-3-[1-[3,5-dimethyl-4-((S)-3-pyrrolidin-1-ylmethyl-piperidine-1-carbonyl)-1H-pyrrol-2-yl]-meth-(Z)-ylidene]-1,3-dihydro-indol-2-one |
| 397 | 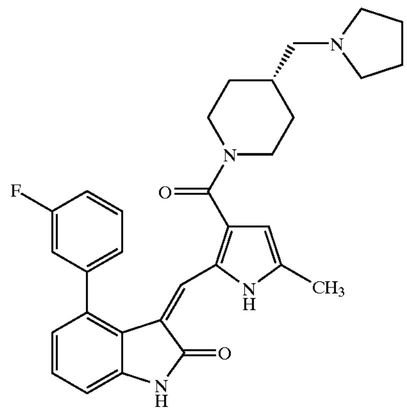 | 4-(3-Fluoro-phenyl)-3-[1-[5-methyl-3-(4-pyrrolidin-1-ylmethyl-piperidine-1-carbonyl)-1H-pyrrol-2-yl]-meth-(Z)-ylidene]-1,3-dihydro-indol-2-one |
| 398 | 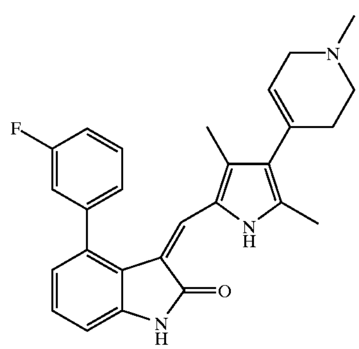 | 3-[1-[3,5-Dimethyl-4-(1-methyl-1,2,3,6-tetrahydro-pyridin-4-yl)-1H-pyrrol-2-yl]-meth-(Z)-ylidene]-4-(3-fluoro-phenyl)-1,3-dihydro-indol-2-one |
| 399 | 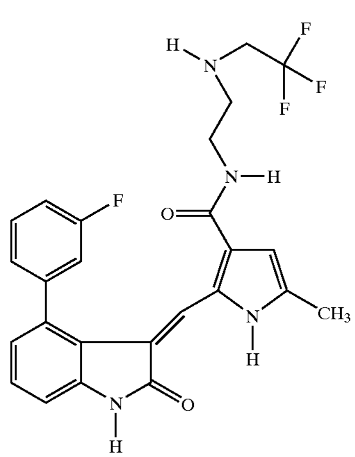 | 2-[4-(3-Fluoro-phenyl)-2-oxo-1,2-dihydro-indol-(3Z)-ylidenemethyl]-5-methyl-1H-pyrrole-3-carboxylic acid [2-(2,2,2-trifluoro-ethylamino)-ethyl]-amide |

TABLE 1-continued

Preferred 4-Aryl Substituted Indolinones

| Example | Structure | Name |
|---|---|---|
| 400 | 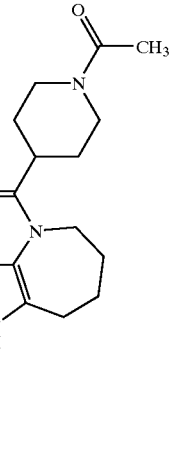 | 3-[1-[4-(1-Acetyl-piperidine-4-carbonyl)-1,4,5,6,7,8-hexahydro-pyrrolo[3,2-b]azepin-2-yl]-meth-(Z)-ylidene]-4-(3-fluoro-phenyl)-1,3-dihydro-indol-2-one |
| 401 | 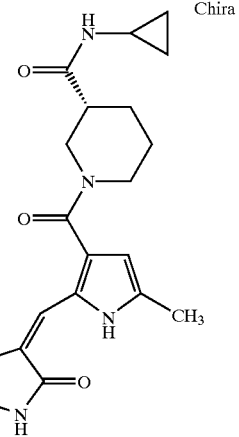 Chiral | (R)-1-{2-[4-(3-Fluoro-phenyl)-2-oxo-1,2-dihydro-indol-(3Z)-ylidenemethyl]-5-methyl-1H-pyrrole-3-carbonyl}-piperidine-3-carboxylic acid cyclopropylamide |
| 402 | 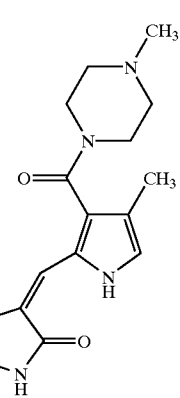 | 4-(3-Fluoro-phenyl)-3-[1-[4-methyl-3-(4-methyl-piperazine-1-carbonyl)-1H-pyrrol-2-yl]-meth-(Z)-ylidene]-1,3-dihydro-indol-2-one |

TABLE 1-continued

Preferred 4-Aryl Substituted Indolinones

| Example | Structure | Name |
|---|---|---|
| 403 | 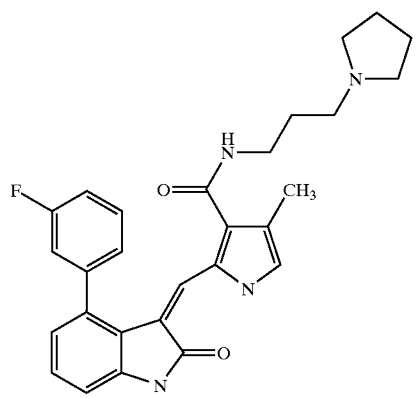 | 2-[4-(3-Fluoro-phenyl)-2-oxo-1,2-dihydro-indol-(3Z)-ylidenemethyl]-4-methyl-1H-pyrrole-3-carboxylic acid (3-pyrrolidin-1-yl-propyl)-amide |
| 404 | 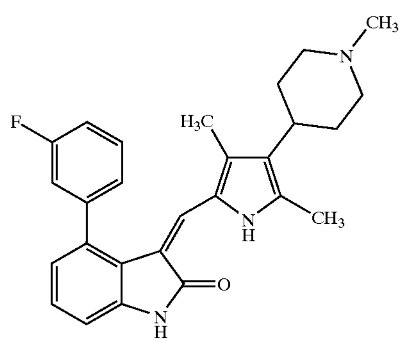 | 3-[1-[3,5-Dimethyl-4-(1-methyl-piperidin-4-yl)-1H-pyrrol-2-yl]-meth-(Z)-ylidene]-4-(3-fluoro-phenyl)-1,3-dihydro-indol-2-one |
| 405 | 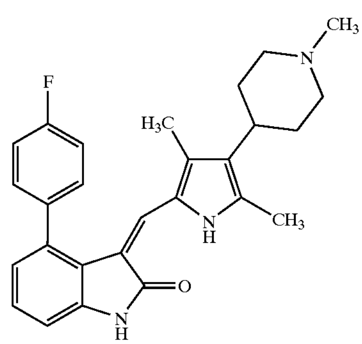 | 3-[1-[3,5-Dimethyl-4-(1-methyl-piperidin-4-yl)-1H-pyrrol-2-yl]-meth-(Z)-ylidene]-4-(4-fluoro-phenyl)-1,3-dihydro-indol-2-one |
| 406 | 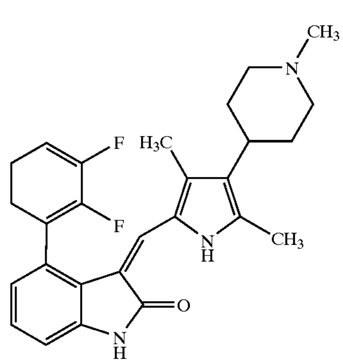 | 4-(2,3-Difluoro-phenyl)-3-[1-[3,5-dimethyl-4-(1-methyl-piperidin-4-yl)-1H-pyrrol-2-yl]-meth-(Z)-ylidene]-1,3-dihydro-indol-2-one |

TABLE 1-continued

Preferred 4-Aryl Substituted Indolinones

| Example | Structure | Name |
|---------|-----------|------|
| 407 | 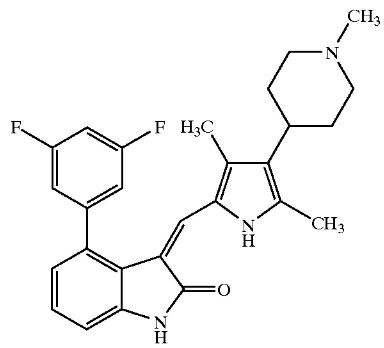 | 4-(3,5-Difluoro-phenyl)-3-[1-[3,5-dimethyl-4-(1-methyl-piperidin-4-yl)-1H-pyrrol-2-yl]-meth-(Z)-ylidene]-1,3-dihydro-indol-2-one |
| 408 | 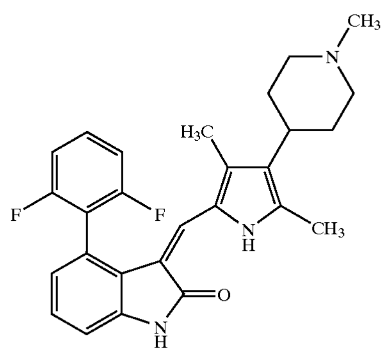 | 4-(2,6-Difluoro-phenyl)-3-[1-[3,5-dimethyl-4-(1-methyl-piperidin-4-yl)-1H-pyrrol-2-yl]-meth-(Z)-ylidene]-1,3-dihydro-indol-2-one |
| 409 | 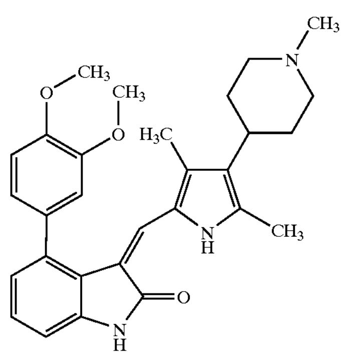 | 4-(3,4-Dimethoxy-phenyl)-3-[1-[3,5-dimethyl-4-(1-methyl-piperidin-4-yl)-1H-pyrrol-2-yl]-meth-(Z)-ylidene]-1,3-dihydro-indol-2-one |
| 410 | 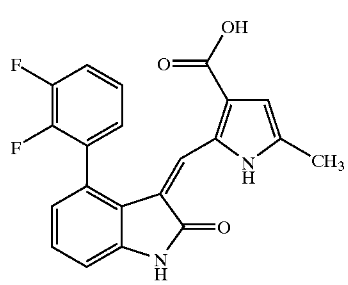 | 2-[4-(2,3-Difluoro-phenyl)-2-oxo-1,2-dihydro-indol-(3Z)-ylidenemethyl]-5-methyl-1H-pyrrole-3-carboxylic acid |

TABLE 1-continued

Preferred 4-Aryl Substituted Indolinones

| Example | Structure | Name |
|---------|-----------|------|
| 411 | 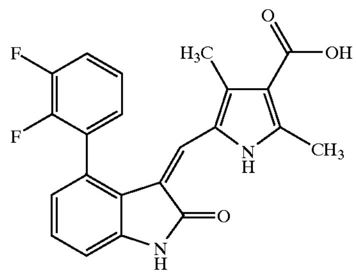 | 5-[4-(2,3-Difluoro-phenyl)-2-oxo-1,2-dihydro-indol-(3Z)-ylidenemethyl]-2,4-dimethyl-1H-pyrrole-3-carboxylic acid |
| 412 | 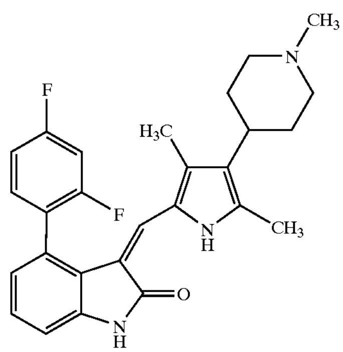 | 4-(2,4-Difluoro-phenyl)-3-[1-[3,5-dimethyl-4-(1-methyl-piperidin-4-yl)-1H-pyrrol-2-yl]-meth-(Z)-ylidene]-1,3-dihydro-indol-2-one |
| 413 | 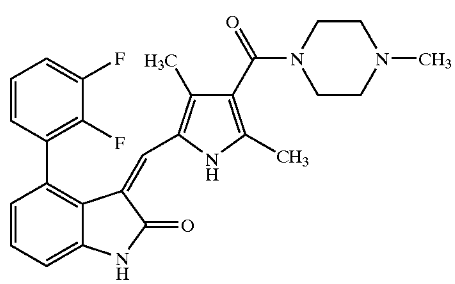 | 4-(2,3-Difluoro-phenyl)-3-[1-[3,5-dimethyl-4-(4-methyl-piperazine-1-carbonyl)-1H-pyrrol-2-yl]-meth-(Z)-ylidene]-1,3-dihydro-indol-2-one |
| 414 | 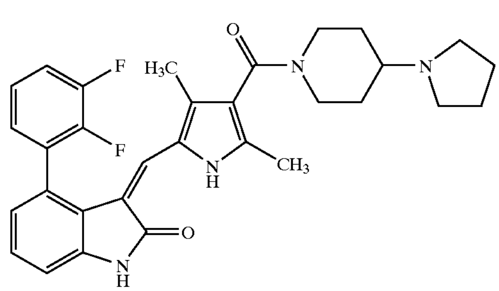 | 4-(2,3-Difluoro-phenyl)-3-[1-[3,5-dimethyl-4-(4-pyrrolidin-1-yl-piperidine-1-carbonyl)-1H-pyrrol-2-yl]-meth-(Z)-ylidene]-1,3-dihydro-indol-2-one |

TABLE 1-continued

Preferred 4-Aryl Substituted Indolinones

| Example | Structure | Name |
|---|---|---|
| 415 | 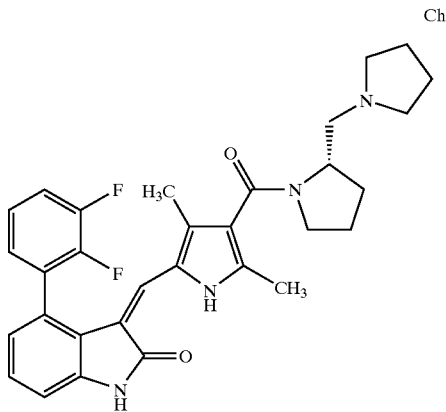 Chiral | 4-(2,3-Difluoro-phenyl)-3-[1-[3,5-dimethyl-4-((S)-2-pyrrolidin-1-ylmethyl-pyrrolidine-1-carbonyl)-1H-pyrrol-2-yl]-meth-(Z)-ylidene]-1,3-dihydro-indol-2-one |
| 416 | 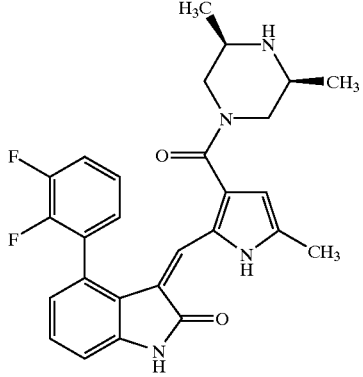 | 4-(2,3-Difluoro-phenyl)-3-[1-[3-((3R,5S)-3,5-dimethyl-piperazine-1-carbonyl)-5-methyl-1H-pyrrol-2-yl]-meth-(Z)-ylidene]-1,3-dihydro-indol-2-one |
| 417 | 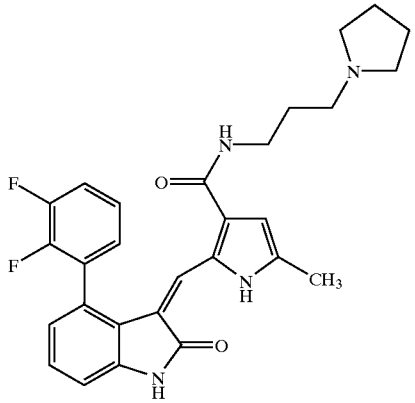 | 2-[4-(2,3-Difluoro-phenyl)-2-oxo-1,2-dihydro-indol-(3Z)-ylidenemethyl]-5-methyl-1H-pyrrole-3-carboxylic acid (3-pyrrolidin-1-yl-propyl)-amide |

TABLE 1-continued

Preferred 4-Aryl Substituted Indolinones

| Example | Structure | Name |
|---|---|---|
| 418 | 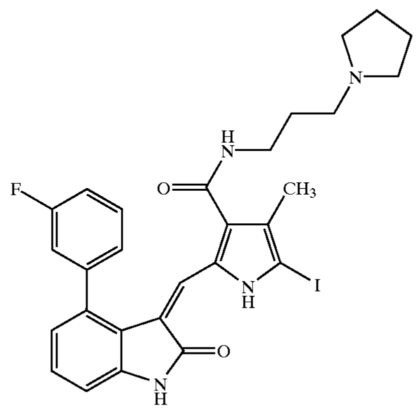 | 2-[4-(3-Fluoro-phenyl)-2-oxo-1,2-dihydro-indol-(3Z)-ylidenemethyl]-5-iodo-4-methyl-1H-pyrrole-3-carboxylic acid (3-pyrrolidin-1-yl-propyl)-amide |
| 419 | 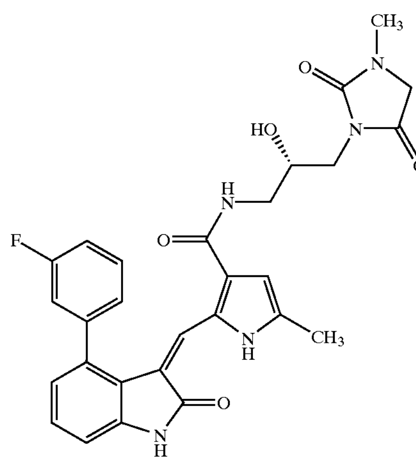 | 2-[4-(3-Fluoro-phenyl)-2-oxo-1,2-dihydro-indol-(3Z)-ylidenemethyl]-5-methyl-1H-pyrrole-3-carboxylic acid [(S)-2-hydroxy-3-(3-methyl-2,5-dioxo-imidazolin-1-yl)-propyl]-amide |
| 420 | 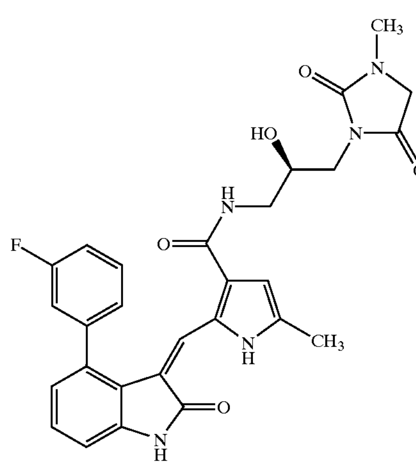 | 2-[4-(3-Fluoro-phenyl)-2-oxo-1,2-dihydro-indol-(3Z)-ylidenemethyl]-5-methyl-1H-pyrrole-3-carboxylic acid [(R)-2-hydroxy-3-(3-methyl-2,5-dioxo-imidazolin-1-yl)-propyl]-amide |

TABLE 1-continued

Preferred 4-Aryl Substituted Indolinones

| Example | Structure | Name |
|---------|-----------|------|
| 421 | 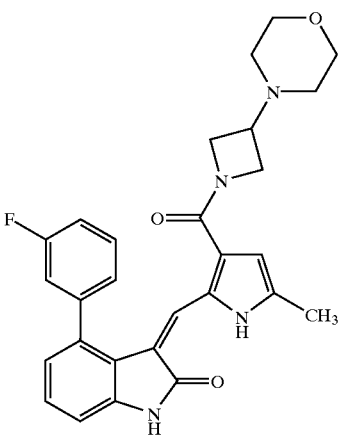 | 4-(3-Fluoro-phenyl)-3-[1-[5-methyl-3-(3-morpholin-4-yl-azetidine-1-carbonyl)-1H-pyrrol-2-yl]-meth-(Z)-ylidene]-1,3-dihydro-indol-2-one |
| 422 | 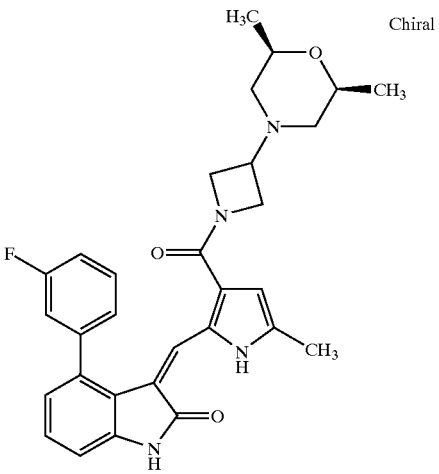 | 3-[1-{3-[3-((2R,6S)-2,6-Dimethyl-morpholin-4-yl)-azetidine-1-carbonyl]-5-methyl-1H-pyrrol-2-yl}-meth-(Z)-ylidene]-4-(3-fluoro-phenyl)-1,3-dihydro-indol-2-one |
| 423 | 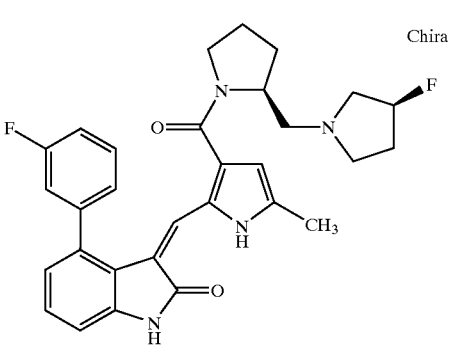 | 4-(3-Fluoro-phenyl)-3-[1-{3-[(S)-2-((S)-3-fluoro-pyrrolidin-1-ylmethyl)-pyrrolidine-1-carbonyl]-5-methyl-1H-pyrrol-2-yl}-meth-(Z)-ylidene]-1,3-dihydro-indol-2-one |

TABLE 1-continued

Preferred 4-Aryl Substituted Indolinones

| Example | Structure | Name |
|---|---|---|
| 424 | 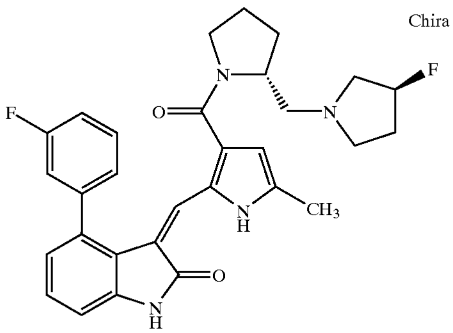 | 4-(3-Fluoro-phenyl)-3-[1-{3-[(R)-2-((S)-3-fluoro-pyrrolidin-1-ylmethyl)-pyrrolidine-1-carbonyl]-5-methyl-1H-pyrrol-2-yl}-meth-(Z)-ylidene]-1,3-dihydro-indol-2-one |
| 425 | 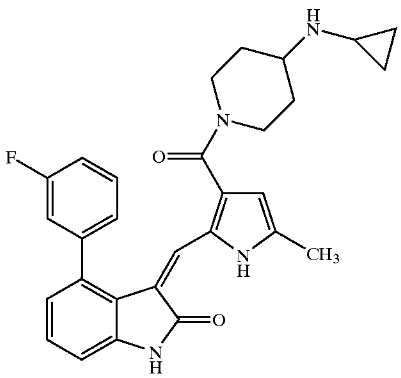 | 3-[1-[3-(4-Cyclopropylamino-piperidine-1-carbonyl)-5-methyl-1H-pyrrol-2-yl]-meth-(Z)-ylidene]-4-(3-fluoro-phenyl)-1,3-dihydro-indol-2-one |
| 426 | 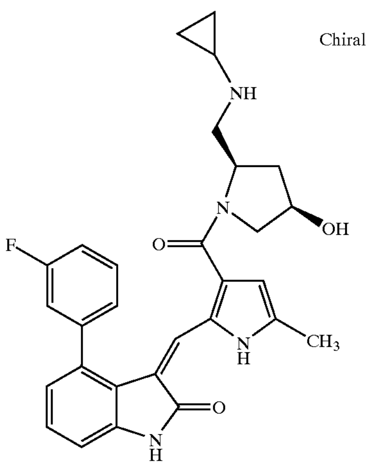 | 3-[1-[3-((2R,4R)-2-Cyclopropylaminomethyl-4-hydroxy-pyrrolidine-1-carbonyl)-5-methyl-1H-pyrrol-2-yl]-meth-(Z)-ylidene]-4-(3-fluoro-phenyl)-1,3-dihydro-indol-2-one |
| 427 | 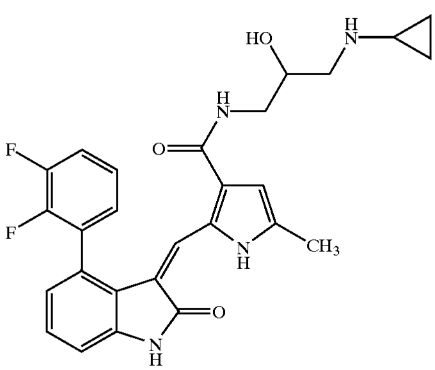 | 2-[4-(2,3-Difluoro-phenyl)-2-oxo-1,2-dihydro-indol-(3Z)-ylidenemethyl]-5-methyl-1H-pyrrole-3-carboxylic acid (3-cyclopropylamino-2-hydroxy-propyl)-amide |

TABLE 1-continued

Preferred 4-Aryl Substituted Indolinones

| Example | Structure | Name |
|---|---|---|
| 428 | 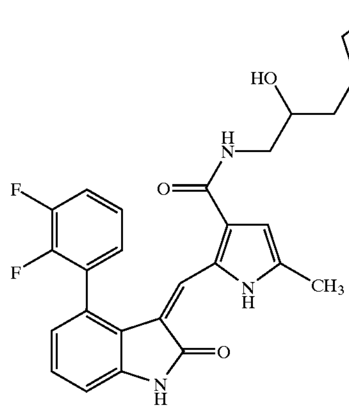 | 2-[4-(2,3-Difluoro-phenyl)-2-oxo-1,2-dihydro-indol-(3Z)-ylidenemethyl]-5-methyl-1H-pyrrole-3-carboxylic acid (2-hydroxy-3-pyrrolidin-1-yl-propyl)-amide |
| 429 | Chira | 4-(2,3-Difluoro-phenyl)-3-[1-{3-[(S)-2-((R)-3-hydroxy-pyrrolidin-1-ylmethyl)-pyrrolidine-1-carbonyl]-5-methyl-1H-pyrrol-2-yl}-meth-(Z)-ylidene]-1,3-dihydro-indol-2-one |
| 430 | Chira | 4-(2,3-Difluoro-phenyl)-3-[1-{3-[(S)-2-((S)-3-fluoro-pyrrolidin-1-ylmethyl)-pyrrolidine-1-carbonyl]-5-methyl-1H-pyrrol-2-yl}-meth-(Z)-ylidene]-1,3-dihydro-indol-2-one |

TABLE 1-continued

Preferred 4-Aryl Substituted Indolinones

| Example | Structure | Name |
|---|---|---|
| 431 | 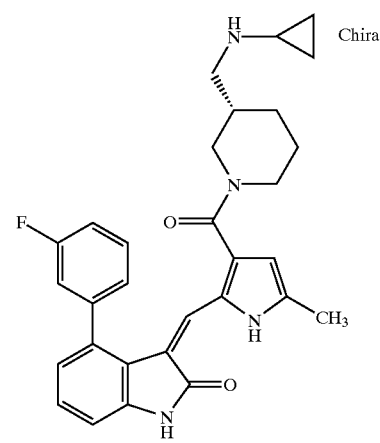 | 3-[1-[3-((S)-3-Cyclopropylaminomethyl-piperidine-1-carbonyl)-5-methyl-1H-pyrrol-2-yl]-meth-(Z)-ylidene]-4-(3-fluoro-phenyl)-1,3-dihydro-indol-2-one |
| 432 | 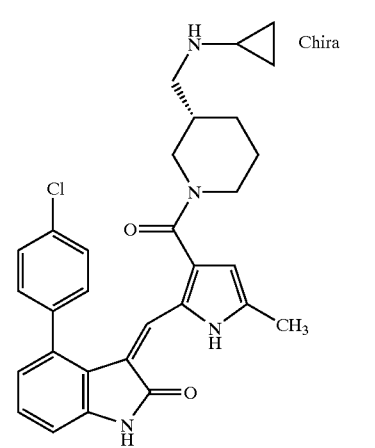 | 4-(4-Chloro-phenyl)-3-[1-[3-((S)-3-cyclopropylaminomethyl-piperidine-1-carbonyl)-5-methyl-1H-pyrrol-2-yl]-meth-(Z)-ylidene]-1,3-dihydro-indol-2-one |
| 433 | 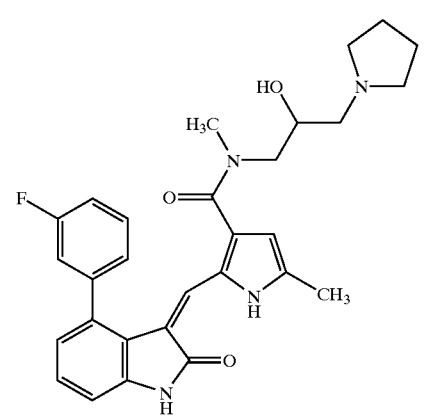 | 2-[4-(3-Fluoro-phenyl)-2-oxo-1,2-dihydro-indol-(3Z)-ylidenemethyl]-5-methyl-1H-pyrrole-3-carboxylic acid (2-hydroxy-3-pyrrolidin-1-yl-propyl)-methyl-amide |

TABLE 1-continued

Preferred 4-Aryl Substituted Indolinones

| Example | Structure | Name |
| --- | --- | --- |
| 434 | 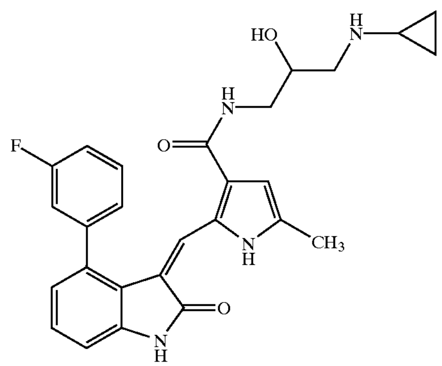 | 2-[4-(3-Fluoro-phenyl)-2-oxo-1,2-dihydro-indol-(3Z)-ylidenemethyl]-5-methyl-1H-pyrrole-3-carboxylic acid (3-cyclopropylamino-2-hydroxy-propyl)-amide |
| 435 | 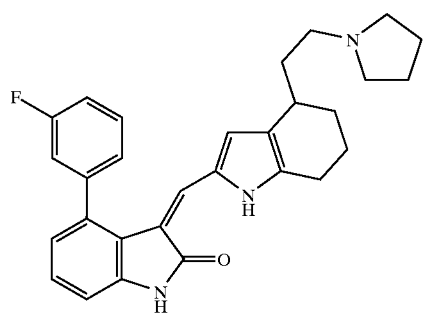 | 4-(3-Fluoro-phenyl)-3-[1-[4-(2-pyrrolidin-1-yl-ethyl)-4,5,6,7-tetrahydro-1H-indol-2-yl]-meth-(Z)-ylidene]-1,3-dihydro-indol-2-one |

In a second aspect, this inventions is directed to a pharmaceutical composition comprising one or more compounds of formula (I) or a pharmaceutically acceptable salt thereof and a pharmaceutically acceptable excipient.

Biochemistry

Another aspect of this invention relates to a method for the modulation of the catalytic activity of a PK by contacting a PK with a compound of this invention or a physiologically acceptable salt thereof.

A further aspect of this invention is that the modulation of the catalytic activity of PKs using a compound of this invention may be carried out in vitro or in vivo.

A still further aspect of this invention is that the protein kinase whose catalytic activity is being modulated by a compound of this invention is selected from the group consisting of receptor protein tyrosine kinases, cellular tyrosine kinases and serine-threonine kinases.

It is an aspect of this invention that the receptor tyrosine protein kinase whose catalytic activity is modulated by a compound of this invention is selected from the group consisting of EGF, HER2, HER3, HER4, IR, IGF-1R, IRR, PDGFRα, PDGFRβ, CSFIR, C-Kit, C-fms, Flk-1R, Flk4, KDR/Flk-1, Flt-1, FGFR-1R, FGFR-2R, FGFR-3R, FGFR-4R, MET, DDR-1 and DDR-2.

In addition, it is an aspect of this invention that the cellular tyrosine kinase whose catalytic activity is modulated by a compound of this invention is selected from the group consisting of Src, Frk, Btk, Csk, Abl, ZAP70, Fes/Fps, Fak, Jak, Ack, Yes, Lyn, Lck, Blk, Hck, Fgr and Yrk.

Another aspect of this invention is that the serine-threonine protein kinase whose catalytic activity is modulated by a compound of this invention is selected from the group consisting of CDK2, Raf, NEK and BUB1.

Another aspect of this inventions relates to a method for treating or preventing a protein kinase related disorder in an organism comprising administering a therapeutically effective amount of a compound or a salt thereof Formula I to an organism.

It is an aspect of this invention that the above-referenced protein kinase related disorder is selected from the group consisting of a receptor protein tyrosine kinase related disorder, a cellular tyrosine kinase disorder and a serine-threonine kinase related disorder.

In yet another aspect of this invention, the above referenced protein kinase related disorder is selected from the group consisting of a Met related disorder, a PDGFR related disorder, an IGFR related disorder and a flk related disorder.

The above referenced protein kinase related disorders include by way of example and not limitation, cancers such as lung cancer, NSCLC (non small cell ling cancer), bone cancer, pancreatic cancer, skin cancer, cancer of the head and neck, cutaneous or intraocular melanoma, uterine cancer, ovarian cancer, rectal cancer, cancer of the anal region, stomach cancer, colon cancer, breast cancer, gynecologic tumors (e.g., uterine sarcomas, carcinoma of the fallopian tubes, carcinoma of the endometrium, carcinoma of the cervix, carcinoma of the vagina or carcinoma of the vulva), Hodgkin's Disease, cancer of the esophagus, cancer of the small intestine, cancer of the endocrine system (e.g., cancer of the thyroid, parathyroid or adrenal glands), sarcomas of soft tissues, cancer of the urethra, cancer of the penis, prostate cancer, chronic or acute leukemia, solid tumors of childhood, lynphocytic lymphomas, cancer of the bladder, cancer of the kidney or uerter (e.g., renal cell carcinoma, carcinoma of the renal pelvis), pediatric malignancy, neoplasms of the central nervous system (e.g., primary CNS lymphoma, spinal axis tumors, brain stem glima or pituitary adenomas), Barrett's esophagus (pre-malignant syndrome), neoplastic cutaneous disease, psoriasis, mycoses fungoides and benign prostatic hypertrophy, diabetes related diseases such as diabetic retinopathy, retinal ischemia and retinal neovascularization, hepatic cirrhosis, cardiovascular disease such as atherosclerosis, immunological disease such as autoimmune disease and renal disease. Preferably, the disease is cancer such as acute myeloid leukemia and colorectal cancer.

The above referenced protein kinase related disorder also includes disorders selected from the group consisting of diabetes, a hyper-proliferation disorder, hyperproliferative disorders of the kidney, von Hippel-Lindau disease, restenosis, fibrosis, psoriasis, osteoarthritis, rheumatoid arthritis, an inflammatory disorder and angiogenesis in yet another aspect of this invention.

Additional disorders which may be treated or prevented using the compounds of this invention are immunological disorders such as autoimmune diseases (e.g., AIDS, lupus, etc.) and cardiovascular disorders such as atherosclerosis.

It is an aspect of this invention that the protein kinase related disorder being treated or prevented by administration of a compound of this invention is a CDK2 related disorder.

The organism in which the protein kinase related disorder is being treated or prevented is a human being in yet another aspect of this invention.

It is as aspect of this invention that a chemical compound that modulates the catalytic activity of a protein kinase may be identified by contacting cells expressing said protein kinase with a compound or a salt thereof of Formula I and then monitoring said cells for an effect.

The above-referenced effect is selected from a change or an absence of change in a cell phenotype, a change or absence of change in the catalytic activity of said protein kinase or a change or absence of change in the interaction of said protein kinase with a natural binding partner in a final aspect of this invention.

It is also an aspect of this invention that a compound described herein, or its salt, might be combined with other chemotherapeutic agents for the treatment of the diseases and disorders discussed above. For instance, a compound or salt of this invention might be combined with alkylating agents such as fluorouracil (5-FU) alone or in further combination with leukovorin; or other alkylating agents such as, without limitation, other pyrimidine analogs such as UFT, capecitabine, gemcitabine and cytarabine, the alkyl sulfonates, e.g., busulfan (used in the treatment of chronic granulocytic leukemia), improsulfan and piposulfan; aziridines, e.g., benzodepa, carboquone, meturedepa and uredepa; ethyleneimines and methylmelamines, e.g., altretamine, triethylenemelamine, triethylenephosphoramide, triethylenethiophosphoramide and trimethylolmelamine; and the nitrogen mustards, e.g., chlorambucil (used in the treatment of chronic lymphocytic leukemia, primary macroglobulinemia and non-Hodgkin's lymphoma), cyclophosphamide (used in the treatment of Hodgkin's disease, multiple myeloma, neuroblastoma, breast cancer, ovarian cancer, lung cancer, Wilm's tumor and rhabdomyosarcoma), estramustine, ifosfamide, novembrichin, prednimustine and uracil mustard (used in the treatment of primary thrombocytosis, non-Hodgkin's lymphoma, Hodgkin's disease and ovarian cancer); and triazines, e.g., dacarbazine (used in the treatment of soft tissue sarcoma).

Likewise a compound or salt of this invention might be expected to have a beneficial effect in combination with other antimetabolite chemotherapeutic agents such as, without limitation, folic acid analogs, e.g. methotrexate (used in the treatment of acute lymphocytic leukemia, choriocarcinoma, mycosis fungiodes breast cancer, head and neck cancer and osteogenic sarcoma) and pteropterin; and the purine analogs such as mercaptopurine and thioguanine which find use in the treatment of acute granulocytic, acute lymphocytic and chronic granulocytic leukemias.

A compound or salt of this invention might also be expected to prove efficacious in combination with natural product based chemotherapeutic agents such as, without limitation, the vinca alkaloids, e.g., vinblastin (used in the treatment of breast and testicular cancer), vincristine and vindesine; the epipodophylotoxins, e.g., etoposide and teniposide, both of which are useful in the treatment of testicular cancer and Kaposi's sarcoma; the antibiotic chemotherapeutic agents, e.g., daunorubicin, doxorubicin, epirubicin, mitomycin (used to treat stomach, cervix, colon, breast, bladder and pancreatic cancer), dactinomycin, temozolomide, plicamycin, bleomycin (used in the treatment of skin, esophagus and genitourinary tract cancer); and the enzymatic chemotherapeutic agents such as L-asparaginase.

In addition to the above, a compound or salt of this invention might be expected to have a beneficial effect used in combination with the platinum coordination complexes (cisplatin, etc.); substituted ureas such as hydroxyurea; methylhydrazine derivatives, e.g., procarbazine; adrenocortical suppressants, e.g., mitotane, aminoglutethimide; and hormone and hormone antagonists such as the adrenocorticosteriods (e.g., prednisone), progestins (e.g., hydroxyprogesterone caproate); estrogens (e.g., diethylstilbesterol); antiestrogens such as tamoxifen; androgens, e.g., testosterone propionate; and aromatase inhibitors (such as anastrozole.

Finally, the combination of a compound of this invention might be expected to be particularly effective in combination with mitoxantrone or paclitaxel for the treatment of solid tumor cancers or leukemias such as, without limitation, acute myelogenous (non-lymphocytic) leukemia.

The above method can be carried out in combination with a chemotherapeutic agent selected from the group consisting of mitotic inhibitors, alkylating agetns, antimetabolites, cell cycle inhibitors, enzymes, topoisomerase inhibitors, biological response modifiers, anti-hormones, antiangiogenic agents such as MMP-2, MMP-9 and COX-2 inhibitors, and anti-androgens.

Examples of useful COX-II inhibitors include Vioxx™, CELEBREX™ (alecoxib), valdecoxib, paracoxib, rofecoxib, and Cox 189. Examples of useful matrix metalloproteinase inhibitors are described in WO 96/33172 (published Oct. 24, 1996), WO 96/27583 (published Mar. 7, 1996), European Patent Application No. 97304971.1 (filed Jul. 8, 1997), European Patent Application No. 99308617.2 (filed Oct. 29, 1999), WO 98/07697 (published Feb. 26, 1998), WO 98/03516 (published Jan. 29, 1998), WO 98/34918 (published Aug. 13, 1998), WO 98/34915 (published Aug. 13, 1998), WO 98/33768 (published Aug. 6, 1998), WO 98/30566 (published Jul. 16, 1998), European Patent Publication 606,046 (published Jul. 13, 1994), European Patent Publication 931,788 (published Jul. 28, 1999), WO 90/05719 (published May 31, 1990), WO 99/52910

(published Oct. 21, 1999), WO 99/52889 (published Oct. 21, 1999), WO 99/29667 (published Jun. 17, 1999), PCT International Application No. PCT/IB98/01113 (filed Jul. 21, 1998), European Patent Application No. 99302232.1 (filed Mar. 25, 1999), Great Britain patent application number 9912961.1 (filed Jun. 3, 1999), U.S. Provisional Application No. 60/148,464 (filed Aug. 12, 1999), U.S. Pat. No. 5,863,949 (issued Jan. 26, 1999), U.S. Pat. No. 5,861,510 (issued Jan. 19, 1999), and European Patent Publication 780,386 (published Jun. 25, 1997), all of which are incorporated herein in their entireties by reference. Preferred MMP-2 and MMP-9 inhibitors are those that have little or no activity inhibiting MMP-1. More preferred, are those that selectively inhibit MMP-2 and/or MMP-9 relative to the other matrix-metalloproteinases (i.e. MMP-1, MMP-3, MMP-4, MMP-5, MMP-6, MMP-7, MMP-8, MMP-10, MMP-11, MMP-12, and MMP-13).

Some specific examples of MMP inhibitors useful in the present invention are AG-3340, RO 32-3555, RS 13-0830, and the compounds recited in the following list:

3-[[4-(4-fluoro-phenoxy)-benzenesulfonyl]-(1-hydroxycarbamoyl-cyclopentyl)-amino]-propionic acid; 3-exo-3-[4-(4-fluoro-phenoxy)-benzenesulfonylamino]-8-oxa-bicyclo[3.2.1]octane-3-carboxylic acid hydroxyamide; (2R,3R) 1-[4-(2-chloro-4-fluoro-benzyloxy)-benzenesulfonyl]-3-hydroxy-3-methyl-piperidine-2-carboxylic acid hydroxyamide; 4-[4-(4-fluoro-phenoxy)-benzenesulfonylamino]-tetrahydro-pyran-4-carboxylic acid hydroxyamide; 3-[[4-(4-fluoro-phenoxy)-benzenesulfonyl]-(1-hydroxycarbamoyl-cyclobutyl)-amino]-propionic acid; 4-[4-(4-chloro-phenoxy)-benzenesulfonylamino]-tetrahydro-pyran-4-carboxylic acid hydroxyamide; (R) 3-[4-(4-chloro-phenoxy)-benzenesulfonylamino]-tetrahydro-pyran-3-carboxylic acid hydroxyamide; (2R,3R) 1-[4-(4-fluoro-2-methyl-benzyloxy)-benzenesulfonyl]-3-hydroxy-3-methyl-piperidine-2-carboxylic acid hydroxyamide; 3-[[(4-(4-fluoro-phenoxy)-benzenesulfonyl]-(1-hydroxycarbamoyl-1-methyl-ethyl)-amino]-propionic acid; 3-[[4-(4-fluoro-phenoxy)-benzenesulfonyl]-(4-hydroxycarbamoyl-tetrahydro-pyran-4-yl)-amino]-propionic acid; 3-exo-3-[4-(4-chloro-phenoxy)-benzenesulfonylamino]-8-oxa-bicyclo[3.2.1]octane-3-carboxylic acid hydroxyamide; 3-endo-3-[4-(4-fluoro-phenoxy)-benzenesulfonylamino]-8-oxa-bicyclo[3.2.1]octane-3-carboxylic acid hydroxyamide; and (R) 3-[4-(4-fluoro-phenoxy)-benzenesulfonylamino]-tetrahydro-furan-3-carboxylic acid hydroxyamide; and pharmaceutically acceptable salts and solvates of said compounds.

Other anti-angiogenesis agents, including other COX-II inhibitors and other MMP inhibitors, can also be used in the present invention.

A compound of Formula (I) can also be used with signal transduction inhibitors, such as agents that can inhibit EGFR (epidermal growth factor receptor) responses, such as EGFR antibodies, EGF antibodies, and molecules that are EGFR inhibitors; VEGF (vascular endothelial growth factor) inhibitors; and erbB2 receptor inhibitors, such as organic molecules or antibodies that bind to the erbB2 receptor, for example, HERCEPTIN.™. (Genentech, Inc. of South San Francisco, Calif., USA). EGFR inhibitors are described in, for example in WO 95/19970 (published Jul. 27, 1995), WO 98/14451 (published Apr. 9, 1998), WO 98/02434 (published Jan. 22, 1998), and U.S. Pat. No. 5,747,498 (issued May 5, 1998), and such substances can be used in the present invention as described herein.

EGFR-inhibiting agents include, but are not limited to, the monoclonal antibodies C225 and anti-EGFR 22Mab (ImClone Systems Incorporated of New York, N.Y., USA), the compounds ZD-1839 (AstraZeneca), BIBX-1382 (Boehringer Ingelheim), MDX-447 (Medarex Inc. of Annandale, N.J., USA), and OLX-103 (Merck & Co. of Whitehouse Station, N.J., USA), VRCTC-310 (Ventech Research) and EGF fusion toxin (Seragen Inc. of Hopkinton, Mass.).

These and other EGFR-inhibiting agents can be used in the present invention.

VEGF inhibitors, for example SU-5416, SU 11248, SU-6668 (Sugen Inc. of South San Francisco, Calif., USA), can also be combined with a compound of Formula (I). VEGF inhibitors are described in, for example in WO 99/24440 (published May 20, 1999), PCT International Application PCT/IB99/00797 (filed May 3, 1999), in WO 95/21613 (published Aug. 17, 1995), WO 99/61422 (published Dec. 2, 1999), U.S. Pat. No. 5,834,504 (issued Nov. 10, 1998), WO 01/60814, WO 98/50356 (published Nov. 12, 1998), U.S. Pat. No. 5,883,113 (issued Mar. 16, 1999), U.S. Pat. No. 5,886,020 (issued Mar. 23, 1999), U.S. Pat. No. 5,792,783 (issued Aug. 11, 1998), WO 99/10349 (published Mar. 4, 1999), WO 97/32856 (published Sep. 12, 1997), WO 97/22596 (published Jun. 26, 1997), WO 98/54093 (published Dec. 3, 1998), WO 98/02438 (published Jan. 22, 1998), WO 99/16755 (published Apr. 8, 1999), and WO 98/02437 (published Jan. 22, 1998), all of which are incorporated herein in their entireties by reference. Other examples of some specific VEGF inhibitors useful in the present invention are IM862 (Cytran Inc. of Kirkland, Wash., USA); anti-VEGF monoclonal antibody of Genentech, Inc. of South San Francisco, Calif.; and angiozyme, a synthetic ribozyme from Ribozyme (Boulder, Colo.) and Chiron (Emeryville, Calif.). These and other VEGF inhibitors can be used in the present invention as described herein.

ErbB2 receptor inhibitors, such as GW-282974 (Glaxo Wellcome plc), and the monoclonal antibodies AR-209 (Aronex Pharmaceuticals Inc. of The Woodlands, Tex., USA) and 2B-1 (Chiron), can furthermore be combined with a compound of Formula (I) for example those indicated in WO 98/02434 (published Jan. 22, 1998), WO 99/35146 (published Jul. 15, 1999), WO 99/35132 (published Jul. 15, 1999), WO 98/02437 (published Jan. 22, 1998), WO 97/13760 (published Apr. 17, 1997), WO 95/19970 (published Jul. 27, 1995), U.S. Pat. No. 5,587,458 (issued Dec. 24, 1996), and U.S. Pat. No. 5,877,305 (issued Mar. 2, 1999), which are all hereby incorporated herein in their entireties by reference. ErbB2 receptor inhibitors useful in the present invention are also described in U.S. Provisional Application No. 60/117,341, filed Jan. 27, 1999, and in U.S. Provisional Application No. 60/117,346, filed Jan. 27, 1999, both of which are incorporated in their entireties herein by reference. The erbB2 receptor inhibitor compounds and substance described in the aforementioned PCT applications, U.S. patents, and U.S. provisional applications, as well as other compounds and substances that inhibit the erbB2 receptor, can be used with a compound of Formula (I), in accordance with the present invention.

A compound of Formula (I) can also be used with other agents useful in treating cancer, including, but not limited to, agents capable of enhancing antitumor immune responses, such as CTLA4 (cytotoxic lymphocite antigen 4) antibodies, and other agents capable of blocking CTLA4; and anti-proliferative agents such as other farnesyl protein transferase inhibitors, for example the farnesyl protein transferase inhibitors described in the references cited in the "Background" section, of U.S. Pat. No. 6,258,824 B1. Specific CTLA4 antibodies that can be used in the present invention include those described in U.S. Provisional Application 60/113,647 (filed Dec. 23, 1998) which is incorporated by reference in its entirety, however other CTLA4 antibodies can be used in the present invention.

The above method can be also be carried out in combination with radiation therapy, wherein the amount of a compound of Formula (I) in combination with the radiation therapy effective in treating the above diseases.

Techniques for administering radiation therapy are known in the art, and these techniques can be used in the combination therapy described herein. The administration of the compound of the invention in this combination therapy can be determined as described herein.

Another aspect of the invention is directed to the use of a compound of Formula (I) in the preparation of a medicament, which is useful in the treatment of a disease mediated by abnormal Met kinase activity.

DETAILED DESCRIPTION OF THE INVENTION

I. Definitions

The terms "indolinone", "2-indolinone" and "indolin-2-one" are used interchangeably herein to refer to a molecule having the chemical structure:

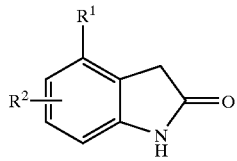

"Pyrrole" refers to a molecule having the chemical structure:

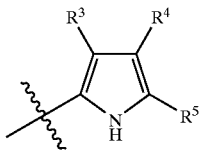

"Pyrrole-substituted 2-indolinone" and "3-pyrrolidinyl-2-indolinone" are used interchangeably herein to refer to a chemical compound having the general structure shown in Formula I.

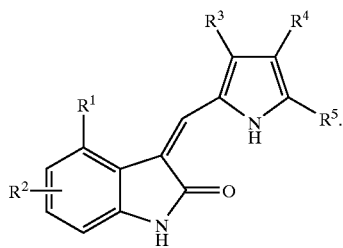

I

"Pharmaceutically acceptable salt" or "pharmaceutically acceptable salt thereof" refer to those salts which retain the biological effectiveness and properties of the free bases and which are obtained by reaction with inorganic or organic acids, such as hydrochloric acid, hydrobromic acid, hydroiodic acid, sulfuric acid, nitric acid, phosphoric acid, methanesulfonic acid, ethanesulfonic acid, p-toluenesulfonic acid, salicylic acid, acetic acid, benzenesulfonic acid (besylate), benzoic acid, camphorsulfonic acid, citric acid, fumaric acid, gluconic acid, glutamic acid, isethionic acid, lactic acid, maleic acid, malic acid, mandelic acid, mucic acid, pamoic acid, pantothenic acid, succinic acid, tartaric acid, and the like.

A "pharmaceutical composition" refers to a mixture of one or more of the compounds described herein, or physiologically acceptable salts thereof, with other chemical components, such as physiologically acceptable carriers and excipients. The purpose of a pharmaceutical composition is to facilitate administration of a compound to an organism.

As used herein, a "physiologically acceptable carrier" refers to a carrier or diluent that does not cause significant irritation to an organism and does not abrogate the biological activity and properties of the administered compound.

An "excipient" refers to an inert substance added to a pharmaceutical composition to further facilitate administration of a compound. Examples, without limitation, of excipients include calcium carbonate, calcium phosphate, various sugars and types of starch, cellulose derivatives (including microcrystalline cellulose), gelatin, vegetable oils, polyethylene glycols, diluents, granulating agents, lubricants, binders, disintegrating agents, and the like.

"Alkyl" refers to a saturated aliphatic hydrocarbon including straight chain, branched chain or cyclic groups. Preferably, the alkyl group has 1 to 20 carbon atoms (whenever a numerical range; e.g., "1–20", is stated herein, it means that the group, in this case the alkyl group, may contain 1 carbon atom, 2 carbon atoms, 3 carbon atoms, etc. up to and including 20 carbon atoms). More preferably, it is a medium size alkyl having 1 to 10 carbon atoms. Most preferably, it is a lower alkyl having 1 to 4 carbon atoms. The alkyl group may be substituted or unsubstituted. When substituted, the substituent group(s) is preferably one or more individually selected from halogen, —OR$^6$, —COR$^6$, —COOR$^6$, OCOR$^6$, —CONR$^6$R$^7$, —R$^6$NCOR$^7$, —NR$^6$R$^7$, —CN, —NO$_2$, —CX$_3$, —SR$^6$, —SOR$^6$, —SO$_2$R$^6$, —SO$_2$OR$^6$, —SO$_2$NR$^6$R$^7$, thiocarbonyl, —R(NSO$_2$R$^7$, perfluoroalkyl, O-carbamyl, N-carbamyl, O-thiocarbamyl, N-thiocarbamyl, silyl, ammonium, lower alkyl, lower alkenyl, lower alkynyl, cycloalkyl, heterocycle, heteroaryl and aryl.

"Alkenyl" refers to an aliphatic hydrocarbon having at least one carbon-carbon double bond, including straight chain, branched chain or cyclic groups having at least one carbon-carbon double bond. Preferably, the alkenyl group has 2 to 20 carbon atoms (whenever a numerical range; e.g., "2–20", is stated herein, it means that the group, in this case the alkenyl group, may contain 2 carbon atoms, 3 carbon atoms, etc. up to and including 20 carbon atoms). More preferably, it is a medium size alkenyl having 2 to 10 carbon atoms. Most preferably, it is a lower alkenyl having 2 to 6 carbon atoms. The alkenyl group may be substituted or unsubstituted.

When substituted, the substituent group(s) is preferably one or more individually selected from halogen, —OR$^6$, —COR$^6$, —COOR$^6$, OCOR$^6$, —CONR$^6$R$^7$, —R$^6$NCOR$^7$, —NR$^6$R$^7$, —CN, —NO$_2$, —CX$_3$, —SR$^6$, —SOR$^6$, —SO$_2$R$^6$, —SO$_2$OR$^6$, —SO$_2$NR$^6$R$^7$, thiocarbonyl, —R$^6$NSO$_2$R$^7$, perfluoroalkyl, O-carbamyl, N-carbamyl, O-thiocarbamyl, N-thiocarbamyl, silyl, ammonium, lower alkyl, lower alkenyl, lower alkynyl, cycloalkyl, heterocycle, heteroaryl and aryl.

"Alkynyl" refers to an aliphatic hydrocarbon having at least one carbon-carbon triple bond, including straight chain, branched chain or cyclic groups having at least one carbon-carbon triple bond. Preferably, the alkenyl group has 2 to 20 carbon atoms (whenever a numerical range; e.g., "2–20", is stated herein, it means that the group, in this case the alkynyl group, may contain 2 carbon atoms, 3 carbon atoms, etc. up to and including 20 carbon atoms). More preferably, it is a medium size alkynyl having 2 to 10 carbon atoms. Most preferably, it is a lower alkynyl having 2 to 6 carbon atoms. The alkynyl group may be substituted or unsubstituted. When substituted, the substituent group(s) is preferably one or more individually selected from halogen, —$OR^6$, —$COR^6$, —$COOR^6$, $OCOR^6$, —$CONR^6R^7$, —$R^6NCOR^7$, —$NR^6R^7$, —CN, —$NO_2$, —$CX_3$, —$SR^6$, —$SOR^6$, —$SO_2R^6$, —$SO_2OR^6$, —$SO_2NR^6R^7$, thiocarbonyl, —$R^6NSO_2R^7$, perfluoroalkyl, O-carbamyl, N-carbamyl, O-thiocarbamyl, N-thiocarbamyl, silyl, ammonium, lower alkyl, lower alkenyl, lower alkynyl, cycloalkyl, heterocycle, heteroaryl and aryl.

A "cycloalkyl" group refers to an all-carbon monocyclic or fused ring (i.e., rings which share an adjacent pair of carbon atoms) group wherein one of more of the rings does not have a completely conjugated pi-electron system. Examples, without limitation, of cycloalkyl groups are cyclopropane, cyclobutane, cyclopentane, cyclopentene, cyclohexane, adamantane, cyclohexadiene, cycloheptane and, cycloheptatriene. A cycloalkyl group may be substituted or unsubstituted. When substituted, the substituent group(s) is preferably one or more individually selected from halogen, —$OR^6$, —$COR^6$, —$COOR^6$, $OCOR^6$, —$CONR^6R^7$, —$R^6NCOR^7$, —$NR^6R^7$, —CN, —$NO_2$, —$CX_3$, —$SR^6$, —$SOR^6$, —$SO_2R^6$, —$SO_2OR^6$, —$SO_2NR^6R^7$, thiocarbonyl, —$R^6NSO_2R^7$, perfluoroalkyl, O-carbamyl, N-carbamyl, O-thiocarbamyl, N-thiocarbamyl, silyl, ammonium, lower alkyl, lower alkenyl, lower alkynyl, cycloalkyl, heterocycle, heteroaryl and aryl.

An "aryl" group refers to an all-carbon monocyclic or fused-ring polycyclic (i.e., rings which share adjacent pairs of carbon atoms) groups having a completely conjugated pi-electron system. Examples, without limitation, of aryl groups are phenyl, naphthalenyl and anthracenyl. The aryl group may be substituted or unsubstituted. When substituted, the substituted group(s) is preferably one or more selected halogen, —$OR^6$, —$COR^6$, —$COOR^6$, $OCOR^6$, —$CONR^6R^7$, —$RNCOR^7$, —$NR^6R^7$, —CN, —$NO_2$, —$CX_3$, —$SR^6$, —$SOR^6$, —$SO_2R^6$, —$SO_2OR^6$, —$SO_2NR^6R^7$, thiocarbonyl, —$R^6NSO_2R^7$, perfluoroalkyl, O-carbamyl, N-carbamyl, O-thiocarbamyl, N-thiocarbamyl, silyl, ammonium, lower alkyl, lower alkenyl, lower alkynyl, cycloalkyl, heterocycle, heteroaryl and aryl.

As used herein, a "heteroaryl" group refers to a monocyclic or fused ring (i.e., rings which share an adjacent pair of atoms) group having in the ring(s) one or more atoms selected from the group consisting of nitrogen, oxygen and sulfur and, in addition, having a completely conjugated pi-electron system. Examples, without limitation, of heteroaryl groups are pyrrole, furan, thiophene, imidazole, oxazole, thiazole, pyrazole, pyridine, pyrimidine, quinoline, isoquinoline, purine and carbazole. The heteroaryl group may be substituted or unsubstituted. When substituted, the substituted group(s) is preferably one or more selected from halogen, —$OR^6$, —$COR^6$, —$COOR^6$, $OCOR^6$, —$CONR^6R^7$, —$R^6NCOR^7$, —$NR^6R^7$, —CN, —$NO_2$, —$CX_3$, —$SR^6$, —$SOR^6$, —$SO_2R^6$, —$SO_2OR^6$, —$SO_2NR^6R^7$, thiocarbonyl, —$R^6NSO_2R^7$, perfluoroalkyl, O-carbamyl, N-carbamyl, O-thiocarbamyl, N-thiocarbamyl, silyl, ammonium, lower alkyl, lower alkenyl, lower alkynyl, cycloalkyl, heterocycle, heteroaryl and aryl, where X is halogen.

A "heterocyclic ring" or "heterocycle" group refers to a monocyclic or fused ring group having in the ring(s) one or more atoms selected from the group consisting of nitrogen, oxygen and sulfur. The rings may also have one or more double bonds. However, the rings may or may not have a completely conjugated pi-electron system. The heterocyclic ring may be substituted or unsubstituted. The heterocyci ring may contain one or more oxo groups. When substituted, the substituted group(s) is preferably one or more selected halogen, —$OR^6$, —$COR^6$, —$COOR^6$, $OCOR^6$, —$CON^6R^7$, —$R^6NCOR^7$, —$NR^6R^7$, —CN, —$NO_2$, —$CX_3$, —$SR^6$, —$SOR^6$, —$SO_2R^6$, —$SO_2OR^6$, —$SO_2NR^6R^7$, thiocarbonyl, —$R^6NSO_2R^7$, perfluoroalkyl, O-carbamyl, N-carbamyl, O-thiocarbamyl, N-thiocarbamyl, silyl, ammonium, lower alkyl, lower alkenyl, lower alkynyl, cycloalkyl, heterocycle, heteroaryl and aryl.

X refers to a halogen group selected from the group consisting of fluorine, chlorine, bromine and iodine.

The definitions of $R^1$–$R^{13}$ are defined in the present specification.

Compounds that have the same molecular formula but difer in the nature or sequence of bonding of their atoms or arrangements of their atoms in space are termed "isomers." Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The compounds of this invention may possess one or more asymmetric centers; such compounds can therefore be produced as individual (R)- or (S)-stereoisomers or as mixtures thereof. For example, if the $R^6$ substituent in a compound of formula (I) is 2-hydroxyethyl, then the carbon to which the hydroxy group is attached is an asymmetric center and therefore the compound of Formula (I) can exist as an (R)- or (S)-stereoisomer. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see discussion in Chapter 4 of "Advanced Organic Chemistry", 4th edition J. March, John Wiley and Sons, New York, 1992).

The compounds of Formula (I) may exhibit the phenomena of tautomerism and structural isomerism. For example, the compounds described herein may adopt an E or a Z configuration about the double bond connecting the 2-indolinone moiety to the pyrrole moiety or they may be a mixture of E and Z. This invention encompasses any tautomeric or structural isomeric form and mixtures thereof which possess the ability to modulate RTK, CTK and/or STK activity and is not limited to any one tautomeric or structural isomeric form.

It is contemplated that a compound of Formula (I) would be metabolized by enzymes in the body of the organism such as human being to generate a metabolite that can modulate the activity of the protein kinases. Such metabolites are within the scope of the present invention.

As used herein, "PK" refers to receptor protein tyrosine kinase (RTKs), non-receptor or "cellular" tyrosine kinase (CTKs) and serine-threonine kinases (STKs).

The term "method" refers to manners, means, techniques and procedures for accomplishing a given task including, but not limited to, those manners, means, techniques and procedures either known to, or readily developed from known manners, means, techniques and procedures by, practitioners of the chemical, pharmaceutical, biological, biochemical and medical arts.

As used herein, the term "modulation" or "modulating" refers to the alteration of the catalytic activity of RTKs, CTKs and STKs. In particular, modulating refers to the activation of the catalytic activity of RTKs, CTKs and STKs, preferably the activation or inhibition of the catalytic activity of RTKs, CTKs and STKs, depending on the concentration of the compound or salt to which the RTK, CTK or STK is exposed or, more preferably, the inhibition of the catalytic activity of RTKs, CTKs and STKs.

The term "catalytic activity" as used herein refers to the rate of phosphorylation of tyrosine under the influence, direct or indirect, of RTKs and/or CTKs or the phosphorylation of serine and threonine under the influence, direct or indirect, of STKs.

The term "contacting" as used herein refers to bringing a compound of this invention and a target PK together in such a manner that the compound can affect the catalytic activity of the PK, either directly, i.e., by interacting with the kinase itself, or indirectly, i.e., by interacting with another molecule on which the catalytic activity of the kinase is dependent. Such "contacting" can be accomplished in vitro, i.e., in a test tube, a petri dish or the like. In a test tube, contacting may involve only a compound and a PK of interest or it may involve whole cells. Cells may also be maintained or grown in cell culture dishes and contacted with a compound in that environment. In this context, the ability of a particular compound to affect a PK related disorder, i.e., the $IC_{50}$ of the compound, defined below, can be determined before use of the compounds in vivo with more complex living organisms is attempted. For cells outside the organism, multiple methods exist, and are well-known to those skilled in the art, to get the PKs in contact with the compounds including, but not limited to, direct cell microinjection and numerous transmembrane carrier techniques.

"In vitro" refers to procedures performed in an artificial environment such as, e.g., without limitation, in a test tube or culture medium. The skilled artisan will understand that, for example, an isolated PK may be contacted with a modulator in an in vitro environment. Alternatively, an isolated cell may be contacted with a modulator in an in vitro environment.

As used herein, "in vivo" refers to procedures performed within a living organism such as, without limitation, a mouse, rat, rabbit, ungulate, bovine, equine, porcine, canine, feline, primate, or human.

As used herein, "PK related disorder," "PK driven disorder," and "abnormal PK activity" all refer to a condition characterized by inappropriate, i.e., under or, more commonly, over, PK catalytic activity, where the particular PK can be an RTK, a CTK or an STK. Inappropriate catalytic activity can arise as the result of either: (1) PK expression in cells which normally do not express PKs, (2) increased PK expression leading to unwanted cell proliferation, differentiation and/or growth, or, (3) decreased PK expression leading to unwanted reductions in cell proliferation, differentiation and/or growth. Over-activity of a PK refers to either amplification of the gene encoding a particular PK or production of a level of PK activity which can correlate with a cell proliferation, differentiation and/or growth disorder (that is, as the level of the PK increases, the severity of one or more of the symptoms of the cellular disorder increases). Under-activity is, of course, the converse, wherein the severity of one or more symptoms of a cellular disorder increase as the level of the PK activity decreases.

As used herein, the terms "prevent", "preventing" and "prevention" refer to a method for barring an organism from acquiring a PK related disorder in the first place.

As used herein, the terms "treat", "treating" and "treatment" refer to a method of alleviating or abrogating a PK mediated cellular disorder and/or its attendant symptoms. With regard particularly to cancer, these terms simply mean that the life expectancy of an individual affected with a cancer will be increased or that one or more of the symptoms of the disease will be reduced.

The term "organism" refers to any living entity comprised of at least one cell. A living organism can be as simple as, for example, a single eukaryotic cell or as complex as a mammal. In a preferred aspect, the organism is a mammal. In a particularly preferred aspect, the mammal is a human being.

The term "therapeutically effective amount" as used herein refers to that amount of the compound being administered which will relieve to some extent one or more of the symptoms of the disorder being treated. In reference to the treatment of cancer, a therapeutically effective amount refers to that amount which has the effect of (1) reducing the size of the tumor, (2) inhibiting (that is, slowing to some extent, preferably stopping) tumor metastasis, (3) inhibiting to some extent (that is, slowing to some extent, preferably stopping) tumor growth, and/or, (4) relieving to some extent (or, preferably, eliminating) one or more symptoms associated with the cancer.

By "monitoring" is meant observing or detecting the effect of contacting a compound with a cell expressing a particular PK. The observed or detected effect can be a change in cell phenotype, in the catalytic activity of a PK or a change in the interaction of a PK with a natural binding partner. Techniques for observing or detecting such effects are well-known in the art. For example, the catalytic activity of a PK may be observed by determining the rate or amount of phosphorylation of a target molecule.

"Cell phenotype" refers to the outward appearance of a cell or tissue or the biological function of the cell or tissue. Examples, without limitation, of a cell phenotype are cell size, cell growth, cell proliferation, cell differentiation, cell survival, apoptosis, and nutrient uptake and use. Such phenotypic characteristics are measurable by techniques well-known in the art.

A "natural binding partner" refers to a polypeptide that binds to a particular PK in a cell. Natural binding partners can play a role in propagating a signal in a PK-mediated signal transduction process. A change in the interaction of the natural binding partner with the PK can manifest itself as an increased or decreased concentration of the PK/natural binding partner complex and, as a result, in an observable change in the ability of the PK to mediate signal transduction.

As used herein, "administer" or "administration" refers to the delivery of a compound or salt of the present invention or of a pharmaceutical composition containing a compound or salt of this invention to an organism for the purpose of prevention or treatment of a PK-related disorder.

A "pharmaceutical composition" refers to a mixture of one or more of the compounds described herein, or pharmaceutically acceptable salts or prodrugs thereof, with other chemical components, such as pharmaceutically acceptable excipients. The purpose of a pharmaceutical composition is to facilitate administration of a compound to an organism.

"Pharmaceutically acceptable excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

"Pharmaceutically acceptable salt" refers to those salts, which retain the biological effectiveness and properties of the parent compound. Such salts include:

(1) acid addition salt which is obtained by reaction of the free base of the parent compound with inorganic acids such as hydrochloric acid, hydrobromic acid, nitric acid, phosphoric acid, sulfuric acid, and perhcloric acid and the like, or with organic acids such as acetic acid, oxalic acid, (D) or (L) malic acid, maleic acid, methanesulfonic acid, ethanesulfonic acid, p-toluenesulfonic acid, salicylic acid, tartaric acid, citric acid, succinic acid or malonic acid and the like, preferably hydrochloric acid or (L)-malic acid; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

The compound of Formula (I) may also act as a prodrug. A "prodrug" refers to an agent, which is converted into the parent drug in vivo. Prodrugs are often usefull because, in some situations, they may be easier to administer than the parent drug. They may, for instance, be bioavailable by oral administration whereas the parent drug is not. The prodrug may also have improved solubility in pharmaceutical compositions over the parent drug. An example, without limitation, of a prodrug would be a compound of the present invention, which is, administered as an ester (the "prodrug"), carbamate or urea.

Indications

The PKs whose catalytic activity is modulated by the compounds of this invention include protein tyrosine kinases of which there are two types, receptor tyrosine kinases (RTKs) and cellular tyrosine kinases (CTKs), and serine-threonine kinases (STKs). RTK mediated signal transduction, is initiated by extracellular interaction with a specific growth factor (ligand), followed by receptor dimerization, transient stimulation of the intrinsic protein tyrosine kinase activity and phosphorylation. Binding sites are thereby created for intracellular signal transduction molecules and lead to the formation of complexes with a spectrum of cytoplasmic signaling molecules that facilitate the appropriate cellular response (e.g., cell division, metabolic effects on the extracellular microenvironment, etc.). See, Schlessinger and Ullrich, Neuron, 9:303–391 (1992).

It has been shown that tyrosine phosphorylation sites on growth factor receptors function as high-affinity binding sites for SH2 (src homology) domains of signaling molecules. Fantl et al., Cell, 69:413–423 (1992), Songyang et al., Mol. Cell. Biol., 14:2777–2785 (1994), Songyang et al., Cell, 72:767–778 (1993), and Koch et al., Science, 252:668–678 (1991). Several intracellular substrate proteins that associate with RTKs have been identified. They may be divided into two principal groups: (1) substrates that have a catalytic domain, and (2) substrates which lack such domain but which serve as adapters and associate with catalytically active molecules. Songyang et al., Cell, 72:767–778 (1993). The specificity of the interactions between receptors and SH2 domains of their substrates is determined by the amino acid residues immediately surrounding the phosphorylated tyrosine residue. Differences in the binding affinities between SH2 domains and the amino acid sequences surrounding the phosphotyrosine residues on particular receptors are consistent with the observed differences in their substrate phosphorylation profiles. Songyang et al., Cell, 72:767–778 (1993). These observations suggest that the function of each RTK is determined not only by its pattern of expression and ligand availability but also by the array of downstream signal transduction pathways that are activated by a particular receptor. Thus, phosphorylation provides an important regulatory step which determines the selectivity of signaling pathways recruited by specific growth factor receptors, as well as differentiation factor receptors.

STKs, being primarily cytosolic, affect the internal biochemistry of the cell, often as a down-line response to a PTK event. STKs have been implicated in the signaling process which initiates DNA synthesis and subsequent mitosis leading to cell proliferation.

Thus, PK signal transduction results in, among other responses, cell proliferation, differentiation, growth and metabolism. Abnormal cell proliferation may result in a wide array of disorders and diseases, including the development of neoplasia such as carcinoma, sarcoma, glioblastoma and hemangioma, disorders such as leukemia, psoriasis, arteriosclerosis, arthritis and diabetic retinopathy and other disorders related to uncontrolled angiogenesis and/or vasculogenesis.

A precise understanding of the mechanism by which the compounds of the invention, in particular, the compounds generated iii vivo from the compounds of the invention, inhibit PKs is not required in order to practice the present invention. However, while not hereby being bound to any particular mechanism or theory, it is believed that the compounds interact with the amino acids in the catalytic region of PKs. PKs typically possess a bi-lobate structure wherein ATP appears to bind in the cleft between the two lobes in a region where the amino acids are conserved among PKs. Inhibitors of PKs are believed to bind by non-covalent interactions such as hydrogen bonding, van der Waals forces and ionic interactions in the same general region where the aforesaid ATP binds to the PKs. More specifically, it is thought that the 2-indolinone component of the compounds of this invention binds in the general space normally occupied by the adenine ring of ATP. Specificity of a particular molecule for a particular PK may then arise as the result of additional interactions between the various substituents on the 2-indolinone core and the amino acid domains specific to particular PKs. Thus, different indolinone substituents may contribute to preferential binding to particular PKs. The ability to select compounds active at different ATP (or other nucleotide) binding sites makes the compounds of this invention useful for targeting any protein with such a site. The compounds disclosed herein may thus have utility as in vitro assays for such proteins as well as exhibiting in vivo therapeutic effects through interaction with such proteins.

In another aspect, the protein kinase, the catalytic activity of which is modulated by contact with a compound of this invention, is a protein tyrosine kinase, more particularly, a receptor protein tyrosine kinase. Among the receptor protein tyrosine kinases whose catalytic activity can be modulated with a compound of this invention, or salt thereof, are, without limitation, selected from the group consisting of Met, Flk, FGFR, PDGFR, HER, IR, IGF, IRR, CSFIR, C-Kit, C-fms, flt. In a preferred aspect, the receptor protein tyrosine kinases whose catalytic activity can be modulated with a compound of this invention, or salt thereof, are, without limitation, Met, Flk-1R, Flk4, KDR/Flk-1, FGFR-1R, FGFR-2R, FGFR-3R, FGFR-4R, PDGFRα, PDGFRβ, HER2, HER3, HER4, IRR, CSFIR, C-Kit and C-fms, preferably Met.

The protein tyrosine kinase whose catalytic activity is modulated by contact with a compound of this invention, or a salt thereof, can also be a non-receptor or cellular protein tyrosine kinase (CTK). Thus, the catalytic activity of CTKs such as, without limitation, Src, Frk, Btk, Csk, Abl, ZAP70, Fes, Fps, Fak, Jak, Ack, Yes, Fyn, Lyn, Lck, Blk, Hck, Fgr, Aur2 and Yrk may be modulated by contact with a compound or salt of this invention.

Still another group of PKs which may have their catalytic activity modulated by contact with a compound of this invention are the serine-threonine protein kinases such as, without limitation, CDK2, Raf, NEK (including NEK 4a, NEK 4b, NEK 5 and NEK 6) and BUB1.

In another aspect, this invention relates to a method for treating or preventing a PK related disorder by administering a therapeutically effective amount of a compound of this invention, or a salt thereof, to an organism.

It is also an aspect of this invention that a pharmaceutical composition containing a compound of this invention, or a salt thereof, is administered to an organism for the purpose of preventing or treating a PK related disorder.

This invention is therefore directed to compounds that modulate PK signal transduction by affecting the enzymatic activity of RTKs, CTKs and/or STKs, thereby interfering with the signals transduced by such proteins. More particularly, the present invention is directed to compounds which modulate RTK, CTK and/or STK mediated signal transduction pathways as a therapeutic approach to cure many kinds of solid tumors, including but not limited to carcinomas, sarcomas including Kaposi's sarcoma, erythroblastoma, glioblastoma, meningioma, astrocytoma, melanoma and myoblastoma. Treatment or prevention of non-solid tumor cancers such as leukemia are also contemplated by this invention. Indications may include, but are not limited to brain cancers, bladder cancers, ovarian cancers, gastric cancers, pancreas cancers, colon cancers, blood cancers, lung cancers and bone cancers.

Further examples, without limitation, of the types of disorders related to inappropriate PK activity that the compounds described herein may be useful in preventing, treating and studying, are cell proliferative disorders, fibrotic disorders, metabolic disorders and infectious diseases.

Cell proliferative disorders, which may be prevented, treated or further studied by the present invention include cancer, blood vessel proliferative disorders and mesangial cell proliferative disorders.

Blood vessel proliferative disorders refer to disorders related to abnormal vasculogenesis (blood vessel formation) and angiogenesis (spreading of blood vessels). While vasculogenesis and angiogenesis play important roles in a variety of normal physiological processes such as embryonic development, corpus luteum formation, wound healing and organ regeneration, they also play a pivotal role in cancer development where they result in the formation of new capillaries needed to keep a tumor alive. Other examples of blood vessel proliferation disorders include arthritis, where new capillary blood vessels invade the joint and destroy cartilage, and ocular diseases, like diabetic retinopathy, where new capillaries in the retina invade the vitreous, bleed and cause blindness.

Two structurally related RTKs have been identified to bind VEGF with high affinity: the fms-like tyrosine 1 (flt-1) receptor (Shibuya et al., *Oncogene*, 5:519–524 (1990); De Vries et al., *Science*, 255:989–991 (1992) and the KDR/FLK-1 receptor, also known as VEGF-R2. Vascular endothelial growth factor (VEGF) has been reported to be an endothelial cell specific mitogen with in vitro endothelial cell growth promoting activity. Ferrara & Henzel, *Biochem. Biophys. Res. Comm.*, 161:851–858 (1989); Vaisman et al., *J. Biol. Chem.*, 265:19461–19566 (1990). Information set forth in U.S. application Ser. Nos. 08/193,829, 08/038,596 and 07/975,750, strongly suggest that VEGF is not only responsible for endothelial cell proliferation, but also is the prime regulator of normal and pathological angiogenesis. See generally, Klagsbum & Soker, *Current Biology*, 3(10):699–702 (1993); Houck, et al., *J. Biol. Chem.*, 267:26031–26037 (1992).

Normal vasculogenesis and angiogenesis play important roles in a variety of physiological processes such as embryonic development, wound healing, organ regeneration and female reproductive processes such as follicle development in the corpus luteum during ovulation and placental growth after pregnancy. Folkman & Shing, *J. Biological Chem.*, 267(16):10931–10934 (1992). Uncontrolled vasculogenesis and/or angiogenesis has been associated with diseases such as diabetes as well as with malignant solid tumors that rely on vascularization for growth. Klagsbum & Soker, *Current Biology*, 3(10):699–702 (1993); Folkham, *J. Natl. Cancer Inst.*, 82:4–6 (1991); Weidner, et al., *New Engl. J. Med.*, 324:1–5 (1991).

As presently understood, the role of VEGF in endothelial cell proliferation and migration during angiogenesis and vasculogenesis indicates an important role for the KDR/FLK-1 receptor in these processes. Diseases such as diabetes mellitus (Folkman, 198, in XIth Congress of Thrombosis and Haemostasis (Verstraeta, et al., eds.), pp. 583–596, Leuven University Press, Leuven) and arthritis, as well as malignant tumor growth may result from uncontrolled angiogenesis. See e.g., Folkman, *N. Engl. J. Med.*, 285:1182–1186 (1971). The receptors to which VEGF specifically binds are an important and powerful therapeutic target for the regulation and modulation of vasculogenesis and/or angiogenesis and a variety of severe diseases which involve abnormal cellular growth caused by such processes. Plowman, et al., *DN&P*, 7(6):334–339 (1994). More particularly, the KDR/FLK-1 receptor's highly specific role in neovascularization make it a choice target for therapeutic approaches to the treatment of cancer and other diseases which involve the uncontrolled formation of blood vessels.

Thus, one aspect of the present invention relates to compounds capable of regulating and/or modulating tyrosine kinase signal transduction including KDR/FLK-1 receptor signal transduction in order to inhibit or promote angiogenesis and/or vasculogenesis, that is, compounds that inhibit, prevent, or interfere with the signal transduced by KDR/FLK-1 when activated by ligands such as VEGF. Although it is believed that the compounds of the present invention act on a receptor or other component along the tyrosine kinase signal transduction pathway, they may also act directly on the tumor cells that result from uncontrolled angiogenesis.

Although the nomenclature of the human and murine counterparts of the generic "flk-I" receptor differ, they are, in many respects, interchangeable. The murine receptor, Flk-1, and its human counterpart, KDR, share a sequence homology of 93.4% within the intracellular domain. Likewise, murine FLK-I binds human VEGF with the same affinity as mouse VEGF, and accordingly, is activated by the ligand derived from either species. Millauer et al., *Cell*, 72:835–846 (1993); Quinn et al., *Proc. Natl. Acad. Sci. USA*, 90:7533–7537 (1993). FLK-1 also associates with and subsequently tyrosine phosphorylates human RTK substrates (e.g., PLC-γ or p85) when co-expressed in 293 cells (human embryonal kidney fibroblasts).

Models which rely upon the FLK-1 receptor therefore are directly applicable to understanding the KDR receptor. For example, use of the murine FLK-1 receptor in methods which identify compounds that regulate the murine signal transduction pathway are directly applicable to the identification of compounds which may be used to regulate the human signal transduction pathway, that is, which regulate activity related to the KDR receptor. Thus, chemical compounds identified as inhibitors of KDR/FLK-1 in vitro, can be confirmed in suitable in vivo models. Both in vivo mouse and rat animal models have been demonstrated to be of excellent value for the examination of the clinical potential of agents acting on the KDR/FLK-1 induced signal transduction pathway.

Thus, in one aspect, this invention is directed to compounds that regulate, modulate and/or inhibit vasculogenesis and/or angiogenesis by affecting the enzymatic activity of the KDR/FLK-1 receptor and interfering with the signal transduced by KDR/FLK-1. In another aspect, the present invention is directed to compounds which regulate, modulate and/or inhibit the KDR/FLK-1 mediated signal transduction pathway as a therapeutic approach to the treatment of many kinds of solid tumors including, but not limited to, glioblastoma, melanoma and Kaposi's sarcoma, and ovarian, lung, mammary, prostate, pancreatic, colon and epidermoid carcinoma. In addition, data suggest the administration of compounds which inhibit the KDR/Flk-1 mediated signal transduction pathway may also be used in the treatment of hemangioma, restenois and diabetic retinopathy.

A further aspect of this invention relates to the inhibition of vasculogenesis and angiogenesis by other receptor-mediated pathways, including the pathway comprising the flt-1 receptor.

Receptor tyrosine kinase mediated signal transduction is initiated by extracellular interaction with a specific growth factor (ligand), followed by receptor dimerization, transient stimulation of the intrinsic protein tyrosine kinase activity and autophosphorylation. Binding sites are thereby created for intracellular signal transduction molecules which leads to the formation of complexes with a spectrum of cytoplasmic signaling molecules that facilitate the appropriate cellular response, e.g., cell division and metabolic effects to the extracellular microenvironment. See, Schlessinger and Ullnich, *Neuron*, 9:1–20 (1992).

The close homology of the intracellular regions of KDR/FLK-1 with that of the PDGF-β receptor (50.3% homology) and/or the related flt-1 receptor indicates the induction of overlapping signal transduction pathways. For example, for the PDGF-β receptor, members of the src family (Twamley et al., *Proc. Natl. Acad. Sci. USA*, 90:7696–7700 (1993)), phosphatidylinositol-3'-kinase (Hu et al., *Mol. Cell. Biol.*, 12:981–990 (1992), phospholipase cγ (Kashishian & Cooper, *Mol. Cell. Biol.*, 4:49–51 (1993)), ras-GTPase-activating protein, (Kashishian et al., *EMBO J.*, 11:1373–1382 (1992), PTP-ID/syp (Kazlauskas et al., *Proc. Natl. Acad. Sci. USA*, 90:6939–6943 (1993)), Grb2 (Arvidsson et al., *Mol. Cell. Biol.*, 14:6715–6726 (1994)), and the adapter molecules Shc and Nck (Nishimura et al., *Mol. Cell. Biol.*, 13:6889–6896 (1993)), have been shown to bind to regions involving different autophosphorylation sites. See generally, Claesson-Welsh, *Prog. Growth Factor Res.*, 5:37–54 (1994). Thus, it is likely that signal transduction pathways activated by KDR/FLK-1 include the ras pathway (Rozakis et al., *Nature*, 360:689–692 (1992)), the PI-3'-kinase, the src-mediated and the plcγ-mediated pathways. Each of these pathways may play a critical role in the angiogenic and/or vasculogenic effect of KDR/FLK-1 in endothelial cells. Consequently, a still further aspect of this invention relates to the use of the organic compounds described herein to modulate angiogenesis and vasculogenesis as such processes are controlled by these pathways.

Conversely, disorders related to the shrinkage, contraction or closing of blood vessels, such as restenosis, are also implicated and may be treated or prevented by the methods of this invention.

Fibrotic disorders refer to the abnormal formation of extracellular matrices. Examples of fibrotic disorders include hepatic cirrhosis and mesangial cell proliferative disorders. Hepatic cirrhosis is characterized by the increase in extracellular matrix constituents resulting in the formation of a hepatic scar. An increased extracellular matrix resulting in a hepatic scar can also be caused by a viral infection such as hepatitis. Lipocytes appear to play a major role in hepatic cirrhosis. Other fibrotic disorders implicated include atherosclerosis.

Mesangial cell proliferative disorders refer to disorders brought about by abnormal proliferation of mesangial cells. Mesangial proliferative disorders include various human renal diseases such as glomerulonephritis, diabetic nephropathy and malignant nephrosclerosis as well as such disorders as thrombotic microangiopathy syndromes, transplant rejection, and glomerulopathies. The RTK PDGFR has been implicated in the maintenance of mesangial cell proliferation. Floege et al., *Kidney International*, 43:47S–54S (1993).

Many cancers are cell proliferative disorders and, as noted previously, PKs have been associated with cell proliferative disorders. Thus, it is not surprising that PKs such as, for example, members of the RTK family have been associated with the development of cancer. Some of these receptors, like EGFR (Tuzi et al., *Br. J. Cancer*, 63:227–233 (1991), Torp et al., *APMIS*, 100:713–719 (1992)) HER2/neu (Slamon et al., *Science*, 244:707–712 (1989)) and PDGF-R (Kumabe et al., *Oncogene*, 7:627–633 (1992)) are over-expressed in many tumors and/or persistently activated by autocrine loops. In fact, in the most common and severe cancers these receptor over-expressions (Akbasak and Suner-Akbasak et al., *J. Neurol. Sci.*, 111:119–133 (1992), Dickson et al., *Cancer Treatment Res.*, 61:249–273 (1992), Korc et al., *J. Clin. Invest.*, 90:1352–1360 (1992)) and autocrine loops (Lee and Donoghue, *J. Cell. Biol.*, 118:1057–1070 (1992), Korc et al., supra, Akbasak and Suner-Akbasak et al., supra) have been demonstrated. For example, EGFR has been associated with squamous cell carcinoma, astrocytoma, glioblastoma, head and neck cancer, lung cancer and bladder cancer. HER2 has been associated with breast, ovarian, gastric, lung, pancreas and bladder cancer. PDGFR has been associated with glioblastoma and melanoma as well as lung, ovarian and prostate cancer. The RTK c-met has also been associated with malignant tumor formation. For example, c-met has been associated with, among other cancers, colorectal, thyroid, pancreatic, gastric and hepatocellular carcinomas and lymphomas. Additionally c-met has been linked to leukemia. Over-expression of the c-met gene has also been detected in patients with Hodgkins disease and Burkitts disease.

IGF-IR, in addition to being implicated in nutritional support and in type-II diabetes, has also been associated with several types of cancers. For example, IGF-I has been implicated as an autocrine growth stimulator for several tumor types, e.g. human breast cancer carcinoma cells (Arteaga et al., *J. Clin. Invest.*, 84:1418–1423 (1989)) and small lung tumor cells (Macauley et al., *Cancer Res.*, 50:2511–2517 (1990)). In addition, IGF-I, while integrally involved in the normal growth and differentiation of the nervous system, also appears to be an autocrine stimulator of human gliomas. Sandberg-Nordqvist et al., *Cancer Res.*, 53:2475–2478 (1993). The importance of IGF-IR and its ligands in cell proliferation is further supported by the fact that many cell types in culture (fibroblasts, epithelial cells, smooth muscle cells, T-lymphocytes, myeloid cells, chondrocytes and osteoblasts (the stem cells of the bone marrow)) are stimulated to grow by IGF-I. Goldring and Goldring, *Eukaryotic Gene Expression*, 1:301–326 (1991). In a series of recent publications; Baserga suggests that IGF-IR plays a central role in the mechanism of transformation and, as such, could be a preferred target for therapeutic interventions for a broad spectrum of human malignancies. Baserga, *Cancer Res.*, 55:249–252 (1995), Baserga, *Cell*, 79:927–930 (1994), Coppola et al., *Mol. Cell. Biol.*, 14:4588–4595 (1994).

STKs have been implicated in many types of cancer including, notably, breast cancer (Cance, et al., *Int. J. Cancer*, 54:571–77 (1993)).

The association between abnormal PK activity and disease is not restricted to cancer. For example, RTKs have been associated with diseases such as psoriasis, diabetes mellitus, endometriosis, angiogenesis, atheromatous plaque development, Alzheimer's disease, von Hippel-Lindau disease, epidermal hyperproliferation, neurodegenerative diseases, age-related macular degeneration and hemangiomas. For example, EGFR has been indicated in corneal and dermal wound healing. Defects in Insulin-R and IGF-IR are indicated in type-II diabetes mellitus. A more complete correlation between specific RTKs and their therapeutic indications is set forth in Plowman et al., *DN&P*, 7:334–339 (1994).

As noted previously, not only RTKs but CTKs including, but not limited to, src, abl, fps, yes, fyn, lyn, lck, blk, hck, fgr and yrk (reviewed by Bolen et al., *FASEB J.*, 6:3403–3409 (1992)) are involved in the proliferative and metabolic signal transduction pathway and thus could be expected, and have been shown, to be involved in many PTK-mediated disorders to which the present invention is directed. For example, mutated src (v-src) has been shown to be an oncoprotein (pp60$^{v\text{-}src}$) in chicken. Moreover, its cellular homolog, the proto-oncogene pp60$^{c\text{-}src}$ transmits oncogenic signals of many receptors. Over-expression of EGFR or HER2/neu in tumors leads to the constitutive activation of pp60$^{c\text{-}src}$, which is characteristic of malignant cells but absent in normal cells. On the other hand, mice deficient in the expression of c-src exhibit an osteopetrotic phenotype, indicating a key participation of c-src in osteoclast function and a possible involvement in related disorders.

Similarly, Zap70 has been implicated in T-cell signaling which may relate to autoimmune disorders.

STKs have been associated with inflammation, autoimmune disease, immunoresponses, and hyperproliferation disorders such as restenosis, fibrosis, psoriasis, osteoarthritis and rheumatoid arthritis.

PKs have also been implicated in embryo implantation. Thus, the compounds of this invention may provide an effective method of preventing such embryo implantation and thereby be useful as birth control agents.

In yet another aspect, the compounds of the instant invention can also be used as anti-infective agents. For example, indolinone compounds are known to exhibit antibacterial and antifungal activities. See, e.g., Singh and Jha, "Indolinone derivatives as potential antimicrobial agents," *Zentralbl. Mikrobiol,*. 144(2):105–109 (1989). In addition, indolinone compounds have been reported to exhibit significant antiviral activity. See, e.g., Maass et al., "Viral resistance to the thiazolo-iso-indolinones, a new class of nonnucleoside inhibitors of human immunodeficiency virus type 1 reverse transcriptase," *Antimicrob. Agents Chemother.*, 37(12):2612–2617 (1993).

Finally, both RTKs and CTKs are currently suspected as being involved in hyperimmune disorders.

A method for identifying a chemical compound that modulates the catalytic activity of one or more of the above discussed protein kinases is another aspect of this invention. The method involves contacting cells expressing the desired protein kinase with a compound of this invention (or its salt) and monitoring the cells for any effect that the compound has on them. The effect may be any observable, either to the naked eye or through the use of instrumentation, change or absence of change in a cell phenotype. The change or absence of change in the cell phenotype monitored may be, for example, without limitation, a change or absence of change in the catalytic activity of the protein kinase in the cells or a change or absence of change in the interaction of the protein kinase with a natural binding partner.

Pharmaceutical Compositions and Use

A compound of the present invention or a physiologically acceptable salt thereof, can be administered as such to a human patient or can be administered in pharmaceutical compositions in which the foregoing materials are mixed with suitable carriers or excipient(s). Techniques for formulation and administration of drugs may be found in "Remington's Pharmacological Sciences," Mack Publishing Co., Easton, Pa., latest edition.

Routes of Administration

Suitable routes of administration may include, without limitation, oral, intraoral, rectal, transmucosal or intestinal administration or intramuscular, epicutaneous, parenteral, subcutaneous, transdermal, intramedullary, intrathecal, direct intraventricular, intravenous, intravitreal, intraperitoneal, intranasal, intramuscular, intradural, intrarespiratory, nasal inhalation or intraocular injections. The preferred routes of administration are oral and parenteral.

Alternatively, one may administer the compound in a local rather than systemic manner, for example, via injection of the compound directly into a solid tumor, often in a depot or sustained release formulation.

Furthermore, one may administer the drug in a targeted drug delivery system, for example, in a liposome coated with tumor-specific antibody. The liposomes will be targeted to and taken up selectively by the tumor.

Composition/Formulation

Pharmaceutical compositions of the present invention may be manufactured by processes well known in the art, e.g., by means of conventional mixing, dissolving, granulating, dragee-making, levigating, emulsifying, encapsulating, entrapping, lyophilizing processes or spray drying.

Pharmaceutical compositions for use in the methods of the present invention may be prepared by any methods of pharmacy, but all methods include the step of bringing in association the active ingredient with the carrier which constitutes one or more necessary ingredients. In particular, pharmaceutical compositions for use in accordance with the present invention may be formulated in conventional manner using one or more physiologically acceptable carriers comprising excipients and auxiliaries which facilitate processing of the active compounds into preparations which can be used pharmaceutically. Proper formulation is dependent upon the route of administration chosen.

Dosage forms include tablets, troches, dispersions, suspensions, solutions, capsules, patches, syrups, elixirs, gels, powders, magmas, lozenges, ointments, creams, pastes, plasters, lotions, discs, suppositories, nasal or oral sprays, aerosols and the like.

For injection, the compounds of the invention may be formulated in aqueous solutions, preferably in physiologically compatible buffers such buffers with or without a low concentration of surfactant or cosolvent, or physiological saline buffer. For transmucosal administration, penetrants appropriate to the barrier to be permeated are used in the formulation. Such penetrants are generally known in the art.

For oral administration, the compounds can be formulated by combining the active compounds with pharmaceutically acceptable carriers well known in the art. Such carriers enable the compounds of the invention to be formulated as tablets, pills, lozenges, dragees, capsules, liquids, gels, syrups, slurries, suspensions and the like, for oral ingestion by a patient. Pharmaceutical preparations for oral use can be made using a solid excipient, optionally grinding the resulting mixture, and processing the mixture of granules, after adding other suitable auxiliaries if desired, to obtain tablets or dragee cores. Useful excipients are, in particular, fillers such as sugars, including lactose, sucrose, mannitol, or sorbitol, cellulose preparations such as, for example, maize starch, wheat starch, rice starch and potato starch and other materials such as gelatin, gum tragacanth, methyl cellulose, hydroxypropylmethyl-cellulose, sodium carboxymethylcellulose, and/or polyvinyl-pyrrolidone (PVP). If desired, disintegrating agents may be added, such as cross-linked polyvinyl pyrrolidone, agar, or alginic acid. A salt such as sodium alginate may also be used.

Dragee cores are provided with suitable coatings. For this purpose, concentrated sugar solutions may be used which may optionally contain gum arabic, talc, polyvinyl pyrrolidone, carbopolgel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical compositions which can be used orally include push-fit capsules made of gelatin, as well as soft, sealed capsules made of gelatin and a plasticizer, such as glycerol or sorbitol. The push-fit capsules can contain the active ingredients in admixture with a filler such as lactose, a binder such as starch, and/or a lubricant such as talc or magnesium stearate and, optionally, stabilizers. In soft capsules, the active compounds may be dissolved or suspended in suitable liquids, such as fatty oils, liquid paraffin, liquid polyethylene glycols, cremophor, capmul, medium or long chain mono- di- or triglycerides. Stabilizers may be added in these formulations, also.

For administration by inhalation, the compounds for use according to the present invention are conveniently delivered in the form of an aerosol spray using a pressurized pack or a nebulizer and a suitable propellant, e.g., without limitation, dichlorodifluoromethane, trichlorofluoromethane, dichlorotetra-fluoroethane or carbon dioxide. In the case of a pressurized aerosol, the dosage unit may be controlled by providing a valve to deliver a metered amount. Capsules and cartridges of, for example, gelatin for use in an inhaler or insufflator may be formulated containing a powder mix of the compound and a suitable powder base such as lactose or starch.

The compounds may also be formulated for parenteral administration, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulating materials such as suspending, stabilizing and/or dispersing agents.

Pharmaceutical compositions for parenteral administration include aqueous solutions of a water soluble form, such as, without limitation, a salt, of the active compound. Additionally, suspensions of the active compounds may be prepared in a lipophilic vehicle. Suitable lipophilic vehicles include fatty oils such as sesame oil, synthetic fatty acid esters such as ethyl oleate and triglycerides, or materials such as liposomes. Aqueous injection suspensions may contain substances which increase the viscosity of the suspension, such as sodium carboxymethyl cellulose, sorbitol, or dextran. Optionally, the suspension may also contain suitable stabilizers and/or agents that increase the solubility of the compounds to allow for the preparation of highly concentrated solutions.

Alternatively, the active ingredient may be in powder form for constitution with a suitable vehicle, e.g., sterile, pyrogen-free water, before use.

The compounds may also be formulated in rectal compositions such as suppositories or retention enemas, using, e.g., conventional suppository bases such as cocoa butter or other glycerides.

In addition to the formulations described previously, the compounds may also be formulated as depot preparations. Such long acting formulations may be administered by implantation (for example, subcutaneously or intramuscularly) or by intramuscular injection. A compound of this invention may be formulated for this route of administration with suitable polymeric or hydrophobic materials (for instance, in an emulsion with a pharmacologically acceptable oil), with ion exchange resins, or as a sparingly soluble derivative such as, without limitation, a sparingly soluble salt.

A non-limiting example of a pharmaceutical carrier for the hydrophobic compounds of the invention is a cosolvent system comprising benzyl alcohol, a nonpolar surfactant, a water-miscible organic polymer and an aqueous phase such as the VPD co-solvent system. VPD is a solution of 3% w/v benzyl alcohol, 8% w/v of the nonpolar surfactant Polysorbate 80™, and 65% w/v polyethylene glycol 300, made up to volume in absolute ethanol. The VPD co-solvent system (VPD:D5W) consists of VPD diluted 1:1 with a 5% dextrose in water solution. This co-solvent system dissolves hydrophobic compounds well, and itself produces low toxicity upon systemic administration. Naturally, the proportions of such a co-solvent system may be varied considerably without destroying its solubility and toxicity characteristics. Furthermore, the identity of the co-solvent components may be varied: for example, other low-toxicity nonpolar surfactants may be used instead of Polysorbate 80™, the fraction size of polyethylene glycol may be varied, other biocompatible polymers may replace polyethylene glycol, e.g., polyvinyl pyrrolidone, and other sugars or polysaccharides may substitute for dextrose.

Alternatively, other delivery systems for hydrophobic pharmaceutical compounds may be employed. Liposomes and emulsions are well known examples of delivery vehicles or carriers for hydrophobic drugs. In addition, certain organic solvents such as dimethylsulfoxide also may be employed, although often at the cost of greater toxicity.

Additionally, the compounds may be delivered using a sustained-release system, such as semipermeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions herein also may comprise suitable solid or gel phase carriers or excipients. Examples of such carriers or excipients include, but are not limited to, calcium carbonate, calcium phosphate, various sugars, starches, cellulose derivatives, gelatin, and polymers such as polyethylene glycols.

Many of the PK modulating compounds of the invention may be provided as physiologically acceptable salts wherein the claimed compound may form the negatively or the positively charged species. Examples of salts in which the compound forms the positively charged moiety include, without limitation, quaternary ammonium (defined elsewhere herein), salts such as the hydrochloride, sulfate, carbonate, lactate, tartrate, maleate, succinate wherein the nitrogen atom of the quaternary ammonium group is a nitrogen of the selected compound of this invention which has reacted with the appropriate acid. Salts in which a compound of this invention forms the negatively charged species include, without limitation, the sodium, potassium, calcium and magnesium salts formed by the reaction of a carboxylic acid group in the compound with an appropriate base (e.g. sodium hydroxide (NaOH), potassium hydroxide (KOH), Calcium hydroxide (Ca(OH)$_2$), etc.).

Dosage

Pharmaceutical compositions suitable for use in the present invention include compositions wherein the active ingredients are contained in an amount sufficient to achieve the intended purpose, i.e., the modulation of PK activity or the treatment or prevention of a PK-related disorder.

More specifically, a therapeutically effective amount means an amount of compound effective to prevent, alleviate or ameliorate symptoms of disease or prolong the survival of the subject being treated.

Determination of a therapeutically effective amount is well within the capability of those skilled in the art, especially in light of the detailed disclosure provided herein.

For any compound used in the methods of the invention, the therapeutically effective amount or dose can be estimated initially from cell culture assays. Then, the dosage can be formulated for use in animal models so as to achieve a circulating concentration range that includes the IC$_{50}$ as determined in cell culture (i.e., the concentration of the test compound which achieves a half-maximal inhibition of the PK activity). Such information can then be used to more accurately determine useful doses in humans.

Toxicity and therapeutic efficacy of the compounds described herein can be determined by standard pharmaceutical procedures in cell cultures or experimental animals, e.g., by determining the IC$_{50}$ and the LD$_{50}$ (both of which are discussed elsewhere herein) for a subject compound. The data obtained from these cell culture assays and animal studies can be used in formulating a range of dosage for use in humans. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p.1).

Dosage amount and interval may be adjusted individually to provide plasma levels of the active species which are sufficient to maintain the kinase modulating effects. These plasma levels are referred to as minimal effective concentrations (MECs). The MEC will vary for each compound but can be estimated from in vitro data, e.g., the concentration necessary to achieve 50–90% inhibition of a kinase may be ascertained using the assays described herein. Dosages necessary to achieve the MEC will depend on individual characteristics and route of administration. HPLC assays or bioassays can be used to determine plasma concentrations.

Dosage intervals can also be determined using MEC value. Compounds should be administered using a regimen that maintains plasma levels above the MEC for 10–90% of the time, preferably between 30–90% and most preferably between 50–90%. At present, the therapeutically effective amounts of compounds of Formula (I) may range from approximately 25 mg/m$^2$ to 150 mg/m$^2$ perday. Even more preferably 25 mg/m$^2$ to 1000 mg/m$^2$.

In cases of local administration or selective uptake, the effective local concentration of the drug may not be related to plasma concentration and other procedures known in the art may be employed to determine the correct dosage amount and interval.

The amount of a composition administered will, of course, be dependent on the subject being treated, the severity of the affliction, the manner of administration, the judgment of the prescribing physician, etc.

Packaging

The compositions may, if desired, be presented in a pack or dispenser device, such as an FDA approved kit, which may contain one or more unit dosage forms containing the active ingredient. The pack may for example comprise metal or plastic foil, such as a blister pack. The pack or dispenser device may be accompanied by instructions for administration. The pack or dispenser may also be accompanied by a notice associated with the container in a form prescribed by a governmental agency regulating the manufacture, use or sale of pharmaceuticals, which notice is reflective of approval by the agency of the form of the compositions or of human or veterinary administration. Such notice, for example, may be of the labeling approved by the U.S. Food and Drug Administration for prescription drugs or of an approved product insert. Compositions comprising a compound of the invention formulated in a compatible pharmaceutical carrier may also be prepared, placed in an appropriate container, and labeled for treatment of an indicated condition. Suitable conditions indicated on the label may include treatment of a tumor, inhibition of angiogenesis, treatment of fibrosis, diabetes, and the like.

EXAMPLES

Compound Synthesis

The compounds of this invention, as well as the precursor indolinones, may be readily synthesized using techniques well known in the chemical arts. It will be appreciated by those skilled in the art that other synthetic pathways for forming the compounds of the invention are available and that the following is offered by way of example and not limitation.

The following syntheses of representative compounds of this invention are shown by way of example only and are not to be construed as limiting the scope of this invention as to synthetic approach or as to the compounds whose syntheses are exemplified.

It will be clear to those skilled in the art, based both on known general principles of organic synthesis and on the disclosures herein appropriate changes and modifications to the following syntheses that may be effected without departing from the scope or spirit of the invention as defined in the appended claims.

HPLC data was obtained with a Zorbax SB C18 column (4.6 mm ID×7.5 cm), a Perkin Elmer series 200 pump programmed to run from 10% acetonitrile/water 0.1% TFA (solvent A) to 90% acetonitrile/water (solvent B) with a flow rate of 1.5 mL/min. After 0.1 min on solvent A, a 5 min linear program to solvent B was run, followed by 3 min on solvent B, before recycling to solvent A (2 min). Detection was with a Perkin Elmer diode array detector recording at 215 and 280 nM). NMR spectra were recorded on a Bruker instrument at 300 MHz.

A. General Synthetic Procedure

The following general methodology may be employed to prepare the compounds of this invention:

The appropriately substituted 2-oxindole (1 equiv.), the appropriately substituted aldehyde (1.2 equiv.) and a base (0.1 equiv.) are mixed in a solvent (1–2 ml/mmol 2-oxindole) and the mixture is then heated for from about 2 to about 12 hours. After cooling, the precipitate that forms is filtered, washed with cold ethanol or ether and vacuum dried to give the solid product. If no precipitate forms, the reaction mixture is concentrated and the residue is triturated with dichloromethane/ether, the resulting solid is collected by filtration and then dried. The product may optionally be further purified by chromatography.

The base may be an organic or an inorganic base. If an organic base is used, preferably it is a nitrogen base. Examples of organic nitrogen bases include, but are not limited to, diisopropylamine, trimethylamine, triethylamine, aniline, pyridine, 1,8-diazabicyclo[5.4.1]undec-7-ene, pyrrolidine and piperidine.

Examples of inorganic bases are, without limitation, ammonia, alkali metal or alkaline earth hydroxides, phosphates, carbonates, bicarbonates, bisulfates and amides.

The alkali metals include, lithium, sodium and potassium while the alkaline earths include calcium, magnesium and barium.

In a presently preferred aspect of this invention, when the solvent is a protic solvent, such as water or alcohol, the base is an alkali metal or an alkaline earth inorganic base, preferably, a alkali metal or an alkaline earth hydroxide.

It will be clear to those skilled in the art, based both on known general principles of organic synthesis and on the disclosures herein which base would be most appropriate for the reaction contemplated.

The solvent in which the reaction is carried out may be a protic or an aprotic solvent, preferably it is a protic solvent. A "protic solvent" is a solvent which has hydrogen atom(s) covalently bonded to oxygen or nitrogen atoms which renders the hydrogen atoms appreciably acidic and thus capable of being "shared" with a solute through hydrogen bonding. Examples of protic solvents include, without limitation, water and alcohols.

An "aprotic solvent" may be polar or non-polar but, in either case, does not contain acidic hydrogens and therefore is not capable of hydrogen bonding with solutes. Examples, without limitation, of non-polar aprotic solvents, are pentane, hexane, benzene, toluene, methylene chloride and carbon tetrachloride. Examples of polar aprotic solvents are chloroform, tetrahydro-furan, dimethylsulfoxide and dimethylformamide.

In a presently preferred aspect of this invention, the solvent is a protic solvent, preferably water or an alcohol such as ethanol.

The reaction is carried out at temperatures greater than room temperature. The temperature is generally from about 30° C. to about 150° C., preferably about 80° C. to about 100° C., most preferable about 75° C. to about 85° C., which is about the boiling point of ethanol. By "about" is meant that the temperature range is preferably within 10 degrees Celsius of the indicated temperature, more preferably within 5 degrees Celsius of the indicated temperature and, most preferably, within 2 degrees Celsius of the indicated temperature. Thus, for example, by "about 75° C." is meant 75° C.±10° C., preferably 75° C.±5° C. and most preferably, 75° C.±2° C.

B. General Procedures for the Syntheses of 4-Aryl-1H-indole

Procedure A:

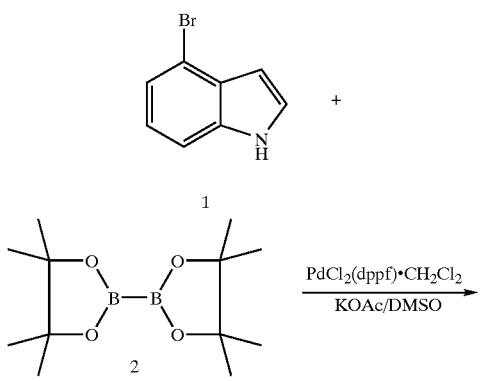

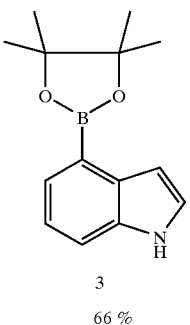

3
66 %

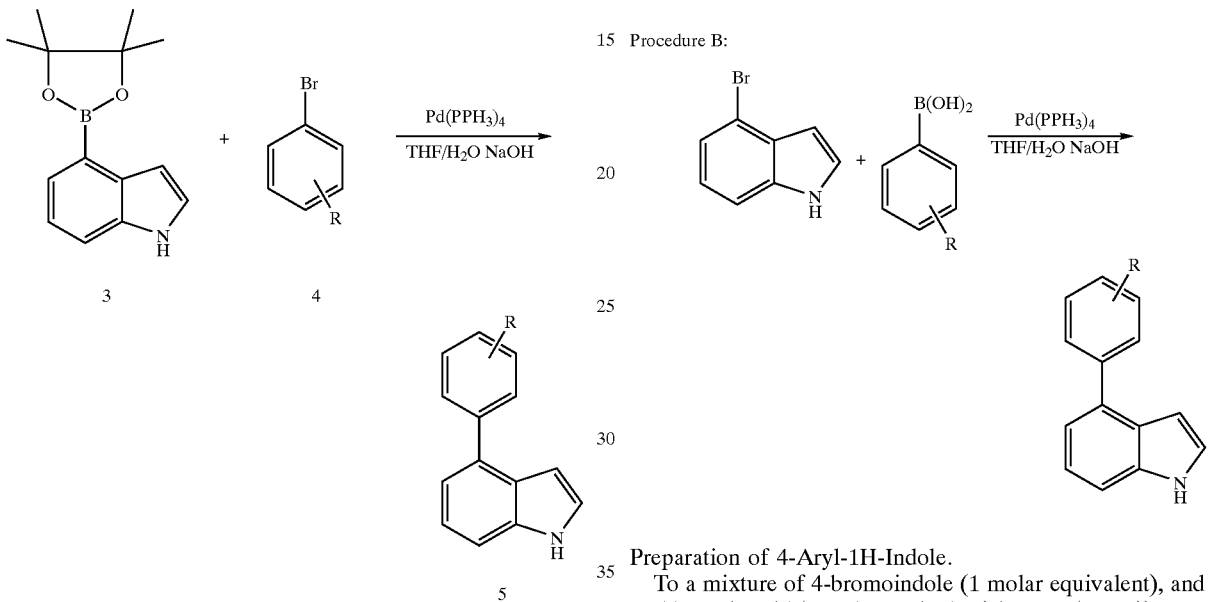

Preparation of 4-(4,4,5,5-Tetramethyl-[1,3,2]dioxaborolan-2-yl)1H-indole

To a mixture of 4-bromoindole (1, 9.80 g, 50 mmol), pinacole diborate (2, 13.97 g, 55 mmol), and KOAc (14.72 g, 150 mmol) in DMSO (200 mL) was added Palladium catalyst $PdCl_2(dppf)$ $CH_2Cl_2$ (1.22 g, 1.5 mmol). The system was degassed, and then charged with nitrogen for three times. The mixture was stirred at 80° C. oil bath under nitrogen for 22 hours. TLC$^2$ showed the complete disappearance of the starting material 4-bromoindole (1). The mixture was cooled to room temperature, and then poured to water (1 L). The product was extracted with ethyl acetate for three times. The combined extracts were washed by brine for five times to remove DMSO solvent, and then dried over $Na_2SO_4$. During the washing step, the catalyst may precipitate out, which was removed by filtration. The ethyl acetate solution was filtered and condensed. The residue was purified on a silica gel column eluting with EtOAc-hexane (9:1). The first fraction provided the side product indole (1.25 g, 21% yield), $R_f$ 0.55 (EtOAc-Hexane 5:1). The second fraction provided the product 4-(4,4,5,5-tetramethyl-[1,3,2]dioxaborolan-2-yl)-1H-indole as a white solid (3, 8.01 g, 66%), $R_f$ 0.46 (EtOAc-Hexane 5:1).

$^1$H NMR (300 MHz, DMSO-$d_6$) δ 11.03 (bs, 1H, N—H)), 7.49 (d, J 7.7 Hz, 1H, H-5), 7.38 (dd, J 0.9 Hz, J 7.0 Hz, 1H, H-7), 7.38 (t, J 2.6 Hz, 1H, H-2), 7.06 (dd, J 7.7 Hz, J 7.0 Hz, 1H, H-6), 6.73 (bd, J 2.2 Hz, 1H, H-3), 1.32 (s, 12H, 4CH$_3$). MS m/z 244 [M$^+$+1].

Preparation of 4-Aryl-1H-Indole.

To a mixture of 4-(4,4,5,5-tetramethyl-[1,3,2]dioxaborolan-2-yl)-1H-indole (3, 1 molar equivalent), and aryl bromide (4, 1.01 molar equivalent) in THF (0.3 M)) were added Palladium catalyst Pd(PPh$_3$)$_4$ (0.03 molar equivalent) and the freshly prepared sodium hydroxide solution (2.76N, 3 equivalent). The system was degassed and then charged with nitrogen. The degas procedure was repeated for three times. The mixture was stirred under nitrogen at 70° C. oil bath for 6–24 hours. TLC showed the completion of the coupling reaction. The mixture was cooled to room temperature, diluted with ethyl acetate, and separated from water layer. The ethyl acetate solution was washed by brine, and dried over Na$_2$SO$_4$. After filtration, the solvents were evaporated, and the crude product was purified by a silica gel column.

Procedure B:

Preparation of 4-Aryl-1H-Indole.

To a mixture of 4-bromoindole (1 molar equivalent), and aryl boronic acid (1 molar equivalent) in THF (0.3 M)) were added Palladium catalyst Pd(PPh$_3$)$_4$ (0.03 molar equivalent) and the freshly prepared sodium hydroxide solution (2.76N, 3 equivalent). The system was degassed and then charged with nitrogen. The degas procedure was repeated for three times. The mixture was stirred under nitrogen at 70° C. oil bath for 6–24 hours. TLC showed the completion of the coupling reaction. The mixture was cooled to room temperature, diluted with ethyl acetate, and separated from water layer. The ethyl acetate solution was washed by brine, and dried over Na$_2$SO$_4$. After filtration, the solvents were evaporated, and the crude product was purified by a silica gel column.

Example A-1

4-Phenyl-1H-indole

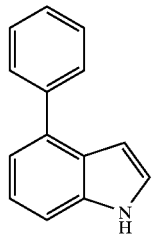

To a mixture of 4-(4,4,5,5-tetramethyl-[1,3,2]dioxaborolan-2-yl)-1H-indole (pinacole 4-indoleboronate (2 g, 8.2 mmol) and 3-bromobenzene (0.87 mL, 8.3 mmol) in THF (28 mL) were added Palladium catalyst Pd(PPh$_3$)$_4$ (284 mg, 0.25 mmol) and the freshly prepared sodium hydroxide solution (984 mg in 9 mL of water). The system was degassed and then charged with nitrogen for three times. The mixture was stirred under nitrogen at 70° C. oil bath for 6 hours. The reaction solution was cooled to room temperature, diluted with ethyl acetate and separated from water layer. The ethyl acetate solution was washed by brine, dried over Na$_2$SO$_4$ and concentrated. The residue was purified on a silica gel column eluting with hexanes:EtOAc 9:1 to give 1.38 g (78%) of 4-phenyl-1H-indole as a colorless liquid.

$^1$H NMR (360 MHz, DMSO-d$_6$) δ 11.26 (br s, 1H, NH), 7.66 (d, J=7.9 Hz, 2H), 7.50 (t, J=7.5 Hz, 2H), 7.35–7.43 (m, 3H), 7.18 (t, J=7.5 Hz, 1H), 7.08 (d, J=7.1 Hz, 1H), 6.41 (brs, 1H). MS m/z 194 [M$^+$+1].

Example A-2

4-(4-Fluoro-phenyl)-1H-indole

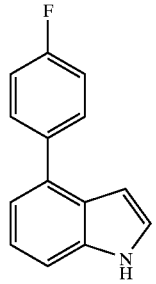

To a mixture of 4-(4,4,5,5-tetramethyl-[1,3,2] dioxaborolan-2-yl)-1H-indole (3, 4.0 g, 16.4 mmol), and 4-bromofluorobenzene (3.45 g, 19.7 mmol) in THF (80 mL)) were added Palladium catalyst Pd(PPh$_3$)$_4$ (0.57 g, 0.49 mmol) and the freshly prepared sodium hydroxide solution (2.0 g, 49.3 mmol in 25 mL water). The system was degassed and then charged with nitrogen. The degas procedure was repeated for three times. The mixture was stirred under nitrogen at 70° C. oil bath for 15 hours. TLC showed the completion of the coupling reaction. The mixture was cooled to room temperature, diluted with ethyl acetate, and separated from water layer. The ethyl acetate solution was washed by brine, dried over Na$_2$SO$_4$, and concentrated. The crude product was purified by a silica gel column eluting with hexanes—EtOAc (9:1) to provide 2.75 g (80%) of the product 4-(4-fluoro-phenyl)-1H-indole as a white solid.

$^1$H-NMR (400 MHz, DMSO-d$_6$) δ 11.26 (br s, 1H, NH), 7.68 (m, 2H, aromatic), 7.41 (m, 2H, aromatic), 7.32 (m, 2H aromatic), 7.17 (m, 1H, aromatic), 7.05 (m, 1H, aromatic), 6.51 (m, 1H, aromatic). MS m/z 212 [M$^+$+1].

Example A-3

4-(3-Fluoro-phenyl)-1H-indole

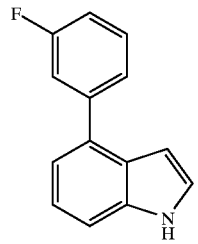

To a mixture of 4-(4,4,5,5-tetramethyl-[1,3,2] dioxaborolan-2-yl)-1H-indole (3, 2.43 g, 10 mmol), and 3-bromofluorobenzene (1.09 mL, 10 mmol) in THF (34 mL)) were added Palladium catalyst Pd(PPh$_3$)$_4$ (347 mg, 0.3 mmol) and the freshly prepared sodium hydroxide solution (1.20 g, 30 mmol in 14 mL water). The system was degassed and then charged with nitrogen. The degas procedure was repeated for three times. The mixture was stirred under nitrogen at 70° C. oil bath for 15 hours. TLC showed the completion of the coupling reaction. The mixture was cooled to room temperature, diluted with ethyl acetate, and separated from water layer. The ethyl acetate solution was washed by brine, dried over Na$_2$SO$_4$, and concentrated. The crude product was purified by a silica gel column eluting with hexanes—EtOAc (9:1) to provide 1.88 g (88%) of the product 4-(3-fluoro-phenyl)-1H-indole as a colorless syrup.

$^1$H-NMR (400 MHz, DMSO-d$_6$) δ 11.30 (br s, 1H, NH), 7.52 (m, 2H, aromatic), 7.45 (m, 3H, aromatic), 7.20 (m, 2H, aromatic), 7.12 (m, 1H, aromatic), 6.55 (m, 1H, aromatic). MS m/z 212 [M$^+$+1].

Example A-4

4-(4-Chloro-phenyl)-1H-indole

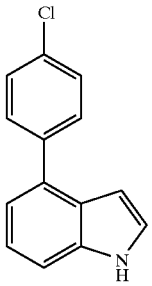

To a mixture of 4-(4,4,5,5-tetramethyl-[1,3,2] dioxaborolan-2-yl)-1H-indole (3, 2.43 g, 10 mmol), and 4-bromochlorobenzene (2.87 g, 15 mmol) in THF (34 mL)) were added Palladium catalyst Pd(PPh$_3$)$_4$ (347 mg, 0.3 mmol) and the freshly prepared sodium hydroxide solution (1.20 g, 30 mmol in 14 mL water). The system was degassed and then charged with nitrogen. The degas procedure was repeated for three times. The mixture was stirred under nitrogen at 70° C. oil bath for 15 hours. TLC showed the completion of the coupling reaction. The mixture was cooled to room temperature, diluted with ethyl acetate, and separated from water layer. The ethyl acetate solution was washed by brine, dried over Na$_2$SO$_4$, and concentrated. The crude product was purified by a silica gel column eluting with hexanes—EtOAc (9:1) to provide 2.02 g (89%) of the product 4-(4-chloro-phenyl)-1H-indole as a white solid.

¹H-NMR (400 MHz, DMSO-d₆) δ 11.29 (brs, 1H, NH), 7.70 (m, 2H, aromatic), 7.55 (m, 2H, aromatic), 7.43 (m, 2H, aromatic), 7.19 (t, 1H, aromatic), 7.08 (m, 1H aromatic), 6.53 (m, 1H, aromatic).

Example A-5

4-(3-Chloro-phenyl)-1H-indole

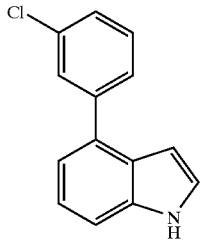

To a mixture of 4-(4,4,5,5-tetramethyl-[1,3,2]dioxaborolan-2-yl)-1H-indole (3, 2.43 g, 10 mmol), and 3-bromochlorobenzene (1.76 mL, 15 mmol) in THF (34 mL)) were added Palladium catalyst Pd(PPh₃)₄ (347 mg, 0.3 mmol) and the freshly prepared sodium hydroxide solution (1.20 g, 30 mmol in 14 mL water). The system was degassed and then charged with nitrogen. The degas procedure was repeated for three times. The mixture was stirred under nitrogen at 70° C. oil bath for 15 hours. TLC showed the completion of the coupling reaction. The mixture was cooled to room temperature, diluted with ethyl acetate, and separated from water layer. The ethyl acetate solution was washed by brine, dried over Na₂SO₄, and concentrated. The crude product was purified by a silica gel column eluting with hexanes—EtOAc (9:1) to provide 2.06 g (91%) of the product 4-(3-chloro-phenyl)-1H-indole as a white solid.

¹H-NMR (400 MHz, DMSO-d₆) δ 11.32 (br s, 1H, NH), 7.66 (m, 2H, aromatic), 7.53 (t, 1H, aromatic), 7.45 (m, 3H, aromatic), 7.20 (t, 1H, aromatic), 7.11 (d, 1H, aromatic), 6.53 (d, 1H, aromatic).

Example A-6

4-(4-Bromo-phenyl)-1H-indole

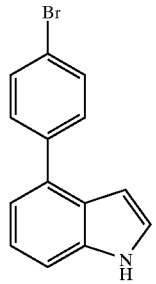

To a mixture of 4-(4,4,5,5-tetramethyl-[1,3,2]dioxaborolan-2-yl)-1H-indole (3, 2.43 g, 10 mmol), and 1,4-dibromobenzene (11.8 g, 50 mmol) in THF (34 mL)) were added Palladium catalyst Pd(PPh₃)₄ (347 mg, 0.3 mmol) and the freshly prepared sodium hydroxide solution (1.20 g, 30 mmol in 14 mL water). The system was degassed and then charged with nitrogen. The degas procedure was repeated for three times. The mixture was stirred under nitrogen at 70° C. oil bath for 15 hours. TLC showed the completion of the coupling reaction. The mixture was cooled to room temperature, diluted with ethyl acetate, and separated from water layer. The ethyl acetate solution was washed by brine, dried over Na₂SO₄, and concentrated. The crude product was purified by a silica gel column eluting with hexanes—EtOAc (9:1) to provide 1.50 g (55%) of the product 4-(4-bromo-phenyl)-1H-indole as a white solid.

¹H-NMR (400 MHz, DMSO-d₆) δ 11.29 (br s, 1H, NH), 7.65 (m, 4H, aromatic), 7.41 (m, 2H, aromatic), 7.17 (t, 1H, aromatic), 7.08 (m, 1H, aromatic), 6.51 (m, 1H, aromatic).

Example A-7

4-(3-Bromo-phenyl)-1H-indole

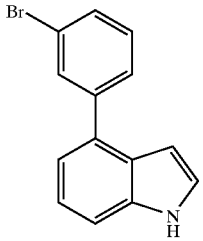

To a mixture of 4-(4,4,5,5-tetramethyl-[1,3,2]dioxaborolan-2-yl)-1H-indole (3, 2.43 g, 10 mmol), and 1,4-dibromobenzene (11.8 g, 50 mmol) in THF (34 mL)) were added Palladium catalyst Pd(PPh₃)₄ (347 mg, 0.3 mmol) and the freshly prepared sodium hydroxide solution (1.20 g, 30 mmol in 14 mL water). The system was degassed and then charged with nitrogen. The degas procedure was repeated for three times. The mixture was stirred under nitrogen at 70° C. oil bath for 15 hours. TLC showed the completion of the coupling reaction. The mixture was cooled to room temperature, diluted with ethyl acetate, and separated from water layer. The ethyl acetate solution was washed by brine, dried over Na₂SO₄, and concentrated. The crude product was purified by a silica gel column eluting with hexanes—EtOAc (9:1) to provide 2.02 g (74%) of the product 4-(3-bromo-phenyl)-1H-indole as a white solid.

¹H-NMR (400 MHz, DMSO-d₆) δ 11.33 (br s, 1H, NH), 7.80 (m, 1H, aromatic), 7.68 (d, 1H, aromatic), 7.57 (m, 1H, aromatic), 7.45 (m, 3H, aromatic), 7.19 (t, 1H, aromatic), 7.10 (d, 1H, aromatic), 6.52 (m, 1H, aromatic). MS m/z 271, 273 [M⁺+1].

Example A-8

4-(4-Methoxy-phenyl)-1H-indole

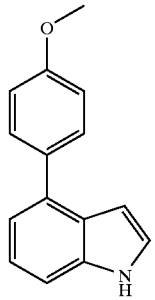

To a mixture of 4-bromoindole (1.96 g, 10 mmol), and 4-methoxyphenylboronic acid (1.52 g, 10 mmol) in THF (34 mL)) were added Palladium catalyst Pd(PPh₃)₄ (347 mg, 0.3 mmol) and the freshly prepared sodium hydroxide solution (1.20 g, 30 mmol in 14 mL water). The system was degassed and then charged with nitrogen. The degas procedure was repeated for three times. The mixture was stirred under nitrogen at 70° C. oil bath for 16 hours. TLC showed the completion of the coupling reaction. The mixture was cooled to room temperature, diluted with ethyl acetate, and separated from water layer. The ethyl acetate solution was washed by brine, dried over $Na_2SO_4$, and concentrated. The crude product was purified by a silica gel column eluting with hexanes—EtOAc (9:1) to provide 1.85 g (83%) of the product 4-(4-Methoxy-phenyl)-1H-indole as a white solid.

$^1$H-NMR (400 MHz, DMSO-$d_6$) δ 11.21 (br s, 1H, NH), 7.61 (m, 2H, aromatic), 7.38 (m, 2H, aromatic), 7.15 (t, 1H, aromatic), 7.05 (m, 3H, aromatic), 6.52 (m, 1H, aromatic), 3.30 (s, 3H, $CH_3$). MS m/z 224 [$M^+$+1].

Example A-9

4-(3-Methoxy-phenyl)-1H-indole

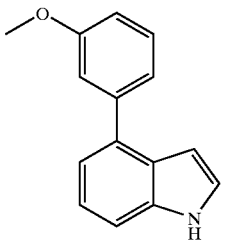

To a mixture of 4-bromoindole (1.96 g, 10 mmol), and 3-methoxyphenylboronic acid (1.52 g, 10 mmol) in THF (34 mL)) were added Palladium catalyst $Pd(PPh_3)_4$ (347 mg, 0.3 mmol) and the freshly prepared sodium hydroxide solution (1.20 g, 30 mmol in 14 mL water). The system was degassed and then charged with nitrogen. The degas procedure was repeated for three times. The mixture was stirred under nitrogen at 70° C. oil bath for 16 hours. TLC showed the completion of the coupling reaction. The mixture was cooled to room temperature, diluted with ethyl acetate, and separated from water layer. The ethyl acetate solution was washed by brine, dried over $Na_2SO_4$, and concentrated. The crude product was purified by a silica gel column eluting with hexanes—EtOAc (9:1) to provide 1.83 g (82%) of the product 4-(3-methoxy-phenyl)-1H-indole as colorless syrup.

$^1$H-NMR (400 MHz, DMSO-$d_6$) δ 11.26 (brs, 1H, NH), 7.41 (m, 3H, aromatic), 7.25 (d, 1H, aromatic), 7.18 (m, 2H, aromatic), 7.11 (d, 1H, aromatic), 6.95 (m, 1H, aromatic), 6.57 (m, 1H, aromatic), 3.82 (s, 3H, $CH_3$). MS m/z 224 [$M^+$+1].

Example A-10

4-(2-Fluoro-phenyl)-1H-indole

To a mixture of 4-(4,4,5,5-tetramethyl-[1,3,2] dioxaborolan-2-yl)-1H-indole (3, 2.431 g, 10.0 mmol), and 2-bromofluorobenzene (1.75 g, 10.1 mmol) in THF (34 mL)) were added Palladium catalyst $Pd(PPh_3)_4$ (0.347 g, 0.30 mmol) and the freshly prepared sodium hydroxide solution (1.20 g, 30.0 mmol in 14 mL water). The system was degassed and then charged with nitrogen. The degas procedure was repeated for three times. The mixture was stirred under nitrogen at 75° C. oil bath for 15 hours. TLC showed the completion of the coupling reaction. The mixture was cooled to room temperature, diluted with ethyl acetate, and separated from water layer. The ethyl acetate solution was washed by brine, dried over $Na_2SO_4$, and concentrated. The crude product was purified by a silica gel column eluting with hexanes—EtOAc (9:1) to provide 1.35 g (64%) of the product 4-(2-fluoro-phenyl)-1H-indole as a white solid.

$^1$H-NMR (400 MHz, DMSO-$d_6$) δ 11.25 (br s, 1H, NH), 7.55 (m, 1H, aromatic), 7.38 (m, 5H, aromatic), 7.18 (t, 1H, aromatic), 7.03 (d, 1H, aromatic), 6.27 (m, 1H, aromatic). MS m/z 212 [$M^+$+1].

Example A-11

4-(3-Trifluoromethyl-phenyl)-1H-indole

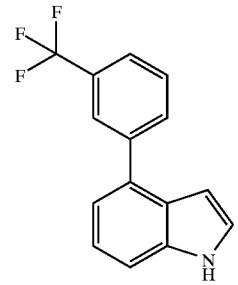

To a mixture of 4-bromoindole (3.00 g, 15.3 mmol), and 3-trifluoromethylphenylboronic acid (2.91 g, 15.3 mmol) in THF (52 mL)) were added Palladium catalyst $Pd(PPh_3)_4$ (530 mg, 0.46 mmol) and the freshly prepared sodium hydroxide solution (1.84 g, 45.9 mmol in 21 mL water). The system was degassed and then charged with nitrogen. The degas procedure was repeated for three times. The mixture was stirred under nitrogen at 75° C. oil bath for 16 hours. TLC showed the completion of the coupling reaction. The mixture was cooled to room temperature, diluted with ethyl acetate, and separated from water layer. The ethyl acetate solution was washed by brine, dried over $Na_2SO_4$, and concentrated. The crude product was purified by a silica gel column eluting with hexanes—EtOAc (9:1) to provide 3.55 g (89%) of the product 4-(3-trifluoromethyl-phenyl)-1H-indole.

$^1$H-NMR (400 MHz, DMSO-d$_6$) δ 11.40 (br s, 1H, NH), 7.98 (t, 1H, aromatic), 7.95 (s, 1H, aromatic), 7.73 (m, 2H, aromatic), 7.50 (d, 1H, aromatic), 7.47 (t, 1H, aromatic), 7.22 (t, 1H, aromatic), 7.16 (d, 1H, aromatic), 6.54 (s, 1H, aromatic). MS m/z 262 [M$^+$+1].

Example A-12

4-(3-Chloro-4-fluoro-phenyl)-1H-indole

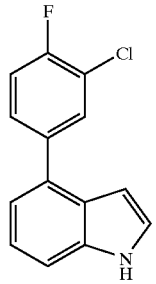

To a mixture of 4-(4,4,5,5-tetramethyl-[1,3,2] dioxaborolan-2-yl)-1H-indole (3, 3.00 g, 12.34 mmol), and 4-bromo-2-chloro-fluorobenzene (2.58 g, 12.34 mmol) in THF (42 mL)) were added Palladium catalyst Pd(PPh$_3$)$_4$ (0.428 g, 0.37 mmol) and the freshly prepared sodium hydroxide solution (1.50 g, 37.02 mmol in 17 mL water). The system was degassed and then charged with nitrogen. The degas procedure was repeated for three times. The mixture was stirred under nitrogen at 75° C. oil bath for 15 hours. TLC showed the completion of the coupling reaction. The mixture was cooled to room temperature, diluted with ethyl acetate, and separated from water layer. The ethyl acetate solution was washed by brine, dried over Na$_2$SO$_4$, and concentrated. The crude product was purified by a silica gel column eluting with hexanes—EtOAc (9:1) to provide 2.11 g (70%) of the product 4-(3-chloro-4-fluoro-phenyl)-1H-indole as a white solid.

$^1$H-NMR (400 MHz, DMSO-d$_6$) δ 11.34 (br s, 1H, NH), 7.79 (dd, 1H, aromatic), 7.67 (m, 1H, aromatic), 7.53 (t, 1H, aromatic), 7.44 (m, 2H, aromatic), 7.19 (t, 1H, aromatic), 7.10 (d, 1H, aromatic), 6.52 (m, 1H, aromatic). MS m/z 244 [M$^-$−1].

Example A-13

4-(3-Trifluoromethoxy-phenyl)-1H-indole

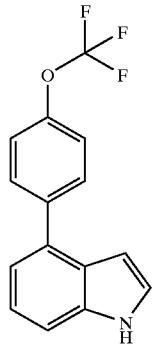

To a mixture of 4-bromoindole (4.50 g, 22.95 mmol), and 4-trifluoromethoxyphenylboronic acid (4.73 g, 22.95 mmol) in THF (78 mL)) were added Palladium catalyst Pd(PPh$_3$)$_4$ (795.6 mg, 0.69 mmol) and the freshly prepared sodium hydroxide solution (2.75 g, 68.9 mmol in 32 mL water). The system was degassed and then charged with nitrogen. The degas procedure was repeated for three times. The mixture was stirred under nitrogen at 75° C. oil bath for 16 hours. TLC showed the completion of the coupling reaction. The mixture was cooled to room temperature, diluted with ethyl acetate, and separated from water layer. The ethyl acetate solution was washed by brine, dried over Na$_2$SO$_4$, and concentrated. The crude product was purified by a silica gel column eluting with hexanes—EtOAc (9:1) to provide 5.56 g (78%) of the product 4-(4-trifluoromethoxy-phenyl)-1H-indole.

$^1$H-NMR (400 MHz, DMSO-d$_6$) δ 11.32 (br s, 1H, NH), 7.78 (d, 2H, aromatic), 7.45 (m, 4H, aromatic), 7.20 (t, 1H, aromatic), 7.10 (d, 1H, aromatic), 6.55 (m, 1H, aromatic). MS m/z 278 [M$^+$+1].

Example A-14

2-Fluoro-5-(1H-indol-4-yl)-benzonitrile

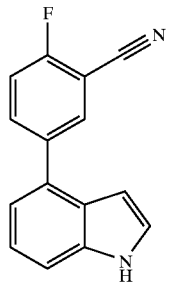

To a mixture of 4-(4,4,5,5-tetramethyl-[1,3,2] dioxaborolan-2-yl)-1H-indole (4 g, 16.4 mmol), and 5-bromo-2-fluorobenzonitrile (3.28 g, 16.4 mmol) in THF (564 mL) were added Palladium catalyst Pd(PPh$_3$)$_4$ (0.6 g, 0.5 mmol) and the freshly prepared sodium carbonate solution (5.22 g in 23 mL of water). The system was degassed and then charged with nitrogen. The degas procedure was repeated for three times. The mixture was stirred under nitrogen at 83° C. oil bath for overnight. TLC showed the completion of the coupling reaction. The mixture was cooled to room temperature, diluted with ethyl acetate, and separated from water layer. The ethyl acetate solution was washed with brine, and dried over Na$_2$SO$_4$. After filtration, the solvents were evaporated, and the crude product was purified by a silica gel column to give 2.18 g (56%) of 2-fluoro-5-(1H-indol-4-yl)-benzonitrile.

Example A-15

4-Biphenyl-3-yl-1H-indole

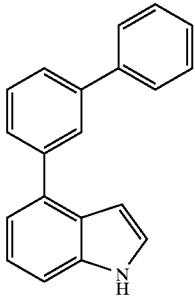

To a mixture of 4-bromoindole (2.1 g, 10 mmol), and 3-biphenylboronic acid (2.2 g, 10 mmol) in THF (34.5 mL) were added Palladium catalyst Pd(PPh$_3$)$_4$ (0.35 g, 0.3 mmol) and the freshly prepared sodium hydroxide solution (1.21 g, 30 mmol in 14 mL of water). The system was degassed and then charged with nitrogen. The degas procedure was repeated for three times. The mixture was stirred under nitrogen at 75° C. oil bath for overnight. TLC showed the completion of the coupling reaction. The mixture was cooled to room temperature, diluted with ethyl acetate, and separated from water layer. The ethyl acetate solution was washed with brine, and dried over Na$_2$SO$_4$. After filtration, the solvents were evaporated, and the crude product was purified on a silica gel column to give 4-biphenyl-3-yl-1H-indole.

Example A-16

4-Biphenyl-2-yl-1H-indole

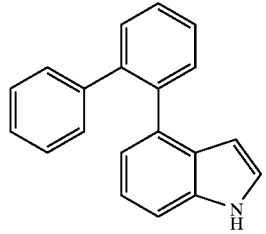

To a mixture of 4-bromoindole (1 g, 5 mmol), and 2-biphenylboronic acid (1 g, 5 mmol) in THF (17 mL) were added Palladium catalyst Pd(PPh$_3$)$_4$ (0.2 g, 0. 17 mmol) and the freshly prepared sodium hydroxide solution (0.6 g, 15 mmol in 7 mL of water). The system was degassed and then charged with nitrogen. The degas procedure was repeated for three times. The mixture was stirred under nitrogen at 75° C. oil bath for overnight. TLC showed the completion of the coupling reaction. The mixture was cooled to room temperature, diluted with ethyl acetate, and separated from water layer. The ethyl acetate solution was washed with brine, and dried over Na$_2$SO$_4$. After filtration, the solvents were evaporated, and the crude product was purified on a silica gel column to give 1.26 g (93%) of 4-biphenyl-2-yl-1H-indole.

Example A-17

4-(3,5-Difluoro-phenyl)-1H-indole

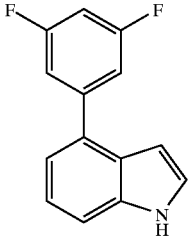

To a mixture of 4-bromoindole (12.42 g, 63.3 mmol), and 3,5-difluorophenylboronic acid (10.0 g, 63.3 mmol) in THF (108 mL) were added Palladium catalyst Pd(PPh$_3$)$_4$ (2.2 g, 1.9 mmol) and the freshly prepared sodium hydroxide solution (7.6 g, 190 mmol in 89 mL water). The system was degassed and then charged with nitrogen. The degas procedure was repeated for three times. The mixture was stirred under nitrogen at 85° C. oil bath for overnight. TLC showed the completion of the coupling reaction. The mixture was cooled to room temperature, filtered through celite, diluted with ethyl acetate, and separated from water layer. The ethyl acetate solution was washed with brine, dried over Na$_2$SO$_4$, and concentrated. The crude product was purified by a silica gel column to provide 4-(3,5-difluoro-phenyl)-1H-indole.

Example A-18

[3-(1H-Indol-4-yl)-phenyl]-acetic Acid

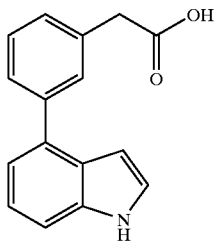

To a mixture of 4-(4,4,5,5-tetramethyl-[1,3,2]dioxaborolan-2-yl)-1H-indole (15.52 g, 63.72 mmol), and 3-bromo-phenylacetic acid (13.78 g, 63.72 mmol) in THF (192 mL) were added Palladium catalyst Pd(PPh$_3$)$_4$ (2.21 g, 1.9 mmol) and the freshly prepared sodium hydroxide solution (7.65 g in 90 mL of water). The system was degassed and then charged with nitrogen. The degas procedure was repeated for three times. The mixture was stirred under nitrogen in a 70° C. oil bath for over the weekend. TLC showed the completion of the coupling reaction. The mixture was cooled to room temperature, diluted with ethyl acetate, and separated from water layer. The water layer was acidified with dil. HCl solution to pH 4–5 and extracted with ethyl acetate. The ethyl acetate solution was washed with water, brine, and dried over Na$_2$SO$_4$. After filtration, the solvents were evaporated, and the crude product was purified on a silica gel column to give 13.5 g (84%) of [3-(1H-indol-4-yl)-phenyl]-acetic acid.

Example A-19

2-[3-(1H-Indol-4-yl)-phenyl]-N,N-Dimethyl-acetamide

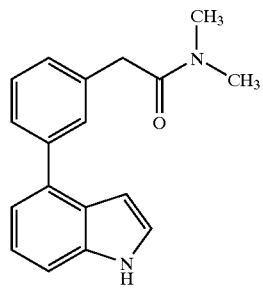

Dimethylamine (2M in THF, 5 mL) was added to a mixture of [3-(1H-indol-4-yl)-phenyl]-acetic acid (1.26 g, 5 mmol), EDC (1.19 g, 1.25 eq.) and HOBt (675 mg, 1 eq.) in THF (10 mL) was stirred at rt for 5 hours. The reaction was concentrated, diluted with ethyl acetate, washed with 10% $Na_2CO_3$ (3x), brine, dried and concentrated. The residue was purified on a silica gel column to give 658 mg of 2-[3-(1H-indol-4-yl)-phenyl]-N,N-dimethyl-acetamide as a solid.

Example A-20

{2-[3-(1H-Indol-4-yl)-phenyl]-ethyl}-dimethyl-amine

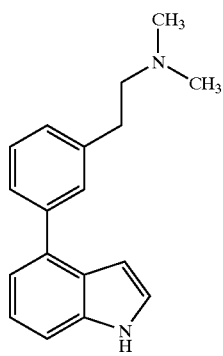

To a suspension of LAH (276 mg, 7.2 mmol) in THF (20 mL) under nitrogen at rt was added dropwise a solution of 2-[3-(1H-indol-4-yl)-phenyl]-N,N-dimethyl-acetamide (500 mg, 1.8 mmol) in THF (10 mL). After stirring at rt for 6 hours, the reaction was quenched with water (0.6 mL) dropwise. The precipitate was filtered off, washed with ethyl acetate (3x), the filtrate was concentrated t give 640 mg of {2-[3-(1H-indol-4-yl)-phenyl]-ethyl}-dimethyl-amine.

Example A-21

5-(1H-Indol-4-yl)-1H-indazol-3-ylamine

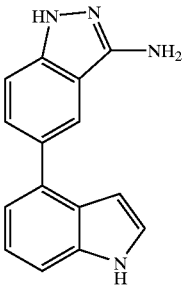

Hydrazine hydrate (0.4 mL, 12.7 mmol) was added to a solution of 2-fluoro-5-(1H-indol-4-yl)-benzonitrile (1.2 g, 5.08 mmol) in n-butanol (25 mL). The mixture was heated to reflux under nitrogen for 3 days. The reaction was cooled to room temperature and the solvent was removed. The residue was purified on a silica gel column eluting with DCM:MeOH (95:5) to give 1.05 g (83%) of 5-(1H-indol-4-yl)-1H-indazol-3-ylamine as a white foam.

$^1$H-NMR (400 MHz, DMSO-$d_6$) δ 11.40 (s, 1H, NH), 11.18 (s, 1H, NH), 7.96 (s, 1H), 7.54 (dd, 1H), 7.29–7.38 (m, 3H), 7.14 (t, 1H), 7.05 (d, 1H), 6.58 (s, 1H), 5.4 (br s, 2H, $NH_2$). MS m/z 249 [M$^+$+1].

Example A-22

4-(2,6-Difluoro-phenyl)-1H-indole

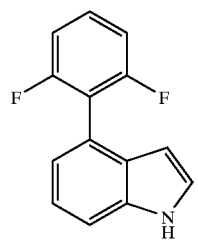

To a mixture of 4-(4,4,5,5-tetramethyl-[1,3,2]dioxaborolan-2-yl)-1H-indole (11.34 g, 46.6 mmol), and 1-bromo-2,6-difluorobenzene (9 g, 46.6 mmol) in 1,2-dimethoxyethane (204 mL) were added Palladium catalyst Pd(PPh$_3$)$_4$ (1.62 g, 1.4 mmol) and the freshly prepared sodium carbonate solution (15.19 g in 66 mL of water). The system was degassed and then charged with nitrogen. The degas procedure was repeated for three times. The mixture was stirred under nitrogen at 110° C. oil bath for overnight. TLC showed the completion of the coupling reaction. The mixture was cooled to room temperature, diluted with ethyl acetate, and separated from water layer. The ethyl acetate solution was washed with brine, and dried over $Na_2SO_4$. After filtration, the solvents were evaporated, and the crude product was purified by a silica gel column to give 9.77 g (91%) of 4-(2,6-difluoro-phenyl)-1H-indole.

Example A-23

3-(1H-Indol-4-yl)-benzoic Acid

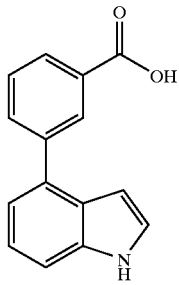

To a mixture of 4-bromoindole (11.81 g, 60.26 mmol), and 3-carboxyphenylboronic acid (10.0 g, 60.6 mmol) in acetonitrile (100 mL) and DMF (100 mL) were added Palladium catalyst Pd(PPh$_3$)$_4$ (2.09 g, 1.81 mmol) and the freshly prepared sodium hydroxide solution (9.64 g, 241 mmol in 80 mL water). The system was degassed and then charged with nitrogen. The degas procedure was repeated for three times. The mixture was stirred under argon at 110° C. oil bath for 4 hours. TLC showed the completion of the coupling reaction. The mixture was cooled to room temperature, filtered through celite, diluted with ethyl acetate, and separated from water layer. The ethyl acetate solution was washed with brine, dried over MgSO$_4$, and concentrated. The crude product was purified by a silica gel column eluting with DCM:Hexanes:acetic acid (100:1:1) to provide 10.2 g (71%) of 3-(1H-indol-4-yl)-benzoic acid as a gray yellow solid.

$^1$H-NMR (400 MHz, DMSO-d$_6$) δ 13.02 (s, 1H, NH), 11.31 (s, 1H), 8.21–8.26 (m, 1H), 7.87–7.97 (m, 2H), 7.58–7.65 (m, 1H), 7.41–7.45 (m, 2H), 7.08–7.22 (m, 2H), 6.51 (brs, 1H). MS m/z 238 [M$^+$+1].

Example A-24

4-(3,4-Dimethoxy-phenyl)-1H-indole

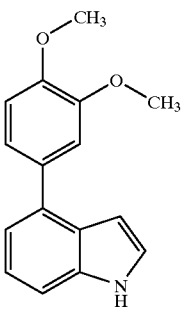

To a mixture of 4-(4,4,5,5-tetramethyl-[1,3,2]dioxaborolan-2-yl)-1H-indole (10 g, 41.1 mmol), and 4-bromoveratrole (8.93 g, 41.1 mmol) in THF (140 mL) were added Palladium catalyst Pd(PPh$_3$)$_4$ (1.43 g, 1.23 mmol) and the freshly prepared sodium hydroxide solution (5.08 g in 58 mL of water). The system was degassed and then charged with nitrogen. The degas procedure was repeated for three times. The mixture was stirred under nitrogen at 80° C. oil bath for overnight. TLC showed the completion of the coupling reaction. The mixture was cooled to room temperature, diluted with ethyl acetate, and separated from water layer. The ethyl acetate solution was washed with brine, and dried over Na$_2$SO$_4$. After filtration, the solvents were evaporated, and the crude product was purified by a silica gel column to give 7.47 g (72%) of 4-(3,4-dimethoxy-phenyl)-1H-indole.

Example A-25

2-[3-(1H-Indol-4-yl)-phenoxy]-ethanol

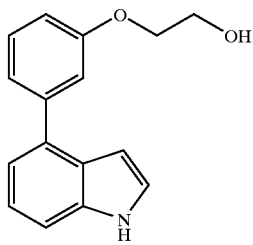

A mixture of 3-bromo-phenol (10 g, 56.64 mmol), 2-bromoethanol (4.65 mL) and cesium carbonate (18.64 g, 1 eq.) in DMF (25 mL) was stirred at rt for overnight. The mixture was then heated in a 70° C. oil bath for about 3 hours. More 2-bromoethanol (3 mL) was added and heating was increased to 80° C. and stirred for overnight. The reaction was allowed to cool to rt and the insolubles were filtered off. The filtrate was poured into water and extracted with ethyl acetate (2×200 mL), washed with 10% Na$_2$CO$_3$ (3×), brine (2×), dried and concentrated. The residue was purified on a silica gel column to give 2-(3-bromo-phenoxy)-ethanol.

To a mixture of 4-(4,4,5,5-tetramethyl-[1,3,2]dioxaborolan-2-yl)-1H-indole (5.49 g, 22.5 mmol) and 2-(3-bromo-phenoxy)-ethanol (4.9 g, 22.5 mmol) in THF (68 mL) was added Palladium catalyst Pd(PPh$_3$)$_4$ (473 mg, 0.03 eq.) and the freshly prepared sodium hydroxide solution (2.7 g in 31.5 mL of water). The system was degassed and then charged with nitrogen. The degas procedure was repeated for three times. The mixture was stirred under nitrogen at 70° C. oil bath for overnight. TLC showed the completion of the coupling reaction. The mixture was cooled to room temperature, diluted with ethyl acetate, and separated from water layer. The ethyl acetate solution was washed with brine (4×), and dried over Na$_2$SO$_4$ and concentrated. The residue was purified on a silica gel column to give 5.4 g (95%) of 2-[3-(1H-indol-4-yl)-phenoxy]-ethanol.

$^1$H-NMR (400 MHz, CDCl$_3$) δ 8.35 (br s, 1H, NH), 7.39 (m, 2H), 7.32 (m, 1H), 7.28 (m, 2H), 7.24 (m, 1H), 7.19 (dd, 1H), 6.93 (m, 1H), 6.73 (m, 1H), 4.15 (m, 3H), 4.0 (m, 2H). MS m/z 254 [M$^+$+1].

Example A-26

4-(2,3-Difluoro-phenyl)-1H-indole

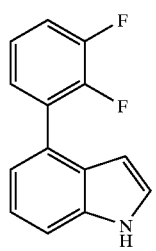

To a mixture of 4-(4,4,5,5-tetramethyl-[1,3,2]dioxaborolan-2-yl)-1H-indole (3,78 g, 15.5 mmol), and 1-bromo-2,3-difluorobenzene (3 g, 15.5 mmol) in THF (55 mL) were added Palladium catalyst Pd(PPh$_3$)$_4$ (0.54 g, 0.47 mmol) and the freshly prepared sodium hydroxide solution (1.865 g, 47 mmol in 22 mL of water). The system was degassed and then charged with nitrogen. The degas procedure was repeated for three times. The mixture was stirred under nitrogen at 75° C. oil bath for overnight. TLC showed the completion of the coupling reaction. The mixture was cooled to room temperature, diluted with ethyl acetate, and separated from water layer. The ethyl acetate solution was washed with brine, and dried over Na$_2$SO$_4$. After filtration, the solvents were evaporated, and the crude product was purified by a silica gel column to give 2.92 g (82%) of 4-(2,3-difluoro-phenyl)-1H-indole.

Example A-27

4-(2,4-Difluoro-phenyl)-1H-indole

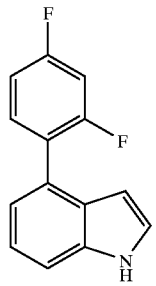

To a mixture of 4-bromoindole (6.2 g, 31.7 mmol), and 2,4-difluorophenylboronic acid (5 g, 31.7 mmol) in THF (108 mL) were added Palladium catalyst Pd(PPh$_3$)$_4$ (0.67 g, 0.95 mmol) and the freshly prepared sodium hydroxide solution (3.8 g, 95 mmol in 45 mL of water). The system was degassed and then charged with nitrogen. The degas procedure was repeated for three times. The mixture was stirred under nitrogen at 80° C. oil bath for over the weekend. TLC showed the completion of the coupling reaction. The mixture was cooled to room temperature, diluted with ethyl acetate, and separated from water layer. The ethyl acetate solution was washed with brine, and dried over Na$_2$SO$_4$. After filtration, the solvents were evaporated, and the crude product was purified by a silica gel column to give 6.55 g (90%) of 4-(2,4-difluoro-phenyl)-1H-indole.

Example A-28

4-(2-Chloro-phenyl)-1H-indole

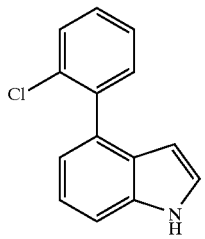

To a mixture of 4-bromoindole (5.5 g, 28 mmol), and 2-chlorophenylboronic acid (4.4 g, 28 mmol) in THF (96 mL) were added Palladium catalyst Pd(PPh$_3$)$_4$ (0.975 g, 0.8 mmol) and the freshly prepared sodium hydroxide solution (3.4 g, 84 mmol in 40 mL of water). The system was degassed and then charged with nitrogen. The degas procedure was repeated for three times. The mixture was stirred under nitrogen at 75° C. oil bath for overnight. TLC showed the completion of the coupling reaction. The mixture was cooled to room temperature, diluted with ethyl acetate, and separated from water layer. The ethyl acetate solution was washed with brine, and dried over Na$_2$SO$_4$. After filtration, the solvents were evaporated, and the crude product was purified by a silica gel column to give 2.41 g (38%) of 4-(2-chloro-phenyl)-1H-indole.

Example A-29

[3-(1H-Indol-4-yl)-phenyl]-acetic Acid Methyl Ester

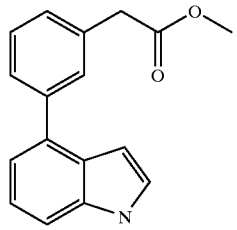

A mixture of [3-(1H-indol-4-yl)-phenyl]-acetic acid (4 g, 15.9 mmol), 4N HCl (20 drops) in methanol (30 mL) and dioxane was stirred at rt for 4 hours. The reaction was concentrated, diluted in ethyl acetate, washed with NaHCO$_3$ (2×), brine (2×), dried and concentrated to give 3.72 g (88%) of [3-(1H-Indol-4-yl)-phenyl]-acetic acid methyl ester.

General Procedure for the Syntheses of the Precursor, 4-Aryl-1,3-dihydro-indol-2-one

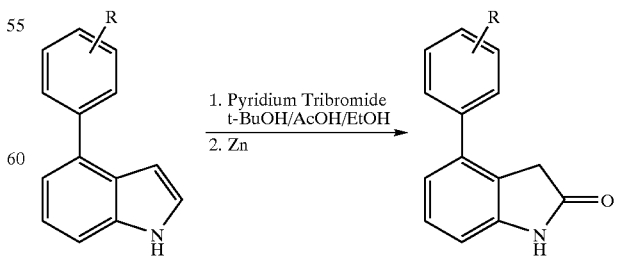

To the suspension of 4-aryl-1H-indole (1 molar equivalent) in 2-methyl-2-propanol-ethanol-acetic acid (3:2:1) (11 mL) (0.1 M) was added pyridinium tribromide (90% purity from Aldrich, 3 molar equivalent) portionwise. The mixture was stirred at 27° C. for 3 hours, and then to the mixture was added acetic acid. Zinc dust (10 molar equivalent) was added to the reaction mixture portionwise, and the reaction mixture was stirred at room temperature for one hour. The unreacted zinc dust was filtered off and washed with ethanol. The filtrate was concentrated and the syrupy residue was suspended in water for 1 hour. The solid product was precipitated out, filtered, and washed repeatedly with water to remove the zinc salt and pyridine salt. After high vacuum dry, a pure product was obtained. If the product couldn't precipitate out, ethyl acetate was used to extract the product from water. The combined extracts were washed with water, 0.5% HCl water solution, sat. $Na_2CO_3$, and brine, dried over $Na_2SO_4$. After filtration, condensation, the crude product was triturated with diethyl ether to provide pure product.

Example A-30

4-Phenyl-1,3-dihydro-indol-2-one

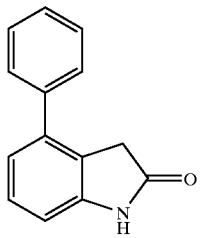

To the suspension of 4-phenyl-1H-indole (1.1 g, 5.7 mmol) in 2-methyl-2-propanol (33 mL), ethanol (22 mL) and acetic acid (11 mL) was added pyridinium tribromide (90% purity from Aldrich, 6.1 g, 17.1 mmol) portionwise over 10 minutes. The mixture was stirred at room temperature for 2 hours, and then to the mixture was added acetic acid (50 mL). After stirring at room temperature for one hour, water (0.5 mL) and zinc (3.7 g, 57 mmol) were added to the reaction mixture and stirring was continued for another hour. The unreacted zinc dust was filtered off and washed with methanol. The filtrate was concentrated and the syrupy residue was suspended in water (100 mL) for overnight. The solid product was filtered, washed repeatedly with water to remove the zinc salt and pyridine salt. After high vacuum dry, 800 mg (67%) of 4-phenyl-1,3-dihydro-indol-2-one as a light yellow solid was obtained.

$^1$H NMR (360 MHz, DMSO-$d_6$) 10.46 (br s, 1H, NH), 7.56 (d, J=7.1 Hz, 1H), 7.45 (t, J=7.6 Hz, 1H), 7.37 (m, 1H), 7.27 (t, J=7.7 Hz, 1H), 7.01 (d, J=7.7 Hz, 1H), 6.82 (d, J=7.7 Hz, 1H), 3.59 (s, 2H, CH$_2$). MS m/z 210 [M$^+$+1].

Example A-31

4-(4-Fluoro-phenyl)-1,3-dihydro-indol-2-one

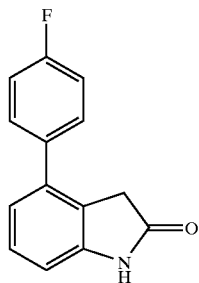

To the suspension of 4-(4-fluoro-phenyl)-1H-indole (2.28 g, 10.79 mmol) in t-BuOH-ethanol-acetic acid (3:2:1) (147 mL) was added pyridinium tribromide (90% purity from Aldrich, 11.51 g, 32.38 mmol)) portionwise. The mixture was stirred at 27° C. for 3 hours, and then to the mixture was added acetic acid (108 mL). Zinc dust (10.52 g, 162 mmol) was added to the reaction mixture portionwise, and the reaction mixture was stirred at room temperature for one hour. The unreacted zinc dust was filtered off and washed with ethanol. The filtrate was concentrated and the syrupy residue was suspended in water for 4 hour. The solid product was precipitated out, filtered, and washed repeatedly with water to remove the zinc salt and pyridine salt. After high vacuum dry, a pure product (2.40 g, 98%) was obtained.

$^1$H NMR (360 MHz, DMSO-$d_6$) 10.47 (br s, 1H, NH), 7.61 (m, 2H, aromatic), 7.27 (m, 3H, aromatic), 7.12 (d, 1H, aromatic), 6.90 (d, 1H, aromatic), 3.59 (s, 2H).

Example A-32

4-(3-Fluoro-phenyl)-1,3-dihydro-indol-2-one

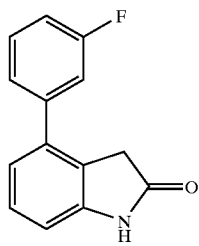

To the suspension of 4-(3-fluoro-phenyl)-1H-indole (1.40 g, 6.63 mmol) in t-BuOH-ethanol-acetic acid (3:2:1) (81 mL) was added pyridinium tribromide (90% purity from Aldrich, 7.07 g, 19.88 mmol)) portionwise. The mixture was stirred at 27° C. for 3 hours, and then to the mixture was added acetic acid (30 mL). Zinc dust was added to the reaction mixture portionwise until the color changed from deep red to light yellow, and the reaction mixture was stirred at room temperature for one hour. The unreacted zinc dust was filtered off and washed with ethanol. The filtrate was concentrated, and the syrupy residue was dissolved in ethyl acetate, which was washed with water, 0.5 N HCl, sat. NaHCO$_3$ and brine, and dried over Na$_2$SO$_4$. After filtration and evaporation, the crude product was triturated with diethyl ether to provide product 4-(3-fluoro-phenyl)-1,3-dihydro-indol-2-one (1.34 g, 89%) as a tan solid.

$^1$H-NMR (400 MHz, DMSO-$d_6$) δ 10.50 (br s, 1H, NH), 7.51 (m, 1H, aromatic), 7.47 (m, 2H, aromatic), 7.43 (t, 1H, aromatic), 7.30 (m, 1H, aromatic), 7.22 (d 1H, aromatic), 6.85 (d, 1H, aromatic), 3.64 (s, 2H, CH$_2$).

Example A-33

4-(4-Chloro-phenyl)-1,3-dihydro-indol-2-one

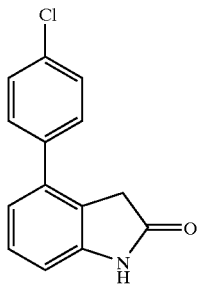

To the suspension of 4-(4-chloro-phenyl)-1H-indole (1.52 g, 6.68 mmol) in t-BuOH-ethanol-acetic acid (3:2:1) (81 mL) was added pyridinium tribromide (90% purity from Aldrich, 7.12 g, 20.0 mmol)) portionwise. The mixture was stirred at 27° C. for 3 hours, and then to the mixture was added acetic acid (30 mL). Zinc dust was added to the reaction mixture portionwise until the color changed from deep red to light yellow, and the reaction mixture was stirred at room temperature for one hour. The unreacted zinc dust was filtered off and washed with ethanol. The filtrate was concentrated, and the syrupy residue was suspended in water (500 mL) for 0.5 hour. The solid product was precipitated out, filtered, and washed repeatedly with water to remove the zinc salt and pyridine salt. After high vacuum dry, a pure product (1.54 g, 94%) was obtained.

$^1$H-NMR (400 MHz, DMSO-d$_6$) δ 11.29 (br s, 1H, NH), 7.70 (m, 2H, aromatic), 7.55 (m, 2H, aromatic), 7.43 (m, 2H, aromatic), 7.19 (t, 1H, aromatic), 7.08 (m, 1H aromatic), 6.53 (m, 1H, aromatic).

Example A-34

4-(3-Chloro-phenyl)-1,3-dihydro-indol-2-one

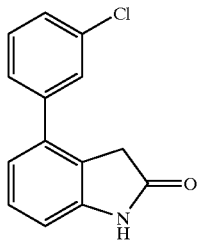

To the suspension of 4-(3-chloro-phenyl)-1H-indole (1.52 g, 6.68 mmol) in t-BuOH-ethanol-acetic acid (3:2:1) (81 mL) was added pyridinium tribromide (90% purity from Aldrich, 7.12 g, 20.0 mmol)) portionwise. The mixture was stirred at 27° C. for 3 hours, and then to the mixture was added acetic acid (30 mL). Zinc dust was added to the reaction mixture portionwise until the color changed from deep red to light yellow, and the reaction mixture was stirred at room temperature for one hour. The unreacted zinc dust was filtered off and washed with ethanol. The filtrate was concentrated, and the syrupy residue was dissolved in ethyl acetate, which was washed with water, 0.5 N HCl, sat. NaHCO$_3$ and brine, and dried over Na$_2$SO$_4$. After filtration and evaporation, the crude product was triturated with diethyl ether to provide product 4-(3-chloro-phenyl)-1,3-dihydro-indol-2-one (1.55 g, 95%) as a tan solid.

$^1$H-NMR (400 MHz, DMSO-d$_6$) δ 10.50 (br s, 1H, NH), 7.62 (m, 1H, aromatic), 7.56 (m, 1H, aromatic), 7.52 (m, 2H, aromatic), 7.29 (t, 1H, aromatic), 7.03 (d, 1H, aromatic), 6.85 (m, 1H, aromatic), 3.63 (s, 2H, CH$_2$).

Example A-35

4-(4-Bromo-phenyl)-1,3-dihydro-indol-2-one

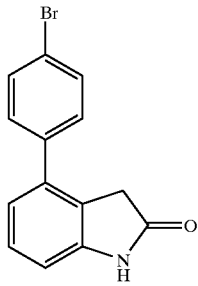

To the suspension of 4-(4-bromo-phenyl)-1H-indole (1.20 g, 4.41 mmol) in t-BuOH-ethanol-acetic acid (3:2:1) (54 mL) was added pyridinium tribromide (4.23 g, 13.23 mmol)) portionwise. The mixture was stirred at 27° C. for 3 hours, and then to the mixture was added acetic acid (30 mL). Zinc dust was added to the reaction mixture portionwise until the color changed from deep red to light yellow, and the reaction mixture was stirred at room temperature for one hour. The unreacted zinc dust was filtered off and washed with ethanol. The filtrate was concentrated, and the syrupy residue was suspended in water (300 mL) for 0.5 hour. The solid product was precipitated out, filtered, and washed repeatedly with water to remove the zinc salt and pyridine salt. After high vacuum dry, a pure product (1.12 g, 88%) was obtained.

$^1$H-NMR (400 MHz, DMSO-d$_6$) δ 10.50 (br s, 1H, NH), 7.64 (d, 2H, aromatic), 7.54 (d, 2H, aromatic), 7.28 (t, 1H, aromatic), 7.01 (d, 1H, aromatic), 6.84 (d, 1H, aromatic), 3.60 (s, 2H, CH$_2$).

Example A-36

4-(3-Bromo-phenyl)-1,3-dihydro-indol-2-one

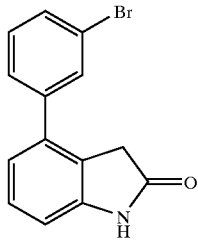

To the suspension of 4-(3-bromo-phenyl)-1H-indole (1.48 g, 5.44 mmol) in t-BuOH-ethanol-acetic acid (3:2:1) (66 mL) was added pyridinium tribromide (90% purity from Aldrich, 5.80 g, 16.3 mmol)) portionwise. The mixture was stirred at 27° C. for 3 hours, and then to the mixture was added acetic acid (26 mL). Zinc dust was added to the reaction mixture portionwise until the color changed from deep red to light yellow, and the reaction mixture was stirred at room temperature for one hour. The unreacted zinc dust was filtered off and washed with ethanol. The filtrate was concentrated, and the syrupy residue was dissolved in ethyl acetate, which was washed with water, 0.5 N HCl, sat. NaHCO$_3$ and brine, and dried over Na$_2$SO$_4$. After filtration and evaporation, the crude product was triturated with diethyl ether to provide product 4-(3-bromo-phenyl)-1,3-dihydro-indol-2-one (1.02 g, 65%) as a tan solid.

$^1$H-NMR (400 MHz, DMSO-d$_6$) δ 10.50 (br s, 1H, NH), 7.74 (m, 1H, aromatic), 7.58 (m, 2H, aromatic), 7.41 (t, 1H, aromatic), 7.28 (t, 1H, aromatic), 7.02 (d, 1H, aromatic), 6.85 (d, 1H, aromatic), 3.62 (s, 2H, CH$_2$).

Example A-37

4-(4-Methoxy-phenyl)-1,3-dihydro-indol-2-one

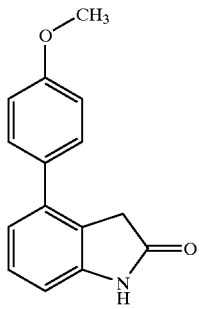

To the suspension of 4-(4-methoxy-phenyl)-1H-indole (1.84 g, 8.24 mmol) in t-BuOH-ethanol-acetic acid (3:2:1) (99 mL) was added pyridinium tribromide (90% purity from Aldrich, 8.78 g, 24.72 mmol)) portionwise. The mixture was stirred at 27° C. for 3 hours, and then to the mixture was added acetic acid (40 mL). Zinc dust was added to the reaction mixture portionwise until the color changed from deep red to light yellow, and the reaction mixture was stirred at room temperature for one hour. The unreacted zinc dust was filtered off and washed with ethanol. The filtrate was concentrated, and the syrupy residue was dissolved in ethyl acetate, which was washed with water, 0.5 N HCl, sat. NaHCO$_3$ and brine, and dried over Na$_2$SO$_4$. After filtration and evaporation, the crude product was triturated with diethyl ether to provide product 4-(4-methoxy-phenyl)-1,3-dihydro-indol-2-one (1.66 g, 84%) as a tan solid.

$^1$H-NMR (400 MHz, DMSO-d$_6$) δ 10.44 (br s, 1H, NH), 7.50 (m, 2H, aromatic), 7.24 (m, 1H, aromatic), 6.97 (m, 3H, aromatic), 6.78 (m, 1H, aromatic), 3.79 (s, 3H, CH$_3$), 3.58 (s, 2H, CH$_2$).

Example A-38

4-(3-Methoxy-phenyl)1,3-dihydro-indol-2-one

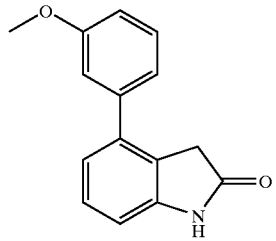

To the suspension of 4-(4-methoxy-phenyl)-1H-indole (1.73 g, 7.75 mmol) in t-BuOH-ethanol-acetic acid (3:2:1) (93 mL) was added pyridinium tribromide (90% purity from Aldrich, 8.26 g, 23.24 mmol)) portionwise. The mixture was stirred at 27° C. for 3 hours, and then to the mixture was added acetic acid (38 mL). Zinc dust was added to the reaction mixture portionwise until the color changed from deep red to light yellow, and the reaction mixture was stirred at room temperature for one hour. The unreacted zinc dust was filtered off and washed with ethanol. The filtrate was concentrated, and the syrupy residue was dissolved in ethyl acetate, which was washed with water, 0.5 N HCl, sat. NaHCO$_3$ and brine, and dried over Na$_2$SO$_4$. After filtration and evaporation, the crude product was triturated with diethyl ether to provide product 4-(3-methoxy-phenyl)-1,3-dihydro-indol-2-one (0.97 g, 52%) as a tan solid.

$^1$H-NMR (400 MHz, DMSO-d$_6$) δ 10.45 (br s, 1H, NH), 7.34 (t, 1H, aromatic), 7.25 (t, 1H, aromatic), 7.12 (d, 1H, aromatic), 7.08 (m, 1H, aromatic), 7.02 (d, 1H, aromatic), 6.93 (m, 1H, aromatic), 6.82 (d, 1H, aromatic), 3.80 (s, 3H, CH$_3$).

Example A-39

4-(2-Fluoro-phenyl)-1,3-dihydro-indol-2-one

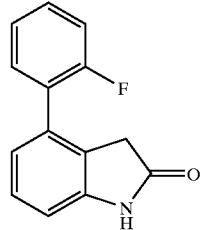

To the suspension of 4-(2-fluoro-phenyl)-1H-indole (1.30 g, 6.15 mmol) in t-BuOH-ethanol-acetic acid (3:2:1) (74 mL) was added pyridinium tribromide (5.90 g, 18.46 mmol)) portionwise. The mixture was stirred at 27° C. for 3 hours, and then to the mixture was added acetic acid (30 mL). Zinc dust was added to the reaction mixture portionwise until the color changed from deep red to light yellow, and the reaction mixture was stirred at room temperature for one hour. The unreacted zinc dust was filtered off and washed with ethanol. The filtrate was concentrated, and the syrupy residue was dissolved in ethyl acetate, which was washed with water, 0.5 N HCl, sat. NaHCO$_3$ and brine, and dried over Na$_2$SO$_4$. After filtration and evaporation, the crude product was triturated with diethyl ether to provide product 4-(2-fluoro-phenyl)-1,3-dihydro-indol-2-one (0.59 g, 42%) as a tan solid.

$^1$H-NMR (400 MHz, DMSO-d$_6$) δ 10.51 (br s, 1H, NH), 7.50 (m, 1H, aromatic), 7.48 (m, 1H, aromatic), 7.29 (m, 3H, aromatic), 6.95 (d, 1H, aromatic), 6.87 (d, 1H, aromatic), 3.39 (s, 2H, CH$_2$).

Example A-40

4-(3-Trifluoromethyl-phenyl)-1,3-dihydro-indol-2-one

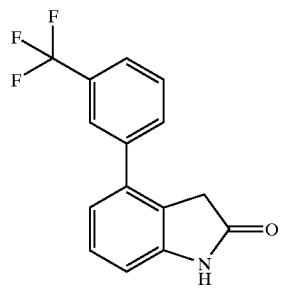

To the suspension of 4-(3-trifluoromethyl-phenyl)-1H-indole (3.37 g, 12.90 mmol) in t-BuOH-ethanol-acetic acid (3:2:1) (155 mL) was added pyridinium tribromide (12.38 g, 38.70 mmol)) portionwise. The mixture was stirred at 27° C. for 3 hours, and then to the mixture was added acetic acid (63 mL). Zinc dust was added to the reaction mixture portionwise until the color changed from deep red to light yellow, and the reaction mixture was stirred at room temperature for one hour. The unreacted zinc dust was filtered off and washed with ethanol. The filtrate was concentrated, and the syrupy residue was dissolved in ethyl acetate, which was washed with water, 0.5 N HCl, sat. NaHCO$_3$ and brine, and dried over Na$_2$SO$_4$. After filtration and evaporation, the crude product was triturated with diethyl ether to provide product 4-(3-trifluoromethyl-phenyl)-1,3-dihydro-indol-2-one (2.07 g, 58%) as a tan solid.

$^1$H-NMR (400 MHz, DMSO-d$_6$) δ 10.52 (br s, 1H, NH), 7.90 (d, 1H, aromatic), 7.87 (s, 1H, aromatic), 7.74 (d, 1H, aromatic), 7.69 (t, 1H, aromatic), 7.31 (t, 1H, aromatic), 7.07 (d, 1H, aromatic), 6.88 (d, 1H, aromatic), 3.64 (s, 2H, CH$_2$).

Example A-41

4-(3-chloro-4-fluoro-phenyl)-1,3-dihydro-indol-2-one

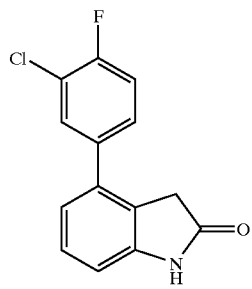

To the suspension of 4-(3-chloro-4-fluoro-phenyl)-1H-indole (2.03 g, 8.26 mmol) in t-BuOH-ethanol-acetic acid (3:2:1) (99 mL) was added pyridinium tribromide (7.93 g, 24.79 mmol)) portionwise. The mixture was stirred at 27° C. for 3 hours, and then to the mixture was added acetic acid (40 mL). Zinc dust was added to the reaction mixture portionwise until the color changed from deep red to light yellow, and the reaction mixture was stirred at room temperature for one hour. The unreacted zinc dust was filtered off and washed with ethanol. The filtrate was concentrated, and the syrupy residue was dissolved in ethyl acetate, which was washed with water, 0.5 N HCl, sat. NaHCO$_3$ and brine, and dried over Na$_2$SO$_4$. After filtration and evaporation, the crude product was triturated with diethyl ether to provide product 4-(3-chloro-4-fluoro-phenyl)-1,3-dihydro-indol-2-one (1.39 g, 64%) as a tan solid.

$^1$H-NMR (400 MHz, DMSO-d$_6$) δ 10.52 (br s, 1H, NH), 7.79 (dd, 1H, aromatic), 7.59 (m, 1H, aromatic), 7.49 (t, 1H, aromatic), 7.28 (t, 1H, aromatic), 7.02 (d, 1H, aromatic), 6.85 (d, 1H, aromatic), 3.63 (s, 2H, CH$_2$).

Example A-42

4-(4-Trifluoromethoxy-phenyl)-1,3-dihydro-indol-2-one

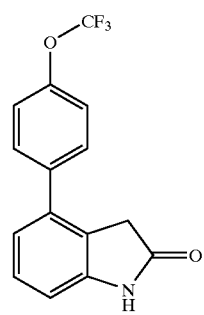

To the suspension of 4-(4-trifluoromethoxy-phenyl)-1H-indole (4.93 g, 17.78 mmol) in t-BuOH-ethanol-acetic acid (3:2:1) (261 mL) was added pyridinium tribromide (17.06 g, 53.34 mmol)) portionwise. The mixture was stirred at 27° C. for 3 hours, and then to the mixture was added acetic acid (105 mL). Zinc dust was added to the reaction mixture portionwise until the color changed from deep red to light yellow, and the reaction mixture was stirred at room temperature for one hour. The unreacted zinc dust was filtered off and washed with ethanol. The filtrate was concentrated, and the syrupy residue was dissolved in ethyl acetate, which was washed with water, 0.5 N HCl, sat. NaHCO$_3$ and brine, and dried over Na$_2$SO$_4$. After filtration and evaporation, the crude product was triturated with diethyl ether to provide product 4-(4-trifluoromethoxy-phenyl)-1,3-dihydro-indol-2-one (2.05 g, 39%) as a tan solid.

$^1$H-NMR (400 MHz, DMSO-d$_6$) δ 10.50 (br s, 1H, NH), 7.71 (d, 2H, aromatic), 7.43 (d, 2H, aromatic), 7.29 (t, 1H, aromatic), 7.03 (d, 1H, aromatic), 6.85 (d, 1H, aromatic), 3.62 (s, 2H, CH$_2$).

Example A-43

4-[3-(2-Hydroxy-ethyl)-phenyl]-1,3-dihydro-indol-2-one

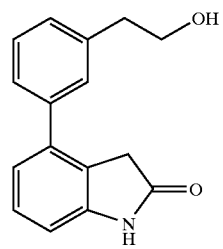

To a suspension of NaBH$_4$ (600 mg, 16 mmol) in 15% H$_2$O/MeOH (6 mL) under nitrogen at rt was added dropwise a solution of [3-(2-oxo-2,3-dihydro-1H-indol-4-yl)-phenyl]-acetic acid methyl ester (450 mg, 1.6 mmol) in THF (3 mL). After stirring at rt for overnight, to the reaction was added $CaCl_2$ (300 mg) and stirring was continued for another 5 hours. The reaction was quenched with acetic acid (2 mL), concentrated, diluted with ethyl acetate, washed with 0.5 N HCl (3×15 mL), 10% $NaHCO_3$ (3×15 mL), brine (1×), dried and concentrated. The oily residue was purified to give 384 mg (95%) of 4-[3-(2-hydroxy-ethyl)-phenyl]-1,3-dihydro-indol-2-one.

$^1$H-NMR (400 MHz, DMSO-$d_6$) δ 10.49 (s, 1H, NH), 7.35–7.43 (m, 3H), 7.28 (t, 1H), 7.23 (d, 1H), 7.03 (d, 1H), 6.83 (d, 1H), 4.68 (t, 1H, OH), 3.67 (m, 2H), 3.62 (s, 2H), 2.80 (t, 2H). MS m/z 254.1 [M$^+$+1].

Example A-44

2-Fluoro-5-(2-oxo-2,3-dihydro-1H-indol-4-yl)-benzonitrile

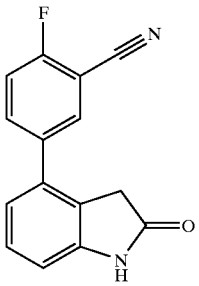

To the suspension of 2-fluoro-5-(1H-indol-4-yl)-benzonitrile (2.68 g, 11.34 mmol) in t-BuOH:ethanol:acetic acid (72 mL:43 mL:23 mL) was added pyridinium tribromide (10.91 g, 34.1 mmol) portionwise. The mixture was stirred at room temperature for 3 hours, and then to the mixture was added acetic acid (55 mL). Zinc dust (4 g, 61.2 mmol) was added to the reaction mixture portionwise. After stirring for one hour, any unreacted zinc was filtered off and most of the solvent was removed under reduced pressure. The residue was diluted with ethyl acetate, washed with water (3×), sat. $NaHCO_3$, brine, dried over $Na_2SO_4$, concentrated and triturated with ether to give 1.93 g (68%) of 2-fluoro-5-(2-oxo-2,3-dihydro-1H-indol-4-yl)-benzonitrile.

$^1$H-NMR (400 MHz, DMSO-$d_6$) δ 10.52 (s, 1H, NH), 8.13 (dd, 1H), 7.96 (m, 1H), 7.59 (t, 1H), 7.28 (t, 1H), 7.03 (d, 1H), 6.85 (d, 1H), 3.64 (s, 2H). MS m/z 251.4 [M−1].

Example A-45

4-Biphenyl-3-yl-1,3-dihydro-indol-2-one

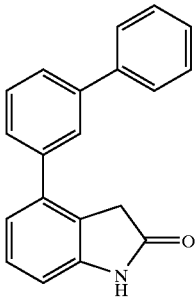

To the suspension of 4-bipheny-3-yl-1H-indole (3.5 g, 13 mmol) in t-BuOH:ethanol:acetic acid (82 mL:49 mL:269 mL) was added pyridinium tribromide (12.7 g, 40 mmol) portionwise. The mixture was stirred at room temperature for 3 hours, and then to the mixture was added acetic acid (63 mL). Zinc dust (4.39 g, 67 mmol) was added to the reaction mixture portionwise. After stirring for one hour, any unreacted zinc was filtered off and most of the solvent was removed under reduced pressure. The residue was diluted with ethyl acetate, washed with water (3×), sat. $NaHCO_3$, brine, dried over $Na_2SO_4$, concentrated and triturated with ether to give 2.67 g (72%) of 4-biphenyl-3-yl-1,3-dihydro-indol-2-one.

$^1$H-NMR (400 MHz, DMSO-$d_6$) δ 10.49 (s, 1H, NH), 7.78 (m, 1H), 7.71 (m, 2H), 7.65 (m, 1H), 7.53 (m, 2H), 7.47 (m, 2H), 7.37 (m, 1H), 7.28 (t, 1H), 7.10 (d, 1H), 6.83 (d, 1H), 3.66 (s, 2H). MS m/z 286 [M$^+$+1].

Example A-46

4-Biphenyl-2-yl-1,3-dihydro-indol-2-one

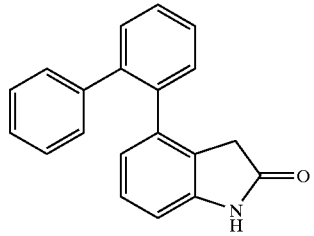

To the suspension of 4-bipheny-2-yl-1H-indole (1.18 g, 4.4 mmol) in t-BuOH:ethanol:acetic acid (28 mL:17 mL:9 mL) was added pyridinium tribromide (4.39 g, 13.7 mmol) portionwise. The mixture was stirred at room temperature for 3 hours, and then to the mixture was added acetic acid (22 mL). Zinc dust (1.63 g, 25 mmol) was added to the reaction mixture portionwise. After stirring for one hour, any unreacted zinc was filtered off and most of the solvent was removed under reduced pressure. The residue was diluted with ethyl acetate, washed with water (3×), sat. $NaHCO_3$, brine, dried over $Na_2SO_4$, concentrated and triturated with ether to give 0.93 g (74%) of 4-biphenyl-2-yl-1,3-dihydro-indol-2-one.

$^1$H-NMR (400 MHz, DMSO-$d_6$) δ 10.30 (s, 1H, NH), 7.35–7.45 (m, 4H), 7.2 (m, 4H), 7.12 (m, 1H), 7.08 (t, 1H), 6.67 (m, 2H), 2.86 (s, 2H).

Example A-47

4-(3,5-Difluoro-phenyl)-1,3-dihydro-indol-2-one

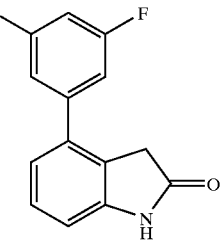

To the suspension of 4-(3,5-difluoro-phenyl)-1H-indole (13.52 g, 59 mmol) in t-BuOH:ethanol:acetic acid (375 mL:225 mL:115 mL) was added pyridinium tribromide (57 g, 177 mmol) portionwise. The mixture was stirred at room temperature for 3 hours, and then to the mixture was added with acetic acid (286 mL). Zinc dust (19.25 g, 295 mmol) was added to the reaction mixture portionwise. After stirring for one hour, any unreacted zinc was filtered off and most of the solvent was removed under reduced pressure. The residue was diluted with ethyl acetate, washed with water (5x), neutralized with 1N HCl, washed with sat. NaHCO$_3$, brine, dried over Na$_2$SO$_4$, concentrated and triturated with ether to give 9.88 g (68%) of 4-(3,5-difluoro-phenyl)-1,3-dihydro-indol-2-one.

$^1$H-NMR (400 MHz, DMSO-d$_6$) δ 10.51 (s, 1H, NH), 7.2–7.35 (m, 5H), 7.04 (dd, 1H), 6.86 (d, 1H), 3.66 (s, 2H). MS m/z 244 [M−1].

Example A-48

[3-(2-oxo-2,3-Dihydro-1H-indol-4-yl)-phenyl]-acetic Acid

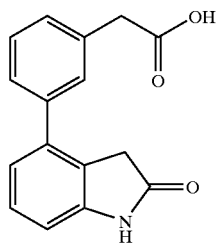

To the suspension of [3-(1H-indol-4-yl)-phenyl]-acetic acid (3.52 g, 14 mmol) in t-BuOH:ethanol:acetic acid (93 mL:56 mL:67 mL) was added pyridinium tribromide (14.14 g, 42 mmol) portionwise. The mixture was stirred at room temperature for 3 hours, and then to the mixture was added acetic acid (60 mL). Water (2 mL) and zinc dust (14 g, excess) were added to the reaction mixture portionwise. After stirring for one hour, any unreacted zinc was filtered off and most of the solvent was removed under reduced pressure. The residue was diluted with ethyl acetate, washed with water (3x), sat. NaHCO$_3$, brine, dried over Na$_2$SO$_4$ and concentrated to give 2.59 g (70%) of [3-(2-oxo-2,3-dihydro-1H-indol-4-yl)-phenyl]-acetic acid.

$^1$H-NMR (400 MHz, DMSO-d$_6$) δ 12.32 (br s, 1H, OH), 10.46 (s, 1H, NH), 7.43 (m, 2H), 7.37 (t, 1H), 7.25 (m, 2H), 6.98 (dd, 1H), 6.80 (d, 1H), 3.63 (s, 2H), 3.58 (s, 2H). MS m/z 266 [M−1].

Example A-49

N,N-Dimethyl-2-[3-(2-oxo-2,3-dihydro-1H-indol-4-yl)-phenyl]-acetamide

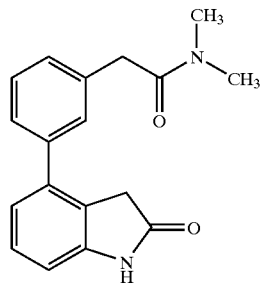

To the suspension of 2-[3-(1H-indol-4-yl)-phenyl]-N,N-dimethyl-acetamide (1.6 g, 5 mmol) in t-BuOH:ethanol:acetic acid (332 mL:20 mL:24 mL) was added pyridinium tribromide (5 g, 15 mmol) portionwise. The mixture was stirred at room temperature for 3 hours, and then to the mixture was added acetic acid (22 mL). Water (0.7 mL) and zinc dust (5 g) were added to the reaction mixture portionwise. After stirring for one hour, any unreacted zinc was filtered off and most of the solvent was removed under reduced pressure. The residue was diluted with ethyl acetate, washed with 0.5 N HCl (2x), 10% Na$_2$CO$_3$ (2x), brine (2x), water, dried over Na$_2$SO$_4$, concentrated and triturated with ether to give N,N-dimethyl-2-[3-(2-oxo-2,3-dihydro-1H-indol-4-yl)-phenyl]-acetamide. MS m/z 293 [M−1].

Example A-50

4-[3-(2-Dimethylamino-ethyl)-phenyl]-1,3-dihydro-indol-2-one

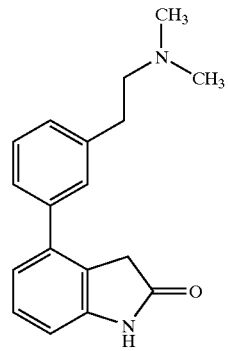

To the suspension of {2-[3-(1H-indol-4-yl)-phenyl]-ethyl}-dimethyl-amine (600 mg, 2.2 mmol) in t-BuOH:ethanol:acetic acid (14.5 mL:8.8 mL:10.5 mL) was added pyridinium tribromide (2.3 g, 6.6 mmol) portionwise. The mixture was stirred at room temperature for 3 hours, and then to the mixture was added acetic acid (9.24 mL). Water (0.32 mL) and zinc dust (2.2 g, 61.2 mmol) was added to the reaction mixture portionwise. After stirring for one hour, any unreacted zinc was filtered off and most of the solvent was removed under reduced pressure. The residue was diluted with ethyl acetate, washed with water (3x), sat. NaHCO$_3$, brine, dried over Na$_2$SO$_4$ and concentrated. The residue was dissolved in methanol (10 mL) and hydrogenated using 10% Pd—C for overnight. The reaction was filtered through celite and the filtrate was concentrated. The residue was purified on a silica gel column to give 4-[3-(2-dimethylamino-ethyl)-phenyl]-1,3-dihydro-indol-2-one $^1$H-NMR (400 MHz, DMSO-d$_6$) δ 10.49 (s, 1H, NH), 7.37–7.46 (m, 3H), 7.26 (t, 2H), 6.81 (d, 1H), 3.60 (s, 2H), 3.08 (m, 2H), 2.93 (m, 2H), 2.62 (s, 6H, 2xCH$_3$).

MS m/z 281.1 [M$^+$+1].

Example A-51

4-(3-Amino-1H-indazol-5-yl)-1,3-dihydro-indol-2-one

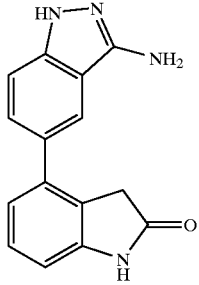

To the suspension of 5-(1H-indol-4-yl)-1H-indazol-3-ylamine (0.82 g, 3.33 mmol) in t-BuOH:ethanol:acetic acid (20.5 mL:12 mL:6 mL) was added pyridinium tribromide (3.17 g, 9.9 mmol) portionwise. The mixture was stirred at room temperature for 3 hours, it immediately became a dark pink color. Zinc dust (excess) was added to the reaction mixture portionwise. After stirring for one hour, the unreacted zinc was filtered off and the solvent was removed under reduced pressure. The residue was washed with ample of water. The solid was triturated with DCM to give 0.563 g (77%) of 4-(3amino-1H-indazol-5-yl)-1,3-dihydro-indol-2-one.

Example A-52

4-(2,6-Difluoro-phenyl)-1,3-dihydro-indol-2-one

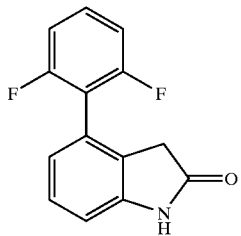

To the suspension of 4-(2,6-difluoro-phenyl)-1H-indole (9.5 g, 41.4 mmol) in t-BuOH:ethanol:acetic acid (262 mL:155 mL:81 mL) was added pyridinium tribromide (40.28 g, 126 mmol) portionwise. The mixture was stirred at room temperature for 3 hours, and then to the mixture was added more acetic acid (200 mL). Zinc dust (14.2 g, 217 mmol) was added to the reaction mixture portionwise. After stirring for one hour, the unreacted zinc was filtered off and most of the solvent was removed under reduced pressure. The residue was diluted with ethyl acetate, washed with water (5×), sat. NaHCO$_3$ (2×), brine (3×), dried over Na$_2$SO$_4$, concentrated, triturated with ether to give 7.1 g (70%) of 4-(2,6-difluoro-phenyl)-1,3-dihydro-indol-2-one as a white solid.

$^1$H-NMR (400 MHz, DMSO-d$_6$) δ 10.53 (s, 1H, NH), 7.50 (m, 1H), 7.25 (m, 3H), 6.90 (m, 2H), 3.25 (s, 2H).

Example A-53

3-(2-oxo-2,3-Dihydro-1H-indol-4-yl)-benzoic Acid

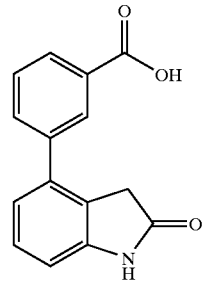

To the suspension of 3-(1H-indol-4-yl)-benzoic acid (7.58 g, 33 mmol) in t-BuOH:ethanol:acetic acid (150 mL:100 mL:50 mL) was added pyridinium tribromide (31.66 g, 99 mmol) portionwise. The mixture was stirred at room temperature for 2 hours, and then to the mixture was added with acetic acid (150 mL). Water (4 mL) and Zinc dust (13.07 g, 200 mmol) was added to the reaction mixture portionwise and stirring was continued at room temperature for 2 hours. The solvent was removed under reduced pressure. The oily residue was suspended in 1N HCl (400 mL) and stirred at room temperature overnight. The precipitate solid was collected by filtration, purified by recrystallization from ethyl acetate to give (6.4 g, 77%) of 3-(2-oxo-2,3-dihydro-1H-indol-4-yl)-benzoic acid as a pinkish white solid.

$^1$H-NMR (400 MHz, DMSO-d$_6$) δ 10.50 (br s, 1H, NH), 8.01–8.05 (m, 1H), 7.90–7.95 (m, 1H), 7.82–7.87 (m, 1H), 7.54–7.60 (m, 1H), 7.26–7.32 (m, 1H), 7.04 (d, J=7.1 Hz, 1H), 6.84 (d, J=7.4 Hz, 1H), 3.58 (s, 2H).

Example A-54

N-Methyl-3-(2-oxo-2,3-dihydro-1H-indol-4-yl)-benzamide

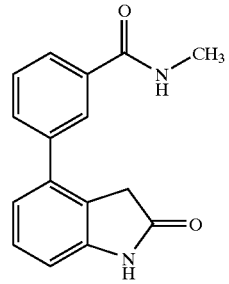

A mixture of 3-(2-oxo-2,3-dihydro-1H-indol-4-yl)-benzoic acid (1.27 g, 5.0 mmol), HOBt (0.68 g, 5.0 mmol) and EDC (1.44 g, 7.5 mmol) in DMF (10 mL) was stirred at room temperature for 30 minutes. To the mixture was added methylamine (2M in THF, 3.75 mL, 7.5 mmol), it was then stirred at room temperature for overnight. Most of the solvent was removed under reduced pressure and the residue was diluted with sat. NaHCO$_3$ (20 mL). The precipitate was collected by filtration, washed with water and dried. The crude product was recrystallized from DCM-hexane to give 1.14 g (86%) of N-methyl-3-(2-oxo-2,3-dihydro-1H-indol-4-yl)-benzamide as a light yellow solid.

$^1$H-NMR (400 MHz, DMSO-d$_6$) δ 8.46–8.53 (m, 1H), 7.94 (m, 1H), 7.80–7.85 (m, 1H), 7.68–7.74 (m, 1H), 7.52 (t,

J=7.8 Hz, 1H), 7.28 (t, J=7.8 Hz, 1H), 7.05 (dd, J=0.8, 7.8 Hz, 1H), 6.83 (d, J=7.4 Hz, 1H), 3.63 (s, 2H), 2.79 (d, J=4.6 Hz, 3H). MS m/z 267 [M$^+$+1].

Example A-55

4-(3,4-Dimethoxy-phenyl)-1,3-dihydro-indol-2-one

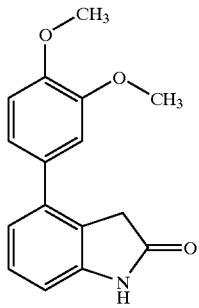

To the suspension of 4-(3,4-dimethoxy-phenyl)-1H-indole (14.7 g, 58 mmol) in t-BuOH:ethanol:acetic acid (367 mL:217 mL:113 mL) was added pyridinium tribromide (55.68 g, 174 mmol) portionwise. The mixture was stirred at room temperature for 3 hours, and then to the mixture was added more acetic acid (287 mL). Zinc dust (18.95 g, 290 mmol) was added to the reaction mixture portionwise. After stirring for one hour, water was added to the reaction. The unreacted zinc was filtered off and most of the solvent was removed under reduced pressure. The residue was diluted with ethyl acetate, washed with water (6×), sat. NaHCO$_3$ (2×), brine (3×), dried over Na$_2$SO$_4$, concentrated and triturated with ether to give 10.14 g (65%) of 4-(3,4-dimethoxy-phenyl)-1,3-dihydro-indol-2-one as an earth colored solid.

$^1$H-NMR (400 MHz, DMSO-d$_6$) δ 10.44 (s, 1H, NH), 7.22 (t, 1H), 7.18 (m, 2H), 7.0 (m, 2H), 6.77 (d, 1H), 3.79 (s, 3H, OCH$_3$), 3.77 (s, 3H, OCH$_3$), 3.6 (s, 2H).

Example A-56

4-[3-(2-Hydroxy-ethoxy)-phenyl]-1,3-dihydro-indol-2-one

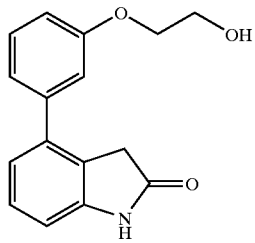

To the suspension of 2-[3-(1H-indol-4-yl)-phenoxy]-ethanol (5.4 g, 21 mmol) in t-BuOH:ethanol:acetic acid (139.5 mL:84 mL:100.5 mL) was added pyridinium tribromide (21.21 g, 63 mmol) portionwise. The mixture was stirred at room temperature for 3 hours, and then to the mixture was added more acetic acid (90 mL) and water (3 mL). Zinc dust (21 g) was added to the reaction mixture portionwise. After stirring for one hour, the unreacted zinc was filtered off and most of the solvent was removed under reduced pressure. The residue was diluted with ethyl acetate, washed with 1N HCl (3×), water (1×), brine (2×), dried over Na$_2$SO$_4$, concentrated. The residue was recrystallized to give 1.82 g (32%) of 4-[3-(2-hydroxy-ethoxy)-phenyl]-1,3-dihydro-indol-2-one.

$^1$H-NMR (400 MHz, DMSO-d$_6$) δ 10.46 (s, 1H, NH), 7.33 (t, 1H), 7.25 (t, 1H), 7.09 (d, 1H), 7.06 (m, 1H), 7.0 (dd, 1H), 6.92 (dd, 1H), 6.80 (d, 1H), 4.86 (t, 1H), 4.02 (t, 2H), 3.71 (q, 2H), 3.58 (s, 2H). MS m/z 270 [M$^+$+1].

Example A-57

4-(2,3-Difluoro-phenyl)-1,3-dihydro-indol-2-one

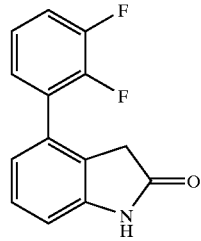

To the suspension of 4-(2,3-difluoro-phenyl)-1H-indole (2.85 g, 12.4 mmol) in t-BuOH:ethanol:acetic acid (78.5 mL:46.5 mL:24.13 mL) was added pyridinium tribromide (11.93 g, 37.3 mmol) portionwise. The mixture was stirred at room temperature for 3 hours, and then to the mixture was added with acetic acid (60 mL). Zinc dust (4.1 g, 62.2 mmol) was added to the reaction mixture portionwise. After stirring for one hour, any unreacted zinc was filtered off and most of the solvent was removed under reduced pressure. The residue was diluted with ethyl acetate, washed with water (5×), sat NaHCO$_3$, brine, dried over Na$_2$SO$_4$, concentrated and triturated with ether to give 2.32 g (76%) of 4-(2,3-difluoro-phenyl)-1,3-dihydro-indol-2-one as an earth colored solid.

$^1$H-NMR (400 MHz, DMSO-d$_6$) δ 10.53 (br s, 1H, NH), 7.45 (m, 1H), 7.29 (m, 3H), 6.96 (d, J=7.8 Hz, 1H), 6.88 (d, J=7.8 Hz, 1H), 3.41 (s, 2H). MS m/z 246.2 [M$^+$+1].

Example A-58

4-Bromo-5-methoxy-1,3-dihydro-indol-2-one

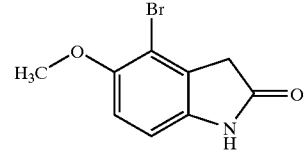

To the suspension of 5-methoxyindole (5.0 g, 34 mmol) in t-BuOH:ethanol:acetic acid (215 mL:127 mL:66 mL) was added pyridinium tribromide (32.6 g, 102 mmol) portionwise. The mixture was stirred at room temperature for 3 hours, and then to the mixture was added with more acetic acid (165 mL). Zinc dust (11.1 g, 170 mmol) was added to the reaction mixture portionwise. After stirring for one hour, the unreacted zinc was filtered off, and the solvent was removed under reduced pressure. The residue was diluted with water, extracted with ethyl acetate. The combined extracts were washed with water (5×), sat. NaHCO$_3$ (2×), brine (3×), dried over Na$_2$SO$_4$, concentrated, triturated with ether to give 2.12 g (26%) of 4-bromo-5-methoxy-1,3-dihydro-indol-2-one.

$^1$H-NMR (400 MHz, DMSO-d$_6$) δ 10.41 (s, 1H, NH), 6.90 (d, J=8 Hz, 1H), 6.74 (d, J=8 Hz, 1H), 3.77 (s, 3H, OCH$_3$), 3.42 (s, 2H).

Example A-59

4-(2,4-Difluoro-phenyl)-1,3-dihydro-indol-2-one

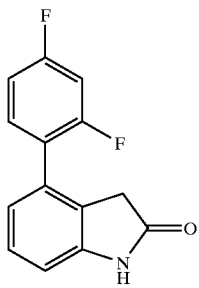

To the suspension of 4-(2,4-difluoro-phenyl)-1H-indole (6.42 g, 28 mmol) in t-BuOH:ethanol:acetic acid (177 mL:105 mL:55 mL) was added pyridinium tribromide (27 g, 84 mmol) portionwise. The mixture was stirred at room temperature for 3 hours, and then to the mixture was added with acetic acid (136 mL). Zinc dust (9.8 g, 150 mmol) was added to the reaction mixture portionwise. After stirring for one hour, any unreacted zinc was filtered off and most of the solvent was removed under reduced pressure. The residue was diluted with ethyl acetate, washed with water (5×), neutralized with 1N HCl, washed with sat. NaHCO$_3$, brine, dried over Na$_2$SO$_4$, concentrated and triturated with ether to give 5.16 g (75%) of 4-(2,4-difluoro-phenyl)-1,3-dihydro-indol-2-one.

$^1$H-NMR (400 MHz, DMSO-d$_6$) δ 10.50 (s, 1H, NH), 7.54 (m, 1H), 7.35 (m, 1H), 7.25 (t, 1H), 7.16 (m, 1H), 6.91 (d, 1H), 6.85 (d, 1H), 3.37 (s, 2H).

Example A-60

4-(2-Chloro-phenyl)-1,3-dihydro-indol-2-one

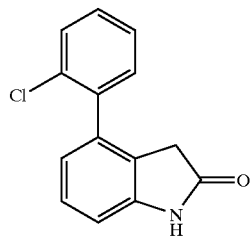

To the suspension of 4-(2-chloro-phenyl)-1H-indole (2.4 g, 10.6 mmol) in t-BuOH:ethanol:acetic acid (67 mL:40 mL:21 mL) was added pyridinium tribromide (10.5 g, 32 mmol) portionwise. The mixture was stirred at room temperature for 3 hours, and then to the mixture was added acetic acid (52 mL). Zinc dust (3.5 g, 53 mmol) was added to the reaction mixture portionwise. After stirring for one hour, any unreacted zinc was filtered off and most of the solvent was removed under reduced pressure. The residue was diluted with ethyl acetate, washed with water (3×), sat. NaHCO$_3$, brine, dried over Na$_2$SO$_4$, concentrated and triturated with ether to give 1.96 g (76%) of 4-(2-chloro-phenyl)-1,3-dihydro-indol-2-one.

$^1$H-NMR (400 MHz, DMSO-d$_6$) δ 10.53 (s, 1H, NH), 7.56 (m, 1H), 7.41 (m, 3H), 7.26 (t, 1H), 6.86 (m, 2H), 3.26 (s, 2H). MS m/z 244.2 [M$^+$+1].

Example A-61

[3-(2-oxo-2,3-Dihydro-1H-indol-4-yl)phenyl]-acetic Acid Methyl Ester

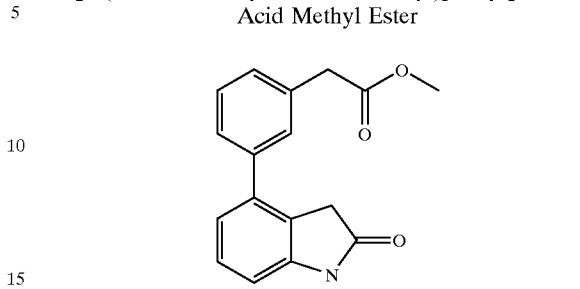

To the suspension of [3-(1H-indol-4-yl)-phenyl]-acetic acid methyl ester (3.72 g, 14 mmol) in t-BuOH:ethanol:acetic acid (93 mL:56 mL:67.2 mL) was added pyridinium tribromide (14.14 g, 44 mmol) portionwise. The mixture was stirred at room temperature for 3 hours, and then to the mixture was added acetic acid (60 mL). Water (2 mL) and zinc dust (14 g, excess) was added to the reaction mixture portionwise. After stirring at rt for one hour, any unreacted zinc was filtered off and most of the solvent was removed under reduced pressure. The residue was diluted with diluted with water (380 mL), extracted with ethyl acetate, washed with 0.5 N HCl (2×), 10% Na$_2$CO$_3$, (2×), brine (2×), water (1×), dried over Na$_2$SO$_4$, concentrated and triturated with ether to give [3-(2-oxo-2,3-dihydro-1H-indol-4-yl)-phenyl]-acetic acid methyl ester.

MS m/z 282 [M$^+$+1].

Syntheses of the Precursor, Pyrrole Aldehydes: 5-Formyl-2,4-dimethyl-1H-pyrrole-3-carboxylic Acid (Pyrrole Aldehyde-1)

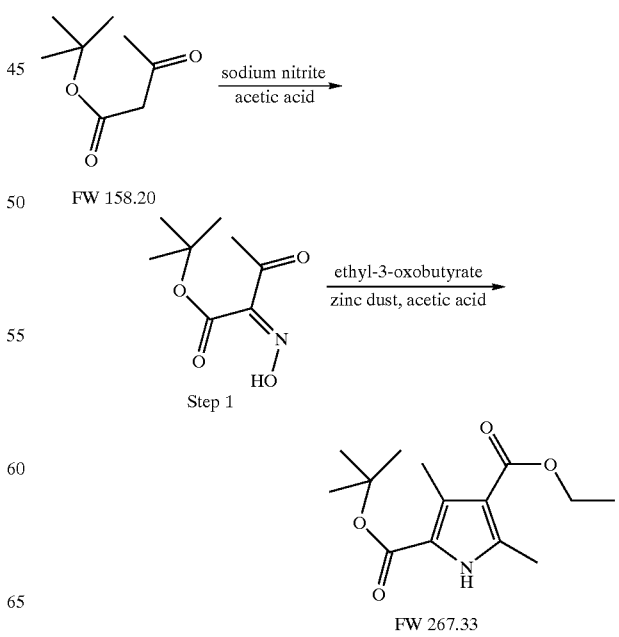

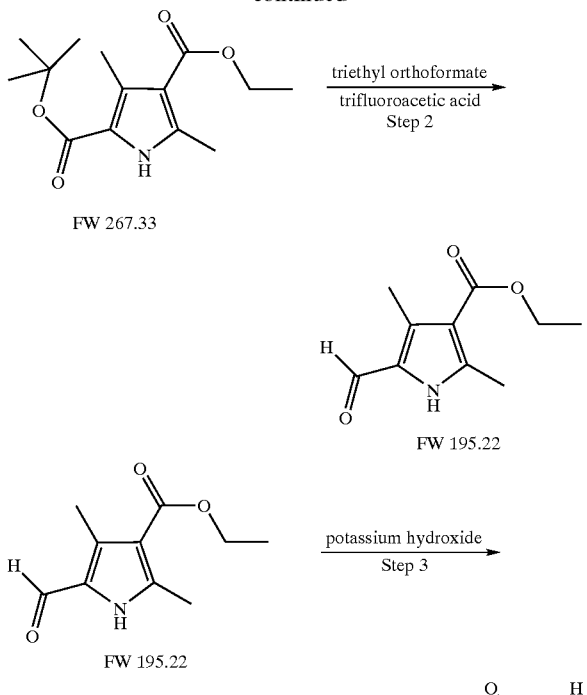

Step 1:

t-Butyl-3-oxobutyrate (158 g, 1 mol) was dissolved in 200 mL of acetic acid in a 500 mL 3-neck round bottom flask equipped with a thermometer, addition funnel and mechanical stirring. The mixture was cooled in an ice bath to about 10° C. Sodium nitrite (69 g, 1 mol) was added over 75 minutes keeping the temperature under 15° C. The cold bath was removed and the mixture stirred for 30 minutes and then allowed to stand for 3.5 hours to give t-butyl-2-hydroximino-3-oxobutyrate.

Ethyl-3-oxobutyrate (130 g, 1 mol) was dissolved in 400 mL of acetic acid in a 2 L 3-neck round bottom flask equipped with a thermometer, an addition funnel, mechanical stirring and placed in an oil bath. Zinc dust (50 g, 0.76 mol) was added and the mixture heated to 60° C. with stirring. The crude t-butyl-2-hydroximino-3-oxobutyrate solution prepared above was cautiously added keeping the temperature at about 65° C. by slowing the addition and cooling the flask. More zinc dust (4×50 g, 3.06 mol) was added in portions during the addition with the last portion added after all the t-butyl ester had been added. The temperature of the mixture reached a maximum of 80° C. At the end of the additions the temperature was 64° C. The temperature was increased by heating to 70–75° C. for one hour and then poured into 5 L of water. The gray floating precipitate was collected by vacuum filtration and washed with 2 L of water to give 354 g of wet crude product. The crude product was dissolved in 1 L of hot methanol and hot filtered to remove zinc. The filtrate was cooled to give a precipitate that was collected by vacuum filtration to give 118 g of product. The filtrate was put in the refrigerator overnight to give a total of 173.2 g of 3,5-dimethyl-1H-pyrrole-2,4-dicarboxylic acid 2-tert-butyl ester 4-ethyl ester.

Step 2:

3,5-Dimethyl-1H-pyrrole-2,4-dicarboxylic acid 2-tert-butyl ester 4-ethyl ester (80.1 g, 0.3 mol) and 400 mL of trifluoroacetic acid were stirred for 5 minutes in a 2 L 3-neck round bottom flask equipped with mechanical stirring and warmed to 40° C. in an oil bath. The mixture was then cooled to −5° C. and triethyl orthoformate (67.0 g, 0.45 mol) was added all at once. The temperature increased to 15° C. The mixture was stirred for about 1 minute, removed from the cold bath and then stirred for 1 hour. The trifluoroacetic acid was removed by rotary evaporation and the residue put in the refrigerator where it solidified. The solid was dissolved by warming and poured into 500 g of ice. The mixture was extracted with 800 mL of dichloromethane to give a red solution and a brown precipitate, both of which were saved. The precipitate was isolated and washed with 150 mL of saturated sodium bicarbonate solution. The dichloromethane phase was washed with 150 mL of sodium bicarbonate and both bicarbonate solutions discarded. The dichloromethane solution was washed with 3 times with 100 mL of water each time. The dichloromethane solution was evaporated to dryness and the dark residue recrystallized twice from hot ethyl acetate after decolorizing with Darco to give golden yellow needles. The brown precipitate was recrystallized from 350 mL of hot ethyl acetate after decolorizing with Darco to give a yellow-red solid. All the recrystallized solids were combined and recrystallized from 500 mL of hot ethanol to give 37.4 g (63.9%) of 5-formyl-2,4-dimethyl-1H-pyrrole-3-carboxylic acid ethyl ester as yellow needles (mp 165.6–166.3° C., lit. 163–164° C.). The evaporated residues from the ethyl acetate and ethanol mother liquors were recrystallized from 500 mL of ethanol to give 10.1 g (17.1%) of a second crop of dirty yellow needles.

Step 3:

5-Formyl-2,4-dimethyl-1H-pyrrole-3-carboxylic acid ethyl ester (2 g, 10 mmol) was added to a solution of potassium hydroxide (3 g, 53 mmol) dissolved in methanol (3 mL) and water (10 mL). The mixture was refluxed for 3 hours, cooled to room temperature and acidified with 6 N hydrochloric acid to pH3. The solid was collected by filtration, washed with water and dried in a vacuum oven overnight to give 1.6 g (93%) of 5-formyl-2,4-dimethyl-1H-pyrrole-3-carboxylic acid.

$^1$H NMR (300 MHz, DMSO-d$_6$) δ 12.09 (s, br, 2H, NH & COOH), 9.59 (s, 1H, CHO), 2.44 (s, 3H, CH$_3$), 2.40 (s, 3H, CH$_3$). MS m/z 167 (M$^+$).

II. General Amidation Procedure

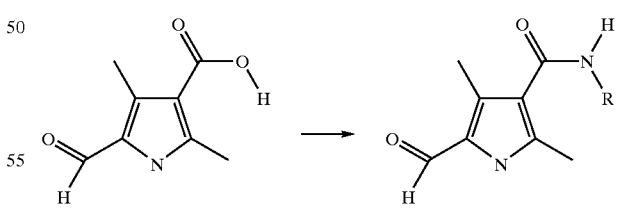

The 5-formyl-2,4-dimethyl-1H-pyrrole-3-carboxylic acid is dissolved in DMF (0.3M) with stirring. To the solution is added 1-ethyl-3-(3-dimethylamino-propylcarbodiimide hydrochloride (EDC, 1.2 equiv.), 1-hydroxybenzotriazole (HOBt, 1.2 eq) followed by the appropriate amine (1.2 eq). The reaction solution is stirred for 12 h, and then DMF solvent was removed. The residue was purified on a silica gel column eluting with 1–5% methanol in dichloromethane to provide the product.

Example B-1

3,5-Dimethyl-4-(4-methyl-piperazine-1-carbonyl)-1H-pyrrole-2-carbaldehyde

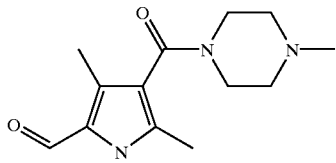

5-Formyl-2,4-dimethyl-1H-pyrrole-3-carboxylic acid (5 g, 29.9 mmol) reacted with N-methylpiperazine (4.0 mL) to give 5.3 g (72%) of 3,5-imethyl-4-(4-methyl-piperazine-1-carbonyl)-1H-pyrrole-2-carbaldehyde.

$^1$H NMR (360 MHz, DMSO-$d_6$) δ 11.82 (s, 1H, NH), 9.50 (s, 1H, CHO), 3.14 (br m, 4H, 2×CH$_2$), 2.29 (br m, 4H, 2×CH$_2$), 2.19 (s, 3H, CH$_3$), 2.17 (s, 3H, CH$_3$), 2.14 (s, 3H, CH$_3$). MS m/z 249 [M]$^+$.

Example B-2

5-Formyl-2,4-dimethyl-1H-pyrrole-3-carboxylic Acid (2-Diethylamino-ethyl)-amide

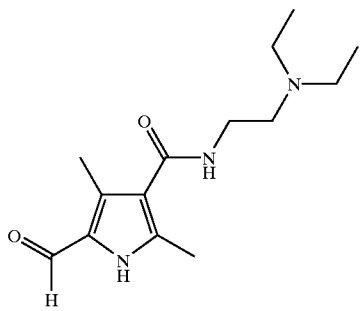

5-Formyl-2,4-dimethyl-1H-pyrrole-3-carboxylic acid (5 g, 2.99 mmol) reacted with N,N-diethylethylenediamine (4.62 mL) to give 6.19 g (78%) of 5-formyl-2,4-dimethyl-1H-pyrrole-3-carboxylic acid (2-diethylamino-ethyl)-amide.

$^1$H NMR (360 MHz, DMSO-$d_6$) δ 11.7 (brs, 1H, NH), 9.52 (s, 1H, CHO), 7.27 (m, 1H, CONH), 3.2 (m, 2H, NCH$_2$), 2.5 (m, 6H, 3×NCH$_2$), 2.35 (s, 3H, CH$_3$), 2.30 (s, 3H, CH$_3$), 0.95 (t, J=6.7 Hz, 6H, 2×NCH$_2$CH$_3$). MS m/z 266 (M$^+$+1)

Example B-3

5-Formyl-2,4-dimethyl-1H-pyrrole-3-carboxylic Acid (2-Pyrrolidin-1-yl-ethyl)-amide

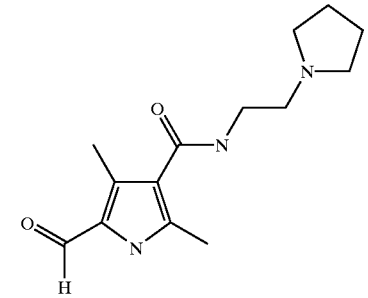

5-Formyl-2,4-dimethyl-1H-pyrrole-3-carboxylic acid (5 g, 29.9 mmol) reacted with 1-(2-aminoethyl)pyrrolidine (4.1 g, 35.9 mmol) to give 5.7 g (73%) of 5-formyl-2,4-dimethyl-1H-pyrrole-3-carboxylic acid (2-pyrrolidin-1-yl-ethyl)-amide.

$^1$H NMR (360 MHz, DMSO-$d_6$) δ 11.79 (br s, 1H, NH), 9.53 (s, 1H, CHO), 7.41 (m, 1H, CONH), 3.28–3.34 (m, 2H, NCH$_2$), 2.53–2.60 (m, 6H, NCH$_2$ and 2×NCH$_2$), 2.35 (s, 3H, CH$_3$), 2.3 (s, 3H, CH$_3$), 1.68 (m, 4H, 2×CH$_2$). MS m/z 264.1 (M$^+$).

Example B-4

5-Formyl-2,4-dimethyl-1H-pyrrole-3-carboxylic Acid (2-[1,2,3]Triazol-1-yl-ethyl)-amide

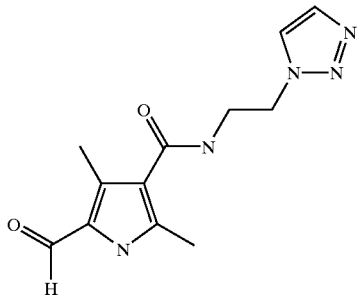

5-Formyl-2,4-dimethyl-1H-pyrrole-3-carboxylic acid (2 g, 11.96 mmol) reacted with 2-[1,2,3]triazol-1-yl-ethylamine (2.66 g, 14.36 mmol) to give 3.05 g (98%) of 5-formyl-2,4-dimethyl-1H-pyrrole-3-carboxylic acid (2-[1,2,3]triazol-1-yl-ethyl)-amide.

$^1$H NMR (360 MHz, DMSO-$d_6$) δ 11.83 (br s, 1H, NH), 9.52 (s, 1H, CHO), 8.12 (d, 1H, J=1.3 Hz, triazole hydrogen), 7.72 (d, 1H, J=1.27 Hz, triazole hydrogen), 7.63 (t, 1H, J=5.6 Hz, CONH), 4.55 (m, 2H, NCH$_2$), 3.66 (m, 2H, CH$_2$), 2.26 (s, 3H, CH$_3$), 2.21 (s, 3H, CH$_3$). MS m/z 262 (M$^+$+1).

Example B-5

3,5-Dimethyl-4-[(cis)-3,5-dimethyl-piperazine-1-carbonyl]-1H-pyrrole-2-carbaldehyde

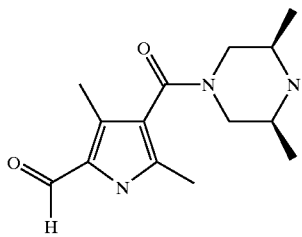

5-Formyl-2,4-dimethyl-1H-pyrrole-3-carboxylic acid (2 g, 11.96 mmol) reacted with cis-2,6-dimethylpiperazine (2.66 g, 14.36 mmol) to give 2.27 g (72%) of 3,5-dimethyl-4-[(cis)-3,5-dimethyl-piperazine-1-carbonyl]-1H-pyrrole-2-carbaldehyde.

$^1$H NMR (360 MHz, DMSO-$d_6$) δ 11.84 (br s, 1H, NH), 9.51 (s, 1H, CHO), 4.30 (br s 1H, NH), 2.50 (m, 4H, 2×CH$_2$), 2.28 (m, 8H, 2×CH$_3$ and 2×CH), 0.96 (m, 6H, 2×CH$_3$). MS m/z 264 (M$^+$+1).

Example B-6

5-Formyl-2,4-dimethyl-1H-pyrrole-3-carboxylic Acid (3-Diethylamino-propyl)-amide

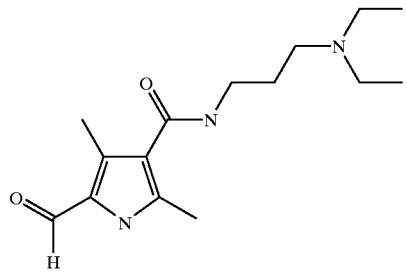

5-Formyl-2,4-dimethyl-1H-pyrrole-3-carboxylic acid (3.0 g, 17.9 mmol) reacted with diethylamino propylamine (2.57 g, 19.7 mmol) to give 3.19 g (64%) of 5-formyl-2,4-dimethyl-1H-pyrrole-3-carboxylic acid (3-diethylamino-propyl)-amide.

$^1$H NMR (360 MHz, DMSO-$d_6$) δ 11.78 (br s, 1H, NH), 9.52 (s, 1H, CHO), 7.5 (m, 1H, CONH), 3.21 (q, J=6.4 Hz, 2H, NCH$_2$CH$_3$), 2.5 (m, 6H, NCH$_2$CH$_3$ and 2×NCH$_2$), 2.35 (s, 3H, CH$_3$), 2.29 (s, 3H, CH$_3$), 1.63 (m, 2H, CH$_2$), 0.96 (t, J=6.8 Hz, 6H, NCH$_2$CH$_3$). MS m/z 280 (M$^+$+1).

Example B-7

5-Formyl-2,4-dimethyl-1H-pyrrole-3-carboxylic Acid (2-Diisopropylamino-ethyl)-amide

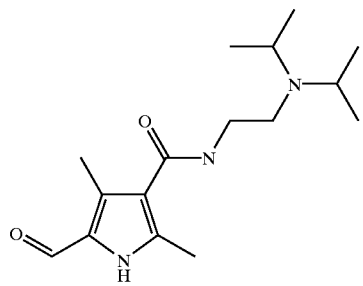

5-Formyl-2,4-dimethyl-1H-pyrrole-3-carboxylic acid (3.0 g, 17.9 mmol) reacted with diisopropylamino ethylamine (3.56 mL, 19.7 mmol) to give 4.93 g (94%) of 5-formyl-2,4-dimethyl-1H-pyrrole-3-carboxylic acid (3-diisopropylamino-ethyl)-amide.

$^1$H NMR (360 MHz, DMSO-$d_6$) δ 11.78 (br s, 1H, NH), 9.54 (s, 1H, CHO), 7.29 (m, 1H, CONH), 3.15 (m, 2H, CH$_2$), 2.51 (m, 4H, CH$_2$ and 2×CH), 2.38 (s, 3H, CH$_3$), 2.32 (s, 3H, CH$_3$), 0.97 (d, 12H, 4×CH$_3$). MS m/z 294 (M$^+$+1).

Example B-8

5-Formyl-4-methyl-1H-pyrrole-3-carboxylic Acid

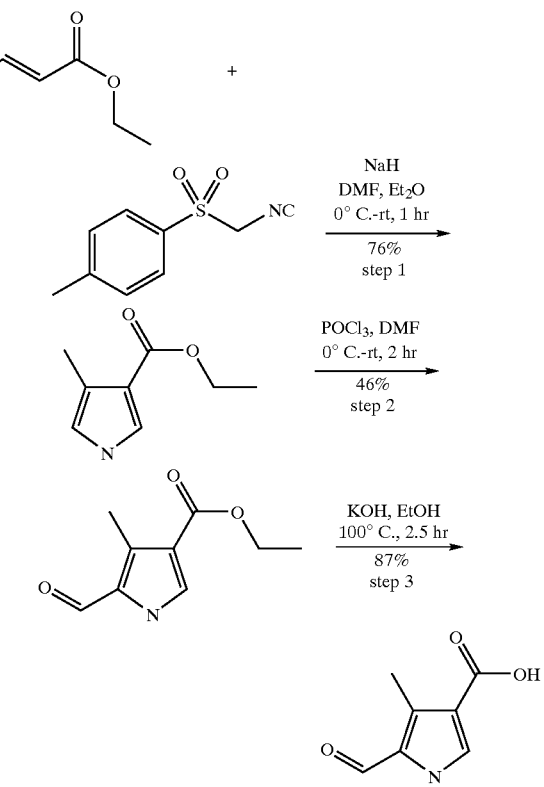

Step 1: Preparation of 4-Methyl-1H-pyrrole-3-carboxylic Acid Ethyl Ester

To a suspension of sodium hydride (4 g of 60% dispersion, 2 eq, washed with diethyl ether) in diethyl ether (200 mL), cooled in an ice bath with stirring was added slowly a solution of ethyl crotonate (6.2 mL, 50 mmol) and p-tosylmethyl isocyanide (9.7 g, 50 mmol) in 80 mL of DMSO and 160 mL diethyl ether. Upon complete addition of the solution, the reaction mixture was stirred at room temperature for 1 hr. The reaction was quenched with 400 mL water and extracted into diethyl ether (2×100 mL), dried (MgSO$_4$) and concentrated to afford 6 g (78%) of 4-methyl-1H-pyrrole-3-carboxylic acid ethyl ester as a brown oil which solidified upon standing.

$^1$H NMR (300 MHz, DMSO-d$_6$) δ 11.1 (br s, 1H, NH), 9.78 (t, J=2.7 Hz, 1H), 6.56 (s, 1H), 4.12 (q, J=7.2 Hz, 2H, OCH$_2$CH$_3$), 2.15 (s, 3H, CH$_3$), 1.22 (t, J=7.2 Hz, 3H, OCH$_2$CH$_3$). MS m/z 153 [M$^+$].

(Lit. ref.: Cheng et al., J. Heterocyclic Chem., 1976, 13, 1145–1147).

Step 2: Preparation of 5-Formyl-4-methyl-1H-pyrrole-3-carboxylic Acid Ethyl Ester POCl$_3$ (4 mL, 1.1 eq) added to 9 mL (3 eq) of DMF cooled in an ice bath. After 15 mins, a solution of the 4-methyl-1H-pyrrole-3-carboxylic acid ethyl ester (6 g, 39.2 mmol) in DMF (2M, 20 mL) was added to the reaction and stirring continued at rt. After 2 hr, the reaction mixture was diluted with water (100 mL) and basified to pH=11 with 1N NaOH. The aqueous layer was extracted into DCM (2×250 mL), washing the combined organic layers with water (2×400 mL), dried (MgSO$_4$), filtered through a plug of silica and concentrated to afford a pinkish solid. Trituration with hexanes afforded 3.3 g (46%) of 5-formyl-4-methyl-1H-pyrrole-3-carboxylic acid ethyl ester as a tan solid $^1$H NMR (300 MHz, DMSO-d$_6$) δ 12.4 (br s, 1H, NH), 9.69 (s, 1H, CHO), 7.59 (s, 1H), 4.16 (q, J=6.8 Hz, 2H, OCH$_2$CH$_3$), 2.48 (s, 3H, CH$_3$), 1.24 (t, J=6.8 Hz, 3H, OCH$_2$CH$_3$). MS m/z 181 [M$^+$].

(Lit. ref.: Bonnett, Raymond; Hamzetash, Dariush; Valles, Maria Asuncion; Soc. Perkin Trans 1; 1987; 1387–1388).

Step 3: Preparation of 5-Formyl-4-methyl-1H-pyrrole-3-carboxylic Acid

KOH (5 g, 2 eq) was added to a suspension of 5-formyl-4-methyl-1H-pyrrole-3-carboxylic acid ethyl ester (8.13 g, 44.8 mmol) in water (100 mL) and EtOH (50 mL) with stirring. The mixture was heated to reflux for 2.5 hr, cooled to rt, concentrated to about 2/3 volume, diluted with water (300 mL) and acidified to pH=3 using 1N HCl. The white solid was collected by filtration and dried to afford 6 g (87%) of 5-formyl-4-methyl-1H-pyrrole-3-carboxylic acid as a tan solid.

$^1$H NMR (300 MHz, DMSO-d$_6$) δ 12.28 (br s, 1H, CO$_2$H), 12.13 (br s, 1H, NH), 9.68 (s, 1H, CHO), 7.55 (d, J=3.6 Hz, 1H), 3.32 (s, 3H, CH$_3$). MS m/z 153 [M$^+$].

A. General Amidation Procedure

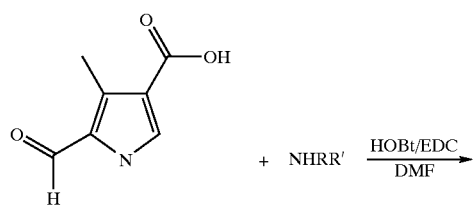

-continued

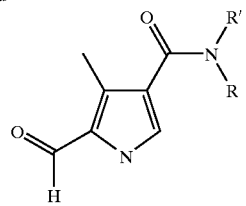

To the solution of 5-formyl-4-methyl-1H-pyrrole-3-carboxylic acid in DMF (0.3M) was added 1-ethyl-3-(3-dimethylamino-propylcarbodiimide hydrochloride (EDC, 1.2 equiv.), 1-hydroxybenzotriazole (HOBt, 1.2 eq) followed by the appropriate amine (1.2 eq). The reaction solution was stirred for 12 h, and then DMF solvent was removed. The residue was purified on a silica gel column eluting with 1–5% methanol in dichloromethane to provide the product.

Example B-9

3-Methyl-4-(4-methyl-piperazine-1-carbonyl)-1H-pyrrole-2-carbaldehyde

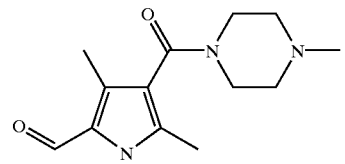

5-Formyl-4-methyl-1H-pyrrole-3-carboxylic acid (500 mg, 3.27 mmol) reacted with 1-methylpiperazine (0.43 mL, 3.92 mmol) to give 3-methyl-4-(4-methyl-piperazine-1-carbonyl)-1H-pyrrole-2-carbaldehyde.

$^1$HNMR (300 MHz, DMSO-d$_6$) δ 12.25 (br s, 1H, NH), 9.66 (s, 1H, CHO), 7.35 (s, 1H), 3.7 (m, 4H, 2×CH$_2$), 3.16 (m, 4H, 2×CH$_2$), 2.73 (s, 3H, CH$_3$), 2.32 (s, 3H, CH$_3$). MS 236 [M$^+$+1].

Example B-10

4-[(cis)-3,5-Dimethyl-piperazine-1-carbonyl]-3-methyl-1H-pyrrole-2-carbaldehyde

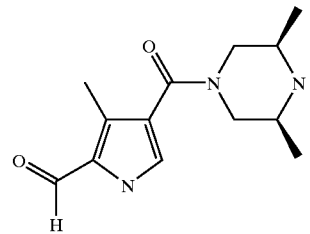

5-Formyl-4-methyl-1H-pyrrole-3-carboxylic acid (1.00 g, 6.54 mmol) reacted with cis-2,6-dimethylpiperazine (822 mg, 7.19 mmol) to give 4-[(cis)-3,5-dimethyl-piperazine-1-carbonyl]-3-methyl-1H-pyrrole-2-carbaldehyde (1.43 g, 88%).

$^1$HNMR (300 MHz, DMSO-d$_6$) δ 12.08 (br s, 1H, NH), 9.65 (s, 1H, CHO), 7.23 (s, 1H), 4.09 (br s, 2H, CH$_2$), 2.62 (m, 2H, CH$_2$), 2.40 (br s, 2H, 2×CH), 2.29 (s, 3H, CH$_3$), 0.93 (br d, 6H, J=4.6 Hz, 2×CH$_3$). MS m/z 248 [M$^-$−1].

Example B-11

5-Formyl-4-methyl-1H-pyrrole-2-carboxylic Acid

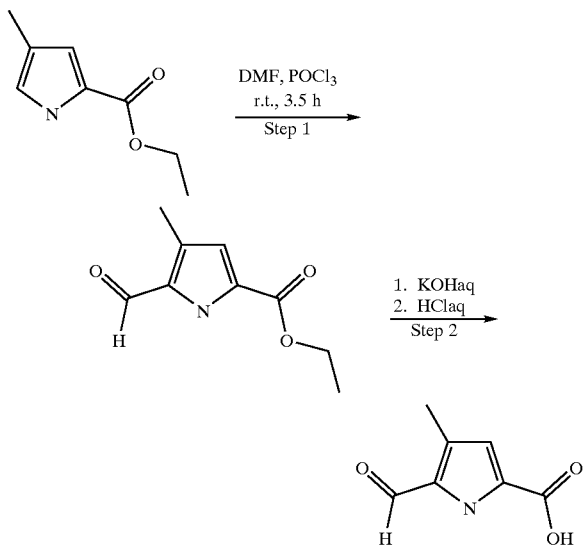

Step 1: Preparation of 5-Formyl-4-methyl-1H-pyrrole-2-carboxylic Acid Ethyl Ester To the ice-cold 3 mL (39.2 mmol) of dimethylformamide (DMF) was added phosphorus oxychloride (0.67 mL, 7.18 mmol) drop wise and the resultant mixture was stirred for 30 minutes. A solution of 1 g (6.53 mmol) of 4-methyl-1H-pyrrole-2-carboxylic acid ethyl ester in 3 mL of DMF was added to the reaction. After 1 h, the reaction was warmed to room temperature for another 2.5 h. The reaction mixture was diluted with water (100 mL) and basified to pH=11 with 1N sodium hydroxide solution. The precipitate was removed by filtration, rinsing with water and dried to afford 0.8 g (68%) of 5-formyl-4-methyl-1H-pyrrole-2-carboxylic acid ethyl ester as a white solid.

$^1$H NMR (360 MHz, DMSO-$d_6$) δ 12.6 (br s, 1H, NH-1), 9.78 (s, 1H, CHO-5), 6.68 (s, 1H, H-3), 4.26 (q, J=7.0 Hz, 2H, OCH$_2$CH$_3$), 2.28 (s, 3H, CH$_3$-4), 1.28 (t, J=7.0 Hz, 3H, OCH$_2$CH$_3$). MS m/z 181 (M$^+$).

Step 2: Preparation of 5-Formyl-4-methyl-1H-pyrrole-2-carboxylic Acid

To a solution of 0.8 g (4.4 mmol) of 5-formyl-4-methyl-1H-pyrrole-2-carboxylic acid ethyl ester in 35 mL of water and 15 mL of ethanol was added 0.5 gram (8.9 mmol) of potassium hydroxide. The reaction mixture was heated to 100° C. for 1 h, cooled to room temperature, and evaporated ethanol. The water layer was acidified to pH=3 using 2N hydrogen chloride solution. The precipitate was filtered and washed with water to afford 0.67 g (68%) of 5-formyl-4-methyl-1H-pyrrole-2-carboxylic acid as a tan solid.

$^1$H NMR (360 MHz, DMSO-$d_6$) δ 12.92 (br s, 1H, CO$_2$H-5), 12.48 (br s, 1H, NH-1), 9.76 (s, 1H, CHO-5), 6.63 (s, 1H, H-3), 2.28 (s, 3H, CH$_3$-4). MS m/z 152 [M$^-$–1].

Example B-12

5-Formyl-4-methyl-1H-pyrrole-2-carboxylic Acid (2-Diethylamino-ethyl)-amide

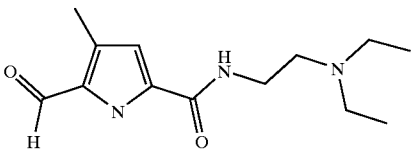

To a solution of 5-formyl-4-methyl-1H-pyrrole-2-carboxylic acid (2.50 g, 16.32 mmol) in DMF (54 mL) was added 1-ethyl-3-(3-dimethylamino-propylcarbodiimide hydrochloride (EDC, 3.76 g, 19.59 mmol), 1-hydroxybenzotriazole (HOBt, 2.65 g, 19.59 mmol) followed by diethylaminoethyl amine (2.75 mL, 19.59 mmol). The reaction solution was stirred for 12 h, and then DMF solvent was removed. The residue was purified on a silica gel column eluting with 1–5% methanol in dichloromethane to provide 3.2 g (78%) of 5-formyl-4-methyl-1H-pyrrole-2-carboxylic acid (2-diethylamino-ethyl)-amide.

$^1$H NMR (360 MHz, DMSO-$d_6$) δ 12.22 (br s, 1H, NH), 9.73 (s, 1H, CHO), 8.29 (t, 1H, J=5.5 Hz, CONH), 6.66 (s, 1H, H-3), 3.28 (m, 2H, CH$_2$), 2.50 (m, 6H, 3×CH$_2$), 2.30 (s, 3H, CH$_3$), 0.94 (t, 6H, J=7.2 Hz, 2×CH$_3$). MS m/z 252 [M$^+$+1].

B. General Amidation Procedure

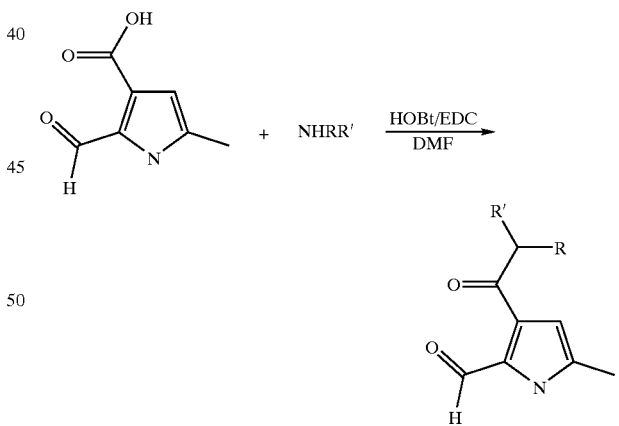

To the solution of 2-formyl-5-methyl-1H-pyrrole-3-carboxylic acid in DMF (0.3M) was added 1-ethyl-3-(3-dimethylamino-propylcarbodiimide hydrochloride (EDC, 1.2 equiv.), 1-hydroxybenzotriazole (HOBt, 1.2 eq) followed by the appropriate amine (1.2 eq). The reaction solution was stirred for 12 h, and then DMF solvent was removed. The residue was purified on a silica gel column eluting with 1–5% methanol in dichloromethane to provide the product.

Example B-13

2-Formyl-5-methyl-1H-pyrrole-3-carboxylic Acid (2-Diethylamino-ethyl)-amide

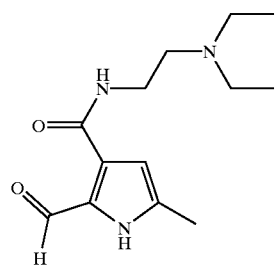

2-Formyl-5-methyl-1H-pyrrole-3-carboxylic acid (3.0 g, 19.6 mmol) reacted with N,N-diethylethylenediamine (3.03 mL, 21.5 mmol) to give 2-formyl-5-methyl-1H-pyrrole-3-carboxylic acid (2-diethylamino-ethyl)-amide (4.65 g, 94%).

¹HNMR (400 MHz, DMSO-$d_6$) δ 12.16 (br s, 1H, NH), 9.96 (s, 1H, CHO), 8,28 (m, 1H, CONH), 6.40 (s, 1H, H-4), 3.27 (m, 2H, $CH_2$), 2.49 (m, 6H, 3×$CH_2$), 2.22 (s, 3H, $CH_3$), 0.95 (t, 6H, J=7.1 Hz, 2×$CH_3$) MS m/z 252 [M$^+$+1].

Example B-14

2-Formyl-5-methyl-1H-pyrrole-3-carboxylic Acid (2-Pyrrolidin-1-yl-ethyl)-amide

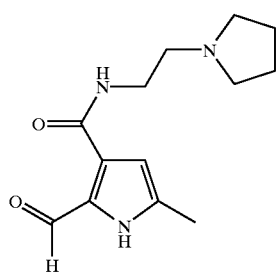

2-Formyl-5-methyl-1H-pyrrole-3-carboxylic acid (3.0 g, 19.6 mmol) reacted with 1-(2-aminoethyl)pyrrolidine (2.73 mL, 21.5 mmol) to give 2-formyl-5-methyl-1H-pyrrole-3-carboxylic acid (2-pyrrolidin-1-yl-ethyl)-amide (3.71 g, 76%).

¹HNMR (400 MHz, DMSO-$d_6$) δ 12.16 (br s, 1H, NH), 9.96 (s, 1H, CHO), 8.32 (m, 1H, CONH), 6.42 (s, 1H, H-4), 3.31 (m, 2H, $CH_2$), 2.54 (m, 6H, 3×$CH_2$), 2.23 (s, 3H, $CH_3$), 1.66 (m, 4H, 2×$CH_2$) MS m/z 250 [M$^+$+1].

Example B-15

2-Formyl-5-methyl-1H-pyrrole-3-carboxylic Acid (2-[1,2,3]Triazol-1-yl-ethyl)-amide

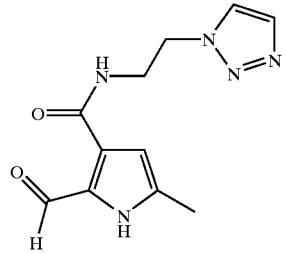

2-Formyl-5-methyl-1H-pyrrole-3-carboxylic acid (2.0 g, 13.06 mmol) reacted with 2-[1,2,3]triazol-1-yl-ethylamine (1.76 g, 15.67 mmol) to give 2-formyl-5-methyl-1H-pyrrole-3-carboxylic acid (2-[1,2,3]triazol-1-yl-ethyl)-amide (2.55 g, 79%).

¹HNMR (400 MHz, DMSO-$d_6$) δ 12.17 (br s, 1H, NH), 9.90 (s, 1H, CHO), 8.32 (t, 1H, J=5.6 Hz, CONH), 8.10 (d, 1H, J=0.85 Hz, triazole CH), 7.70 (d, 1H, J=0.85 Hz, triazole CH), 6.37 (s, 1H, H-4), 4.56 (m, 2H, $CH_2$), 3.65 (m, 2H, $CH_2$), 2.22 (s, 3H, $CH_3$). MS m/z 248 [M$^+$+1].

Example B-16

3-[(3R)-3-Dimethylamino-pyrrolidine-1-carbonyl]-5-methyl-1H-pyrrole-2-carbaldehyde

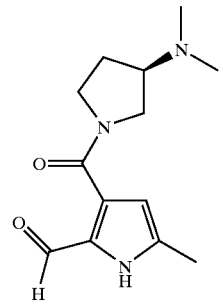

2-Formyl-5-methyl-1H-pyrrole-3-carboxylic acid (536 mg, 3.50 mmol) reacted with (3R)-(+)-3-dimethylamino-pyrrolidine (480 mg, 4.20 mmol) to give 3-[(3R)-3-dimethylamino-pyrrolidine-1-carbonyl]-5-methyl-1H-pyrrole-2-carbaldehyde (600 mg, 69%).

¹HNMR (400 MHz, DMSO-$d_6$) δ 12.23 (br s, 1H, NH), 9.63 (s, 1H, CHO), 6,28 (s, 1H, H-4), 3.89 (m, 2H, $CH_2$), 3.70 (m, 2H, $CH_2$), 2.76 (m, 7H, 2×$CH_3$ and CH), 2.29 (m, 1H, $CH_2$), 2.24 (s, 3H, $CH_3$), 2.15 (m, 1H, $CH_2$). MS m/z 250 [M$^+$+1].

Example B-17

3-[(3S)-3-Dimethylamino-pyrrolidine-1-carbonyl]-5-methyl-1H-pyrrole-2-carbaldehyde

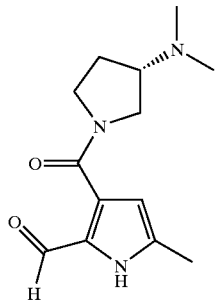

2-Formyl-5-methyl-1H-pyrrole-3-carboxylic acid (548 mg, 3.58 mmol) reacted with (3S)-(−)-3-dimethylamino-pyrrolidine (490 mg, 4.29 mmol) to give 3-[(3S)-dimethylamino-pyrrolidine-1-carbonyl]-5-methyl-1H-pyrrole-2-carbaldehyde (460 mg, 52%).

$^1$HNMR (400 MHz, DMSO-$d_6$) δ 12.22 (br s, 1H, NH), 9.63 (s, 1H, CHO), 6.28 (s, 1H, H-4), 3.90 (m, 2H, CH$_2$), 3.73 (m, 2H, CH$_2$), 2.73 (m, 7H, 2×CH$_3$ and CH), 2.28 (m, 1H, CH$_2$), 2.24 (s, 3H, CH$_3$), 2.21 (m, 1H, CH$_2$). MS m/z 250 [M$^+$+1].

Example B-18

3-[(cis)-3,5-Dimethyl-piperazine-1-carbonyl]-5-methyl-1H-pyrrole-2-carbaldehyde

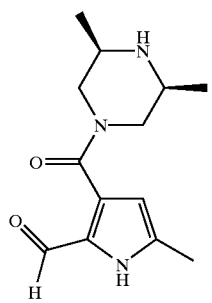

2-Formyl-5-methyl-1H-pyrrole-3-carboxylic acid (1.00 g, 6.53 mmol) reacted with cis-2,6-dimethylpiperazine (900 mg, 7.84 mmol) to give 3-[(cis)-3,5-dimethyl-piperazine-1-carbonyl]-5-methyl-1H-pyrrole-2-carbaldehyde (1.20 g, 74%).

$^1$HNMR (400 MHz, DMSO-$d_6$) δ 12.12 (br s, 1H, NH), 9.40 (s, 1H, CHO), 6.05 (s, 1H, H-4), 4.15 (m, 1H, CH$_2$), 3.65 (m, 1H, CH$_2$), 2.59 (m, 2H, CH$_2$), 2.30 (m, 2H, 2×CH), 2.24 (s, 3H, CH$_3$), 0.94 (m, 7H, 2×CH$_3$ and NH). MS m/z 250 [M$^+$+1].

Example B-19

3,5-Dimethyl-4-[3-(4-methyl-piperazin-1-yl)-3-oxopropyl]-1H-pyrrole-2-carbaldehyde

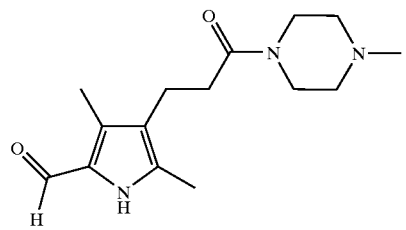

3-(5-Formyl-2,4-dimethyl-1H-pyrrol-3-yl)-propionic acid (1.37 g, 6.50 mmol) reacted with 1-methylpiperazine (719.6 mg, 7.15 mmol) to give 3,5-dimethyl-4-[3-(4-methyl-piperazin-1-yl)-3-oxo-propyl]-1H-pyrrole-2-carbaldehyde (1.30 g, 72%).

$^1$HNMR (400 MHz, DMSO-$d_6$) δ 11.40 (br s, 1H, NH), 9.42 (s, 1H, CHO), 3.41 (m, 2H, CH$_2$), 3.31 (m, 2H, CH$_2$), 2.54 (m, 2H, CH$_2$), 2.37 (m, 2H, CH$_2$), 2.19 (s, 3H, CH$_3$), 2.18 (m, 2H, CH$_2$), 2.15 (s, 3H, CH$_3$), 2.12 (s, 3H, CH$_3$). MS m/z 278 [M$^+$+1].

Example B-20

3,5-Dimethyl-4-[3-[(cis)-3,5-dimethyl-piperazin-1-yl)]-3-oxo-propyl]-1H-pyrrole-2-carbaldehyde

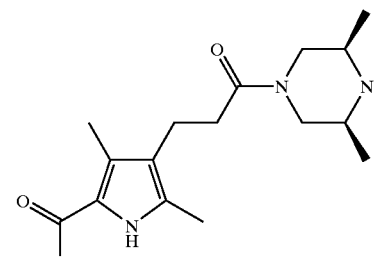

3-(5-Formyl-2,4-dimethyl-1H-pyrrol-3-yl)-propionic acid (1.37 g, 6.50 mmol reacted with cis-2,6-dimethylpiperazine (822 mg, 7.15 mmol) to give 3,5-dimethyl-4-[3-[(cis)-3,5-dimethyl-piperazin-1-yl)]-3-oxo-propyl]-1H-pyrrole-2-carbaldehyde (1.42 g, 75%).

$^1$HNMR (400 MHz, DMSO-$d_6$) δ 11.39 (br s, 1H, NH), 9.42 (s, 1H, CHO), 4.25 (m, 1H, CH$_2$), 3.54 (m, 1H, CH$_2$), 2.54 (m, 2H, CH$_2$), 2.45 (m, 2H, 2×CH), 2.36 (m, 4H, 2×CH$_2$), 2.20 (s, 3H, CH$_3$), 2.14 (s, 3H, CH$_3$), 1.94 (t, 1H, J=11.5 Hz, NH), 0.93 (d, 3H, J=5.9 Hz, CH$_3$), 0.88 (d, 3H, J=5.6 Hz, CH$_3$). MS m/z 292 [M$^+$+1].

Example B-21

4-(3-Piperidin-1-yl-propionyl)-1,4,5,6,7,8-hexahydro-pyrrolo[3,2-b]azepine-2-carbaldehyde

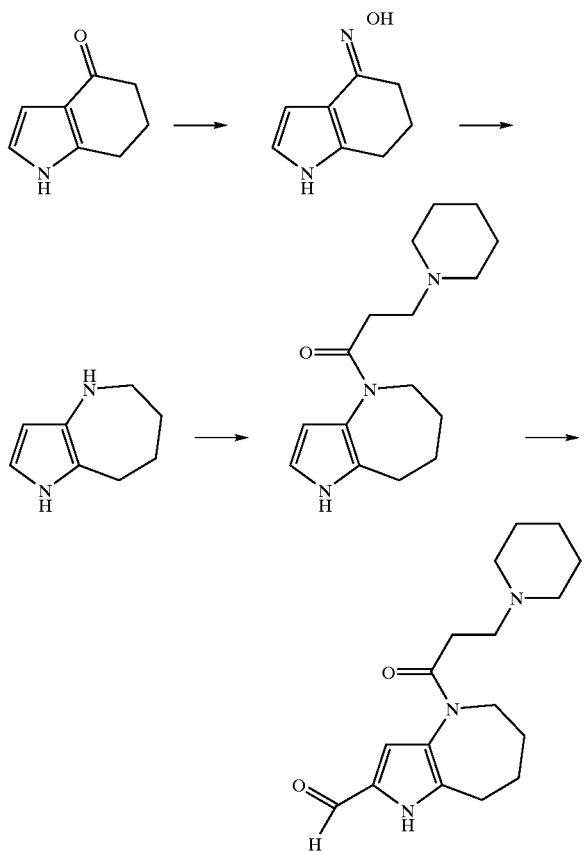

To a stirred solution of 1,5,6,7-tetrahydro-indol-4-one (5.4 g) in pyridine (40 mL) was added hydroxyammonium chloride (2 eq.) at rt. After 2 hours, the solvent was removed and the residue was diluted with water and extracted with ethyl acetate. The combined extracts were washed with brine, dried and concentrated to give 5.5 g of 1,5,6,7-tetrahydro-indol-4-one oxime as a pale yellow solid.

$^1$H NMR (400 MHz, DMSO-d$_6$) δ 10.85 (br s, 1H, NH), 9.85 (s, 1H, N—OH), 6.66 (m, 1H), 6.58 (m, 1H), 2.62 (m, 2H), 2.28 (m, 2H), 1.82 (m, 2H). MS m/z 151.01 [M$^+$+1].

To a stirred solution of 1,5,6,7-tetrahydro-indol-4-one oxime (1.2 g, 7.7 mmol) in DCM (anhydrous, 250 mL) was added DIBAL-H (1M solution in DCM, 35 mL) at 0° C. under nitrogen. After 2 hours, NaF (7 g) was added followed by water (2.24 g). After 20 mins, the reaction was filtered through celite and the solvent was removed to give 350 mg of 1,4,5,6,7,8-hexahydro-pyrrolo[3,2-b]azepine as a brown oil $^1$H NMR (400 MHz, DMSO-d$_6$) δ 9.74 (s, 1H, NH), 6.14 (m, 1H), 5.47 (m, 1H), 4.2 (br s, 1H, NH), 2.78 (m, 2H), 2.47 (m, 2H), 1.60 (m, 2H), 1.46 (m, 2H).

To a solution of 3-piperidin-1-yl-propionic acid (472 mg, 3 mmol) in DCM (15 mL) at 0° C. was added oxalyl chloride (4.5 mmol) followed by one drop of DMF. After stirring for 2 hours at rt, the solvent was removed to give 3-piperidin-1-yl-propionyl chloride as a white solid. To a solution of 1,4,5,6,7,8-hexahydro-pyrrolo[3,2-b]azepine (347 mg, 2.55 mmol) in DCM (10 mL) was added TEA (1 eq.) and 1-piperidinepropionic acid chloride. The mixture was stirred at rt for overnight. The reaction was diluted with DCM, washed with NaHCO$_3$, brine, dried and concentrated. The residue was purified on a silica gel column to give 230 mg of 3-piperidin-1-yl-1-(5,6,7,8-tetrahydro-1H-pyrrolo[3,2-b]azepin-4-yl)-propan-1-one as a light brown gel.

$^1$H NMR (400 MHz, DMSO-d$_6$) δ 10.59 (s, 1H, NH), 6.42 (m, 1H), 5.91 (m, 1H), 3.45 (m, 2H), 2.56 (m, 2H), 2.41 (m, 4H), 2.19 (m, 4H), 1.66 (m, 2H), 1.51 (m, 2H), 1.40 (m, 4H), 1.29 (m, 2H). MS m/z 276.4 [M$^+$+1].

3-Piperidin-1-yl-1-(5,6,7,8-tetrahydro-1H-pyrrolo[3,2-b]azepin-4-yl)-propan-1-one (225 mg, 0.8 mmol) was formylated with POCl$_3$ (91 μL, 1.2 eq.) and DMF(1 mL) using standard Vilsmierer condition to give 96 mg of 4-(3-piperidin-1-yl-propioyl)-1,4,5,6,7,8-hexahydro-pyrrolo[3,2-b]azepine-2-carbaldehyde as a light yellow solid.

$^1$H NMR (400 MHz, DMSO-d$_6$) δ 12.09 (br s, 1H, NH), 9.30 (s, 1H, NH), 6.96 (s, 1H), 3.48 (m, 2H), 2.67 (m, 2H), 2.43 (m, 4H), 2.17 (m, 4H), 1.69 (m, 2H), 1.56 (m, 2H), 1.40 (m, 4H), 1.31 (m, 2H). MS m/z 304.4 [M$^+$+1].

Example B-22

4-((S)-Pyrrolidine-2-carbonyl)-1,4,5,6,7,8-hexahydro-pyrrolo[3,2-b]azepine-2-carbaldehyde

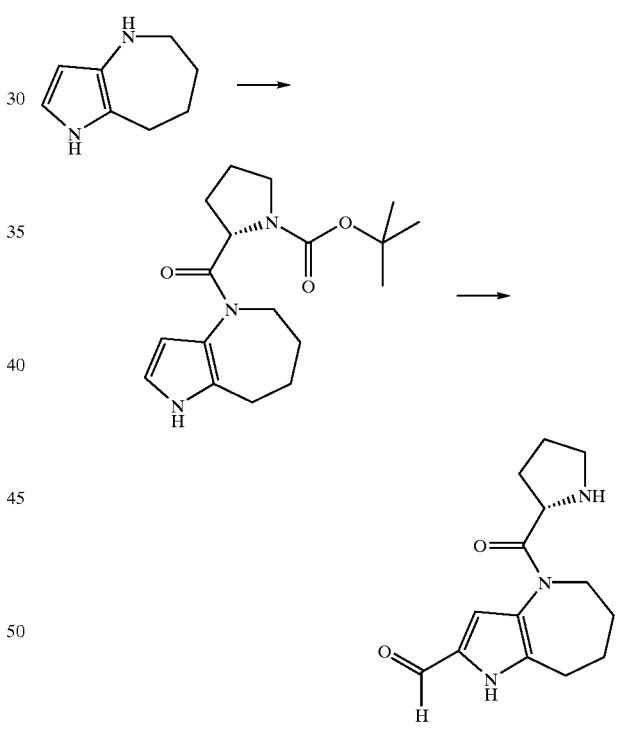

To a solution of (S)-pyrrolidine-1,2-dicarboxylic acid 1-tert-butyl ester (664 mg) in DCM (10 mL) at 0° C. was added oxalyl chloride (4.7 mmol), followed by one drop of DMF. After stirring at rt for 2 hours, the solvent was concentrated to give S)-2-chlorocarbonyl-pyrrolidine-1-carboxylic acid tert-butyl ester. To a solution of 1,4,5,6,7,8-hexahydro-pyrrolo[3,2-b]azepine (350 mg, 2.6 mmol) was added TEA (362μL) and (S)-2-chlorocarbonyl-pyrrolidine-1-carboxylic acid tert-butyl ester (dissolved in 10 mL of DCM). After stirring at rt for overnight, the reaction was diluted with DCM, washed with NaHCO$_3$, brine, dried and concentrated. The residue was purified on a silica gel column to give 410 mg of (S)-2-(5,6,7,8-tetrahydro-1H-pyrrolo[3,2-b]azepine-4-carbonyl)-pyrrolidine-1-carboxylic acid tert-butyl ester as a light brown liquid.

MS m/z 232.5 [M+−Boc].

(S)-2-(5,6,7,8-Tetrahydro-1H-pyrrolo[3,2-b]azepine-4-carbonyl)-pyrrolidine-1-carboxylic acid tert-butyl ester (400 mg, 1.2 mmol) was formylated with POCl$_3$ (134 μL, 1.2 eq.) using standard Vilsmierer condition to give 225 mg of 4-((S)-pyrrolidine-2-carbonyl)-1,4,5,6,7,8-hexahydro-pyrrolo[3,2-b]azepine-2-carbaldehyde as a light yellow solid.

MS m/z 260.4 [M−1].

Example B-23

4-(1-Acetyl-piperidine-4-carbonyl)-1,4,5,6,7,8-hexahydro-pyrrolo[3,2-b]azepine-2-carbaldehyde

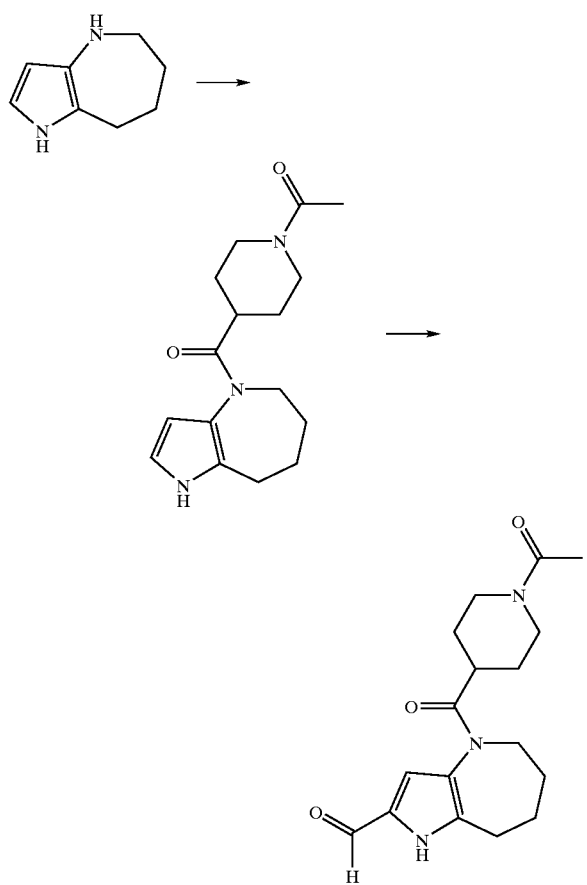

To a mixture of 1-acetyl-piperidine-4-carboxylic acid (822 mg, 4.8 mmol, 1.2 eq.), EDC (920 mg, 1.2 eq.), HOBt (648 mg, 1.2 eq.) in DCM (15 mL) was added TEA (1.3 mL, 2 eq.) and 1,4,5,6,7,8-hexahydro-pyrrolo[3,2-b]azepine (550 mg, 4 mmol). The mixture was stirred at rt for 2 days. The reaction was diluted with DCM, washed with water, sat. NaHCO$_3$, brine, dried and concentrated. The residue was purified on a silica gel column to give 1.1 g of 1-[4-(5,6,7,8-tetrahydro-1H-pyrrolo[3,2-b]azepine-4-carbonyl)-piperidin-1-yl]-ethanone as a white solid.

MS m/z 290.2 [M++1].

1-[4-(5,6,7,8-Tetrahydro-1H-pyrrolo[3,2-b]azepine-4-carbonyl)-piperidin-1-yl]-ethanone (1.1 g) was formylated with POCl$_3$ (186 μL, 1.2 eq.) and DMF using standard Vilsmierer condition to give 240 mg of 4-(1-acetyl-piperidine-4-carbonyl)-1,4,5,6,7,8-hexahydro-pyrrolo[3,2-b]azepine-2-carbaldehyde as a gold colored solid.

MS m/z 318.2 [M++1].

Example B-24

4-(2-Pyrrolidin-1-yl-ethyl)-4,5,6,7-tetrahydro-1H-indole-2-carbaldehyde

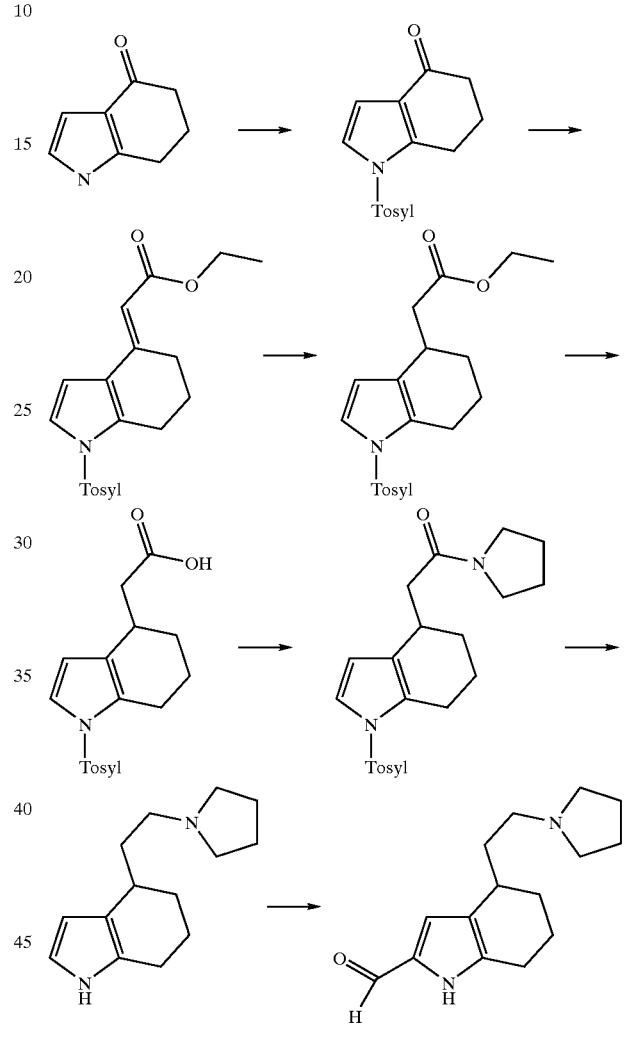

To a mixture of 1,5,6,7-tetrahydro-4H-indol-4-one (2.7 g, 20 mmol) and tosyl chloride (3.8 g, 20 mmol) in THF (30 mL) was added DIPEA (5.3 mL, 30 mmol). After heating at 70° C. for 18 hours, the solvent was removed and the residue dissolved in ethyl acetate, washed (3×) with NaHCO$_3$ (sat.). The solid was recrystallized to give 4.35 g of 1-(p-tosyl)-1,5,6,7-tetrahydro-indol-4-one as a brown solid.

$^1$H NMR (400 MHz, DMSO-d$_6$) δ 7.90 (d, 2H), 7.48 (d, 2H), 7.41 (d, 1H), 6.51 (d, 1H), 2.95 (t, 2H), 2.39 (s, 3H, CH$_3$), 2.33 (t, 2H), 1.99 (m, 2H). MS m/z 290 [M++1].

Triethyl phosphonoacetate (9.5 mL, 48 mmol) was added to sodium hydride (60%) suspended in THF (80 mL) at 0° C., followed by 1-(p-tosyl)-1,5,6,7-tetrahydro-indol-4-one (11.56 g, 40 mmol). The mixture was heated to reflux for 18 hours. The reaction was quenched with NH$_4$Cl (sat.) and extracted with ethyl acetate. After washing with NaHCO$_3$ (sat.) and brine, the solvent was removed and the residue was recrystallized to give 8.2 g of as [1-(p-tosyl)-1,5,6,7-tetrahydro-indol-(4E)-ylidene]-acetic acid ethyl ester a brown solid.

$^1$H NMR (400 MHz, DMSO-d$_6$) δ 7.81 (d, 2H), 7.45 (d, 2H), 7.33 (d, 1H), 6.74 (d, 1H), 5.98 (br s, 1H), 4.04 (q, 2H), 2.88 (m, 2H), 2.78 (t, 2H), 2.37 (s, 3H, CH$_3$), 1.73 (m, 2H), 1.17 (t, 3H). MS m/z 360 [M$^+$+1].

[1-(p-Tosyl)-1,5,6,7-tetrahydro-indol-(4E)-ylidene]-acetic acid ethyl ester (6.2 g) was hydrogenated using 1% Pd—C (0.6 g) in methanol (280 mL) to give 6.5 g of [1-(p-tosyl)-4,5,6,7-tetrahydro-1H-indol-4-yl]-acetic acid ethyl ester.

$^1$H NMR (400 MHz, DMSO-d$_6$) δ 7.72 (d, 2H), 7.42 (d, 2H), 7.21 (br d, 1H), 6.18 (br d, 1H), 4.04 (m, 2H), 2.86 (m, 1H), 2.58 (m, 3H), 2.36 (s, 3H, CH$_3$), 2.23 (dd, 1H), 1.74 (m, 2H), 1.54 (m, 1H), 1.24 (m, 1H), 1.14 (t, 3H). MS m/z 362 [M$^+$+1].

[1-(p-Tosyl)-4,5,6,7-tetrahydro-1H-indol-4-yl]-acetic acid ethyl ester (3 g) was hydrolyzed using NaOH (4N, 10 mL) in MeOH (10 mL) and THF (10 mL) at rt for 1 hour. The reaction was adjusted to pH 3 and extracted with ethyl acetate, dried and concentrated to give 2 g of [1-(p-tosyl)-4,5,6,7-tetrahydro-1H-indol-4-yl]-acetic acid as a white solid.

$^1$H NMR (400 MHz, DMSO-d$_6$) δ 7.71 (d, 2H), 7.42 (d, 2H), 7.18 (d, 1H), 6.21 (d, 1H), 2.83 (m, 1H), 2.56 (m, 2H), 2.45 (m, 1H), 2.36 (s, 3H, CH$_3$), 2.07 (dd, 1H) 1.73 (m, 2H), 1.52 (m, 1H), 1.2 (m, 1H). MS m/z 334 [M$^+$+1].

To a mixture of [1-(p-Tosyl)-4,5,6,7-tetrahydro-1H-indol-4-yl]-acetic acid (1 g, 3 mmol), HOBt (486 mg, 1.2 eq.), EDC (690 mg, 1.2 eq.) in DMF (5 mL) was added TEA (1 mL, 2.5 eq.) and pyrrolidine (0.3 mL, 1.2 eq.). The mixture was stirred at rt for overnight. The reaction was diluted with DCM, washed with NaHCO$_3$, citric acid (3% aq.), water, brine, dried and concentrated. The residue was purified on a silica gel column to give 913 mg of 1-pyrrolidin-1-yl-2-[1-(toluene-4-sulfonyl)-4,5,6,7-tetrahydro-1H-indol-4-yl]-ethanone as a white semi-solid.

$^1$H NMR (400 MHz, DMSO-d$_6$) δ 7.73 (d, 2H), 7.43 (d, 2H), 7.19 (d, 1H), 6.17 (d, 1H), 3.3 (m, 4H), 2.92 (m, 1H), 2.58 (m, 2H), 2.44 (d, 1H), 3.77 (s, 3H, CH$_3$), 2.18 (dd, 1H), 1.74 (m, 6H), 1.55 (m, 1H), 1.24 (m, 1H).

Pyrrolidin-1-yl-2-[1-(toluene-4-sulfonyl)-4,5,6,7-tetrahydro-1H-indol-4-yl]-ethanone (840 mg) was reduced using lithium aluminum hydride (4 eq.) in THF (80 mL) at reflux for 5 hours to give 480 mg of mainly 4-(2-pyrrolidin-1-yl-ethyl)-4,5,6,7-tetrahydro-1H-indole as an oil.

MS m/z 373 [M$^+$+1].

4-(2-Pyrrolidin-1-yl-ethyl)-4,5,6,7-tetrahydro-1H-indole (475 mg, 2.2 mmol) was formylated with POCl$_3$ (0.25 mL, 1.2 eq.) and DMF (2 ml) using standard Vilsmierer condition to give 250 mg of 4-(2-pyrrolidin-1-yl-ethyl)-4,5,6,7-tetrahydro-1H-indole-2-carbaldehyde as a light yellow solid.

$^1$H NMR (400 MHz, DMSO-d$_6$) δ 13.63 (br s, 1H, NH), 9.26 (s, 1H, CHO), 6.77 (s, 1H), 4.2 (br s, 1H), 3.15 (s, 2H), 2.5 (m, 6H), 1.83 (m, 3H), 1.68 (m, 4H), 1.57 (m, 1H), 1.50 (m, 1H), 1.27 (m, 1H). MS m/z [M$^+$+1].

General Procedure for 3,5-Dimethyl-4-methylaminopyrrole Aldehydes

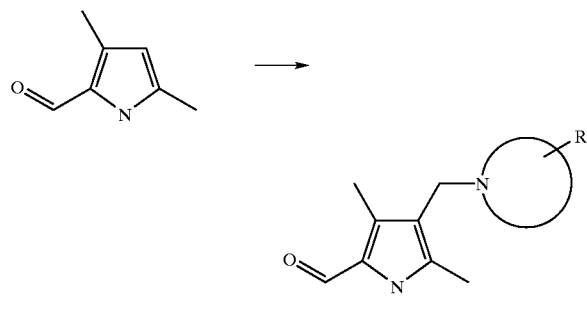

A mixture of 3,5-dimethyl-1H-pyrrole-2-carbaldehyde (20 mmol) in THF (40 mL), water (20 mL), acetic acid (3 mL), formaldehyde (37% wt. % solution in water, 5 mL) and the appropriate amine (30 mL) was heated to reflux (oil bath 90–100° C.) for 6 hours. The reaction was concentrated to a volume of 30 mL, basified with 2N NaOH and extracted with ethyl acetate (2×150 mL) and DCM (4×100 mL). The combined organic layers were concentrated and the residue was purified on a silica gel column to give the desired product.

Example B-25

4-(4-Hydroxy-piperidin-1-ylmethyl)-3,5-dimethyl-1H-pyrrole-2-carbaldehyde

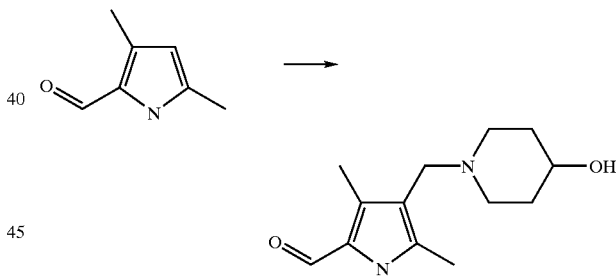

A mixture of 3,5-dimethyl-1H-pyrrole-2-carbaldehyde (2.5 g, 20 mmol) in THF (40 mL), water (20 mL), acetic acid (3 mL), formaldehyde (37% wt. % solution in water, 5 mL) and the appropriate amine (30 mL) was heated to reflux (oil bath 90–100° C.) for 6 hours and then stirred at rt for overnight. The reaction was concentrated to a volume of 30 mL, basified with 2N NaOH and extracted with ethyl acetate (2×150 mL) and DCM (4×100 mL). The combined organic layers were concentrated and the residue was purified on a silica gel column to give 2.3 g (49%) of 4-(4-hydroxy-piperidin-1-ylmethyl)-3,5-dimethyl-1H-pyrrole-2-carbaldehyde as a solid.

$^1$H NMR (400 MHz, DMSO-d$_6$) δ 11.50 (br s, 1H, NH), 9.43 (s, 1H, CHO), 4.50 (br s, 1H), 3.41 (v br s, 1H, OH), 3.15 (s, 2H), 2.60 (m, 2H), 2.22 (s, 3H, CH$_3$), 2.16 (s, 3H, CH$_3$), 1.94 (m, 2H), 1.66 (m, 2H), 1.27 (m, 2H).

Example B-26

3,5-Dimethyl-4-morpholin-4-ylmethyl-1H-pyrrole-2-carbaldehyde

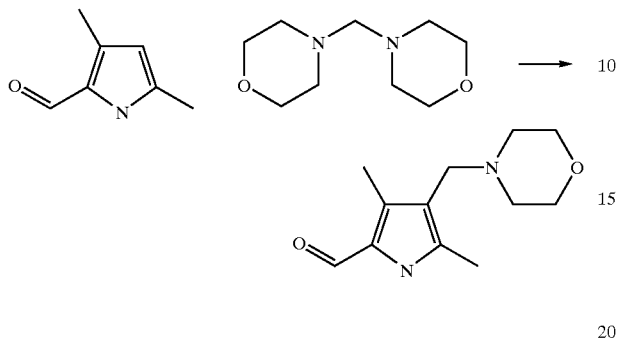

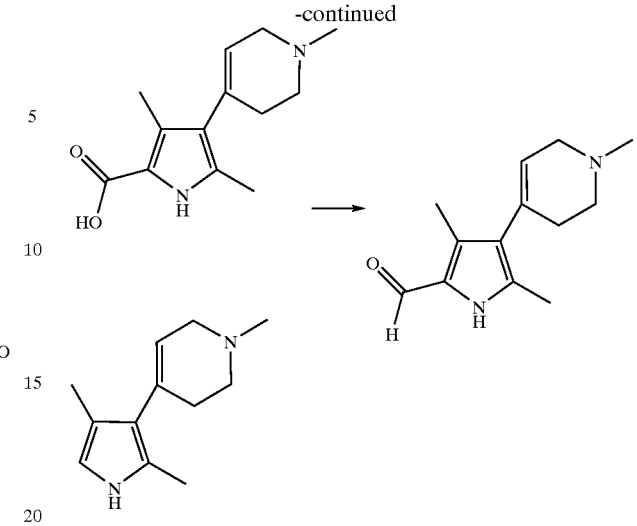

A mixture of 3,5-dimethyl-1H-pyrrole-2-carbaldehyde (1.85 g, 15 mmol), dimorpholine-methane (5 mL, 27 mL) in THF (40 mL), water (15 mL) and acetic acid (4 mL) was heated to reflux (oil bath 90–95° C.) for 6 hours. The reaction was concentrated to a volume of 20 mL, basified with $Na_2CO_3$ and extracted with ethyl acetate (3×75 mL). The combined extracts were dried, concentrated and the residue was purified on a silica gel column to give 2 g (36%) of 3,5-dimethyl-4-morpholin-4-ylmethyl-1H-pyrrole-2-carbaldehyde as a solid.

$^1$H NMR (400 MHz, DMSO-$d_6$) δ 11.51 (br s, 1H, NH), 9.44 (s, 1H, CHO), 3.51 (m, 4H), 3.19 (s, 2H), 2.28 (m, 4H), 2.23 (s, 3H, $CH_3$), 2.17 (s, 3H, $CH_3$).

Example B-27

3,5-Dimethyl-4-(1-methyl-1,2,3,6-tetrahydro-pyridin-4-yl)-1H-pyrrole-2-carbaldehyde

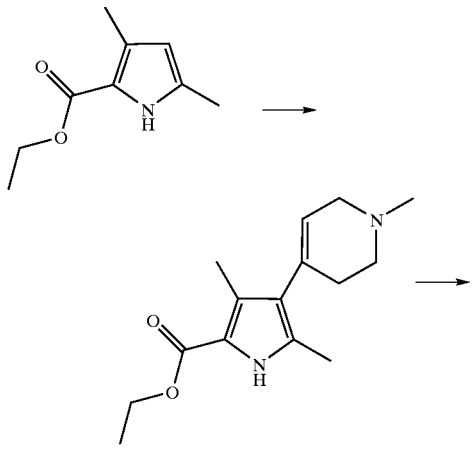

To a solution of 3,5-dimethyl-1H-pyrrole-2-carboxylic acid ethyl ester (836 mg, 5 mmol) in acetic acid (10 mL) and TFA (5 mL) under nitrogen was added 1-methyl-piperidin-4-one (0.8 mL, 6.67 mmol). The mixture was then heated in a 95° C. oil bath for overnight. The reaction was concentrated, dissolved in ethyl acetate, washed with $NaHCO_3$, brine, dried and concentrated. The residue was purified on a silica gel column to give 1.12 g (85%) of 3,5-dimethyl-4-(1-methyl-1,2,3,6-tetrahydro-pyridin-4-yl)-1H-pyrrole-2-carboxylic acid ethyl ester.

$^1$H NMR (400 MHz, $CDCl_3$) δ 8.56 (s, 1H, NH), 5.49 (m, 1H), 4.29 (q, 2H), 3.09 (m, 2H), 2.63 (t, 2H), 2.41 (s, 3H, $CH_3$), 2.34 (m, 2H), 2.26 (s, 3H, $CH_3$), 2.21 (s, 3H, $CH_3$), 1.34 (t, 3H). MS m/z 263 [$M^+$+1].

A mixture of 3,5-dimethyl-4-(1-methyl-1,2,3,6-tetrahydro-pyridin-4-yl)-1H-pyrrole-2-carboxylic acid ethyl ester (1.02 g, 3.9 mmol), KOH (0.287 g, 5.1 mmol) in water (5 mL) and methanol (10 mL) was heated to reflux under nitrogen for 3 days. The cooled reaction was extracted with ethyl acetate (3×), dried and concentrated to give 380 mg of 4-(2,4-dimethyl-1H-pyrrol-3-yl)-1-methyl-1,2,3,6-tetrahydro-pyridine. The aqueous layer was adjusted to pH 7, the resulted precipitate was collected by filtration, washed with water to give 380 mg of 4-(2,4-dimethyl-1H-pyrrol-3-yl)-1-methyl-1,2,3,6-tetrahydro-pyridine and 480 mg of 3,5-dimethyl-4-(1-methyl-1,2,3,6-tetrahydro-pyridin-4-yl)-1H-pyrrole-2-carboxylic acid.

$^1$H NMR (400 MHz, DMSO-$d_6$) δ 10.05 (br s, 1H, NH), 6.25 (s, 1H), 5.30 (m, 1H), 2.92 (m, 2H), 2.48 (m, 2H), 2.24 (m, 2H), 2.23 (s, 3H, $CH_3$), 2.06 (s, 3H, $CH_3$), 1.88 (d, 3H, $CH_3$).

Triethyl orthoformate (6 mL) was added to a solution of 4-(2,4-dimethyl-1H-pyrrol-3-yl)-1-methyl-1,2,3,6-tetrahydro-pyridine (360 mg) in TFA (6 mL) at 0° C. The mixture was stirred at 0° C. for 10 mins and then at rt for 40 mins. The solvent was removed and to the residue was added $NaHCO_3$, extracted with ethyl acetate, dried and concentrated to give 356 mg of 3,5-dimethyl-4-(1-methyl-1,2,3,6-tetrahydro-pyridin-4-yl)-1H-pyrrole-2-carbaldehyde.

$^1$H NMR (400 MHz, $CDCl_3$) δ 9.49 (s, 1H, CHO), 9.10 (br s, 1H, NH), 5.52 (m, 1H), 3.12 (m, 2H), 2.66 (t, 2H), 2.43 (s, 3H), 2.35 (m, 2H), 2.26 (s, 3H), 2.24 (s, 3H).

Example B-28

3,5-Dimethyl-4-(1-methyl-piperidin-4-yl)-1H-pyrrole-2-carbaldehyde

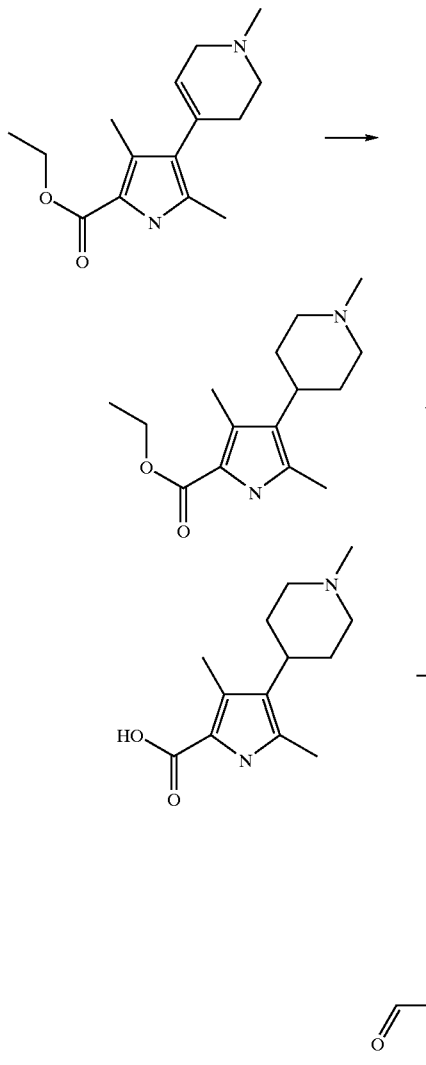

3,5-Dimethyl-1H-pyrrole-2-carboxylic acid ethyl ester (7.97 g) in methanol (200 mL) and acetic acid (5 mL) was hydrogenated using 10% Pd—C at rt overnight to give 10.25 g of 3,5-dimethyl-4-(1-methyl-piperidin-4-yl)-1H-pyrrole-2-carboxylic acid ethyl ester as acetic acid salt.

$^1$H NMR (400 MHz, DMSO-d$_6$) δ 10.97 (br s, 1H, NH), 4.15 (q, 2H), 2.84 (m, 2H), 2.35 (m, 1H), 2.20 (s, 3H, CH$_3$), 2.18 (s, 3H, CH$_3$), 2.15 (s, 3H, CH$_3$), 1.95 (m, 2H), 1.82 (m, 2H), 1.47 (m, 2H), 1.23 (t, 3H). MS m/z 265 [M$^+$+1].

A solution of 3,5-dimethyl-4-(1-methyl-piperidin-4-yl)-1H-pyrrole-2-carboxylic acid ethyl ester, di-acetic acid salt (4.87 g, 12.67 mmol), LiOH (1.8 g, 75 mmol) in methanol (20 mL) and water (10 mL) was heated in a 90° C. oil bath for 6 hours. The cooled reaction was adjusted to pH 7 with 6N HCl and concentrated to give 3,5-dimethyl-4-(1-methyl-piperidin-4-yl)-1H-pyrrole-2-carboxylic acid, LiCl salt. This was used in the next step without further purification.

A solution of 3,5-dimethyl-4-(1-methyl-piperidin-4-yl)-1H-pyrrole-2-carboxylic acid (12.67 mmol) in TFA (75 mL) was stirred at 0° C. for 30 mins. To the mixture was added triethyl orthoformate (20 mL), it was then allowed to warm up slowly to rt for 2 hours. The solvent was removed and to the residue was added NaHCO$_3$, extracted with ethyl acetate, dried and concentrated to give 2.56 g of 3,5-dimethyl-4-(1-methyl-piperidin-4-yl)-1H-pyrrole-2-carbaldehyde as a light yellow solid.

$^1$H NMR (400 MHz, DMSO-d$_6$) δ 11.43 (br s, 1H, NH), 9.41 (s, 1H, CHO), 2.82 (m, 2H), 2.65 (m, 5H), 2.24 (s, 3H, CH$_3$), 2.19 (s, 3H, CH$_3$), 1.95 (m, 3H), 1.64 (m, 2H).

Example B-29

(2-Formyl-5-methyl-1H-pyrrol-3-yl)-acetic Acid

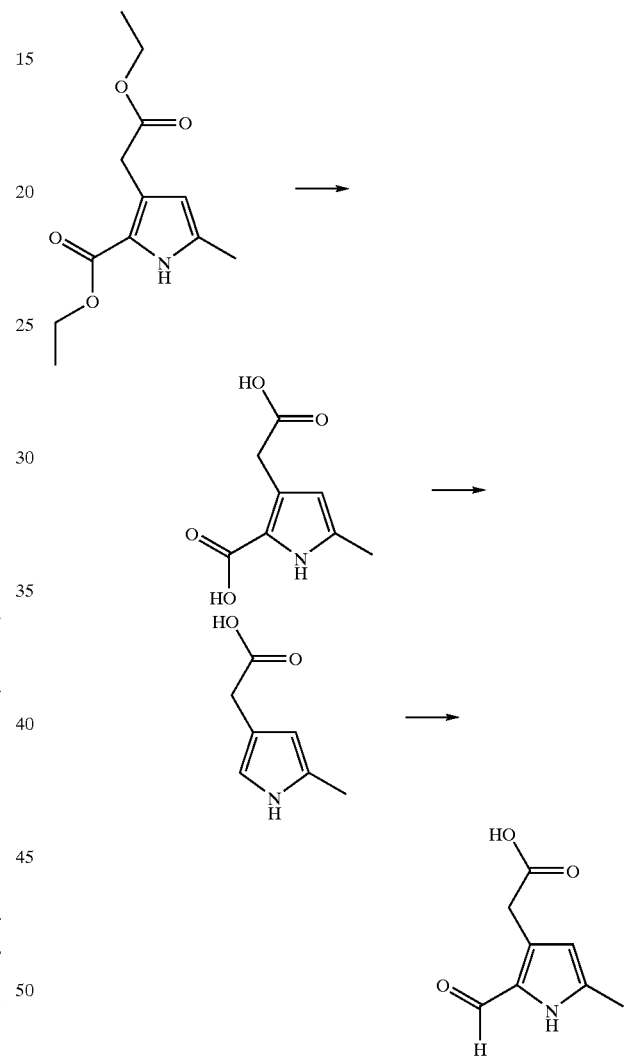

A solution of 3-ethoxycarbonylmethyl-5-methyl-1H-pyrrole-2-carboxylic acid ethyl ester (7 g, 29.26 mmol), LiOH (7 g, 10 eq.) in methanol (90 mL) and water (30 mL) was heated in a 70° C. oil bath for 3 hours. The cooled reaction was adjusted to pH 3 with 3N HCl, the resulted precipitate was collected by filtration, washed with water and dried to give 4.67 g (87%) of 3-carboxymethyl-5-methyl-1H-pyrrole-2-carboxylic acid.

$^1$H NMR (400 MHz, DMSO-d$_6$) δ 11.88 (s, 2H, 2×COOH), 11.2 (s, 1H, NH), 5.68 (s, 1H), 3.6 (s, 2H), 2.14 (s, 3H, CH$_3$). MS m/z 182 [M−1].

A suspension of 3-carboxymethyl-5-methyl-1H-pyrrole-2-carboxylic acid (1.5, 8.2 mmol) in TFA (6 mL) was heated under nitrogen in a 55° C. oil bath until all of the solid had dissolved and no more $CO_2$ gas given off. The reaction was cooled to 0° C. and used in the next step.

To a solution of(5-methyl-1H-pyrrol-3-yl)-acetic acid (8.2 mmol) in TFA (6 mL) at 0° C. was added triethyl orthoformate (6 mL), it was then at 0° C. for 10 mins and at rt for 0.5 hours. The reaction was poured into water, extracted with ethyl acetate, dried and concentrated. The residue was purified on a silica gel column to give 1.15 g (84%) of (2-formyl-5-methyl-1H-pyrrol-3-yl)-acetic acid.

$^1$H NMR (400 MHz, DMSO-d$_6$) δ 12.26 (br s, 1H, COOH), 11.67 (s, 1H, NH), 9.41 (s, 1H, CHO), 5.90 (d, 1H), 3.64 (s, 2H), 2.18 (s, 3H, CH$_3$).

Example B-30

5-Formyl-4-(3-methanesulfonyl-propyl)-2-methyl-1H-pyrrole-3-carboxylic Acid

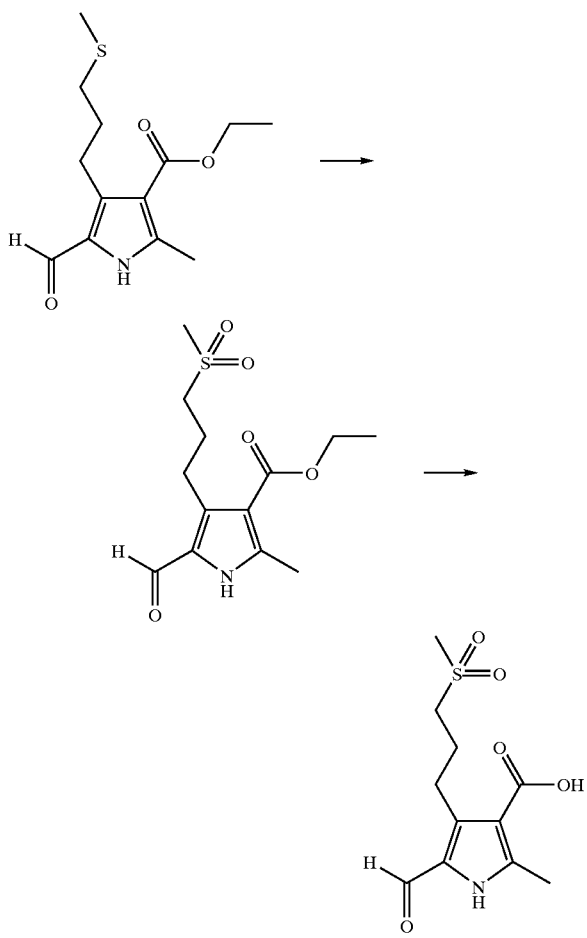

Oxone (614 mg, 1 mmol) dissolved in water (2 mL) was added portionwise to a solution of 5-formyl-2-methyl-4-(3-methylsulfanyl-propyl)-1H-pyrrole-3-carboxylic acid ethyl ester (269 mg, 1 mmol) in methanol (4 mL) cooled in an ice bath. The mixture was stirred for 3 hours, keeping the temp between 0° C. and rt. The reaction was diluted with 10 mL of water, the resulted precipitate was collected by vacuum filtration, washed with water and dried to give 95 mg of the desired product. The water filtrate was extracted with ethyl acetate, dried and concentrated to give another 74 mg of the product. Total of 169 mg (56%) of 5-formyl-4-(3-methanesulfonyl-propyl)-2-methyl-1H-pyrrole-3-carboxylic acid ethyl ester was obtained.

$^1$H NMR (400 MHz, DMSO-d$_6$) δ 12.26 (br s, 1H, NH), 9.61 (s, 1H, CHO), 4.19 (q, 2H), 3.06 (m, 4H), 2.93 (s, 3H, CH$_3$), 2.42 (s, 3H, CH$_3$), 1.93 (m, 2H), 1.27 (t, 3H).

Lithium hydroxide (179.6 mg, 7.5 mmol) was added to a suspension of 5-formyl-4-(3-methanesulfonyl-propyl)-2-methyl-1H-pyrrole-3-carboxylic acid ethyl ester (450 mg, 1.5 mmol) in methanol (6 mL) and water (6 mL). The mixture was heated under nitrogen in a 65° C. oil bath for 20 hours. The cooled reaction was adjusted to pH 2 using 1N HCl, the resulted precipitate was collected by vacuum filtration, washed with water and dried to give 356 mg (87%) of 5-formyl-4-(3-methanesulfonyl-propyl)-2-methyl-1H-pyrrole-3-carboxylic acid.

$^1$H NMR (400 MHz, DMSO-d$_6$) δ 12.20 (br s, 2H, OH, NH), 9.59 (s, 1H, CHO), 3.07 (m, 4H), 2.92 (s, 3H, CH$_3$), 2.41 (s, 3H, CH$_3$), 1.96 (m, 2H).

General Procedure for the Synthesis of 3-Substituted 4-Aryl-1,3-dihydro-indol-2-one

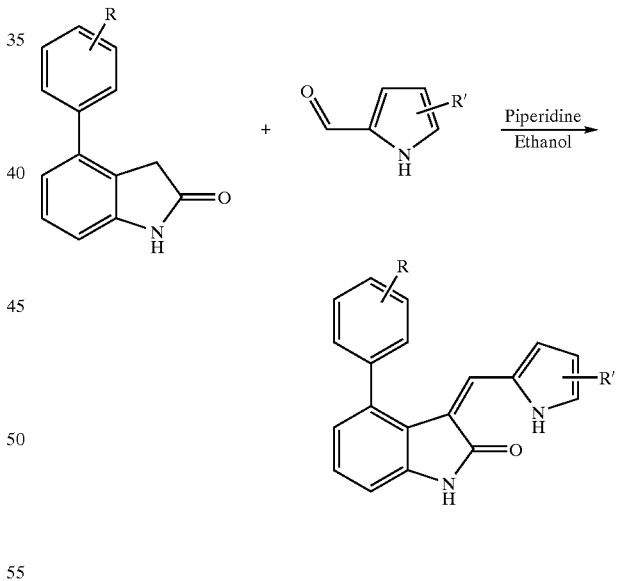

To a solution of 4-aryl-1,3-dihydro-indol-2-one (1 molar equivalent) and pyrrole aldehyde (1 molar equivalent in ethanol (0.125 M) was added catalytic amount of piperidine. The reaction mixture was stirred at room temperature for three days, and a yellow solid product was precipitated out, or a yellow solution was observed. If it was precipitated out, the yellow solid product was filtered, washed by ethanol, and dried under high vacuum. If it was not precipitated, the product was purified on a silica gel column eluting with MeOH—CH$_2$Cl$_2$.

Example 1

2-Methyl-4-[3-(4-methyl-piperazin-1-yl)-propyl]-5-(2-oxo-4-phenyl-1,2-dihydro-indol-3-ylidenemethyl)-1H-pyrrole-3-carboxylic Acid Ethyl Ester

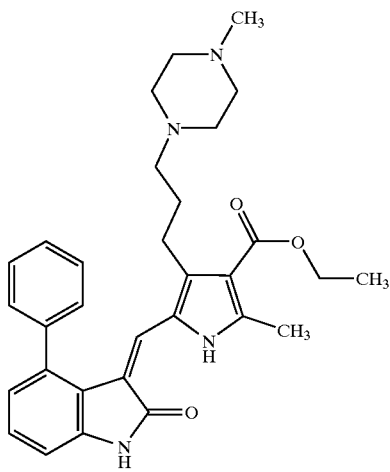

To a solution of 4-phenyl-1,3-dihydro-indol-2-one (41.9 mg, 0.20 mmol) and 5-formyl-2-methyl-4-[3-(4-methyl-piperazin-1-yl)-propyl]-1H-pyrrole-3-carboxylic acid ethyl ester (64.2 mg, 0.20 mmol) in ethanol (1 mL) was added piperidine (0.1 mL). The reaction mixture was stirred at 70° C. for over-night. The solvent was evaporated and the residue was purified on a silica gel column eluting with MeOH—CH$_2$CL$_2$ 1:9 to provide 2-methyl-4-[3-(4-methyl-piperazin-1-yl)-propyl]-5-(2-oxo-4-phenyl-1,2-dihydro-indol-3-ylidenemethyl)-1H-pyrrole-3-carboxylic acid ethyl ester as a yellow solid (30 mg, 29%).

$^1$H-NMR (400 MHz, DMSO-d$_6$) δ 13.85 (br s, 1H, pyrrole NH), 11.12 (br s, 1H, CONH), 7.53 (m, 3H, aromatic), 7.44 (m, 2H, aromatic), 7.21 (t, 1H, aromatic), 6.94 (d, 1H, aromatic), 6.89 (s, 1H, aromatic), 6.78 (d, 1H, aromatic), 4.24 (q, 2H, OCH$_2$), 2.50 (m, 11H, 3×CH$_2$+CH$_3$), 2.33 (s, 3H, CH$_3$), 2.10 (m, 4H, 2×CH$_2$), 1.26 (m, 5H, CH$_2$+CH$_3$). MS m/z 511 [M$^-$−1].

Example 2

3-[3,5-Dimethyl-4-(4-methyl-piperazine-1-carbonyl)-1H-pyrrol-2-ylmethylene]-4-phenyl-1,3-dihydro-indol-2-one

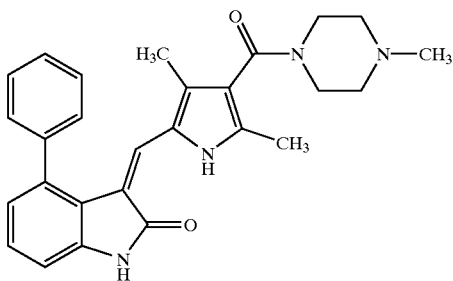

To a solution of 4-phenyl-1,3-dihydro-indol-2-one (41.9 mg, 0.20 mmol) and 3,5-dimethyl-4-(4-methyl-piperazine-1-carbonyl)-1H-pyrrole-2-carbaldehyde (49.9 mg, 0.20 mmol) in ethanol (1 mL) was added piperidine (0.1 mL). The reaction mixture was stirred at 70° C. for over-night. The solvent was evaporated and the residue was crystallized from EtOAc-hexanes to provide 3-[3,5-dimethyl-4-(4-methyl-piperazine-1-carbonyl)-1H-pyrrol-2-ylmethylene]-4-phenyl-1,3-dihydro-indol-2-one as a yellow solid (50 mg, 57%).

$^1$H-NMR (400 MHz, CD$_3$OD) δ 7.53 (m, 2H, aromatic), 7.47 (m, 1H, aromatic), 7.40 (m, 2H, aromatic), 7.18 (t, 1H, aromatic), 6.93 (d, 1H, aromatic), 6.87 (s, 1H, aromatic), 6.81 (d, 1H, aromatic), 3.71 (br s, 2H, CH$_2$), 3.45 (br s, 2H, CH$_2$), 2.42 (br s, 4H, 2×CH$_2$), 2.30 (s, 3H, CH$_3$), 2.28 (s, 3H, CH$_3$), 1.60 (s, 3H, CH$_3$). MS m/z 441 [M$^+$+1].

Example 3

2,4-Dimethyl-5-(2-oxo-4-phenyl-1,2-dihydro-indol-3-ylidenemethyl)-1H-pyrrole-3-carboxylic Acid (2-Diethylamino-ethyl)-amide

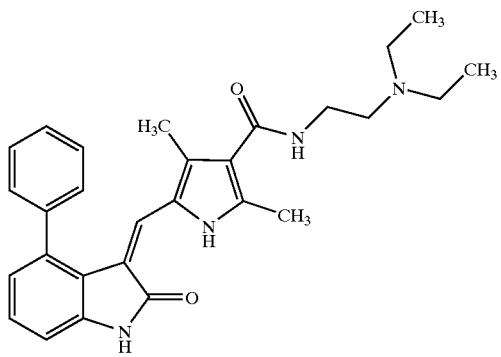

To a solution of 4-phenyl-1,3-dihydro-indol-2-one (41.9 mg, 0.20 mmol) and 5-formyl-2,4-dimethyl-1H-pyrrole-3-carboxylic acid (2-diethylamino-ethyl)-amide (53.1 mg, 0.20 mmol) in ethanol (1 mL) was added piperidine (0.1 mL). The reaction mixture was stirred at room temperature for three days. A yellow solid product was precipitated out, filtered, washed by ethanol for three times, and dried under high vacuum to provide 2,4-dimethyl-5-(2-oxo-4-phenyl-1,2-dihydro-indol-3-ylidenemethyl)-1H-pyrrole-3-carboxylic acid (2-diethylamino-ethyl)-amide (51 mg, 56%)

$^1$H-NMR (400 MHz, DMSO-d$_6$) δ 13.48 (br s, 1H, pyrrole NH), 11.03 (br s, 1H, CONH), 7.43 (m, 6H, aromatic), 7.18 (t, 1H, CONH), 7.18 (t, 1H, aromatic), 6.93 (m, 1H, aromatic), 6.77 (m, 2H, aromatic), 3.21 (m, 2H, CH$_2$), 2.48 (m, 6H, 3×CH$_2$), 2.38 (s, 3H, CH$_3$), 1.66 (s, 3H, CH$_3$), 0.87 (t, 6H, 2×CH$_3$). MS m/z 455 [M$^-$−1].

Example 4

3-[3,5-Dimethyl-4-(4-methyl-piperazine-1-carbonyl)-1H-pyrrol-2-ylmethylene]-4-(4-fluoro-phenyl)-1,3-dihydro-indol-2-one

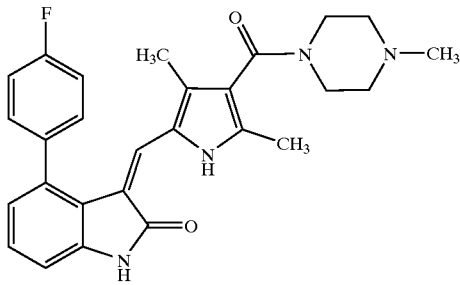

To a solution of 4-(4-fluoro-phenyl)-1,3-dihydro-indol-2-one (56.8 mg, 0.25 mmol) and 3,5-dimethyl-4-(4-methyl-piperazine-1-carbonyl)-1H-pyrrole-2-carbaldehyde (64.8 mg, 0.26 mmol) in ethanol (2 mL) was added piperidine (3 drops). The reaction mixture was stirred at room temperature for three days. A yellow solid product was precipitated out, filtered, washed by ethanol for three times, and dried under high vacuum to provide 3-[3,5-Dimethyl-4-(4-methyl-piperazine-1-carbonyl)-1H-pyrrol-2-ylmethylene]-4-(4-fluoro-phenyl)-1,3-dihydro-indol-2-one as a yellow solid (63.9 mg, 56%)

$^1$H-NMR (400 MHz, DMSO-$d_6$) δ 13.45 (br s, 1H, pyrrole NH), 11.04 (br s, 1H, CONH), 7.47 (m, 2H, aromatic), 7.39 (m, 2H, aromatic), 7.19 (t, 1H, aromatic), 6.92 (m, 1H, aromatic), 6.79 (m, 1H, aromatic), 6.71 (s, 1H, aromatic), 3.31 (s, 4H, 2×CH$_2$), 2.38 (m, 7H, 2×CH$_2$+CH$_3$), 2.17 (s, 3H, CH$_3$), 1.60 (s, 3H, CH$_3$). MS m/z 457 [M$^-$−1].

Example 5

5-[4-(4-Fluoro-phenyl)-2-oxo-1,2-dihydro-indol-3-ylidenemethyl]-2,4-dimethyl-1H-pyrrole-3-carboxylic Acid (2-Diethylamino-ethyl)-amide

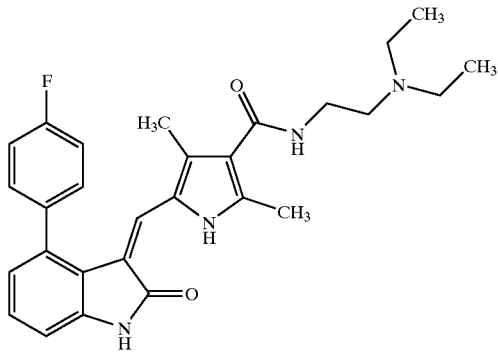

To a solution of 4-(4-fluoro-phenyl)-1,3-dihydro-indol-2-one (56.8 mg, 0.25 mmol) and 5-formyl-2,4-dimethyl-1H-pyrrole-3-carboxylic acid (2-diethylamino-ethyl)-amide (69.0 mg, 0.26 mmol) in ethanol (2 mL) was added piperidine (3 drops). The reaction mixture was stirred at room temperature for three days. A yellow solid product was precipitated out, filtered, washed by ethanol for three times, and dried under high vacuum to provide 5-[4-(4-Fluoro-phenyl)-2-oxo-1,2-dihydro-indol-3-ylidenemethyl]-2,4-dimethyl-1H-pyrrole-3-carboxylic acid (2-diethylamino-ethyl)-amide as a yellow solid (82.9 mg, 70%)

$^1$H-NMR (400MHz, DMSO-$d_6$) δ 13.47 (br s, 1H, pyrrole NH), 11.04 (br s, 1H, CONH), 7.46 (m, 2H, aromatic), 7.38 (m, 2H, aromatic), 7.32 (t, 1H, CONH), 7.18 (t, 1H, aromatic), 6.93 (m, 1H, aromatic), 6.79 (m, 1H, aromatic), 6.71 (s, 1H, aromatic), 3.20 (m, 2H, CH$_2$), 2.49 (m, 6H, 3×CH$_2$), 2.39 (s, 3H, CH$_3$), 1.74 (s, 3H, CH$_3$), 0.95 (t, 6H, 2×CH$_3$). MS m/z 473 [M$^-$−1].

Example 6

5-[4-(4-Fluoro-phenyl)-2-oxo-1,2-dihydro-indol-3-ylidenemethyl]-2,4-dimethyl-1H-pyrrole-3-carboxylic Acid (2-Pyrrolidin-1-yl-ethyl)-amide

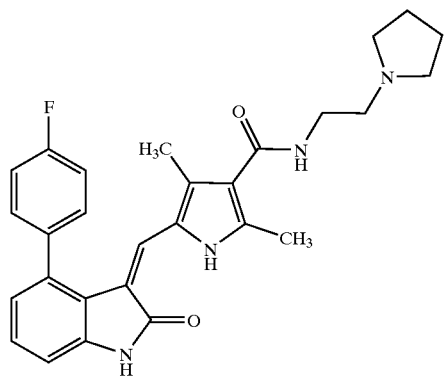

To a solution of 4-(4-fluoro-phenyl)-1,3-dihydro-indol-2-one (56.8 mg, 0.25 mmol) and 5-formyl-2,4-dimethyl-1H-pyrrole-3-carboxylic acid (2-pyrrolidin-1-yl-ethyl)-amide (68.5 mg, 0.26 mmol) in ethanol (2 mL) was added piperidine (3 drops). The reaction mixture was stirred at room temperature for three days. A yellow solid product was precipitated out, filtered, washed by ethanol for three times, and dried under high vacuum to provide pure product 5-[4-(4-fluoro-phenyl)-2-oxo-1,2-dihydro-indol-3-ylidenemethyl]-2,4-dimethyl-1H-pyrrole-3-carboxylic acid (2-pyrrolidin-1-yl-ethyl)-amide as a yellow solid (90.0 mg, 76%).

$^1$H-NMR (400 MHz, DMSO-$d_6$) δ 13.46 (br s, 1H, pyrrole NH), 11.04 (br s, 1H, CONH), 7.42 (m, 5H, aromatic+CONH), 7.18 (t, 1H, aromatic), 6.92 (m, 1H, aromatic), 6.79 (m, 1H, aromatic), 6.71 (s, 1H, aromatic), 3.32 (m, 2H, CH$_2$), 2.49 (m, 2H, CH$_2$), 2.45 (m, 4H, 2×CH$_2$), 2.38 (s, 3H, CH$_3$), 1.73 (s, 3H, CH$_3$), 1.67 (m, 4H, 2×CH$_2$). MS m/z 471 [M$^-$−1].

Example 7

5-[4-(4-Fluoro-phenyl)-2-oxo-1,2-dihydro-indol-3-ylidenemethyl]-2,4-dimethyl-1H-pyrrole-3-carboxylic Acid (2-[1,2,3]Triazol-1-yl-ethyl)-amide

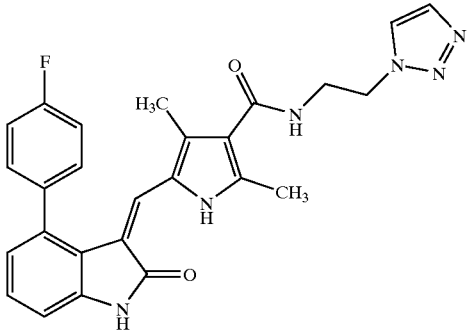

To a solution of 4-(4-fluoro-phenyl)-1,3-dihydro-indol-2-one (56.8 mg, 0.25 mmol) and 5-formyl-2,4-dimethyl-1H-pyrrole-3-carboxylic acid (2-[1,2,3]triazol-1-yl-ethyl)-amide (67.9 mg, 0.26 mmol) in ethanol (2 mL) was added piperidine (3 drops). The reaction mixture was stirred at room temperature for three days. A yellow solid product was precipitated out, filtered, washed by ethanol for three times, and dried under high vacuum to provide pure product 5-[4-(4-Fluoro-phenyl)-2-oxo-1,2-dihydro-indol-3-ylidenemethyl]-2,4-dimethyl-1H-pyrrole-3-carboxylic acid (2-[1,2,3]triazol-1-yl-ethyl)-amide as a yellow solid (42.8 mg, 36%).

$^1$H-NMR (400 MHz, DMSO-$d_6$) δ 13.47 (br s, 1H, pyrrole NH), 11.04 (br s, 1H, CONH), 8.10 (m, 1H, aromatic), 7.71 (m, 1H, aromatic), 7.61 (m, 1H, CONH), 7.60 (m, 2H, aromatic), 7.38 (m, 2H, aromatic), 7.20 (m, 1H, aromatic), 6.93 (m, 1H, aromatic), 6.78 (m, 1H, aromatic), 6.70 (s, 1H, aromatic), 4.53 (m, 2H, CH$_2$), 3.63 (m, 2H, CH$_2$), 2.30 (s, 3H, CH$_3$), 1.65 (s, 3H, CH$_3$). MS m/z 469 [M$^-$–1].

Example 8

4-(4-Fluoro-phenyl)-3-[5-methyl-3-(4-methyl-piperazine-1-carbonyl)-1H-pyrrol-2-ylmethylene]-1,3-dihydro-indol-2-one

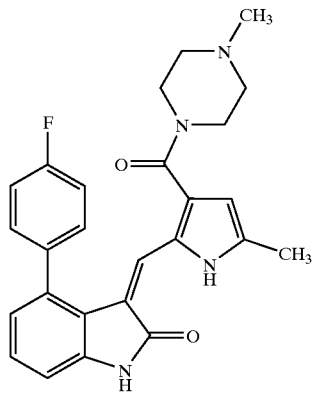

To a solution of 4-(4-fluoro-phenyl)-1,3-dihydro-indol-2-one (56.8 mg, 0.25 mmol) and 5-methyl-3-(4-methyl-piperazine-1-carbonyl)-1H-pyrrole-2-carbaldehyde (61.2 mg, 0.26 mmol) in ethanol (2 mL) was added piperidine (3 drops). The reaction mixture was stirred at room temperature for three days. A yellow solid product was precipitated out, filtered, washed by ethanol for three times, and dried under high vacuum to provide pure product 4-(4-fluoro-phenyl)-3-[5-methyl-3-(4-methyl-piperazine-1-carbonyl)-1H-pyrrol-2-ylmethylene]-1,3-dihydro-indol-2-one as a yellow solid (44.1 mg, 40%).

$^1$H-NMR (400 MHz, DMSO-$d_6$) δ 13.63 (br s, 1H, pyrrole NH), 11.10 (br s, 1H, CONH), 7.40 (m, 2H, aromatic), 7.24 (m, 3H, aromatic), 6.97 (s, 1H, vinyl), 6.91 (m, 1H, aromatic), 6.75 (m, 1H, aromatic), 6.07 (s, 1H, aromatic), 3.44, 3.30 (2×m, 4H, 2×CH$_2$), 2.32 (s, 3H, CH$_3$), 2.18 (m, 7H, 2×CH$_2$+CH$_3$). MS m/z 443 [M$^-$–1].

Example 9

2-[4-(4-Fluoro-phenyl)-2-oxo-1,2-dihydro-indol-3-ylidenemethyl]-5-methyl-1H-pyrrole-3-carboxylic Acid (2-[1,2,3]Triazol-1-yl-ethyl)-amide

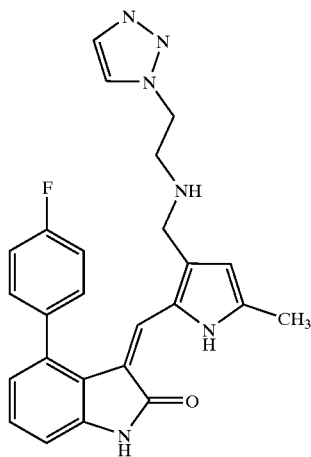

To a solution of 4-(4-fluoro-phenyl)-1,3-dihydro-indol-2-one (56.8 mg, 0.25 mmol) and 2-formyl-5-methyl-1H-pyrrole-3-carboxylic acid (2-[1,2,3]triazol-1-yl-ethyl)-amide (64.8 mg, 0.26 mmol) in ethanol (2 mL) was added piperidine (3 drops). The reaction mixture was stirred at room temperature for three days. A yellow solid product was precipitated out, filtered, washed by ethanol for three times, and dried under high vacuum to provide pure product as a yellow solid 2-[4-(4-fluoro-phenyl)-2-oxo-1,2-dihydro-indol-3-ylidenemethyl]-5-methyl-1H-pyrrole-3-carboxylic acid (2-[1,2,3]triazol-1-yl-ethyl)-amide (74.3 mg, 65%).

$^1$H-NMR (400MHz, DMSO-$d_6$) δ 13.84 (br s, 1H, pyrrole NH), 11.12 (br s, 1H, CONH), 7.98 (m, 2H, aromatic), 7.93 (s, 1H, aromatic), 7.73 (m, 1H, aromatic), 7.38 (m, 2H, aromatic), 7.23 (m, 3H, aromatic+CONH), 6.92 (m, 1H, aromatic), 6.77 (m, 1H, aromatic), 6.32 (m, 1H, aromatic), 4.53 (m, 2H, CH$_2$), 3.63 (m, 2H, CH$_2$), 2.30 (s, 3H, CH$_3$), 1.65 (s, 3H, CH$_3$). MS m/z 455 [M$^-$–1].

Example 10

3-[3-((S)-3-Dimethylamino-pyrrolidine-1-carbonyl)-5-methyl-1H-pyrrol-2-ylmethylene]-4-(4-fluoro-phenyl)-1,3-dihydro-indol-2-one

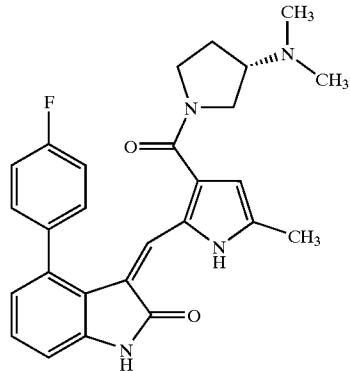

To a solution of 4-(4-fluoro-phenyl)-1,3-dihydro-indol-2-one (56.8 mg, 0.25 mmol) and 3-[3-(3S)-dimethylamino-pyrrolidine-1-carbonyl]-5-methyl-1H-pyrrole-2-carbaldehyde (64.8 mg, 0.26 mmol) in ethanol (2 mL) was added piperidine (3 drops). The reaction mixture was stirred at room temperature for three days. A yellow solid product was precipitated out, filtered, washed by ethanol for three times, and dried under high vacuum to provide pure product 3-[3-[3-(3S)-dimethylamino-pyrrolidine-1-carbonyl]-5-methyl-1H-pyrrol-2-ylmethylene]-4-(4-fluoro-phenyl)-1,3-dihydro-indol-2-one as a yellow solid (64.4 mg, 56%).

$^1$H-NMR (400 MHz, DMSO-$d_6$) δ 13.69 (br d, 1H, pyrrole NH), 11.10 (br s, 1H, CONH), 7.40 (m, 2H, aromatic), 7.20 (m, 4H, aromatic), 6.92 (m, 1H, aromatic), 6.75 (m, 1H, aromatic), 6.20 (m, 1H, aromatic), 3.30 (m, 4H, 4×CH), 3.00 (m, 1H, CH), 2.60 (m, 1H, CH), 2.33 (s, 3H, CH$_3$), 2.21 (s, 3H, CH$_3$), 2.08 (s, 3H, CH$_3$), 1.64 (m, 1H, CH). MS m/z 457 [M$^-$−1].

Example 11

3-[3-((R)-3-Dimethylamino-pyrrolidine-1-carbonyl)-5-methyl-1H-pyrrol-2-ylmethylene]-4-(4-fluoro-phenyl)-1,3-dihydro-indol-2-one

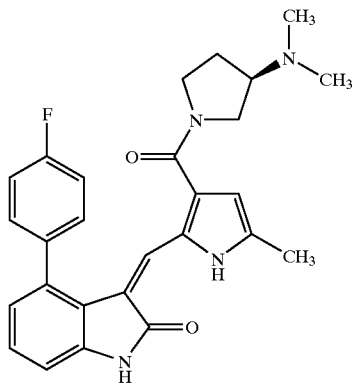

To a solution of 4-(4-fluoro-phenyl)-1,3-dihydro-indol-2-one (56.8 mg, 0.25 mmol) and 3-[3-(3R)-dimethylamino-pyrrolidine-1-carbonyl]-5-methyl-1H-pyrrole-2-carbaldehyde (64.8 mg, 0.26 mmol) in ethanol (2 mL) was added piperidine (3 drops). The reaction mixture was stirred at room temperature for three days. A yellow solid product was precipitated out, filtered, washed by ethanol for three times, and dried under high vacuum to provide pure product 3-[3-[3-(3R)-dimethylamino-pyrrolidine-1-carbonyl]-5-methyl-1H-pyrrol-2-ylmethylene]-4-(4-fluoro-phenyl)-1,3-dihydro-indol-2-one as a yellow solid (63.9, 56%).

$^1$H-NMR (400 MHz, DMSO-$d_6$) δ 13.69 (br d, 1H, pyrrole NH), 11.10 (br s, 1H, CONH), 7.40 (m, 2H, aromatic), 7.20 (m, 4H, aromatic), 6.92 (m, 1H, aromatic), 6.75 (m, 1H, aromatic), 6.20 (m, 1H, aromatic), 3.33 (m, 4H, 4×CH), 3.00 (m, 1H, CH), 2.60 (m, 1H, CH), 2.33 (s, 3H, CH$_3$), 2.21 (s, 3H, CH$_3$), 2.08 (s, 3H, CH$_3$), 1.64 (m, 1H, CH). MS m/z 457 [M$^-$−1].

Example 12

3-[3,5-Dimethyl-4-(4-methyl-piperazine-1-carbonyl)-1H-pyrrol-2-ylmethylene]4-(3-fluoro-phenyl)-1,3-dihydro-indol-2-one

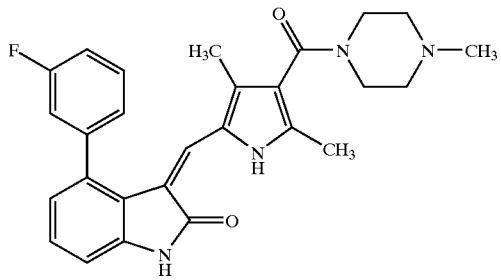

To a solution of 4-(3-fluoro-phenyl)-1,3-dihydro-indol-2-one (56.8 mg, 0.25 mmol) and 3,5-dimethyl-4-(4-methyl-piperazine-1-carbonyl)-1H-pyrrole-2-carbaldehyde (64.8 mg, 0.26 mmol) in ethanol (2 mL) was added piperidine (3 drops). The reaction mixture was stirred at room temperature for three days. A yellow solid product was precipitated out, filtered, washed by ethanol for three times, and dried under high vacuum to provide 3-[3,5-dimethyl-4-(4-methyl-piperazine-1-carbonyl)-1H-pyrrol-2-ylmethylene]-4-(3-fluoro-phenyl)-1,3-dihydro-indol-2-one as a yellow solid (65 mg, 57%)

$^1$H-NMR (400 MHz, DMSO-$d_6$) δ 13.45 (br s, 1H, pyrrole NH), 11.06 (br s, 1H, CONH), 7.59 (m, 1H, aromatic), 7.33 (m, 3H, aromatic), 7.20 (t, 1H, aromatic), 6.94 (d, 1H, aromatic), 6.80 (d, 1H, aromatic), 6.77 (s, 1H, aromatic), 3.38 (m, 4H, 2×CH$_2$), 2.24 (m, 7H, 2×CH$_2$+CH$_3$), 2.16 (s, 3H, CH$_3$), 1.59 (s, 3H, CH$_3$). MS m/z 459 [M$^+$+1].

Example 13

5-[4-(3-Fluoro-phenyl)-2-oxo-1,2-dihydro-indol-3-ylidenemethyl]-2,4-dimethyl-1H-pyrrole-3-carboxylic Acid (2-Diethylamino-ethyl)-amide

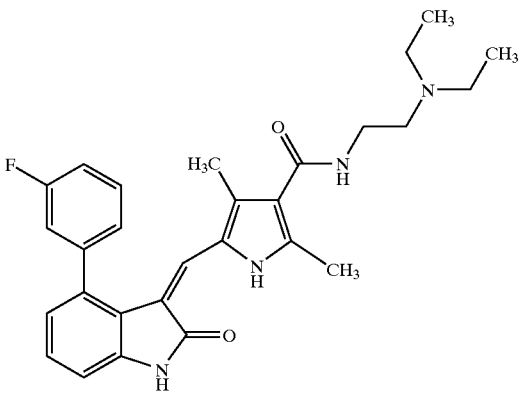

To a solution of 4-(3-fluoro-phenyl)-1,3-dihydro-indol-2-one (56.8 mg, 0.25 mmol) and 5-formyl-2,4-dimethyl-1H-pyrrole-3-carboxylic acid (2-diethylamino-ethyl)-amide (69.0 mg, 0.26 mmol) in ethanol (2 mL) was added piperidine (3 drops). The reaction mixture was stirred at room temperature for three days. A yellow solid product was precipitated out, filtered, washed by ethanol for three times, and dried under high vacuum to provide 5-[4-(3-fluoro-phenyl)-2-oxo-1,2-dihydro-indol-3-ylidenemethyl]-2,4-dimethyl-1H-pyrrole-3-carboxylic acid (2-diethylamino-ethyl)-amide as a yellow solid (70 mg, 59%)

$^1$H-NMR (400 MHz, DMSO-$d_6$) δ 13.48 (br s, 1H, pyrrole NH), 11.07 (br s, 1H, CONH), 7.59 (m, 1H, aromatic), 7.32 (m, 4H, aromatic), 7.20 (t, 1H, CONH), 6.95 (d, 1H, aromatic), 6.80 (m, 2H, aromatic), 3.22 (m, 2H, CH$_2$), 2.49 (m, 6H, 3×CH$_2$), 2.39 (s, 3H, CH$_3$), 1.73 (s, 3H, CH$_3$), 0.95 (t, 6H, 2×CH$_3$). MS m/z 475 [M$^+$+1].

Example 14

5-[4-(3-Fluoro-phenyl)-2-oxo-1,2-dihydro-indol-3-ylidenemethyl]-2,4-dimethyl-1H-pyrrole-3-carboxylic Acid (2-Pyrrolidin-1-yl-ethyl)-amide

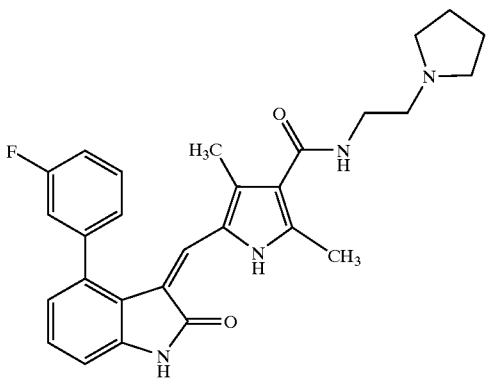

To a solution of 4-(3-fluoro-phenyl)-1,3-dihydro-indol-2-one (56.8 mg, 0.25 mmol) and 5-formyl-2,4-dimethyl-1H-pyrrole-3-carboxylic acid (2-pyrrolidin-1-yl-ethyl)-amide (68.5 mg, 0.26 mmol) in ethanol (2 mL) was added piperidine (3 drops). The reaction mixture was stirred at room temperature for three days. A yellow solid product was precipitated out, filtered, washed by ethanol for three times, and dried under high vacuum to provide pure product 5-[4-(3-fluoro-phenyl)-2-oxo-1,2-dihydro-indol-3-ylidenemethyl]-2,4-dimethyl-1H-pyrrole-3-carboxylic acid (2-pyrrolidin-1-yl-ethyl)-amide as a yellow solid (56.4 mg, 48%).

$^1$H-NMR (400 MHz, DMSO-$d_6$) δ 13.47 (br s, 1H, pyrrole NH), 11.06 (br s, 1H, CONH), 7.59 (m, 1H, aromatic), 7.46 (t, 1H, CONH), 7.34 (m, 3H, aromatic), 7.20 (t, 1H, aromatic), 6.95 (d, 1H, aromatic), 6.80 (m, 2H, aromatic), 3.27 (m, 2H, CH$_2$), 2.50 (m, 2H, CH$_2$), 2.45 (m, 4H, 2×CH$_2$), 2.38 (s, 3H, CH$_3$), 1.72 (s, 3H, CH$_3$), 1.67 (m, 4H 2×CH$_2$). MS m/z 473 [M$^+$+1].

Example 15

5-[4-(3-Fluoro-phenyl)-2-oxo-1,2-dihydro-indol-3-ylidenemethyl]-2,4-dimethyl-1H-pyrrole-3-carboxylic Acid (2-[1,2,3]Triazol-1-yl-ethyl)-amide

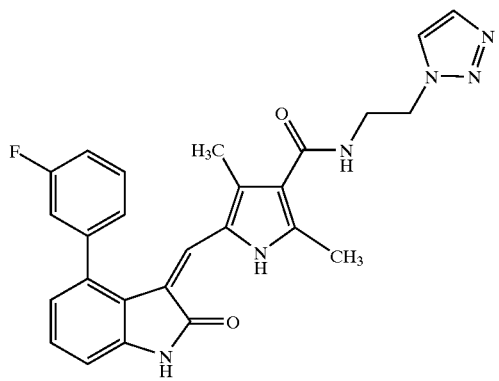

To a solution of 4-(3-fluoro-phenyl)-1,3-dihydro-indol-2-one (56.8 mg, 0.25 mmol) and 5-formyl-2,4-dimethyl-1H-pyrrole-3-carboxylic acid (2-[1,2,3]triazol-1-yl-ethyl)-amide (67.9 mg, 0.26 mmol) in ethanol (2 mL) was added piperidine (3 drops). The reaction mixture was stirred at room temperature for three days. A yellow solid product was precipitated out, filtered, washed by ethanol for three times, and dried under high vacuum to provide pure product 5-[4-(3-fluoro-phenyl)-2-oxo-1,2-dihydro-indol-3-ylidenemethyl]-2,4-dimethyl-1H-pyrrole-3-carboxylic acid (2-[1,2,3]triazol-1-yl-ethyl)-amide as a yellow solid (49.9 mg, 42%).

$^1$H-NMR (400 MHz, DMSO-$d_6$) δ 13.47 (br s, 1H, pyrrole NH), 11.06 (br s, 1H, CONH), 8.10 (s, 1H, aromatic), 7.72 (m, 1H, aromatic), 7.63 (m, 2H, CONH+ aromatic), 7.33 (m, 3H, aromatic), 7.20 (t, 1H, aromatic), 6.95 (d, 1H, aromatic), 6.80 (m, 2H, aromatic), 4.53 (m, 2H, CH$_2$), 3.63 (m, 2H, CH$_2$), 2.29 (s, 3H, CH$_3$), 1.64 (s, 3H, CH$_3$). MS m/z 471 [M$^+$+1].

Example 16

3-[3-((S)-3-Dimethylamino-pyrrolidine-1-carbonyl)-5-methyl-1H-pyrrol-2-ylmethylene]-4-(3-fluoro-phenyl)-1,3-dihydro-indol-2-one

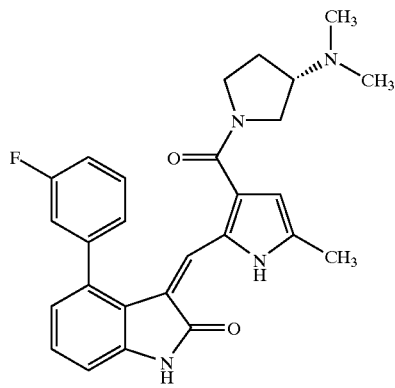

To a solution of 4-(3-fluoro-phenyl)-1,3-dihydro-indol-2-one (56.8 mg, 0.25 mmol) and 3-[(3S)-3-dimethylamino-pyrrolidine-1-carbonyl]-5-methyl-1H-pyrrole-2-carbaldehyde (64.8 mg, 0.26 mmol) in ethanol (2 mL) was added piperidine (3 drops). The reaction mixture was stirred at room temperature for three days. A yellow solid product was precipitated out, filtered, washed by ethanol for three times, and dried under high vacuum to provide pure product 3-[3-[(3S)-3-dimethylamino-pyrrolidine-1-carbonyl]-5-methyl-1H-pyrrol-2-ylmethylene]-4-(3-fluoro-phenyl)-1,3-dihydro-indol-2-one as a yellow solid (60.9 mg, 53%).

$^1$H-NMR (400 MHz, DMSO-d$_6$) δ 13.63 (br d, 1H, pyrrole NH), 11.12 (br s, 1H, CONH), 7.47 (m, 1H, aromatic), 7.21 (m, 5H, aromatic), 6.94 (d, 1H, aromatic), 6.77 (d, 1H, aromatic), 6.19 (m, 1H, aromatic), 3.30 (m, 4H, 4×CH), 3.00 (m, 1 H, CH), 2.60 (m, 1H, CH), 2.33 (s, 3H, CH$_3$), 2.21 (s, 3H, CH$_3$), 2.07 (s, 3H, CH$_3$), 1.61 (m, 1H, CH). MS m/z 459 [M$^+$+1].

Example 17

3-[3-((R)-3-Dimethylamino-pyrrolidine-1-carbonyl)-5-methyl-1H-pyrrol-2-ylmethylene]-4-(3-fluoro-phenyl)-1,3-dihydro-indol-2-one

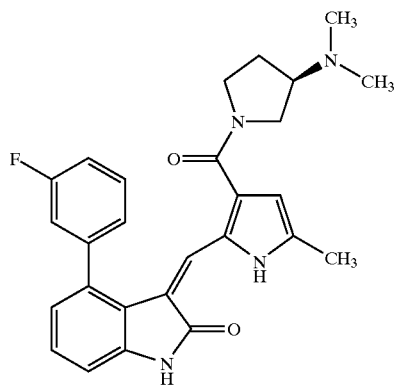

To a solution of 4-(3-fluoro-phenyl)-1,3-dihydro-indol-2-one (56.8 mg, 0.25 mmol) and 3-[(3R)-3-dimethylamino-pyrrolidine-1-carbonyl]-5-methyl-1H-pyrrole-2-carbaldehyde (64.8 mg, 0.26 mmol) in ethanol (2 mL) was added piperidine (3 drops). The reaction mixture was stirred at room temperature for three days. A yellow solid product was precipitated out, filtered, washed by ethanol for three times, and dried under high vacuum to provide pure product 3-[3-[(3R)-3-dimethylamino-pyrrolidine-1-carbonyl]-5-methyl-1H-pyrrol-2-ylmethylene]-4-(3-fluoro-phenyl)-1,3-dihydro-indol-2-one as a yellow solid (63.5, 55%).

$^1$H-NMR (400 MHz, DMSO-d$_6$) δ 13.64 (br d, 1H, pyrrole NH), 11.12 (br s, 1H, CONH), 7.47 (m, 1H, aromatic), 7.22 (m, 5H, aromatic), 6.94 (d, 1H, aromatic), 6.78 (d, 1H, aromatic), 6.19 (m, 1H, aromatic), 3.31 (m, 4H, 4×CH), 3.00 (m, 1H, CH), 2.60 (m, 1H, CH), 2.33 (s, 3H, CH$_3$), 2.21 (s, 3H, CH$_3$), 2.07 (s, 3H, CH$_3$), 1.61 (m, 1H, CH). MS m/z 459 [M$^+$+1].

Example 18

5-[4-(3-Fluoro-phenyl)-2-oxo-1,2-dihydro-indol-3-ylidenemethyl]-2-methyl-4-[3-(4-methyl-piperazin-1-yl)-propyl]-1H-pyrrole-3-carboxylic Acid Ethyl Ester

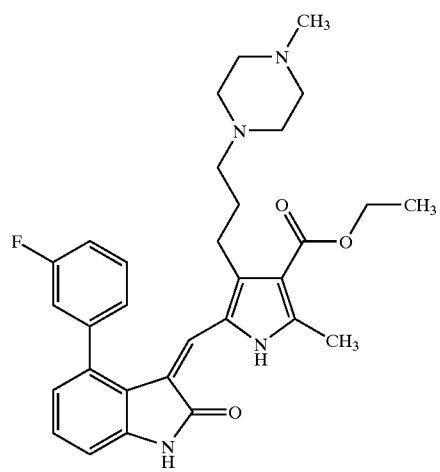

To a solution of 4-(3-fluoro-phenyl)-1,3-dihydro-indol-2-one (56.8 mg, 0.25 mmol) and 5-formyl-2-methyl-4-[3-(4-methyl-piperazin-1-yl)-propyl]-1H-pyrrole-3-carboxylic acid ethyl ester (80.3 mg, 0.26 mmol) in ethanol (2 mL) was added piperidine (3 drops). The reaction mixture was stirred at room temperature for three days. A yellow solid product was precipitated out, filtered, washed by ethanol for three times, and dried under high vacuum to provide pure product 5-[4-(3-fluoro-phenyl)-2-oxo-1,2-dihydro-indol-3-ylidenemethyl]-2-methyl-4-[3-(4-methyl-piperazin-1-yl)-propyl]-1H-pyrrole-3-carboxylic acid ethyl ester as a yellow solid (60.9 mg, 53%).

$^1$H-NMR (400 MHz, DMSO-d$_6$) δ 13.85 (br s, 1H, pyrrole NH), 11.33 (br s, 1H, CONH), 7.58 (m, 1H, aromatic), 7.32 (m, 3H, aromatic), 7.22 (t, 1H, aromatic), 6.95 (d, 1H, aromatic), 6.90 (m, 1H, aromatic), 6.80 (d, 1H, aromatic), 4.17 (q, 2H, OCH$_2$), 3.30 (s, 1H, CH$_3$), 2.26 (m, 10H, 5×CH$_2$), 2.11 (s, 3H, CH$_3$), 2.00 (m, 2H, CH$_2$), 1.26 (m, 5H, CH$_2$+CH$_3$). MS m/z 531 [M$^+$+1].

Example 19

3-[3-(cis)-3,5-Dimethyl-piperazine-1-carbonyl)-5-methyl-1H-pyrrol-2-ylmethylene]-4-(3-fluoro-phenyl)-1,3-dihydro-indol-2-one

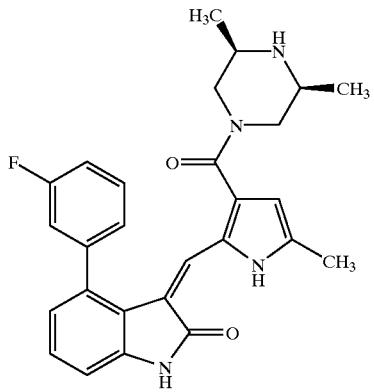

To a solution of 4-(3-fluoro-phenyl)-1,3-dihydro-indol-2-one (56.8 mg, 0.25 mmol) and 3-[(cis)-3,5-dimethyl-piperazine-1-carbonyl]-5-methyl-1H-pyrrole-2-carbaldehyde (64.8 mg, 0.26 mmol) in ethanol (2 mL) was added piperidine (3 drops). The reaction mixture was stirred at room temperature for three days. The reaction solution was evaporated, and purified on a silica gel column eluting with MeOH—CH$_2$Cl$_2$ 95:5 to provide pure product 3-[3-[(cis)-3,5-Dimethyl-piperazine-1-carbonyl)]-5-methyl-1H-pyrrol-2-ylmethylene]-4-(3-fluoro-phenyl)-1,3-dihydro-indol-2-one as a yellow solid (74.5 mg, 65%).

$^1$H-NMR (400 MHz, DMSO-d$_6$) δ 13.60 (br s, 1H, pyrrole NH), 11.11 (br s, 1H, CONH), 7.48 (m, 1H, aromatic), 7.20 (m, 4H, aromatic), 6.94 (m, 2H, aromatic), 6.77 (d, 1H, aromatic), 6.06 (d, 1H, aromatic), 4.13 (m, 1H, CH), 3.41 (m, 1H, CH), 2.37 (m, 6H, CH+CH$_2$+CH$_3$), 2.05 (m, 1H, CH), 1.04 (m, 3H, CH$_3$), 0.80 (m, 3H, CH$_3$). MS m/z 459 [M$^+$+1].

Example 20

4-(4-Chloro-phenyl)-3-[3,5-dimethyl-4-(4-methyl-piperazine-1-carbonyl)-1H-pyrrol-2-ylmethylene]-1,3-dihydro-indol-2-one

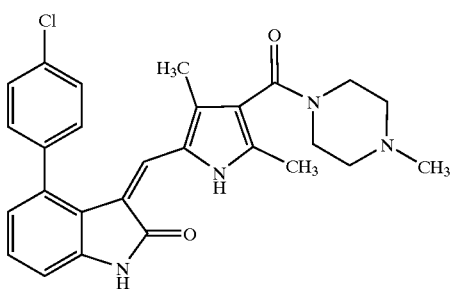

To a solution of 4-(4-chloro-phenyl)-1,3-dihydro-indol-2-one (60.9 mg, 0.25 mmol) and 3,5-dimethyl-4-(4-methyl-piperazine-1-carbonyl)-1H-pyrrole-2-carbaldehyde (64.8 mg, 0.26 mmol) in ethanol (2 mL) was added piperidine (3 drops). The reaction mixture was stirred at room temperature for three days. A yellow solid product was precipitated out, filtered, washed by ethanol for three times, and dried under high vacuum to provide 4-(4-Chloro-phenyl)-3-[3,5-dimethyl-4-(4-methyl-piperazine-1-carbonyl)-1H-pyrrol-2-ylmethylene]-1,3-dihydro-indol-2-one as a yellow solid (54 mg, 45%)

$^1$H-NMR (400 MHz, DMSO-d$_6$) δ 13.42 (br s, 1H, pyrrole NH), 11.05 (br s, 1H, CONH), 7.62 (d, 2H, aromatic), 7.45 (d, 2H, aromatic), 7.19 (t, 1H, aromatic), 6.95 (d, 1H, aromatic), 6.79 (d, 1H, aromatic), 6.66 (s, 1H, aromatic), 3.31 (m, 4H, 2×CH$_2$), 2.38 (m, 7H, 2×CH$_2$+CH$_3$), 2.17 (s, 3H, CH$_3$), 1.60 (s, 3H, CH$_3$. MS m/z 475 [M$^+$+1].

Example 21

5-[4-(4-Chloro-phenyl)-2-oxo-1,2-dihydro-indol-3-ylidenemethyl]-2,4-dimethyl-1H-pyrrole-3-carboxylic Acid (2-Diethylamino-ethyl)-amide

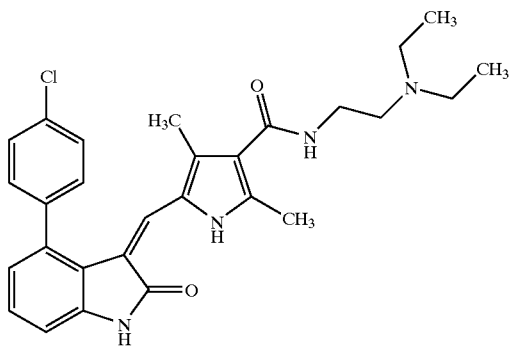

To a solution of 4-(4-chloro-phenyl)-1,3-dihydro-indol-2-one (60.9 mg, 0.25 mmol) and 5-formyl-2,4-dimethyl-1H-pyrrole-3-carboxylic acid (2-diethylamino-ethyl)-amide (69.0 mg, 0.26 mmol) in ethanol (2 mL) was added piperidine (3 drops). The reaction mixture was stirred at room temperature for three days. A yellow solid product was precipitated out, filtered, washed by ethanol for three times, and dried under high vacuum to provide 5-[4-(4-chloro-phenyl)-2-oxo-1,2-dihydro-indol-3-ylidenemethyl]-2,4-dimethyl-1H-pyrrole-3-carboxylic acid (2-diethylamino-ethyl)-amide as a yellow solid (59.4 mg, 48%).

$^1$H-NMR (400 MHz, DMSO-d$_6$) δ 13.44 (br s, 1H, pyrrole NH), 11.05 (br s, 1H, CONH), 7.61 (m, 2H, aromatic), 7.44 (m, 2H, aromatic), 7.33 (t, 1H, CONH), 7.19 (t, 1H, aromatic), 6.95 (m, 1H, aromatic), 6.80 (m, 1H, aromatic), 6.71 (s, 1H, aromatic), 3.20 (m, 2H, CH$_2$), 2.49 (m, 6H, 3×CH$_2$), 2.39 (s, 3H, CH$_3$), 1.74 (s, 3H, CH$_3$), 0.95 (t, 6H, 2×CH$_3$). MS m/z 491 [M$^+$+1].

Example 22

5-[4-(4-Chloro-phenyl)-2-oxo-1,2-dihydro-indol-3-ylidenemethyl]-2,4-dimethyl-1H-pyrrole-3-carboxylic Acid (2-Pyrrolidin-1-yl-ethyl)-amide

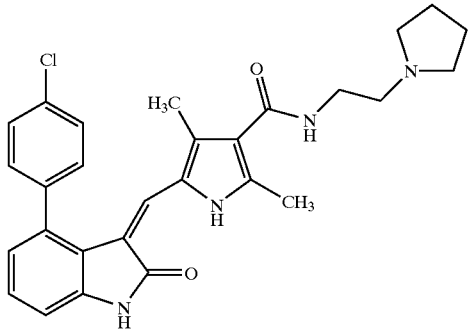

To a solution of 4-(4-chloro-phenyl)-1,3-dihydro-indol-2-one (60.9 mg, 0.25 mmol) and 5-formyl-2,4-dimethyl-1H-pyrrole-3-carboxylic acid (2-pyrrolidin-1-yl-ethyl)-amide (68.5 mg, 0.26 mmol) in ethanol (2 mL) was added piperidine (3 drops). The reaction mixture was stirred at room temperature for three days. A yellow solid product was precipitated out, filtered, washed by ethanol for three times, and dried under high vacuum to provide pure product 5-[4-(4-chloro-phenyl)-2-oxo-1,2-dihydro-indol-3-ylidenemethyl]-2,4-dimethyl-1H-pyrrole-3-carboxylic acid (2-pyrrolidin-1-yl-ethyl)-amide as a yellow solid (54.9 mg, 45%).

$^1$H-NMR (400 MHz, DMSO-$d_6$) δ 13.43 (br s, 1H, pyrrole NH), 11.05 (br s, 1H, CONH), 7.61 (m, 2H, aromatic), 7.44 (m, 3H, aromatic), 7.19 (t, 1H, aromatic), 6.93 (m, 1H, aromatic), 6.79 (m, 1H, aromatic), 6.66 (s, 1H, aromatic), 3.30 (m, 2H, CH$_2$), 2.50 (m, 2H, CH$_2$), 2.47 (m, 4H, 2×CH$_2$), 2.38 (s, 3H, CH$_3$), 1.73 (s, 3H, CH$_3$), 1.67 (m, 4H 2×CH$_2$). MS m/z 489 [M$^+$+1].

Example 23

5-[4-(4-Chloro-phenyl)-2-oxo-1,2-dihydro-indol-3-ylidenemethyl]-2,4-dimethyl-1H-pyrrole-3-carboxylic Acid (2-[1,2,3]Triazol-1-yl-ethyl)amide

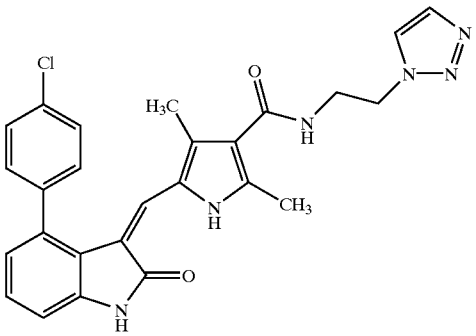

To a solution of 4-(4-chloro-phenyl)-1,3-dihydro-indol-2-one (60.9 mg, 0.25 mmol) and 5-formyl-2,4-dimethyl-1H-pyrrole-3-carboxylic acid (2-[1,2,3]triazol-1-yl-ethyl)-amide (67.9 mg, 0.26 mmol) in ethanol (2 mL) was added piperidine (3 drops). The reaction mixture was stirred at room temperature for three days. A yellow solid product was precipitated out, filtered, washed by ethanol for three times, and dried under high vacuum to provide pure product 5-[4-(4-chloro-phenyl)-2-oxo-1,2-dihydro-indol-3-ylidenemethyl]-2,4-dimethyl-1H-pyrrole-3-carboxylic acid (2-[1,2,3]triazol-1-yl-ethyl)-amide as a yellow solid (43.4 mg, 36%).

$^1$H-NMR (400 MHz, DMSO-$d_6$) δ 13.44 (br s, 1H, pyrrole NH), 11.05 (br s, 1H, CONH), 8.10 (m, 1H, aromatic), 7.71 (m, 1H, aromatic), 7.62 (m, 3H, aromatic), 7.46 (m, 2H, aromatic), 7.20 (m, 1H, aromatic), 6.93 (m, 1H, aromatic), 6.78 (m, 1H, aromatic), 6.65 (s, 1H, aromatic), 4.53 (m, 2H, CH$_2$), 3.64 (m, 2H, CH$_2$), 2.30 (s, 3H, CH$_3$), 1.64 (s, 3H, CH$_3$). MS m/z 487 [M$^+$+1].

Example 24

4-(4-Chloro-phenyl)-3-[3-((S)-3-dimethylamino-pyrrolidine-1-carbonyl)-5-methyl-1H-pyrrol-2-ylmethylene]-1,3-dihydro-indol-2-one

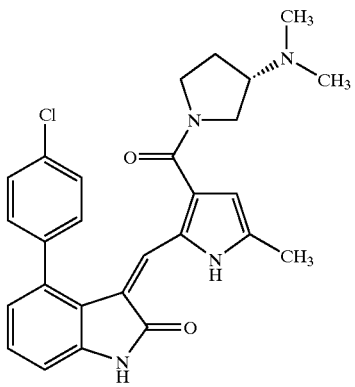

To a solution of 4-(4-chloro-phenyl)-1,3-dihydro-indol-2-one (60.9 mg, 0.25 mmol) and 3-[(3S)-3-dimethylamino-pyrrolidine-1-carbonyl]-5-methyl-1H-pyrrole-2-carbaldehyde (64.8 mg, 0.26 mmol) in ethanol (2 mL) was added piperidine (3 drops). The reaction mixture was stirred at room temperature for three days. A yellow solid product was precipitated out, filtered, washed by ethanol for three times, and dried under high vacuum to provide pure product 4-(4-Chloro-phenyl)-3-[3-[(3S)-3-dimethylamino-pyrrolidine-1-carbonyl]-5-methyl-1H-pyrrol-2-ylmethylene]-1,3-dihydro-indol-2-one as a yellow solid (60.1 mg, 51%).

$^1$H-NMR (400 MHz, DMSO-$d_6$) δ 13.71 (br d, 1H, pyrrole NH), 11.13 (br s, 1H, CONH), 7.47 (m, 2H, aromatic), 7.40 (m, 2H, aromatic), 7.27 (d, 1H, aromatic), 7.20 (t, 1H, aromatic), 6.93 (d, 1H, aromatic), 6.74 (m, 1H, aromatic), 6.20 (m, 1H, aromatic), 3.30 (m, 4H, 4×CH), 3.00 (m, 1H, CH), 2.60 (m, 1H, CH), 2.33 (s, 3H, CH$_3$), 2.21 (s, 3H, CH$_3$), 2.08 (s, 3H, CH$_3$), 1.64 (m, 1H, CH). MS m/z 475 [M$^+$+1].

Example 25

4-(4-Chloro-phenyl)-3-[3-((R)-3-dimethylamino-pyrrolidine-1-carbonyl)-5-methyl-1H-pyrrol-2-ylmethylene]-1,3-dihydro-indol-2-one

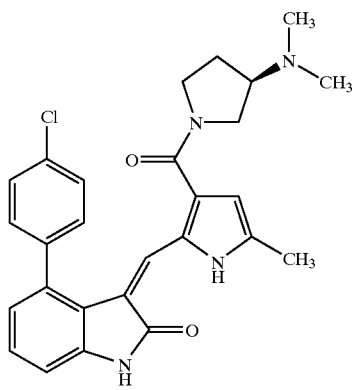

To a solution of 4-(4-chloro-phenyl)-1,3-dihydro-indol-2-one (60.9 mg, 0.25 mmol) and 3-[(3R)-3-dimethylamino-pyrrolidine-1-carbonyl]-5-methyl-1H-pyrrole-2-carbaldehyde (64.8 mg, 0.26 mmol) in ethanol (2 mL) was added piperidine (3 drops). The reaction mixture was stirred at room temperature for three days. A yellow solid product was precipitated out, filtered, washed by ethanol for three times, and dried under high vacuum to provide pure product 4-(4-chloro-phenyl)-3-[3-[(3R)-3-dimethylamino-pyrrolidine-1-carbonyl)-5-methyl-1H-pyrrol-2-ylmethylene]-1,3-dihydro-indol-2-one as a yellow solid (44.8, 38%).

$^1$H-NMR (400 MHz, DMSO-$d_6$) δ 13.72 (br d, 1H, pyrrole NH), 11.13 (br s, 1H, CONH), 7.47 (m, 2H, aromatic), 7.40 (m, 2H, aromatic), 7.26 (d, 1H, aromatic), 7.20 (t, 1H, aromatic), 6.92 (m, 1H, aromatic), 6.73 (m, 1H, aromatic), 6.22 (m, 1H, aromatic), 3.33 (m, 4H, 4×CH), 3.00 (m, 1H, CH), 2.60 (m, 1H, CH), 2.33 (s, 3H, CH$_3$), 2.21 (s, 3H, CH$_3$), 2.08 (s, 3H, CH$_3$), 1.64 (m, 1H, CH). MS m/z 475 [M$^+$+1].

Example 26

5-[4-(4-Chloro-phenyl)-2-oxo-1,2-dihydro-indol-3-ylidenemethyl]-2-methyl-4-[3-(4-methyl-piperazin-1-yl)-propyl]-1H-pyrrole-3-carboxylic Acid Ethyl Ester

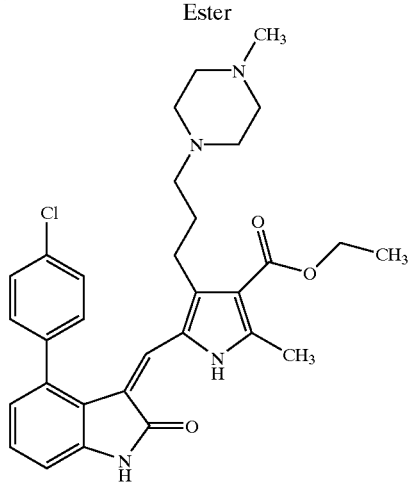

To a solution of 4-(4-chloro-phenyl)-1,3-dihydro-indol-2-one (60.9 mg, 0.25 mmol) and 5-formyl-2-methyl-4-[3-(4-methyl-piperazin-1-yl)-propyl]-1H-pyrrole-3-carboxylic acid ethyl ester (80.3 mg, 0.26 mmol) in ethanol (2 mL) was added piperidine (3 drops). The reaction mixture was stirred at room temperature for three days. A yellow solid product was precipitated out, filtered, washed by ethanol for three times, and dried under high vacuum to provide pure product 5-[4-(4-chloro-phenyl)-2-oxo-1,2-dihydro-indol-3-ylidenemethyl]-2-methyl-4-[3-(4-methyl-piperazin-1-yl)-propyl]-1H-pyrrole-3-carboxylic acid ethyl ester as a yellow solid (38.8 mg, 28%).

$^1$H-NMR (400 MHz, DMSO-$d_6$) δ 13.88 (br s, 1H, pyrrole NH), 11.17 (br s, 1H, CONH), 7.60 (m, 2H, aromatic), 7.50 (m, 2H, aromatic), 7.22 (t, 1H, aromatic), 6.94 (m, 2H, aromatic), 6.77 (d, 1H, aromatic), 4.17 (q, 2H, OCH$_2$), 3.30 (s, 1H, CH$_3$), 2.25 (m, 10H, 5×CH$_2$), 2.11 (s, 3H, CH$_3$), 2.06 (m, 2H, CH$_2$), 1.26 (m, 5H, CH$_2$+CH$_3$). MS m/z 547 [M$^+$+1].

Example 27

4-(4-Chloro-phenyl)-3-[3-(cis)-3,5-dimethyl-piperazine-1-carbonyl)-5-methyl-1H-pyrrol-2-ylmethylene]-1,3-dihydro-indol-2-one

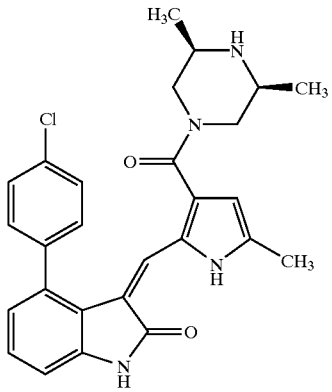

To a solution of 4-(4-chloro-phenyl)-1,3-dihydro-indol-2-one (60.9 mg, 0.25 mmol) and 3-[(cis)-3,5-dimethyl-piperazine-1-carbonyl]-5-methyl-1H-pyrrole-2-carbaldehyde (64.8 mg, 0.26 mmol) in ethanol (2 mL) was added piperidine (3 drops). The reaction mixture was stirred at room temperature for three days. A yellow solid product was precipitated out, filtered, washed by ethanol for three times, and dried under high vacuum to provide pure product 3-[3-[(cis)-3,5-dimethyl-piperazine-1-carbonyl)]-5-methyl-1H-pyrrol-2-ylmethylene]-4-(4-chloro-phenyl)-1,3-dihydro-indol-2-one as a yellow solid (22.1 mg, 19%).

$^1$H-NMR (400 MHz, DMSO-$d_6$) δ 13.70 (br s, 1H, pyrrole NH), 11.13 (br s, 1H, CONH), 7.47 (m, 2H, aromatic), 7.40 (m, 2H, aromatic), 7.20 (t, 1H, aromatic), 7.08 (s, 1H, aromatic), 6.93 (m, 1H, aromatic), 6.73 (d, 1H, aromatic), 6.07 (m, 1H, aromatic), 4.20 (m, 1H, CH), 3.43 (m, 2H, CH$_2$), 2.33 (m, 5H, CH$_2$+CH$_3$), 2.05 (m, 1H, CH), 1.04 (m, 3H, CH$_3$), 0.80 (m, 3H, CH$_3$). MS m/z 475 [M$^+$+1].

Example 28

4-(3-Chloro-phenyl)-3-[3,5-dimethyl-4-(4-methyl-piperazine-1-carbonyl)-1H-pyrrol-2-ylmethylene]-1,3-dihydro-indol-2-one

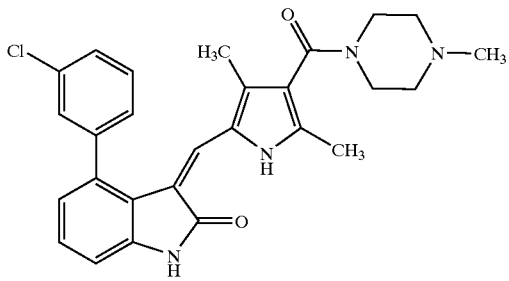

To a solution of 4-(3-chloro-phenyl)-1,3-dihydro-indol-2-one (60.9 mg, 0.25 mmol) and 3,5-dimethyl-4-(4-methyl-piperazine-1-carbonyl)-1H-pyrrole-2-carbaldehyde (64.8 mg, 0.26 mmol) in ethanol (2 mL) was added piperidine (3 drops). The reaction mixture was stirred at room temperature for three days. A yellow solid product was precipitated out, filtered, washed by ethanol for three times, and dried under high vacuum to provide 3-[3,5-dimethyl-4-(4-methyl-piperazine-1-carbonyl)-1H-pyrrol-2-ylmethylene]-4-(3-chloro-phenyl)-1,3-dihydro-indol-2-one as a yellow solid (61 mg, 51%).

$^1$H-NMR (400 MHz, DMSO-$d_6$) δ 13.45 (br s, 1H, pyrrole NH), 11.06 (br s, 1H, CONH), 7.57 (m, 2H, aromatic), 7.53 (m, 1H, aromatic), 7.20 (t, 1H, aromatic), 6.95 (d, 1H, aromatic), 6.80 (d, 1H, aromatic), 6.77 (s, 1H, aromatic), 3.30 (m, 4H, 2×CH$_2$), 2.24 (m, 7H, 2×CH$_2$+CH$_3$), 2.17 (s, 3H, CH$_3$), 1.61 (s, 3H, CH$_3$). MS m/z 475 [M$^+$+1].

Example 29

5-[4-(3-Chloro-phenyl)-2-oxo-1,2-dihydro-indol-3-ylidenemethyl]-2,4-dimethyl-1H-pyrrole-3-carboxylic Acid (2-Diethylamino-ethyl)-amide

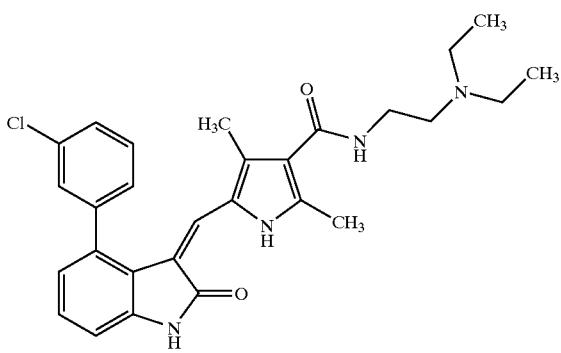

To a solution of 4-(3-chloro-phenyl)-1,3-dihydro-indol-2-one (60.9 mg, 0.25 mmol) and 5-formyl-2,4-dimethyl-1H-pyrrole-3-carboxylic acid (2-diethylamino-ethyl)-amide (69.0 mg, 0.26 mmol) in ethanol (2 mL) was added piperidine (3 drops). The reaction mixture was stirred at room temperature for three days. The reaction solution was evaporated, and purified on a silica gel column eluting with MeOH—CH$_2$Cl$_2$ 5:95 to provide pure product 5-[4-(3-chloro-phenyl)-2-oxo-1,2-dihydro-indol-3-ylidenemethyl]-2,4-dimethyl-1H-pyrrole-3-carboxylic acid (2-diethylamino-ethyl)-amide as a yellow solid (73 mg, 59%).

$^1$H-NMR (400 MHz, DMSO-$d_6$) δ 13.51 (br s, 1H, pyrrole NH), 11.09 (br s, 1H, CONH), 7.69 (m, 1H, aromatic), 7.57 (m, 2H, aromatic), 7.53 (m, 1H, aromatic), 7.41 (m, 1H, aromatic), 7.21 (t, 1H, aromatic), 6.96 (d, 1H, aromatic), 6.80 (m, 2H, aromatic), 3.22 (m, 2H, CH$_2$), 2.49 (m, 6H, 3×CH$_2$), 2.42 (s, 3H, CH$_3$), 1.76 (s, 3H, CH$_3$), 0.80 (t, 6H, 2×CH$_3$). MS m/z 491 [M$^+$+1].

Example 30

5-[4-(3-Chloro-phenyl)-2-oxo-1,2-dihydro-indol-3-ylidenemethyl]-2,4-dimethyl-1H-pyrrole-3-carboxylic Acid (2-Pyrrolidin-1-yl-ethyl)-amide

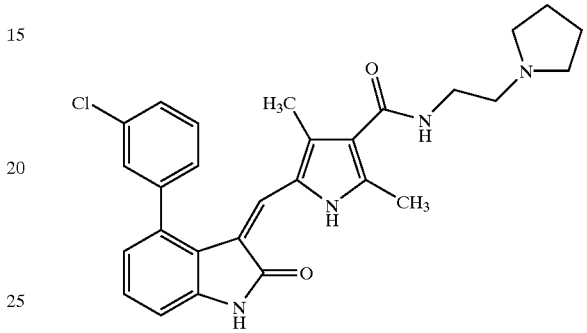

To a solution of 4-(3-chloro-phenyl)-1,3-dihydro-indol-2-one (60.9 mg, 0.25 mmol) and 5-formyl-2,4-dimethyl-1H-pyrrole-3-carboxylic acid (2-pyrrolidin-1-yl-ethyl)-amide (68.5 mg, 0.26 mmol) in ethanol (2 mL) was added piperidine (3 drops). The reaction mixture was stirred at room temperature for three days. The reaction solution was evaporated, and purified on a silica gel column eluting with MeOH—CH$_2$Cl$_2$ 5:95 to provide pure product 5-[4-(3-chloro-phenyl)-2-oxo-1,2-dihydro-indol-3-ylidenemethyl]-2,4-dimethyl-1H-pyrrole-3-carboxylic acid (2-pyrrolidin-1-yl-ethyl)-amide as a yellow solid (75 mg, 61%).

$^1$H-NMR (400 MHz, DMSO-$d_6$) δ 13.48 (br s, 1H, pyrrole NH), 11.06 (br s, 1H, CONH), 7.66 (m, 1H, aromatic), 7.58 (m, 2H, aromatic), 7.52 (s, 1H, aromatic), 7.47 (t, 1H, CONH), 7.04 (m, 2H, aromatic), 7.20 (t, 1H, aromatic), 6.95 (d, 1H, aromatic), 6.80 (d, 1H, aromatic), 6.78 (s, 1H, aromatic), 3.30 (m, 2H, CH$_2$), 2.50 (m, 2H, CH$_2$), 2.45 (m, 4H, 2×CH$_2$), 2.38 (s, 3H, CH$_3$), 1.74 (s, 3H, CH$_3$), 1.67 (m, 4H, 2×CH$_2$). MS m/z 489 [M$^+$+1].

Example 31

5-[4-(3-Chloro-phenyl)-2-oxo-1,2-dihydro-indol-3-ylidenemethyl]-2,4-dimethyl-1H-pyrrole-3-carboxylic Acid (2-[1,2,3]Triazol-1-yl-ethyl)-amide

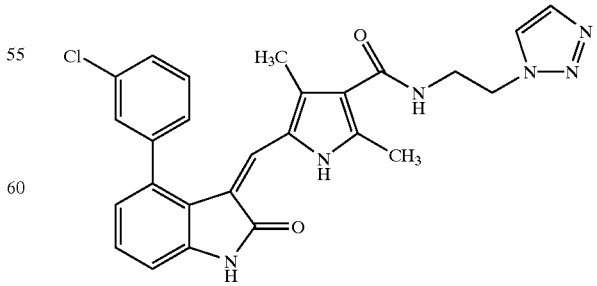

To a solution of 4-(3-chloro-phenyl)-1,3-dihydro-indol-2-one (60.9 mg, 0.25 and 5-formyl-2,4-dimethyl-1H-pyrrole- 3-carboxylic acid (2-[1,2,3]triazol-yl-ethyl)-amide (67.9 mg, 0.26 mmol) in ethanol (2 mL) was added piperidine (3 The reaction mixture was stirred at room temperature for three days. A yellow solid product was precipitated out, filtered, washed by ethanol for three times, and dried under high vacuum to provide pure product 5-[4-(3-chloro-phenyl)-2-oxo-1,2-dihydro-indol-3-ylidenemethyl]-2,4-dimethyl-1H-pyrrole-3-carboxylic acid (2-[1,2,3]triazol-1-yl-ethyl)-amide as a yellow solid (54 mg, 44%).

$^1$H-NMR (400 MHz, DMSO-$d_6$) δ 13.48 (br s, 1H, pyrrole NH), 11.07 (br s, 1H, CONH), 8.10 (m, 1H, aromatic), 7.72 (s, 1H, aromatic), 7.64 (t, 1H, CONH), 7.58 (m, 2H, aromatic), 7.52 (m, 1H, aromatic), 7.41 (m, 1H, aromatic), 7.20 (t, 1H, aromatic), 6.94 (d, 1H, aromatic), 6.80 (d, 1H, aromatic), 6.77 (s, 1H, aromatic), 4.53 (m, 2H, CH$_2$), 3.64 (m, 2H, CH$_2$), 2.29 (s, 3H, CH$_3$), 1.66 (s, 3H, CH$_3$). MS m/z 487 [M$^+$+1].

Example 32

4-(3-Chloro-phenyl)-3-[3-((S)-3-dimethylamino-pyrrolidine-1-carbonyl)-5-methyl-1H-pyrrol-2-ylmethylene]-1,3-dihydro-indol-2-one

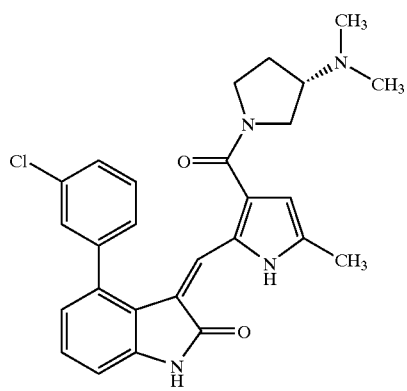

To a solution of 4-(3-chloro-phenyl)-1,3-dihydro-indol-2-one (60.9 mg, 0.25 mmol) and 3-[(3S)-3-dimethylamino-pyrrolidine-1-carbonyl]-5-methyl-1H-pyrrole-2-carbaldehyde (64.8 mg, 0.26 mmol) in ethanol (2 mL) was added piperidine (3 drops). The reaction mixture was stirred at room temperature for three days. A yellow solid product was precipitated out, filtered, washed by ethanol for three times, and dried under high vacuum to provide pure product 4-(3-Chloro-phenyl)-3-[3-[(3S)-3-dimethylamino-pyrrolidine-1-carbonyl)-5-methyl-1H-pyrrol-2-ylmethylene]-1,3-dihydro-indol-2-one as a yellow solid (70 mg, 59%).

$^1$H-NMR (400 MHz, DMSO-$d_6$) δ 13.64 (br d, 1H, pyrrole NH), 11.12 (br s, 1H, CONH), 7.50 (m, 2H, aromatic), 7.41 (s, 1H, aromatic), 7.36 (m, 1H, aromatic), 7.21 (m, 2H, aromatic), 6.94 (d, 1H, aromatic), 6.78 (d, 1H, aromatic), 6.21 (m, 1H, aromatic), 3.54, 3.26 (2×m, 1H, CH), 3.39 (m, 2H, CH$_2$), 3.04 (m, 1H, CH), 2.60 (m, 1H, CH), 2.33 (s, 3H, CH$_3$), 2.23 (s, 3H, CH$_3$), 2.08 (s, 3H, CH$_3$), 1.96 (m, 1H, CH), 1.63 (m, 1H, CH). MS m/z 475 [M$^+$+1].

Example 33

4-(3-Chloro-phenyl)-3-[3-((R)-3-dimethylamino-pyrrolidine-1-carbonyl)-5-methyl-1H-pyrrol-2-ylmethylene]-1,3-dihydro-indol-2-one

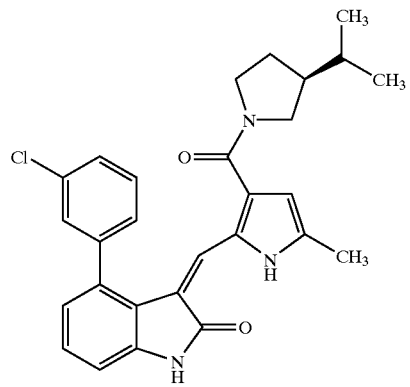

To a solution of 4-(3-chloro-phenyl)-1,3-dihydro-indol-2-one (60.9 mg, 0.25 mmol) and 3-[(3R)-3-dimethylamino-pyrrolidine-1-carbonyl]-5-methyl-1H-pyrrole-2-carbaldehyde (64.8 mg, 0.26 mmol) in ethanol (2 mL) was added piperidine (3 drops). The reaction mixture was stirred at room temperature for three days. A yellow solid product was precipitated out, filtered, washed by ethanol for three times, and dried under high vacuum to provide pure product 4-(3-chloro-phenyl)-3-[3-[(3R)-3-dimethylamino-pyrrolidine-1-carbonyl)-5-methyl-1H-pyrrol-2-ylmethylene)-1,3-dihydro-indol-2-one as a yellow solid (71 mg, 60%).

$^1$H-NMR (400 MHz, DMSO-$d_6$) δ 13.63 (br m, 1H, pyrrole NH), 11.12 (br s, 1H, CONH), 7.45 (m, 2H, aromatic), 7.41 (s, 1H, aromatic), 7.36 (m, 1H, aromatic), 7.21 (m, 2H, aromatic), 6.94 (d, 1H, aromatic), 6.78 (d, 1H, aromatic), 6.21 (m, 1H, aromatic), 3.54, 3.26 (2×m, 1H, CH), 3.39 (m, 2H, CH$_2$), 3.04 (m, 1H, CH), 2.60 (m, 1H, CH), 2.33 (s, 3H, CH$_3$), 2.23 (s, 3H, CH$_3$), 2.08 (s, 3H, CH$_3$), 1.96 (m, 1H, CH), 1.63 (m, 1H, CH). MS m/z 475 [M$^+$+1].

Example 34

2-[4-(3-Chloro-phenyl)-2-oxo-1,2-dihydro-indol-3-ylidenemethyl]-5-methyl-1H-pyrrole-3-carboxylic Acid (2-[1,2,3]Triazol-1-yl-ethyl)-amide

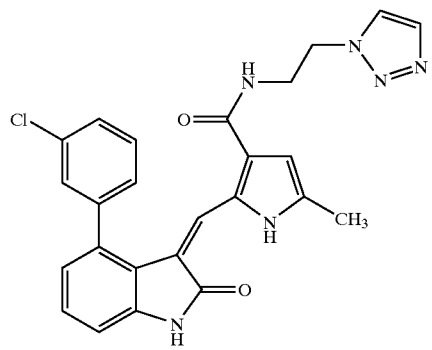

To a solution of 4-(3-chloro-phenyl)-1,3-dihydro-indol-2-one (60.9 mg, 0.25 mmol) and 2-formyl-5-methyl-1H- pyrrole-3-carboxylic acid (2-[1,2,3]triazol-1-yl-ethyl)-amide (64.8 mg, 0.26 mmol) in ethanol (2 mL) was added piperidine (3 drops). The reaction mixture was stirred at room temperature for three days. A yellow solid product was precipitated out, filtered, washed by ethanol for three times, and dried under high vacuum to provide pure product 2-[4-(3-chloro-phenyl)-2-oxo-1,2-dihydro-indol-3-ylidenemethyl]-5-methyl-1H-pyrrole-3-carboxylic acid (2-[1,2,3]triazol-1-yl-ethyl)-amide as a yellow solid (64 mg, 54%).

$^1$H-NMR (400 MHz, DMSO-d$_6$) δ 13.82 (br s, 1H, pyrrole NH), 11.14 (br s, 1H, CONH), 8.02 (m, 3H, aromatic), 7.74 (s, 1H, aromatic), 7.46 (m, 2H, aromatic), 7.40 (m, 1H, aromatic), 7.33 (m, 1H, aromatic), 7.22 (t, 1H, aromatic), 6.94 (d, 1H, aromatic), 6.78 (d, 1H, aromatic), 6.34 (m, 1H, aromatic), 4.51 (m, 2H, CH$_2$), 3.50 (m, 2H, CH$_2$), 2.31 (s, 3H, CH$_3$). MS m/z 473 [M$^+$+1].

Example 35

4-(3-Chloro-phenyl)-3-[3-((cis)-3,5-dimethyl-piperazine-1-carbonyl)-5-methyl-1H-pyrrol-2-ylmethylene]-1,3-dihydro-indol-2-one

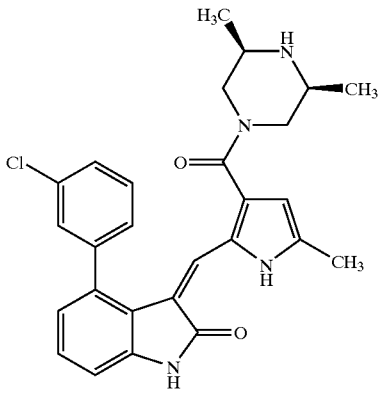

To a solution of 4-(3-chloro-phenyl)-1,3-dihydro-indol-2-one (60.9 mg, 0.25 mmol) and 3-[(cis)-3,5-dimethyl-piperazine-1-carbonyl]-5-methyl-1H-pyrrole-2-carbaldehyde (64.8 mg, 0.26 mmol) in ethanol (2 mL) was added piperidine (3 drops). The reaction mixture was stirred at room temperature for three days. The reaction solution was evaporated, and purified on a silica gel column eluting with MeOH—CH$_2$Cl$_2$ 5:95 to provide pure product 3-[3-[(cis)-3,5-dimethyl-piperazine-1-carbonyl]-5-methyl-1H-pyrrol-2-ylmethylene]-4-(3-chloro-phenyl)-1,3-dihydro-indol-2-one as a yellow solid (67 mg, 56%).

$^1$H-NMR (400 MHz, DMSO-d$_6$) δ 13.60 (br s, 1H, pyrrole NH), 11.12 (br s, 1H, CONH), 7.45 (m, 2H, aromatic), 7.40 (s, 1H, aromatic), 7.33 (m, 1H, aromatic), 7.20 (t, 1H, aromatic), 6.94 (m, 2H, aromatic), 6.77 (d, 1H, aromatic), 6.06 (m, 1H, aromatic), 4.13 (m, 1H, CH), 3.32 (m, 1H, CH), 2.39 (m, 6H, CH+CH$_2$+CH$_3$), 2.05 (m, 1H, CH), 1.04 (m, 3H, CH$_3$), 0.80 (m, 3H, CH$_3$). MS m/z 475 [M$^+$+1].

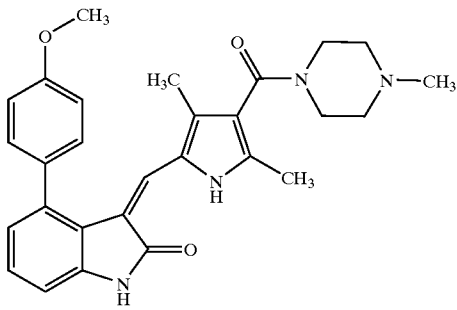

Example 36

3-[3,5-Dimethyl-4-(4-methyl-piperazine-1-carbonyl)-1H-pyrrol-2-ylmethylene]-4-(4-methoxy-phenyl)-1,3-dihydro-indol-2-one To a solution of 4-(4-methoxy-phenyl)-1,3-dihydro-indol-2-one (59.8 mg, 0.25 mmol) and 3,5-dimethyl-4-(4-methyl-piperazine-1-carbonyl)-1H-pyrrole-2-carbaldehyde (64.8 mg, 0.25 mmol) in ethanol (2 mL) was added piperidine (3 drops). The reaction mixture was stirred at room temperature for three days. A yellow solid product was precipitated out, filtered, washed by ethanol for three times, and dried under high vacuum to provide 3-[3,5-dimethyl-4-(4-methyl-piperazine-1-carbonyl)-1H-pyrrol-2-ylmethylene]-4-(4-methoxy-phenyl)-1,3-dihydro-indol-2-one as a yellow solid (85 mg, 72%)

$^1$H-NMR (400 MHz, DMSO-d$_6$) δ 13.42 (br s, 1H, pyrrole NH), 10.98 (br s, 1H, CONH), 7.30 (m, 2H, aromatic), 7.15 (t, 1H, aromatic), 7.10 (m, 2H, aromatic), 6.89 (d, 1H, aromatic), 6.76 (m, 2H, aromatic), 3.80 (s, 3H, OCH$_3$), 3.31 (m, 4H, 2×CH$_2$), 2.22 (m, 7H, 2×CH$_2$+CH$_3$), 2.15 (s, 3H, CH$_3$), 1.60 (s, 3H, CH$_3$). MS m/z 471 [M$^+$+1].

Example 37

5-[4-(4-Methoxy-phenyl)-2-oxo-1,2-dihydro-indol-3-ylidenemethyl]-2,4-dimethyl-1H-pyrrole-3-carboxylic Acid (2-Diethylamino-ethyl)-amide

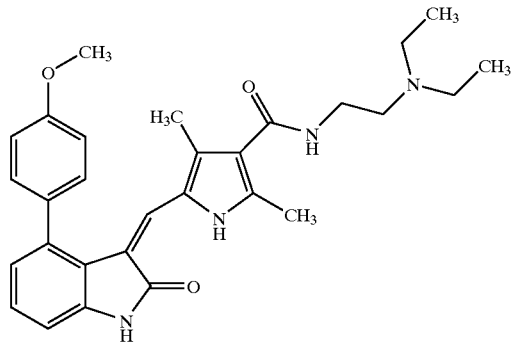

To a solution of 4-(4-methoxy-phenyl)-1,3-dihydro-indol-2-one (59.8 mg, 0.25 mmol) and 5-formyl-2,4-dimethyl]-1H-pyrrole-3-carboxylic acid (2-diethylamino-ethyl)-amide (69.0 mg, 0.25 mmol) in ethanol (2 mL) was added piperidine (3 drops). The reaction mixture was stirred at room temperature for three days. A yellow solid product was precipitated out, filtered, washed by ethanol for three times, and dried under high vacuum to provide 5-[4-(4-methoxy-phenyl)-2-oxo-1,2-dihydro-indol-3-ylidenemethyl]-2,4-dimethyl-1H-pyrrole -3-carboxylic acid (2-diethylamino-ethyl)-amide as a yellow solid (87 mg, 72%).

$^{1}$H-NMR (400 MHz, DMSO-d$_{6}$) δ 13.44 (br s, 1H, pyrrole NH), 10.98 (br s, 1H, CONH), 7.31 (m, 3H, aromatic), 7.16 (t, 1H, aromatic), 7.11 (m, 2H, aromatic), 6.90 (m, 1H, aromatic), 6.78 (m, 2H, aromatic), 3.82 (s, 3H, OCH$_{3}$), 3.22 (m, 2H, CH$_{2}$), 2.49 (m, 6H, 3×CH$_{2}$), 2.39 (s, 3H, CH$_{3}$), 1.73 (s, 3H, CH$_{3}$), 0.95 (t, 6H, 2×CH$_{3}$). MS m/z 487 [M$^{+}$+1].

Example 38

5-[4-(4-Methoxy-phenyl)-2-oxo-1,2-dihydro-indol-3-ylidenemethyl]-2,4-dimethyl-1H-pyrrole-3-carboxylic Acid (2-Pyrrolidin-1-yl-ethyl)-amide

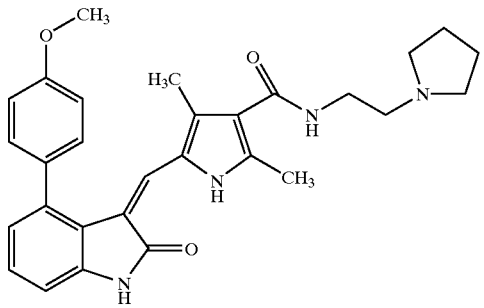

To a solution of 4-(4-methoxy-phenyl)-1,3-dihydro-indol-2-one (59.8 mg, 0.25 mmol) and 5-formyl-2,4-dimethyl-1H-pyrrole-3-carboxylic acid (2-pyrrolidin-1-yl-ethyl)-amide (68.5 mg, 0.25 mmol) in ethanol (2 mL) was added piperidine (3 drops). The reaction mixture was stirred at room temperature for three days. A yellow solid product was precipitated out, filtered, washed by ethanol for three times, and dried under high vacuum to provide pure product 5-[4-(4-Methoxy-phenyl)-2-oxo-1,2-dihydro-indol-3-ylidenemethyl]-2,4-dimethyl-1H-pyrrole-3-carboxylic acid (2-pyrrolidin-1-yl-ethyl)-amide as a yellow solid (86 mg, 71%).

$^{1}$H-NMR (400 MHz, DMSO-d$_{6}$) δ 13.46 (br s, 1H, pyrrole NH), 10.99 (br s, 1H, CONH), 7.41 (m, 1H, CONH), 7.32 (m, 2H, aromatic), 7.16 (t, 1H, aromatic), 7.11 (m, 2H, aromatic), 6.90 (m, 1H, aromatic), 6.78 (m, 2H, aromatic), 3.82 (s, 3H, OCH$_{3}$), 3.28 (m, 2H, CH$_{2}$), 2.50 (m, 2H, CH$_{2}$), 2.46 (m, 4H, 2×CH$_{2}$), 2.37 (s, 3H, CH$_{3}$), 1.73 (s, 3H, CH$_{3}$), 1.67 (m, 4H, 2×CH$_{2}$). MS m/z 485 [M$^{+}$+1].

Example 39

5-[4-(4-Methoxy-phenyl)-2-oxo-1,2-dihydro-indol-3-ylidenemethyl]-2,4-dimethyl-1H-pyrrole-3-carboxylic Acid (2-[1,2,3]Triazol-1-yl-ethyl)-amide

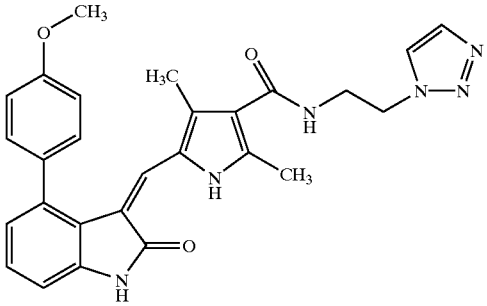

To a solution of 4-(4-methoxy-phenyl)-1,3-dihydro-indol-2-one (59.8 mg, 0.25 mmol) and 5-formyl-2,4-dimethyl-1H-pyrrole-3-carboxylic acid (2-[1,2,3]triazol-1-yl-ethyl)-amide (67.9 mg, 0.25 mmol) in ethanol (2 mL) was added piperidine (3 drops). The reaction mixture was stirred at room temperature for three days. A yellow solid product was precipitated out, filtered, washed by ethanol for three times, and dried under high vacuum to provide pure product 5-[4-(4-methoxy-phenyl)-2-oxo-1,2-dihydro-indol-3-ylidenemethyl]-2,4-dimethyl-1H-pyrrole-3-carboxylic acid (2-[1,2,3]triazol-1-yl-ethyl)-amide as a yellow solid (54 mg, 45%).

$^{1}$H-NMR (400 MHz, DMSO-d$_{6}$) δ 13.47 (br s, 1H, pyrrole NH), 11.00 (br s, 1H, CONH), 8.10 (m, 1H, aromatic), 7.71 (m, 1H, aromatic), 7.60 (m, 1H, CONH), 7.31 (m, 2H, aromatic), 7.16 (t, 1H, aromatic), 7.10 (m, 2H, aromatic), 6.89 (m, 1H, aromatic), 6.78 (m, 2H, aromatic), 4.53 (m, 2H, CH$_{2}$), 3.82 (s, 3H, OCH$_{3}$), 3.63 (m, 2H, CH$_{2}$), 2.29 (s, 3H, CH$_{3}$), 1.61 (s, 3H, CH$_{3}$). MS m/z 483 [M$^{+}$+1].

Example 40

3-[4-((cis)-3,5-Dimethyl-piperazine-1-carbonyl)-3,5-dimethyl-1H-pyrrol-2-ylmethylene]-4-(4-methoxy-phenyl)-1,3-dihydro-indol-2-one

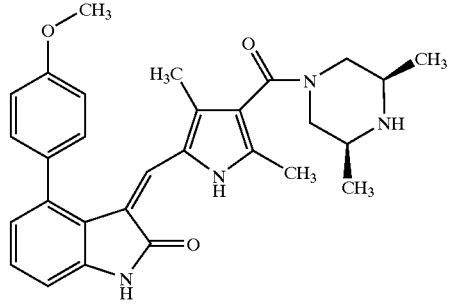

To a solution of 4-(4-methoxy-phenyl)-1,3-dihydro-indol-2-one (59.8 mg, 0.25 mmol) and 4-[(cis)-3,5-dimethyl-piperazine-1-carbonyl)-3,5-dimethyl-1H-pyrrole-2-carbaldehyde (68.5 mg, 0.25 mmol) in ethanol (2 mL) was added piperidine (3 drops). The reaction mixture was stirred at room temperature for three days. A yellow solid product was precipitated out, filtered, washed by ethanol for three times, and dried under high vacuum to provide pure product 3-[4-[(cis)-3,5-Dimethyl-piperazine-1-carbonyl)-3,5-dimethyl-1H-pyrrol-2-ylmethylene]-4-(4-methoxy-phenyl)-1,3-dihydro-indol-2-one as a yellow solid (88 mg, 73%).

$^1$H-NMR (400 MHz, DMSO-$d_6$) δ 13.40 (br s, 1H, pyrrole NH), 10.99 (br s, 1H, CONH), 7.33 (m, 2H, aromatic), 7.16 (t, 1H, aromatic), 7.10 (m, 2H, aromatic), 6.90 (m, 1H, aromatic), 6.77 (m, 2H, aromatic), 3.80 (s, 3H, OCH$_3$), 3.43 (m, 1H, CH), 2.52 (m, 1H, CH), 2.23 (m, 4H, 2×CH$_2$), 1.57 (m, 3H, CH$_3$), 1.04 (m, 3H, CH$_3$), 0.90 (m, 6H, 2×CH$_3$). MS m/z 485 [M$^+$+1].

Example 41

2-[4-(4-Methoxy-phenyl)-2-oxo-1,2-dihydro-indol-3-ylidenemethyl]-5-methyl-1H-pyrrole-3-carboxylic Acid (2-Pyrrolidin-1-yl-ethyl)-amide

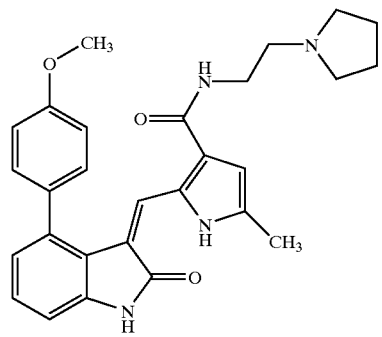

To a solution of 4-(4-methoxy-phenyl)-1,3-dihydro-indol-2-one (59.8 mg, 0.25 mmol) and 2-Formyl-5-methyl-1H-pyrrole-3-carboxylic acid (2-pyrrolidin-1-yl-ethyl)-amide (64.8 mg, 0.25 mmol) in ethanol (2 mL) was added piperidine (3 drops). The reaction mixture was stirred at room temperature for three days. A yellow solid product was precipitated out, filtered, washed by ethanol for three times, and dried under high vacuum to provide pure product 2-[4-(4-Methoxy-phenyl)-2-oxo-1,2-dihydro-indol-3-ylidenemethyl]-5-methyl-1H-pyrrole-3-carboxylic acid (2-pyrrolidin-1-yl-ethyl)-amide as a yellow solid (90 mg, 77%).

$^1$H-NMR (400 MHz, DMSO-$d_6$) δ 13.73 (br s, 1H, pyrrole NH), 11.05 (br s, 1H, CONH), 7.99 (s, 1H, aromatic), 7.67 (t, 1H, CONH), 7.26 (m, 2H, aromatic), 7.17 (t, 1H, aromatic), 6.98 (m, 2H, aromatic), 6.87 (m, 1H, aromatic), 6.74 (m, 1H, aromatic), 6.35 (m, 1H, aromatic), 3.81 (s, 3H, OCH$_3$), 3.13 (m, 2H, CH$_2$), 2.46 (m, 6H, 3×CH$_2$), 2.31 (s, 3H, CH$_3$), 1.68 (m, 4H, 2×CH$_2$). MS m/z 471 [M$^+$+1].

Example 42

2-[4-(4-Methoxy-phenyl)-2-oxo-1,2-dihydro-indol-3-ylidenemethyl]-5-methyl-1H-pyrrole-3-carboxylic Acid (2-[1,2,3]Triazol-1-yl-ethyl)-amide

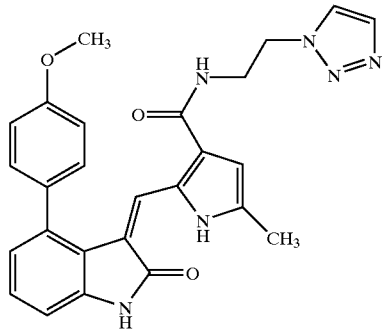

To a solution of 4-(4-methoxy-phenyl)-1,3-dihydro-indol-2-one (59.8 mg, 0.25 mmol) and 2-Formyl-5-methyl-1H-pyrrole-3-carboxylic acid (2-[1,2,3]triazol-1-yl-ethyl)-amide (64.8 mg, 0.25 mmol) in ethanol (2 mL) was added piperidine (3 drops). The reaction mixture was stirred at room temperature for three days. A yellow solid product was precipitated out, filtered, washed by ethanol for three times, and dried under high vacuum to provide pure product 2-[4-(4-Methoxy-phenyl)-2-oxo-1,2-dihydro-indol-3-ylidenemethyl]-5-methyl-1H-pyrrole-3-carboxylic acid (2-[1,2,3]triazol-1-yl-ethyl)-amide as a yellow solid (61 mg, 52%).

$^1$H-NMR (400 MHz, DMSO-$d_6$) δ 13.84 (br s, 1H, pyrrole NH), 11.12 (br s, 1H, CONH), 7.98 (m, 3H, aromatic), 7.73 (s, 1H, aromatic), 7.27 (m, 2H, aromatic), 7.18 (t, 1H, aromatic), 6.99 (m, 2H, aromatic), 6.88 (m, 1H, aromatic), 6.75 (m, 1H, aromatic), 6.30 (m, 1H, aromatic), 4.47 (t, 2H, CH$_2$), 3.75 (m, 3H, OCH$_3$), 3.45 (m, 2H, CH$_2$), 2.30 (s, 3H, CH$_3$). MS m/z 469 [M$^+$+1].

Example 43a

3-[3-((3S)-3-Dimethylamino-pyrrolidine-1-carbonyl)-5-methyl-1H-pyrrol-2-ylmethylene]-4-(4-methoxy-phenyl)-1,3-dihydro-indol-2-one

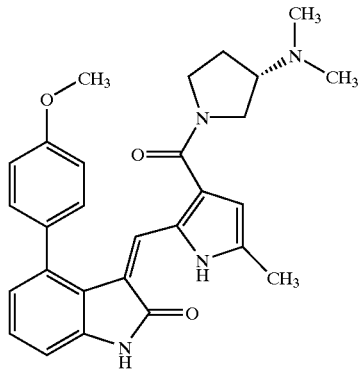

To a solution of 4-(4-methoxy-phenyl)-1,3-dihydro-indol-2-one (59.8 mg, 0.25 mmol) and 3-[(3S)-3-Dimethylamino-pyrrolidine-1-carbonyl]-5-methyl-1H-pyrrole-2-carbaldehyde (64.8 mg, 0.25 mmol) in ethanol (2 mL) was added piperidine (3 drops). The reaction mixture was stirred at room temperature for three days. A yellow solid product was precipitated out, filtered, washed by ethanol for three times, and dried under high vacuum to provide pure product 3-[3-[(3S)-3-dimethylamino-pyrrolidine-1-carbonyl)-5-methyl-1H-pyrrol-2-ylmethylene]-4-(4-methoxy-phenyl)-1,3-dihydro-indol-2-one as a yellow solid (94 mg, 80%).

$^1$H-NMR (400 MHz, DMSO-$d_6$) δ 13.69 (br m, 1H, pyrrole NH), 11.10 (br s, 1H, CONH), 7.29 (m, 2H, aromatic), 7.18 (m, 2H, aromatic), 6.98 (m, 2H, aromatic), 6.88 (d, 1H, aromatic), 6.73 (d, 1H, aromatic), 6.15 (s, 1H, aromatic), 3.84 (m, 3H, OCH$_3$), 3.32 (m, 1H, CH), 3.00 (4×m, 2H, 2×CH), 2.60 (m, 1H, CH), 2.55, 2.00 (4×m, 2H, 2×CH), 2.33 (m, 3H, CH$_3$), 2.19 (s, 3H, CH$_3$), 2.05 (s, 3H, CH$_3$), 1.6 (m, 1H, CH). MS m/z 471 [M$^+$+1].

Example 44

3-[3-((R)-3-Dimethylamino-pyrrolidine-1-carbonyl)-5-methyl-1H-pyrrol-2-ylmethylene]-4-(4-methoxy-phenyl)-1,3-dihydro-indol-2-one

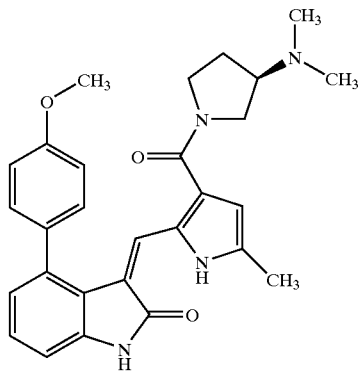

To a solution of 4-(4-methoxy-phenyl)-1,3-dihydro-indol-2-one (59.8 mg, 0.25 mmol) and 3-[(3R)-3-Dimethylamino-pyrrolidine-1-carbonyl]-5-methyl-1H-pyrrole-2-carbaldehyde (64.8 mg, 0.25 mmol) in ethanol (2 mL) was added piperidine (3 drops). The reaction mixture was stirred at room temperature for three days. A yellow solid product was precipitated out, filtered, washed by ethanol for three times, and dried under high vacuum to provide pure product 3-[3-((R)-3-dimethylamino-pyrrolidine-1-carbonyl)-5-methyl-1H-pyrrol-2-ylmethylene]-4-(4-methoxy-phenyl)-1,3-dihydro-indol-2-one as a yellow solid (95 mg, 81%).

$^1$H-NMR (400 MHz, DMSO-$d_6$) δ 13.69 (br d, 1H, pyrrole NH), 11.10 (br s, 1H, CONH), 7.29 (m, 2H, aromatic), 7.18 (m, 2H, aromatic), 6.98 (m, 2H, aromatic), 6.88 (d, 1H, aromatic), 6.73 (d, 1H, aromatic), 6.15 (s, 1H, aromatic), 3.84 (m, 3H, OCH$_3$), 3.32 (m, 1H, CH), 3.00 (4×m, 2H, 2×CH), 2.52 (m, 1H, CH), 2.55 (m, 1H, CH), 2.00, 1.90 (2×m, 1H, CH), 2.32 (m, 3H, CH$_3$), 2.20 (s, 3H, CH$_3$), 2.05 (s, 3H, CH$_3$), 1.64 (m, 1H, CH). MS m/z 471 [M$^+$+1].

Example 45

3-[3,5-Dimethyl-4-(4-methyl-piperazine-1-carbonyl)-1H-pyrrol-2-ylmethylene]-4-(3-methoxy-phenyl)-1,3-dihydro-indol-2-one

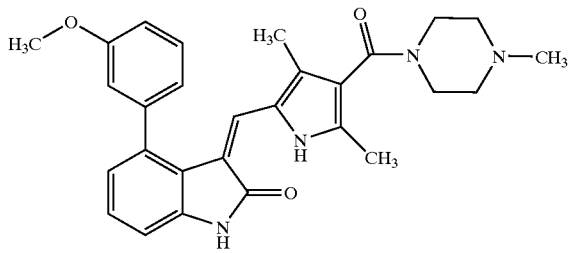

To a solution of 4-(3-methoxy-phenyl)-1,3-dihydro-indol-2-one (59.8 mg, 0.25 mmol) and 3,5-dimethyl-4-(4-methyl-piperazine-1-carbonyl)-1H-pyrrole-2-carbaldehyde (64.8 mg, 0.25 mmol) in ethanol (2 mL) was added piperidine (3 drops). The reaction mixture was stirred at room temperature for three days. The reaction solution was evaporated, and purified on a silica gel column eluting with MeOH—CH$_2$Cl$_2$ 5:95 to provide 3-[3,5-dimethyl-4-(4-methyl-piperazine-1-carbonyl)-1H-pyrrol-2-ylmethylene]-4-(3-methoxy-phenyl)-1,3-dihydro-indol-2-one as a yellow solid (62 mg, 53%)

$^1$H-NMR (400 MHz, DMSO-$d_6$) δ 13.45 (br s, 1H, pyrrole NH), 11.02 (br s, 1H, CONH), 7.46 (t, 1H, aromatic), 7.18 (t, 1H, aromatic), 7.04 (m, 1H, aromatic), 6.97 (m, 2H, aromatic), 6.92 (d, 1H, aromatic), 6.83 (s, 1H, aromatic), 6.80 (d, 1H, aromatic), 3.77 (s, 3H, OCH$_3$), 3.30 (m, 4H, 2×CH$_2$), 2.24 (m, 7H, 2×CH$_2$+C), 2.17 (s, 3H, CH$_3$), 1.58 (s, 3H, CH$_3$). MS m/z 471 [M$^+$+1].

Example 46

5-[4-(3-Methoxy-phenyl)-2-oxo-1,2-dihydro-indol-3-ylidenemethyl]-2,4-dimethyl-1H-pyrrole-3-carboxylic Acid (2-Diethylamino-ethyl)-amide

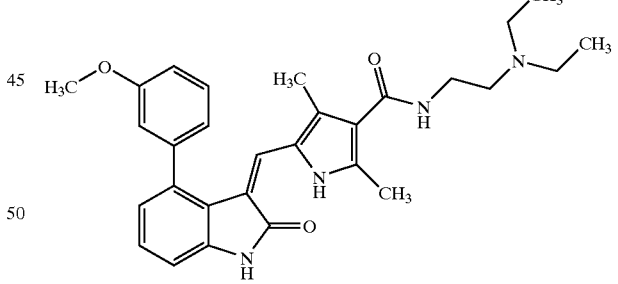

To a solution of 4-(3-methoxy-phenyl)-1,3-dihydro-indol-2-one (59.8 mg, 0.25 mmol) and 5-formyl-2,4-dimethyl-1H-pyrrole-3-carboxylic acid (2-diethylamino-ethyl)-amide (69.0 mg, 0.25 mmol) in ethanol (2 mL) was added piperidine (3 drops). The reaction mixture was stirred at room temperature for three days. The reaction solution was evaporated, and purified on a silica gel column eluting with MeOH—CH$_2$Cl$_2$ 5:95 to provide 5-[4-(3-methoxy-phenyl)-2-oxo-1,2-dihydro-indol-3-ylidenemethyl]-2,4-dimethyl-1H-pyrrole-3-carboxylic acid (2-diethylamino-ethyl)-amide as a yellow solid (94 mg, 78%).

$^1$H-NMR (400 MHz, DMSO-$d_6$) δ 13.48 (br s, 1H, pyrrole NH), 11.02 (br s, 1H, CONH), 7.47 (t, 1H, aromatic), 7.35 (t, 1H, CONH), 7.19 (t, 1H, aromatic), 7.06 (m, 1H, aromatic), 6.98 (m, 2H, aromatic), 6.92 (d, 1H, aromatic), 6.88 (s, 1H, aromatic), 6.80 (d, 1H, aromatic), 3.77 (s, 1H, CH₃), 3.25 (m, 2H, CH₂), 2.38 (s, 3H, CH₃), 2.50 (m, 6H, 3×CH₂), 1.73 (s, 3H, CH₃), 0.95 (t, 6H, 2×CH₃). MS m/z 487 [M⁺+1].

Example 47

5-[4-(3-Methoxy-phenyl)-2-oxo-1,2-dihydro-indol-3-ylidenemethyl]-2,4-dimethyl-1H-pyrrole-3-carboxylic Acid (2-Pyrrolidin-1-yl-ethyl)-amide

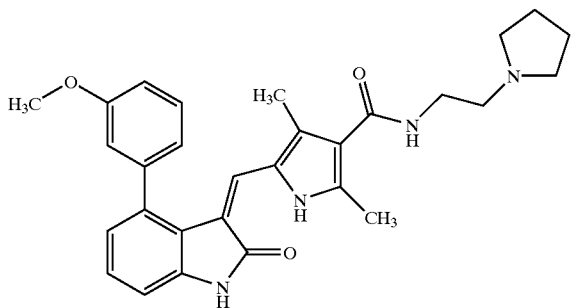

To a solution of 4-(3-methoxy-phenyl)-1,3-dihydro-indol-2-one (59.8 mg, 0.25 mmol) and 5-formyl-2,4-dimethyl-1H-pyrrole-3-carboxylic acid (2-pyrrolidin-1-yl-ethyl)-amide (68.5 mg, 0.25 mmol) in ethanol (2 mL) was added piperidine (3 drops). The reaction mixture was stirred at room temperature for three days. The reaction solution was evaporated, and purified on a silica gel column eluting with MeOH—CH₂Cl₂ 5:95 to provide pure product 5-[4-(3-Methoxy-phenyl)-2-oxo-1,2-dihydro-indol-3-ylidenemethyl]-2,4-dimethyl-1H-pyrrole-3-carboxylic acid (2-pyrrolidin-1-yl-ethyl)-amide as a yellow solid (97 mg, 80%).

¹H-NMR (400 MHz, DMSO-d₆) δ 13.48 (br s, 1H, pyrrole NH), 11.01 (br s, 1H, CONH), 7.50 (m, 2H, aromatic), 7.17 (t, 1H, aromatic), 7.11 (m, 1H, aromatic), 6.97 (m, 2H, aromatic), 6.92 (d, 1H, aromatic), 6.87 (s, 1H, aromatic), 6.80 (d, 1H, aromatic), 3.78 (s, 3H, OCH₃), 3.30 (m, 2H, CH₂), 2.50 (m, 6H, 3×CH₂), 2.37 (s, 3H, CH₃), 1.70 (s, 3H, CH₃), 1.68 (m, 4H, 2×CH₂). MS m/z 485 [M⁺+1].

Example 48

5-[4-(3-Methoxy-phenyl)-2-oxo-1,2-dihydro-indol-3-ylidenemethyl]-2,4-dimethyl-1H-pyrrole-3-carboxylic Acid (2-[1,2,3]Triazol-1-yl-ethyl)-amide

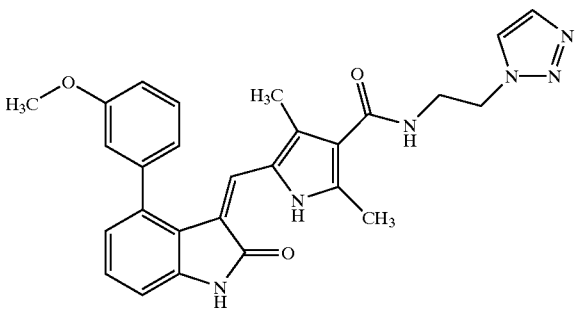

To a solution of 4-(3-methoxy-phenyl)-1,3-dihydro-indol-2-one (59.8 mg, 0.25 mmol) and 5-formyl-2,4-dimethyl-1H-pyrrole-3-carboxylic acid (2-[1,2,3]triazol-1-yl-ethyl)-amide (67.9 mg, 0.25 mmol) in ethanol (2 mL) was added piperidine (3 drops). The reaction mixture was stirred at room temperature for three days. A yellow solid product was precipitated out, filtered, washed by ethanol for three times, and dried under high vacuum to provide pure product 5-[4-(3-methoxy-phenyl)-2-oxo-1,2-dihydro-indol-3-ylidenemethyl]-2,4-dimethyl-1H-pyrrole-3-carboxylic acid (2-[1,2,3]triazol-1-yl-ethyl)-amide as a yellow solid (18 mg, 15%).

¹H-NMR (400 MHz, DMSO-d₆) δ 13.47 (br s, 1H, pyrrole NH), 11.02 (br s, 1H, CONH), 8.10 (s, 1H, aromatic), 7.71 (s, 1H, aromatic), 7.62 (t, 1H, CONH), 7.46 (t, 1H, aromatic), 7.16 (t, 1H, aromatic), 7.07 (m, 1H, aromatic), 6.97 (m, 2H, aromatic), 6.95 (d, 1H, aromatic), 6.84 (s, 1H, aromatic), 6.80 (d, 1H, aromatic), 4.53 (m, 2H, CH₂), 3.78 (s, 3H, OCH₃), 3.63 (m, 2H, CH₂), 2.29 (s, 3H, CH₃), 1.61 (s, 3H, CH₃). MS m/z 483 [M⁺+1].

Example 49

3-[4-((cis)-3,5-Dimethyl-piperazine-1-carbonyl)-3,5-dimethyl-1H-pyrrol-2-ylmethylene]-4-(3-methoxy-phenyl)-1,3-dihydro-indol-2-one

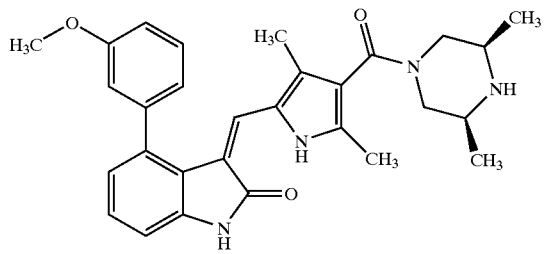

To a solution of 4-(3-methoxy-phenyl)-1,3-dihydro-indol-2-one (59.8 mg, 0.25 mmol) and 4-[(cis)-3,5-dimethyl-piperazine-1-carbonyl)-3,5-dimethyl-1H-pyrrole-2-carbaldehyde (68.5 mg, 0.25 mmol) in ethanol (2 mL) was added piperidine (3 drops). The reaction mixture was stirred at room temperature for three days. The reaction solution was evaporated, and purified on a silica gel column eluting with MeOH—CH₂Cl₂ 5:95 to provide pure product 3-[4-((cis)-3,5-Dimethyl-piperazine-1-carbonyl)-3,5-dimethyl-1H-pyrrol-2-ylmethylene]-4-(3-methoxy-phenyl)-1,3-dihydro-indol-2-one as a yellow solid (95 mg, 79%).

¹H-NMR (400 MHz, DMSO-d₆) δ 13.40 (br s, 1H, pyrrole NH), 11.00 (br s, 1H, CONH), 7.46 (t, 1H, aromatic), 7.17 (t, 1H, aromatic), 7.05 (m, 1H, aromatic), 6.98 (m, 2H, aromatic), 6.92 (d, 1H, aromatic), 6.85 (s, 1H, aromatic), 6.80 (d, 1H, aromatic), 3.80 (s, 3H, OCH₃), 3.43 (m, 1H, CH), 2.52 (m, 1H, CH), 2.23 (m, 4H, 2×CH₂), 1.57 (m, 3H, CH₃), 1.04 (m, 3H, CH₃), 0.90 (m, 6H, 2×CH₃). MS m/z 485 [M⁺+1].

Example 50

2-[4-(3-Methoxy-phenyl)-2-oxo-1,2-dihydro-indol-3-ylidenemethyl]-5-methyl-1H-pyrrole-3-carboxylic Acid (2-Pyrrolidin-1-yl-ethyl)-amide

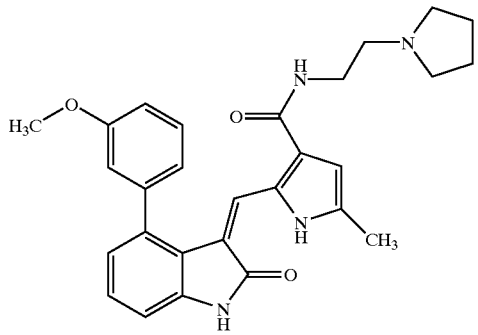

To a solution of 4-(3-methoxy-phenyl)-1,3-dihydro-indol-2-one (59.8 mg, 0.25 mmol) and 2-Formyl-5-methyl-1H-pyrrole-3-carboxylic acid (2-pyrrolidin-1-yl-ethyl)-amide (64.8 mg, 0.25 mmol) in ethanol (2 mL) was added piperidine (3 drops). The reaction mixture was stirred at room temperature for three days. A yellow solid product was precipitated out, filtered, washed by ethanol for three times, and dried under high vacuum to provide pure product 2-[4-(3-Methoxy-phenyl)-2-oxo-1,2-dihydro-indol-3-ylidenemethyl]-5-methyl-1H-pyrrole-3-carboxylic acid (2-pyrrolidin-1-yl-ethyl)-amide as a yellow solid (40 mg, 34%).

$^1$H-NMR (400 MHz, DMSO-$d_6$) δ 13.80 (br s, 1H, pyrrole NH), 11.09 (br s, 1H, CONH), 8.03 (s, 1H, aromatic), 7.71 (t, 1H, CONH), 7.32 (m, 1H, aromatic), 7.28 (t, 1H, aromatic), 6.90 (m, 4H, aromatic), 6.78 (d, 1H, aromatic), 6.35 (m, 1H, aromatic), 3.74 (s, 3H, OCH$_3$), 3.14 (m, 2H, CH$_2$), 2.50 (m, 6H, 3×CH$_2$), 2.32 (s, 3H, CH$_3$), 1.69 (m, 4H, 2×CH$_2$). MS m/z 471 [M$^+$+1].

Example 51

2-[4-(3-Methoxy-phenyl)-2-oxo-1,2-dihydro-indol-3-ylidenemethyl]-5-methyl-1H-pyrrole-3-carboxylic Acid (2-[1,2,3]Triazol-1-yl-ethyl)-amide

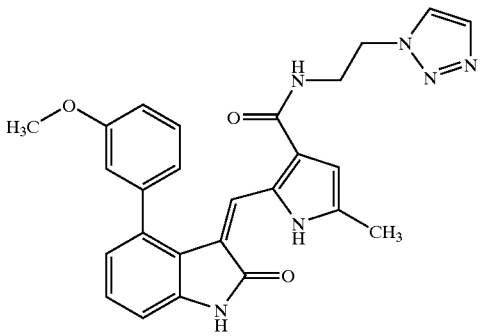

To a solution of 4-(3-methoxy-phenyl)-1,3-dihydro-indol-2-one (59.8 mg, 0.25 mmol) and 2-Formyl-5-methyl-1H-pyrrole-3-carboxylic acid (2-[1,2,3]triazol-1-yl-ethyl)-amide (64.8 mg, 0.25 mmol) in ethanol (2 mL) was added piperidine (3 drops). The reaction mixture was stirred at room temperature for three days. A yellow solid product was precipitated out, filtered, washed by ethanol for three times, and dried under high vacuum to provide pure product 2-[4-(3-Methoxy-phenyl)-2-oxo-1,2-dihydro-indol-3-ylidenemethyl]-5-methyl-1H-pyrrole-3-carboxylic acid (2-[1,2,3]triazol-1-yl-ethyl)-amide as a yellow solid (51 mg, 43%).

$^1$H-NMR (400 MHz, DMSO-$d_6$) δ 13.86 (br s, 1H, pyrrole NH), 11.02 (br s, 1H, CONH), 8.00 (m, 3H, aromatic), 7.72 (s, 1H, aromatic), 7.65 (t, 1H, aromatic), 7.39 (t, 1H, aromatic), 6.92 (m, 4H, aromatic), 6.79 (d, 1H, aromatic), 6.30 (m, 1H, aromatic), 4.49 (t, 2H, CH$_2$), 3.76 (s, 3H, OCH$_3$), 3.47 (m, 2H, CH$_2$), 2.29 (s, 3H, CH$_3$). MS m/z 469 [M$^+$+1].

Example 52

5-[4-(3-Methoxy-phenyl)-2-oxo-1,2-dihydro-indol-3-ylidenemethyl]-2,4-dimethyl-1H-pyrrole-3-carboxylic Acid (2-Diisopropylamino-ethyl)-amide

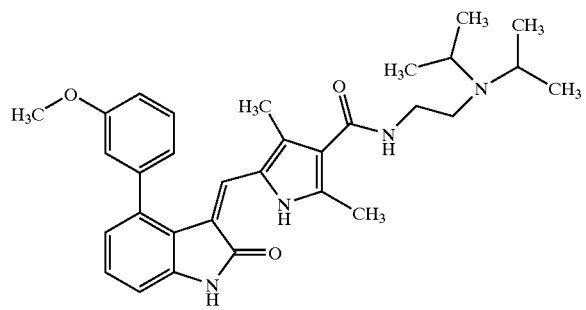

To a solution of 4-(3-methoxy-phenyl)-1,3-dihydro-indol-2-one (59.8 mg, 0.25 mmol) and 5-formyl-2,4-dimethyl-1H-pyrrole-3-carboxylic acid (2-diisopropylamino-ethyl)-amide (73 mg, 0.25 mmol) in ethanol (2 mL) was added piperidine (3 drops). The reaction mixture was stirred at room temperature for three days. The reaction solution was evaporated, and purified on a silica gel column eluting with MeOH—CH$_2$Cl$_2$ 5:95 to provide pure product 5-[4-(3-methoxy-phenyl)-2-oxo-1,2-dihydro-indol-3-ylidenemethyl]-2,4-dimethyl-1H-pyrrole-3-carboxylic acid (2-diisopropylamino-ethyl)-amide as a yellow solid (95 mg, 79%).

$^1$H-NMR (400 MHz, DMSO-$d_6$) δ 13.49 (br s, 1H, pyrrole NH), 11.03 (br s, 1H, CONH), 7.47 (m, 1H, aromatic), 7.33 (m, 1H, aromatic), 7.17 (t, 1H, aromatic), 7.06 (m, 1H, aromatic), 6.98 (m, 2H, aromatic), 6.92 (d, 1H, aromatic), 6.88 (s, 1H, aromatic), 6.80 (d, 1H, aromatic), 3.77 (s, 1H, CH$_3$), 3.31 (m, 2H, CH$_2$), 3.29 (m, 2H, CH$_2$), 2.39 (s, 3H, CH$_3$), 1.73 (m, 3H, CH$_3$), 0.99 (m, 12H, 4×CH$_3$). MS m/z 515 [M$^+$+1].

Example 53

4-(4-Bromo-phenyl)-3-[3,5-dimethyl-4-(4-methyl-piperazine-1-carbonyl-1H-pyrrol-2-ylmethylene]-1,3-dihydro-indol-2-one

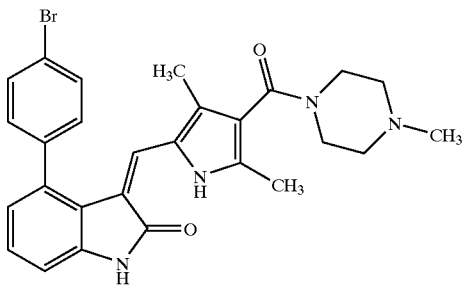

To a solution of 4-(4-bromo-phenyl)-1,3-dihydro-indol-2-one (72 mg, 0.25 mmol) and 3,5-dimethyl-4-(4-methyl-piperazine-1-carbonyl)-1H-pyrrole-2-carbaldehyde (64.8 mg, 0.26 mmol) in ethanol (2 mL) was added piperidine (3 drops). The reaction mixture was stirred at room temperature for three days. A yellow solid product was precipitated out, filtered, washed by ethanol for three times, and dried under high vacuum to provide 4-(4-bromo-phenyl)-3-[3,5-dimethyl-4-(4-methyl-piperazine-1-carbonyl)-1H-pyrrol-2-ylmethylene]-1,3-dihydro-indol-2-one as a yellow solid (38 mg, 29%)

$^1$H-NMR (400 MHz, DMSO-$d_6$) δ 13.41 (br s, 1H, pyrrole NH), 11.04 (br s, 1H, CONH), 7.75 (d, 2H, aromatic), 7.395 (d, 2H, aromatic), 7.19 (t, 1H, aromatic), 6.93 (d, 1H, aromatic), 6.79 (d, 1H, aromatic), 6.64 (s, 1H, aromatic), 3.31 (m, 4H, 2×CH$_2$), 2.25 (m, 7H, 2×CH$_2$+CH$_3$), 2.17 (s, 3H, CH$_3$), 1.61 (s, 3H, CH$_3$). MS m/z 519 [M$^+$+1].

Example 54

5-[4-(4-Bromo-phenyl)-2-oxo-1,2-dihydro-indol-3-ylidenemethyl]-2,4-dimethyl-1H-pyrrole-3-carboxylic Acid (2-Diethylamino-ethyl)-amide

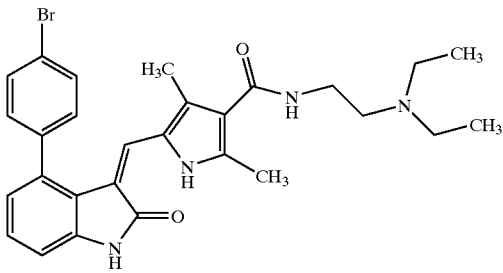

To a solution of 4-(4-bromo-phenyl)-1,3-dihydro-indol-2-one (72 mg, 0.25 mmol) and 5-formyl-2,4-dimethyl-1H-pyrrole-3-carboxylic acid (2-diethylamino-ethyl)-amide (69.0 mg, 0.26 mmol) in ethanol (2 mL) was added piperidine (3 drops). The reaction mixture was stirred at room temperature for three days. A yellow solid product was precipitated out, filtered, washed by ethanol for three times, and dried under high vacuum to provide 5-[4-(4-bromo-phenyl)-2-oxo-1,2-dihydro-indol-3-ylidenemethyl]-2,4-dimethyl-1H-pyrrole-3-carboxylic acid (2-diethylamino-ethyl)-amide as a yellow solid (59 mg, 44%)

$^1$H-NMR (400 MHz, DMSO-$d_6$) δ 13.44 (br s, 1H, pyrrole NH), 11.04 (br s, 1H, CONH), 7.74 (d, 2H, aromatic), 7.37 (d, 2H, aromatic), 7.33 (t, 1H, CONH), 7.19 (t, 1H, aromatic), 6.93 (d, 1H, aromatic), 6.80 (m, 1H, aromatic), 6.66 (s, 1H, aromatic), 3.24 (m, 2H, CH$_2$), 2.49 (m, 6H, 3×CH$_2$), 2.39 (s, 3H, CH$_3$), 1.75 (s, 3H, CH$_3$), 0.96 (t, 6H, 2×CH$_3$). MS m/z 535 [M$^+$+1].

Example 55

5-[4-(4-Bromo-phenyl)-2-oxo-1,2-dihydro-indol-3-ylidenemethyl]-2,4-dimethyl-1H-pyrrole-3-carboxylic Acid (2-Pyrrolidin-1-yl-ethyl)-amide

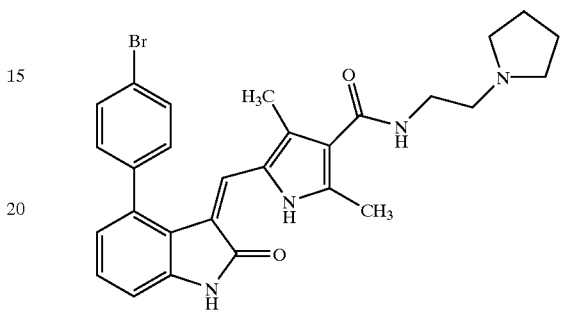

To a solution of 4-(4-bromo-phenyl)-1,3-dihydro-indol-2-one (72 mg, 0.25 mmol) and 5-formyl-2,4-dimethyl-1H-pyrrole-3-carboxylic acid (2-pyrrolidin-1-yl-ethyl)-amide (68.5 mg, 0.26 mmol) in ethanol (2 mL) was added piperidine (3 drops). The reaction mixture was stirred at room temperature for three days. A yellow solid product was precipitated out, filtered, washed by ethanol for three times, and dried under high vacuum to provide pure product 5-[4-(4-bromo-phenyl)-2-oxo-1,2-dihydro-indol-3-ylidenemethyl]-2,4-dimethyl-1H-pyrrole-3-carboxylic acid (2-pyrrolidin-1-yl-ethyl)-amide as a yellow solid (63 mg, 47%).

$^1$H-NMR (400 MHz, DMSO-$d_6$) δ 13.43 (br s, 1H, pyrrole NH), 11.04 (br s, 1H, CONH), 7.74 (m, 2H, aromatic), 7.42 (t, 1H, CONH), 7.36 (d, 2H, aromatic), 7.19 (t, 1H, aromatic), 6.95 (d, 1H, aromatic), 6.79 (m, 1H, aromatic), 6.65 (s, 1H, aromatic), 3.30 (m, 2H, CH$_2$), 2.50 (m, 2H, CH$_2$), 2.46 (m, 4H, 2×CH$_2$), 2.37 (s, 3H, CH$_3$), 1.73 (s, 3H, CH$_3$), 1.67 (m, 4H, 2×CH$_2$). MS m/z 533 [M$^+$+1].

Example 56

5-[4-(4-Bromo-phenyl)-2-oxo-1,2-dihydro-indol-3-ylidenemethyl]-2,4-dimethyl-1H-pyrrole-3-carboxylic Acid (2-[1,2,3]Triazol-1-yl-ethyl)-amide

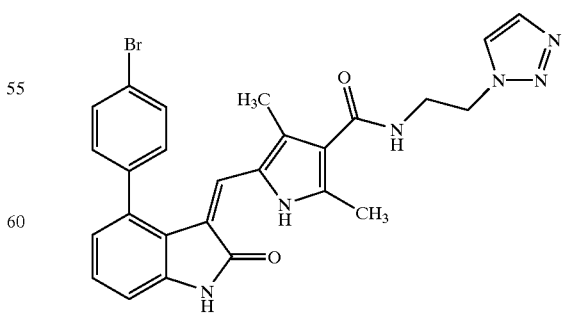

To a solution of 4-(4-bromo-phenyl)-1,3-dihydro-indol-2-one (72 mg, 0.25 mmol) and 5-formyl-2,4-dimethyl-1H- pyrrole-3-carboxylic acid (2-[1,2,3]triazol-1-yl-ethyl)-amide (67.9 mg, 0.26 mmol) in ethanol (2 mL) was added piperidine (3 drops). The reaction mixture was stirred at room temperature for three days. A yellow solid product was precipitated out, filtered, washed by ethanol for three times, and dried under high vacuum to provide pure product 5-[4-(4-bromo-phenyl)-2-oxo-1,2-dihydro-indol-3-ylidenemethyl]-2,4-dimethyl-1H-pyrrole-3-carboxylic acid (2-[1,2,3]triazol-1-yl-ethyl)-amide as a yellow solid (50 mg, 38%).

$^1$H-NMR (400 MHz, DMSO-$d_6$) δ 13.43 (br s, 1H, pyrrole NH), 11.05 (br s, 1H, CONH), 8.10 (s, 1H, aromatic), 7.72 (m, 3H, aromatic), 7.62 (t, 1H, CONH), 7.47 (d, 2H, aromatic), 7.19 (t, 1H, aromatic), 6.93 (d, 1H, aromatic), 6.78 (d, 1H, aromatic), 6.63 (s, 1H, aromatic), 4.53 (m, 2H, CH$_2$), 3.64 (m, 2H, CH$_2$), 2.30 (s, 3H, CH$_3$), 1.64 (s, 3H, CH$_3$). MS m/z 531 [M$^+$+1].

Example 57

4-(4-Bromo-phenyl)-3-[4-[(cis)-3,5-dimethyl-piperazine-1-carbonyl)-3,5-dimethyl-1H-pyrrol-2-ylmethylene]-1,3-dihydro-indol-2-one

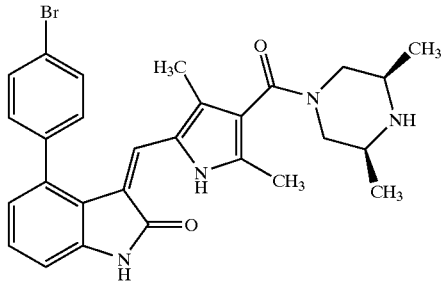

To a solution of 4-(4-bromo-phenyl)-1,3-dihydro-indol-2-one (72 mg, 0.25 mmol) and 4-[(cis)-3,5-dimethyl-piperazine-1-carbonyl)-3,5-dimethyl-1H-pyrrole-2-carbaldehyde (68.5 mg, 0.25 mmol) in ethanol (2 mL) was added piperidine (3 drops). The reaction mixture was stirred at room temperature for three days. A yellow solid product was precipitated out, filtered, washed by ethanol for three times, and dried under high vacuum to provide pure product 4-(4-bromo-phenyl)-3-[4-[(cis)-3,5-dimethyl-piperazine-1-carbonyl)-3,5-dimethyl-1H-pyrrol-2-ylmethylene]-1,3-dihydro-indol-2-one as a yellow solid (38 mg, 28%).

$^1$H-NMR (400 MHz, DMSO-$d_6$) δ 13.40 (br m, 1H, pyrrole NH), 11.03 (br s, 1H, CONH), 7.74 (d, 2H, aromatic), 7.39 (d, 2H, aromatic), 7.19 (t, 1H, aromatic), 6.93 (d, 1H, aromatic), 6.79 (d, 1H, aromatic), 6.62 (s, 1H, aromatic), 4.20 (m, 1H, NH), 3.43 (m, 4H, 2×CH$_2$), 2.52 (m, 2H, 2×CH), 2.23 (m, 3H, CH$_3$), 1.59 (m, 3H, CH$_3$), 0.90 (m, 6H, 2×CH$_3$). MS m/z 533 [M$^+$+1 ).

Example 58

2-[4-(4-Bromo-phenyl)-2-oxo-1,2-dihydro-indol-3-ylidenemethyl]-5-methyl-1H-pyrrole-3-carboxylic Acid (2-Pyrrolidin-1-yl-ethyl)-amide

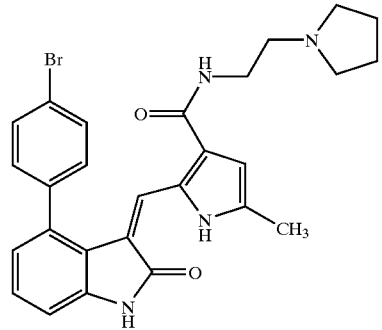

To a solution of 4-(4-bromo-phenyl)-1,3-dihydro-indol-2-one (72 mg, 0.25 mmol) and 2-formyl-5-methyl-1H-pyrrole-3-carboxylic acid (2-pyrrolidin-1-yl-ethyl)-amide (64.8 mg, 0.25 mmol) in ethanol (2 mL) was added piperidine (3 drops). The reaction mixture was stirred at room temperature for three days. A yellow solid product was precipitated out, filtered, washed by ethanol for three times, and dried under high vacuum to provide pure product 2-[4-(4-bromo-phenyl)-2-oxo-1,2-dihydro-indol-3-ylidenemethyl]-5-methyl-1H-pyrrole-3-carboxylic acid (2-pyrrolidin-1-yl-ethyl)-amide as a yellow solid (78 mg, 60%).

$^1$H-NMR (400 MHz, DMSO-$d_6$) δ 13.73 (br s, 1H, pyrrole NH), 11.05 (br s, 1H, CONH), 8.05 (s, 1H, aromatic), 7.72 (t, 1H, CONH), 7.58 (d, 2H, aromatic), 7.30 (d, 2H, aromatic), 7.19 (t, 1H, aromatic), 6.93 (d, 1H, aromatic), 6.75 (d, 1H, aromatic), 6.41 (s, 1H, aromatic), 3.30 (m, 2H, CH$_2$), 2.50 (m, 6H, 3×CH$_2$), 2.31 (s, 3H, CH$_3$), 1.67 (m, 4H, 2×CH$_2$). MS m/z 519 [M$^+$+1].

Example 59

2-[4-(4-Bromo-phenyl)-2-oxo-1,2-dihydro-indol-3-ylidenemethyl]-5-methyl-1H-pyrrole-3-carboxylic Acid (2-[1,2,3]Triazol-1-yl-ethyl)-amide

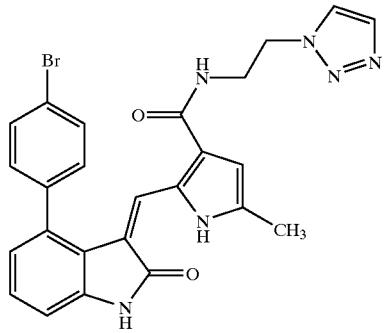

To a solution of 4-(4-bromo-phenyl)-1,3-dihydro-indol-2-one (72 mg, 0.25 mmol) and 2-formyl-5-methyl-1H-pyrrole-3-carboxylic acid (2-[1,2,3]triazol-1-yl-ethyl)-amide (64.8 mg, 0.25 mmol) in ethanol (2 mL) was added piperidine (3 drops). The reaction mixture was stirred at room temperature for three days. A yellow solid product was precipitated out, filtered, washed by ethanol for three times, and dried under high vacuum to provide pure product 2-[4-(4-bromo-phenyl)-2-oxo-1,2-dihydro-indol-3-ylidenemethyl]-5-methyl-1H-pyrrole-3-carboxylic acid (2-[1,2,3]triazol-1-yl-ethyl)-amide as a yellow solid (88 mg, 68%).

$^1$H-NMR (400 MHz, DMSO-$d_6$) δ 13.84 (br s, 1H, pyrrole NH), 11.13 (br s, 1H, CONH), 8.00 (m, 3H, aromatic), 7.73 (s, 1H, aromatic), 7.63 (m, 2H, aromatic), 7.32 (d, 2H, aromatic), 7.21 (t, 1H, aromatic), 6.93 (d, 1H, aromatic), 6.76 (d, 1H, aromatic), 6.33 (m, 1H, aromatic), 4.53 (m, 2H, CH$_2$), 3.54 (m, 2H, CH$_2$), 2.29 (s, 3H, CH$_3$). MS m/s 517 [M$^+$+1].

Example 60

5-[4-(4-Bromo-phenyl)-2-oxo-1,2-dihydro-indol-3-ylidenemethyl]-2,4-dimethyl-1H-pyrrole-3-carboxylic Acid (2-Diisopropylamino-ethyl)-amide

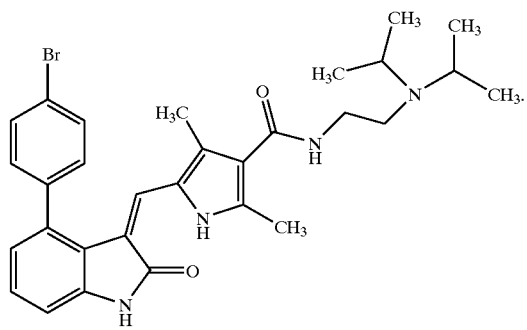

To a solution of 4-(4-bromo-phenyl)-1,3-dihydro-indol-2-one (72 mg, 0.25 mmol) and 5-formyl-2,4-dimethyl-1H-pyrrole-3-carboxylic acid (2-diisopropylamino-ethyl)-amide (73 mg, 0.25 mmol) in ethanol (2 mL) was added piperidine (3 drops). The reaction mixture was stirred at room temperature for three days. A yellow solid product was precipitated out, filtered, washed by ethanol for three times, and dried under high vacuum to provide pure product 5-[4-(4-bromo-phenyl)-2-oxo-1,2-dihydro-indol-3-ylidenemethyl]-2,4-dimethyl-1H-pyrrole-3-carboxylic acid (2-diisopropylamino-ethyl)-amide as a yellow solid (40 mg, 28%).

$^1$H-NMR (400 MHz, DMSO-$d_6$) δ 13.44 (br s, 1H, pyrrole NH), 11.04 (br s, 1H, CONH), 7.74 (d, 2H, aromatic), 7.38 (d, 2H, aromatic), 7.29 (t, 1H, CONH), 7.19 (t, 1H, aromatic), 6.93 (d, 1H, aromatic), 6.80 (d, 1H, aromatic), 6.72 (s, 1H, aromatic), 3.31 (m, 2H, CH$_2$), 3.29 2.50 (m, 2H, 2×CH), (m, 2H, CH$_2$), 2.39 (s, 3H, CH$_3$), 1.73 (m, 3H, CH$_3$), 0.99 (m, 12H, 4×CH$_3$). MS m/z 563 [M$^+$+1].

Example 61

5-[4-(4-Bromo-phenyl)-2-oxo-1,2-dihydro-indol-3-ylidenemethyl]-4-methyl-1H-pyrrole-3-carboxylic Acid (2-Diethylamino-ethyl)-amide

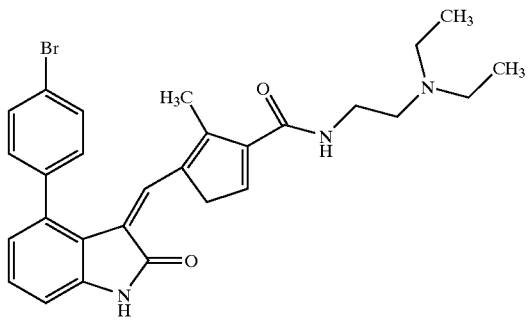

To a solution of 4-(4-bromo-phenyl)-1,3-dihydro-indol-2-one (72 mg, 0.25 mmol) and 5-formyl-4-methyl-1H-pyrrole-3-carboxylic acid (2-diethylamino-ethyl)-amide (62.8 mg, 0.25 mmol) in ethanol (2 mL) was added piperidine (3 drops). The reaction mixture was stirred at room temperature for three days. A yellow solid product was precipitated out, filtered, washed by ethanol for three times, and dried under high vacuum to provide pure product 5-[4-(4-bromo-phenyl)-2-oxo-1,2-dihydro-indol-3-ylidenemethyl]-4-methyl-1H-pyrrole-3-carboxylic acid (2-diethylamino-ethyl)-amide (82 mg, 63%).

$^1$H-NMR (400 MHz, DMSO-$d_6$) δ 13.41 (br s, 1H, pyrrole NH), 11.10 (br s, 1H, CONH), 7.75 (d, 2H, aromatic), 7.66 (m, 2H, aromatic), 7.39 (d, 2H, aromatic), 7.21 (t, 1H, aromatic), 6.93 (d, 1H, aromatic), 6.81 (m, 1H, aromatic), 6.73 (s, 1H, aromatic), 3.20 (m, 2H, CH$_2$), 2.49 (m, 6H, 3×CH$_2$), 1.74 (s, 3H, CH$_3$), 0.95 (t, 6H, 2×CH$_3$). MS m/z 521 [M$^+$+1].

Example 62

4-(3-Bromo-phenyl)-3-[3,5-dimethyl-4-(4-methyl-piperazine-1-carbonyl)-1H-pyrrol-2-ylmethylene]-1,3-dihydro-indol-2-one

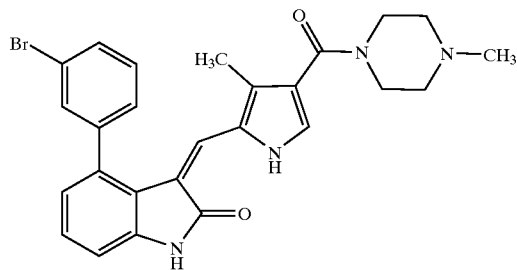

To a solution of 4-(3-bromo-phenyl)-1,3-dihydro-indol-2-one (72 mg, 0.25 mmol) and 3,5-dimethyl-4-(4-methyl-piperazine-1-carbonyl)-1H-pyrrole-2-carbaldehyde (64.8 mg, 0.26 mmol) in ethanol (2 mL) was added piperidine (3 drops). The reaction mixture was stirred at room temperature for three days. A yellow solid product was precipitated out, filtered, washed by ethanol for three times, and dried under high vacuum to provide 4-(3-bromo-phenyl)-3-[3,5-dimethyl-4-(4-methyl-piperazine-1-carbonyl)-1H-pyrrol-2-ylmethylene]-1,3-dihydro-indol-2-one as a yellow solid (48 mg, 37%)

$^1$H-NMR (400 MHz, DMSO-$d_6$) δ 13.45 (br s, 1H, pyrrole NH), 11.06 (br s, 1H, CONH), 7.69 (d, 1H, aromatic), 7.65 (s, 1H, aromatic), 7.52 (t, 1H, aromatic), 7.45 (d, 1H, aromatic), 7.20 (t, 1H, aromatic), 6.94 (d, 1H, aromatic), 6.81 (d, 1H, aromatic), 6.76 (s, 1H, aromatic), 3.33 (m, 4H, 2×CH$_2$), 2.24 (m, 7H, 2×CH$_2$+CH$_3$), 2.17 (s, 3H, CH$_3$), 1.62 (s, 3H, CH$_3$). MS m/z 519 [M$^+$+1].

Example 63

5-[4-(3-Bromo-phenyl)-2-oxo-1,2-dihydro-indol-3-ylidenemethyl]-2,4-dimethyl-1H-pyrrole-3-carboxylic Acid (2-Diethylamino-ethyl)-amide

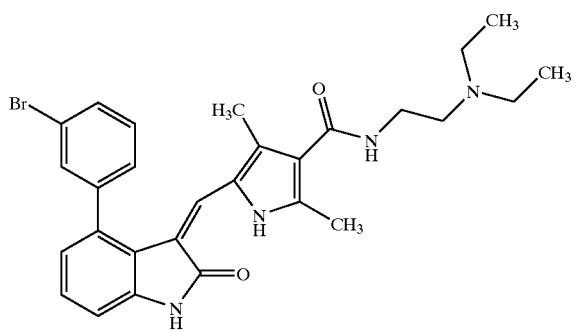

To a solution of 4-(3-bromo-phenyl)-1,3-dihydro-indol-2-one (72 mg, 0.25 mmol) and 5-formyl-2,4-dimethyl-1H-pyrrole-3-carboxylic acid (2-diethylamino-ethyl)-amide (69.0 mg, 0.26 mmol) in ethanol (2 mL) was added piperidine (3 drops). The reaction mixture was stirred at room temperature for three days. A yellow solid product was precipitated out, filtered, washed by ethanol for three times, and dried under high vacuum to provide 5-[4-(3-bromo-phenyl)-2-oxo-1,2-dihydro-indol-3-ylidenemethyl]-2,4-dimethyl-1H-pyrrole-3-carboxylic acid (2-diethylamino-ethyl)-amide as a yellow solid (89.7 mg, 67%)

$^1$H-NMR (400 MHz, DMSO-d$_6$) δ 13.48 (br s, 1H, pyrrole NH), 11.06 (br s, 1H, CONH), 7.71 (d, 1H, aromatic), 7.65 (s, 1H, aromatic), 7.53 (t, 1H, aromatic), 7.44 (d, 1H, aromatic), 7.37 (t, 1H, CONH), 7.20 (t, 1H, aromatic), 6.94 (d, 1H, aromatic), 6.80 (d, 1H, aromatic), 6.78 (s, 1H, aromatic), 3.23 (m, 2H, CH$_2$), 2.49 (m, 6H, 3×CH$_2$), 2.39 (s, 3H, CH$_3$), 1.76 (s, 3H, CH$_3$), 0.95 (t, 6H, 2×CH$_3$). MS m/z 535 [M$^+$+1].

Example 64

5-[4-(3-Bromo-phenyl)-2-oxo-1,2-dihydro-indol-3-ylidenemethyl]-2,4-dimethyl-1H-pyrrole-3-carboxylic Acid (2-Pyrrolidin-1-yl-ethyl)-amide

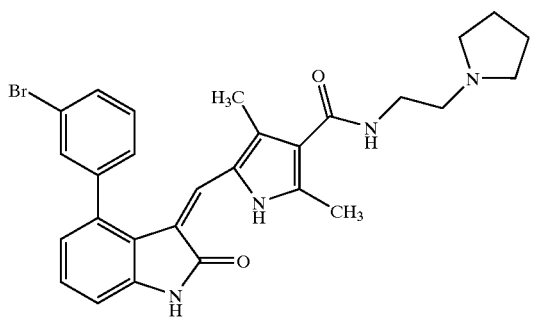

To a solution of 4-(3-bromo-phenyl)-1,3-dihydro-indol-2-one (72 mg, 0.25 mmol) and 5-formyl-2,4-dimethyl-1H-pyrrole-3-carboxylic acid (2-pyrrolidin-1-yl-ethyl)-amide (68.5 mg, 0.26 mmol) in ethanol (2 mL) was added piperidine (3 drops). The reaction mixture was stirred at room temperature for three days. The reaction solution was evaporated, and purified on a silica gel column eluting with MeOH—CH$_2$Cl$_2$ 5:95 to provide pure product 5-[4-(3-bromo-phenyl)-2-oxo-1,2-dihydro-indol-3-ylidenemethyl)-2,4-dimethyl-1H-pyrrole-3-carboxylic acid (2-pyrrolidin-1-yl-ethyl)-amide as a yellow solid (84 mg, 63%).

$^1$H-NMR (400 MHz, DMSO-d$_6$) δ 13.48 (br s, 1H, pyrrole NH), 11.06 (br s, 1H, CONH), 7.71 (d, 1H, aromatic), 7.65 (s, 1H, aromatic), 7.52 (t, 1H, aromatic), 7.45 (m, 2H, CONH and aromatic), 7.20 (t, 1H, aromatic), 6.95 (d, 1H, aromatic), 6.80 (d, 1H, aromatic), 6.78 (s, 1H, aromatic), 3.30 (m, 2H, CH$_2$), 2.52 (m, 6H, 3×CH$_2$), 2.37 (s, 3H, CH$_3$), 1.74 (s, 3H, CH$_3$), 1.68 (m, 4H, 2×CH$_2$). MS m/z 531 [M$^-$−1].

Example 65

5-[4-(3-Bromo-phenyl)-2-oxo-1,2-dihydro-indol-3-ylidenemethyl]-2,4-dimethyl-1H-pyrrole-3-carboxylic Acid (2-[1,2,3]Triazol-1-yl-ethyl)-amide

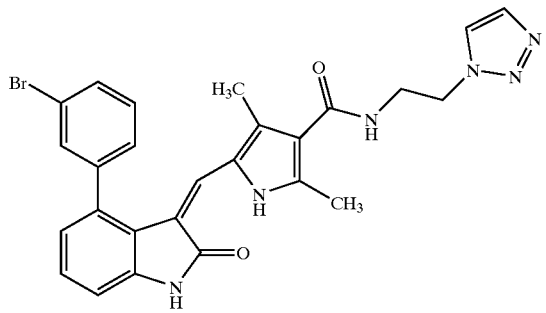

To a solution of 4-(3-bromo-phenyl)-1,3-dihydro-indol-2-one (72 mg, 0.25 mmol) and 5-formyl-2,4-dimethyl-1H-pyrrole-3-carboxylic acid (2-[1,2,3]triazol-1-yl-ethyl)-amide (67.9 mg, 0.26 mmol) in ethanol (2 mL) was added piperidine (3 drops). The reaction mixture was stirred at room temperature for three days. A yellow solid product was precipitated out, filtered, washed by ethanol for three times, and dried under high vacuum to provide pure product 5-[4-(3-bromo-phenyl)-2-oxo-1,2-dihydro-indol-3-ylidenemethyl]-2,4-dimethyl-1H-pyrrole-3-carboxylic acid (2-[1,2,3]triazol-1-yl-ethyl)-amide as a yellow solid (46.6 mg, 35%).

$^1$H-NMR (400 MHz, DMSO-d$_6$) δ 13.48 (br s, 1H, pyrrole NH), 11.07 (br s, 1H, CONH), 8.10 (s, 1H, aromatic), 7.72 (m, 2H, aromatic), 7.65 (m, 2H, aromatic), 7.52 (t, 1H, CONH), 7.42 (d, 1H, aromatic), 7.20 (t, 1H, aromatic), 6.94 (d, 1H, aromatic), 6.80 (d, 1H, aromatic), 6.76 (s, 1H, aromatic), 4.53 (m, 2H, CH$_2$), 3.64 (m, 2H, CH$_2$), 2.26 (s, 3H, CH$_3$), 1.67 (s, 3H, CH$_3$). MS m/z 531 [M$^+$+1].

Example 66

4-(3-Bromo-phenyl)-3-[4-(cis)-3,5-dimethyl-piperazine-1-carbonyl)-3,5-dimethyl-1H-pyrrol-2-ylmethylene]-1,3-dihydro-indol-2-one

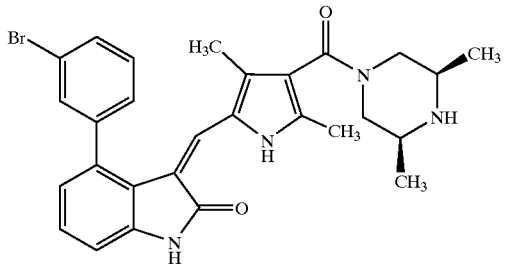

To a solution of 4-(3-bromo-phenyl)-1,3-dihydro-indol-2-one (72 mg, 0.25 mmol) and 4-[(cis)-3,5-dimethyl-piperazine-1-carbonyl)-3,5-dimethyl-1H-pyrrole-2-carbaldehyde (68.5 mg, 0.25 mmol) in ethanol (2 mL) was added piperidine (3 drops). The reaction mixture was stirred at room temperature for three days. The reaction solution was evaporated, and purified on a silica gel column eluting with MeOH—$CH_2Cl_2$ 5:95 to provide pure product 4-(3-bromo-phenyl)-3-[4-[(cis)-3,5-dimethyl-piperazine-1-carbonyl)-3,5-dimethyl-1H-pyrrol-2-ylmethylene]-1,3-dihydro-indol-2-one as a yellow solid (95 mg, 70%).

$^1$H-NMR (400 MHz, DMSO-$d_6$) δ 13.43 (br m, 1H, pyrrole NH), 11.06 (br s, 1H, CONH), 7.70 (d, 1H, aromatic), 7.65 (s, 1H, aromatic), 7.52 (t, 1H, aromatic), 7.45 (d, 1H, aromatic), 7.20 (t, 1H, aromatic), 6.94 (d, 1H, aromatic), 6.80 (d, 1H, aromatic), 6.76 (s, 1H, aromatic), 3.30 (m, 4H, 2×$CH_2$), 2.54 (m, 2H, 2×CH), 2.30 (brs, 1H, NH), 2.23 (s, 3H, $CH_3$), 1.61 (s, 3H, $CH_3$), 0.93 (m, 6H, 2×$CH_3$). MS m/z 531 [M$^-$−1].

Example 67

2-[4-(3-Bromo-phenyl)-2-oxo-1,2-dihydro-indol-3-ylidenemethyl]-5-methyl-1H-pyrrole-3-carboxylic Acid (2-Pyrrolidin-1-yl-ethyl)-amide

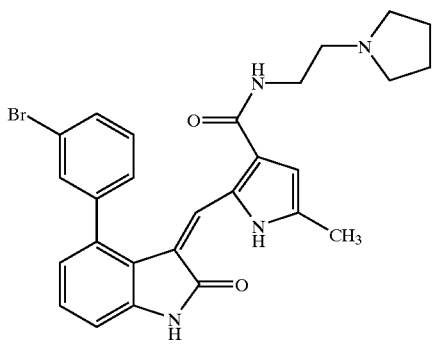

To a solution of 4-(3-bromo-phenyl)-1,3-dihydro-indol-2-one (72 mg, 0.25 mmol) and 2-formyl-5-methyl-1H-pyrrole-3-carboxylic acid (2-pyrrolidin-1-yl-ethyl)-amide (64.8 mg, 0.25 mmol) in ethanol (2 mL) was added piperidine (3 drops). The reaction mixture was stirred at room temperature for three days. A yellow solid product was precipitated out, filtered, washed by ethanol for three times, and dried under high vacuum to provide pure product 2-[4-(3-bromo-phenyl)-2-oxo-1,2-dihydro-indol-3-ylidenemethyl]-5-methyl-1H-pyrrole-3-carboxylic acid (2-pyrrolidin-1-yl-ethyl)-amide as a yellow solid (93 mg, 72%).

$^1$H-NMR (400 MHz, DMSO-$d_6$) δ 13.80 (br s, 1H, pyrrole NH), 11.12 (br s, 1H, CONH), 8.02 (s, 1H, aromatic), 7.77 (t, 1H, CONH), 7.52 (m, 2H, aromatic), 7.38 (m, 2H, aromatic), 7.21 (t, 1H, aromatic), 6.93 (d, 1H, aromatic), 6.77 (d, 1H, aromatic), 6.39 (s, 1H, aromatic), 3.18 (dd, 2H, $CH_2$), 2.48 (m, 6H, 3×$CH_2$), 2.32 (s, 3H, $CH_3$), 1.70 (m, 4H, 2×$CH_2$). MS m/z 519 [M$^+$+1].

Example 68

2-[4-(3-Bromo-phenyl)-2-oxo-1,2-dihydro-indol-3-ylidenemethyl]-5-methyl-1H-pyrrole-3-carboxylic Acid (2-[1,2,3]Triazol-1-yl-ethyl)-amide

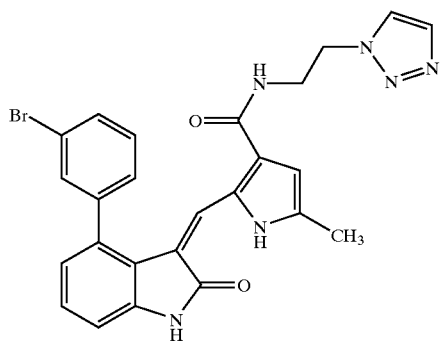

To a solution of 4-(3-bromo-phenyl)-1,3-dihydro-indol-2-one (72 mg, 0.25 mmol) and 2-formyl-5-methyl-1H-pyrrole-3-carboxylic acid (2-[1,2,3]triazol-1-yl-ethyl)-amide (64.8 mg, 0.25 mmol) in ethanol (2 mL) was added piperidine (3 drops). The reaction mixture was stirred at room temperature for three days. A yellow solid product was precipitated out, filtered, washed by ethanol for three times, and dried under high vacuum to provide pure product 2-[4-(3-bromo-phenyl)-2-oxo-1,2-dihydro-indol-3-ylidenemethyl]-5-methyl-1H-pyrrole-3-carboxylic acid (2-[1,2,3]triazol-1-yl-ethyl)-amide as a yellow solid (96 mg, 74%).

$^1$H-NMR (400 MHz, DMSO-$d_6$) δ 13.82 (br s, 1H, pyrrole NH), 11.14 (br s, 1H, CONH), 8.03 (t, 1H, CONH), 8.00 (s, 2H, aromatic), 7.74 (s, 1H, aromatic), 7.61 (m, 1H, aromatic), 7.53 (m, 1H, aromatic), 7.41 (t, 1H, aromatic), 7.35 (m, 1H, aromatic), 7.21 (t, 1H, aromatic), 6.94 (d, 1H, aromatic), 6.78 (d, 1H, aromatic), 6.34 (d, 1H, aromatic), 4.52 (m, 2H, $CH_2$), 3.51 (m, 2H, $CH_2$), 2.31 (s, 3H, $CH_3$). MS m/z 517 [M$^+$+1].

Example 69

5-[4-(3-Bromo-phenyl)-2-oxo-1,2-dihydro-indol-3-ylidenemethyl]-2,4-dimethyl-1H-pyrrole-3-carboxylic Acid (2-Diisopropylamino-ethyl)-amide

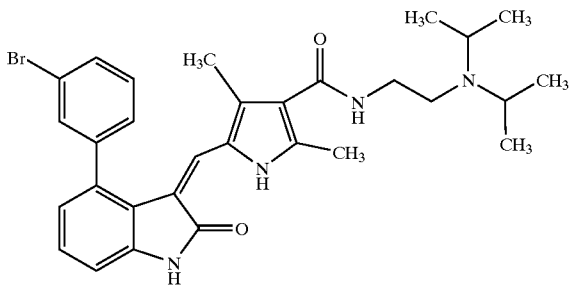

To a solution of 4-(3-bromo-phenyl)-1,3-dihydro-indol-2-one (72 mg, 0.25 mmol) and 5-formyl-2,4-dimethyl-1H-pyrrole-3-carboxylic acid (2-diisopropylamino-ethyl)-amide (73 mg, 0.25 mmol) in ethanol (2 mL) was added piperidine (3 drops). The reaction mixture was stirred at room temperature for three days. A yellow solid product was precipitated out, filtered, washed by ethanol for three times, and dried under high vacuum to provide pure product 5-[4-(3-bromo-phenyl)-2-oxo-1,2-dihydro-indol-3-ylidenemethyl]-2,4-dimethyl-1H-pyrrole-3-carboxylic acid (2-diisopropylamino-ethyl)-amide as a yellow solid (43 mg, 30%).

$^1$H-NMR (400 MHz, DMSO-$d_6$) δ 13.50 (br s, 1H, pyrrole NH), 11.06 (br s, 1H, CONH), 7.71 (d, 1H, aromatic), 7.66 (s, 1H, aromatic), 7.52 (t, 1H, aromatic), 7.44 (d, 1H, aromatic), 7.34 (t, 1H, CONH), 7.20 (t, 1H, aromatic), 6.94 (d, 1H, aromatic), 6.80 (d, 1H, aromatic), 6.78 (s, 1H, aromatic), 3.13 (m, 2H, CH$_2$), 2.97 (m, 2H, 2×CH), 2.50 (m, 2H, CH$_2$), 2.40 (s, 3H, CH$_3$), 1.76 (s, 3H, CH$_3$), 0.97 (d, 12H, 4×CH$_3$). MS m/z 563 [M$^+$+1].

Example 70

5-[4-(4-Fluoro-phenyl)-2-oxo-1,2-dihydro-indol-3-ylidenemethyl]-4-methyl-1H-pyrrole-2-carboxylic Acid (2-Diethylamino-ethyl)-amide

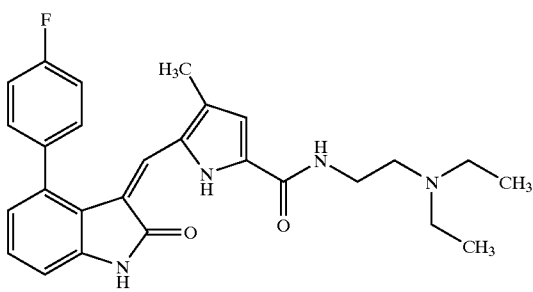

To a solution of 4-(4-fluoro-phenyl)-1,3-dihydro-indol-2-one (56.8 mg, 0.25 mmol) and 5-formyl-4-methyl-1H-pyrrole-2-carboxylic acid (2-diethylamino-ethyl)-amide (65.3 mg, 0.26 mmol) in ethanol (2 mL) was added piperidine (3 drops). The reaction mixture was stirred at room temperature for three days. The reaction solution was evaporated, and purified on a silica gel column eluting with MeOH—CH$_2$Cl$_2$ 5:95 to provide pure product 5-[4-(4-fluoro-phenyl)-2-oxo-1,2-dihydro-indol-3-ylidenemethyl]-4-methyl-1H-pyrrole-2-carboxylic acid (2-diethylaminoethyl)-amide as a yellow solid (52 mg, 45%).

$^1$H-NMR (400 MHz, DMSO-$d_6$) δ 13.51 (br s, 1H, pyrrole NH), 11.10 (br s, 1H, CONH), 8.26 (t, 1H, CONH), 7.48 (m, 2H, aromatic), 7.39 (m, 2H, aromatic), 7.23 (t, 1H, aromatic), 6.94 (d, 1H, aromatic), 6.80 (d, 1H, aromatic), 6.73 (s, 1H, aromatic), 6.68 (d, 1H, aromatic), 3.30 (m, 2H, CH$_2$), 2.50 (m, 6H, 3×CH$_2$), 1.69 (s, 3H, CH$_3$), 0.96 (t, 6H, 2×CH$_3$). MS m/z 461 [M$^+$+1].

Example 71

5-[4-(3-Fluoro-phenyl)-2-oxo-1,2-dihydro-indol-3-ylidenemethyl]-4-methyl-1H-pyrrole-2-carboxylic Acid (2-Diethylamino-ethyl)-amide

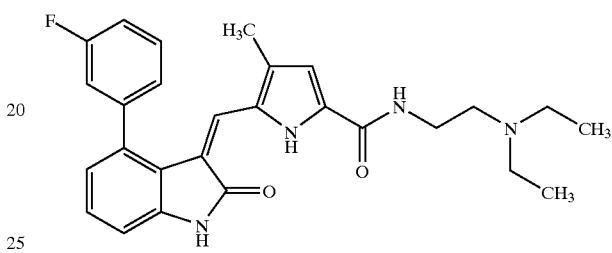

To a solution of 4-(3-fluoro-phenyl)-1,3-dihydro-indol-2-one (56.8 mg, 0.25 mmol) and 5-formyl-4-methyl-1H-pyrrole-2-carboxylic acid (2-diethylamino-ethyl)-amide (65.3 mg, 0.26 mmol) in ethanol (2 mL) was added piperidine (3 drops). The reaction mixture was stirred at room temperature for three days. The reaction solution was evaporated, and purified on a silica gel column eluting with MeOH—CH$_2$Cl$_2$ 5:95 to provide pure product 5-[4-(3-fluoro-phenyl)-2-oxo-1,2-dihydro-indol-3-ylidenemethyl]-4-methyl-1H-pyrrole-2-carboxylic acid (2-diethylaminoethyl)-amide as a yellow solid (26 mg, 23%).

$^1$H-NMR (400 MHz, DMSO-$d_6$) δ 13.55 (br s, 1H, pyrrole NH), 11.12 (br s, 1H, CONH), 8.30 (t, 1H, CONH), 7.60 (dd, 1H, aromatic), 7.33 (m, 3H, aromatic), 7.25 (t, 1H, aromatic), 6.95 (d, 1H, aromatic), 6.83 (d, 1H, aromatic), 6.81 (s, 1H, aromatic), 6.69 (d, 1H, aromatic), 3.30 (m, 2H, CH$_2$), 2.50 (m, 6H, 3×CH$_2$), 1.69 (s, 3H, CH$_3$), 0.96 (t, 6H, 2×CH$_3$). MS m/z 461 [M$^+$+1].

Example 72

5-[4-(4-Chloro-phenyl)-2-oxo-1,2-dihydro-indol-3-ylidenemethyl]-4-methyl-1H-pyrrole-2-carboxylic Acid (2-Diethylamino-ethyl)-amide

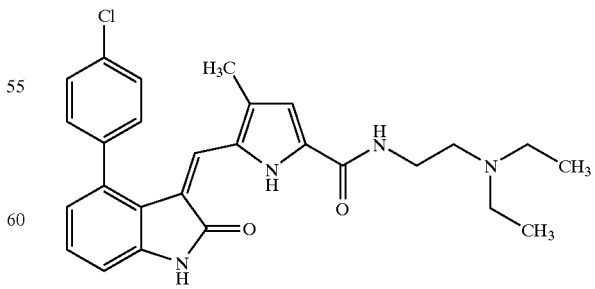

To a solution of 4-(4-Chloro-phenyl)-1,3-dihydro-indol-2-one (60.9 mg, 0.25 mmol) and 5-formyl-4-methyl-1H-pyrrole-2-carboxylic acid (2-diethylamino-ethyl)-amide (65.3 mg, 0.26 mmol) in ethanol (2 mL) was added piperidine (3 drops). The reaction mixture was stirred at room temperature for three days. The reaction solution was evaporated, and purified on a silica gel column eluting with MeOH—CH$_2$Cl$_2$ 5:95 to provide pure product 5-[4-(4-chloro-phenyl)-2-oxo-1,2-dihydro-indol-3-ylidenemethyl]-4-methyl-1H-pyrrole-2-carboxylic acid (2-diethylamino-ethyl)-amide as a yellow solid (80 mg, 67%).

$^1$H-NMR (400 MHz, DMSO-d$_6$) δ 13.50 (br s, 1H, pyrrole NH), 11.10 (br s, 1H, CONH), 8.29 (brs, 1H, CONH), 7.63 (d, 2H, aromatic), 7.47 (d, 2H, aromatic), 7.24 (t, 1H, aromatic), 6.94 (d, 1H, aromatic), 6.82 (d, 1H, aromatic), 6.70 (m, 2H, aromatic), 3.30 (m, 2H, CH$_2$), 2.57 (m, 6H, 3×CH$_2$), 1.69 (s, 3H, CH$_3$), 0.98 (t, 6H, 2×CH$_3$). MS m/z 477 [M$^+$+1].

Example 73

5-[4-(3-Chloro-phenyl)-2-oxo-1,2-dihydro-indol-3-ylidenemethyl]-4-methyl-1H-pyrrole-2-carboxylic Acid (2-Diethylamino-ethyl)-amide

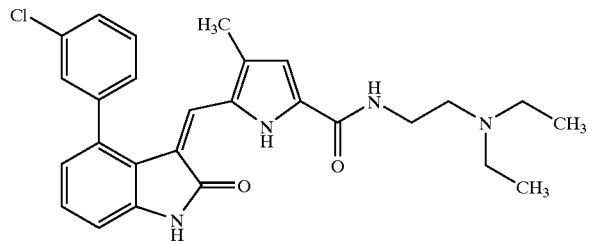

To a solution of 4-(3-Chloro-phenyl)-1,3-dihydro-indol-2-one (60.9 mg, 0.25 mmol) and 5-formyl-4-methyl-1H-pyrrole-2-carboxylic acid (2-diethylamino-ethyl)-amide (65.3 mg, 0.26 mmol) in ethanol (2 mL) was added piperidine (3 drops). The reaction mixture was stirred at room temperature for three days. The reaction solution was evaporated, and purified on a silica gel column eluting with MeOH—CH$_2$Cl$_2$ 5:95 to provide pure product 5-[4-(3-chloro-phenyl)-2-oxo-1,2-dihydro-indol-3-ylidenemethyl]-4-methyl-1H-pyrrole-2-carboxylic acid (2-diethylamino-ethyl)-amide as a yellow solid (65 mg, 54%).

$^1$H-NMR (400 MHz, DMSO-d$_6$) δ 13.53 (br s, 1H, pyrrole NH), 11.12 (br s, 1H, CONH), 8.31 (brs, 1H, CONH), 7.58 (m, 3H, aromatic), 7.42 (m, 1H, aromatic), 7.25 (t, 1H, aromatic), 6.92 (d, 1H, aromatic), 6.82 (d, 1H, aromatic), 6.80 (s, 1H, aromatic), 6.69 (d, 1H, aromatic), 3.30 (m, 2H, CH$_2$), 2.57 (m, 6H, 3×CH$_2$), 1.70 (s, 3H, CH$_3$), 0.98 (t, 6H, 2×CH$_3$). MS m/z 475 [M$^-$−1].

Example 74

5-[4-(4-Bromo-phenyl)-2-oxo-1,2-dihydro-indol-3-ylidenemethyl]-4-methyl-1H-pyrrole-2-carboxylic Acid (2-Diethylamino-ethyl)-amide

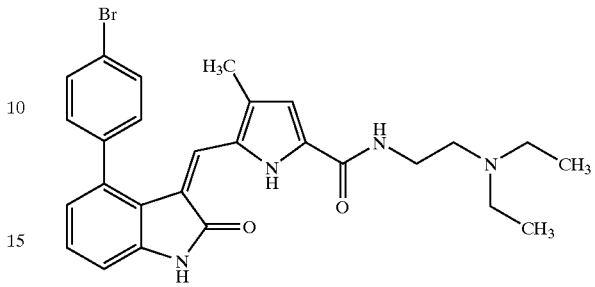

To a solution of 4-(4-bromo-phenyl)-1,3-dihydro-indol-2-one (72.0 mg, 0.25 mmol) and 5-formyl-4-methyl-1H-pyrrole-2-carboxylic acid (2-diethylamino-ethyl)-amide (65.3 mg, 0.26 mmol) in ethanol (2 mL) was added piperidine (3 drops). The reaction mixture was stirred at room temperature for three days. A yellow solid product was precipitated out, filtered, washed by ethanol for three times, and dried under high vacuum to provide pure product 5-[4-(4-bromo-phenyl)-2-oxo-1,2-dihydro-indol-3-ylidenemethyl]-4-methyl-1H-pyrrole-2-carboxylic acid (2-diethylamino-ethyl)-amide as a yellow solid (26 mg, 20%).

$^1$H-NMR (400 MHz, DMSO-d$_6$) δ 13.48 (br s, 1H, pyrrole NH), 11.10 (br s, 1H, CONH), 8.24 (t, 1H, CONH), 7.76 (d, 2H, aromatic), 7.38 (d, 2H, aromatic), 7.24 (t, 1H, aromatic), 6.94 (d, 1H, aromatic), 6.81 (d, 1H, aromatic), 6.69 (m, 2H, aromatic), 3.26 (m, 2H, CH$_2$), 2.50 (m, 6H, 3×CH$_2$), 1.70 (s, 3H, CH$_3$), 0.95 (t, 6H, 2×CH$_3$). MS m/z 521 [M$^+$+1].

Example 75

5-[4-(3-Bromo-phenyl)-2-oxo-1,2-dihydro-indol-3-ylidenemethyl]-4-methyl-1H-pyrrole-2-carboxylic Acid (2-Diethylamino-ethyl)-amide

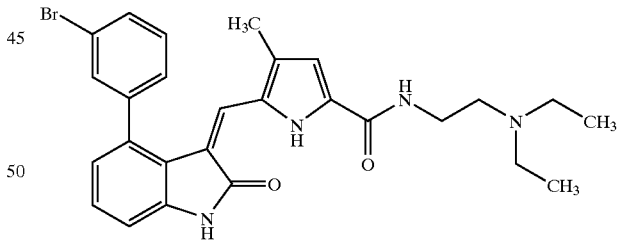

To a solution of 4-(3-bromo-phenyl)-1,3-dihydro-indol-2-one (72 mg, 0.25 mmol) and 5-formyl-4-methyl-1H-pyrrole-2-carboxylic acid (2-diethylamino-ethyl)-amide (65.3 mg, 0.26 mmol) in ethanol (2 mL) was added piperidine (3 drops). The reaction mixture was stirred at room temperature for three days. The reaction solution was evaporated, and purified on a silica gel column eluting with MeOH—CH$_2$Cl$_2$ 5:95 to provide pure product 5-[4-(3-bromo-phenyl)-2-oxo-1,2-dihydro-indol-3-ylidenemethyl]-4-methyl-1H-pyrrole-2-carboxylic acid (2-diethylamino-ethyl)-amide as a yellow solid (45 mg, 35%).

$^1$H-NMR (400 MHz, DMSO-d$_6$) δ 13.52 (br s, 1H, pyrrole NH), 11.12 (br s, 1H, CONH), 8.27 (t, 1H, CONH), 7.72 (d, 1H, aromatic), 7.68 (s, 1H, aromatic), 7.53 (t, 1H, aromatic), 7.46 (d, 1H, aromatic), 7.25 (t, 1H, aromatic), 6.95 (d, 1H, aromatic), 6.82 (d, 1H, aromatic), 6.79 (s, 1H, aromatic), 6.69 (s, 1H, aromatic), 3.29 (m, 2H, CH$_2$), 2.50 (m, 6H, 3×CH$_2$), 1.71 (s, 3H, CH$_3$), 0.96 (t, 6H, 2CH$_3$). MS m/z 519 [M$^-$−1].

Example 76

5-[4-(4-Methoxy-phenyl)-2-oxo-1,2-dihydro-indol-3-ylidenemethyl]-4-methyl-1H-pyrrole-2-carboxylic Acid (2-Diethylamino-ethyl)-amide

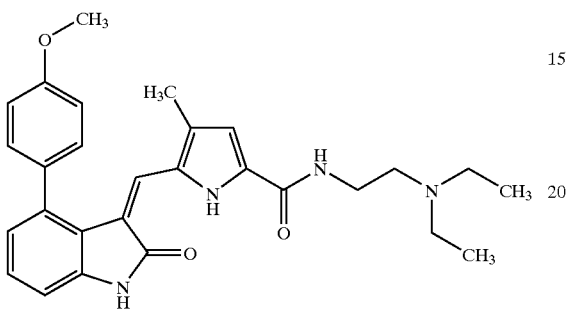

To a solution of 4-(4-methoxy-phenyl)-1,3-dihydro-indol-2-one (59.8 mg, 0.25 mmol) and 5-formyl-4-methyl-1H-pyrrole-2-carboxylic acid (2-diethylamino-ethyl)-amide (65.3 mg, 0.26 mmol) in ethanol (2 mL) was added piperidine (3 drops). The reaction mixture was stirred at room temperature for three days. A yellow solid product was precipitated out, filtered, washed by ethanol for three times, and dried under high vacuum to provide pure product 5-[4-(4-methoxy-phenyl)-2-oxo-1,2-dihydro-indol-3-ylidenemethyl]-4-methyl-1H-pyrrole-2-carboxylic acid (2-diethylamino-ethyl)-amide as a yellow solid (65 mg, 55%).

$^1$H-NMR (400 MHz, DMSO-d$_6$) δ 13.85 (br s, 1H, pyrrole NH), 8.18 (m, 1H, CONH), 7.33 (d, 2H, aromatic), 7.16 (t, 1H, aromatic), 7.10 (d, 2H, aromatic), 6.86 (d, 1H, aromatic), 6.76 (s, 1H, aromatic), 6.73 (d, 1H, aromatic), 6.65 (s, 1H, aromatic), 3.82 (s, 3H, OCH$_3$), 3.25 (m, 2H, CH$_2$), 2.47 (m, 6H, 3×CH$_2$), 1.67 (s, 3H, CH$_3$), 0.95 (t, 6H, 2×CH$_3$). MS m/z 473 [M$^+$+1].

Example 77

5-[4-(3-Methoxy-phenyl)-2-oxo-1,2-dihydro-indol-3-ylidenemethyl]-4-methyl-1H-pyrrole-2-carboxylic Acid (2-Diethylamino-ethyl)-amide

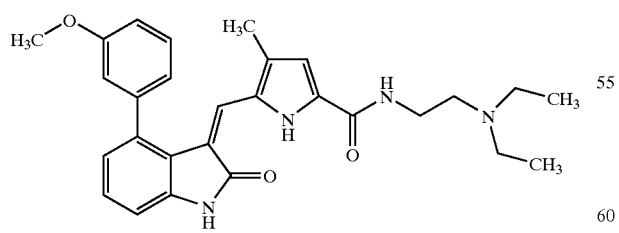

To a solution of 4-(3-methoxy-phenyl)-1,3-dihydro-indol-2-one (72 mg, 0.25 mmol) and 5-formyl-4-methyl-1H-pyrrole-2-carboxylic acid (2-diethylamino-ethyl)-amide (65.3 mg, 0.26 mmol) in ethanol (2 mL) was added piperidine (3 drops). The reaction mixture was stirred at room temperature for three days. The reaction solution was evaporated, and purified on a silica gel column eluting with MeOH—CH$_2$Cl$_2$ 5:95 to provide pure product 5-[4-(3-methoxy-phenyl)-2-oxo-1,2-dihydro-indol-3-ylidenemethyl]-4-methyl-1H-pyrrole-2-carboxylic acid (2-diethylamino-ethyl)-amide as a yellow solid (40 mg, 34%).

$^1$H-NMR (400 MHz, DMSO-d$_6$) δ 13.52 (br s, 1H, pyrrole NH), 11.07 (br s, 1H, CONH), 8.26 (m, 1H, CONH), 7.48 (t, 1H, aromatic), 7.22 (t, 1H, aromatic), 7.06 (dd, 1H, aromatic), 7.00 (m, 2H, aromatic), 6.92 (d, 1H, aromatic), 6.89 (s, 1H, aromatic), 6.82 (d, 1H, aromatic), 6.67 (m, 1H, aromatic), 3.78 (s, 3H, CH$_3$), 3.29 (m, 2H, CH$_2$), 2.55 (m, 6H, 3×CH$_2$), 1.67 (s, 3H, CH$_3$), 0.97 (t, 6H, 2×CH$_3$). MS m/z 471 [M$^-$−1].

Example 78

3-(3,5-Dimethyl-1H-pyrrol-2-ylmethylene)-4-(4-fluoro-phenyl)-1,3-dihydro-indol-2-one

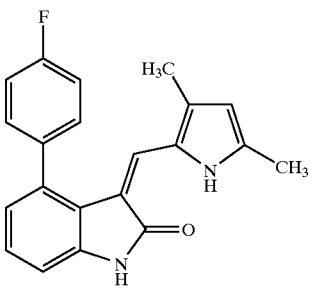

To a solution of 4-(4-fluoro-phenyl)-1,3-dihydro-indol-2-one (56.8 mg, 0.25 mmol) and 3,5-dimethyl-1H-pyrrole-2-carbaldehyde (32 mg, 0.26 mmol) in ethanol (2 mL) was added piperidine (3 drops). The reaction mixture was stirred at room temperature for three days. A yellow solid product was precipitated out, filtered, washed by ethanol for three times, and dried under high vacuum to provide pure product 3-(3,5-Dimethyl-1H-pyrrol-2-ylmethylene)-4-(4-fluoro-phenyl)-1,3-dihydro-indol-2-one as a yellow solid (35 mg, 45%).

$^1$H-NMR (400 MHz, DMSO-d$_6$) δ 13.23 (br s, 1H, pyrrole NH), 10.93 (br s, 1H, CONH), 7.47 (dd, 2H, aromatic), 7.37 (t, 2H, aromatic), 7.14 (t, 1H, aromatic), 6.91 (d, 1H, aromatic), 6.76 (d, 1H, aromatic), 6.68 (s, 1H, aromatic), 5.91 (d, 1H, aromatic), 2.27 (s, 3H, CH$_3$), 1.67 (s, 3H, CH$_3$). MS m/z 333 [M$^+$+1].

Example 79

3-(3,5-Dimethyl-1H-pyrrol-2-ylmethylene)-4-(3-fluoro-phenyl)-1,3-dihydro-indol-2-one

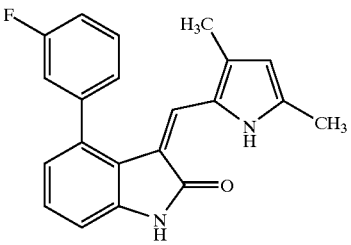

To a solution of 4-(3-fluoro-phenyl)-1,3-dihydro-indol-2-one (56.8 mg, 0.25 mmol) and 3,5-dimethyl-1H-pyrrole-2- carbaldehyde (32 mg, 0.26 mmol) in ethanol (2 mL) was added piperidine (3 drops). The reaction mixture was stirred at room temperature for three days. A yellow solid product was precipitated out, filtered, washed by ethanol for three times, and dried under high vacuum to provide pure product 3-(3,5-Dimethyl-1H-pyrrol-2-ylmethylene)-4-(3-fluoro-phenyl)-1,3-dihydro-indol-2-one as a yellow solid (37 mg, 46%).

$^{1}$H-NMR (400 MHz, DMSO-$d_6$) δ 13.24 (br s, 1H, pyrrole NH), 10.95 (br s, 1H, CONH), 7.59 (dd, 1H, aromatic), 7.31 (m, 3H, aromatic), 7.16 (t, 1H, aromatic), 6.93 (d, 1H, aromatic), 6.78 (d, 1H, aromatic), 6.76 (s, 1H, aromatic), 5.91 (d, 1H, aromatic), 2.27 (s, 3H, CH$_3$), 1.65 (s, 3H, CH$_3$). MS m/z 333 [M$^+$+1].

Example 80

3-(3,5-Dimethyl-1H-pyrrol-2-ylmethylene)-4-(4-chloro-phenyl)-1,3-dihydro-indol-2-one

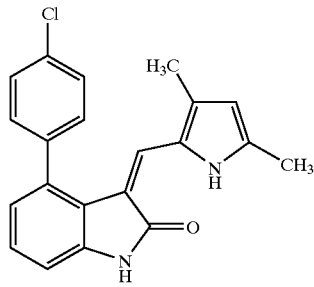

To a solution of 4-(4-chloro-phenyl)-1,3-dihydro-indol-2-one (60.9 mg, 0.25 mmol) and 3,5-dimethyl-1H-pyrrole-2-carbaldehyde (32 mg, 0.26 mmol) in ethanol (2 mL) was added piperidine (3 drops). The reaction mixture was stirred at room temperature for three days. A yellow solid product was precipitated out, filtered, washed by ethanol for three times, and dried under high vacuum to provide pure product 3-(3,5-Dimethyl-1H-pyrrol-2-ylmethylene)-4-(4-chloro-phenyl)-1,3-dihydro-indol-2-one as a yellow solid (36 mg, 41%).

$^{1}$H-NMR (400 MHz, DMSO-$d_6$) δ 13.21 (br s, 1H, pyrrole NH), 10.94 (br s, 1H, CONH), 7.60 (d, 2H, aromatic), 7.44 (d, 2H, aromatic), 7.15 (t, 1H, aromatic), 6.92 (d, 1H, aromatic), 6.77 (d, 1H, aromatic), 6.65 (s, 1H, aromatic), 5.91 (d, 1H, aromatic), 2.27 (s, 3H, CH$_3$), 1.66 (s, 3H, CH$_3$). MS m/z 349 [M$^+$+1].

Example 81

3-(3,5-Dimethyl-1H-pyrrol-2-ylmethylene)-4-(3-chloro-phenyl)-1,3-dihydro-indol-2-one

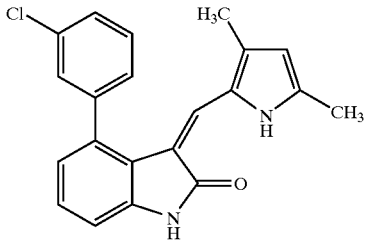

To a solution of 4-(3-chloro-phenyl)-1,3-dihydro-indol-2-one (60.9 mg, 0.25 mmol) and 3,5-dimethyl-1H-pyrrole-2- carbaldehyde (32 mg, 0.26 mmol) in ethanol (2 mL) was added piperidine (3 drops). The reaction mixture was stirred at room temperature for three days. A yellow solid product was precipitated out, filtered, washed by ethanol for three times, and dried under high vacuum to provide pure product 3-(3,5-Dimethyl-1H-pyrrol-2-ylmethylene)-4-(3-chloro-phenyl)-1,3-dihydro-indol-2-one as a yellow solid (60 mg, 68%).

$^{1}$H-NMR (400 MHz, DMSO-$d_6$) δ 13.24 (br s, 1H, pyrrole NH), 10.96 (br s, 1H, CONH), 7.56 (m, 2H, aromatic), 7.50 (s, 1H, aromatic), 7.39 (m, 1H, aromatic), 7.16 (t, 1H, aromatic), 6.93 (d, 1H, aromatic), 6.78 (d, 1H, aromatic), 6.75 (s, 1H, aromatic), 5.92 (d, 1H, aromatic), 2.28 (s, 3H, CH$_3$), 1.66 (s, 3H, CH$_3$). MS m/z 349 [M$^+$+1].

Example 82

3-(3,5-Dimethyl-1H-pyrrol-2-ylmethylene)-4-(4-bromo-phenyl)-1,3-dihydro-indol-2-one

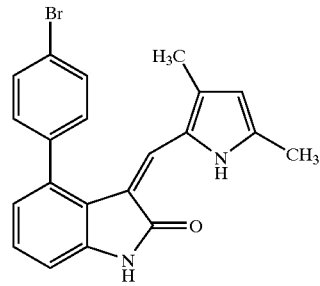

To a solution of 4-(4-bromo-phenyl)-1,3-dihydro-indol-2-one (72 mg, 0.25 mmol) and 3,5-dimethyl-1H-pyrrole-2-carbaldehyde (32 mg, 0.26 mmol) in ethanol (2 mL) was added piperidine (3 drops). The reaction mixture was stirred at room temperature for three days. A yellow solid product was precipitated out, filtered, washed by ethanol for three times, and dried under high vacuum to provide pure product 3-(3,5-Dimethyl-1H-pyrrol-2-ylmethylene)-4-(4-bromo-phenyl)-1,3-dihydro-indol-2-one as a yellow solid (50 mg, 51%).

$^{1}$H-NMR (400 MHz, DMSO-$d_6$) δ 13.21 (br s, 1H, pyrrole NH), 10.94 (br s, 1H, CONH), 7.73 (d, 2H, aromatic), 7.38 (d, 2H, aromatic), 7.15 (t, 1H, aromatic), 6.92 (d, 1H, aromatic), 6.77 (d, 1H, aromatic), 6.63 (s, 1H, aromatic), 5.91 (d, 1H, aromatic), 2.27 (s, 3H, CH$_3$), 1.66 (s, 3H, CH$_3$). MS m/z 393 [M$^+$+1].

Example 83

3-(3,5-Dimethyl-1H-pyrrol-2-ylmethylene)-4-(3-bromo-phenyl)-1,3-dihydro-indol-2-one

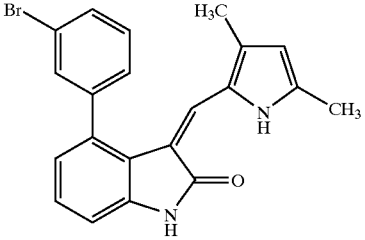

To a solution of 4-(3-bromo-phenyl)-1,3-dihydro-indol-2-one (72 mg, 0.25 mmol) and 3,5-dimethyl-1H-pyrrole-2- carbaldehyde (32 mg, 0.26 mmol) in ethanol (2 mL) was added piperidine (3 drops). The reaction mixture was stirred at room temperature for three days. A yellow solid product was precipitated out, filtered, washed by ethanol for three times, and dried under high vacuum to provide pure product 3-(3,5-Dimethyl-1H-pyrrol-2-ylmethylene)-4-(3-bromo-phenyl)-1,3-dihydro-indol-2-one as a yellow solid (71 mg, 71%).

$^1$H-NMR (400 MHz, DMSO-d$_6$) δ 13.24 (br s, 1H, pyrrole NH), 10.95 (br s, 1H, CONH), 7.70 (m, 1H, aromatic), 7.64 (s, 1H, aromatic), 7.51 (t, 1H, aromatic), 7.44 (d, 1H, aromatic), 7.16 (t, 1H, aromatic), 6.93 (d, 1H, aromatic), 6.78 (d, 1H, aromatic), 6.74 (s, 1H, aromatic), 5.92 (d, 1H, aromatic), 2.28 (s, 3H, CH$_3$), 1.67 (s, 3H, CH$_3$). MS m/z 393 [M$^+$+1].

Example 84

3-(3,5-Dimethyl-1H-pyrrol-2-ylmethylene)-4-(4-methoxy-phenyl)-1,3-dihydro-indol-2-one

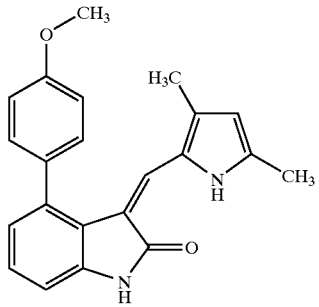

To a solution of 4-(4-methoxy-phenyl)-1,3-dihydro-indol-2-one (59.8 mg, 0.25 mmol) and 3,5-dimethyl-1H-pyrrole-2-carbaldehyde (32 mg, 0.26 mmol) in ethanol (2 mL) was added piperidine (3 drops). The reaction mixture was stirred at room temperature for three days. A yellow solid product was precipitated out, filtered, washed by ethanol for three times, and dried under high vacuum to provide pure product 3-(3,5-Dimethyl-1H-pyrrol-2-ylmethylene)-4-(4-methoxy-phenyl)-1,3-dihydro-indol-2-one as a yellow solid (57 mg, 66%).

$^1$H-NMR (400 MHz, DMSO-d$_6$) δ 13.22 (br s, 1H, pyrrole NH), 10.89 (br s, 1H, CONH), 7.32 (d, 2H, aromatic), 7.11 (m, 3H, aromatic), 6.87 (d, 1H, aromatic), 6.75 (m, 2H, aromatic), 5.89 (d, 1H, aromatic), 3.82 (s, 3H, CH$_3$), 2.27 (s, 3H, CH$_3$), 1.64 (s, 3H, CH$_3$). MS m/z 345 [M$^+$+1].

Example 85

3-(3,5-Dimethyl-1H-pyrrol-2-ylmethylene)-4-(3-methoxy-phenyl)-1,3-dihydro-indol-2-one

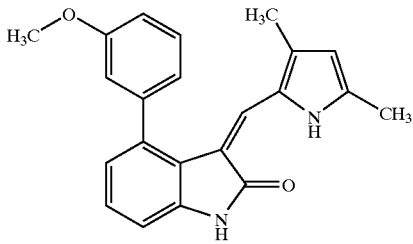

To a solution of 4-(3-methoxy-phenyl)-1,3-dihydro-indol-2-one (59.8 mg, 0.25 mmol) and 3,5-dimethyl-1H-pyrrole-2-carbaldehyde (32 mg, 0.26 mmol) in ethanol (2 mL) was added piperidine (3 drops). The reaction mixture was stirred at room temperature for three days. A yellow solid product was precipitated out, filtered, washed by ethanol for three times, and dried under high vacuum to provide pure product 3-(3,5-Dimethyl-1H-pyrrol-2-ylmethylene)-4-(3-methoxy-phenyl)-1,3-dihydro-indol-2-one as a yellow solid (60 mg, 69%).

$^1$H-NMR (400 MHz, DMSO-d$_6$) δ 13.23 (br s, 1H, pyrrole NH), 10.91 (br s, 1H, CONH), 7.45 (t, 1H, aromatic), 7.14 (t, 1H, aromatic), 7.04 (m, 1H, aromatic), 6.97 (m, 2H, aromatic), 6.90 (d, 1H, aromatic), 6.85 (s, 1H, aromatic), 6.78 (d, 1H, aromatic), 5.90 (d, 1H, aromatic), 3.77 (s, 3H, OCH$_3$), 2.27 (s, 3H, CH$_3$), 1.64 (s, 3H, CH$_3$). MS m/z 345 [M$^+$+1].

Example 86

5-[4-(4-Fluoro-phenyl)-2-oxo-1,2-dihydro-indol-3-ylidenemethyl]-4-methyl-1H-pyrrole-3-carboxylic Acid (2-Diethylamino-ethyl)-amide

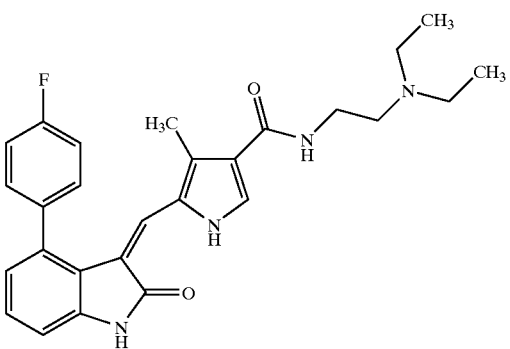

To a solution of 4-(4-fluoro-phenyl)-1,3-dihydro-indol-2-one (56.8 mg, 0.25 mmol) and 5-formyl-4-methyl-1H-pyrrole-3-carboxylic acid (2-diethylamino-ethyl)-amide (65.3 mg, 0.26 mmol) in ethanol (2 mL) was added piperidine (3 drops). The reaction mixture was stirred at room temperature for three days. A yellow solid product was precipitated out, filtered, washed by ethanol for three times, and dried under high vacuum to provide pure product 5-[4-(4-fluoro-phenyl)-2-oxo-1,2-dihydro-indol-3-ylidenemethyl]-4-methyl-1H-pyrrole-3-carboxylic acid (2-diethylamino-ethyl)-amide (98.6 mg, 86%).

$^1$H-NMR (400 MHz, DMSO-d$_6$) δ 13.45 (br s, 1H, pyrrole NH), 11.11 (br s, 1H, CONH), 7.68 (m, 2H, CONH and aromatic), 7.42 (m, 4H, aromatic), 7.21 (t, 1H, aromatic), 6.93 (d, 1H, aromatic), 6.79 (m, 3H, aromatic), 3.21 (m, 2H, $CH_2$), 2.49 (m, 6H, 3×$CH_2$), 1.84 (s, 3H, $CH_3$), 0.95 (t, 6H, 2×$CH_3$). MS m/z 461 [$M^+$+1].

Example 87

5-[4-(3-Fluoro-phenyl)-2-oxo-1,2-dihydro-indol-3-ylidenemethyl]-4-methyl-1H-pyrrole-3-carboxylic Acid (2-Diethylamino-ethyl)-amide

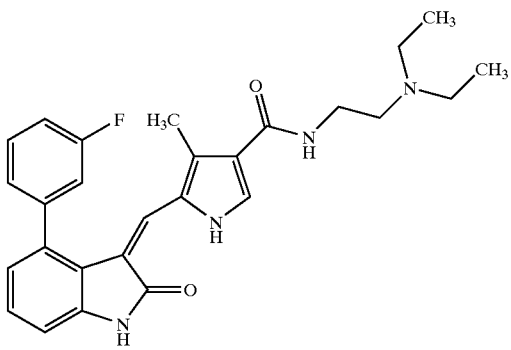

To a solution of 4-(3-fluoro-phenyl)-1,3-dihydro-indol-2-one (56.8 mg, 0.25 mmol) and 5-formyl-4-methyl-1H-pyrrole-3-carboxylic acid (2-diethylamino-ethyl)-amide (65.3 mg, 0.26 mmol) in ethanol (2 mL) was added piperidine (3 drops). The reaction mixture was stirred at room temperature for three days. A yellow solid product was precipitated out, filtered, washed by ethanol for three times, and dried under high vacuum to provide pure product 5-[4-(3-fluoro-phenyl)-2-oxo-1,2-dihydro-indol-3-ylidenemethyl]-4-methyl-1H-pyrrole-3-carboxylic acid (2-diethylamino-ethyl)-amide (71.0 mg, 62%).

$^1$H-NMR (400 MHz, DMSO-$d_6$) δ 13.48 (br s, 1H, pyrrole NH), 11.12 (br s, 1H, CONH), 7.72 (t, 1H, CONH), 7.67 (d, 1H, aromatic), 7.60 (dd, 1H, aromatic), 7.33 (m, 3H, aromatic), 7.22 (t, 1H, aromatic), 6.94 (d, 1H, aromatic), 6.87 (s, 1H, aromatic), 6.82 (d, 2H, aromatic), 3.20 (m, 2H, $CH_2$), 2.46 (m, 6H, 3×$CH_2$), 1.84 (s, 3H, $CH_3$), 0.95 (t, 6H, 2×$CH_3$). MS m/z 461 [$M^+$+1].

Example 88

5-[4-(4-Chloro-phenyl)-2-oxo-1,2-dihydro-indol-3-ylidenemethyl]-4-methyl-1H-pyrrole-3-carboxylic Acid (2-Diethylamino-ethyl)-amide

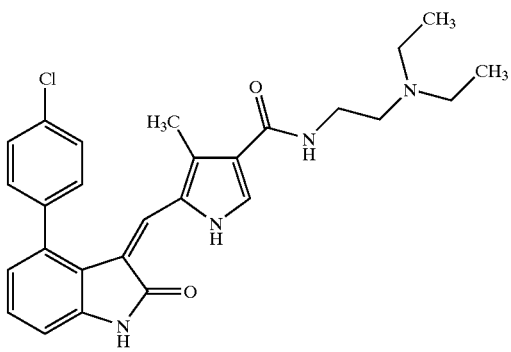

To a solution of 4-(4-chloro-phenyl)-1,3-dihydro-indol-2-one (60.9 mg, 0.25 mmol) and 5-formyl-4-methyl-1H-pyrrole-3-carboxylic acid (2-diethylamino-ethyl)-amide (65.3 mg, 0.26 mmol) in ethanol (2 mL) was added piperidine (3 drops). The reaction mixture was stirred at room temperature for three days. A yellow solid product was precipitated out, filtered, washed by ethanol for three times, and dried under high vacuum to provide pure product 5-[4-(4-chloro-phenyl)-2-oxo-1,2-dihydro-indol-3-ylidenemethyl]-4-methyl-1H-pyrrole-3-carboxylic acid (2-diethylamino-ethyl)-amide (76.6 mg, 64%).

$^1$H-NMR (400 MHz, DMSO-$d_6$) δ 13.45 (br s, 1H, pyrrole NH), 11.11 (br s, 1H, CONH), 7.70 (t, 1H, CONH), 7.67 (d, 1H, aromatic), 7.62 (d, 2H, aromatic), 7.46 (d, 2H, aromatic), 7.22 (t, 1H, aromatic), 6.93 (d, 1H, aromatic), 6.81 (d, 1H, aromatic), 6.74 (s, 1H, aromatic), 3.20 (m, 2H, $CH_2$), 2.49 (m, 6H, 3×$CH_2$), 1.84 (s, 3H, $CH_3$), 0.95 (t, 6H, 2×$CH_3$). MS m/z 477 [$M^+$+1].

Example 89

5-[4-(3-Chloro-phenyl)-2-oxo-1,2-dihydro-indol-3-ylidenemethyl]-4-methyl-1H-pyrrole-3-carboxylic Acid (2-Diethylamino-ethyl)-amide

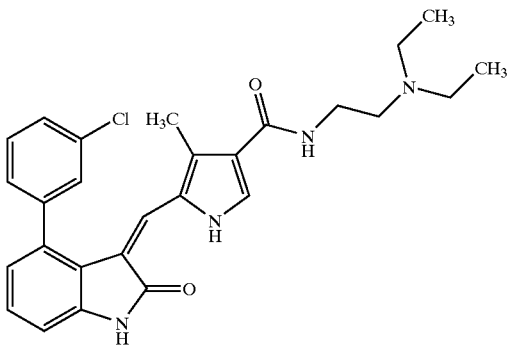

To a solution of 4-(3-chloro-phenyl)-1,3-dihydro-indol-2-one (60.9 mg, 0.25 mmol) and 5-formyl-4-methyl-1H-pyrrole-3-carboxylic acid (2-diethylamino-ethyl)-amide (65.3 mg, 0.26 mmol) in ethanol (2 mL) was added piperidine (3 drops). The reaction mixture was stirred at room temperature for three days. A yellow solid product was precipitated out, filtered, washed by ethanol for three times, and dried under high vacuum to provide pure product 5-[4-(3-chloro-phenyl)-2-oxo-1,2-dihydro-indol-3-ylidenemethyl]-4-methyl-1H-pyrrole-3-carboxylic acid (2-diethylamino-ethyl)-amide (86.2 mg, 72%).

$^1$H-NMR (400 MHz, DMSO-$d_6$) δ 13.47 (br s, 1H, pyrrole NH), 11.13 (br s, 1H, CONH), 7.73 (t, 1H, CONH), 7.68 (d, 1H, aromatic), 7.58 (m, 2H, aromatic), 7.53 (s, 1H, aromatic), 7.41 (m, 1H, aromatic), 7.22 (t, 1H, aromatic), 6.94 (d, 1H, aromatic), 6.87 (s, 1H, aromatic), 6.82 (d, 1H, aromatic), 3.20 (m, 2H, $CH_2$), 2.47 (m, 6H, 3×$CH_2$), 1.85 (s, 3H, $CH_3$), 0.95 (t, 6H, 2×$CH_3$). MS m/z 477 [$M^+$+1].

Example 90

5-[4-(3-Bromo-phenyl)-2-oxo-1,2-dihydro-indol-3-ylidenemethyl]-4-methyl-1H-pyrrole-3-carboxylic Acid (2-Diethylamino-ethyl)-amide

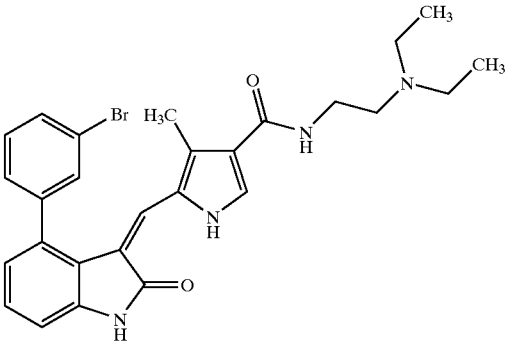

To a solution of 4-(3-bromo-phenyl)-1,3-dihydro-indol-2-one (72.0 mg, 0.25 mmol) and 5-formyl-4-methyl-1H-pyrrole-3-carboxylic acid (2-diethylamino-ethyl)-amide (65.3 mg, 0.26 mmol) in ethanol (2 mL) was added piperidine (3 drops). The reaction mixture was stirred at room temperature for three days. A yellow solid product was precipitated out, filtered, washed by ethanol for three times, and dried under high vacuum to provide pure product 5-[4-(3-bromo-phenyl)-2-oxo-1,2-dihydro-indol-3-ylidenemethyl]-4-methyl-1H-pyrrole-3-carboxylic acid (2-diethylamino-ethyl)-amide (93.5 mg, 72%).

$^1$H-NMR (400 MHz, DMSO-$d_6$) δ 13.47 (br s, 1H, pyrrole NH), 11.13 (br s, 1H, CONH), 7.72 (m, 2H, CONH and aromatic), 7.67 (m, 2H, aromatic), 7.53 (t, 1H, aromatic), 7.45 (d, 1H, aromatic), 7.22 (t, 1H, aromatic), 6.94 (d, 1H, aromatic), 6.86 (s, 1H, aromatic), 6.82 (d, 1H, aromatic), 3.20 (m, 2H, CH$_2$), 2.47 (m, 6H, 3×CH$_2$), 1.86 (s, 3H, CH$_3$), 0.95 (t, 6H, 2×CH$_3$). MS m/z 521 [M$^+$+1].

Example 91

5-[4-(4-Methoxy-phenyl)-2-oxo-1,2-dihydro-indol-3-ylidenemethyl]-4-methyl-1H-pyrrole-3-carboxylic Acid (2-Diethylamino-ethyl)-amide

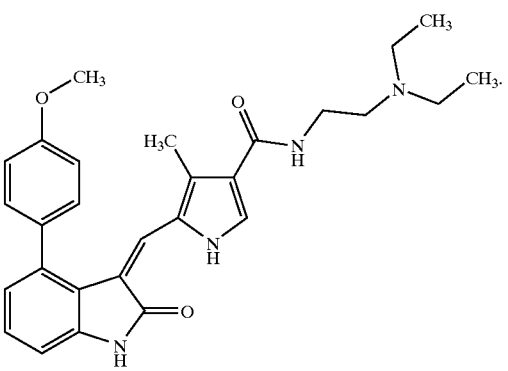

To a solution of 4-(4-methoxy-phenyl)-1,3-dihydro-indol-2-one (59.8 mg, 0.25 mmol) and 5-formyl-4-methyl-1H-pyrrole-3-carboxylic acid (2-diethylamino-ethyl)-amide (65.3 mg, 0.26 mmol) in ethanol (2 mL) was added piperidine (3 drops). The reaction mixture was stirred at room temperature for three days. A yellow solid product was precipitated out, filtered, washed by ethanol for three times, and dried under high vacuum to provide pure product 5-[4-(4-methoxy-phenyl)-2-oxo-1,2-dihydro-indol-3-ylidenemethyl]-4-methyl-1H-pyrrole-3-carboxylic acid (2-diethylamino-ethyl)-amide (90.4 mg, 76.5%).

$^1$H-NMR (400 MHz, DMSO-$d_6$) δ 13.46 (br s, 1H, pyrrole NH), 11.06 (br s, 1H, CONH), 7.69 (t, 1H, CONH), 7.65 (d, 1H, aromatic), 7.33 (d, 2H, aromatic), 7.19 (t, 1H, aromatic), 7.11 (d, 2H, aromatic), 6.89 (d, 1H, aromatic), 6.86 (s, 1H, aromatic), 6.79 (d, 1H, aromatic), 3.83 (S, 3H, OCH$_3$), 3.20 (m, 2H, CH$_2$), 2.47 (m, 6H, 3×CH$_2$), 1.83 (s, 3H, CH$_3$), 0.95 (t, 6H, 2×CH$_3$). MS m/z 473 [M$^+$+1].

Example 92

5-[4-(3-Methoxy-phenyl)-2-oxo-1,2-dihydro-indol-3-ylidenemethyl]-4-methyl-1H-pyrrole-3-carboxylic Acid (2-Diethylamino-ethyl)-amide

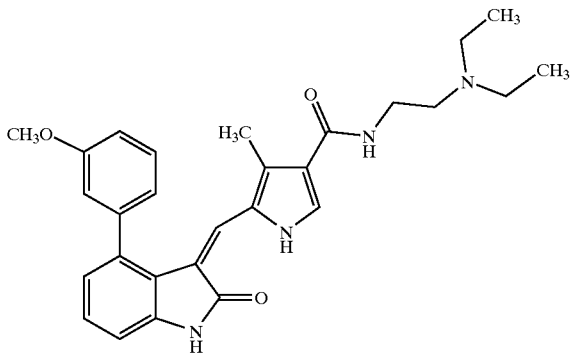

To a solution of 4-(3-methoxy-phenyl)-1,3-dihydro-indol-2-one (59.8 mg, 0.25 mmol) and 5-formyl-4-methyl-1H-pyrrole-3-carboxylic acid (2-diethylamino-ethyl)-amide (65.3 mg, 0.26 mmol) in ethanol (2 mL) was added piperidine (3 drops). The reaction mixture was stirred at room temperature for three days. The solvent was evaporated and the solid was washed by ether for three times to provide pure product 5-[4-(3-methoxy-phenyl)-2-oxo-1,2-dihydro-indol-3-ylidenemethyl]-4-methyl-1H-pyrrole-3-carboxylic acid (2-diethylamino-ethyl)-amide (67.5 mg, 57%).

$^1$H-NMR (400 MHz, DMSO-$d_6$) δ 13.48 (br s, 1H, pyrrole NH), 11.06 (br s, 1H, CONH), 7.70 (t, 1H, CONH), 7.66 (d, 1H, aromatic), 7.47 (t, 1H, aromatic), 7.20 (t, 1H, aromatic), 7.07 (dd, 1H, aromatic), 6.98 (m, 2H, aromatic), 6.86 (s, 1H, aromatic), 6.91 (d, 1H, aromatic), 6.81 (d, 1H, aromatic), 3.78 (s, 3H, OCH$_3$), 3.20 (m, 2H, CH$_2$), 2.48 (m, 6H, 3×CH$_2$), 1.82 (s, 3H, CH$_3$), 0.95 (t, 6H, 2CH$_3$). MS m/z 473 [M$^+$+1].

Example 93

3-[3,5-Dimethyl-4-(4-methyl-piperazine-1-carbonyl)-1H-pyrrol-2-ylmethylene]-4-(2-fluoro-phenyl)-1,3-dihydro-indol-2-one

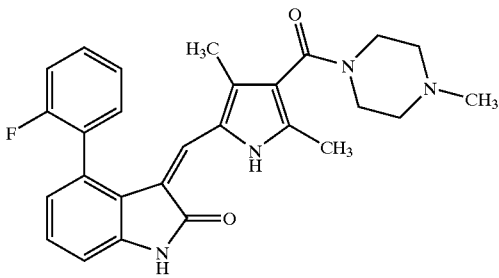

To a solution of 4-(2-fluoro-phenyl)-1,3-dihydro-indol-2-one (56.8 mg, 0.25 mmol) and 3,5-dimethyl-4-(4-methyl-piperazine-1-carbonyl)-1H-pyrrole-2-carbaldehyde (64.8 mg, 0.26 mmol) in ethanol (2 mL) was added piperidine (3 drops). The reaction mixture was stirred at room temperature for three days. The solvent was evaporated and the solid was washed by ether for three times to provide pure product 3-[3,5-dimethyl-4-(4-methyl-piperazine-1-carbonyl)-1H-pyrrol-2-ylmethylene]-4-(2-fluoro-phenyl)-1,3-dihydro-indol-2-one (59.5 mg, 52%)

$^1$H-NMR (400 MHz, DMSO-$d_6$) δ 13.47 (br s, 1H, pyrrole NH), 11.07 (br s, 1H, CONH), 7.56 (m, 1H, aromatic), 7.43 (m, 3H, aromatic), 7.21 (t, 1H, aromatic), 6.97 (d, 1H, aromatic), 6.83 (d, 1H, aromatic), 6.62 (s, 1H, aromatic), 3.37 (m, 4H, 2×CH$_2$), 2.24 (m, 7H, 2×CH$_2$+CH$_3$), 2.16 (s, 3H, CH$_3$), 1.55 (s, 3H, CH$_3$). MS m/z 457 [M$^-$−1].

Example 94

5-[4-(2-Fluoro-phenyl)-2-oxo-1,2-dihydro-indol-3-ylidenemethyl]-2,4-dimethyl-1H-pyrrole-3-carboxylic Acid (2-Diethylamino-ethyl)-amide

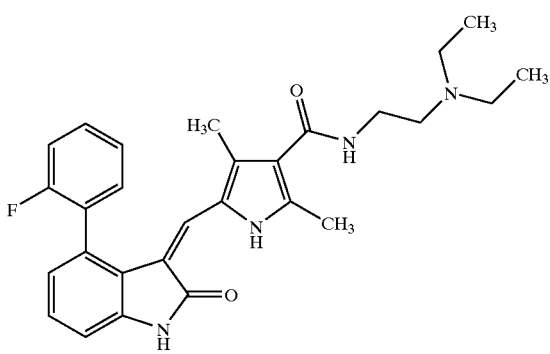

To a solution of 4-(2-fluoro-phenyl)-1,3-dihydro-indol-2-one (56.8 mg, 0.25 mmol) and 5-formyl-2,4-dimethyl-1H-pyrrole-3-carboxylic acid (2-diethylamino-ethyl)-amide (69.0 mg, 0.26 mmol) in ethanol (2 mL) was added piperidine (3 drops). The reaction mixture was stirred at room temperature for three days. A yellow solid product was precipitated out, filtered, washed by ethanol for three times, and dried under high vacuum to provide 5-[4-(2-Fluoro-phenyl)-2-oxo-1,2-dihydro-indol-3-ylidenemethyl]-2,4-dimethyl-1H-pyrrole-3-carboxylic acid (2-diethylamino-ethyl)-amide as a yellow solid (98 mg, 83%).

$^1$H-NMR (400 MHz, DMSO-$d_6$) δ 13.49 (br s, 1H, pyrrole NH), 11.08 (br s, 1H, CONH), 7.57 (m, 1H, aromatic), 7.42 (m, 4H, aromatic and CONH), 7.22 (t, 1H, aromatic), 6.97 (d, 1H, aromatic), 6.83 (d, 1H, aromatic), 6.65 (s, 1H, aromatic), 3.22 (dd, 2H, CH$_2$), 2.49 (m, 6H, 3×CH$_2$), 2.39 (s, 3H, CH$_3$), 1.69 (s, 3H, CH$_3$), 0.95 (6H, 6H, 2×CH$_3$). MS m/z 473 [M$^-$−1].

Example 95

5-[4-(2-Fluoro-phenyl)-2-oxo-1,2-dihydro-indol-3-ylidenemethyl]-2,4-dimethyl-1H-pyrrole-3-carboxylic Acid (2-Pyrrolidin-1-yl-ethyl)-amide

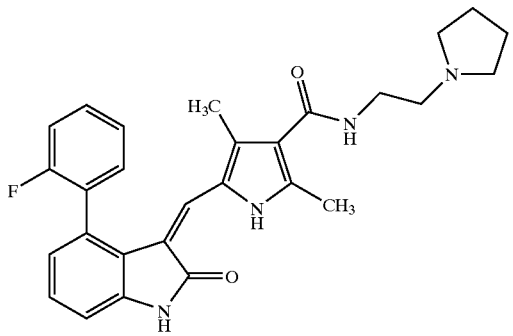

To a solution of 4-(2-fluoro-phenyl)-1,3-dihydro-indol-2-one (56.8 mg, 0.25 mmol) and 5-formyl-2,4-dimethyl-1H-pyrrole-3-carboxylic acid (2-pyrrolidin-1-yl-ethyl)-amide (68.5 mg, 0.26 mmol) in ethanol (2 mL) was added piperidine (3 drops). The reaction mixture was stirred at room temperature for three days. A yellow solid product was precipitated out, filtered, washed by ethanol for three times, and dried under high vacuum to provide pure product 5-[4-(2-fluoro-phenyl)-2-oxo-1,2-dihydro-indol-3-ylidenemethyl]-2,4-dimethyl-1H-pyrrole-3-carboxylic acid (2-pyrrolidin-1-yl-ethyl)-amide as a yellow solid (62.5 mg, 53%).

$^1$H-NMR (400 MHz, DMSO-$d_6$) δ 13.49 (br s, 1H, pyrrole NH), 11.08 (br s, 1H, CONH), 7.57 (m, 1H, aromatic), 7.45 (m, 4H, aromatic and CONH), 7.22 (t, 1H, aromatic), 6.97 (d, 1H, aromatic), 6.83 (d, 1H, aromatic), 6.65 (s, 1H, aromatic), 3.28 (dd, 2H, CH$_2$), 2.52 (m, 6H, 3×CH$_2$), 2.37 (s, 3H, CH$_3$), 1.68 (m, 7H, CH$_3$ and 2×CH$_2$). MS m/z 471 [M$^-$−1].

Example 96

5-[4-(2-Fluoro-phenyl)-2-oxo-1,2-dihydro-indol-3-ylidenemethyl]-2,4-dimethyl-1H-pyrrole-3-carboxylic Acid (2-[1,2,3]Triazol-1-yl-ethyl)-amide

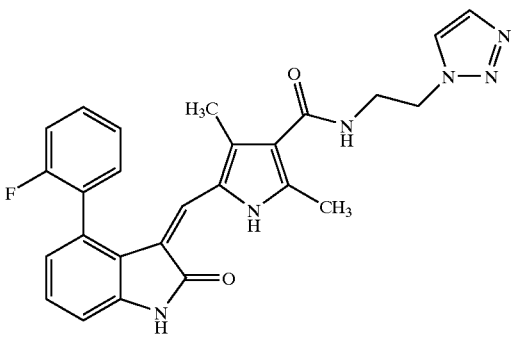

To a solution of 4-(2-fluoro-phenyl)-1,3-dihydro-indol-2-one (56.8 mg, 0.25 mmol) and 5-formyl-2,4-dimethyl-1H- pyrrole-3-carboxylic acid (2-[1,2,3]triazol-1-yl-ethyl)-amide (67.9 mg, 0.26 mmol) in ethanol (2 mL) was added piperidine (3 drops). The reaction mixture was stirred at room temperature for three days. A yellow solid product was precipitated out, filtered, washed by ethanol for three times, and dried under high vacuum to provide pure product 5-[4-(2-fluoro-phenyl)-2-oxo-1,2-dihydro-indol-3-ylidenemethyl]-2,4-dimethyl-1H-pyrrole-3-carboxylic acid (2-[1,2,3]triazol-1-yl-ethyl)-amide as a yellow solid (52.8 mg, 45%).

$^1$H-NMR (400 MHz, DMSO-$d_6$) δ 13.49 (br s, 1H, pyrrole NH), 11.07 (br s, 1H, CONH), 8.10 (s, 1H, aromatic), 7.71 (s, 1H, aromatic), 7.59 (m, 2H, aromatic) 7.44 (m, 3H, aromatic and CONH), 7.21 (t, 1H, CONH), 6.96 (d, 1H, aromatic), 6.83 (d, 1H, aromatic), 6.63 (d, 1H, aromatic), 4.53 (t, 2H, CH$_2$), 3.63 (q, 2H, CH$_2$), 2.29 (s, 3H, CH$_3$), 1.59 (s, 3H, CH$_3$). MS m/z 469 [M$^-$−1].

Example 97

2-[4-(2-Fluoro-phenyl)-2-oxo-1,2-dihydro-indol-3-ylidenemethyl]-5-methyl-1H-pyrrole-3-carboxylic Acid (2-Diethylamino-ethyl)-amide

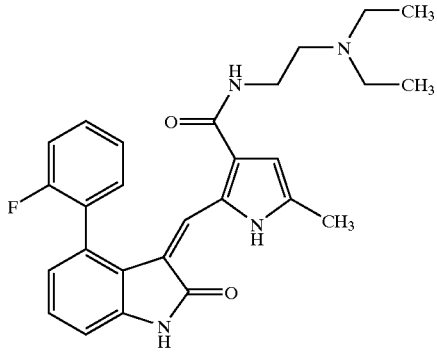

To a solution of 4-(2-fluoro-phenyl)-1,3-dihydro-indol-2-one (56.8 mg, 0.25 mmol) and 2-formyl-5-methyl-1H-pyrrole-3-carboxylic acid (2-diethylamino-ethyl)-amide (65.3 mg, 0.26 mmol) in ethanol (2 mL) was added piperidine (3 drops). The reaction mixture was stirred at room temperature for three days. A yellow solid product was precipitated out, filtered, washed by ethanol for three times, and dried under high vacuum to provide pure product 2-[4-(2-fluoro-phenyl)-2-oxo-1,2-dihydro-indol-3-ylidenemethyl]-5-methyl-1H-pyrrole-3-carboxylic acid (2-diethylamino-ethyl)-amide as a yellow solid (57.5 mg, 50%).

$^1$H-NMR (400 MHz, DMSO-$d_6$) δ 13.90 (br s, 1H, pyrrole NH), 11.16 (br s, 3 H, CONH), 7.90 (s, 1H, aromatic), 7.50 (t, 1H, CONH), 7.40 (m, 2H, aromatic), 7.29 (d, 1H, aromatic), 7.25 (m, 2H, aromatic), 6.96 (d, 1H, aromatic), 6.78 (d, 1H, aromatic), 6.38 (s, 1H, aromatic), 3.20 (dd, 2H, CH$_2$), 2.50 (m, 6H, 3×CH$_2$), 2.32 (s, 3H, CH$_3$), 1.24 (m, 6H, 2×CH$_3$). MS m/z 461 [M$^+$+1].

Example 98

2-[4-(2-Fluoro-phenyl)-2-oxo-1,2-dihydro-indol-3-ylidenemethyl]-5-methyl-1H-pyrrole-3-carboxylic Acid (2-Pyrrolidin-1-yl-ethyl)-amide

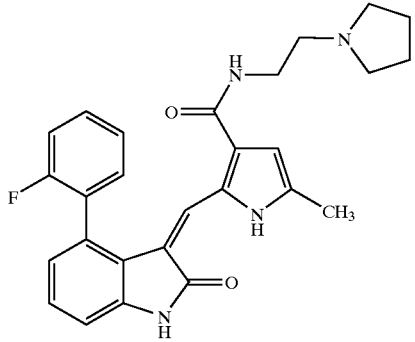

To a solution of 4-(2-fluoro-phenyl)-1,3-dihydro-indol-2-one (56.8 mg, 0.25 mmol) and 2-formyl-5-methyl-1H-pyrrole-3-carboxylic acid (2-pyrrolidin-1-yl-ethyl)-amide (64.8 mg, 0.26 mmol) in ethanol (2 mL) was added piperidine (3 drops). The reaction mixture was stirred at room temperature for three days. A yellow solid product was precipitated out, filtered, washed by ethanol for three times, and dried under high vacuum to provide pure product 2-[4-(2-fluoro-phenyl)-2-oxo-1,2-dihydro-indol-3-ylidenemethyl]-5-methyl-1H-pyrrole-3-carboxylic acid (2-pyrrolidin-1-yl-ethyl)-amide as a yellow solid (58.4 mg, 51%).

$^1$H-NMR (400 MHz, DMSO-$d_6$) δ 13.85 (br s, 1H, pyrrole NH), 11.36 (br s, 1H, CONH), 7.86 (d, 1H, aromatic), 7.75 (t, 1H, CONH), 7.42 (m, 2H, aromatic), 7.30 (m, 2H, aromatic), 7.23 (t, 1H, aromatic), 6.95 (d, 1H, aromatic), 6.78 (d, 1H, aromatic), 6.37 (d, 1H, aromatic), 3.14 (dd, 2H, CH$_2$), 2.48 (m, 6H, 3×CH$_2$), 2.31 (s, 3H, CH$_3$), 1.70 (m, 4H, 2×CH$_2$). MS m/z 457 [M$^-$−1].

Example 99

2-[4-(2-Fluoro-phenyl)-2-oxo-1,2-dihydro-indol-3-ylidenemethyl]-5-methyl-1H-pyrrole-3-carboxylic Acid (2-[1,2,3]Triazol-1-yl-ethyl)-amide

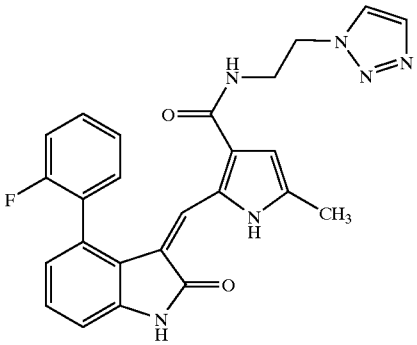

To a solution of 4-(2-fluoro-phenyl)-1,3-dihydro-indol-2-one (56.8 mg, 0.25 mmol) and 2-formyl-5-methyl-1H-pyrrole-3-carboxylic acid (2-[1,2,3]triazol-1-yl-ethyl)-amide (61.8 mg, 0.26 mmol) in ethanol (2 mL) was added piperidine (3 drops). The reaction mixture was stirred at room temperature for three days. A yellow solid product was precipitated out, filtered, washed by ethanol for three times, and dried under high vacuum to provide pure product 2-[4-(2-fluoro-phenyl)-2-oxo-1,2-dihydro-indol-3-ylidenemethyl]-5-methyl-1H-pyrrole-3-carboxylic acid (2-[1,2,3]triazol-1-yl-ethyl)-amide as a yellow solid (74.1 mg, 65%).

$^1$H-NMR (400 MHz, DMSO-d$_6$) δ 13.86 (br s, 1H, pyrrole NH), 11.15 (br s, 1H, CONH), 8.01 (t, 1H, CONH), 7.84 (d, 1H, aromatic), 7.74 (d, 1H, aromatic), 7.47 (m, 1H, aromatic), 7.40 (m, 1H, aromatic), 7.32 (t, 1H, aromatic), 7.35 (m, 2H, aromatic), 7.23 (t, 1H, aromatic), 6.97 (d, 1H, aromatic), 6.80 (d, 1H, aromatic), 6.32 (d, 1H, aromatic), 4.50 (t, 2H, CH$_2$), 3.50 (m, 2H, CH$_2$), 2.32 (s, 3H, CH$_3$). MS m/z 455 [M$^{31}$ −1].

Example 100

3-[3-((cis)-3,5-Dimethyl-piperazine-1-carbonyl]-5-methyl-1H-pyrrol-2-ylmethylene]-4-(2-fluoro-phenyl)-1,3-dihydro-indol-2-one

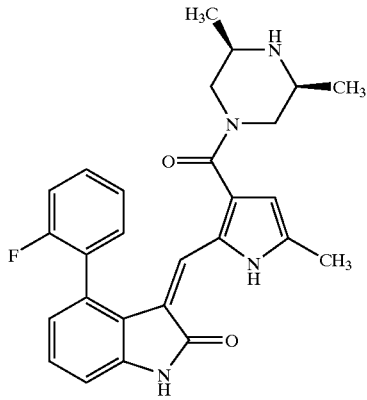

To a solution of 4-(2-fluoro-phenyl)-1,3-dihydro-indol-2-one (56.8 mg, 0.25 mmol) and 3-[(cis)-3,5-dimethyl-piperazine-1-carbonyl]-5-methyl-1H-pyrrole-2-carbaldehyde (62.3 mg, 0.26 mmol) in ethanol (2 mL) was added piperidine (3 drops). The reaction mixture was stirred at room temperature for three days. A yellow solid product was precipitated out, filtered, washed by ethanol for three times, and dried under high vacuum to provide pure product 3-{3-((cis)-3,5-dimethyl-piperazine-1-carbonyl]-5-methyl-1H-pyrrol-2-ylmethylene}-4-(2-fluoro-phenyl)-1,3-dihydro-indol-2-one as a yellow solid (103.5 mg, 90%).

$^1$H-NMR (400 MHz, DMSO-d$_6$) δ 13.66 (br s, 1H, pyrrole NH), 11.13 (br s, 1H, CONH), 7.46 (m, 1H, aromatic), 7.24 (m, 4H, aromatic), 6.96 (d, 1H, aromatic), 6.82 (s, 1H, aromatic), 6.78 (d, 2H, aromatic), 6.04 (s, 1H, aromatic), 4.12 (m, 1H, CH), 3.41 (m, 1H, CH), 2.44 (m, 6H, CH+CH$_2$+CH$_3$), 2.05 (m, 1H, CH), 1.04 (m, 3H, CH$_3$), 0.81 (m, 3H, CH$_3$). MS m/z 457 [M$^-$−1].

Example 101

5-[4-(4-Fluoro-phenyl)-2-oxo-1,2-dihydro-indol-3-ylidenemethyl]-2,4-dimethyl-1H-pyrrole-3-carboxylic Acid (3-Diethylamino-propyl)-amide

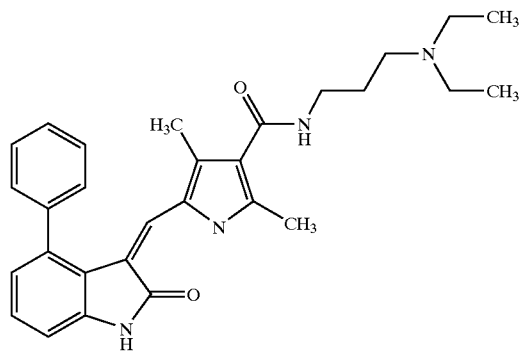

To a solution of 4-(4-fluoro-phenyl)-1,3-dihydro-indol-2-one (56.8 mg, 0.25 mmol) and 5-formyl-2,4-dimethyl-1H-pyrrole-3-carboxylic acid (3-diethylamino-propyl)-amide (69.8 mg, 0.26 mmol) in ethanol (2 mL) was added piperidine (3 drops). The reaction mixture was stirred at room temperature for three days. A yellow solid product was precipitated out, filtered, washed by ethanol for three times, and dried under high vacuum to provide pure product 5-[4-(4-fluoro-phenyl)-2-oxo-1,2-dihydro-indol-3-ylidenemethyl]-2,4-dimethyl-1H-pyrrole-3-carboxylic acid (3-diethylamino-propyl)-amide as a yellow solid (74.4 mg, 61%).

$^1$H-NMR (400 MHz, DMSO-d$_6$) δ 13.47 (br s, 1H, pyrrole NH), 11.04 (br s, 1H, CONH), 7.55 (t, 1H, aromatic), 7.45 (m, 2H, aromatic), 7.37 (t, 1H, aromatic), 7.18 (t, 1H, CONH), 6.92 (d, 1H, aromatic), 6.78 (d, 1H, aromatic), 6.71 (s, 1H, aromatic), 3.18 (m, 2H, CH$_2$), 2.44 (m, 6H, 3×CH$_2$), 2.37 (s, 3H, CH$_3$), 1.73 (s, 3H, CH$_3$), 1.57 (m, 2H, CH$_2$), 0.96 (t, 6H, 2×CH$_3$). MS m/z 487 [M$^-$−1].

Example 102

2-[4-(4-Fluoro-phenyl)-2-oxo-1,2-dihydro-indol-3-ylidenemethyl]-5-methyl-1H-pyrrole-3-carboxylic Acid (3-Pyrrolidin-1-yl-propyl)-amide

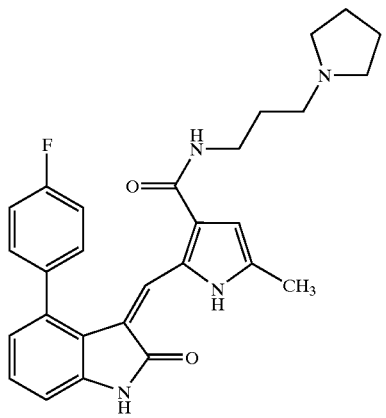

To a solution of 4-(4-fluoro-phenyl)-1,3-dihydro-indol-2-one (56.8 mg, 0.25 mmol) and 2-formyl-5-methyl-1H-pyrrole-3-carboxylic acid (3-pyrrolidin-1-yl-propyl)-amide (68.5 mg, 0.26 mmol) in ethanol (2 mL) was added piperidine (3 drops). The reaction mixture was stirred at room temperature for three days. A yellow solid product was precipitated out, filtered, washed by ethanol for three times, and dried under high vacuum to provide pure product 2-[4-(4-fluoro-phenyl)-2-oxo-1,2-dihydro-indol-3-ylidenemethyl]-5-methyl-1H-pyrrole-3-carboxylic acid (3-pyrrolidin-1-yl-propyl)-amide as a yellow solid (93.2 mg, 79%).

$^1$H-NMR (400 MHz, DMSO-d$_6$) δ 13.88 (br s, 1H, pyrrole NH), 11.04 (br s, 1H, CONH), 7.93 (s, 1H, aromatic), 7.86 (t, 1H, CONH), 7.36 (m, 2H, aromatic), 7.20 (m, 3H, aromatic), 6.90 (d, 1H, aromatic), 6.74 (d, 1H, aromatic), 6.34 (s, 1H, aromatic), 3.10 (m, 2H, CH$_2$), 2.40 (m, 6H, 3×CH$_2$), 2.29 (s, 3H, CH$_3$), 1.68 (m, 4H, 2×CH$_2$), 1.59 (m, 2H, CH$_2$). MS m/z 471 [M$^-$−1].

Example 103

5-[4-(3-Fluoro-phenyl)-2-oxo-1,2-dihydro-indol-3-ylidenemethyl]-2,4-dimethyl-1H-pyrrole-3-carboxylic Acid (3-Diethylamino-propyl)-amide

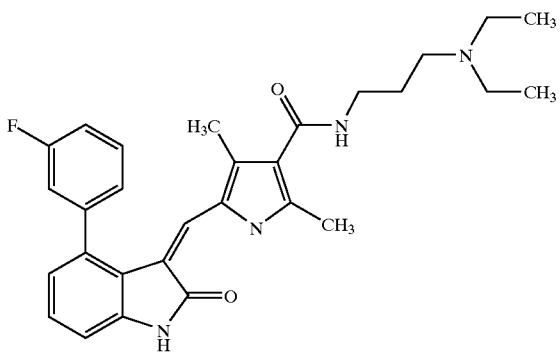

To a solution of 4-(3-fluoro-phenyl)-1,3-dihydro-indol-2-one (56.8 mg, 0.25 mmol) and 5-formyl-2,4-dimethyl-1H-pyrrole-3-carboxylic acid (3-diethylamino-propyl)-amide (69.8 mg, 0.26 mmol) in ethanol (2 mL) was added piperidine (3 drops). The reaction mixture was stirred at room temperature for three days. A yellow solid product was precipitated out, filtered, washed by ethanol for three times, and dried under high vacuum to provide pure product 5-[4-(3-fluoro-phenyl)-2-oxo-1,2-dihydro-indol-3-ylidenemethyl]-2,4-dimethyl-1H-pyrrole-3-carboxylic acid (3-diethylamino-propyl)-amide as a yellow solid (57.3 mg, 47%).

$^1$H-NMR (400 MHz, DMSO-d$_6$) δ 13.49 (br s, 1H, pyrrole NH), 11.07 (br s, 1H, CONH), 7.59 (m, 2H, aromatic), 7.32 (m, 3H, aromatic), 7.20 (t, 1H, CONH), 6.94 (d, 1H, aromatic), 6.73 (m, 2H, aromatic), 3.18 (m, 2H, CH$_2$), 2.45 (m, 6H, 3×CH$_2$), 2.37 (s, 3H, CH$_3$), 1.72 (s, 3H, CH$_3$), 1.57 (m, 2H, CH$_2$), 0.93 (t, 6H, 2×CH$_3$). MS m/z 487 [M$^-$−1].

Example 104

3-[3,5-Dimethyl-4-(4-methyl-piperazine-1-carbonyl)-H-pyrrol-2-ylmethylene]-4-(3-trifluoromethyl-phenyl)-1,3-dihydro-indol-2-one

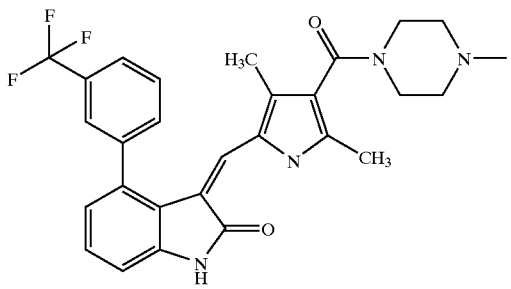

To a solution of 4-(3-trifluoromethyl-phenyl)-1,3-dihydro-indol-2-one (69.3 mg, 0.25 mmol) and 3,5-dimethyl-4-(4-methyl-piperazine-1-carbonyl)-1H-pyrrole-2-carbaldehyde (64.8 mg, 0.26 mmol) in ethanol (2 mL) was added piperidine (3 drops). The reaction mixture was stirred at room temperature for three days. The solvent was evaporated and the solid was washed by ether for three times to provide pure product 3-[3,5-dimethyl-4-(4-methyl-piperazine-1-carbonyl)-1H-pyrrol-2-ylmethylene]-4-(3-trifluoromethyl-phenyl)-1,3-dihydro-indol-2-one (96.5 mg, 76%).

$^1$H-NMR (400 MHz, DMSO-d$_6$) δ 13.44 (br s, 1H, pyrrole NH), 11.10 (br s, 1H, CONH), 7.76 (m, 4H, aromatic), 7.22 (t, 1H, aromatic), 6.95 (d, 1H, aromatic), 6.83 (d, 1H, aromatic), 6.58 (s, 1H, aromatic), 3.38 (m, 4H, 2×CH$_2$), 2.29 (m, 7H, 2×CH$_2$+CH$_3$), 2.17 (s, 3H, CH$_3$), 1.54 (s, 3H, CH$_3$). MS m/z 507 [M$^-$−1].

Example 105

2,4-Dimethyl-5-[2-oxo-4-(3-trifluoromethyl-phenyl)-1,2-dihydro-indol-3-ylidenemethyl]-1H-pyrrole-3-carboxylic Acid (2-Diethylamino-ethyl)-amide

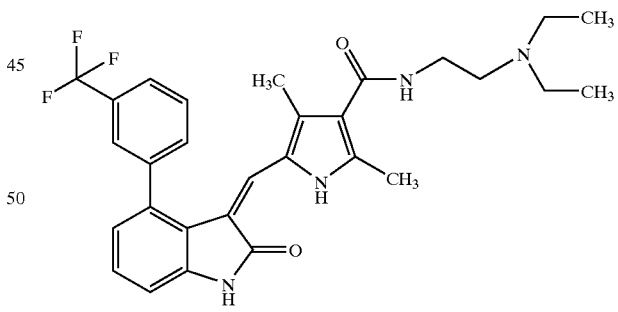

To a solution of 4-(3-trifluoromethyl-phenyl)-1,3-dihydro-indol-2-one (69.3 mg, 0.25 mmol) and 5-formyl-2,4-dimethyl-1H-pyrrole-3-carboxylic acid (2-diethylamino-ethyl)-amide (69.0 mg, 0.26 mmol) in ethanol (2 mL) was added piperidine (3 drops). The reaction mixture was stirred at room temperature for three days. A yellow solid product was precipitated out, filtered, washed by ethanol for three times, and dried under high vacuum to provide 2,4-dimethyl-5-[2-oxo-4-(3-trifluoromethyl-phenyl)-1,2-dihydro-indol-3-ylidenemethyl]-1H-pyrrole-3-carboxylic acid (2-diethylamino-ethyl)-amide as a yellow solid (68 mg, 52%).

¹H-NMR (400 MHz, DMSO-d₆) δ 13.49 (br s, 1H, pyrrole NH), 11.10 (br s, 1H, CONH), 7.80 (m, 1H, aromatic), 7.7 (m, 3H, aromatic), 7.31 (s, 1H, CONH), 7.21 (m, 1H, aromatic), 6.97 (d, 1H, aromatic), 6.83 (d, 1H, aromatic), 6.61 (s, 1H, aromatic), 3.22 (m, 2H, CH₂), 2.40 (m, 6H, 3×CH₂), 2.34 (s, 3H, CH₃), 1.68 (s, 3H, CH₃), 0.94 (m, 6H, 2×CH₃). MS m/z 523 [M⁻−1].

Example 106

2,4-Dimethyl-5-[2-oxo-4-(3-trifluoromethyl-phenyl)-1,2-dihydro-indol-3-ylidenemethyl]-1H-pyrrole-3-carboxylic Acid (2-Pyrrolidin-1-yl-ethyl)-amide

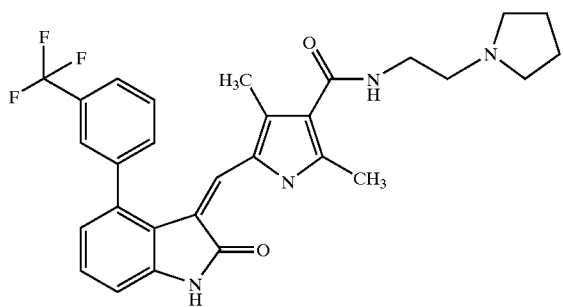

To a solution of 4-(3-trifluoromethyl-phenyl)-1,3-dihydro-indol-2-one (69.3 mg, 0.25 mmol) and 5-formyl-2,4-dimethyl-1H-pyrrole-3-carboxylic acid (2-pyrrolidin-1-yl-ethyl)-amide (68.5 mg, 0.26 mmol) in ethanol (2 mL) was added piperidine (3 drops). The reaction mixture was stirred at room temperature for three days. A yellow solid product was precipitated out, filtered, washed by ethanol for three times, and dried under high vacuum to provide pure product 2,4-dimethyl-5-[2-oxo-4-(3-trifluoromethyl-phenyl)-1,2-dihydro-indol-3-ylidenemethyl]-1H-pyrrole-3-carboxylic acid (2-pyrrolidin-1-yl-ethyl)-amide as a yellow solid (69.2 mg, 53%).

¹H-NMR (400 MHz, DMSO-d₆) δ 13.47 (br s, 1H, pyrrole NH), 11.10 (br s, 1H, CONH), 7.82 (m, 4H, aromatic), 7.44 (t, 1H, CONH), 7.22 (t, 1H, aromatic), 6.97 (dd, 1H, aromatic), 6.43 (dd, 1H, aromatic), 6.61 (s, 2H, aromatic), 3.28 (m, 2H, CH₂), 2.51 (m, 2H, CH₂), 2.44 (m, 4H, 2×CH₂), 2.37 (s, 3H, CH₃), 1.66 (s, 3H, CH₃), 1.62 (m, 4H, 2×CH₂). MS m/z 523 [M⁺+1].

Example 107

2,4-Dimethyl-5-[2-oxo-4-(3-trifluoromethyl-phenyl)-1,2-dihydro-indol-3-ylidenemethyl]-1H-pyrrole-3-carboxylic Acid (2-[1,2,3]Triazol-1-yl-ethyl)-amide

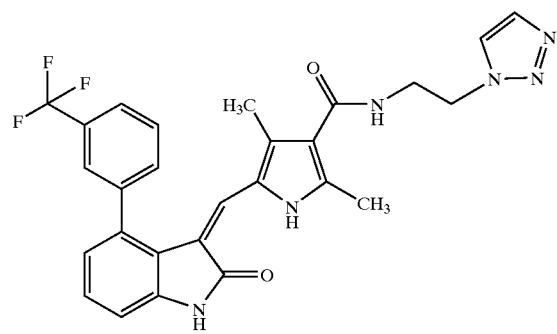

To a solution of 4-(3-trifluoromethyl-phenyl)-1,3-dihydro-indol-2-one (69.3 mg, 0.25 mmol) and 5-formyl-2,4-dimethyl-1H-pyrrole-3-carboxylic acid (2-[1,2,3]triazol-1-yl-ethyl)-amide (67.9 mg, 0.26 mmol) in ethanol (2 mL) was added piperidine (3 drops). The reaction mixture was stirred at room temperature for three days. A yellow solid product was precipitated out, filtered, washed by ethanol for three times, and dried under high vacuum to provide pure product 2,4-dimethyl-5-[2-oxo-4-(3-trifluoromethyl-phenyl)-1,2-dihydro-indol-3-ylidenemethyl]-1H-pyrrole-3-carboxylic acid (2-[1,2,3]triazol-1-yl-ethyl)-amide as a yellow solid (53 mg, 41%).

¹H-NMR (400 MHz, DMSO-d₆) δ 13.48 (br s, 1H, pyrrole NH), 11.06 (br s, 1H, CONH), 8.10 (s, 1H, aromatic), 7.81 (m, 4H, aromatic), 7.71 (d, 1H, aromatic), 7.63 (s, 1H, CONH+aromatic), 7.22 (t, 1H, aromatic), 6.66 (dd, 1H, aromatic), 6.83 (dd, 1H, aromatic), 6.59 (s, 1H, aromatic), 4.52 (t, 2H, CH₂), 3.64 (m, 2H, CH₂), 2.28 (s, 3H, CH₃), 1.54 (s, 3H, CH₃). MS m/z 519 [M⁻−1].

Example 108

5-Methyl-2-[2-oxo-4-(3-trifluoromethyl-phenyl)-1,2-dihydro-indol-3-ylidenemethyl]-1H-pyrrole-3-carboxylic Acid (2-Diethylamino-ethyl)-amide

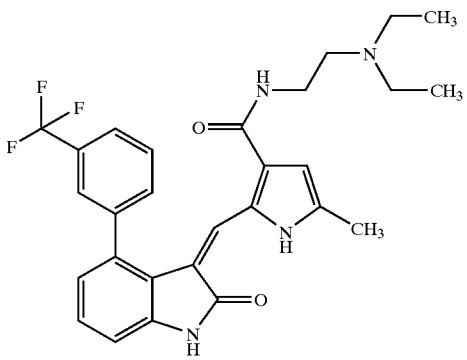

To a solution of 4-(3-trifluoromethyl-phenyl)-1,3-dihydro-indol-2-one (69.3 mg, 0.25 mmol) and 2-formyl-5-methyl-1H-pyrrole-3-carboxylic acid (2-diethylamino-ethyl)-amide (65.3 mg, 0.26 mmol) in ethanol (2 mL) was added piperidine (3 drops). The reaction mixture was stirred at room temperature for three days. A yellow solid product was precipitated out, filtered, washed by ethanol for three times, and dried under high vacuum to provide pure product 5-methyl-2-[2-oxo-4-(3-trifluoromethyl-phenyl)-1,2-dihydro-indol-3-ylidenemethyl]-1H-pyrrole-3-carboxylic acid (2-diethylamino-ethyl)-amide as a yellow solid (28 mg, 22%).

¹H-NMR (400 MHz, DMSO-d₆) δ 13.81 (br s, 1H, pyrrole NH), 11.15 (br s, 1H, CONH), 8.01 (s, 1H, aromatic), 7.66 (m, 5H, CONH+aromatic), 7.23 (t, 1H, aromatic), 6.95 (d, 1H, aromatic), 6.80 (dd, 1H, aromatic), 6.36 (d, 1H, aromatic), 3.33 (m, 2H, CH₂), 2.50 (m, 6H, 3×CH₂), 2.31 (s, 3H, CH₃), 0.98 (t, 6H, 2×CH₃). MS m/z 509 [M⁻−1].

Example 109

5-Methyl-2-[2-oxo-4-(3-trifluoromethyl-phenyl)-1,2-dihydro-indol-3-ylidenemethyl]-1H-pyrrole-3-carboxylic Acid (2-Pyrrolidin-1-yl-ethyl)-amide

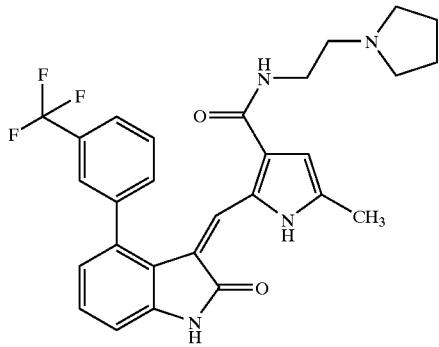

To a solution of 4-(3-trifluoromethyl-phenyl)-1,3-dihydro-indol-2-one (69.3 mg, 0.25 mmol) and 2-formyl-5-methyl-1H-pyrrole-3-carboxylic acid (2-pyrrolidin-1-yl-ethyl)-amide (64.8 mg, 0.26 mmol) in ethanol (2 mL) was added piperidine (3 drops). The reaction mixture was stirred at room temperature for three days. A yellow solid product was precipitated out, filtered, washed by ethanol for three times, and dried under high vacuum to provide pure product 5-methyl-2-[2-oxo-4-(3-trifluoromethyl-phenyl)-1,2-dihydro-indol-3-ylidenemethyl]-1H-pyrrole-3-carboxylic acid (2-pyrrolidin-1-yl-ethyl)-amide as a yellow solid (95 mg, 75%).

$^1$H-NMR (400 MHz, DMSO-$d_6$) δ 13.79 (br s, 1H, pyrrole NH), 11.15 (br s, 1H, CONH), 7.99 (s, 1H, aromatic), 7.70 (m, 5H, CONH+aromatic), 7.23 (t, 1H, aromatic), 6.95 (dd, 1H, aromatic), 6.82 (dd, 1H, aromatic), 6.39 (m, 1H, aromatic), 3.13 (m, 2H, CH$_2$), 2.47 (m, 6H, 3×CH$_2$), 2.31 (s, 3H, CH$_3$), 1.69 (m, 4H, 2×CH$_2$). MS m/z 509 [M$^+$+1].

Example 110

5-Methyl-2-[2-oxo-4-(3-trifluoromethyl-phenyl)-1,2-dihydro-indol-3-ylidenemethyl]-1H-pyrrole-3-carboxylic Acid (2-[1,2,3]Triazol-1-yl-ethyl)-amide

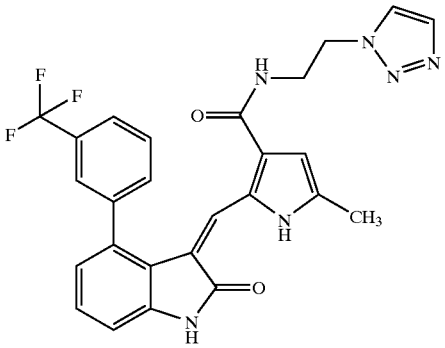

To a solution of 4-(3-trifluoromethyl-phenyl)-1,3-dihydro-indol-2-one (69.3 mg, 0.25 mmol) and 2-formyl-5-methyl-1H-pyrrole-3-carboxylic acid (2-[1,2,3]triazol-1-yl-ethyl)-amide (61.8 mg, 0.26 mmol) in ethanol (2 mL) was added piperidine (3 drops). The reaction mixture was stirred at room temperature for three days. A yellow solid product was precipitated out, filtered, washed by ethanol for three times, and dried under high vacuum to provide pure product 5-methyl-2-[2-oxo-4-(3-trifluoromethyl-phenyl)-1,2-dihydro-indol-3-ylidenemethyl]-1H-pyrrole-3-carboxylic acid (2-[1,2,3]triazol-1-yl-ethyl)-amide as a yellow solid (93.6 mg, 74%).

$^1$H-NMR (400 MHz, DMSO-$d_6$) δ 13.80 (br s, 1H, pyrrole NH), 11.17 (br s, 1H, CONH), 8.01 (m, 1H, aromatic), 7.96 (dd, 2H, aromatic), 7.77 (m, 1H, aromatic), 7.73 (d, 1H, aromatic), 7.68 (m, 3H, aromatic), 7.72 (t, 1H, aromatic), 6.96 (dd, 1H, aromatic), 6.83 (dd, 1H, aromatic), 6.34 (d, 1H, aromatic), 4.45 (t, 2H, CH$_2$), 3.44 (m, 2H, CH$_2$), 2.30 (s, 3H, CH$_3$). MS m/z 505 [M$^-$−1].

Example 111

3-[3-((cis)-3,5-Dimethyl-piperazine-1-carbonyl]-5-methyl-1H-pyrrol-2-ylmethylene]-4-(2-trifluoromethyl-phenyl)-1,3-dihydro-indol-2-one

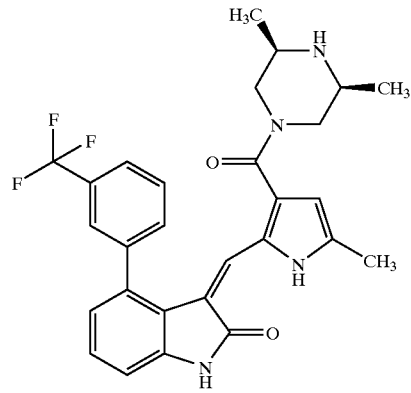

To a solution of 4-(3-trifluoromethyl-phenyl)-1,3-dihydro-indol-2-one (56.8 mg, 0.25 mmol) and 3-[(cis)-3,5-dimethyl-piperazine-1-carbonyl]-5-methyl-1H-pyrrole-2-carbaldehyde (62.3 mg, 0.26 mmol) in ethanol (2 mL) was added piperidine (3 drops). The reaction mixture was stirred at room temperature for three days. A yellow solid product was precipitated out, filtered, washed by ethanol for three times, and dried under high vacuum to provide pure product 3-[3-((cis)-3,5-dimethyl-piperazine-1-carbonyl]-5-methyl-1H-pyrrol-2-ylmethylene]-4-(2-trifluoromethyl-phenyl)-1,3-dihydro-indol-2-one as a yellow solid (92.7 mg, 73%).

$^1$H-NMR (400 MHz, DMSO-$d_6$) δ 13.61 (br s, 1H, pyrrole NH), 11.15 (br s, 1H, CONH), 7.70 (m, 4H, aromatic), 7.22 (t, 1H, aromatic), 6.95 (dd, 1H, aromatic), 6.90 (s, 1H, aromatic), 6.69 (d, 1H, aromatic), 6.00 (d, 1H, aromatic), 4.01 (m, 1H, CH), 3,47 (m, 1H, CH), 2.32 (m, 4H, 2×CH$_2$), 2.32 (m, 3H, CH$_3$), 0.96 (m, 6H, 2×CH$_3$). MS m/z 507 [M$^-$−1].

Example 112

2,4-Dimethyl-5-[2-oxo-4-(3-trifluoromethyl-phenyl)-1,2-dihydro-indol-3-ylidenemethyl]-1H-pyrrole-3-carboxylic Acid (3-Diethylamino-propyl)-amide

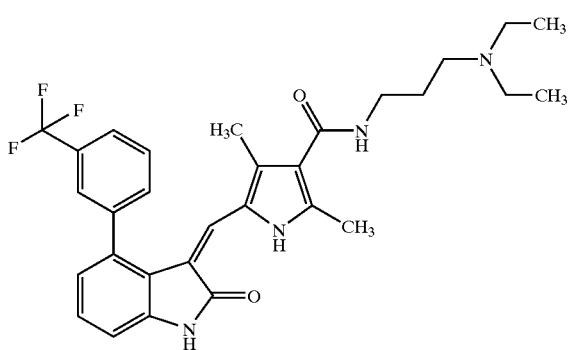

To a solution of 4-(3-trifluoromethyl-phenyl)-1,3-dihydro-indol-2-one (69.3 mg, 0.25 mmol) and 5-formyl-2,4-dimethyl-1H-pyrrole-3-carboxylic acid (3-diethylamino-propyl)-amide (69.8 mg, 0.26 mmol) in ethanol (2 mL) was added piperidine (3 drops). The reaction mixture was stirred at room temperature for three days. A yellow solid product was precipitated out, filtered, washed by ethanol for three times, and dried under high vacuum to provide pure product 2,4-dimethyl-5-[2-oxo-4-(3-trifluoromethyl-phenyl)-1,2-dihydro-indol-3-ylidenemethyl]-1H-pyrrole-3-carboxylic acid (3-diethylamino-propyl)-amide as a yellow solid (72.6 mg, 54%).

$^1$H-NMR (400 MHz, DMSO-$d_6$) δ 13.48 (br s, 1H, pyrrole NH), 11.00 (br s, 1H, CONH), 7.88 (m, 1H, aromatic), 7.78 (m, 3H, aromatic), 7.60 (m, 1H, aromatic), 7.22 (t, 1H, aromatic), 6.97 (d, 1H, aromatic), 6.83 (d, 1H, aromatic), 6.61 (s, 1H, aromatic), 3.32 (m, 2H, CH$_2$), 3.20 (m, 2H, CH$_2$), 2.49 (m, 6H, 3×CH$_2$), 2.37 (s, 3H, CH$_3$), 1.61 (s, 3H, CH$_3$), 0.96 (s, 6H, 2×CH$_3$). MS m/z 537 [M$^-$−1].

Example 113

5-Methyl-2-[2-oxo-4-(3-trifluoromethyl-phenyl)-1,2-dihydro-indol-3-ylidenemethyl]-1H-pyrrole-3-carboxylic Acid (3-Pyrrolidin-1-yl-propyl)-amide

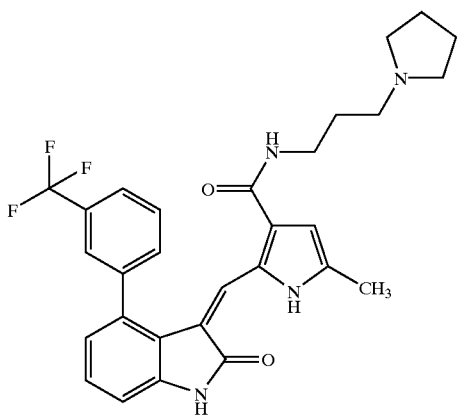

To a solution of 4-(3-trifluoromethyl-phenyl)-1,3-dihydro-indol-2-one (69.3 mg, 0.25 mmol) and 5-formyl-2,4-dimethyl-1H-pyrrole-3-carboxylic acid (3-pyrrolidin-1-yl-propyl)-amide (69.8 mg, 0.26 mmol) in ethanol (2 mL) was added piperidine (3 drops). The reaction mixture was stirred at room temperature for three days. A yellow solid product was precipitated out, filtered, washed by ethanol for three times, and dried under high vacuum to provide pure product 5-methyl-2-[2-oxo-4-(3-trifluoromethyl-phenyl)-1,2-dihydro-indol-3-ylidenemethyl]-1H-pyrrole-3-carboxylic acid (3-pyrrolidin-1-yl-propyl)-amide as a yellow solid (52.2 mg, 40%).

$^1$H-NMR (400 MHz, DMSO-$d_6$) δ 13.85 (br s, 1H, pyrrole NH), 11.05 (br s, 1H, CONH), 7.95 (s, 1H, aromatic), 7.85 (t, 1H, CONH), 7.67 (m, 4H, aromatic), 7.22 (t, 1H, aromatic), 6.96 (d, 1H, aromatic), 6.80 (dd, 1H, aromatic), 6.35 (d, 1H, aromatic), 3.42 (s, 2H, CH2), 3.10 (q, 2H, CH$_2$), 2.49 (m, 6H, 3×CH$_2$), 2.30 (s, 3H, CH$_3$), 1.69 (m, 4H, 2×CH$_2$). MS m/z 521 [M$^-$−1].

Example 114

3-[3-Methyl-4-(4-methyl-piperazine-1-carbonyl)-1H-pyrrol-2-ylmethylene]-4-(3-trifluoromethyl-phenyl)-1,3-dihydro-indol-2-one

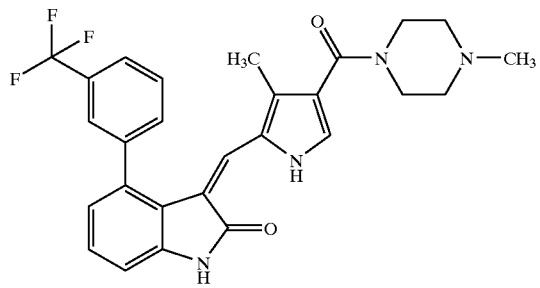

To a solution of 4-(3-trifluoromethyl-phenyl)-1,3-dihydro-indol-2-one (69.3 mg, 0.25 mmol) and 3-methyl-4-(4-methyl-piperazine-1-carbonyl)-1H-pyrrole-2-carbaldehyde (61.2 mg, 0.26 mmol) in ethanol (2 mL) was added piperidine (3 drops). The reaction mixture was stirred at room temperature for three days. A yellow solid product was precipitated out, filtered, washed by ethanol for three times, and dried under high vacuum to provide pure product 3-[3-methyl-4-(4-methyl-piperazine-1-carbonyl)-1H-pyrrol-2-ylmethylene]-4-(3-trifluoromethyl-phenyl)-1,3-dihydro-indol-2-one as a yellow solid (46.9 mg, 38%).

$^1$H-NMR (400 MHz, DMSO-$d_6$) δ 13.45 (br s, 1H, pyrrole NH), 11.16 (br s, 1H, CONH), 7.98 (m, 1H, aromatic), 7.80 (m, 3H, aromatic), 7.39 (d, 1H, aromatic), 7.25 (t, 1H, aromatic), 6.96 (dd, 1H, aromatic), 6.85 (d, 1H, aromatic), 6.66 (s, 1H, aromatic), 3.38 (m, 4H, 2×CH$_2$), 2.25 (m, 4H, 2×CH$_2$), 2.17 (s, 3H, CH$_3$), 1.56 (s, 3H, CH$_3$). MS m/z 493 [M$^-$−1].

Example 115

3-[4-((cis)-3,5-Dimethyl-piperazine-1-carbonyl]-3-methyl-1H-pyrrol-2-ylmethylene]-4-(3-trifluoromethyl-phenyl)-1,3-dihydro-indol-2-one

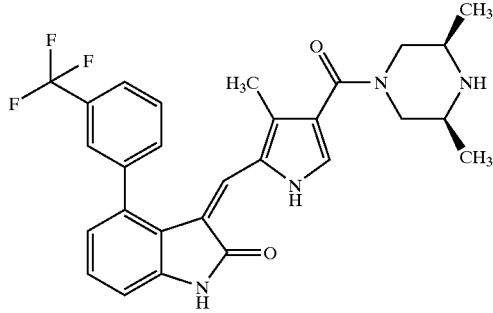

To a solution of 4-(3-trifluoromethyl-phenyl)-1,3-dihydro-indol-2-one (69.3 mg, 0.25 mmol) and 4-[(cis)-3,5-dimethyl-piperazine-1-carbonyl]-3-methyl-1H-pyrrol-2-carbaldehyde (64.8 mg, 0.26 mmol) in ethanol (2 mL) was added piperidine (3 drops). The reaction mixture was stirred at room temperature for three days. A yellow solid product was precipitated out, filtered, washed by ethanol for three times, and dried under high vacuum to provide pure product 3-{4-((cis)-3,5-dimethyl-piperazine-1-carbonyl]-3-methyl-1H-pyrrol-2-ylmethylene}-4-(3-trifluoromethyl-phenyl)-1,3-dihydro-indol-2-one as a yellow solid (34.3 mg, 27%).

$^1$H-NMR (400 MHz, DMSO-$d_6$) δ 13.47 (br s, 1H, pyrrole NH), 11.16 (br s, 1H, CONH), 7.88 (m, 1H, aromatic), 7.81 (m, 3H, aromatic), 7.6 (dd, 1H, aromatic), 7.25 (t, 1H, aromatic), 6.96 (d, 1H, aromatic), 6.85 (d, 1H, aromatic), 6.66 (s, 1H, aromatic), 3.32 (m, 1H, CH), 2.46 (m, 1H, CH), 2.50 (m, 4H, 2×CH$_2$), 1.54 (s, 3H, CH$_3$), 0.92 (m, 6H, 2×CH$_3$). MS m/z 507 [M$^-$–1].

Example 116

4-(3-Chloro-4-fluoro)-3-[3,5-dimethyl-4-(4-methyl-piperazine-1-carbonyl)-1H-pyrrol-2-ylmethylene]-1,3-dihydro-indol-2-one

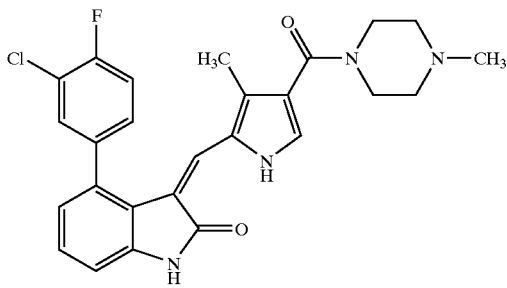

To a solution of 4-(3-chloro-4-fluoro-phenyl)-1,3-dihydro-indol-2-one (65.4 mg, 0.25 mmol) and 3,5-dimethyl-4-(4-methyl-piperazine-1-carbonyl)-1H-pyrrole-2-carbaldehyde (64.8 mg, 0.26 mmol) in ethanol (2 mL) was added piperidine (3 drops). The reaction mixture was stirred at room temperature for three days. The solvent was evaporated and the solid was washed by ether for three times to provide pure product 4-(3-chloro-4-fluoro)-3-[3,5-Dimethyl-4-(4-methyl-piperazine-1-carbonyl)-1H-pyrrol-2-ylmethylene]-1,3-dihydro-indol-2-one (59 mg, 48%).

Example 117

5-[4-(3-Chloro-4-fluoro-phenyl)-2-oxo-1,2-dihydro-indol-3-ylidenemethyl]-2,4-dimethyl-1H-pyrrole-3-carboxylic Acid (2-Diethylamino-ethyl)-amide

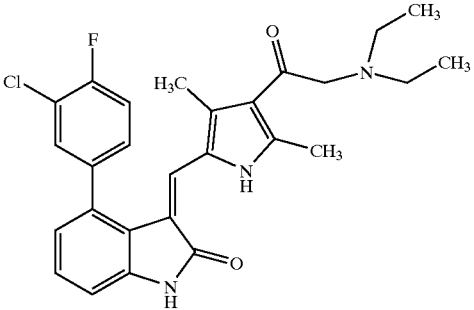

To a solution a solution of 4-(3-Chloro-4-fluoro-phenyl)-2-oxo-1,2-dihydro-indol-2-one (65.4 mg, 0.25 mmol) and 5-formyl-2,4-dimethyl-1H-pyrrole-3-carboxylic acid (2-diethylamino-ethyl)-amide (69.0 mg, 0.26 mmol) in ethanol (2 ml) was added piperidine (3 drops). The reaction mixture was stirred at room temperature for three days. A yellow solid product was precipitated out, filtered, washed by ethanol for three times, and dried under high vacuum to provide 5-[4-(3-Chloro-4-fluoro-phenyl)-2-oxo-1,2-dihydro-indol-3-ylidenemethyl]-2,4-dimethyl-1H-pyrrole-3-carboxylic acid (2-diethylamino-ethyl)-amide (72 mg, 57%).

$^1$H-NMR (400 MHz), DMSO-$d_6$) δ 13.47 (br s, 1H, pyrrole NH), 11.07 (br s, 1H, CONH), 7.70 (d, 1H, aromatic), 7.61 (t, 1H, CONH), 7.46 (m, 1H, aromatic), 7.35 (m, 1H, aromatic), 7.20 (t, 1H, aromatic), 6.95 (d, 1H, aromatic), 6.82 (d, 1H, aromatic), 6.73 (d, 1H, aromatic), 3,24 (m, 2H, CH$_2$), 2.50 (m, 6H, 3×CH$_2$), 2.38 (s, 3H, CH$_3$), 1.78 (s, 3H, CH$_3$), 0.95 (t, 6H, 2×CH$_3$). MS m/z 507 [M$^-$–1].

Example 118

5-[4-(3-Chloro-4-fluoro-phenyl)-2-oxo-1,2-dihydro-indol-3-ylidenemethyl]-2,4-dimethyl-1H-pyrrole-3-carboxylic Acid (2-[1,2,3]Triazol-1-yl-ethyl)-amide

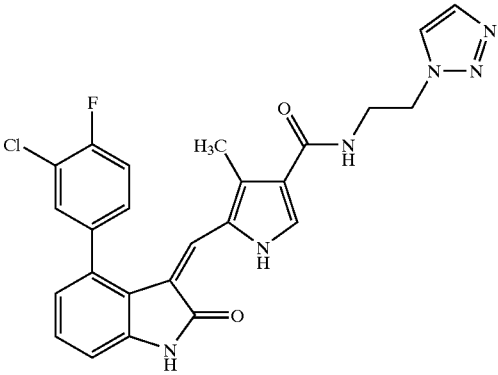

To a solution of 4-(3-chloro-4-fluoro-phenyl)-1,3-dihydro-indol-2-one (65.4 mg, 0.25 mmol) and 5-formyl-2,4-dimethyl-1H-pyrrole-3-carboxylic acid (2-[1,2,3]triazol-1-yl-ethyl)-amide (67.9 mg, 0.26 mmol) in ethanol (2 mL) was added piperidine (3 drops). The reaction mixture was stirred at room temperature for three days. A yellow solid product was precipitated out, filtered, washed by ethanol for three times, and dried under high vacuum to provide pure product 5-[4-(3-chloro-4-fluoro-phenyl)-2-oxo-1,2-dihydro-indol-3-ylidenemethyl]-2,4-dimethyl-1H-pyrrole-3-carboxylic acid (2-[1,2,3]triazol-1-yl-ethyl)-amide as a yellow solid (53 mg, 45%).

$^1$H-NMR (400 MHz, DMSO-d$_6$) δ 13.47 (br s, 1H, pyrrole NH), 11.07 (br s, 1H, CONH), 8.10 (s, 1H, aromatic), 7.70 (m, 2H, aromatic), 7.63 (t, 2H, CONH+ aromatic), 7.46 (m, 1H, aromatic), 7.19 (t, 1H, aromatic), 6.93 (d, 1H, aromatic), 6.80 (d, 1H, aromatic), 6.71 (s, 1H, aromatic), 4.53 (m, 2H, CH$_2$), 3.64 (m, 2H, CH$_2$), 2.30 (s, 3H, CH$_3$), 1.69 (s, 3H, CH$_3$). MS m/z 503 [M$^-$–1].

Example 119

2-[4-(3-Chloro-4-fluoro-phenyl)-2-oxo-1,2-dihydro-indol-3-ylidenemethyl]-5-methyl-1H-pyrrole-3-carboxylic Acid (2-Pyrrolidin-1-yl-ethyl)-amide

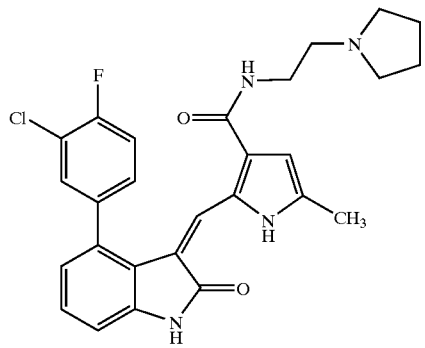

To a solution of 4-(3-chloro-4-fluoro-phenyl)-1,3-dihydro-indol-2-one (65.4 mg, 0.25 mmol) and 2-formyl-5-methyl-1H-pyrrole-3-carboxylic acid (2-pyrrolidin-1-yl-ethyl)-amide (64.8 mg, 0.26 mmol) in ethanol (2 mL) was added piperidine (3 drops). The reaction mixture was stirred at room temperature for three days. A yellow solid product was precipitated out, filtered, washed by ethanol for three times, and dried under high vacuum to provide pure product 2-[4-(3-chloro-4-fluoro-phenyl)-2-oxo-1,2-dihydro-indol-3-ylidenemethyl]-5-methyl-1H-pyrrole-3-carboxylic acid (2-pyrrolidin-1-yl-ethyl)-amide as a yellow solid (89 mg, 72%).

$^1$H-NMR (400 MHz, DMSO-d$_6$) δ 13.79 (br s, 1H, pyrrole NH), 11.13 (br s, 1H, CONH), 8.03 (s, 1H, aromatic), 7.80 (t, 1H, CONH), 7.50 (d, 1H, aromatic), 7.42 (t, 1H, aromatic), 7.32 (m, 1H, aromatic), 7.21 (t, 1H, aromatic), 6.93 (d, 1H, aromatic), 6.78 (d, 1H, aromatic), 6.43 (s, 1H, aromatic), 3.21 (m, 2H, CH$_2$), 2.50 (m, 6H, 3×CH$_2$), 2.31 (s, 3H, CH$_3$), 1.67 (m, 4H, 2×CH$_2$). MS m/z 491 [M$^-$–1].

Example 120

2-[4-(3-Chloro-4-fluoro-phenyl)-2-oxo-1,2-dihydro-indol-3-ylidenemethyl]-5-methyl-1H-pyrrole-3-carboxylic Acid (2-[1,2,3]Triazol-1-yl-ethyl)-amide

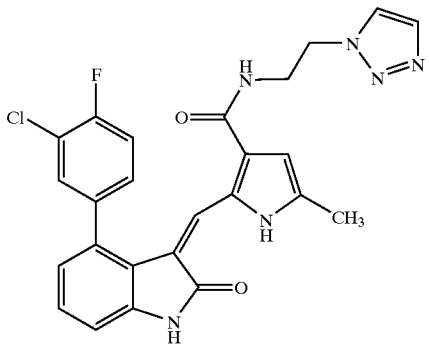

To a solution of 4-(3-chloro-4-fluoro-phenyl)-1,3-dihydro-indol-2-one (65.4 mg, 0.25 mmol) and 2-formyl-5-methyl-1H-pyrrole-3-carboxylic acid (2-[1,2,3]triazol-1-yl-ethyl)-amide (61.8 mg, 0.26 mmol) in ethanol (2 mL) was added piperidine (3 drops). The reaction mixture was stirred at room temperature for three days. A yellow solid product was precipitated out, filtered, washed by ethanol for three times, and dried under high vacuum to provide pure product 2-[4-(3-chloro-4-fluoro-phenyl)-2-oxo-1,2-dihydro-indol-3-ylidenemethyl]-5-methyl-1H-pyrrole-3-carboxylic acid (2-[1,2,3]triazol-1-yl-ethyl)-amide as a yellow solid (85 mg, 69%).

$^1$H-NMR (400 MHz, DMSO-d$_6$) δ 13.81 (br s, 1H, pyrrole NH), 11.15 (br s, 1H, CONH), 8.07 (m, 1H, aromatic), 7.98 (d, 2H, aromatic), 7.74 (s, 1H, aromatic), 7.52 (d, 1H, aromatic), 7.47 (t, 1H, aromatic), 7.32 (m, 1H, aromatic), 7.22 (t, 1H, aromatic), 6.94 (d, 1H, aromatic), 6.78 (d, 1H, aromatic), 6.36 (s; 1H, aromatic), 4.53 (m, 2H, CH$_2$), 3.53 (m, 2H, CH$_2$), 2.30 (s, 3H, CH$_3$). MS m/z 489 [M$^{31}$ –1].

Example 121

2-[4-(3-Chloro-4-fluoro-phenyl)-2-oxo-1,2-dihydro-indol-3-ylidenemethyl]-5-methyl-1H-pyrrole-3-carboxylic Acid (3-Pyrrolidin-1-yl-propyl)-amide

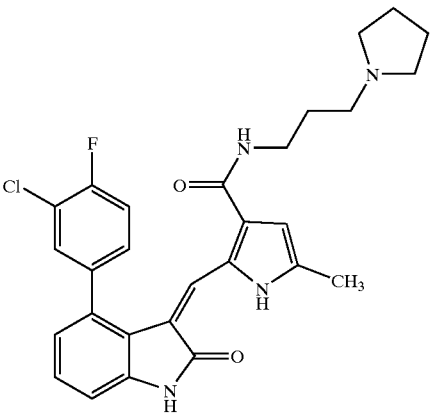

To a solution of 4-(3-chloro-4-fluoro-phenyl)-1,3-dihydro-indol-2-one (65.4 mg, 0.25 mmol) and 2-formyl-5- methyl-1H-pyrrole-3-carboxylic acid (3-pyrrolidin-1-yl-propyl)-amide (68.5 mg, 0.26 mmol) in ethanol (2 mL) was added piperidine (3 drops). The reaction mixture was stirred at room temperature for three days. A yellow solid product was precipitated out, filtered, washed by ethanol for three times, and dried under high vacuum to provide pure product 2-[4-(3-chloro-4-fluoro-phenyl)-2-oxo-1,2-dihydro-indol-3-ylidenemethyl]-5-methyl-1H-pyrrole-3-carboxylic acid (3-pyrrolidin-1-yl-propyl)-amide as a yellow solid (103 mg, 81%).

$^1$H-NMR (400 MHz, DMSO-d$_6$) δ 13.86 (br s, 1H, pyrrole NH), 11.05 (br s, 1H, CONH), 8.01 (s, 1H, aromatic), 7.91 (t, 1H, CONH), 7.50 (d, 1H, aromatic), 7.41 (t, 1H, aromatic), 7.31 (m, 1H, aromatic), 7.20 (t, 1H, aromatic), 6.93 (d, 1H, aromatic), 6.77 (d, 1H, aromatic), 6.40 (s, 1H, aromatic), 3.32 (m, 2H, CH$_2$), 3.14 (m, 2H, CH$_2$), 2.41 (m, 6H, 3×CH$_2$), 2.31 (s, 3H, CH$_3$), 1.67 (m, 4H, 2×CH$_2$). MS m/z 506 [M$^-$−1].

Example 122

4-(4-Chloro-phenyl)-3-{3,5-dimethyl-4-[3-(4-methyl-piperazin-1-yl)-3-oxo-propyl]-1H-pyrrol-2-ylmethylene}-1,3-dihydro-indol-2-one

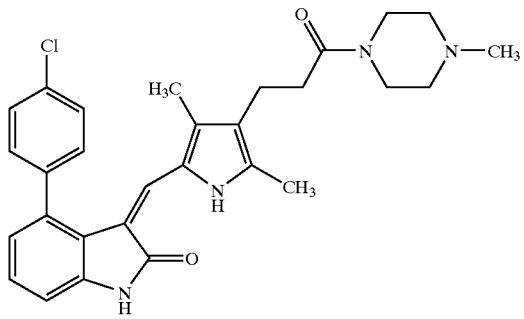

To a solution of 4-(4-chloro-phenyl)-1,3-dihydro-indol-2-one (60.9 mg, 0.25 mmol) and 3,5-dimethyl-4-[3-(4-methyl-piperazin-1-yl)-3-oxo-propyl]-1H-pyrrole-2-carbaldehyde (72.1 mg, 0.26 mmol) in ethanol (2 mL) was added piperidine (3 drops). The reaction mixture was stirred at room temperature for three days. A yellow solid product was precipitated out, filtered, washed by ethanol for three times, and dried under high vacuum to provide pure product 4-(4-chloro-phenyl)-3-{3,5-dimethyl-4-[3-(4-methyl-piperazin-1-yl)-3-oxo-propyl]-1H-pyrrol-2-ylmethylene}-1,3-dihydro-indol-2-one as a yellow solid (47.4 mg, 38%).

$^1$H-NMR (400 MHz, DMSO-d$_6$) δ 13.27 (br s, 1H, pyrrole NH), 11.40 (br s, 1H, CONH), 7.60 (d, 2H, aromatic), 7.42 (dd, 2H, aromatic), 7.10 (t, 1H, aromatic), 6.91 (d, 1H, aromatic), 6.75 (d, 1H, aromatic), 6.66 (s, 1H, aromatic), 3.40 (m, 4H, 2×CH$_2$), 2.52 (m, 4H, 2×CH$_2$), 2.36 (m, 4H, 2×CH$_2$), 2.24 (s, 3H, CH$_3$), 2.19 (s, 3H, CH$_3$), 1.59 (s, 3H, CH$_3$). MS m/z 503 [M$^+$+1].

Example 123

4-(2-Fluoro-phenyl)-3-[3-methyl-4-(4-methyl-piperazine-1-carbonyl)-1H-pyrrol-2-ylmethylene]-1,3-dihydro-indol-2-one

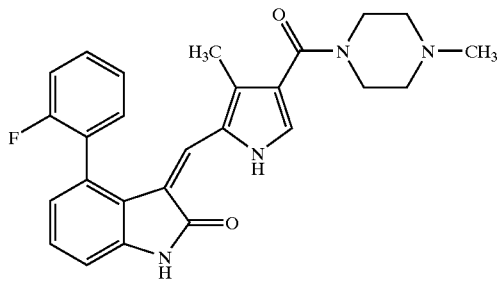

To a solution of 4-(2-fluoro-phenyl)-1,3-dihydro-indol-2-one (56.8 mg, 0.25 mmol) and 3-methyl-4-(4-methyl-piperazine-1-carbonyl)-1H-pyrrole-2-carbaldehyde (61.2 mg, 0.26 mmol) in ethanol (2 mL) was added piperidine (3 drops). The reaction mixture was stirred at room temperature for three days. A yellow solid product was precipitated out, filtered, washed by ethanol for three times, and dried under high vacuum to provide pure product 4-(2-fluoro-phenyl)-3-[3-methyl-4-(4-methyl-piperazine-1-carbonyl)-1H-pyrrol-2-ylmethylene]-1,3-dihydro-indol-2-one as a yellow solid (40 mg, 36%).

$^1$H-NMR (400 MHz, DMSO-d$_6$) δ 13.51 (br s, 1H, pyrrole NH), 11.15 (br s, 1H, CONH), 7.57 (m, 1H, aromatic), 7.42 (m, 4H, aromatic), 7.25 (t, 1H, aromatic), 6.97 (d, 1H, aromatic), 6.85 (d, 1H, aromatic), 6.69 (s, 1H, aromatic), 3.40 (m, 4H, 2×CH$_2$), 2.25 (m, 4H, 2×CH$_2$), 2.17 (s, 3H, CH$_3$), 1.62 (s, 3H, CH$_3$). MS m/z 445 [M$^+$+1].

Example 124

4-(4-Fluoro-phenyl)-3-[3-methyl-4-(4-methyl-piperazine-1-carbonyl)-1H-pyrrol-2-ylmethylene]-1,3-dihydro-indol-2-one

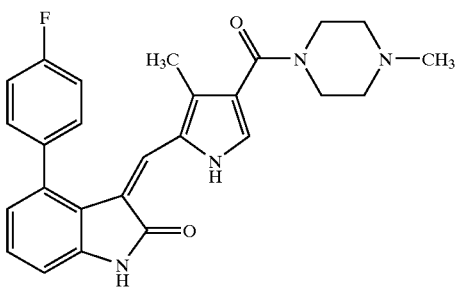

To a solution of 4-(4-fluoro-phenyl)-1,3-dihydro-indol-2-one (56.8 mg, 0.25 mmol) and 3-methyl-4-(4-methyl-piperazine-1-carbonyl)-1H-pyrrole-2-carbaldehyde (61.2 mg, 0.26 mmol) in ethanol (2 mL) was added piperidine (3 drops). The reaction mixture was stirred at room temperature for three days. A yellow solid product was precipitated out, filtered, washed by ethanol for three times, and dried under high vacuum to provide pure product 4-(4-fluoro-phenyl)-3-[3-methyl-4-(4-methyl-piperazine-1-carbonyl)-1H-pyrrol-2-ylmethylene]-1,3-dihydro-indol-2-one as a yellow solid (39 mg, 36%).

$^1$H-NMR (400 MHz, DMSO-d$_6$) δ 13.50 (br s, 1H, pyrrole NH), 11.12 (br s, 1H, CONH), 7.48 (m, 2H, aromatic), 7.39 (m, 3H, aromatic), 7.22 (t, 1H, aromatic), 6.93 (d, 1H, aromatic), 6.80 (t, 2H, aromatic), 3.45 (m, 4H, 2×CH$_2$), 2.26 (m, 4H, 2×CH$_2$), 2.17 (s, 3H, CH$_3$), 1.67 (s, 3H, CH$_3$). MS m/z 445 [M$^+$+1].

Example 125

4-(4-Chloro-phenyl)-3-[3-methyl-4-(4-methyl-piperazine-1-carbonyl)-1H-pyrrol-2-ylmethylene]-1,3-dihydro-indol-2-one

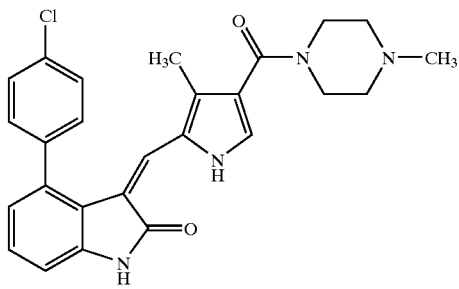

To a solution of 4-(4-chloro-phenyl)-1,3-dihydro-indol-2-one (60.9 mg, 0.25 mmol) and 3-methyl-4-(4-methyl-piperazine-1-carbonyl)-1H-pyrrole-2-carbaldehyde (61.2 mg, 0.26 mmol) in ethanol (2 mL) was added piperidine (3 drops). The reaction mixture was stirred at room temperature for three days. A yellow solid product was precipitated out, filtered, washed by ethanol for three times, and dried under high vacuum to provide pure product 4-(4-chloro-phenyl)-3-[3-methyl-4-(4-methyl-piperazine-1-carbonyl)-1H-pyrrol-2-ylmethylene]-1,3-dihydro-indol-2-one as a yellow solid (47 mg, 35%).

$^1$H-NMR (400 MHz, DMSO-d$_6$) δ 13.46 (br s, 1H, pyrrole NH), 11.12 (br s, 1H, CONH), 7.60 (dd, 2H, aromatic), 7.42 (d, 2H, aromatic), 7.30 (d, 1H, aromatic), 7.20 (t, 1H, aromatic), 6.90 (d, 1H, aromatic), 6.80 (d, 1H, aromatic), 6.72 (s, 1H, aromatic), 3.44 (m, 4H, 2×CH$_2$), 2.26 (m, 4H, 2×CH$_2$), 2.17 (s, 3H, CH$_3$), 1.67 (s, 3H, CH$_3$). MS m/z 461 [M$^+$+1].

Example 126

4-(4-Bromo-phenyl)-3-[3-methyl-4-(4-methyl-piperazine-1-carbonyl)-1H-pyrrol-2-ylmethylene]-1,3-dihydro-indol-2-one

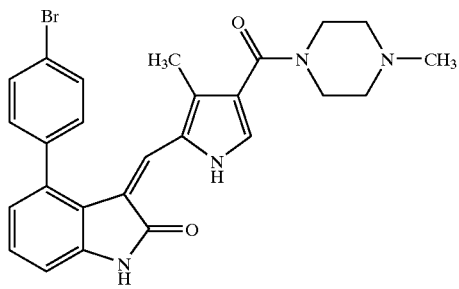

To a solution of 4-(4-bromo-phenyl)-1,3-dihydro-indol-2-one (72.0 mg, 0.25 mmol) and 3-methyl-4-(4-methyl-piperazine-1-carbonyl)-1H-pyrrole-2-carbaldehyde (61.2 mg, 0.26 mmol) in ethanol (2 mL) was added piperidine (3 drops). The reaction mixture was stirred at room temperature for three days. A yellow solid product was precipitated out, filtered, washed by ethanol for three times, and dried under high vacuum to provide pure product 4-(4-bromo-phenyl)-3-[3-methyl-4-(4-methyl-piperazine-1-carbonyl)-1H-pyrrol-2-ylmethylene]-1,3-dihydro-indol-2-one as a yellow solid (42.8 mg, 34%).

$^1$H-NMR (400 MHz, DMSO-d$_6$) δ 13.46 (br s, 1H, pyrrole NH), 11.12 (br s, 1H, CONH), 7.75 (d, 2H, aromatic), 7.40 (d, 3H, aromatic), 7.23 (t, 1H, aromatic), 6.93 (d, 1H, aromatic), 6.81 (d, 1H, aromatic), 6.71 (s, 1H, aromatic), 3.46 (m, 4H, 2×CH$_2$), 2.26 (m, 4H, 2×CH$_2$), 2.17 (s, 3H, CH$_3$), 1.67 (s, 3H, CH$_3$). MS m/z 507 [M$^+$+1].

Example 127

4-(3-Bromo-phenyl)-3-[3-methyl-4-(4-methyl-piperazine-1-carbonyl)-1H-pyrrol-2-ylmethylene]-1,3-dihydro-indol-2-one

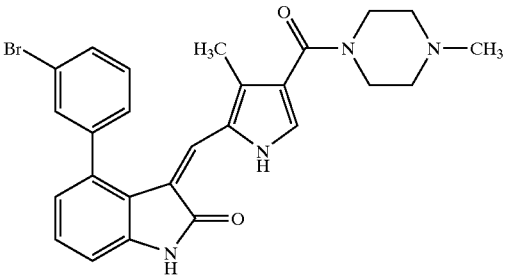

To a solution of 4-(3-bromo-phenyl)-1,3-dihydro-indol-2-one (72.0 mg, 0.25 mmol) and 3-methyl-4-(4-methyl-piperazine-1-carbonyl)-1H-pyrrole-2-carbaldehyde (61.2 mg, 0.26 mmol) in ethanol (2 mL) was added piperidine (3 drops). The reaction mixture was stirred at room temperature for three days. A yellow solid product was precipitated out, filtered, washed by ethanol for three times, and dried under high vacuum to provide pure product 4-(3-bromo-phenyl)-3-[3-methyl-4-(4-methyl-piperazine-1-carbonyl)-1H-pyrrol-2-ylmethylene]-1,3-dihydro-indol-2-one as a yellow solid (61.4 mg, 49%).

$^1$H-NMR (400 MHz, DMSO-d$_6$) δ 13.50 (br s, 1H, pyrrole NH), 11.14 (br s, 1H, CONH), 7.72 (dd, 1H, aromatic), 7.67 (d, 1H, aromatic), 7.53 (t, 1H, aromatic), 7.45 (d, 1H, aromatic), 7.40 (d, 1H, aromatic), 7.23 (d, 1H, aromatic), 6.94 (s, 1H, aromatic), 6.82 (d, 2H, aromatic), 3.46 (m, 4H, 2×CH$_2$), 2.26 (m, 4H, 2×CH$_2$), 2.17 (s, 3H, CH$_3$), 1.67 (s, 3H, CH$_3$). MS m/z 504 [M$^+$+1].

Example 128

4-(4-Methoxy-phenyl)-3-[3-methyl-4-(4-methyl-piperazine-1-carbonyl)-1H-pyrrol-2-ylmethylene]-1,3-dihydro-indol-2-one

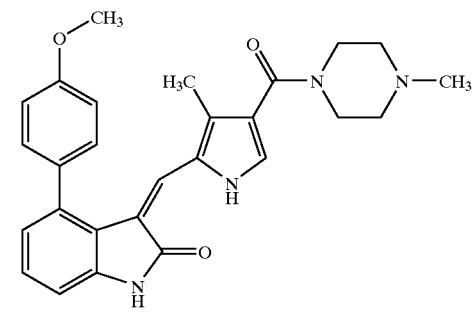

To a solution of 4-(4-methoxy-phenyl)-1,3-dihydro-indol-2-one (59.8 mg, 0.25 mmol) and 3-methyl-4-(4-methylpiperazine-1-carbonyl)-1H-pyrrole-2-carbaldehyde (61.2 mg, 0.26 mmol) in ethanol (2 mL) was added piperidine (3 drops). The reaction mixture was stirred at room temperature for three days. A yellow solid product was precipitated out, filtered, washed by ethanol for three times, and dried under high vacuum to provide pure product 4-(4-methoxy-phenyl)-3-[3-methyl-4-(4-methyl-piperazine-1-carbonyl)-1H-pyrrol-2-ylmethylene]-1,3-dihydro-indol-2-one as a yellow solid (94 mg, 82%).

$^1$H-NMR (400 MHz, DMSO-d$_6$) δ 13.49 (br s, 1H, pyrrole NH), 11.08 (br s, 1H, CONH), 7.74 (d, 1H, aromatic), 7.35 (d, 1H, aromatic), 7.33 (s, 1H, aromatic), 7.20 (t, 1H, aromatic), 7.11 (m, 2H, aromatic), 6.89 (d, 1H, aromatic), 6.84 (s, 1H, aromatic), 6.79 (d, 1H, aromatic), 3.82 (s, 3H, OCH$_3$), 3.45 (m, 4H, 2×CH$_2$), 2.25 (m, 4H, 2×CH$_2$), 2.17 (s, 3H, CH$_3$), 1.66 (s, 3H, CH$_3$). MS m/z 457 [M$^+$+1].

Example 129

4-(3-Methoxy-phenyl)-3-[3-methyl-4-(4-methyl-piperazine-1-carbonyl)-1H-pyrrol-2-ylmethylene]-1,3-dihydro-indol-2-one

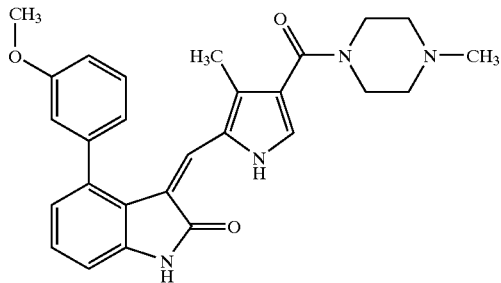

To a solution of 4-(3-methoxy-phenyl)-1,3-dihydro-indol-2-one (59.8 mg, 0.25 mmol) and 3-methyl-4-(4-methyl-piperazine-1-carbonyl)-1H-pyrrole-2-carbaldehyde (61.2 mg, 0.26 mmol) in ethanol (2 mL) was added piperidine (3 drops). The reaction mixture was stirred at room temperature for three days. A yellow solid product was precipitated out, filtered, washed by ethanol for three times, and dried under high vacuum to provide pure product 4-(3-methoxy-phenyl)-3-[3-methyl-4-(4-methyl-piperazine-1-carbonyl)-1H-pyrrol-2-ylmethylene]-1,3-dihydro-indol-2-one as a yellow solid (46.4 mg, 41%).

$^1$H-NMR (400 MHz, DMSO-d$_6$) δ 13.50 (br s, 1H, pyrrole NH), 11.10 (br s, 1H, CONH), 7.47 (t, 1H, aromatic), 7.38 (d, 1H, aromatic), 7.20 (t, 1H, aromatic), 7.06 (dd, 1H, aromatic), 6.99 (dd, 2H, aromatic), 6.91 (d, 2H, aromatic), 6.81 (d, 1H, aromatic), 3.78 (s, 3H, OCH$_3$), 3.45 (m, 4H, 2×CH$_2$), 2.26 (m, 4H, 2×CH$_2$), 2.17 (s, 3H, CH$_3$), 1.65 (s, 3H, CH$_3$). MS m/z 457 [M$^+$+1].

Example 130

3-[3-Methyl-4-(4-methyl-piperazine-1-carbonyl)-1H-pyrrol-2-ylmethylene]-4-phenyl-1,3-dihydro-indol-2-one

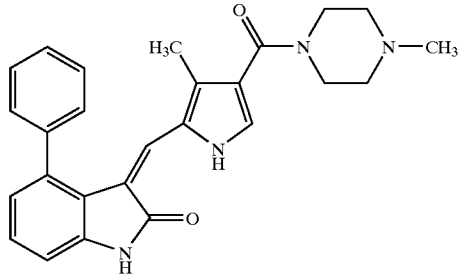

To a solution of 4-phenyl-1,3-dihydro-indol-2-one (52.3 mg, 0.25 mmol) and 3-methyl-4-(4-methyl-piperazine-1-carbonyl)-1H-pyrrole-2-carbaldehyde (61.2 mg, 0.26 mmol) in ethanol (2 mL) was added piperidine (3 drops). The reaction mixture was stirred at room temperature for three days. A yellow solid product was precipitated out, filtered, washed by ethanol for three times, and dried under high vacuum to provide pure product 3-[3-methyl-4-(4-methyl-piperazine-1-carbonyl)-1H-pyrrol-2-ylmethylene]-4-phenyl-1,3-dihydro-indol-2-one as a yellow solid (40.6 mg, 38%).

$^1$H-NMR (400 MHz, DMSO-d) δ 13.50 (br s, 1H, pyrrole NH), 11.11 (br s, 1H, CONH), 7.57 (m, 3H, aromatic), 7.44 (dd, 2H, aromatic), 7.36 (d, 1H, aromatic), 7.21 (t, 1H, aromatic), 6.92 (dd, 1H, aromatic), 6.80 (d, 2H, aromatic), 3.44 (s, 3H, OCH$_3$), 3.41 (m, 4H, 2×CH$_2$), 2.25 (m, 4H, 2×CH$_2$), 2.17 (s, 3H, CH$_3$), 1.59 (s, 3H, CH$_3$). MS m/z 427 [M$^+$+1].

Example 131

3-[4-((cis)-3,5-Dimethyl-piperazine-1-carbonyl]-3-methyl-1H-pyrrol-2-ylmethylene]-4-(4-fluoro-phenyl)-1,3-dihydro-indol-2-one

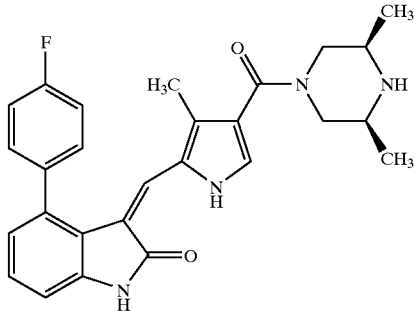

To a solution of 4-(4-fluoro-phenyl)-1,3-dihydro-indol-2-one (56.8 mg, 0.25 mmol) and 4-[(cis)-3,5-dimethyl-piperazine-1-carbonyl]-3-methyl-1H-pyrrole-2-carbaldehyde (64.8 mg, 0.26 mmol) in ethanol (2 mL) was added piperidine (3 drops). The reaction mixture was stirred at room temperature for three days. A yellow solid product was precipitated out, filtered, washed by ethanol for three times, and dried under high vacuum to provide pure product 3-{4-((cis)-3,5-dimethyl-piperazine-1-carbonyl]-3-methyl-1H-pyrrol-2-ylmethylene}-4-(4-fluoro-phenyl)-1,3-dihydro-indol-2-one as a yellow solid (57.8 mg, 50%).

¹H-NMR (400 MHz, DMSO-d₆) δ 13.49 (br s, 1H, pyrrole NH), 11.12 (br s, 1H, CONH), 7.49 (m, 2H, aromatic), 7.39 (m, 3H, aromatic), 7.21 (t, 1H, aromatic), 6.92 (d, 1H, aromatic), 6.80 (t, 2H, aromatic), 4.09 (br, 1H, CH), 3.67 (br, 1H, CH), 2.57 (m, 2H, CH₂), 2.26 (m, 2H, 2×CH), 1.66 (s, 3H, CH₃), 0.92 (s, 6H, 2×CH₃). MS m/z 458 [M⁻–1].

Example 132

4-(4-Chloro-phenyl)-3-[4-[(cis)-3,5-dimethyl-piperazine-1-carbonyl]-3-methyl-1H-pyrrol-2-ylmethylene]-1,3-dihydro-indol-2-one

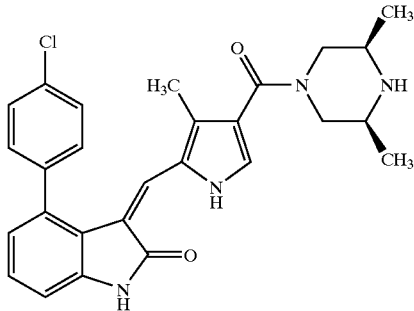

To a solution of 4-(4-chloro-phenyl)-1,3-dihydro-indol-2-one (60.9 mg, 0.25 mmol) and 4-[(cis)-3,5-dimethyl-piperazine-1-carbonyl]-3-methyl-1H-pyrrole-2-carbaldehyde (64.8 mg, 0.26 mmol) in ethanol (2 mL) was added piperidine (3 drops). The reaction mixture was stirred at room temperature for three days. A yellow solid product was precipitated out, filtered, washed by ethanol for three times, and dried under high vacuum to provide pure product 4-(4-chloro-phenyl)-3-{4-[(cis)-3,5-dimethyl-piperazine-1-carbonyl]-3-methyl-1H-pyrrol-2-ylmethylene]-1,3-dihydro-indol-2-one as a yellow solid (29 mg, 25%).

¹H-NMR (400 MHz, DMSO-d₆) δ 13.44 (br s, 1H, pyrrole NH), 11.12 (br s, 1H, CONH), 7.61 (m, 2H, aromatic), 7.46 (dd, 2H, aromatic), 7.37 (d, 1H, aromatic), 7.22 (t, 1H, aromatic), 6.93 (t, 1H, aromatic), 6.82 (d, 1H, aromatic), 6.72 (s, 1H, aromatic), 4.21 (br, 1H, CH), 3.61 (br, 1H, CH), 2.57 (m, 2H, CH₂), 2.28 (m, 2H, 2×CH), 1.61 (s, 3H, CH₃), 0.92 (m, 6H, 2×CH₃). MS m/z 473 [M⁻–1].

Example 133

4-(4-Bromo-phenyl)-3-[4-(3,5-dimethyl-piperazine-1-carbonyl)-3-methyl-1H-pyrrol-2-ylmethylene]-1,3-dihydro-indol-2-one

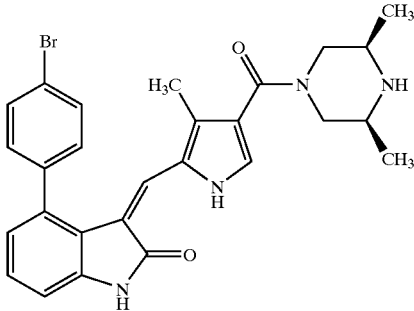

To a solution of 4-(4-bromo-phenyl)-1,3-dihydro-indol-2-one (72.0 mg, 0.25 mmol) and 4-[(cis)-3,5-dimethyl-piperazine-1-carbonyl]-3-methyl-1H-pyrrole-2-carbaldehyde (64.8 mg, 0.26 mmol) in ethanol (2 mL) was added piperidine (3 drops). The reaction mixture was stirred at room temperature for three days. A yellow solid product was precipitated out, filtered, washed by ethanol for three times, and dried under high vacuum to provide pure product 4-(4-bromo-phenyl)-3-[4-[(cis)-3,5-dimethyl-piperazine-1-carbonyl]-3-methyl-1H-pyrrol-2-ylmethylene]-1,3-dihydro-indol-2-one as a yellow solid (79 mg, 61%).

¹H-NMR (400 MHz, DMSO-d₆) δ 13.43 (br s, 1H, pyrrole NH), 11.12 (br s, 1H, CONH), 7.76 (dd, 2H, aromatic), 7.39 (m, 3H, aromatic), 7.22 (t, 1H, aromatic), 6.93 (d, 1H, aromatic), 6.81 (d, 1H, aromatic), 6.70 (s, 1H, aromatic), 4.20 (br, 1H, CH), 3.60 (br, 1H, CH), 2.58 (m, 2H, CH₂), 2.27 (m, 2H, CH), 1.63 (s, 3H, CH₃), 0.92 (s, 6H, 2×CH₃). MS m/z 519 [M⁺+1].

Example 134

3-[4-((cis)-3,5-Dimethyl-piperazine-1-carbonyl]-3-methyl-1H-pyrrol-2-ylmethylene}-4-(4-methoxy-phenyl)-1,3-dihydro-indol-2-one

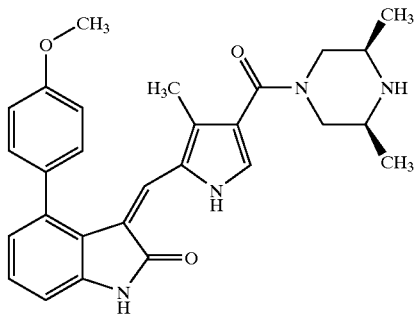

To a solution of 4-(4-methoxy-phenyl)-1,3-dihydro-indol-2-one (59.8 mg, 0.25 mmol) and 4-[(cis)-3,5-dimethyl-piperazine-1-carbonyl]-3-methyl-1H-pyrrole-2-carbaldehyde (64.8 mg, 0.26 mmol) in ethanol (2 mL) was added piperidine (3 drops). The reaction mixture was stirred at room temperature for three days. A yellow solid product was precipitated out, filtered, washed by ethanol for three times, and dried under high vacuum to provide pure product 3-{4-((cis)-3,5-dimethyl-piperazine-1-carbonyl]-3-methyl-1H-pyrrol-2-ylmethylene}-4-(4-methoxy-phenyl)-1,3-dihydro-indol-2-one as a yellow solid (74 mg, 63%).

¹H-NMR (400 MHz, DMSO-d₆) δ 13.47 (br s, 1H, pyrrole NH), 11.08 (br s, 1H, CONH), 7.34 (m, 3H, aromatic), 7.19 (t, 1H, aromatic), 7.11 (dd, 2H, aromatic), 6.89 (d, 1H, aromatic), 6.84 (s, 1H, aromatic), 6.78 (s, 1H, aromatic), 3.82 (s, 3H, OCH₃), 4.45 (br, 1H, CH), 4.0 (br, 1H, CH), 2.58 (m, 2H, CH₂), 2.29 (m, 2H, CH), 1.65 (s, 3H, CH₃), 0.92 (s, 6H, 2×CH₃). MS m/z 471 [M⁺+1].

Example 135

3-[4-((cis)-3,5-Dimethyl-piperazine-1-carbonyl]-3-methyl-1H-pyrrol-2-ylmethylene]-4-(3-methoxy-phenyl)-1,3-dihydro-indol-2-one

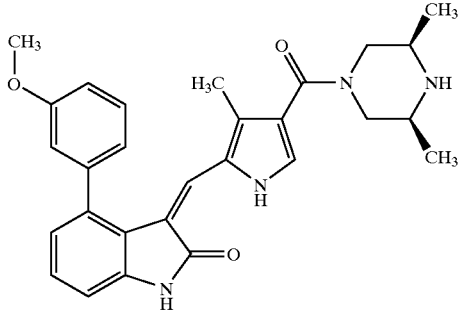

To a solution of 4-(3-methoxy-phenyl)-1,3-dihydro-indol-2-one (59.8 mg, 0.25 mmol) and 4-[(cis)-3,5-dimethyl-piperazine-1-carbonyl]-3-methyl-1H-pyrrole-2-carbaldehyde (64.8 mg, 0.26 mmol) in ethanol (2 mL) was added piperidine (3 drops). The reaction mixture was stirred at room temperature for three days. A yellow solid product was precipitated out, filtered, washed by ethanol for three times, and dried under high vacuum to provide pure product 3-[4-((cis)-3,5-dimethyl-piperazine-1-carbonyl]-3-methyl-1H-pyrrol-2-ylmethylene]-4-(3-methoxy-phenyl)-1,3-dihydro-indol-2-one as a yellow solid (42 mg, 36%).

$^1$H-NMR (400 MHz, DMSO-d$_6$) δ 13.43 (br s, 1H, pyrrole NH), 11.10 (br s, 1H, CONH), 7.46 (q, 1H, aromatic), 7.36 (d, 1H, aromatic), 7.21 (t, 1H, aromatic), 7.06 (dd, 1H, aromatic), 6.99 (dd, 2H, aromatic), 6.91 (d, 2H, aromatic), 6.81 (d, 1H, aromatic), 3.78 (s, 3H, OCH$_3$), 4.30 (br, 1H, CH), 4.00 (br, 1H, CH), 2.58 (m, 2H, CH$_2$), 2.29 (m, 2H, CH), 1.64 (s, 3H, CH$_3$), 0.92 (s, 6H, 2×CH$_3$). MS m/z 469 [M$^-$−1].

Example 136

3-[4-((cis)-3,5-Dimethyl-piperazine-1-carbonyl]-3-methyl-1H-pyrrol-2-ylmethylene]-4-phenyl-1,3-dihydro-indol-2-one

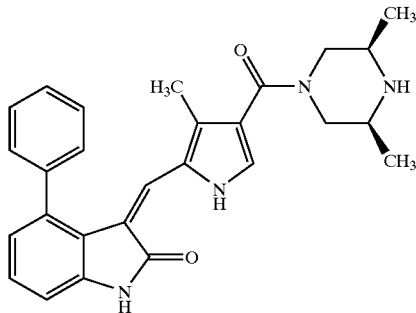

To a solution of 4-phenyl-1,3-dihydro-indol-2-one (52.3 mg, 0.25 mmol) and 4-[(cis)-3,5-dimethyl-piperazine-1-carbonyl]-3-methyl-1H-pyrrole-2-carbaldehyde (64.8 mg, 0.26 mmol) in ethanol (2 mL) was added piperidine (3 drops). The reaction mixture was stirred at room temperature for three days. A yellow solid product was precipitated out, filtered, washed by ethanol for three times, and dried under high vacuum to provide pure product 3-[4-((cis)-3,5-dimethyl-piperazine-1-carbonyl]-3-methyl-1H-pyrrol-2-ylmethylene]-4-phenyl-1,3-dihydro-indol-2-one as a yellow solid (21.5 mg, 20%).

$^1$H-NMR (400 MHz, DMSO-d$_6$) δ 13.49 (br s, 1H, pyrrole NH), 11.10 (br s, 1H, CONH), 7.56 (m, 3H, aromatic), 7.44 (d, 2H, aromatic), 7.35 (d, 1H, aromatic), 7.22 (d, 1H, aromatic), 6.92 (d, 1H, aromatic), 6.81 (m, 2H, aromatic), 4.35 (br, 1H, CH), 3.70 (br, 1H, CH), 2.58 (m, 2H, CH$_2$), 2.29 (m, 2H, CH), 1.58 (s, 3H, CH$_3$), 0.92 (s, 6H, 2×CH$_3$). MS m/z 469 [M$^-$−1].

Example 137

4-(4-Chloro-phenyl)-3-[4-[3-((cis)-3,5-dimethyl-piperazin-1-yl]-3-oxo-propyl]-3,5-dimethyl-1H-pyrrol-2-ylmethylene]-1,3-dihydro-indol-2-one

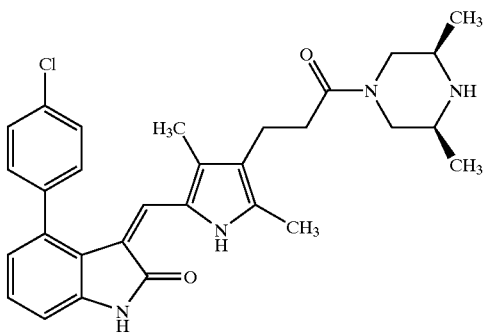

To a solution of 4-(4-chloro-phenyl)-1,3-dihydro-indol-2-one (60.9 mg, 0.25 mmol) and 3-[(cis)-3,5-dimethyl-piperazin-1-yl]-3-oxo-propyl]-3,5-dimethyl-1H-pyrrole-2-carbaldehyde (75.8 mg, 0.26 mmol) in ethanol (2 mL) was added piperidine (3 drops). The reaction mixture was stirred at room temperature for three days. A yellow solid product was precipitated out, filtered, washed by ethanol for three times, and dried under high vacuum to provide pure product 4-(4-chloro-phenyl)-3-[4-[3-((cis)-3,5-dimethyl-piperazin-1-yl]-3-oxo-propyl]-3,5-dimethyl-1H-pyrrol-2-ylmethylene}-1,3-dihydro-indol-2-one as a yellow solid (76.7 mg, 60%).

$^1$H-NMR (400 MHz, DMSO-d$_6$) δ 13.25 (br s, 1H, pyrrole NH), 10.90 (br s, 1H, CONH), 7.61 (d, 2H, aromatic), 7.42 (d, 2H, aromatic), 7.17 (t, 1H, aromatic), 6.91 (d, 1H, aromatic), 6.75 (d, 1H, aromatic), 6.64 (s, 1H, aromatic), 4.24 (d, 1H, CH), 3.49 (d, 1H, CH), 3.40 (m, 4H, 2×CH$_2$), 2.35 (m, 4H, 2×CH$_2$), 2.23 (s, 3H, CH$_3$), 1.59 (s, 3H, CH$_3$), 0.92 (d, 3H, CH$_3$), 0.84 (d, 3H, CH$_3$). MS m/z 517 [M$^+$+1].

Example 138

3-[4-[3-((cis)-3,5-Dimethyl-piperazin-1-yl)-3-oxo-propyl]-3,5-dimethyl-1H-pyrrol-2-ylmethylene]-4-(4-fluoro-phenyl)-1,3-dihydro-indol-2-one

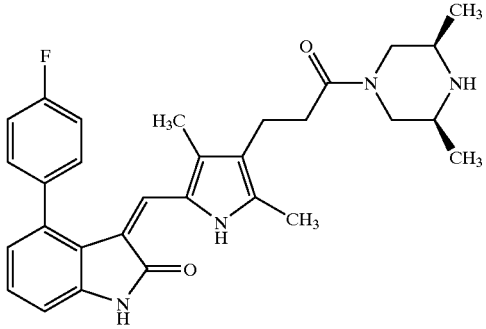

To a solution of 4-(4-fluoro-phenyl)-1,3-dihydro-indol-2-one (56.8 mg, 0.25 mmol) and 3-[(cis)-3,5-dimethyl-piperazin-1-yl]-3-oxo-propyl]-3,5-dimethyl-1H-pyrrole-2-carbaldehyde (75.8 mg, 0.26 mmol) in ethanol (2 mL) was added piperidine (3 drops). The reaction mixture was stirred at room temperature for three days. A yellow solid product was precipitated out, filtered, washed by ethanol for three times, and dried under high vacuum to provide pure product 3-[4-[3-((cis)-3,5-dimethyl-piperazin-1-yl]-3-oxo-propyl]-3,5-dimethyl-1H-pyrrol-2-ylmethylene}-4-(4-fluoro-phenyl)-1,3-dihydro-indol-2-one as a yellow solid (60.7 mg, 49%).

$^1$H-NMR (400 MHz, DMSO-$d_6$) δ 13.27 (br s, 1H, pyrrole NH), 10.89 (br s, 1H, CONH), 7.45 (m, 2H, aromatic), 7.36 (t, 2H, aromatic), 7.12 (t, 1H, aromatic), 6.90 (d, 1H, aromatic), 6.75 (d, 1H, aromatic), 6.66 (s, 1H, aromatic), 4.23 (d, 1H, CH), 3.46 (d, 1H, CH), 3.40 (m, 4H, 2×CH$_2$), 2.37 (m, 4H, 2×CH$_2$), 2.23 (s, 3H, CH$_3$), 1.60 (s, 3H, CH$_3$), 0.92 (d, 3H, CH$_3$), 0.84 (d, 3H, CH$_3$). MS m/z 501 [M$^+$+1].

Example 139

3-[3,5-Dimethyl-4-(4-methyl-piperazine-1-carbonyl)-1H-pyrrol-2-ylmethylene]-4-(4-trifluoromethoxy-phenyl)-1,3-dihydro-indol-2-one

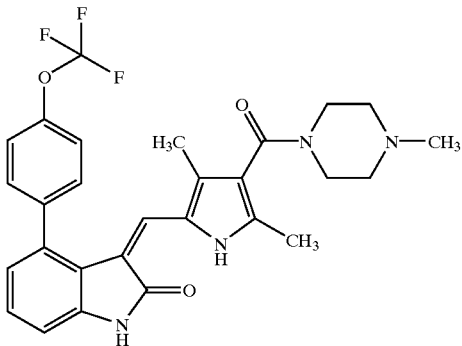

To a solution of 4-(4-trifluoromethoxy-phenyl)-1,3-dihydro-indol-2-one (73.3 mg, 0.25 mmol) and 3,5-dimethyl-4-(4-methyl-piperazine-1-carbonyl)-1H-pyrrole-2-carbaldehyde (64.8 mg, 0.26 mmol) in ethanol (2 mL) was added piperidine (3 drops). The reaction mixture was stirred at room temperature for three days. The solvent was evaporated and the solid was washed by ether for three times to provide pure product 3-[3,5-dimethyl-4-(4-methyl-piperazine-1-carbonyl)-1H-pyrrol-2-ylmethylene]-4-(4-trifluoromethoxy-phenyl)-1,3-dihydro-indol-2-one (79.9 mg, 61%).

$^1$H-NMR (400 MHz, DMSO-$d_6$) δ 13.43 (br s, 1H, pyrrole NH), 11.06 (br s, 1H, CONH), 7.57 (m, 4H, aromatic), 7.20 (t, 1H, aromatic), 6.38 (d, 1H, aromatic), 6.80 (d, 1H, aromatic), 6.73 (s, 1H, aromatic), 3.32 (m, 4H, 2×CH$_2$), 2.24 (m, 7H, 2×CH$_2$+CH$_3$), 2.16 (s, 3H, CH$_3$), 1.56 (s, 3H, CH$_3$). MS m/z 523 [M$^-$−1].

Example 140

2,4-Dimethyl-5-[2-oxo-4-(4-trifluoromethoxy-phenyl)-1,2-dihydro-indol-3-ylidenemethyl]-1H-pyrrole-3-carboxylic Acid (2-Diethylamino-ethyl)-amide

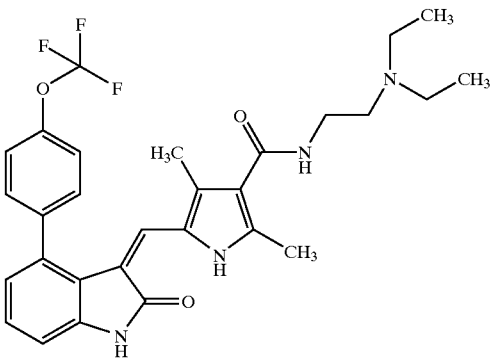

To a solution of 4-(4-trifluoromethoxy-phenyl)-1,3-dihydro-indol-2-one (73.3 mg, 0.25 mmol) and 5-formyl-2,4-dimethyl-1H-pyrrole-3-carboxylic acid (2-diethylamino-ethyl)-amide (69.0 mg, 0.26 mmol) in ethanol (2 mL) was added piperidine (3 drops). The reaction mixture was stirred at room temperature for three days. A yellow solid product was precipitated out, filtered, washed by ethanol for three times, and dried under high vacuum to provide 2,4-dimethyl-5-[2-oxo-4-(4-trifluoromethoxy-phenyl)-1,2-dihydro-indol-3-ylidenemethyl]-1H-pyrrole-3-carboxylic acid (2-diethylamino-ethyl)-amide as a yellow solid (75.6 mg, 56%).

$^1$H-NMR (400 MHz, DMSO-$d_6$) δ 13.49 (br s, 1H, pyrrole NH), 11.07 (br s, 1H, CONH), 7.57 (m, 3H, aromatic), 7.29 (t, 1H, aromatic), 7.20 (t, 1H, aromatic), 6.94 (d, 1H, aromatic), 6.80 (d, 1H, aromatic), 6.74 (s, 1H, aromatic), 3.23 (q, 2H, CH$_2$), 2.49 (m, 6H, 3×CH$_2$), 2.39 (s, 3H, CH$_3$), 1.70 (s, 3H, CH$_3$), 0.95 (t, 6H, 2×CH$_3$). MS m/z 539 [M$^-$−1].

Example 141

2,4-Dimethyl-5-[2-oxo-4-(4-trifluoromethoxy-phenyl)-1,2-dihydro-indol-3-ylidenemethyl]-1H-pyrrole-3-carboxylic Acid (2-[1,2,3]Triazol-1-yl-ethyl)-amide

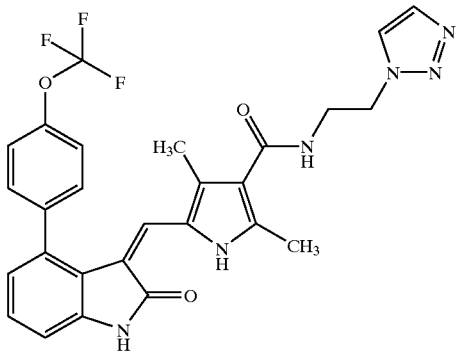

To a solution of 4-(4-trifluoromethoxy-phenyl)-1,3-dihydro-indol-2-one (73.3 mg, 0.25 mmol) and 5-formyl-2,4-dimethyl-1H-pyrrole-3-carboxylic acid (2-[1,2,3]triazol-1-yl-ethyl)-amide (67.9 mg, 0.26 mmol) in ethanol (2 mL) was added piperidine (3 drops). The reaction mixture was stirred at room temperature for three days. A yellow solid product was precipitated out, filtered, washed by ethanol for three times, and dried under high vacuum to provide pure product 2,4-dimethyl-5-[2-oxo-4-(4-trifluoromethoxy-phenyl)-1,2-dihydro-indol-3-ylidenemethyl]-1H-pyrrole-3-carboxylic acid (2-[1,2,3]triazol-1-yl-ethyl)-amide as a yellow solid (49.6 mg, 37%).

$^1$H-NMR (400 MHz, DMSO-$d_6$) δ 13.47 (br s, 1H, pyrrole NH), 11.07 (br s, 1H, CONH), 8.10 (s, 1H, aromatic), 7.67 (m, 1H, aromatic), 7.57 (m, 5H, aromatic+CONH), 7.20 (t, 1H, aromatic), 6.93 (d, 1H, aromatic), 6.78 (d, 1H, aromatic), 6.73 (s, 1H, aromatic), 4.53 (t, 2H, CH$_2$), 3.64 (q, 2H, CH$_2$), 2.29 (s, 3H, CH$_3$), 1.59 (s, 3H, CH$_3$). MS m/z 535 [M$^-$–1].

Example 142

5-Methyl-2-[2-oxo-4-(4-trifluoromethoxy-phenyl)-1,2-dihydro-indol-3-ylidenemethyl]-1H-pyrrole-3-carboxylic Acid (2-Pyrrolidin-1-yl-ethyl)-amide

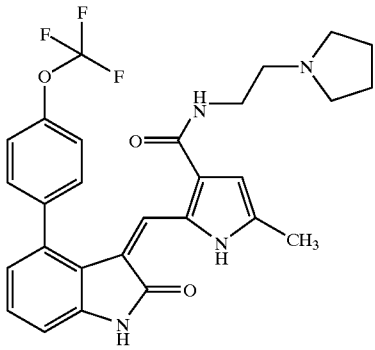

To a solution of 4-(4-trifluoromethoxy-phenyl)-1,3-dihydro-indol-2-one (73.3 mg, 0.25 mmol) and 2-formyl-5-methyl-1H-pyrrole-3-carboxylic acid (2-pyrrolidin-1-yl-ethyl)-amide (64.8 mg, 0.26 mmol) in ethanol (2 mL) was added piperidine (3 drops). The reaction mixture was stirred at room temperature for three days. A yellow solid product was precipitated out, filtered, washed by ethanol for three times, and dried under high vacuum to provide pure product 5-methyl-2-[2-oxo-4-(4-trifluoromethoxy-phenyl)-1,2-dihydro-indol-3-ylidenemethyl]-1H-pyrrole-3-carboxylic acid (2-pyrrolidin-1-yl-ethyl)-amide as a yellow solid (93 mg, 71%).

$^1$H-NMR (400 MHz, DMSO-$d_6$) δ 13.87 (br s, 1H, pyrrole NH), 11.13 (br s, 1H), 8.07 (s, 1H, aromatic), 7.74 (t, 1H, CONH), 7.47 (d, 2H, aromatic), 7.37 (d, 2H, aromatic), 7.21 (t, 1H, aromatic), 6.93 (d, 1H, aromatic), 6.77 (d, 1H, aromatic), 6.41 (d, 1H, aromatic), 3.17 (q, 2H, CH$_2$), 2.49 (m, 6H, 3×CH$_2$), 2.31 (s, 3H, CH$_3$), 1.68 (m, 4H, 2×CH$_2$). MS m/z 523 [M$^-$–1].

Example 143

5-Methyl-2-[2-oxo-4-(4-trifluoromethoxy-phenyl)-1,2-dihydro-indol-3-ylidenemethyl]-1H-pyrrole-3-carboxylic Acid (2-[1,2,3]Triazol-1-yl-ethyl)-amide

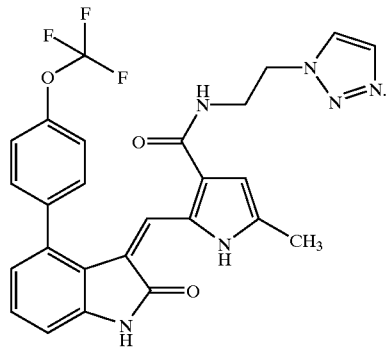

To a solution of 4-(4-trifluoromethoxy-phenyl)-1,3-dihydro-indol-2-one (73.3 mg, 0.25 mmol) and 2-formyl-5-methyl-1H-pyrrole-3-carboxylic acid (2-[1,2,3]triazol-1-yl-ethyl)-amide (61.8 mg, 0.26 mmol) in ethanol (2 mL) was added piperidine (3 drops). The reaction mixture was stirred at room temperature for three days. A yellow solid product was precipitated out, filtered, washed by ethanol for three times, and dried under high vacuum to provide pure product 5-methyl-2-[2-oxo-4-(4-trifluoromethoxy-phenyl)-1,2-dihydro-indol-3-ylidenemethyl]-1H-pyrrole-3-carboxylic acid (2-[1,2,3]triazol-1-yl-ethyl)-amide as a yellow solid (96.6 mg, 74%).

$^1$H-NMR (400 MHz, DMSO-$d_6$) δ 13.87 (brs, 1H, pyrrole NH), 11.15 (brs, 1H, CONH), 8.00 (m, 3H, aromatic), 7.72 (s, 1H, CONH), 7.49 (m, 2H, aromatic), 7.41 (d, 2H, aromatic), 7.21 (t, 1H, aromatic), 6.94 (d, 1H, aromatic), 6.78 (d, 1H, aromatic), 6.34 (d, 1H, aromatic), 4.52 (t, 2H, CH$_2$), 3.48 (m, 2H, CH$_2$), 2.29 (s, 3H, CH$_3$) MS m/z 521 [M$^-$–1].

Example 144

5-Methyl-2-[2-oxo-4-(4-trifluoromethoxy-phenyl)-1,2-dihydro-indol-3-ylidenemethyl]-1H-pyrrole-3-carboxylic Acid (3-Pyrrolidin-1-yl-propyl)-amide

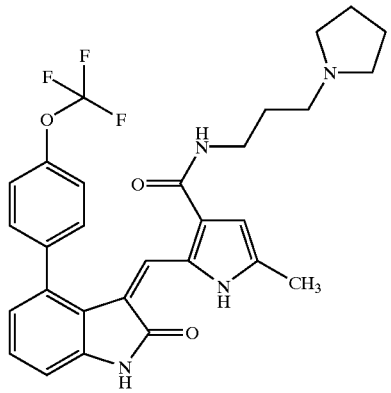

To a solution of 4-(4-trifluoromethoxy-phenyl)-1,3-dihydro-indol-2-one (69.3 mg, 0.25 mmol) and 5-formyl-2,4-dimethyl-1H-pyrrole-3-carboxylic acid (3-pyrrolidin-1-yl-propyl)-amide (69.8 mg, 0.26 mmol) in ethanol (2 mL) was added piperidine (3 drops). The reaction mixture was stirred at room temperature for three days. A yellow solid product was precipitated out, filtered, washed by ethanol for three times, and dried under high vacuum to provide pure product 5-methyl-2-[2-oxo-4-(4-trifluoromethoxy-phenyl)-1,2-dihydro-indol-3-ylidenemethyl]-1H-pyrrole-3-carboxylic acid (3-pyrrolidin-1-yl-propyl)-amide as a yellow solid (96.8 mg, 72%).

$^1$H-NMR (400 MHz, DMSO-d$_6$) δ 13.93 (br s, 1H, pyrrole NH), 11.05 (br s, 1H, CONH), 8.04 (s, 1H, aromatic), 7.85 (t, 1H, CONH), 7.47 (m, 2H, aromatic), 7.35 (d, 1H, aromatic), 7.19 (t, 1H, aromatic), 6.92 (d, 1H, aromatic), 6.75 (d, 1H, aromatic), 6.40 (d, 1H, aromatic), 3.32 (m, 2H, CH$_2$), 3.08 (q, 2H, CH$_2$), 2.40 (m, 6H, 3×CH$_2$), 2.30 (s, 3H, CH$_3$), 1.67 (m, 4H, 2×CH$_2$), MS m/z 537 [M$^-$−1].

Example 145

4-(2-Fluoro-phenyl)-3-[1-[5-(2-pyrrolidin-1-yl-ethyl)-4,5,6,7-tetrahydro-1H-indol-2-yl]-meth-(Z)-ylidene]-1,3-dihydro-indol-2-one

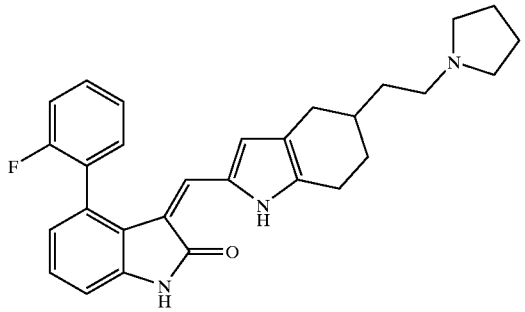

$^1$H NMR (400 MHz, DMSO-d$_6$) δ 13.09 (s, NH, 1H), 10.97 (s, NH, 1H), 7.56 (m, 1H), 7.36 (m, 3H), 7.16 (t, J=7.8 Hz, 1H), 6.93 (d, J=7.8 Hz, 1H), 6.79 (d, J=7.8 Hz, 1H), 6.40 (s, 1H), 5.86 (s, 1H), 2.66 (m, 2H), 2.56 (m, 2H), 2.43 (m, 6H), 2.03 (m, 1H), 1.85 (m, 1H), 1.64 (m, 4H), 1.44 (m, 3H). MS m/z 456.2 [M$^+$+1].

Example 146

4-(3-Fluoro-phenyl)-3-[1-[5-(2-pyrrolidin-1-yl-ethyl)-4,5,6,7-tetrahydro-1H-indol-2-yl]-meth-(Z)-ylidene]-1,3-dihydro-indol-2-one

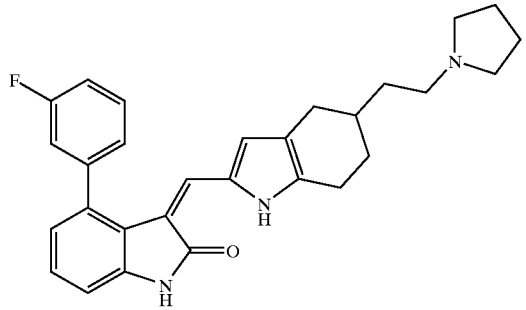

$^1$H NMR (400 MHz, DMSO-d$_6$) δ 13.12 (s, NH, 1H), 10.99 (s, NH, 1H), 7.55 (m, 1H), 7.32 (m, 1H), 7.26 (m, 2H), 7.18 (m, 1H), 6.90 (d, J=7.8 Hz, 1H), 6.76 (d, J=7.4 Hz, 1H), 6.50 (s, 1H), 5.93 (s, 1H), 3.06 (m, 6H), 2.68 (m, 2H), 2.51 (m, 2H), 2.06 (m, 1H), 1.84 (m, 4H), 1.62 (m, 3H), 1.42 (m, 1H). MS m/z 454 [M$^-$−1].

Example 147

4-(2-Fluoro-phenyl)-3-[1-[-5-(2-morpholin-4-yl-ethyl)-4,5,6,7-tetrahydro-1H-indol-2-yl]-meth-(Z)-ylidene]-1,3-dihydro-indol-2-one

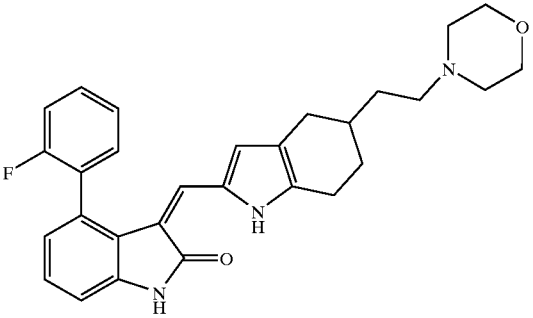

$^1$H NMR (400 MHz, DMSO-d$_6$) δ 13.11 (s, NH, 1H), 10.99 (s, NH, 1H), 7.58 (m, 1H), 7.41 (m, 3H), 7.18 (m, 1H), 6.94 (d, J=7.4 Hz, 1H), 6.80 (d, J=8.2 Hz, 1H), 6.42 (s, 1H), 5.88 (s, 1H), 3.54 (m, 4H), 2.69 (m, 2H), 2.56 (m, 1H), 2.32 (m, 6H), 2.04 (m, 1H), 1.85 (m, 1H), 1.66 (m, 1H), 1.44 (m, 3H). MS m/z 470 [M$^-$−1].

Example 148

4-(3-Fluoro-phenyl)-3-[1-[5-(2-morpholin-4-yl-ethyl)-4,5,6,7-tetrahydro-1H-indol-2-yl]-meth-(Z)-ylidene]-1,3-dihydro-indol-2-one

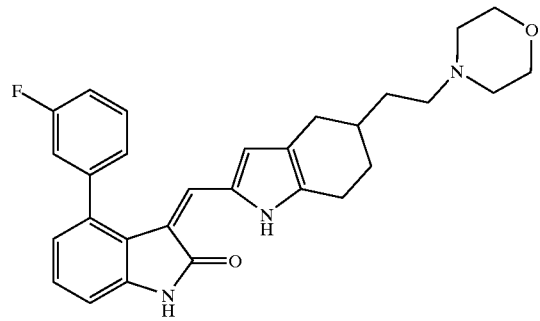

¹H NMR (400 MHz, DMSO-d₆) δ 13.10 (s, NH, 1H), 10.96 (s, NH, 1H), 7.55 (m, 1H), 7.25 (m, 3H), 7.15 (t, J=7.8 Hz, 1H), 6.90 (d, J=7.4 Hz, 1H), 6.76 (d, J=7.4 Hz, 1H), 6.55 (s, 1H), 5.92 (s, 1H), 3.53 (m, 4H), 2.68 (m, 2H), 2.56 (m, 1H), 2.31 (m, 6H), 2.04 (m, 1H), 1.85 (m, 1H), 1.64 (m, 1H), 1.45 (m, 3H). MS m/z 470 [M−1].

Example 149

4-(2-Fluoro-phenyl)-3-[1-{5-[2-(4-methyl-piperazin-1-yl)-ethyl]-4,5,6,7-tetrahydro-1H-indol-2-yl}-meth-(Z)-ylidene]-1,3-dihydro-indol-2-one

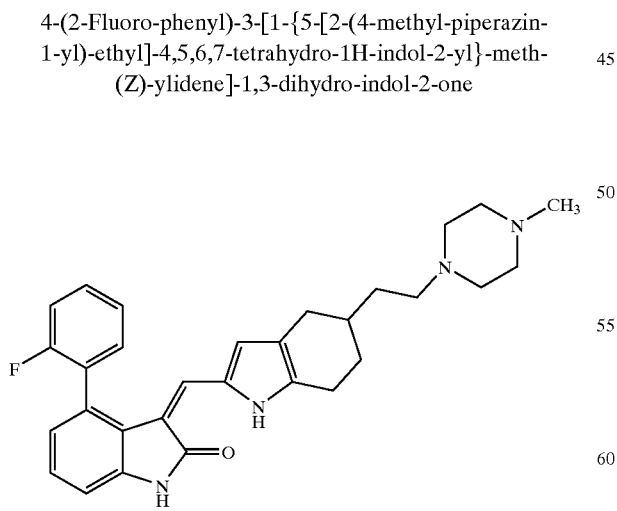

MS m/z 483 [M−1].

Example 150

4-(3-Fluoro-phenyl)-3-[1-{5-[2-(4-methyl-piperazin-1-yl)-ethyl]-4,5,6,7-tetrahydro-1H-indol-2-yl}-meth-(Z)-ylidene]-1,3-dihydro-indol-2-one

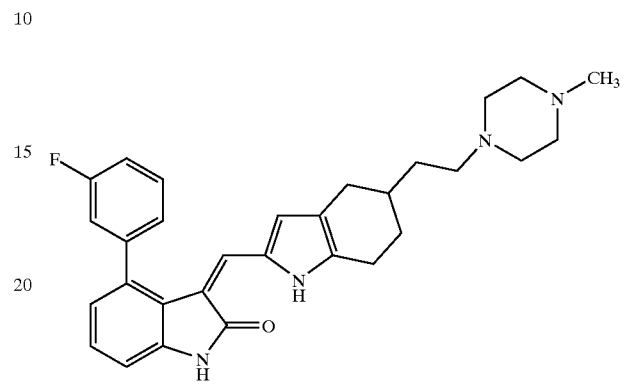

MS m/z 483 [M−1].

Example 151

5-[4-(4-Fluoro-phenyl)-2-oxo-1,2-dihydro-indol-(3Z)-ylidenemethyl]-4-methyl-1H-pyrrole-3-carboxylic Acid (2-Diethylamino-ethyl)-amide

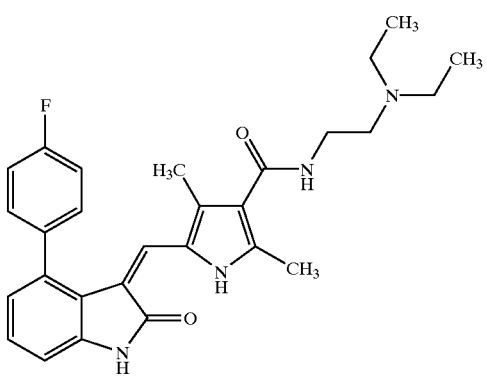

¹H NMR (400 MHz, DMSO-d₆) δ 13.48 (s, NH, 1H), 11.11 (s, NH, 1H), 7.68 (m, 2H), 7.43 (m, 4H), 7.21 (t, J=7.7 Hz, 1H), 6.93 (dd, J=0.9 Hz, J=7.6 Hz, 1H), 6.79 (m, 2H), 3.21 (m, 2H), 2.45 (m, 6H), 1.84 (s, 3H), 0.94 (t, J=7.4 Hz, 6H); MS m/z 461 [M⁺+1].

Example 152

5-[4-(3-Chloro-phenyl)-2-oxo-1,2-dihydro-indol-(3Z)-ylidenemethyl]-4-methyl-1H-pyrrole-3-carboxylic Acid (2-Diethylamido-ethyl)-amide

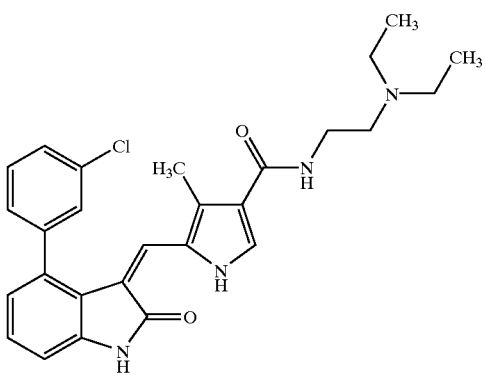

$^1$H NMR (400 MHz, DMSO-d$_6$) δ 13.47 (s, NH, 1H), 11.13 (s, NH, 1H), 7.72 (m, 1H), 7.67 (d, J=3.5 Hz, 1H), 7.58 (m, 2H), 7.53 (m, 1H), 7.41 (m, 1H), 7.2 (t, J=7.7 Hz, 1H), 6.94 (dd, J=0.7 Hz, J=7.8 Hz, 1H), 6.86 (s, 1H), 6.82 (dd, J=0.8 Hz, J=7.7 Hz, 1H), 3.19 (m, 2H), 2.44 (m, 6H), 1.85 (s, 3H), 0.95 (t, J=7.3 Hz 6H). MS m/z 477 [M$^+$+1].

Example 153

5-[4-(3-Fluoro-phenyl)-2-oxo-1,2-dihydro-indol-(3Z)-ylidenemethyl]-2,4-dimethyl-1H-pyrrole-3-carboxylic Acid Methyl-(1-methyl-piperidin-4-yl)-amide

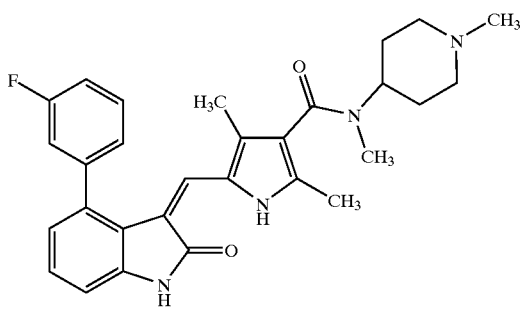

$^1$H NMR (400 MHz, DMSO-d$_6$) δ 13.40 (s, NH, 1H), 11.05 (s, NH, 1H), 7.56 (m, 1H), 7.28 (m, 3H), 7.17 (t, J=7.8 Hz, 1H), 6.92 (d, J=7.4 Hz, 1H), 6.78 (d, J=7.6 Hz, 1H), 6.74 (s, 1H), 3.30 (m, 4H), 2.72 (m, 4H), 2.19 (s, 3H), 2.12 (br s, 3H), 1.92 (m, 1H), 1.74 (m, 2H), 1.54 (s, 3H), 1.40 (m, 1H). MS m/z 485 [M−1].

Example 154

5-Methoxy-3-[1-[3-methyl-4-(morpholine-4-carbonyl)-1H-pyrrol-2-yl]-meth-(Z)-ylidene]-4-phenyl-1,3-dihydro-indol-2-one

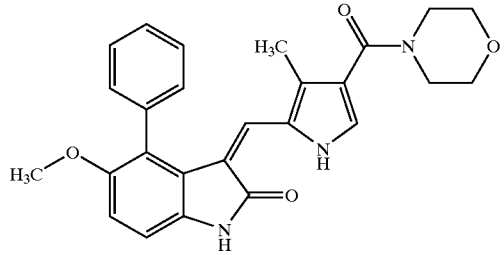

To a mixture of 4-bromo-5-methoxy-3-[1-[3-methyl-4-(morpholine-4-carbonyl)-1H-pyrrol-2-yl]-meth-(Z)-ylidene]-1,3-dihydro-indol-2-one (223 mg, 0.5 mmol) and phenylboronic acid (73 mg, 0.6 mmol) in DME/water (5 mL) were added Palladium catalyst Pd(PPh$_3$)$_2$Cl$_2$ (10.5 mg) and sodium carbonate (106 mg, 1 mmol). The system was degassed and then charged with nitrogen. The degas procedure was repeated for three times. The mixture was stirred under nitrogen at 85° C. oil bath for overnight. TLC showed some de-bromination of the starting material. The degass procedure was repeated for three more times and the heating was continued for 3 more days. The mixture was cooled to room temperature, the unreacted starting material was filtered off and the mother liquor was concentrated. The residue was purified on a silica gel column to give 21 mg of 5-methoxy-3-[1-[3-methyl-4-(morpholine-4-carbonyl)-1H-pyrrol-2-yl]-meth-(Z)-ylidene]-4-phenyl-1,3-dihydro-indol-2-one.

$^1$H NMR (400 MHz, DMSO-d$_6$) δ 13.60 (s, NH, 1H), 10.91 (s, NH, 1H), 7.55 (m, 2H), 7.46 (m, 1H), 7.36 (d, J=3.5 Hz, 1H), 7.29 (m, 2H), 6.93 (m, 1H), 6.86 (m, 1H), 6.43 (s, 1H), 3.62 (s, 3H), 3.53 (m, 4H), 3.44 (m, 4H), 1.54 (s, 3H). MS m/z 444 [M$^+$+1].

Example 155

5-[4-(3-Fluoro-phenyl)-2-oxo-1,2-dihydro-indol-(3Z)-ylidenemethyl]-2,4-dimethyl-1H-pyrrole-3-carboxylic Acid (2-Hydroxy-3-[1,2,3]triazol-1-yl-propyl)-amide

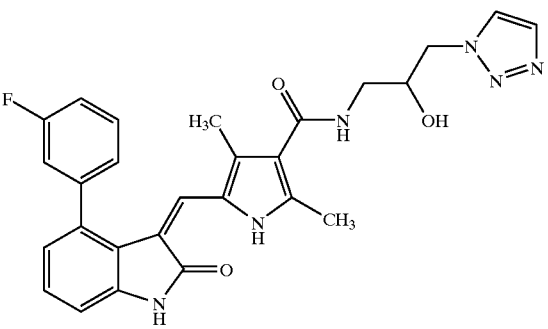

$^1$H NMR (400 MHz, DMSO-d$_6$) δ 13.51 (s, NH, 1H), 11.09 (s, NH, 1H), 8.06 (d, J=0.8 Hz, 1H), 7.71 (d, J=0.8 Hz, 1H), 7.61 (m, 2H), 7.32 (m, 3H), 7.19 (t, J=7.8 Hz, 1H), 6.94 (dd, J=0.8 Hz, J=7.8 Hz, 1H), 6.81 (m, 2H), 5.36 (d, J=5.9 Hz, 1H), 4.47 (m, 1H), 4.26 (m, 1H), 3.96 (m, 1H), 3.24 (m, 2H), 2.41 (s, 3H), 1.76 (s, 3H). MS m/z 499 [M−1].

Example 156

2-[4-(3-Fluoro-phenyl)-2-oxo-1,2-dihydro-indol-(3Z)-ylidenemethyl]-5-methyl-1H-pyrrole-3-carboxylic Acid (2-Hydroxy-3-[1,2,3]triazol-1-yl-propyl)-amide

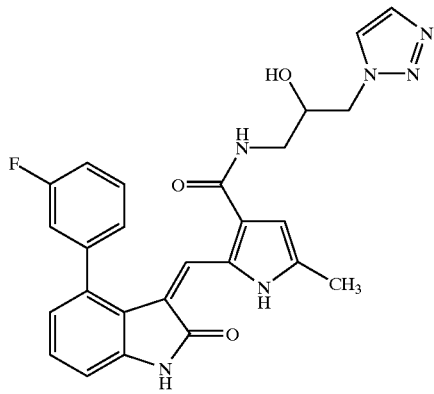

$^1$H NMR (400 MHz, DMSO-d$_6$) δ 13.90 (s, NH, 1H), 11.16 (s, NH, 1H), 8.11 (s, 1H), 8.04 (s, 1H), 8.01 (m, 1H), 7.75 (s, 1H), 7.39 (m, 1H), 7.18 (m, 3H), 7.12 (m, 1H), 6.93 (dd, J=1.2 Hz, J=7.8 Hz, 1H), 6.77 (d, J=7.8 Hz, 1H), 6.48 (m, 1H), 5.33 (d, J=5.5 Hz, 1H), 4.43 (m, 1H), 4.22 (m, 1H), 3.90 (m, 1H), 3.19 (m, 1H), 3.08 (m, 1H), 2.32 (s, 3H). MS m/z 485 [M$^-$–1].

Example 157

2-[4-(3-Fluoro-phenyl)-2-oxo-1,2-dihydro-indol-(3Z)-ylidenemethyl]-5-methyl-1H-pyrrole-3-carboxylic Acid (2-Hydroxy-3-[1,2,3]triazol-2-yl-propyl)-amide

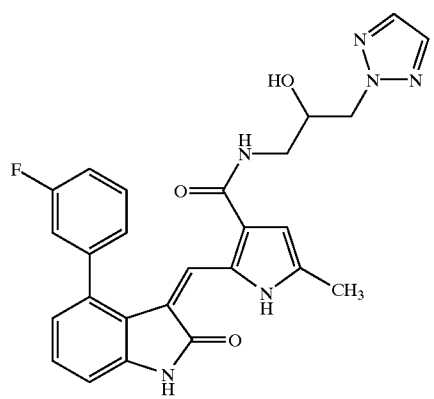

$^1$H NMR (400 MHz, DMSO-d$_6$) δ 13.88 (s, NH, 1H), 11.15 (s, NH, 1H), 8.02 (s, 1H), 7.97 (s, 1H), 7.82 (s, 2H), 7.40 (m, 1H), 7.17 (m, 4H), 6.93 (d, J=7.8 Hz, 1H), 6.77 (d, J=7.8 Hz, 1H), 6.47 (m, 1H), 5.17 (d, J=5.9 Hz, 1H), 4.35 (m, 2H), 4.19 (m, 1H), 3.51 (m, 2H), 3.24 (m, 1H), 3.10 (m, 1H), 2.32 (s, 3H). MS m/z 485 [M–1].

Example 158

2-[4-(3-Fluoro-phenyl)-2-oxo-1,2-dihydro-indol-(3Z)-ylidenemethyl]-5-methyl-1H-pyrrole-3-carboxylic Acid (2-Hydroxy-3-morpholin-4-yl-propyl)-amide

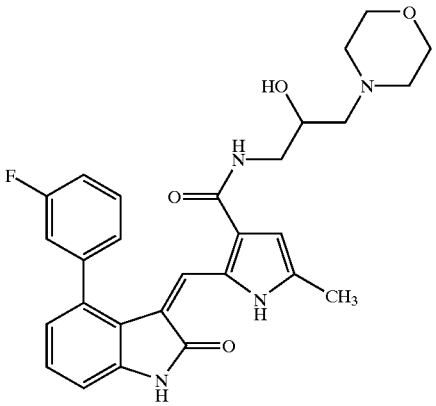

$^1$H NMR (400 MHz, DMSO-d$_6$) δ 13.88 (s, NH, 1H), 11.15 (s, NH, 1H), 8.02 (s, 1H), 7.82 (m, 1H), 7.46 (m, 1H), 7.18 (m, 4H), 6.93 (d, J=7.0 Hz, 1H), 6.77 (d, J=7.4 Hz, 1H), 6.45 (m, 1H), 4.69 (m, 1H), 3.72 (m, 1H), 3.60 (m, 4H), 3.24 (m, 1H), 2.95 (m, 1H), 2.50 (m, 2H), 2.45 (m, 3H), 2.32 (s, 3H), 2.28 (m, 1H); MS m/z 503 [M–1].

Example 159

4-(3-Fluoro-phenyl)-3-[1-{5-methyl-3-[2-(4-methyl-piperazin-1-yl)-2-oxo-ethyl]-1H-pyrrol-2-yl}-meth-(Z)-ylidene]-1,3-dihydro-indol-2-one

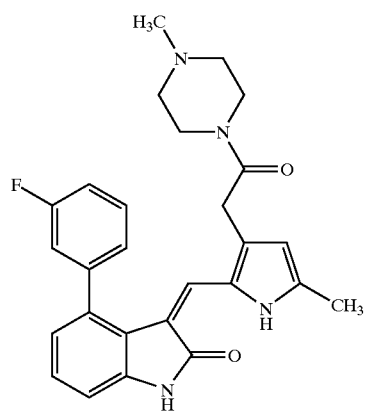

$^1$H NMR (400 MHz, DMSO-d$_6$) δ 13.39 (s, NH, 1H), 11.02 (s, NH, 1H), 7.54 (m, 1H), 7.29 (m, 3H), 7.17 (t, J=7.8 Hz, 1H), 6.93 (dd, J=0.8 Hz, J=7.4 Hz 1H), 6.77 (m, 2H), 5.90 (m, 1H), 3.39 (m, 2H), 3.25 (m, 2H), 2.99 (s, 2H), 2.94 (s, 3H), 2.22 (m, 4H), 2.17 (s, 3H). MS m/z 457 [M–1].

Example 160

2-{2-[4-(3-Fluoro-phenyl)-2-oxo-1,2-dihydro-indol-(3Z)-ylidenemethyl]-5-methyl-1H-pyrrol-3-yl}-N-methyl-N-(1-methyl-piperidin-4-yl)-acetamide

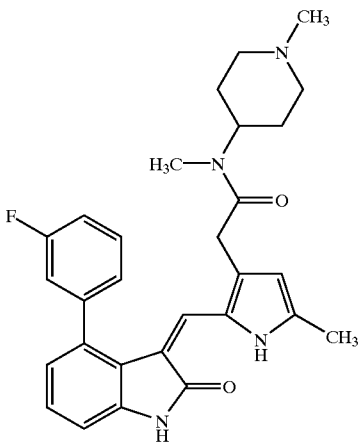

MS m/z 485 [M−1].

Example 161

3-[1-{3-[2-((cis)-3,5-Dimethyl-piperazin-1-yl)-2-oxo-ethyl]-5-methyl-1H-pyrrol-2-yl}-meth-(Z)-ylidene]-4-(3-dihydro-indol-2-one

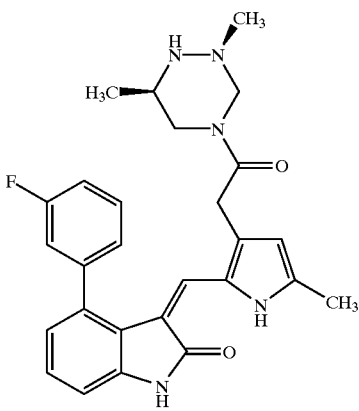

$^1$H NMR (400 MHz, DMSO-d$_6$) δ 13.39 (s, NH, 1H), 11.07 (s, NH, 1H), 7.54 (m, 1H), 7.29 (m, 3H), 7.17 (t, J=7.8 Hz, 1H), 6.93 (d, J=7.0 Hz, 1H), 6.77 (m, 2H), 5.89 (d, J=2.3 Hz, 1H), 4.14 (m, 1H), 3.36 (m, 1H), 2.98 (m, 2H), 2.42 (m, 4H), 2.00 (t, J=10.9 Hz, 1H), 2.29 (s, 3H), 0.92 (d, J=6.3 Hz, 3H), 0.88 (d, J=5.1 Hz, 3H). MS m/z 471 [M −1].

Example 162

4-(3-Fluoro-phenyl)-3-[1-[5-methyl-3-(2-morpholin-4-yl-2-oxo-ethyl)-1H-pyrrol-2-yl]-meth-(Z)-ylidene]-1,3-dihydro-indol-2-one

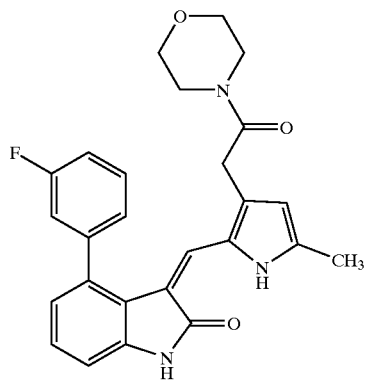

$^1$H NMR (400 MHz, DMSO-d$_6$) δ 13.41 (s, NH, 1H), 11.05 (s, NH, 1H), 7.54 (m, 1H), 7.34 (m, 1H), 7.27 (m, 2H), 7.17 (t, J=7.8 Hz, 1H), 6.93 (d, J=7.8 Hz, 1H), 6.77 (dd, J=0.8 Hz, J=7.8 Hz, 1H), 6.75 (s, 1H), 5.92 (d, J=2.3 Hz, 1H), 3.53 (m, 4H), 3.39 (m, 2H), 3.34 (m, 4H), 3.01 (s, 2H), 2.29 (s, 3H). MS m/z 444 [M−1].

Example 163

4-(3-Fluoro-phenyl)-3-[1-{5-methyl-3-[2-oxo-2-(4-pyrrolidin-1-yl-piperidin-1-yl)-ethyl]-1H-pyrrol-2-yl}-meth-(Z)-ylidene]-1,3-dihydro-indol-2-one

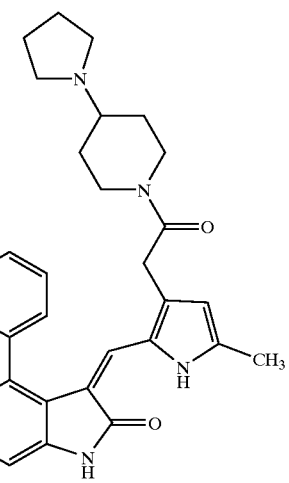

$^1$H NMR (400 MHz, DMSO-d$_6$) δ 13.38 (s, NH, 1H), 11.00 (s, NH, 1H), 7.52 (m, 1H), 7.32 (m, 1H), 7.26 (m, 2H), 7.15 (t, J=7.8 Hz, 1H), 6.91 (dd, J=1.2 Hz, J=7.8 Hz, 1H), 6.76 (m, 2H), 5.88 (d, J=2.3 Hz, 1H), 4.07 (m, 1H), 3.49 (m, 1H), 2.97 (m, 3H), 2.70 (m, 1H), 2.42 (m, 4H), 2.27 (s, 3H), 2.14 (m, 1H), 1.75 (m, 2H), 1.64 (m, 4H), 1.18 (m, 2H). MS m/z 511 [M−1].

Example 164

4-(3-Fluoro-phenyl)-3-[1-{5-methyl-3-[2-oxo-2-((S)-2-pyrrolidin-1-ylmethyl-pyrrolidin-1-yl)-ethyl]-1H-pyrrol-2-yl}-meth-(Z)-ylidene]-1,3-dihydro-indol-2-one

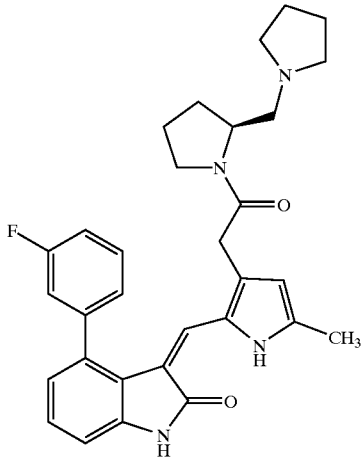

$^1$H NMR (400 MHz, DMSO-d$_6$) δ 13.38 (s, NH, 1H), 11.00 (s, NH, 1H), 7.52 (m, 1H), 7.24 (m, 3H), 7.14 (t, J=7.8 Hz, 1H), 6.91 (d, J=7.0 Hz, 1H), 6.76 (m, 2H), 5.88 (d, J=2.3 Hz, 1H), 3.99 (m, 1H), 3.21 (m, 2H), 2.90 (m, 2H), 2.55 (m, 2H), 2.40 (m, 4H), 2.31 (s, 3H), 1.86 (m, 4H), 1.62 (m, 4H). MS m/z 511 [M$^-$−1].

Example 165

2-{2-[4-(3-Fluoro-phenyl)-2-oxo-1,2-dihydro-indol-(3Z)-ylidenemethyl]-5-methyl-1H-pyrrol-3-yl}-N-(2-hydroxy-3-[1,2,3]triazol-1-yl-propyl)-acetamide

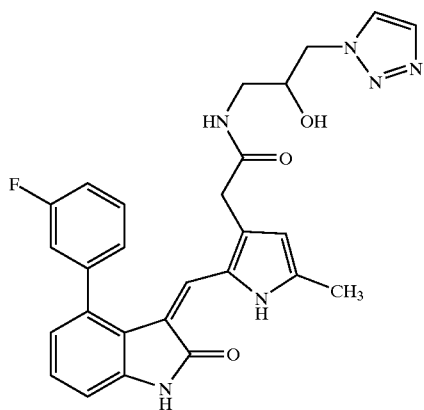

$^1$H NMR (400 MHz, DMSO-d$_6$) δ 13.35 (s, NH, 1H), 11.00 (s, NH, 1H), 8.03 (d, J=0.8 Hz, 1H), 7.82 (m, 1H), 7.71 (d, J=0.8 Hz, 1H), 7.50 (m, 1H), 7.26 (m, 3H), 7.17 (t, J=7.8 Hz, 1H), 6.93 (dd, J=1.2 Hz, J=7.8 Hz, 1H), 6.78 (m, 2H), 5.96 (d, J=2.3 Hz, 1H), 5.34 (d, J=5.4 Hz, 1H), 4.40 (m, 1H), 4.21 (m, 1H), 3.86 (m, 1H), 3.08 (m, 2H), 2.82 (s, 2H), 2.29 (s, 3H). MS m/z 499 [M−1].

Example 166

{2-[4-(3-Fluoro-phenyl)-2-oxo-1,2-dihydro-indol-(3Z)-ylidenemethyl]-5-methyl-1H-pyrrol-3-yl}-N-(2-pyrrolidin-1-yl-ethyl)-acetamide

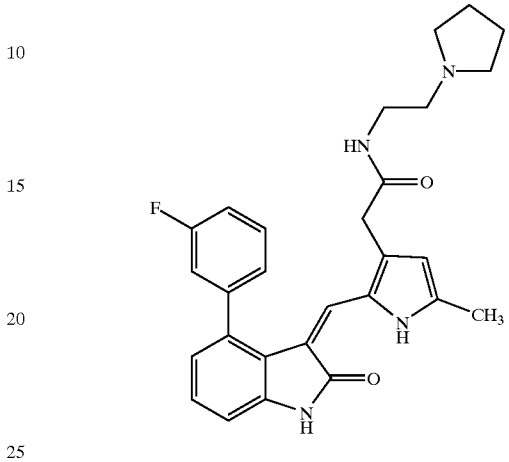

$^1$H NMR (400 MHz, DMSO-d$_6$) δ 13.34 (s, NH, 1H), 11.00 (s, NH, 1H), 7.53 (m, 2H), 7.25 (m, 3H), 7.17 (t, J=7.4 Hz, 1H), 6.94 (dd, J=0.8 Hz, J=7.8 Hz, 1H), 6.79 (m, 2H), 5.93 (d, J=2.3 Hz, 1H), 3.11 (m, 2H), 2.76 (s, 2H), 2.42 (m, 6H), 2.28 (s, 3H), 1.66 (m, 4H). MS m/z 471 [M−1].

Example 167

2-{2-[4-(3-Fluoro-phenyl)-2-oxo-1,2-dihydro-indol-(3Z)-ylidenemethyl]-5-methyl-1H-pyrrol-3-yl}-N-(3-pyrrolidin-1-yl-propyl)-acetamide

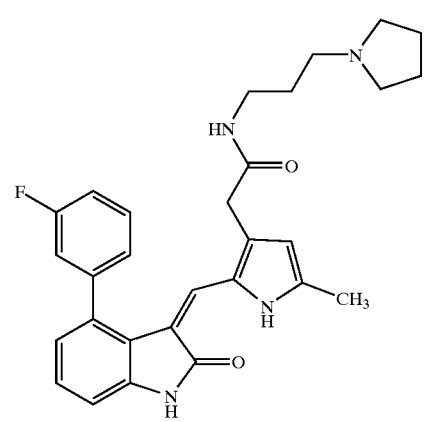

$^1$H NMR (400 MHz, DMSO-d$_6$) δ 13.34 (s, NH, 1H), 11.01 (s, NH, 1H), 7.58 (m, 1H), 7.51 (m, 1H), 7.25 (m, 3H), 7.17 (t, J=7.8 Hz, 1H), 6.93 (d, J=7.8 Hz, 1H), 6.79 (m, 2H), 5.91 (d, J=2.3 Hz, 1H), 3.20 (m, 2H), 2.74 (s, 2H), 2.37 (m, 5H), 2.28 (s, 3H), 1.64 (m, 3H), 1.53 (m, 2H). MS m/z 485 [M−1].

Example 168

N-(2,4-Dioxo-1,2,3,4-tetrahydro-pyrimidin-5-ylmethyl)-2-{2-[4-(3-fluoro-phenyl)-2-oxo-1,2-dihydro-indol-(3Z)-ylidenemethyl]-5-methyl-1H-pyrrol-3-yl}-acetamide

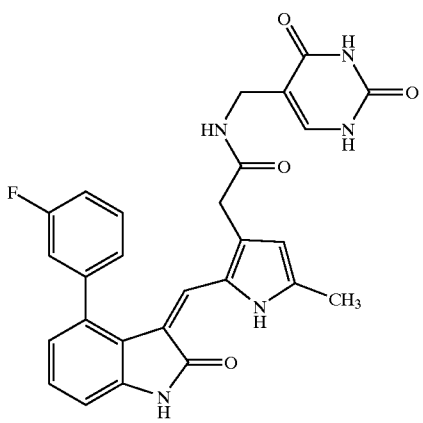

$^1$H NMR (400 MHz, DMSO-d$_6$) δ 13.38 (s, NH, 1H), 11.02 (s, NH, 1H), 10.93 (s, 2H), 8.07 (m, 1H), 7.48 (m, 1H), 7.24 (m, 3H), 7.17 (t, J=7.4 Hz, 1H), 6.94 (dd, J=0.8 Hz, J=7.8 Hz, 1H), 6.78 (m, 2H), 5.96 (d, J=2.3 Hz, 1H), 5.18 (s, 1H), 3.89 (d, J=5.5 Hz, 2H), 2.86 (s, 2H), 2.29 (s, 3H). MS m/z 498 [M−1].

Example 169

4-(2-Fluoro-phenyl)-3-[1-{5-methyl-3-[2-(4-methyl-piperazin-1-yl)-2-oxo-ethyl]-1H-pyrrol-2-yl}-meth-(Z)-ylidene]-1,3-dihydro-indol-2-one

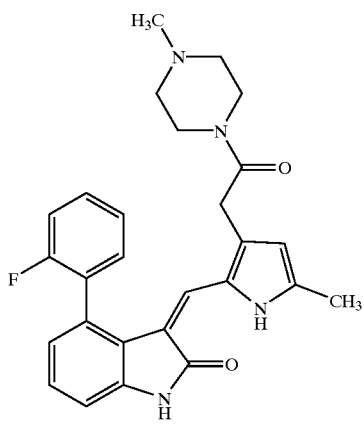

$^1$H NMR (400 MHz, DMSO-d$_6$) δ 13.42 (s, NH, 1H), 11.02 (s, NH, 1H), 7.56 (m, 1H), 7.45 (m, 1H), 7.36 (m, 2H), 7.19 (t, J=7.4 Hz, 1H), 6.95 (d, J=7.8 Hz, 1H), 6.80 (d, J=7.4 Hz, 1H), 6.59 (d, J=1.2 Hz, 1H), 5.89 (d, J=2.3 Hz, 1H), 3.39 (m, 2H), 3.24 (m, 2H), 2.94 (m, 2H), 2.29 (s, 3H), 2.22 (m, 4H), 2.18 (s, 3H). MS m/z 457 [M−1].

Example 170

2-{2-[4-(2-Fluoro-phenyl)-2-oxo-1,2-dihydro-indol-(3Z)-ylidenemethyl]-5-methyl-1H-pyrrol-3-yl}-N-methyl-N-(1-methyl-piperidin-4-yl)-acetamide

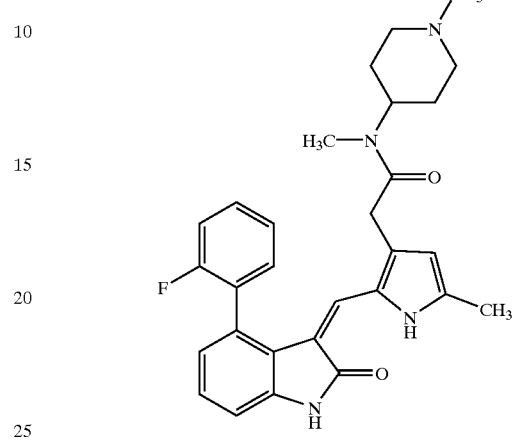

MS m/z 485 [M−1].

Example 171

3-[1-{3-[2-((cis)-3,5-Dimethyl-piperazin-1-yl)-2-oxo-ethyl]-5-methyl-1H-pyrrol-2-yl}-meth-(Z)-ylidene]-4-(2-fluoro-phenyl)-1,3-dihydro-indol-2-one

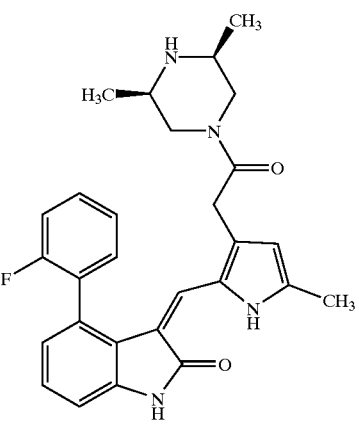

$^1$H NMR (400 MHz, DMSO-d$_6$) δ 13.41 (s, NH, 1H), 11.04 (s, NH, 1H), 7.54 (m, 1H), 7.44 (m, 1H), 7.36 (m, 2H), 7.19 (t, J=7.4 Hz, 1H), 6.96 (dd, J=0.8 Hz, J=7.8 Hz, 1H), 6.81 (d, J=7.4 Hz, 1H), 6.62 (s, 1H), 5.88 (d, J=2.0 Hz, 1H), 4.16 (m, 1H), 3.38 (m, 1H), 2.95 (m, 2H), 2.45 (m, 1H), 2.29 (s, 3H), 2.00 (t, J=10.7 Hz, 1H), 0.95 (d, J=6.3 Hz, 3H), 0.88 (d, J=6.3 Hz, 3H). MS m/z 471 [M−1].

Example 172

4-(2-Fluoro-phenyl)-3-[1-[5-methyl-3-(2-morpholin-4-yl-2-oxo-ethyl)-1H-pyrrol-2-yl]-meth-(Z)-ylidene]-1,3-dihydro-indol-2-one

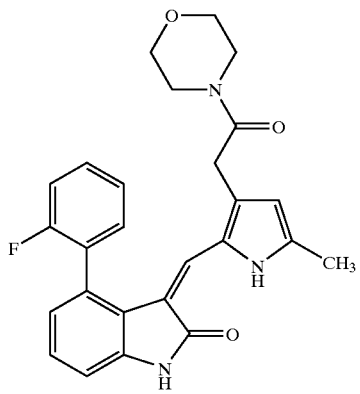

$^1$H NMR (400 MHz, DMSO-d$_6$) δ 13.42 (s, NH, 1H), 11.03 (s, NH, 1H), 7.56 (m, 1H), 7.44 (m, 1H), 7.36 (m, 2H), 7.19 (t, J=7.8 Hz, 1H), 6.96 (dd, J=0.8 Hz, J=7.8 Hz, 1H), 6.81 (d, J=7.4 Hz, 1H), 6.59 (s, 1H), 5.92 (d, J=2.3 Hz, 1H), 3.53 (m, 4H), 3.39 (m, 2H), 3.27 (m, 2H), 2.95 (m, 2H), 2.29 (s, 3H). MS m/z 444 [M−1].

Example 173

4-(2-Fluoro-phenyl)-3-[1-{5-methyl-3-[2-oxo-2-(4-pyrrolidin-1-yl-piperidin-1-yl)-ethyl]-1H-pyrrol-2-yl}-meth-(Z)-ylidene]-1,3-dihydro-indol-2-one

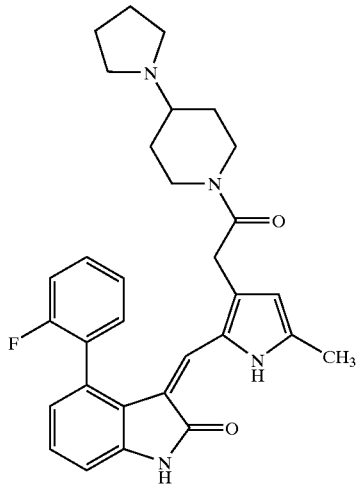

$^1$H NMR (400 MHz, DMSO-d$_6$) δ 13.41 (s, NH, 1H), 11.05 (s, NH, 1H), 7.56 (m, 1H), 7.46 (m, 1H), 7.35 (m, 2H), 7.19 (t, J=7.8 Hz, 1H), 6.96 (dd, J=6.6 Hz, 1H), 6.80 (dd, J=0.8 Hz, J=7.8 Hz, 1H), 6.60 (s, 1H), 5.89 (d, J=2.0 Hz, 1H), 4.11 (m, 1H), 3.48 (m, 1H), 3.34 (m, 4H), 2.42 (m, 3H), 2.71 (m, 1H), 2.29 (s, 3H), 2.42 (m, 1H), 1.78 (m, 2H), 1.67 (m, 4H), 1.21 (m, 2H). MS m/z 511 [M−1].

Example 174

4-(4-Chloro-phenyl)-3-[1-{3,5-dimethyl-4-[3-(4-methyl-piperazin-1-yl)-3-oxo-propyl]-1H-pyrrol-2-yl}-meth-(Z)-ylidene]-1,3-dihydro-indol-2-one

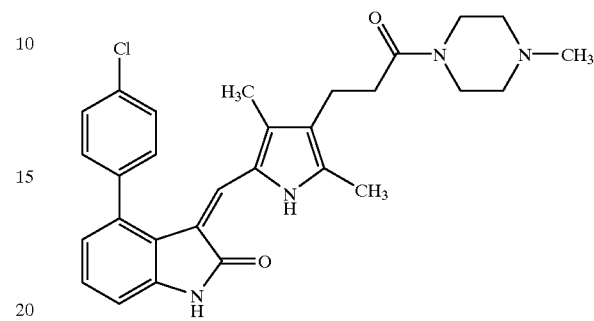

$^1$H NMR (400 MHz, DMSO-d$_6$) δ 13.26 (s, NH, 1H), 10.89 (s, NH, 1H), 7.60 (d, J=8.9 Hz, 2H), 7.42 (d, J=7.9 Hz, 2H), 7.13 (t, J=7.6 Hz, 1H), 6.91 (d, J=7.4 Hz, 1H), 6.75 (d, J=7.5 Hz, 1H), 6.64 (s, 1H), 3.39 (m, 4H), 2.54 (m, 4H), 2.36 (m, 4H), 2.24 (s, 3H), 2.19 (s, 3H), 1.59 (s, 3H). MS m/z 503 [M−1].

Example 175

4-(4-Chloro-phenyl)-3-[1-{4-[3-((cis)-3,5-dimethyl-piperazin-1-yl)-3-oxo-propyl]-3,5-dimethyl-1H-pyrrol-2-yl}-meth-(Z)-ylidene]-1,3-dihydro-indol-2-one

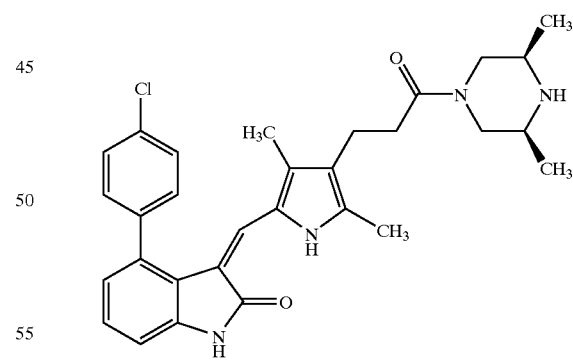

$^1$H NMR (400 MHz, DMSO-d$_6$) δ 13.25 (s, NH, 1H), 10.89 (s, NH, 1H), 7.59 (d, J=8.8 Hz, 2H), 7.42 (d, J=7.8 Hz, 2H), 7.13 (t, J=7.8 Hz, 1H), 6.91 (d, J=8.0 Hz, 1H), 6.75 (d, J=7.4 Hz, 1H), 6.64 (s, 1H), 4.22 (d, J=12.0 Hz, 1H), 3.49 (d, J=10.4 Hz, 1H), 2.53 (m, 2H), 2.32 (m, 5H), 2.23 (s, 3H), 2.15 (m, 1H), 1.92 (t, J=1.6 Hz, 1H), 1.60 (s, 3H), 0.93 (d, J=6.3 Hz, 3H), 0.85 (d, J=5.6 Hz, 3H). MS m/z 517 [M−1].

Example 176

3-[1-{3,5-Dimethyl-4-[3-(4-methyl-piperazin-1-yl)-3-oxo-propyl]-1H-pyrrol-2-yl}-meth-(Z)-ylidene]-4-(4-fluoro-phenyl)-1,3-dihydro-indol-2-one

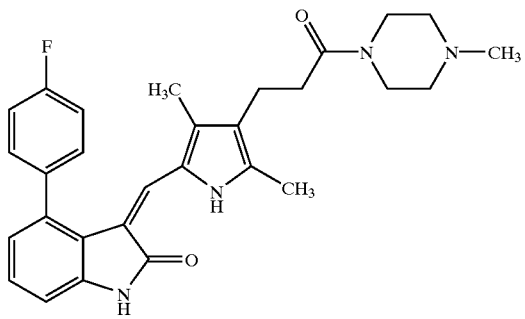

$^1$H NMR (400 MHz, DMSO-$d_6$) δ 13.28 (s, NH, 1H), 10.89 (s, NH, 1H), 7.44 (m, 2H), 7.37 (m, H), 7.13 (t, J=7.5 Hz, 1H), 6.90 (d, J=7.4 Hz, 1H), 6.75 (d, J=8.0 Hz, 1H), 6.68 (s, 1H), 3.38 (m, 2H), 3.28 (m, 2H), 2.53 (m, 2H), 2.33 (t, J=7.4 Hz, 2H), 2.24 (s, 3H), 2.17 (m, 2H), 2.10 (m, 5H), 1.60 (s, 3H). MS m/z 487 [M$^+$+1].

Example 177

5-[4-[3-(2-Hydroxy-ethyl)-phenyl]-2-oxo-1,2-dihydro-indol-(3Z)-ylidenemethyl]-2,4-dimethyl-1H-pyrrole-3-carboxylic Acid (2-Pyrrolidin-1-yl-ethyl)-amide

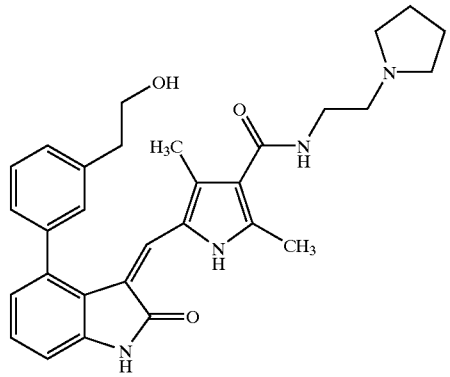

$^1$H NMR (400 MHz, DMSO-$d_6$) δ 13.42 (s, 1H, NH), 11.03 (s, 1H, NH), 7.45 (m, 2H), 7.35 (d, 1H), 7.26 (s, 1H), 7.20 (d, 1H), 7.15 (t, 1H), 6.89 (d, 1H), 6.75 (d, 1H), 6.74 (s, 1H), 4.66 (t, 1H), 3.61 (m, 2H), 3.28 (m, 2H), 2.79 (m, 2H), 2.54 (m, 6H), 2.36 (s, 3H), 1.68 (m, 4H), 1.64 (s, 3H). MS m/z 497 [M−1].

Example 178

5-[4-[3-(2-Hydroxy-ethyl)-phenyl]-2-oxo-1,2-dihydro-indol-(3Z)-ylidenemethyl]-2,4-dimethyl-1H-pyrrole-3-carboxylic Acid (2-[1,2,3]Triazol-1-yl-ethyl)-amide

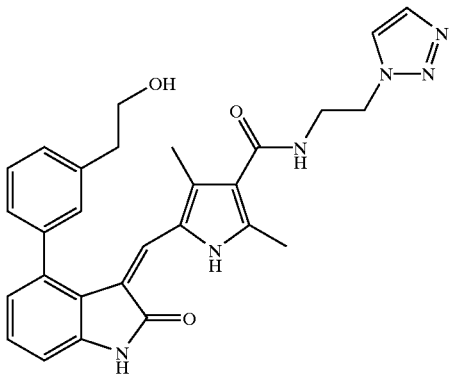

$^1$H NMR (400 MHz, DMSO-$d_6$) δ 13.45 (s, NH, 1H), 11.01 (s, NH, 1H), 8.08 (s, 1H), 7.69 (s, 1H), 7.59 (t, J=5.9 Hz, 1H), 7.42 (t, J=7.6 Hz, 1H), 7.31 (d, J=7.8 Hz, 1H), 7.24 (s, 1H), 7.19 (d, J=7.4 Hz, 1H), 7.15 (t, J=7.8 Hz, 1H), 6.88 (d, J=7.8 Hz, 1H), 6.75 (d, J=7.4 Hz, 1H), 6.72 (s, 1H), 4.66 (t, J=5.1 Hz, 1H), 4.50 (t, J=5.8 Hz, 2H), 3.60 (m, 4H), 2.76 (t, J=7.0 Hz, 2H), 2.25 (s, 3H), 1.54 (s, 3H). MS m/z 495 [M−1].

Example 179

2-[4-[3-(2-Hydroxy-ethyl)-phenyl]-2-oxo-1,2-dihydro-indol-(3Z)-ylidenemethyl]-5-methyl-1H-pyrrole-3-carboxylic Acid (2-[1,2,3]Triazol-1-yl-ethyl)-amide

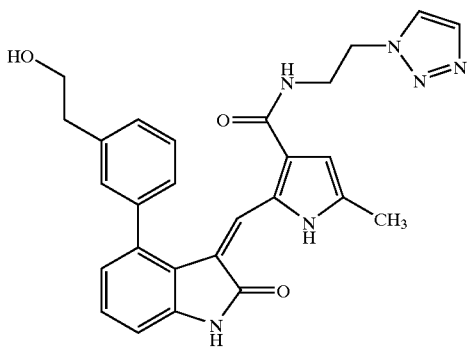

$^1$H NMR (400 MHz, DMSO-$d_6$) δ 13.79 (s, 1H, NH), 11.10 (s, 1H, NH), 8.05 (t, 1H), 7.98 (s, 1H), 7.85 (s, 1H), 7.72 (s, 1H), 7.29 (t, 1H), 7.23 (d, 1H), 7.21 (s, 1H), 7.17 (t, 1H), 7.12 (d, 1H), 6.88 (d, 1H), 6.73 (d, 1H), 6.29 (s, 1H), 4.51 (t, 1H), 4.44 (t, 2H), 3.63 (dd, 2H), 3.42 (m, 2H), 2.74 (t, 2H), 2.26 (s, 3H). MS m/z 481 [M−1].

Example 180

3-[1-[3,5-Dimethyl-4-(4-pyrrolidin-1-yl-piperidine-1-carbonyl)-1H-pyrrol-2-yl]-meth-(Z)-ylidene]-4-(3-methoxy-phenyl)-1,3-dihydro-indol-2-one

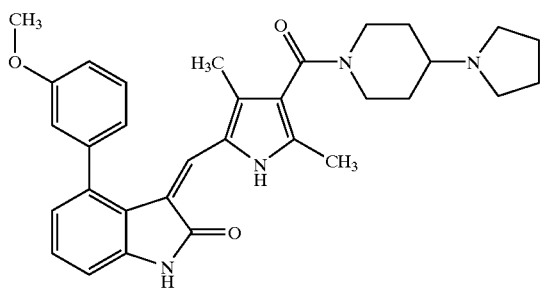

$^1$H NMR (400 MHz, DMSO-d$_6$) δ 13.41 (s, NH, 1H), 11.00 (s, NH, 1H), 7.43 (t, 1H), 7.15 (t, 1H), 7.02 (d, 1H), 6.96 (m, 2H), 6.89 (d, 1H), 6.82 (s, 1H), 6.77 (d, 1H), 4.20 (m, 1H), 3.74 (s, 3H), 3.60 (m, 1H), 2.92 (m, 2H), 2.43 (m, 4H), 2.21 (s, 3H), 1.78 (m, 2H), 1.63 (m, 4H), 1.55 (s, 3H), 1.22 (m, 3H). MS m/z 523 [M−1].

Example 181

4-(2-Chloro-phenyl)-3-[1-[3,5-dimethyl-4-(4-pyrrolidin-1-yl-piperidine-1-carbonyl)-1H-pyrrol-2-yl]-meth-(Z)-ylidene]-1,3-dihydro-indol-2-one

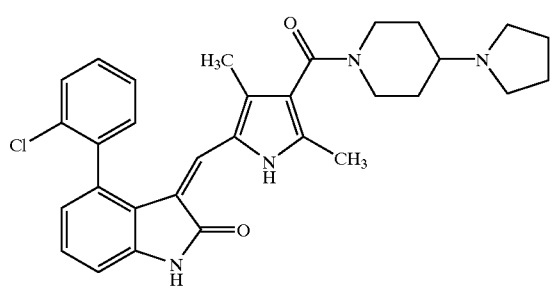

$^1$H NMR (400 MHz, DMSO-d$_6$) δ 13.40 (s, NH, 1H), 10.50 (br s, NH, 1H), 7.66 (m, 1H), 7.51 (m, 2H), 7.43 (m, 1H), 7.19 (t, 1H), 6.94 (d, 1H), 6.74 (d, 1H), 6.38 (s, 1H), 4.20 (m, 1H), 3.60 (m, 1H), 2.92 (m, 2H), 2.43 (m, 4H), 2.21 (s, 3H), 1.78 (m, 2H), 1.63 (m, 4H), 1.55 (s, 3H), 1.22 (m, 3H). MS m/z 528 [M−1].

Example 182

4-(4-Chloro-phenyl)-3-[1-[3,5-dimethyl-4-(4-pyrrolidin-1-yl-piperidine-1-carbonyl)-1H-pyrrol-2-yl]-meth-(Z)-ylidene]-1,3-dihydro-indol-2-one

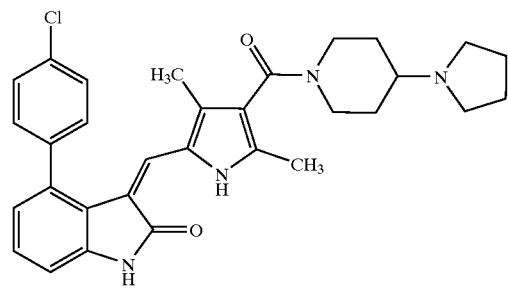

$^1$H NMR (400 MHz, DMSO-d$_6$) δ 13.38 (s, NH, 1H), 11.02 (s, NH, 1H), 7.59 (d, 2H), 7.43 (d, 2H), 7.17 (t, 1H), 6.91 (d, 1H), 6.77 (d, 1H), 6.63 (s, 1H), 4.20 (m, 1H), 3.40 (d, 2H), 2.92 (t, 2H), 2.44 (d, 4H), 2.21 (s, 3H), 2.85 (s, 1H), 1.77 (m, 2H), 1.64 (m, 5H), 1.53 (s, 3H), 1.22 (m, 1H). MS m/z 528 [M−1].

Example 183

4-(3-Chloro-phenyl)-3-[1-[3,5-dimethyl-4-(4-pyrrolidin-1-yl-piperidine-1-carbonyl)-1H-pyrrol-2-yl]-meth-(Z)-ylidene]-1,3-dihydro-indol-2-one

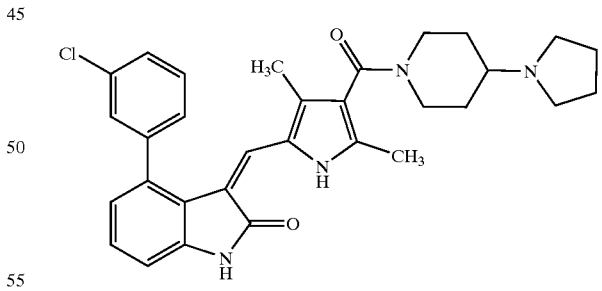

$^1$H NMR (400 MHz, DMSO-d$_6$) δ 13.38 (s, NH, 1H), 10.50 (br s, NH, 1H), 7.52 (m, 2H), 7.39 (m, 1H), 7.17 (t, J=7.8 Hz, 1H), 7.04 (t, J=8.2 Hz, 1H), 6.92 (m, 1H), 6.78 (d, J=7.4 Hz, 1H), 6.74 (s, 1H), 4.20 (m, 1H), 3.40 (m, 1H), 2.92 (m, 2H), 2.44 (m, 4H), 2.21 (s, 3H), 2.85 (m, 1H), 1.77 (m, 2H), 1.64 (m, 5H), 1.53 (s, 3H), 1.22 (m, 1H). MS m/z 528 [M$^-$−1].

Example 184

3-[1-[3,5-Dimethyl-4-(4-pyrrolidin-1-yl-piperidine-1-carbonyl)-1H-pyrrol-2-yl]-meth-(Z)-ylidene]-4-(3-fluoro-phenyl)-1,3-dihydro-indol-2-one

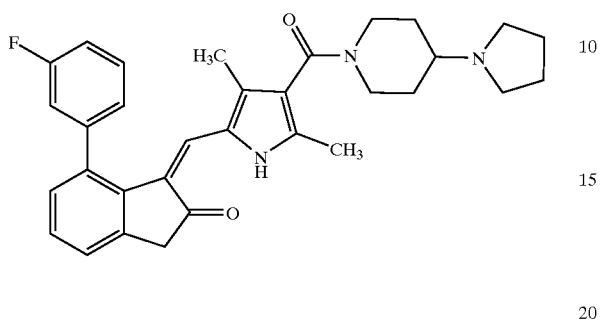

$^1$H NMR (400 MHz, DMSO-d$_6$) δ 13.41 (s, NH, 1H), 11.05 (s, NH, 1H), 7.57 (m, 1H), 7.28 (m, 3H), 7.17 (t, 1H), 6.92 (d, 1H), 6.78 (d, 1H), 6.74 (s, 1H), 4.15 (m, 1H), 3.49 (m, 1H), 2.93 (m, 2H), 2.43 (m, 4H), 2.21 (s, 3H), 2.14 (m, 1H), 1.77 (m, 2H), 1.63 (m, 5H), 1.56 (s, 3H), 1.22 (m, 1H). MS m/z 511 [M−1].

Example 185

3-[1-[5-Methyl-3-(4-pyrrolidin-1-yl-piperidine-1-carbonyl)-1H-pyrrol-2-yl]-meth-(Z)-ylidene]-4-phenyl-1,3-dihydro-indol-2-one

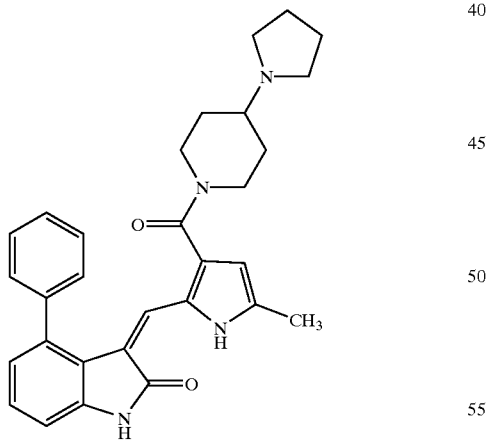

$^1$H NMR (400 MHz, DMSO-d$_6$) δ 13.65 (s, NH, 1H), 11.12 (s, NH, 1H), 7.43 (m, 3H), 7.37 (m, 2H), 7.20 (t, J=7.8 Hz, 1H), 6.95 (s, 1H), 6.92 (d, J=7.8 Hz, 1H), 6.76 (d, J=7.4 Hz, 1H), 6.06 (d, J=2.3 Hz, 1H), 4.05 (m, 1H), 3.45 (m, 1H), 2.87 (m, 2H), 2.45 (m, 4H), 2.35 (s, 3H), 2.20 (m, 1H), 1.85 (m, 1H), 1.65 (m, 5H), 1.30 (m, 1H), 1.15 (m, 1H). MS m/z 479 [M−1].

Example 186

4-(4-Chloro-phenyl)-3-[1-[5-methyl-3-(4-pyrrolidin-1-yl-piperidine-1-carbonyl)-1H-pyrrol-2-yl]-meth-(Z)-ylidene]-1,3-dihydro-indol-2-one

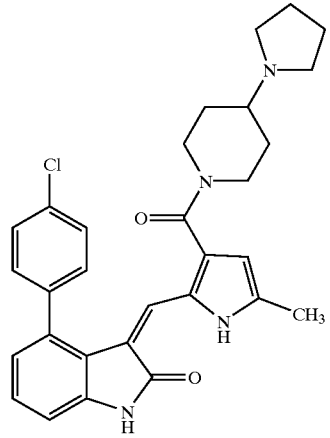

$^1$H NMR (400 MHz, DMSO-d$_6$) δ 13.67 (s, NH, 1H), 11.15 (s, NH, 1H), 7.49 (d, 2H), 7.40 (d, 2H), 7.21 (t, 1H), 7.06 (s, 1H), 6.94 (d, 1H), 6.74 (d, 1H), 6.10 (s, 1H), 4.11 (m, 1H), 3.55 (m, 1H), 2.87 (m, 2H), 2.47 (m, 4H), 2.34 (s, 3H), 2.21 (m, 1H), 1.82 (m, 1H), 1.69 (m, 5H), 1.30 (m, 1H), 1.20 (m, 1H). MS m/z 514 [M−1].

Example 187

4-(3-Fluoro-phenyl)-3-[1-[5-methyl-3-(4-pyrrolidin-1-yl-piperidine-1-carbonyl)-1H-pyrrol-2-yl]-meth-(Z)-ylidene]-1,3-dihydro-indol-2-one

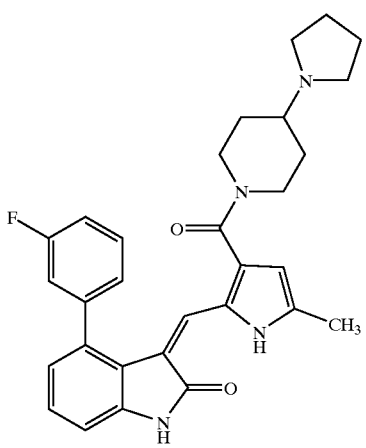

$^1$H NMR (400 MHz, DMSO-d$_6$) δ 13.60 (s, NH, 1H), 11.12 (s, NH, 1H), 7.48 (m, 1H), 7.23 (m, 4H), 6.95 (d, 1H), 6.94 (s, 1H), 6.78 (d, 1H), 6.09 (d, 1H), 4.08 (m, 1H), 3.52 (m, 1H), 2.81 (m, 2H), 2.47 (m, 4H), 2.32 (s, 3H), 2.18 (m, 1H), 1.82 (m, 1H), 1.67 (m, 5H), 1.21 (m, 2H). MS m/z 497 [M−1].

Example 188

3-[1-[5-Methyl-3-(morpholine-4-carbonyl)-1H-pyrrol-2-yl]-meth-(Z)-ylidene]-4-phenyl-1,3-dihydro-indol-2-one

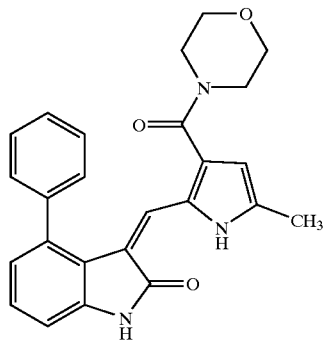

$^1$H NMR (400 MHz, DMSO-d$_6$) δ 13.63 (s, NH, 1H), 11.10 (s, NH, 1H), 7.39 (m, 5H), 7.18 (t, J=7.6 Hz, 1H), 6.96 (s, 1H), 6.89 (d, J=6.6, 1H), 6.73 (dd, J=0.8 Hz, J=7.8 Hz, 1H), 6.06 (d, J=2.3 Hz, 1H), 3.52 (m, 2H), 3.35 (m, 4H), 3.18 (m, 2H), 2.26 (s, 3H). MS m/z 412 [M−1].

Example 189

4-(2-Chloro-phenyl)-3-[1-[5-methyl-3-(morpholine-4-carbonyl)-1H-pyrrol-2-yl]-meth-(Z)-ylidene]-1,3-dihydro-indol-2-one

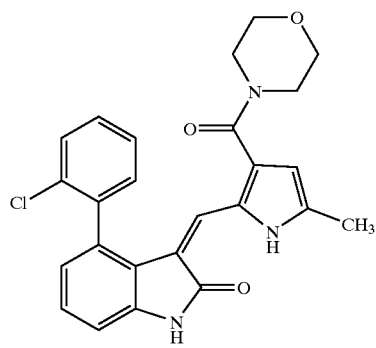

$^1$H NMR (400 MHz, DMSO-d$_6$) δ 13.65 (s, NH, 1H), 11.15 (s, NH, 1H), 7.54 (dd, J=1.6 Hz, J=8.2 Hz, 1H), 7.44 (m, 2H), 3.33 (dd, J=2.0 Hz, J=7.0 Hz, 1H), 7.20 (t, J=7.6 Hz, 1H), 6.95 (dd, J=0.8 Hz, J=7.8 Hz, 1H), 6.69 (d, J=7.8 Hz, 1H), 6.57 (s, 1H), 6.07 (d, J=2.7 Hz, 1H), 3.58 (m, 2H), 3.44 (m, 4H), 3.22 (m, 2H), 2.31 (s, 3H). MS m/z 446 [M−1].

Example 190

4-(4-Chloro-phenyl)-3-[1-[5-methyl-3-(morpholine-4-carbonyl)-1H-pyrrol-2-yl]-meth-(Z)-ylidene]-1,3-dihydro-indol-2-one

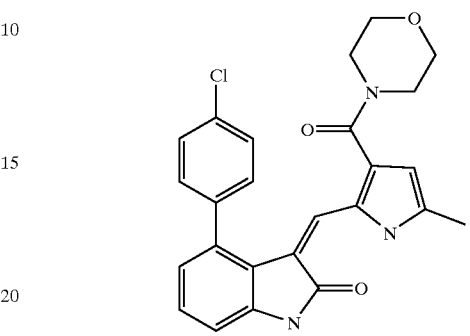

$^1$H NMR (400 MHz, DMSO-d$_6$) δ 13.67 (s, NH, 1H), 11.14 (s, NH, 1H), 7.48 (dd, J=2.0 Hz, J=6.6 Hz, 2H), 7.38 (dd, J=2.0 Hz, J=6.6 Hz, 2H), 7.19 (t, J=7.6 Hz, 1H), 7.07 (s, 1H), 6.91 (dd, J=0.8 Hz, J=7.8 Hz, 1H), 6.73 (d, J=7.4 Hz, 1H), 6.10 (d, J=2.3 Hz, 1H), 3.54 (m, 2H), 3.42 (m, 4H), 3.27 (m, 2H), 2.31 (s, 3H). MS m/z 446 [M−1].

Example 191

4-(3-Fluoro-phenyl)-3-[1-[5-methyl-3-(morpholine-4-carbonyl)-1H-pyrrol-2-yl]-meth-(Z)-ylidene]-1,3-dihydro-indol-2-one

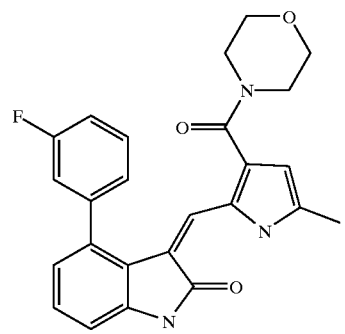

$^1$H NMR (400 MHz, DMSO-d$_6$) δ 13.62 (s, NH, 1H), 11.12 (s, NH, 1H), 7.48 (m, 1H), 7.21 (m, 2H), 7.18 (dd, J=1.6 Hz, J=7.0 Hz, 2H), 6.96 (s, 1H), 6.92 (dd, J=1.2 Hz, J=7.8 Hz, 1H), 6.76 (dd, J=0.8 Hz, J=7.4 Hz, 1H), 6.09 (d, J=2.3 Hz, 1H), 3.54 (m, 2H), 3.40 (m, 4H), 3.28 (m, 2H), 2.30 (s, 3H). MS m/z 430 [M−1].

Example 192

2-[4-(3-Chloro-phenyl)-2-oxo-1,2-dihydro-indol-(3Z)-ylidenemethyl]-5-methyl-1H-pyrrole-3-carboxylic Acid (2,6-Dioxo-1,2,3,6-tetrahydro-pyrimidin-4-ylmethyl)-amide

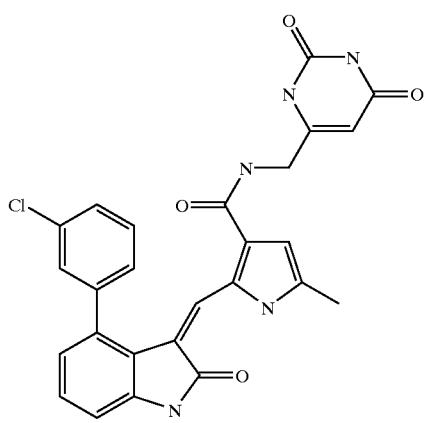

$^1$H NMR (400 MHz, DMSO-d$_6$) δ 13.82 (s, NH, 1H), 11.15 (s, NH, 1H), 10.99 (s, 1H), 10.85 (s, 1H), 8.31 (br t, 1H), 7.92 (s, 1H), 7.34 (m, 3H), 7.27 (m, 1H), 7.19 (t, J=7.8 Hz, 1H), 6.91 (d, J=7.4 Hz, 1H), 6.76 (d, J=7.4 Hz, 1H), 6.45 (s, 1H), 5.20 (s, 1H), 3.94 (br d, 2H), 2.31 (s, 3H). MS m/z 500 [M−1].

Example 193

4-(3-Chloro-phenyl)-3-[1-[3-methyl-4-(4-pyrrolidin-1-yl-piperidine-1-carbonyl)-1H-pyrrol-2-yl]-meth-(Z)-ylidene]-1,3-dihydro-indol-2-one

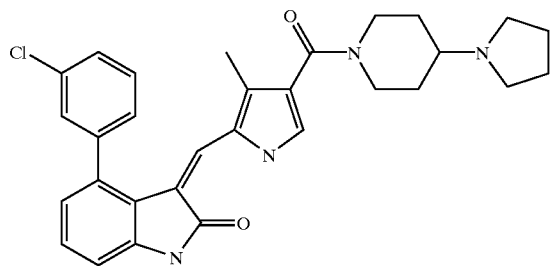

$^1$H NMR (400 MHz, DMSO-d$_6$) δ 13.48 (s, NH, 1H), 11.18 (s, NH, 1H), 7.56 (m, 2H), 7.52 (m, 1H), 7.40 (m, 1H), 7.37 (d, J=3.1 Hz, 1H), 7.21 (t, J=7.8 Hz, 1H), 6.93 (dd, J=0.8 Hz, J=7.4 Hz, 1H), 6.81 (s, 1H), 6.80 (d, J=7.4 Hz, 1H), 3.90 (br m, 2H), 2.94 (m, 2H), 2.44 (m, 4H), 2.16 (m, 1H), 1.78 (m, 2H), 1.65 (s, 3H), 1.64 (m, 4H), 1.26 (m, 2H). MS m/z 513 [M−1].

Example 194

4-(3-Chloro-phenyl)-3-[1-[3-methyl-4-(2-pyrrolidin-1-ylmethyl-pyrrolidiue-1-carbonyl)-1H-pyrrol-2-yl]-meth-(Z)-ylidene]-1,3-dibydro-indol-2-one

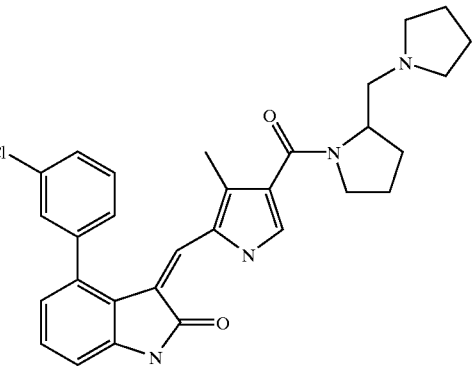

$^1$H NMR (400 MHz, DMSO-d$_6$) δ 13.45 (s, NH, 1H), 11.13 (s, NH, 1H), 7.57 (d, J=2.3 Hz, 1H), 7.56 (d, J=1.2 Hz, 1H), 7.52 (m, 2H), 7.40 (m, 1H), 7.21 (t, J=7.6 Hz, 1H), 6.93 (dd, J=0.8 Hz, J=7.0 Hz, 1H), 6.83 (s, 1H), 6.80 (d, J=7.4 Hz, 1H), 4.19 (m, 1H), 3.41 (m, 2H), 2.55 (m, 2H), 2.43 (m, 4H), 1.86 (m, 4H), 1.70 (s, 3H), 1.63 (m, 4H). MS m/z 514 [M−1]1.

Example 195

5-[4-(3-Chloro-phenyl)-2-oxo-1,2-dihydro-indol-(3Z)-ylidenemethyl]-4-methyl-1H-pyrrole-3-carboxylic Acid (2-Morpholin-4-yl-ethyl)-amide

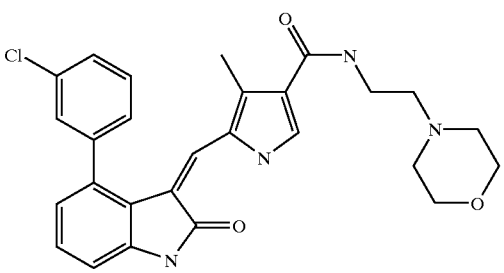

$^1$H NMR (400 MHz, DMSO-d$_6$) δ 13.46 (s, NH, 1H), 11.12 (s, NH, 1H), 7.56 (t, J=5.6 Hz, 1H), 7.67 (d, J=3.1 Hz, 1H), 7.58 (d, J=3.1 Hz, 1H), 7.57 (d, J=0.8 Hz, 1H), 7.52 (s, 1H), 7.40 (m, 1H), 7.21 (t, J=7.6 Hz, 1H), 6.93 (d, J=7.8 Hz, 1H), 6.85 (s, 1H), 6.80 (d, J=7.8 Hz, 1H), 3.54 (m, 4H), 3.26 (m, 4H), 2.37 (m, 4H), 1.84 (s, 3H). MS m/z 489 [M−1].

Example 196

5-[4-(3-Chloro-phenyl)-2-oxo-1,2-dihydro-indol-(3Z)-ylidenemethyl]-4-methyl-1H-pyrrole-3-carboxylic Acid [3-(2-Methyl-piperidin-1-yl)-propyl]-amide

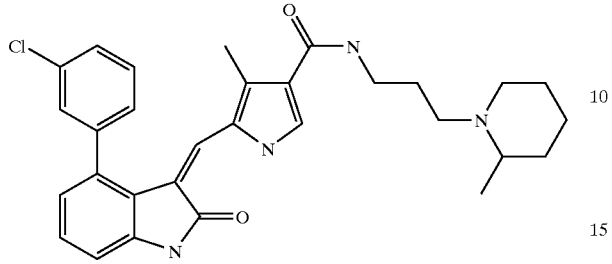

$^1$H NMR (400 MHz, DMSO-d$_6$) δ 13.45 (s, NH, 1H), 11.13 (s, NH, 1H), 7.56 (m, 1H), 7.67 (d, J=3.1 Hz, 1H), 7.58 (d, J=2.3 Hz, 1H), 7.57 (d, J=0.8 Hz, 1H), 7.52 (s, 1H), 7.40 (m, 1H), 7.21 (t, J=7.8 Hz, 1H), 6.93 (d, J=7.8 Hz, 1H), 6.85 (s, 1H), 6.80 (d, J=7.4 Hz, 1H), 3.32 (m, 2H), 3.12 (m, 2H), 2.71 (m, 2H), 2.26 (m, 2H), 1.83 (s, 3H), 1.56 (m, 4H), 1.41 (m, 1H), 1.20 (m, 2H), 0.96 (d, J=5.9 Hz, 3H). MS m/z 516 [M−1].

Example 197

5-[4-(3-Chloro-phenyl)-2-oxo-1,2-dihydro-indol-(3Z)-ylidenemethyl]-4-methyl-1H-pyrrole-3-carboxylic Acid (2-Piperidin-1-yl-ethyl)-amide

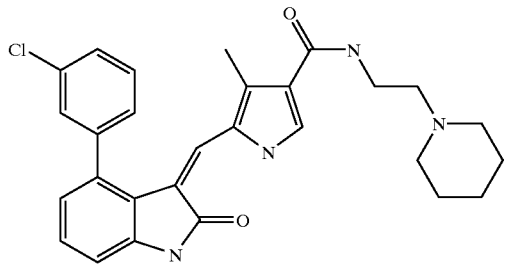

$^1$H NMR (400 MHz, DMSO-d$_6$) δ 13.51 (s, NH, 1H), 11.15 (s, NH, 1H), 8.27 (m, 1H), 7.82 (d, J=3.1 Hz, 1H), 7.58 (d, J=3.1 Hz, 1H), 7.57 (d, J=1.2 Hz, 1H), 7.52 (s, 1H), 7.40 (m, 1H), 7.22 (t, J=7.8 Hz, 1H), 6.93 (d, J=7.8 Hz, 1H), 6.85 (s, 1H), 6.81 (d, J=7.8 Hz, 1H), 3.51 (m, 4H), 3.12 (m, 2H), 2.87 (m, 2H), 1.86 (s, 3H), 1.72 (m, 5H), 1.36 (m, 1H). MS m/z 488 [M−1].

Example 198

5-[4-(3-Chloro-phenyl)-2-oxo-1,2-dihydro-indol-(3Z)-ylidenemethyl]-4-methyl-1H-pyrrole-3-carboxylic Acid (2-Pyridin-4-yl-ethyl)-amide

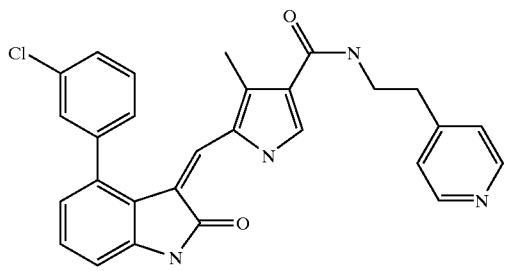

$^1$H NMR (400 MHz, DMSO-d$_6$) δ 13.45 (s, NH, 1H), 11.11 (s, NH, 1H), 8.43 (m, 2H), 7.96 (t, J=5.5 Hz, 1H), 7.64 (d, J=3.5 Hz, 1H), 7.57 (dd, J=1.7 Hz, J=4.3 Hz, 2H), 7.52 (s, 1H), 7.40 (m, 1H), 7.21 (m, 3H), 6.93 (d, J=7.8 Hz, 1H), 6.84 (s, 1H), 6.80 (d, J=7.8 Hz, 1H), 3.40 (m, 2H), 2.78 (t, J=7.2 Hz, 2H), 1.81 (s, 3H). MS m/z 481 [M−1].

Example 199

5-[4-(3-Chloro-phenyl)-2-oxo-1,2-dihydro-indol-(3Z)-ylidenemethyl]-4-methyl-1H-pyrrole-3-carboxylic Acid (2-Pyrrolidin-1-yl-ethyl)-amide

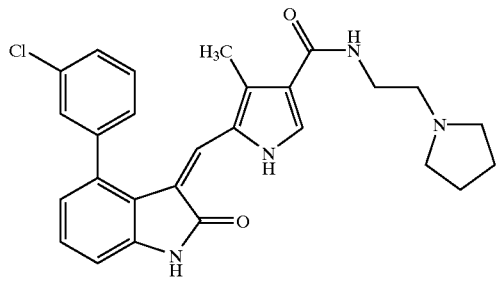

$^1$H NMR (400 MHz, DMSO-d$_6$) δ 13.46 (s, NH, 1H), 11.12 (s, NH, 1H), 7.83 (t, J=5.9 Hz, 1H), 7.69 (d, J=3.5 Hz, 1H), 7.58 (d, J=2.0 Hz, 1H), 7.57 (d, J=1.2 Hz, 1H), 7.52 (d, J=1.2 Hz, 1H), 7.40 (m, 1H), 7.21 (t, J=7.8 Hz, 1H), 6.93 (dd, J=0.8 Hz, J=7.8 Hz, 1H), 6.85 (s, 1H), 6.80 (dd, J=0.8 Hz, J=7.4 Hz, 1H), 3.26 (m, 2H), 2.50 (m, 6H), 1.84 (s, 3H), 1.67 (m, 4H). MS m/z 473 [M−1].

Example 200

5-[4-(3-Chloro-phenyl)-2-oxo-1,2-dihydro-indol-(3Z)-ylidenemethyl]-4-methyl-1H-pyrrole-3-carboxylic Acid [3-(2-oxo-Pyrrolidin-1-yl)-propyl]-amide

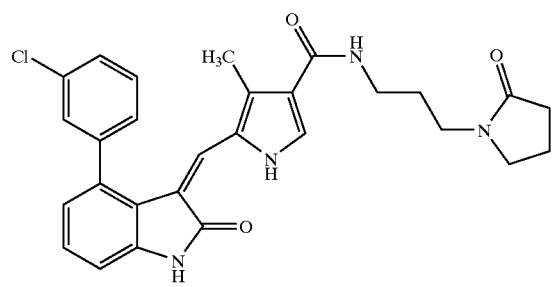

$^1$H NMR (400 MHz, DMSO-d$_6$) δ 13.44 (s, NH, 1H), 11.12 (s, NH, 1H), 7.82 (br t, 1H), 7.67 (d, J=3.5 Hz, 1H), 7.58 (m, 2H), 7.52 (d, J=1.2 Hz, 1H), 7.40 (m, 1H), 7.21 (t, J=7.8 Hz, 1H), 6.93 (dd, J=0.8 Hz, J=7.8 Hz, 1H), 6.85 (s, 1H), 6.80 (d, J=7.4 Hz, 1H), 3.31 (m, 2H), 3.17 (t, J=7.2 Hz, 2H), 3.10 (m, 2H), 2.19 (t, J=8.0 Hz, 2H), 1.89 (m, 2H), 1.84 (s, 3H), 1.62 (m, 2H). MS m/z 501 [M−1].

Example 201

5-[4-(3-Chloro-phenyl)-2-oxo-1,2-dihydro-indol-(3Z)-ylidenemethyl]-4-methyl-1H-pyrrole-3-carboxylic Acid (2-Hydroxy-3-morpholin-4-yl-propyl)-amide

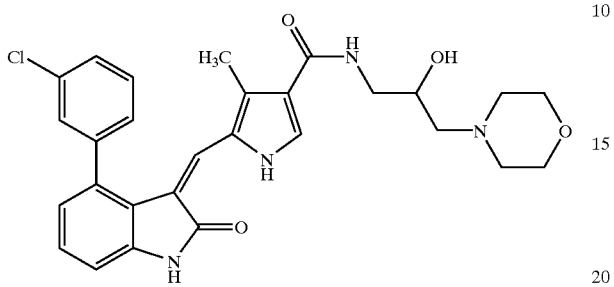

¹H NMR (400 MHz, DMSO-d₆) δ 13.47 (s, NH, 1H), 11.13 (s, NH, 1H), 7.80 (d, J=5.5 Hz, 1H), 7.72 (m, 1H), 7.57 (m, 2H), 7.53 (m, 1H), 7.40 (m, 1H), 7.21 (m, 1H), 6.94 (t, J=6.4 Hz, 1H), 6.85 (d, J=5.1 Hz, 1H), 6.81 (t, J=6.3 Hz, 1H), 4.73 (m, 1H), 3.73 (m, 1H), 3.32 (d, J=5.1 Hz, 2H), 3.28 (m, 1H), 3.04 (m, 1H), 2.58 (m, 2H), 2.38 (m, 4H), 2.25 (m, 2H), 1.84 (m, 3H). MS m/z 519 [M−1].

Example 202

5-[4-(3-Chloro-phenyl)-2-oxo-1,2-dihydro-indol-(3Z)-ylidenemethyl]-4-methyl-1H-pyrrole-3-carboxylic Acid (2-Hydroxy-3-[1,2,3]triazol-1-yl-propyl)-amide

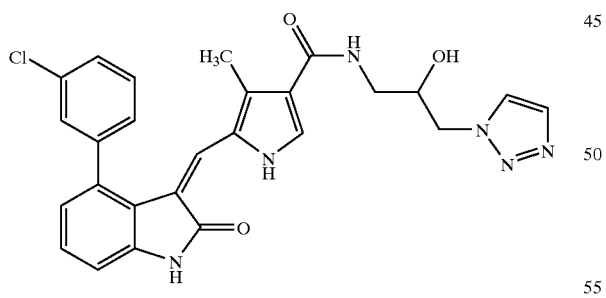

¹H NMR (400 MHz, DMSO-d₆) δ 13.46 (s, NH, 1H), 11.12 (s, NH, 1H), 8.05 (s, 1H), 7.97 (t, J=5.7 Hz, 1H), 7.75 (d, J=3.1 Hz, 1H), 7.68 (s, 1H), 7.58 (m, 2H), 7.52 (m, 1H), 7.40 (m, 1H), 7.21 (t, J=7.8 Hz, 1H), 6.93 (d, J=7.8 Hz, 1H), 6.86 (s, 1H), 6.80 (d, J=7.4 Hz, 1H), 3.36 (d, J=5.5 Hz, 1H), 4.45 (dd, J=3.5 Hz, J=14.5 Hz, 1H), 4.23 (dd, J=7.2 Hz, J=14.1 Hz, 1H), 3.95 (m, 1H), 3.24 (t, J=6.0 Hz, 1H), 3.20 (t, J=6.0 Hz, 1H), 1.86 (s, 3H). MS m/z 501 [M−1].

Example 203

3-[1-{3,5-Dimethyl-4-[2-oxo-2-(4-pyrrolidin-1-yl-piperidin-1-yl)-ethyl]-1H-pyrrol-2-yl}-meth-(Z)-ylidene]-4-(2-fluoro-phenyl)-1,3-dihydro-indol-2-one

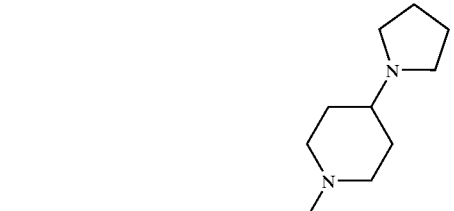
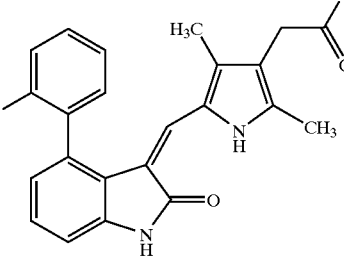

¹H NMR (400 MHz, DMSO-d₆) δ 13.29 (s, NH, 1H), 10.93 (s, NH, 1H), 7.52 (m, 1H), 7.40 (m, 3H), 7.13 (t, J=7.8 Hz, 1H), 6.92 (dd, J=0.78 Hz, J=7.8 Hz, 1H), 6.77 (dd, J=1.2 Hz, J=7.8 Hz, 1H), 6.58 (s, 1H), 4.10 (d, J=14.1 Hz, 1H), 3.79 (d, J=12.9 Hz, 1H), 3.36 (m, 2H), 3.01 (t, J=11.8 Hz, 1H), 2.67 (t, J=11.1 Hz, 1H), 2.42 (m, 4H), 2.17 (s, 3H), 2.12 (m, 1H), 1.75 (d, J=1.7 Hz, 2H), 1.62 (m, 4H), 1.45 (s, 3H), 1.16 (m, 2H). MS m/z 525 [M−1].

Example 204

3-[1-{3,5-Dimethyl-4-[2-oxo-2-((S)-2-pyrrolidin-1-ylmethyl-pyrrolidin-1-yl)-ethyl]-1H-pyrrol-2-yl}-meth-(Z)-ylidene]-4-(2-fluoro-phenyl)-1,3-dihydro-indol-2-one

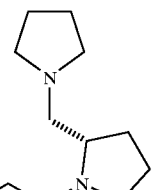
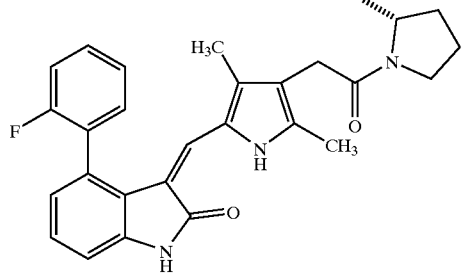

¹H NMR (400 MHz, DMSO-d₆) δ 13.29 (s, NH, 1H), 10.93 (s, NH, 1H), 7.52 (m, 1H), 7.40 (m, 3H), 7.13 (t, J=7.8 Hz, 1H), 6.92 (dd, J=0.78 Hz, J=7.8 Hz, 1H), 6.77 (dd, J=0.8 Hz, J=7.4 Hz, 1H), 6.58 (s, 1H), 4.05 (m, 1H), 3.42 (m, 2H), 3.27 (m, 2H), 2.44 (m, 2H), 2.37 (m, 4H), 2.17 (s, 3H), 1.84 (m, 4H), 1.62 (m, 4H), 1.46 (s, 3H). MS m/z 525 [M−1].

Example 205

2-{5-[4-(2-Fluoro-phenyl)-2-oxo-1,2-dihydro-indol-(3Z)-ylidenemethyl]-2,4-dimethyl-1H-pyrrol-3-yl}-N-(2-morpholin-4-yl-ethyl)-acetamide

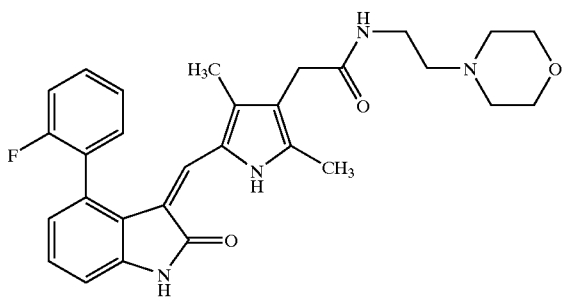

¹H NMR (400 MHz, DMSO-d₆) δ 13.31 (s, NH, 1H), 10.93 (s, NH, 1H), 7.51 (m, 2H), 7.40 (m, 3H), 7.14 (t, J=7.6 Hz, 1H), 6.92 (d, J=7.8 Hz, 1H), 6.77 (d, J=7.4 Hz, 1H), 6.59 (s, 1H), 3.47 (m, 4H), 3.11 (s, 2H), 3.07 (m, 2H), 2.27 (m, 6H), 2.22 (s, 3H), 1.52 (s, 3H). MS m/z 501 [M−1].

Example 206

3-[1-{4-[2-((cis)-3,5-Dimethyl-piperazin-1-yl)-2-oxo-ethyl]-3,5-dimethyl-1H-pyrrol-2-yl}-meth-(Z)-ylidene]-4-(2-fluoro-phenyl)-1,3-dihydro-indol-2-one

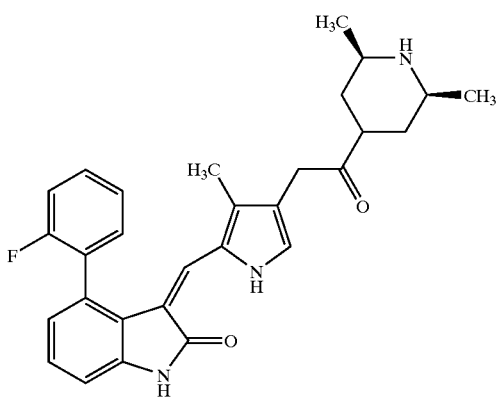

¹H NMR (400 MHz, DMSO-d₆) δ 13.29 (s, NH, 1H), 10.96 (s, NH, 1H), 7.51 (m, 1H), 7.40 (m, 3H), 7.14 (t, J=7.8 Hz, 1H), 6.92 (d, J=0.8 Hz, J=7.8 Hz, 1H), 6.77 (d, J=0.8 Hz, J=8.6 Hz, 1H), 6.58 (s, 1H), 4.15 (d, J=12.1 Hz, 1H), 3.71 (t, J=8.2 Hz, 1H), 3.28 (m, 2H), 2.43 (m, 4H), 2.17 (s, 3H), 1.96 (t, J=1.5 Hz, 1H), 1.45 (s, 3H), 0.89 (d, J=6.6 Hz, 6H).

Example 207

2-{5-[4-(2-Fluoro-phenyl)-2-oxo-1,2-dihydro-indol-(3Z)-ylidenemethyl]-2,4-dimethyl-1H-pyrrol-3-yl}-N-(2-piperidin-1-yl-ethyl)-acetamide

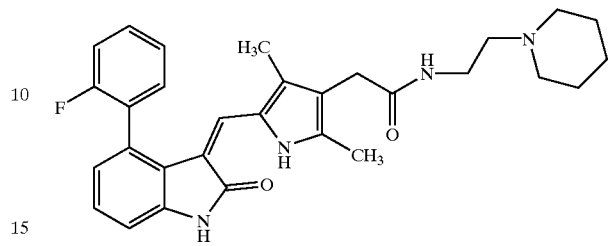

¹H NMR (400 MHz, DMSO-d₆) δ 13.32 (s, NH, 1H), 10.94 (s, NH, 1H), 7.52 (m, 1H), 7.39 (m, 4H), 7.14 (t, J=7.6 Hz, 1H), 6.92 (d, J=7.0 Hz, 1H), 6.77 (d, J=7.4 Hz, 1H), 6.60 (s, 1H), 3.11 (s, 2H), 3.06 (m, 2H), 2.24 (m, 6H), 2.21 (s, 3H), 1.51 (s, 3H), 1.38 (m, 4H), 1.30 (m, 2H). MS m/z 499 [M−1].

Example 208

2-{5-[4-(2-Fluoro-phenyl)-2-oxo-1,2-dihydro-indol-(3Z)-ylidenemethyl]-2,4-dimethyl-1H-pyrrol-3-yl}-N-(2-pyridin-4-yl-ethyl)-acetamide

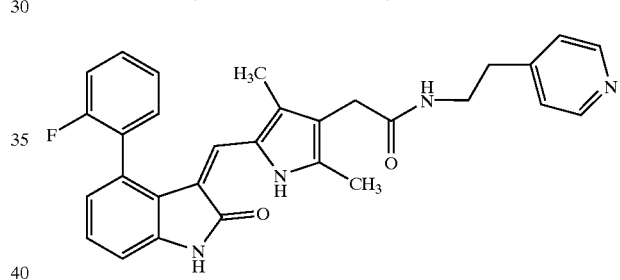

¹H NMR (400 MHz, DMSO-d₆) δ 13.29 (s, NH, 1H), 10.93 (s, NH, 1H), 8.40 (m, 2H), 7.72 (t, J=5.5 Hz, 1H), 7.55 (m, 1H), 7.40 (m, 3H), 7.14 (m, 3H), 6.92 (dd, J=0.8 Hz, J=7.8 Hz, 1H), 6.77 (dd, J=0.8 Hz, J=8.6 Hz, 1H), 6.58 (s, 1H), 3.25 (m, 2H), 3.08 (s, 2H), 2.68 (m, 2H), 2.16 (s, 3H), 1.43 (s, 3H). MS m/z 493 [M−1].

Example 209

2-{5-[4-(2-Fluoro-phenyl)-2-oxo-1,2-dihydro-indol-(3Z)-ylidenemethyl]-2,4-dimethyl-1H-pyrrol-3-yl}-N-(2-pyrrolidin-1-yl-ethyl)-acetamide

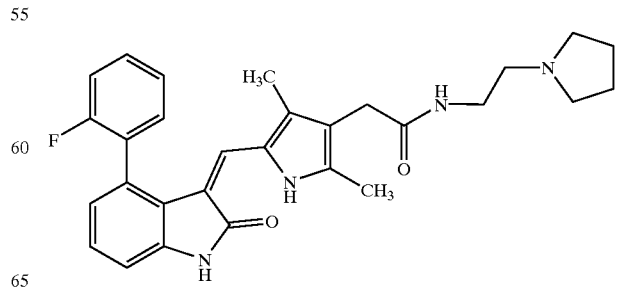

¹H NMR (400 MHz, DMSO-d₆) δ 13.30 (s, NH, 1H), 10.93 (s, NH, 1H), 7.60 (t, J=5.5 Hz, 1H), 7.53 (m, 1H), 7.42 (t, J=7.4 Hz, 1H), 7.37 (d, J=7.4 Hz, 1H), 7.34 (d, J=1.5 Hz, 1H), 7.14 (t, J=7.8 Hz, 1H), 6.92 (dd, J=0.8 Hz, J=7.8 Hz, 1H), 6.77 (d, J=7.8 Hz, 1H), 6.60 (s, 1H), 3.11 (s, 2H), 3.07 (m, 2H), 2.37 (m, 6H), 2.21 (s, 3H), 1.61 (m, 4H), 1.50 (s, 3H). MS m/z 485 [M−1].

Example 210

3-[1-{3,5-Dimethyl-4-[2-(4-methyl-piperazin-1-yl)-2-oxo-ethyl]-1H-pyrrol-2-yl}-meth-(Z)-ylidene]-4-(2-fluoro-phenyl)-1,3-dihydro-indol-2-one

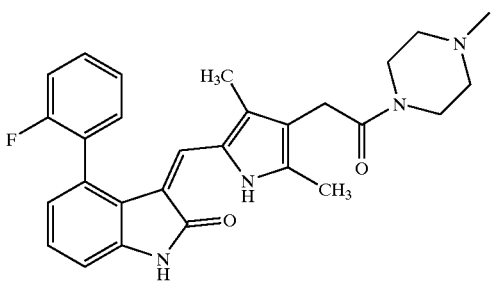

¹H NMR (400 MHz, DMSO-d₆) δ 13.29 (s, NH, 1H), 10.94 (s, NH, 1H), 7.52 (m, 1H), 7.42 (m, 3H), 7.14 (t, J=7.8 Hz, 1H), 6.92 (dd, J=1.0 Hz, J=7.4 Hz, 1H), 6.77 (dd, J=0.8 Hz, J=7.8 Hz, 1H), 6.58 (s, 1H), 3.40 (m, 4H), 3.31 (s, 2H), 1.20 (m, 4H), 2.16 (s, 3H), 2.13 (s, 3H), 1.45 (s, 3H). MS m/z 471 [M−1].

Example 211

3-[1-[3,5-Dimethyl-4-(2-morpholin-4-yl-2-oxo-ethyl]-1H-pyrrol-2-yl]-meth-(Z)-ylidene]-4-(2-fluoro-phenyl)-1,3-dihydro-indol-2-one

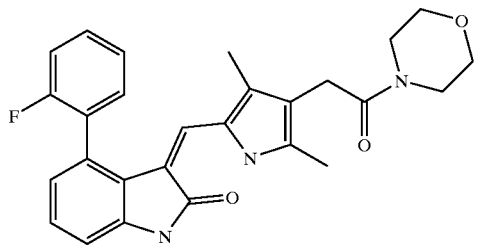

¹H NMR (400 MHz, DMSO-d₆) δ 13.30 (s, NH, 1H), 10.95 (s, NH, 1H), 7.51 (m, 1H), 7.40 (m, 3H), 7.14 (t, J=7.8 Hz, 1H), 6.92 (dd, J=0.8 Hz, J=7.8 Hz, 1H), 6.77 (dd, J=1.0 Hz, J=7.4 Hz, 1H), 6.59 (s, 1H), 3.50 (m, 4H), 3.46 (m, 2H), 3.31 (m, 4H), 2.17 (s, 3H), 1.45 (s, 3H). MS m/z 458 [M−1].

Example 212

N-(2-Diethylamino-ethyl)-2-{5-[4-(2-fluoro-phenyl)-2-oxo-1,2-dihydro-indol-(3Z)-ylidenemethyl]-2,4-dimethyl-1H-pyrrol-3-yl}-acetamide

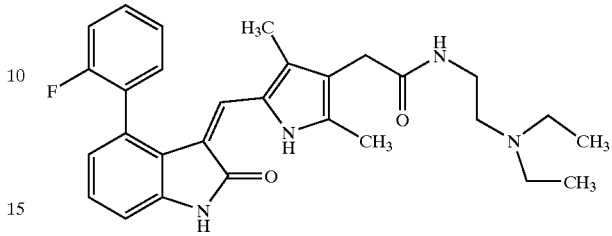

¹H NMR (400 MHz, DMSO-d₆) δ 13.31 (s, NH, 1H), 10.93 (s, NH, 1H), 7.53 (m, 1H), 7.40 (m, 4H), 7.14 (t, J=7.8 Hz, 1H), 6.92 (d, J=7.8 Hz, 1H), 6.77 (d, J=7.4 Hz, 1H), 6.59 (s, 1H), 3.11 (s, 2H), 3.03 (m, 2H), 2.40 (m, 6H), 2.21 (s, 3H), 1.50 (s, 3H), 0.87 (t, J=7.0 Hz, 6H). MS m/z 487 [M−1].

Example 213

4-(2-Chloro-phenyl)-3-[1-[3,5-dimethyl-4-(4-methyl-piperazine-1-carbonyl)-1H-pyrrol-2-yl]-meth-(Z)-ylidene]-1,3-dihydro-indol-2-one

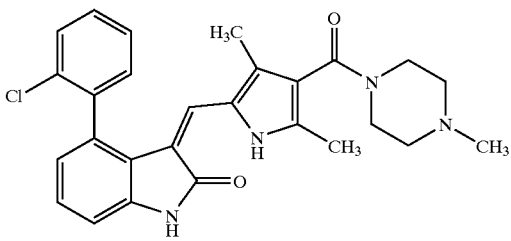

¹H NMR (400 MHz, DMSO-d₆) δ 13.41 (s, 1H, NH), 11.04 (s, 1H, NH), 7.64 (m, 1H), 7.5 (m, 2H), 7.41 (m, 1H), 7.18 (t, J=8.7 Hz, 1H), 6.93 (dd, J=0.9 Hz, J=9.1 Hz, 1H), 6.73 (dd, J=1.1 Hz, J=9.1 Hz, 1H), 6.37 (s, 1H), 3.28 (m, 4H), 2.22 (m, 4H), 2.19 (s, 3H), 2.13 (s, 3H), 1.48 (s, 3H); MS m/z 473 [M−1].

Example 214

2-[4-(2-Chloro-phenyl)-2-oxo-1,2-dihydro-indol-(3Z)-ylidenemethyl]-5-methyl-1H-pyrrole-3-carboxylic Acid (2-Pyrrolidin-1-yl-ethyl)-amide

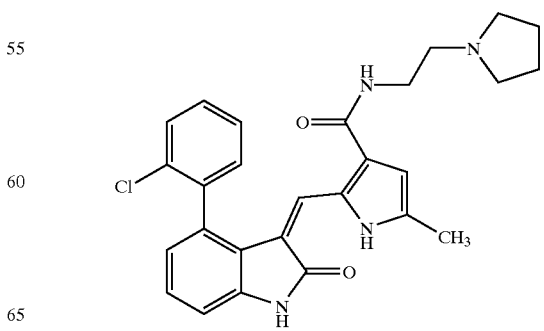

¹H NMR (400 MHz, DMSO-d₆) δ 13.80 (s, 1H, NH), 11.18 (br s, 1H, NH), 7.72 (t, 1H), 7.62 (s, 1H), 7.47 (m, 1H), 7.37 (m, 2H), 7.30 (m, 1H), 7.18 (t, 1H), 6.92 (dd, 1H), 6.67 (dd, 1H), 6.32 (d, 1H), 3.1 (m, 2H), 2.42 (m, 6H), 2.27 (s, 3H), 1.67 (m, 4H). MS m/z 473 [M−1].

Example 215

2-[4-(2-Chloro-phenyl)-2-oxo-1,2-dihydro-indol-(3Z)-ylidenemethyl]-5-methyl-1H-pyrrole-3-carboxylic Acid (3-Pyrrolidin-1-yl-propyl)-amide

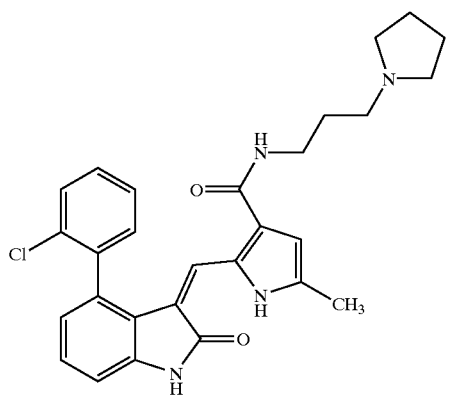

¹H NMR (400 MHz, DMSO-d₆) δ 13.81 (s, 1H, NH), 7.82 (t, 1H), 7.59 (s, 1H), 7.46 (m, 1H), 7.37 (m, 2H), 7.29 (m, 1H), 7.17 (t, 1H), 6.91 (dd, 1H), 6.66 (dd, 1H), 6.29 (t, 1H), 3.05 (m, 2H), 2.40 (m, 6H), 2.22 (s, 3H), 1.7 (m, 4H), 1.49 (m, 2H). MS m/z 488 [M−1].

Example 216

4-(2-Chloro-phenyl)-3-[1-[3-methyl-4-(4-methyl-piperazine-1-carbonyl)-1H-pyrrol-2-yl]-meth-(Z)-ylidene]-1,3-dihydro-indol-2-one

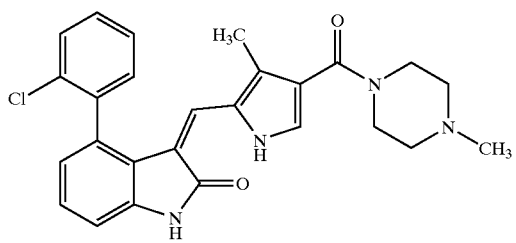

¹H NMR (400 MHz, DMSO-d₆) δ 13.45 (s, 1H, NH), 11.12 (s, 1H, NH), 7.66 (m, 2H), 7.52 (m, 2H), 7.43 (m, 1H), 7.35 (d, J=3.1 Hz, 1H), 7.21 (t, J=7.8 Hz, 2H), 6.93 (dd, J=0.8 Hz, J=7.8 Hz, 1H), 6.76 (dd, J=0.8 Hz, J=7.4 Hz, 1H), 6.45 (s, 1H), 3.42 (m, 4H), 2.22 (m, 4H), 2.18 (s, 3H), 1.60 (s, 3H); MS m/z 459 [M−1].

Example 217

4-(3-Methoxy-phenyl)-3-[1-[3-methyl-4-(morpholine-4-carbonyl)-1H-pyrrol-2-yl]-meth-(Z)-ylidene]-1,3-dihydro-indol-2-one

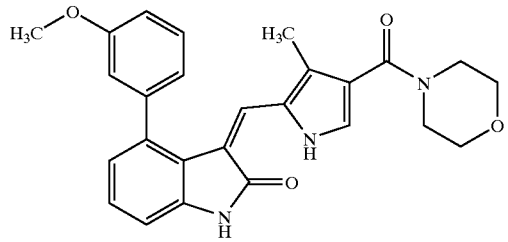

¹H NMR (400 MHz, DMSO-d₆) δ 13.49 (s, 1H, NH), 11.08 (s, 1H, NH), 7.44 (t, J=8.2 Hz, 1H), 7.38 (d, J=3.1 Hz, 1H), 7.17 (t, J=7.6 Hz, 1H), 7.09 (m, 1H), 6.95 (m, 2H), 6.89 (s, 1H), 6.87 (d, J=0.8 Hz, 1H), 6.78 (dd, J=0.8 Hz, J=7.4 Hz, 1H), 3.75 (s, 3H), 3.51 (m, 4H), 3.43 (m, 4H), 1.63 (s, 3H). MS m/z 442 [M−1].

Example 218

4-(3-Chloro-4-fluoro-phenyl)-3-[1-[3-methyl-4-(morpholine-4-carbonyl)-1H-pyrrol-2-yl]-meth-(Z)-ylidene]-1,3-dihydro-indol-2-one

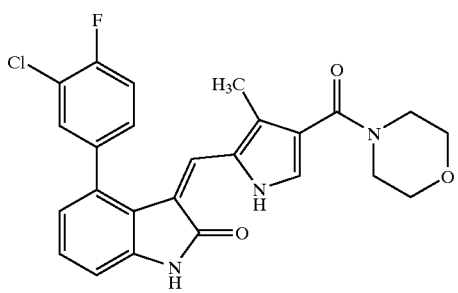

¹H NMR (400 MHz, DMSO-d₆) δ 13.41 (s, 1H, NH), 11.13 (s, 1H, NH), 7.70 (dd, J=2.2 Hz, J=7.4 Hz, 1H), 7.59 (t, J=9.0 Hz, 1H), 7.46 (m, 1H), 7.40 (d, J=3.1 Hz, 1H), 7.19 (t, J=7.6 Hz, 1H), 7.19 (t, J=7.6 Hz, 1H), 6.92 (dd, J=0.8 Hz, J=7.4 Hz, 1H), 6.80 (dd, J=0.8 Hz, J=7.4 Hz, 1H), 6.76 (s, 1H), 3.5 (m, 4H), 3.38 (m, 4H), 1.69 (s, 3H). MS m/z 464 [M−1].

Example 219

3-[1-{3,5-Dimethyl-4-[2-oxo-2-(4-pyrrolidin-1-yl-piperidin-1-yl)-ethyl]-1H-pyrrol-2-yl}-meth-(Z)-ylidene]-4-(3-fluoro-phenyl)-1,3-dihydro-indol-2-one

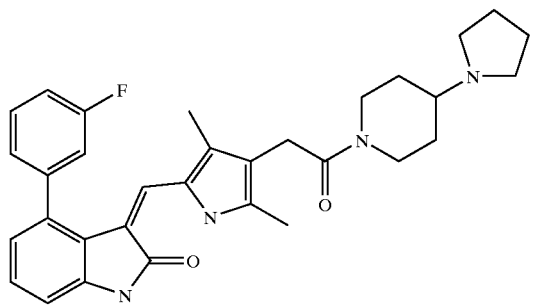

$^1$H NMR (400 MHz, DMSO-d$_6$) δ 13.28 (s, 1H, NH), 10.93 (s, 1H, NH), 7.56 (m, 1H), 7.28 (m, 3H), 7.13 (t, 1H), 6.90 (dd, 1H), 6.75 (dd, 1H), 6.74 (s, 1H), 4.13 (m, 1H), 3.58 (m, 1H), 3.39 (s, 2H), 3.05 (m, 1H), 2.71 (m, 1H), 2.47 (m, 4H), 2.19 (m, 5H), 1.79 (m, 2H), 1.65 (m, 4H), 1.52 (s, 3H), 1.2 (m, 1H). MS m/z 525 [M−1].

Example 220

2-{5-[4-(3-Fluoro-phenyl)-2-oxo-1,2-dihydro-indol-(3Z)-ylidenemethyl]-2,4-dimethyl-1H-pyrrol-3-yl}-N-(2-hydroxy-3-[1,2,3]triazol-2-yl-propyl)-acetamide

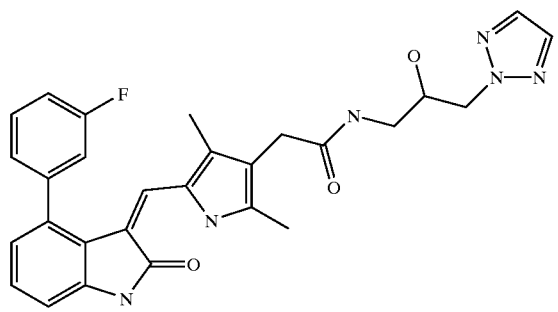

$^1$H NMR (400 MHz, DMSO-d$_6$) δ 13.30 (s, 1H, NH), 10.93 (s, 1H, NH), 7.87 (t, 1H), 7.74 (s, 2H), 7.55 (m, H), 7.26 (m, 3H), 7.13 (t, 1H), 6.90 (d, H), 6.75 (m, H), 5.22 (m, 1H), 4.29 (m, 2H), 4.02 (m, 1H), 3.17 (s, 2H), 3.06 (m, 2H), 2.23 (s, 3H), 1.56 (s, 3H). MS m/z 513 [M−1].

Example 221

3-[1-[3,5-Dimethyl-4-(2-morpholin-4-yl-2-oxo-ethyl)-1H-pyrrol-2-yl]-meth-(Z)-ylidene]-4-(3-fluoro-phenyl)-1,3-dihydro-indol-2-one

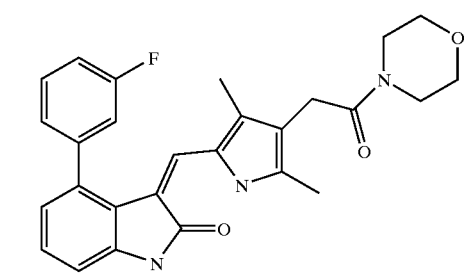

$^1$H NMR (400 MHz, DMSO-d$_6$) δ 13.29 (s, 1H, NH), 10.92 (s, 1H, NH), 7.56 (m, 1H), 7.28 (m, 3H), 7.13 (t, J=7.8 Hz, 1H), 6.90 (dd, J=0.8 Hz, J=7.8 Hz, 1H), 6.75 (dd, J=1.0 Hz, J=7.4 Hz, 1H), 6.75 (s, 1H), 3.49 (m, 6H), 3.39 (m, 4H), 2.19 (s, 3H), 1.51 (s, 3H). MS m/z 458 [M−1].

Example 222

4-(3-Fluoro-phenyl)-3-[1-{4-[2-(4-hydroxy-piperidin-1-yl)-2-oxo-ethyl]-3,5-dimethyl-1H-pyrrol-2-yl}-meth-(Z)-ylidene]-1,3-dihydro-indol-2-one

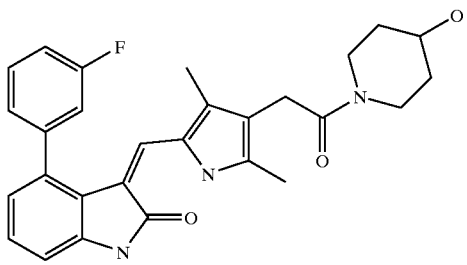

$^1$H NMR (400 MHz, DMSO-d$_6$) δ 13.29 (s, 1H, NH), 10.92 (s, 1H, NH), 7.56 (m, 1H), 7.28 (m, 3H), 7.13 (t, J=7.8 Hz, 1H), 6.90 (d, J=7.4 Hz, 1H), 6.75 (dd, J=0.78 Hz, J=7.8 Hz, 1H), 6.74 (s, 1H), 4.72 (d, J=3.9 Hz, 1H), 3.89 (m, 1H), 3.68 (m, 2H), 3.39 (m, 2H), 3.15 (m, 1H), 2.95 (m, 1H), 2.19 (s, 3H), 1.67 (m, 2H), 1.52 (s, 3H), 1.19 (m, 2H). MS m/z 472 [M−1].

Example 223

2-{5-[4-(3-Fluoro-phenyl)-2-oxo-1,2-dihydro-indol-(3Z)-ylidenemethyl]-2,4-dimethyl-1H-pyrrol-3-yl}-N-(2-morpholin-4-yl-ethyl)-acetamide

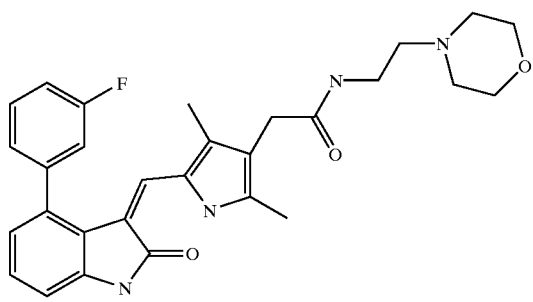

$^1$H NMR (400 MHz, DMSO-d$_6$) δ 13.31 (s, 1H, NH), 10.94 (s, 1H, NH), 7.56 (m, 2H), 7.28 (m, 3H), 7.13 (t, J=7.6 Hz, 1H), 6.90 (dd, J=0.8 Hz, J=7.8 Hz, 1H), 6.76 (d, J=0.8 Hz, 1H), 6.74 (s, 1H), 3.54 (m, 2H), 3.50 (m, H), 3.15 (s, 2H), 3.19 (m, 2H), 2.29 (m, 6H), 2.25 (s, 3H), 1.60 (s, 3H). MS m/z 501 [M−1].

Example 224

N-(2-Diethylamino-ethyl)-2-{5-[4-(3-fluoro-phenyl)-2-oxo-1,2-dihydro-indol-(3Z)-ylidenemethyl]-2,4-dimethyl-1H-pyrrol-3-yl}-acetamide

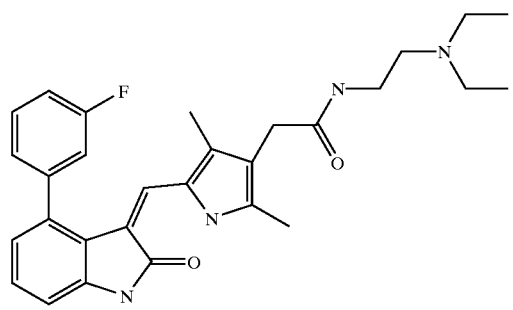

$^1$H NMR (400 MHz, DMSO-d$_6$) δ 13.30 (s, 1H, NH), 10.93 (s, 1H, NH), 7.56 (m, H), 7.41 (t, J=5.6 Hz, 1H), 7.28 (m, 3H), 7.13 (t, J=7.8 Hz, 1H), 6.90 (d, J=7.0 Hz, 1H), 6.75 (d, J=8.6 Hz, 1H), 6.74 (s, 1H), 3.14 (s, 2H), 3.04 (m, 2H), 2.38 (m, 6H), 2.24 (s, 3H), 1.57 (s, 3H), 0.88 (t, J=7.2 Hz, 6H). MS m/z 487 [M−1].

Example 225

2-{5-[4-(3-Fluoro-phenyl)-2-oxo-1,2-dihydro-indol-(3Z)-ylidenemethyl]-2,4-dimethyl-1H-pyrrol-3-yl}-N-(2-pyrrolidin-1-yl-ethyl)-acetamide

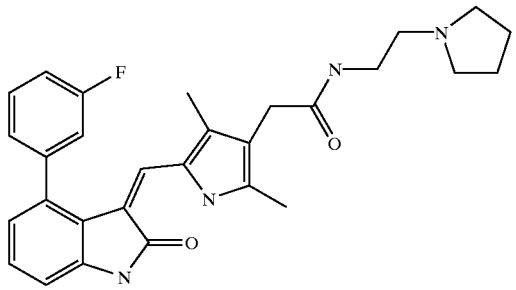

$^1$H NMR (400 MHz, DMSO-d$_6$) δ 13.29 (s, 1H, NH), 10.92 (s, 1H, NH), 7.64 (t, 1H), 7.56 (m, 1H), 7.27 (m, 3H), 7.13 (t, J=7.8 Hz, 1H), 6.90 (dd, J=0.78 Hz, J=7.8 Hz, 1H), 6.75 (dd, J=0.78 Hz, J=7.8 Hz, 1H), 6.74 (s, 1H), 3.14 (s, 2H), 3.11 (m, 2H), 2.42 (m, 6H), 2.24 (s, 3H), 1.65 (m, 4H), 1.57 (s, 3H). MS m/z 485 [M−1].

Example 226

3-[1-{4-[2-((cis)-3,5-Dimethyl-piperazin-1-yl)-2-oxo-ethyl]-3,5-dimethyl-1H-pyrrol-2-yl}-meth-(Z)-ylidene]-4-(3-fluoro-phenyl)-1,3-dihydro-indol-2-one

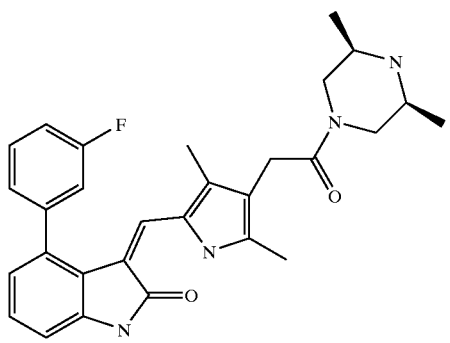

$^1$H NMR (400 MHz, DMSO-d$_6$) δ 13.29 (s, 1H, NH), 10.92 (s, 1H, NH), 7.56 (m, 1H), 7.27 (m, 3H), 7.14 (t, J=7.6 Hz, 1H), 6.92 (dd, J=0.77 Hz, J=7.8 Hz, 1H), 6.75 (dd, J=0.78 Hz, J=7.8 Hz, 1H), 6.74 (s, 1H), 4.19 (m, 1H), 3.75 (m, 1H), 3.45 (d, J=16.8 Hz, 1H), 3.13 (d, J=16.8 Hz, 1H), 2.45 (m, 3H), 2.20 (m, 1H), 2.19 (s, 3H), 1.99 (m, 1H), 1.52 (s, 3H), 0.91 (m, 6H). MS m/z 485 [M−1].

Example 227

2-{5-[4-(3-Fluoro-phenyl)-2-oxo-1,2-dihydro-indol-(3Z)-ylidenemethyl]-2,4-dimethyl-1H-pyrrol-3-yl}-N-(2-pyridin-4-yl-ethyl)-acetamide

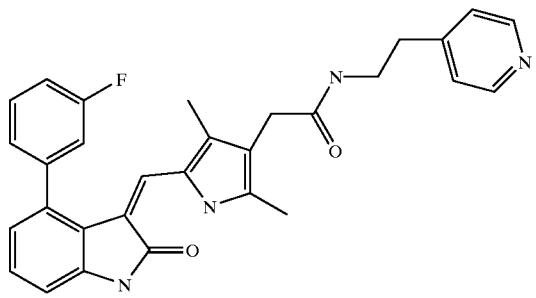

$^1$H NMR (400 MHz, DMSO-d$_6$) δ 13.29 (s, 1H, NH), 10.92 (s, 1H, NH), 8.41 (dd, 2H), 7.74 (t, 1H), 7.57 (m, 1H), 7.29 (m, 3H), 7.13 (m, 3H), 6.90 (d, 1H), 6.76 (d, 1H), 6.73 (s, 1H), 3.28 (m, 2H), 3.11 (s, 2H), 2.69 (t, 2H), 2.19 (s, 3H), 1.51 (s, 3H). MS m/z 493 [M−1].

Example 228

2-Fluoro-5-{3-[1-[5-methyl-3-(4-pyrrolidin-1-yl-piperidine-1-carbonyl)-1H-pyrrol-2-yl]-meth-(Z)-ylidene]-2-oxo-2,3-dihydro-1H-indol-4-yl}-benzonitrile

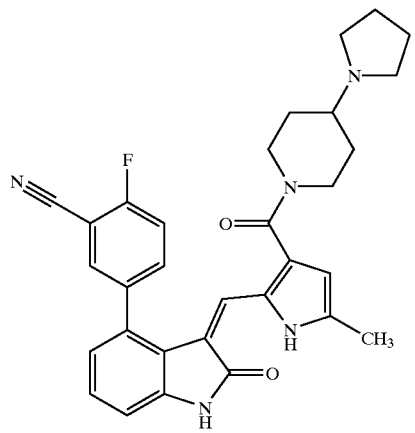

$^1$H NMR (400 MHz, DMSO-d$_6$) δ 13.59 (s, NH, 1H), 11.17 (s, NH, 1H), 7.93 (dd, J=2.3 Hz, J=6.3 Hz, 1H), 7.73 (m, 1H), 7.63 (m, 1H), 7.21 (t, J=7.6 Hz, 1H), 6.94 (dd, J=0.8 Hz, J=7.8 Hz, 1H), 6.87 (m, 1H), 6.78 (d, J=6.6 Hz, 1H), 6.11 (d, J=1.9 Hz, 1H), 4.25 (m, 1H), 3.85 (m, 1H), 2.95 (m, 8H), 1.90 (m, 6H), 1.42 (m, 1H). MS m/z 522 [M−1].

Example 229

2-[4-(3-Cyano-4-fluoro-phenyl)-2-oxo-1,2-dihydro-indol-(3Z)-ylidenemethyl]-5-methyl-1H-pyrrole-3-carboxylic Acid (2-Hydroxy-3-[1,2,3]triazol-2-yl-propyl)-amide

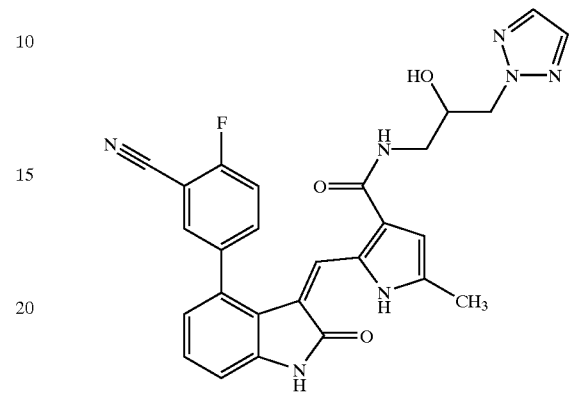

$^1$H NMR (400 MHz, DMSO-d$_6$) δ 13.79 (s, NH, 1H), 11.17 (s, NH, 1H), 8.00 (t, 1H), 7.93 (s, 1H), 7.91 (dd, 1H), 7.75 (s, 2H), 7.68 (m, 1H), 7.50 (t, 1H), 7.21 (t, 1H), 6.94 (d, 1H), 6.78 (d, 1H), 6.51 (d, 1H), 5.14 (d, 1H), 4.32 (m, 2H), 4.09 (m, 1H), 3.12 (m, 2H), 2.30 (s, 3H). MS m/z 510 [M−1].

Example 230

5-{3-[1-[3-((cis)-3,5-Dimethyl-piperazine-1-carbonyl)-5-methyl-1H-pyrrol-2-yl]-meth-(Z)-ylidene]-2-oxo-2,3-dihydro-1H-indol-4-yl}-2-fluoro-benzonitrile

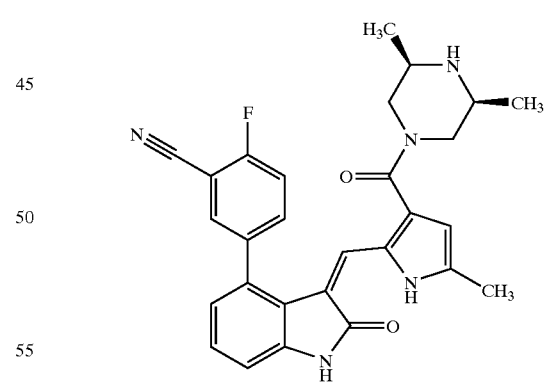

$^1$H NMR (400 MHz, DMSO-d$_6$) δ 13.59 (s, NH, 1H), 11.15 (s, NH, 1H), 7.93 (dd, J=2.3 Hz, J=6.3 Hz, 1H), 7.72 (m, 1H), 7.54 (m, 1H), 7.20 (t, J=7.6 Hz, 1H), 6.94 (dd, J=0.8 Hz, J=7.8 Hz, 1H), 6.87 (s, 1H), 6.76 (dd, J=0.8 Hz, J=7.8 Hz, 1H), 6.08 (d, J=2.0 Hz, 1H), 4.18 (m, 1H), 3.57 (m, 1H), 2.42 (m, 2H), 2.31 (s, 3H), 2.26 (m, 1H), 2.07 (m, 1H), 1.02 (m, 3H), 0.96 (m, 3H), 0.82 (m, 3H). MS m/z 482 [M−1].

Example 231

3-[1-[3-(3-Dimethylamino-propyl)-4,5,6,7-tetrahydro-1H-indol-2-yl]-meth-(Z)-ylidene]-4-(4-fluoro-phenyl)-1,3-dihydro-indol-2-one

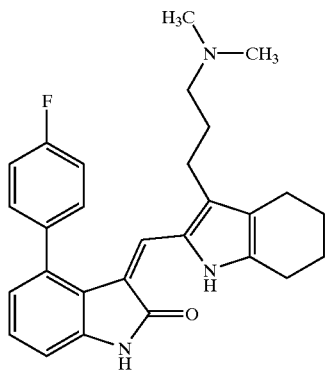

$^1$H NMR (400 MHz, DMSO-d$_6$) δ 13.25 (s, 1H. NH), 10.91 (s, 1H, NH), 7.45 (m, 2H), 7.34 (m, 2H), 7.11 (t, J=7.6 Hz, 1H), 6.88 (dd, J=0.78 Hz, J=7.8 Hz, 1H), 6.82 (s, 1H), 6.71 (d, J=7.8 Hz, 1H), 2.62 (m, 2H), 2.33 (m, 2H), 2.07 (s, 6H), 1.97 (m, 4H), 1.69 (m, 4H), 1.20 (m, 2H). MS m/z 444 [M$^+$+1].

Example 232

3-[1-[3-(3-Dimethylamino-propyl)-4,5,6,7-tetrahydro-1H-indol-2-yl]-meth-(Z)-ylidene]-4-(2-fluoro-phenyl)-1,3-dihydro-indol-2-one

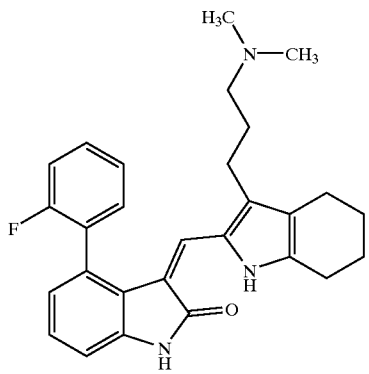

$^1$H NMR (400 MHz, DMSO-d$_6$) δ 13.25 (s, 1H, NH), 10.93 (s, 1H, NH), 7.57 (m, H), 7.44 (m, 1H), 7.37 (m, 2H), 7.14 (t, J=7.8 Hz, 1H), 6.92 (d, J=7.8 Hz, 1H), 6.75 (d, J=7.4 Hz, 1H), 6.7 (s, 1H), 2.62 (t, J=5.9 Hz, 2H), 2.32 (m, 2H), 2.06 (s, 6H), 1.91 (m, 4H), 1.68 (m, 4H), 1.18 (m, 2H). MS m/z 444 [M$^+$+1].

Example 233

4-(4-Chloro-phenyl)-3-[1-[3-(3-dimethylamino-propyl)-4,5,6,7-tetrahydro-1H-indol-2-yl]-meth-(Z)-ylidene]-1,3-dihydro-indol-2-one

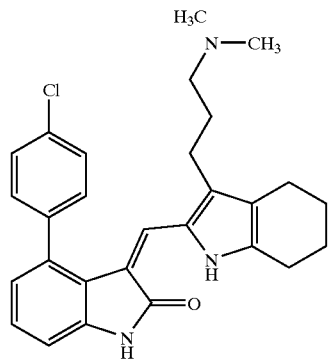

$^1$H NMR (400 MHz, DMSO-d$_6$) δ 13.25 (s, 1H, NH), 10.92 (s, 1H, NH), 7.56 (m, 2H), 7.45 (m, 2H), 7.12 (t, J=7.6 Hz, 1H), 6.89 (dd, J=0.78 Hz, J=7.8 Hz, 1H), 6.85 (s, 1H), 6.71 (dd, J=0.78 Hz, J=7.8 Hz, 1H), 2.62 (m, 2H), 2.32 (m, 2H), 2.07 (s, 6H), 1.97 (m, 4H), 1.68 (m, 4H), 1.18 (m, 2H). MS m/z 459 [M−1].

Example 234

4-(3-Chloro-phenyl)-3-[1-[3-(3-dimethylamino-propyl)-4,5,6,7-tetrahydro-1H-indol-2-yl]-meth-(Z)-ylidene]-1,3-dihydro-indol-2-one

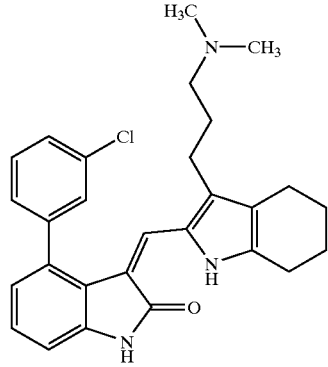

$^1$H NMR (400 MHz, DMSO-d$_6$) δ 13.25 (s, 1H, NH), 10.93 (s, 1H, NH), 7.54 (m, H), 7.48 (m, 1H), 7.39 (m, 1H), 7.12 (t, J=7.8 Hz, 1H), 6.90 (d, J=6.6 Hz, 1H), 6.83 (s, 1H), 6.73 (dd, J=0.78 Hz, J=7.8 Hz, 1H), 2.62 (m, 2H), 2.33 (m, 2H), 2.05 (s, 6H), 1.94 (m, 4H), 1.68 (m, 4H), 1.18 (m, 2H). MS m/z 460 [M$^+$+1].

Example 235

4-(2-Chloro-phenyl)-3-[1-[3-(3-dimethylamino-propyl)-4,5,6,7-tetrahydro-1H-indol-2-yl]-meth-(Z)-ylidene]-1,3-dihydro-indol-2-one

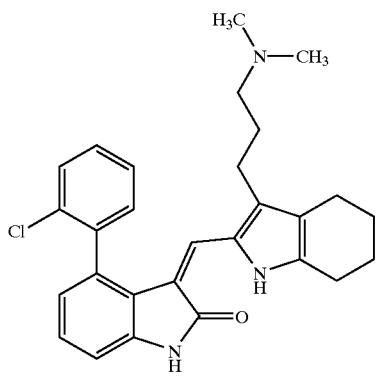

¹H NMR (400 MHz, DMSO-d₆) δ 13.25 (s, 1H, NH), 10.93 (s, 1H, NH), 7.63 (dd, J=1.2 Hz, J=7.8 Hz, 1H), 7.53 (m, 2H), 7.42 (m, 1H), 7.14 (t, J=7.6 Hz, 1H), 6.91 (d, J=7.8 Hz, 1H), 6.68 (d, J=7.8 Hz, 1H), 6.49 (s, 1H), 2.61 (m, 2H), 2.31 (m, 2H), 2.11 (s, 6H), 2.01 (m, 2H), 1.85 (m, 2H), 1.68 (m, 4H), 1.21 (m, 2H). MS m/z 460 [M⁺+1].

Example 236

4-Biphenyl-3-yl-3-[1-[3,5-dimethyl-4-(4-pyrrolidin-1-yl-piperidine-1-carbonyl)-1H-pyrrol-2-yl]-meth-(Z)-ylidene]-1,3-dihydro-indol-2-one

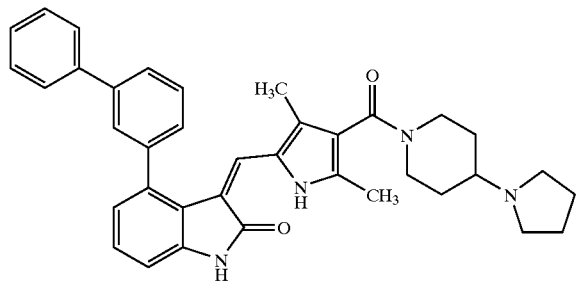

MS m/z 569 [M−1].

Example 237

5-[4-Biphenyl-3-yl-2-oxo-1,2-dihydro-indol-(3Z)-ylidenemethyl]-2,4-dimethyl-1H-pyrrole-3-carboxylic Acid (2-Hydroxy-3-[1,2,3]triazol-1-yl-propyl)-amide

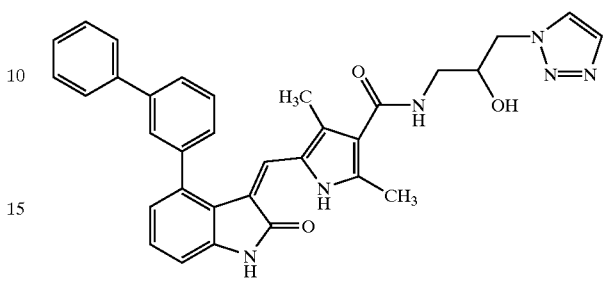

¹H NMR (400 MHz, DMSO-d₆) δ 13.49 (s, 1H, NH), 11.06 (s, 1H, NH), 8.03 (d, J=0.78 Hz, 1H), 7.67 (m, 6H), 7.39 (m, 5H), 7.20 (t, J=7.6 Hz, 1H), 6.93 (dd, J=0.78 Hz, J=7.8 Hz, 1H), 6.87 (s, 1H), 6.85 (s, 1H), 5.32 (m, 1H), 4.22 (m, 1H), 3.20 (m, 4H), 2.36 (s, 3H), 1.61 (s, 3H). MS m/z 557 [M−1].

Example 238

4-Biphenyl-3-yl-3-[1-[4-((cis)-3,5-dimethyl-piperazine-1-carbonyl)-3,5-dimethyl-1H-pyrrol-2-yl]-meth-(Z)-ylidene]-1,3-dihydro-indol-2-one

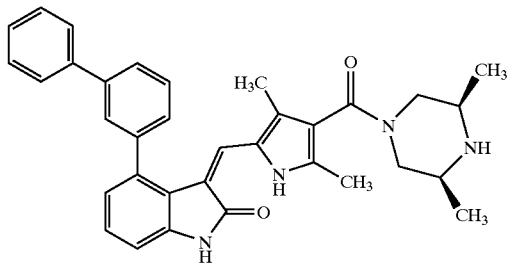

MS m/z 529 [M−1].

Example 239

4-(3-Fluoro-phenyl)-3-[1-[4-(4-hydroxy-piperidine-1-carbonyl)-3,5-dimethyl-1H-pyrrol-2-yl]-meth-(Z)-ylidene]-1,3-dihydro-indol-2-one

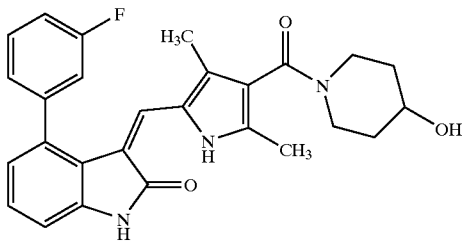

¹H NMR (400 MHz, DMSO-d₆) δ 13.41 (s, 1H, NH), 11.05 (s, 1H, NH), 7.57 (m, 1H), 7.28 (m, 3H), 7.17 (t, J=7.6 Hz, 1H), 6.92 (dd, J=0.78 Hz, J=7.8 Hz, 1H), 6.78 (dd, J=0.78 Hz, J=7.8 Hz, 1H), 6.75 (s, 1H), 4.7 (d, J=4.3 Hz,

1H), 3.95 (br m, 1H), 3.67 (m, 1H), 3.45 (br m, 1H), 3.07 (m, 2H), 2.23 (s, 3H), 1.69 (m, 2H), 1.58 (s, 3H), 1.24 (m, 2H). MS m/z 458 [M−1].

Example 240

3-[1-[3,5-Dimethyl-4-(4-pyridin-2-yl-piperazine-1-carbonyl)-1H-pyrrol-2-yl]-meth-(Z)-ylidene]-4-(3-fluoro-phenyl)-1,3-dihydro-indol-2-one

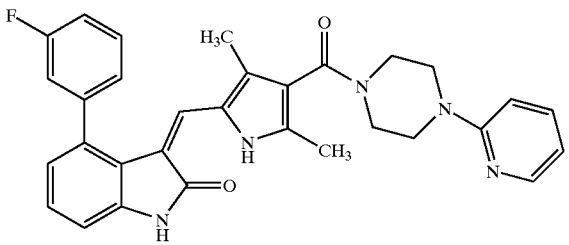

¹H NMR (400 MHz, DMSO-d₆) δ 13.47 (s, 1H, NH), 11.07 (s, 1H, NH), 8.10 (dd, J=1.7 Hz, J=4.7 Hz, 1H), 7.54 (m, 2H), 7.29 (m, 3H), 7.18 (t, J=7.6 Hz, 1H), 6.93 (dd, J=0.78 Hz, J=7.8 Hz, 1H), 6.79 (m, 3H), 6.64 (m, 1H), 3.47 (m, 4H), 3.49 (m, 4H), 2.26 (s, 3H), 1.62 (s, 3H). MS m/z 520 [M−1].

Example 241

5-[4-(3-Fluoro-phenyl)-2-oxo-1,2-dihydro-indol-(3Z)-ylidenemethyl]-2,4-dimethyl-1H-pyrrole-3-carboxylic Acid (2-Piperidin-1-yl-ethyl)-amide

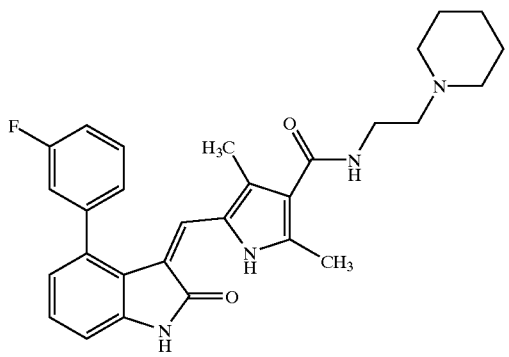

¹H NMR (400 MHz, DMSO-d₆) δ 13.45 (s, 1H, NH), 11.05 (s, 1H, NH), 7.58 (m, 1H), 7.30 (m, 4H), 7.17 (t, J=7.8 Hz, 1H), 6.92 (dd, J=1.2 Hz, J=7.8 Hz, 1H), 6.79 (dd, J=0.78 Hz, J=7.8 Hz, 1H), 6.77 (s, 1H), 3.27 (m, 2H), 2.39 (s, 3H), 2.36 (m, 6H), 1.73 (s, 3H), 1.47 (m, 4H), 1.38 (m, 2H). MS m/z 485 [M−1].

Example 242

5-[4-Biphenyl-2-yl-2-oxo-1,2-dihydro-indol-(3Z)-ylidenemethyl]-2,4-dimethyl-1H-pyrrole-3-carboxylic Acid (2-Diethylamino-ethyl)-amide

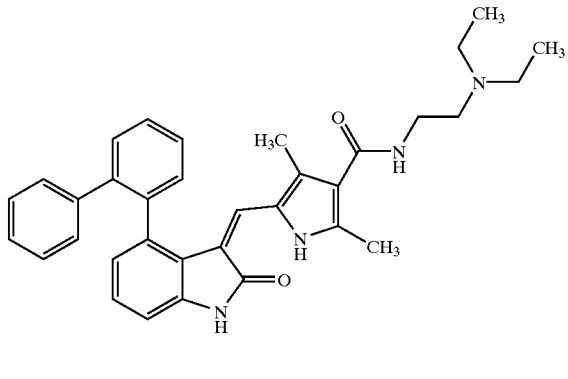

¹H NMR (400 MHz, DMSO-d₆) δ 13.45 (s, 1H, NH), 11.05 (s, 1H, NH), 7.53 (m, 3H), 7.35 (m, 2H), 7.07 (m, 6H); 7.77 (d, J=7.0 Hz, 1H), 6.73 (d, J=7.4 Hz, 1H), 6.56 (s, 1H), 3.34 (s, 2H), 2.48 (m, 6H), 2.36 (s, 3H), 1.73 (s, 3H), 0.95 (t, 6H). MS m/z 531 [M−1].

Example 243

2-[4-Biphenyl-2-yl-2-oxo-1,2-dihydro-indol-(3Z)-ylidenemethyl]-5-methyl-1H-pyrrole-3-carboxylic Acid (3-Pyrrolidin-1-yl-propyl)-amide

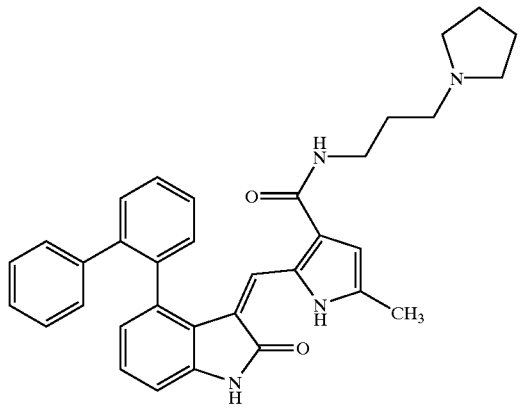

¹H NMR (400 MHz,DMSO-d₆) δ 13.71 (s, 1H, NH), 10.91 (s, 1H, NH), 7.84 (t, 1H), 7.64 (s, 1H), 7.41 (m, 3H), 7.24 (d, 1H), 7.07 d (m, H), 6.76 (dd, 1H), 6.38 (dd, 1H), 6.28 (d, 1H), 3.19 (m, 2H), 2.50 (m, 4H), 2.41 (m, 2H), 2.28 (s, 3H), 1.65 (m, 6H). MS m/z 529 [M−1].

Example 244

2-[4-(4-Chloro-phenyl)-2-oxo-1,2-dihydro-indol-(3Z)-ylidenemethyl]-5-methyl-1H-pyrrole-3-carboxylic Acid (3-Pyrrolidin-1-yl-propyl)-amide

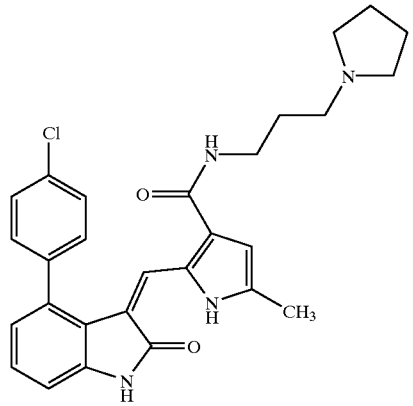

$^{1}$H NMR (400 MHz, DMSO-d$_{6}$) δ 13.81 (s, NH, 1H), 11.12 (br s, NH, 1H), 7.99 (s, 1H), 7.88 (m, 1H), 7.44 (m, 2H), 7.35 (m, 2H), 7.19 (t, J=7.8 Hz, 1H), 6.92 (d, J=7.4 Hz, 1H), 6.75 (d, J=7.4 Hz, 1H), 6.36 (s, 1H), 3.12 (m, 2H), 2.42 (m, 6H), 2.30 (s, 3H), 1.67 (m, 4H), 1.60 (m, 2H). MS m/z 487 [M−1].

Example 245

2-[4-(3-Chloro-phenyl)-2-oxo-1,2-dihydro-indol-(3Z)-ylidenemethyl]-5-methyl-1H-pyrrole-3-carboxylic Acid (3-Pyrrolidin-1-yl-propyl)-amide

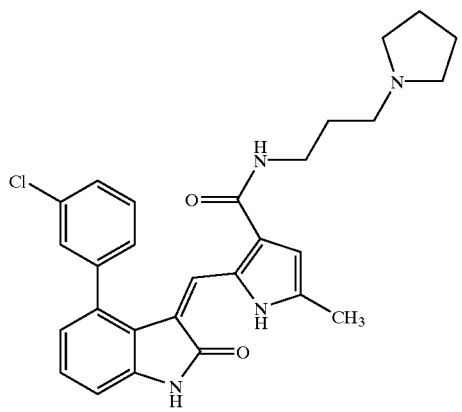

$^{1}$H NMR (400 MHz, DMSO-d$_{6}$) δ 13.81 (s, NH, 1H), 11.16 (br s, NH, 1H), 7.099 (s, 1H), 7.88 (m, 1H), 7.42 (d, J=7.4 Hz, 1H), 7.39 (m, 2H), 7.32 (d, J=7.0 Hz, 1H), 7.20 (t, J=7.6 Hz, 1H), 6.92 (d, J=7.8 Hz, 1H), 6.76 (d, J=7.8 Hz, 1H), 6.35 (s, 1H), 3.12 (m, 2H), 2.42 (m, 6H), 2.30 (s, 3H), 1.69 (m, 4H), 1.60 (m, 2H). MS m/z 487 [M−1].

Example 246

2-[4-(3-Fluoro-phenyl)-2-oxo-1,2-dihydro-indol-(3Z)-ylidenemethyl]-5-methyl-1H-pyrrole-3-carboxylic Acid (3-Pyrrolidin-1-yl-propyl)-amide

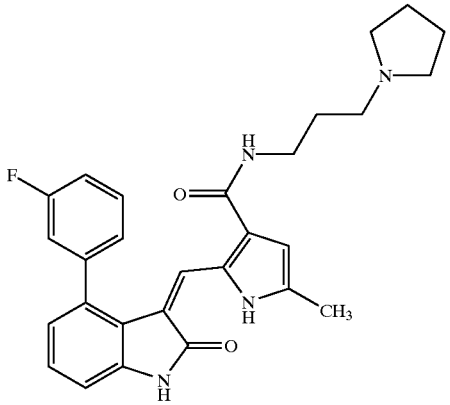

$^{1}$H NMR (400 MHz, DMSO-d$_{6}$) δ 13.81 (s, NH, 1H), 11.14 (br s, NH, 1H), 7.98 (s, 1H), 7.88 (m, 1H), 7.44 (m, 1H), 7.18 (m, 4H), 6.92 (d, J=7.0 Hz, 1H), 6.77 (d, J=7.0 Hz, 1H), 6.34 (s, 1H), 3.07 (m, 2H), 2.42 (m, 6H), 2.30 (s, 3H), 1.69 (m, 4H), 1.59 (m, 2H). MS m/z 47.1 [M−1].

Example 247

2-[4-(4-Bromo-phenyl)-2-oxo-1,2-dihydro-indol-(3Z)-ylidenemethyl]-5-methyl-1H-pyrrole-3-carboxylic Acid (3-Pyrrolidin-1-yl-propyl)-amide

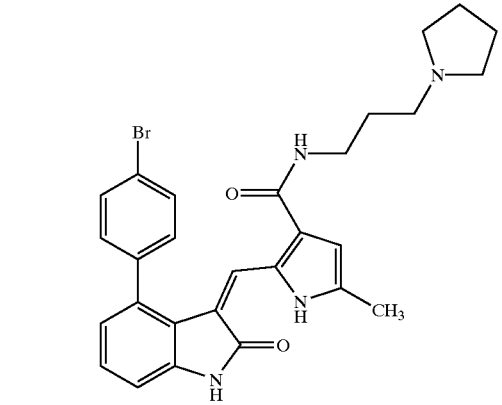

$^{1}$H NMR (400 MHz, DMSO-d$_{6}$) δ 13.81 (s, NH, 1H), 11.16 (br s, NH, 1H), 8.01 (s, 1H), 7.87 (m, 1H), 7.57 (m, 2H), 7.29 (m, 2H), 7.19 (t, J=7.8 Hz, 1H), 6.91 (d, J=7.8 Hz, 1H), 6.75 (dd, J=1.2 Hz, J=7.8 Hz, 1H), 6.36 (m, 1H), 3.15 (m, 2H), 2.42 (m, 6H), 2.30 (s, 3H), 1.67 (m, 4H), 1.61 (m, 2H). MS m/z 531, 533 [M−1].

Example 248

5-Methyl-2-[2-oxo-4-phenyl-1,2-dihydro-indol-(3Z)-ylidenemethyl]-1H-pyrrole-3-carboxylic Acid (3-Pyrrolidin-1-yl-propyl)-amide

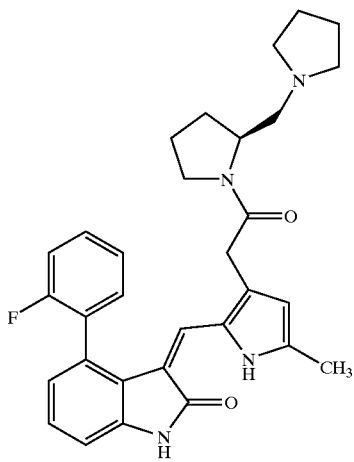

$^1$H NMR (400 MHz, DMSO-$d_6$) δ 13.80 (s, NH, 1H), 11.16 (s, NH, 1H), 7.89 (s, 1H), 7.82 (m, 1H), 7.37 (m, 5H), 7.17 (t, J=7.8 Hz, 1H), 6.90 (d, J=7.0 Hz, 1H), 6.75 (d, J=7.0 Hz, 1H), 6.29 (m, 1H), 3.03 (m, 2H), 2.42 (m, 6H), 2.29 (s, 3H), 1.68 (m, 4H), 1.56 (m, 2H). MS m/z 453 [M−1].

Example 249

5-[4-(3,5-Difluoro-phenyl)-2-oxo-1,2-dihydro-indol-(3Z)-ylidenemethyl]-2,4-dimethyl-1H-pyrrole-3-carboxylic Acid (2-Pyrrolidin-1-yl-ethyl)-amide

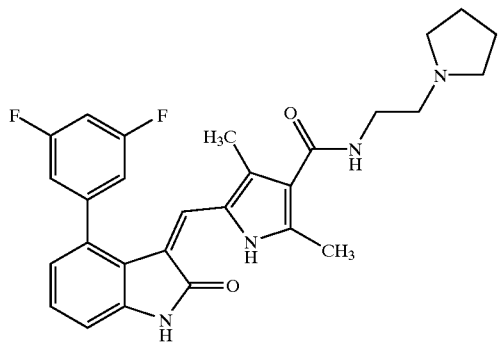

$^1$H NMR (400 MHz, DMSO-$d_6$) δ 13.45 (s, NH, 1H), 11.08 (s, NH, 1H), 7.48 (m, 1H), 7.40 (m, 1H), 7.22 (m, 2H), 7.18 (t, J=7.8 Hz, 1H), 6.92 (dd, J=0.8 Hz, J=7.4 Hz, 1H), 6.80 (m, 2H), 3.26 (m, 2H), 2.51 (m, 2H), 2.44 (m, 4H), 2.36 (s, 3H), 1.78 (s, 3H), 1.64 (m, 4H). MS m/z 489 [M−1].

Example 250

2-[4-(3,5-Difluoro-phenyl)-2-oxo-1,2-dihydro-indol-(3Z)-ylidenemethyl]-5-methyl-1H-pyrrole-3-carboxylic Acid (3-Pyrrolidin-1-yl-propyl)-amide

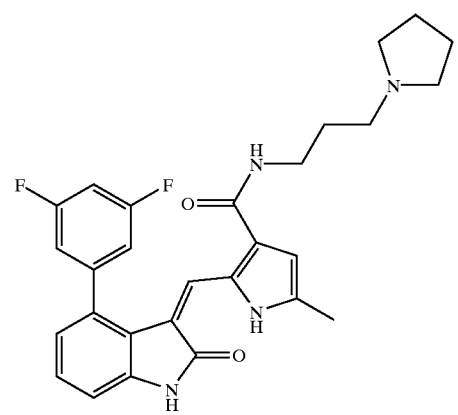

$^1$H NMR (400 MHz, DMSO-$d_6$) δ 13.77 (s, NH, 1H), 11.13 (s, NH, 1H), 8.05 (s, 1H), 7.94 (m, 1H), 7.19 (t, J=7.8 Hz, 1H), 7.11 (m, 1H), 7.05 (m, 2H), 6.93 (d, J=7.8 Hz, 1H), 6.78 (d, J=7.8 Hz, 1H), 6.38 (m, 1H), 3.10 (m, 2H), 2.42 (m, 6H), 2.30 (s, 3H), 1.68 (m, 4H), 1.59 (m, 2H). MS m/z 489 [M−1].

Example 251

4-(3,5-Difluoro-phenyl)-3-[1-[3,5-dimethyl-4-(4-methyl-piperazine-1-carbonyl)-1H-pyrrol-2-yl]-meth-(Z)-ylidene]-1,3-dihydro-indol-2-one

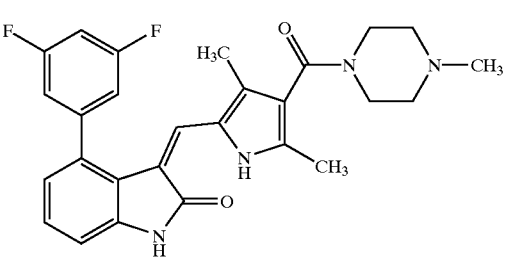

$^1$H NMR (400 MHz, DMSO-$d_6$) δ 13.43 (s, NH, 1H), 11.08 (s, NH, 1H), 7.39 (m, 1H), 7.20 (m, 3H), 6.94 (d, J=7.4 Hz, 1H), 6.80 (m, 2H), 3.42 (m, 4H), 2.26 (m, 4H), 2.22 (s, 3H), 2.15 (s, 3H), 1.65 (s, 3H). MS m/z 475 [M−1].

Example 252

4-(3,5-Difluoro-phenyl)-3-[1-[5-methyl-3-(4-pyrrolidin-1-yl-piperidine-1-carbonyl)-1H-pyrrol-2-yl]-meth-(Z)-ylidene]-1,3-dihydro-indol-2-one

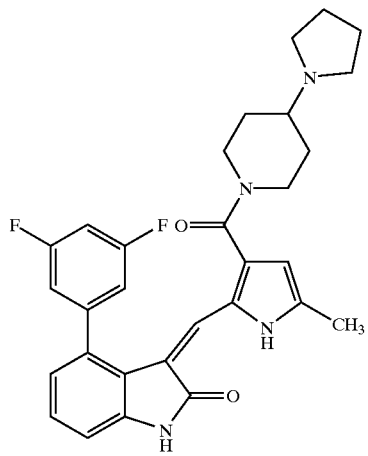

$^1$H NMR (400 MHz, DMSO-d$_6$) δ 13.54 (s, NH, 1H), 11.12 (s, NH, 1H), 7.24 (m, H), 7.18 (m, 1H), 7.06 (m, 2H), 6.93 (m, 2H), 6.76 (d, J=7.0 Hz, 1H), 6.09 (s, 1H), 4.11 (m, 1H), 3.59 (m, 1H), 2.84 (m, 2H), 2.45 (m, 4H), 2.31 (s, 3H), 2.17 (m, 1H), 1.58 (m, 1H), 1.65 (m, 5H), 1.21 (m, 2H). MS m/z 515 [M−1].

Example 253

3-[1-{3,5-Dimethyl-4-[3-(4-methyl-piperazin-1-yl)-3-oxo-propyl]-1H-pyrrol-2-yl}-meth-(Z)-ylidene]-4-[3-(2-hydroxy-ethyl)-phenyl]-1,3-dihydro-indol-2-one

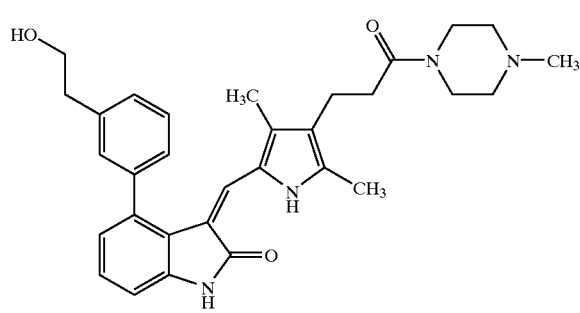

$^1$H NMR (400 MHz, DMSO-d$_6$) δ 13.27 (s, NH, 1H), 10.85 (s, NH, 1H), 7.41 (t, J=7.4 Hz, 1H), 7.31 (d, J=7.4 Hz, 1H), 7.23 (s, 1H), 7.18 (d, J=7.8 Hz, 1H), 7.09 (t, J=7.8 Hz, 1H), 6.86 (d, J=7.8 Hz, 1H), 6.71 (m, 2H), 4.64 (m, 1H), 3.60 (m, 2H), 3.37 (m, 2H), 3.24 (m, 2H), 2.76 (t, J=7.4 Hz, 2H), 2.35 (m, 4H), 2.21 (s, 3H), 2.13 (m, 4H), 2.07 (s, 3H), 1.49 (s, 3H). MS m/z 511 [M−1].

Example 254

3-[1-{4-[3-((cis)-3,5-Dimethyl-piperazin-1-yl)-3-oxo-propyl]-3,5-dimethyl-1H-pyrrol-2-yl}-meth-(Z)-ylidene]-4-[3-(2-hydroxy-ethyl)-phenyl]-1,3-dihydro-indol-2-one

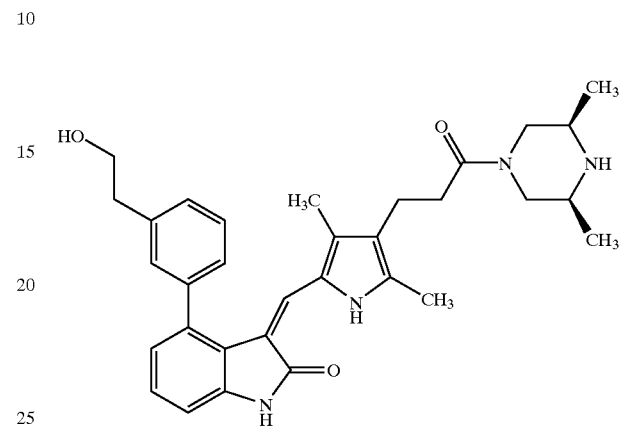

MS m/z 525 [M−1].

Example 255

4-[3-(2-Hydroxy-ethyl)-phenyl]-3-[1-[3-methyl-4-(4-methyl-piperazine-1-carbonyl)-1H-pyrrol-2-yl]-meth-(Z)-ylidene]-1,3-dihydro-indol-2-one

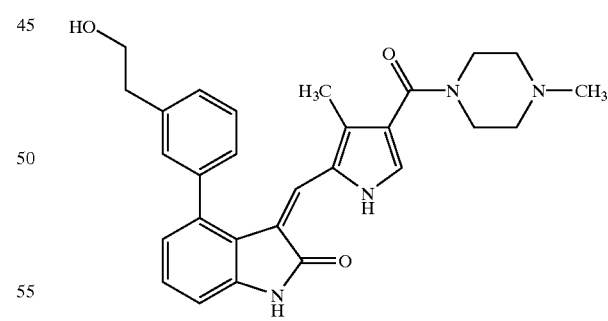

$^1$H NMR (400 MHz, DMSO-d$_6$) δ 13.48 (s, NH, 1H), 11.08 (s, NH, 1H), 7.44 (t, J=7.4 Hz, 1H), 7.35 (d, J=3.1 Hz, 1H), 7.33 (d, J=7.8 Hz, 1H), 7.26 (s, 1H), 7.22 (m, 1H), 7.18 (t, J=7.8 Hz, 1H), 6.90 (d, J=7.8 Hz, 1H), 6.78 (m, 2H), 4.64 (t, J=5.1 Hz, 1H), 3.60 (m, 2H), 3.43 (m, 4H), 2.77 (t, J=7.0 Hz, 2H), 2.24 (m, 4H), 2.15 (s, 3H), 1.57 (s, 3H). MS m/z 469 [M−1].

Example 256

3-[1-[4-((cis)-3,5-Dimethyl-piperazine-1-carbonyl)-3-methyl-1H-pyrrol-2-yl]-meth-(Z)-ylidene]-4-[3-(2-hydroxy-ethyl)-phenyl]-1,3-dihydro-indol-2-one

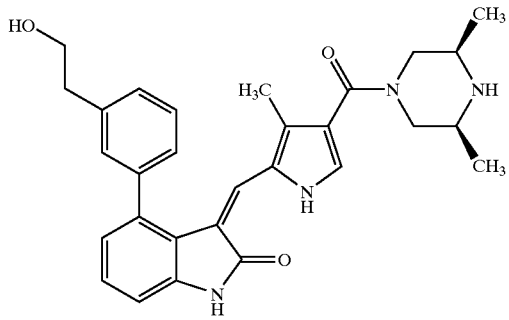

$^1$H NMR (400 MHz, DMSO-d$_6$) δ 13.46 (s, NH, 1H), 11.08 (s, NH, 1H), 7.44 (t, J=7.8 Hz, 1H), 7.34 (m, 2H), 7.26 (s, 1H), 7.21 (d, J=7.4 Hz, 1H), 7.18 (t, J=7.8 Hz, 1H), 6.89 (d, J=7.8 Hz, 1H), 6.77 (m, 2H), 4.63 (t, J=5.1 Hz, 1H), 4.10 (m, 1H), 3.60 (m, 2H), 2.77 (t, J=7.0 Hz, 2H), 2.56 (m, 4H), 2.30 (m, 2H), 1.56 (s, 3H), 0.90 (m, 6H). MS m/z 483 [M−1].

Example 257

2-[4-[3-(2-Hydroxy-ethyl)-phenyl]-2-oxo-1,2-dihydro-indol-(3Z)-ylidenemethyl]-5-methyl-1H-pyrrole-3-carboxylic Acid (3-Pyrrolidin-1-yl-propyl)-amide

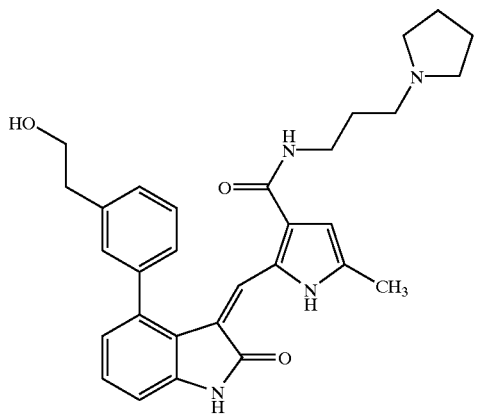

$^1$H NMR (400 MHz, DMSO-d$_6$) δ 13.79 (s, NH, 1H), 11.08 (s, NH, 1H), 7.95 (m, 1H), 7.86 (s, 1H), 7.26 (d, J=7.8 Hz, 1H), 7.16 (m, 3H), 7.11 (d, J=7.8 Hz, 1H), 6.88 (d, J=7.8 Hz, 1H), 6.73 (dd, J=1.2 Hz, J=7.8 Hz, 1H), 6.32 (m, 1H), 4.55 (br m, 1H), 3.61 (m, 2H), 3.02 (m, 2H), 2.72 (t, J=6.6 Hz, 2H), 2.43 (m, 6H), 2.28 (s, 3H), 1.67 (m, 4H), 1.57 (m, 2H). MS m/z 497 [M−1].

Example 258

3-[1-[3-((cis)-3,5-Dimethyl-piperazine-1-carbonyl)-5-methyl-1H-pyrrol-2-yl]-meth-(Z)-ylidene]-4-[3-(2-hydroxy-ethyl)-phenyl]-1,3-dihydro-indol-2-one

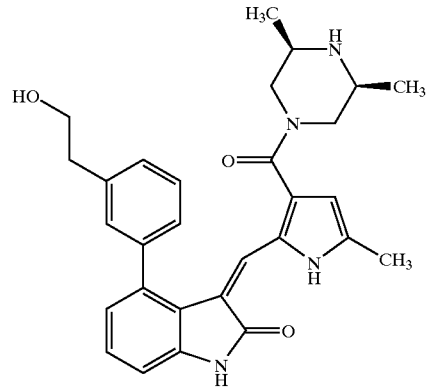

$^1$H NMR (400 MHz, DMSO-d$_6$) δ 13.65 (s, NH, 1H), 11.20 (s, NH, 1H), 7.30 (br m, 1H), 7.20 (m, 1H), 7.18 (m, 3H), 6.96 (br m, 1H), 6.88 (dd, J=0.8 Hz, J=7.8 Hz, 1H), 6.71 (dd, J=0.8 Hz, J=7.4 Hz, 1H), 6.02 (d, J=2.3 Hz, 1H), 4.61 (m, 1H), 4.06 (m, 1H), 3.63 (m, 2H), 2.75 (m, 2H), 2.46 (m, 4H), 2.29 (s, 3H), 2.0 (m, 2H), 1.03 (m, 3H), 0.77 (m, 3H). MS m/z 483 [M−1].

Example 259

(3-{3-[1-[3-Methyl-4-(morpholine-4-carbonyl)-1H-pyrrol-2-yl]-meth-(Z)-ylidene]-2-oxo-2,3-dihydro-1H-indol-4-yl}-phenyl)-acetic Acid

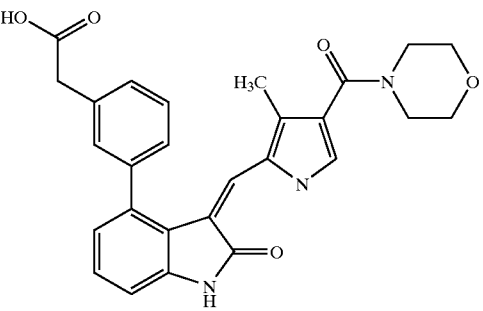

[3-(2-Oxo-2,3-dihydro-1H-indol-4-yl)-phenyl]-acetic acid (80.1 mg, 0.3 mmol) was condensed with 3-methyl-4-(morpholine-4-carbonyl)-1H-pyrrole-2-carbaldehyde (66.7 mg, 0.3 mmol) in ethanol to give 75.3 mg of the titled compound.

$^1$H NMR (400 MHz, DMSO-d$_6$) δ 13.50 (s, NH, 1H), 12.29 (s, 1H), 11.09 (s, NH, 1H), 7.48 (t, J=7.4 Hz, 1H), 7.37 (m, 2H), 7.30 (s, 1H), 7.27 (d, J=7.4 Hz, 1H), 7.19 (t, J=7.4 Hz, 1H), 6.90 (dd, J=0.8 Hz, J=7.8 Hz, 1H), 6.76 (m, 2H), 3.64 (s, 2H), 3.52 (m, 4H), 3.44 (m, 4H), 1.58 (s, 3H). MS m/z 472 [M$^+$+1].

Example 260

4-{3-[2-((cis)-3,5-Dimethyl-piperazin-1-yl)-2-oxo-ethyl]-phenyl}-3-[1-[3-methyl-4-(morpholine-4-carbonyl)-1H-pyrrol-2-yl]-meth-(Z)-ylidene]-1,3-dihydro-indol-2-one

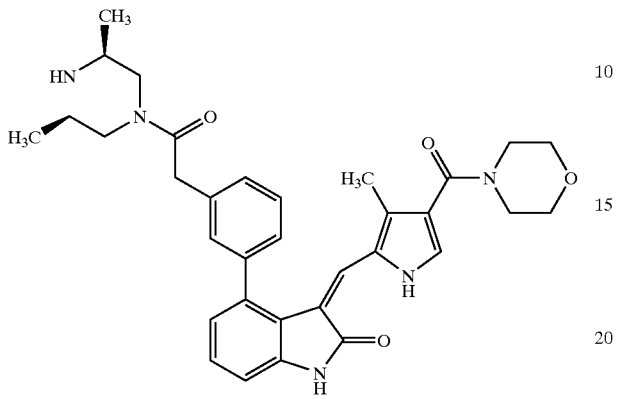

(3-{3-[1-[3-Methyl-4-(morpholine-4-carbonyl)-1H-pyrrol-2-yl]-meth-(Z)-ylidene]-2-oxo-2,3-dihydro-1H-indol-4-yl}-phenyl)-acetic acid was coupled with (2S,6R)-2,6-dimethyl-piperazine (3 eq.), EDC (1.5 eq.) and HOBt (1 eq.) in THF using the general amidation procedure to give the titled compound.

$^1$H NMR (400 MHz, DMSO-d$_6$) δ 13.50 (s, NH, 1H), 11.09 (s, NH, 1H), 7.46 (t, J=7.8 Hz, 1H), 7.38 (d, J=3.1 Hz, 1H), 7.34 (br m, 1H), 7.27 (m, 2H), 7.19 (t, J=7.8 Hz, 1H), 6.90 (d, J=7.4 Hz, 1H), 6.79 (s, 1H), 6.75 (d, J=7.8 Hz, 1H), 4.21 (m, 1H), 3.82 (m, 1H), 3.76 (s, 2H), 3.51 (m, 4H), 3.44 (m, 4H), 2.42 (m, 4H), 1.97 (m, 1H), 1.60 (s, 3H), 0.90 (d, 3H), 0.81 (d, 3H). MS m/z 566 [M−1].

Example 261

N-(2-Dimethylamino-ethyl)-2-(3-{3-[1-[3-methyl-4-(morpholine-4-carbonyl)-1H-pyrrol-2-yl]-meth-(Z)-ylidene]-2-oxo-2,3-dihydro-1H-indol-4-yl}-phenyl)-acetamide

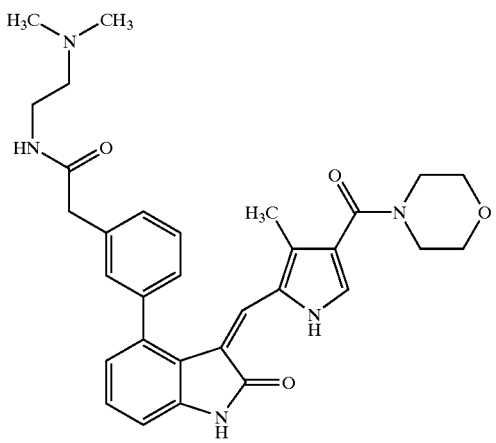

(3-{3-[1-[3-Methyl-4-(morpholine-4-carbonyl)-1H-pyrrol-2-yl]-meth-(Z)-ylidene]-2-oxo-2,3-dihydro-1H-indol-4-yl}-phenyl)-acetic acid (117.6 mg, 0.25 mmol) was coupled with N,N-dimethylethylenediamine (2 eq.), EDC (1.5 eq.) and HOBt (1 eq.) in DMF (1 mL) using the general amidation procedure to give 117.3 mg of the titled compound.

$^1$H NMR (400 MHz, DMSO-d$_6$) δ 13.50 (s, NH, 1H), 11.09 (s, NH, 1H), 7.98 (m, 1H), 7.45 (t, J=7.8 Hz, 1H), 7.36 (m, 3H), 7.24 (d, J=7.4 Hz, 1H), 7.19 (t, J=7.6 Hz, 1H), 6.90 (d, J=7.8 Hz, 1H), 6.76 (m, 2H), 3.52 (m, 4H), 3.44 (m, 4H), 3.31 (s, 2H), 3.05 (m, 2H), 2.16 (t, J=7.0 Hz, 2H), 2.03 (s, 6H), 1.57 (s, 3H). MS m/z 540 [M−1].

Example 262

5-[4-(2-Fluoro-phenyl)-2-oxo-1,2-dihydro-indol-(3Z)-ylidenemethyl]-4-phenyl-1H-pyrrole-3-carboxylic Acid Methyl-(1-methyl-piperidin-4-yl)-amide

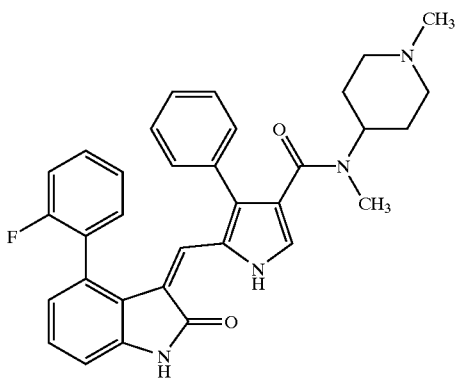

MS m/z 533 [M−1].

Example 263

5-[4-(2-Fluoro-phenyl)-2-oxo-1,2-dihydro-indol-(3Z)-ylidenemethyl]-4-phenyl-1H-pyrrole-3-carboxylic Acid (2-Diethylamino-ethyl)-amide

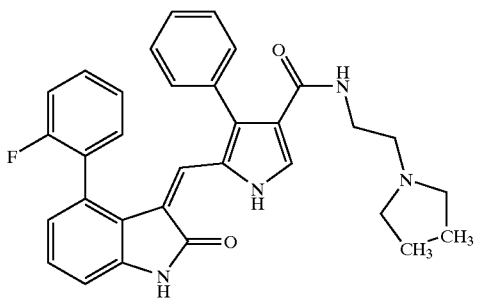

$^1$H NMR (400 MHz, DMSO-d$_6$) δ 13.99 (s, NH, 1H), 11.21 (s, NH, 1H), 7.69 (d, J=2.9 Hz, 1H), 7.32 (m, 1H), 7.21 (m, 4H), 7.04 (m, 1H), 6.98 (m, 1H), 6.92 (m, 4H), 6.79 (m, 1H), 6.69 (s, 1H), 6.68 (d, J=7.8 Hz, 1H), 3.05 (m, 2H), 2.30 (m, 6H), 0.82 (t, J=7.0 Hz, 6H). MS m/z 521 [M−1].

Example 264

5-[4-(2-Fluoro-phenyl)-2-oxo-1,2-dihydro-indol-(3Z)-ylidenemethyl]-4-phenyl-1H-pyrrole-3-carboxylic Acid (2-Pyrrolidin-1-yl-ethyl)-amide

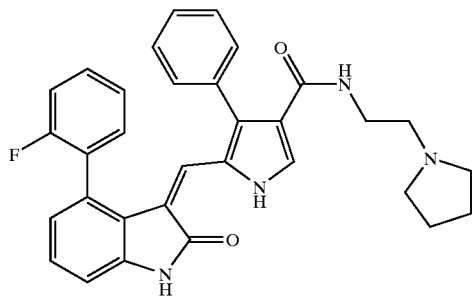

$^1$H NMR (400 MHz, DMSO-d$_6$) δ 13.99 (s, NH, 1H), 11.21 (s, NH, 1H), 7.70 (d, J=3.4 Hz, 1H), 7.32 (t, J=7.3 Hz, 1H), 7.23 (t, J=7.4 Hz, 1H), 7.18 (m, 3H), 7.04 (m, 1H), 6.97 (m, 1H), 6.90 (m, 3H), 6.83 (m, 1H), 6.78 (m, 1H), 6.67 (m, 2H), 3.10 (m, 2H), 2.27 (m, 6H), 1.57 (m, 4H). MS m/z 519 [M−1].

Example 265

N,N-Dimethyl-2-(3-{3-[1-[3-methyl-4-(4-methyl-piperazine-1-carbonyl)-1H-pyrrol-2-yl]-meth-(Z)-ylidene]-2-oxo-2,3-dihydro-1H-indol-4-yl}-phenyl)-acetamide

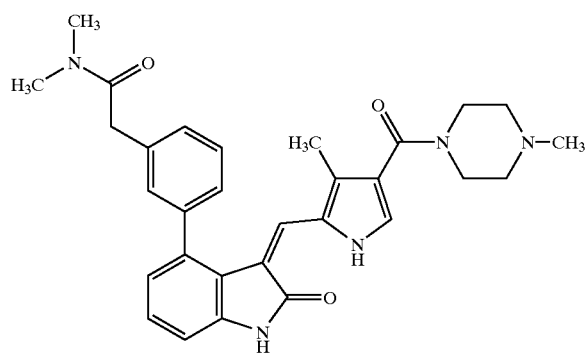

$^1$H NMR (400 MHz, DMSO-d$_6$) δ 13.47 (s, NH, 1H), 11.08 (s, NH, 1H), 7.46 (m, 1H), 7.35 (m, 2H), 7.26 (m, 2H), 7.19 (t, J=7.8 Hz, 1H), 6.90 (dd, J=0.8 Hz, J=7.8 Hz, 1H), 6.77 (m, 2H), 3.73 (s, 2H), 3.42 (m, 4H), 2.96 (s, 3H), 2.76 (s, 3H), 2.23 (m, 4H), 2.15 (s, 3H), 1.57 (s, 3H). MS m/z 510 [M−1].

Example 266

2-(3-{3-[1-[3,5-Dimethyl-4-(4-pyrrolidin-1-yl-piperidine-1-carbonyl)-1H-pyrrol-2-yl]-meth-(Z)-ylidene]-2-oxo-2,3-dihydro-1H-indol-4-yl}-phenyl)-N,N-dimethyl-acetamide

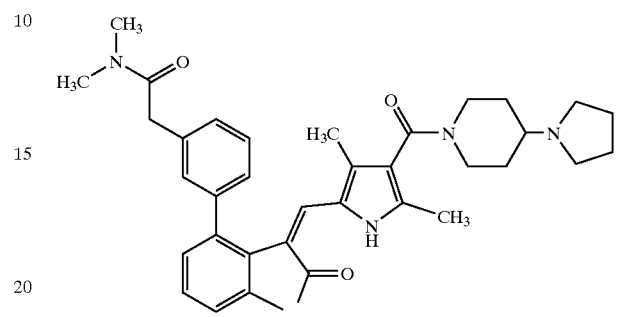

$^1$H NMR (400 MHz, DMSO-d$_6$) δ 13.40 (s, NH, 1H), 11.01 (s, NH, 1H), 7.46 (m, 1H), 7.31 (m, 1H), 7.25 (m, 2H), 7.16 (t, J=7.4 Hz, 1H), 6.90 (d, J=7.8 Hz, 1H), 6.75 (d, J=7.4 Hz, 1H), 6.69 (s, 1H), 4.08 (m, 1H), 3.73 (s, 2H), 3.40 (m, 1H), 2.95 (s, 3H), 2.90 (m, 2H), 2.76 (s, 3H), 2.43 (m, 4H), 2.20 (s, 3H), 2.16 (m, 1H), 1.74 (m, 2H), 1.63 (m, 4H), 1.50 (s, 3H), 1.15 (m, 1H). MS m/z 578 [M−1].

Example 267

5-[4-(3-Dimethylcarbamoylmethyl-phenyl)-2-oxo-1,2-dihydro-indol-(3Z)-ylidenemethyl]-2,4-dimethyl-1H-pyrrole-3-carboxylic Acid (2-Diethylamino-ethyl)-amide

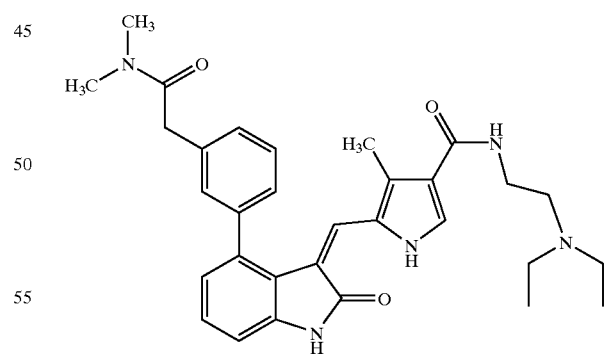

$^1$H NMR (400 MHz, DMSO-d$_6$) δ 13.46 (s, NH, 1H), 11.03 (s, NH, 1H), 7.45 (m, 1H), 7.34 (m, 2H), 7.25 (m, 2H), 7.16 (t, J=7.8 Hz, 1H), 6.90 (dd, J=0.8 Hz, J=7.8 Hz, 1H), 6.75 (m, 2H), 3.73 (s, 2H), 3.23 (m, 2H), 2.95 (s, 3H), 2.77 (s, 3H), 2.52 (m, 6H), 2.36 (s, 3H), 1.64 (s, 3H), 0.95 (m, 6H) or (t, J=7.0 Hz, 6H); MS m/z 540 [M−1].

Example 268

3-[1-[3,5-Dimethyl-4-(4-pyrrolidin-1-yl-piperidine-1-carbonyl)-1H-pyrrol-2-yl]-meth-(Z)-ylidene]-4-[3-(2-hydroxy-ethyl)-phenyl]-1,3-dihydro-indol-2-one

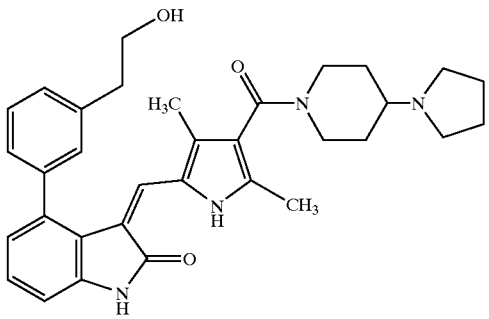

$^1$H NMR (400 MHz, DMSO-d$_6$) δ 13.40 (s, NH, 1H), 10.99 (s, NH, 1H), 7.43 (m, 1H), 7.31 (m, 1H), 7.24 (s, 1H), 7.20 (d, J=7.4 Hz, 1H), 7.15 (t, J=7.4 Hz, 1H), 6.89 (dd, J=0.8 Hz, J=7.4 Hz, 1H), 6.75 (dd, J=0.8 Hz, J=7.4 Hz, 1H), 6.71 (s, 1H), 4.63 (t, J=5.1 Hz, 1H), 4.17 (m, 1H), 3.59 (m, 3H), 2.92 (m, 2H), 2.76 (t, J=7.4 Hz, 2H), 2.43 (s, 3H), 2.20 (m, 5H), 1.78 (m, 2H), 1.64 (m, 5H), 1.49 (s, 3H), 1.22 (m, 1H). MS m/z 537 [M−1].

Example 269

4-[3-(2-Dimethylamino-ethyl)-phenyl]-3-[1-[3-methyl-4-(morpholine-4-carbonyl)-1H-pyrrol-2-yl]-meth-(Z)-ylidene]-1,3-dihydro-indol-2-one

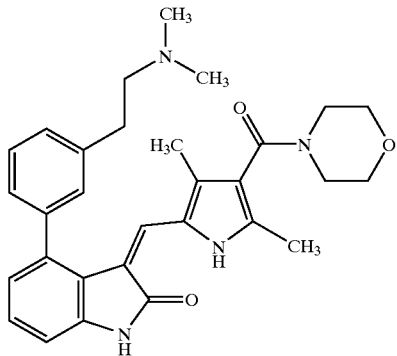

$^1$H NMR (400 MHz, DMSO-d$_6$) δ 13.50 (s, NH, 1H), 11.09 (s, NH, 1H), 7.44 (m, 1H), 7.38 (d, J=3.1 Hz, 1H), 7.33 (m, 1H), 7.26 (m, 1H), 7.19 (m, 2H), 6.89 (dd, J=1.2 Hz, J=7.8 Hz, 1H), 6.77 (m, 2H), 3.51 (m, 4H), 3.44 (m, 4H), 2.76 (t, J=7.4 Hz, 2H), 2.45 (m, 2H), 2.14 (s, 6H), 1.59 (s, 3H). MS m/z 483 [M−1].

Example 270

4-[3-(2-Dimethylamino-ethyl)-phenyl]-3-[1-[4-(4-hydroxy-piperidine-1-carbonyl)-3,5-dimethyl-1H-pyrrol-2-yl]-meth-(Z)-ylidene]-1,3-dihydro-indol-2-one

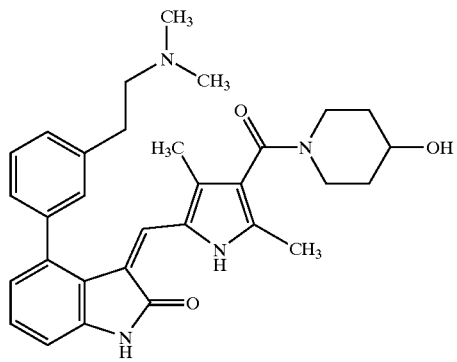

$^1$H NMR (400 MHz, DMSO-d$_6$) δ 13.41 (s, NH, 1H), 11.01 (br s, NH, 1H), 7.41 (m, 1H), 7.32 (m, 1H), 7.24 (s, 1H), 7.20 (m, 1H), 7.15 (t, J=7.8 Hz, 1H), 6.89 (dd, J=1.2 Hz, J=6.6 Hz, 1H), 6.75 (dd, J=0.8 Hz, J=7.8 Hz, 1H), 6.69 (s, 1H), 4.73 (m, 1H), 3.65 (m, 1H), 3.11 (m, 4H), 2.74 (t, J=7.4 Hz, 2H), 2.43 (m, 2H), 2.20 (s, 3H), 2.11 (s, 6H), 1.69 (m, 3H), 1.50 (s, 3H), 1.22 (m, 1H). MS m/z 511 [M−1].

Example 271

3-{3-[1-[3-Methyl-4-(morpholine-4-carbonyl)-1H-pyrrol-2-yl-meth-(Z)-ylidene]-2-oxo-2,3-dihydro-1H-indol-4-yl}-N-(2-pyrrolidin-1-yl-ethyl)-benzamide

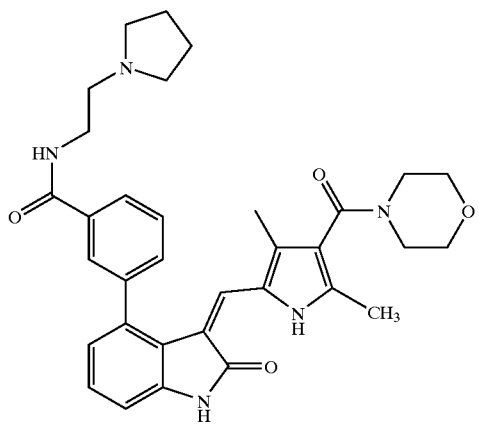

$^1$H NMR (400 MHz, DMSO-d$_6$) δ 13.50 (s, 1H, NH), 11.13 (s, 1H, NH), 8.53 (t, 1H), 7.93–7.97 (m, 2H), 7.64 (t, 1H), 7.58 (d, 1H), 7.39 (d, 1H), 7.22 (t, 1H), 6.93 (d, 1H), 6.82 (d, 1H), 6.80 (s, 1H), 3.51 (m, 4H), 3.43 (m, 4H), 3.3 (m, 2H), 2.54 (m, 2H), 2.45 (m, 4H), 1.62 (m, 4H), 1.54 (s, 3H, CH$_3$). MS m/z 554.3 [M$^+$+1].

Example 272

3-{3-[1-[3-Methyl-4-(morpholine-4-carbonyl)-1H-pyrrol-2-yl]-meth-(Z)-ylidene]-2-oxo-2,3-dihydro-1H-indol-4-yl}-N-(3-pyrrolidin-1-yl-propyl)-benzamide

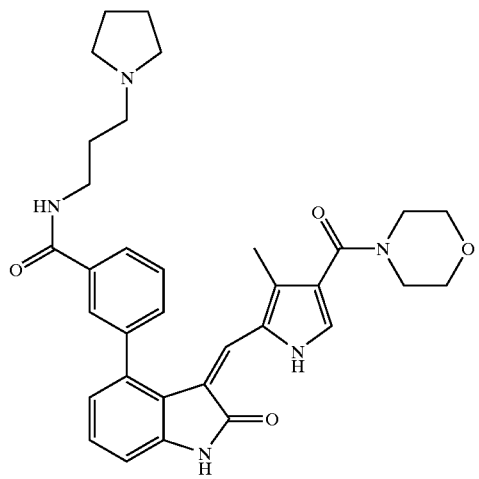

$^1$H NMR (400 MHz, DMSO-d$_6$) δ 13.51 (s, 1H, NH), 11.14 (s, 1H, NH), 8.65 (t, 1H), 7.95 (m, 1H), 7.90 (m, 1H), 7.64 (t, 1H), 7.57 (m, 1H), 7.39 (d, 1H), 7.23 (t, 1H), 6.94 (d, 1H), 6.83 (d, 1H), 6.81 (s, 1H), 3.52 (m, 4H), 3.43 (m, 4H), 3.28 (m, 2H), 2.38 (m, 6H), 1.64 (m, 6H), 1.55 (s, 3H). MS m/z 568.3 [M$^+$+1].

Example 273

N-(2-Dimethylamino-ethyl)-3-{3-[1-[3-methyl-4-(morpholine-4-carbonyl)-1H-pyrrol-2-yl]-meth-(Z)-ylidene]-2-oxo-2,3-dihydro-1H-indol-4-yl}-benzamide

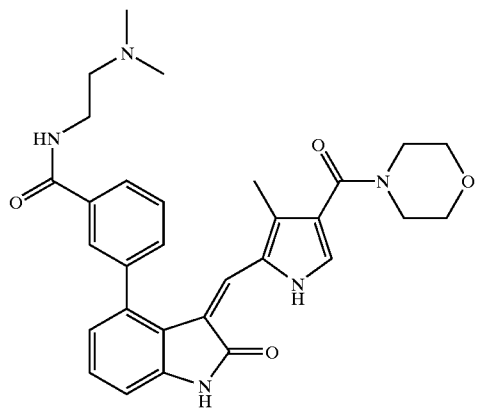

$^1$H NMR (400 MHz, DMSO-d$_6$) δ 13.52 (s, 1H, NH), 11.15 (s, 1H, NH), 8.48 (t, 1H), 7.96 (m, 1H), 7.93 (m, 1H), 7.64 (t, 1H), 7.58 (m, 1H), 7.39 (d, 1H), 7.23 (t, 1H), 6.94 (d, 1H), 6.83 (d, 1H), 6.80 (s, 1H), 3.51 (m, 4H), 3.44 (m, 4H), 3.3 (m, 2H), 2.34 (t, 2H), 2.12 (s, 6H, 2×CH$_3$), 1.55 (s, 3H, CH$_3$). MS m/z 528.2 [M$^+$+1].

Example 274

N-(3-Dimethylamino-propyl)-3-{3-[1-[3-methyl-4-(morpholine-4-carbonyl)-1H-pyrrol-2-yl]-meth-(Z)-ylidene]-2-oxo-2,3-dihydro-1H-indol-4-yl}-benzamide

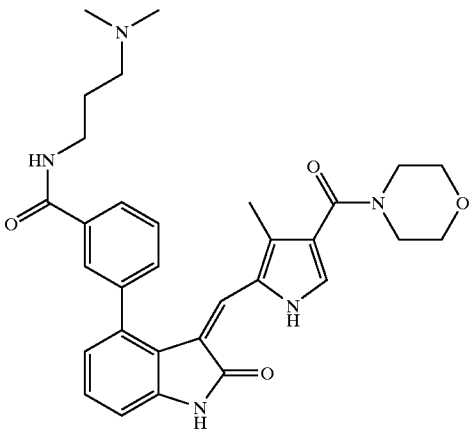

$^1$H NMR (400 MHz, DMSO-d$_6$) δ 13.52 (s, 1H, NH), 11.14 (s, 1H, NH), 8.59 (t, 1H), 7.95 (m, 1H), 7.92 (m, 1H), 7.64 (t, 1H), 7.57 (m, 1H), 7.39 (d, 1H), 7.23 (t, 1H), 6.94 (d, 1H), 6.83 (d, 1h), 6.81 (s, 1H), 3.51 (m, 4H), 3.43 (m, 4H), 3.25 (m, 2H), 2.19 (t, 2H), 2.06 (s, 6H), 1.60 (m, 2H), 1.55 (s, 3H, 2×CH$_3$). MS m/z 542.3 [M$^+$+1].

Example 275

N-Methyl-3-{3-[1-[3-methyl-4-(morpholine-4-carbonyl)-1H-pyrrol-2-yl]-meth-(Z)-ylidene]-2-oxo-2,3-dihydro-1H-indol-4-yl}-N-(1-methyl-piperidin-4-yl)-benzamide

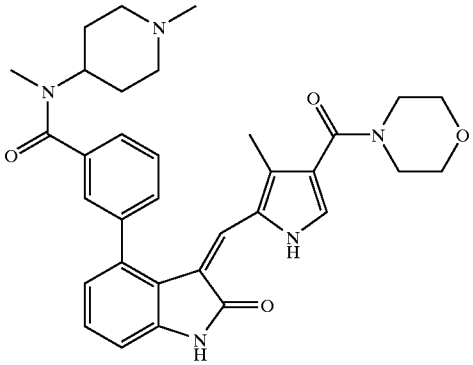

MS m/z 568 [M$^+$+1].

Example 276

2-{2-[4-(2-Fluoro-phenyl)-2-oxo-1,2-dihydro-indol-(3Z)-ylidenemethyl]-5-methyl-1H-pyrrol-3-yl}-N-(2-pyrrolidin-1-yl-ethyl)-acetamide

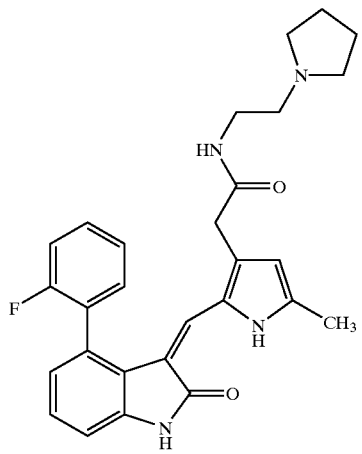

$^1$H NMR (400 MHz, DMSO-d$_6$) δ 13.33 (s, NH, 1H), 10.98 (s, NH, 1H), 7.49 (m, 2H), 7.41 (m, 1H), 7.31 (m, 2H), 7.17 (t, J=7.8 Hz, 1H), 6.93 (d, J=7.4 Hz, 1H), 6.79 (d, J=7.4 Hz, 1H), 6.57 (s, 1H), 5.91 (s, 1H), 3.09 (m, 2H), 2.68 (m, 2H), 2.40 (m, 6H), 2.26 (s, 3H), 1.63 (m, 4H). MS m/z 471 [M−1].

Example 277

N-(2,4-Dioxo-1,2,3,4-tetrahydro-pyrimidin-5-ylmethyl)-2-{2-[4-(2-fluoro-phenyl)-2-oxo-1,2-dihydro-indol-(3Z)-ylidenemethyl]-5-methyl-1H-pyrrol-3-yl}-acetamide

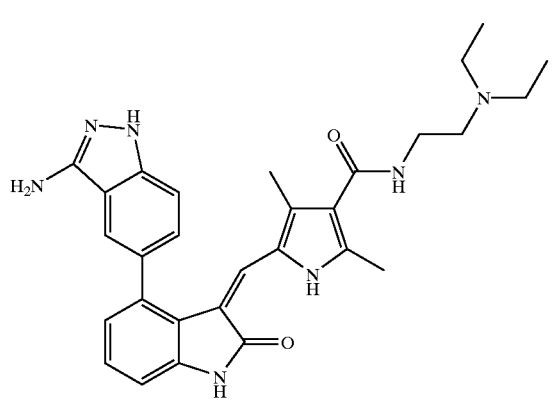

$^1$H NMR (400 MHz, DMSO-d$_6$) δ 13.39 (s, NH, 1H), 11.02 (s, NH, 1H), 10.81 (br s, NH, 2H), 8.04 (m, 1H), 7.52 (m, 1H), 7.42 (m, 1H), 7.32 (m, 2H), 7.19 (t, J=7.8 Hz, 1H), 6.96 (dd, J=1.2 Hz, J=7.8 Hz, 1H), 6.81 (dd, J=0.8 Hz, J=7.4 Hz, 1H), 6.62 (s, 1H), 5.93 (d, J=2.3 Hz, 1H), 5.18 (s, 1H), 3.88 (m, 2H), 2.81 (d, J=11.3 Hz, 2H), 2.29 (s, 3H). MS m/z 498 [M−1].

Example 278

5-[4-(3-Amino-1H-indazol-5-yl)-2-oxo-1,2-dihydro-indol-(3Z)-ylidenemethyl]-2,4-dimethyl-1H-pyrrole-3-carboxylic Acid (2-Diethylamino-ethyl)-amide

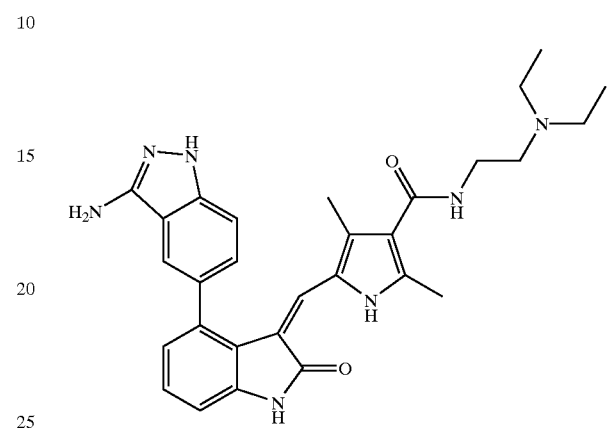

MS m/z 510.5 [M−1].

Example 279

5-[4-(3-Amino-1H-indazol-5-yl)-2-oxo-1,2-dihydro-indol-(3Z)-ylidenemethyl]-2,4-dimethyl-1H-pyrrole-3-carboxylic Acid (2-Pyrrolidin-1-yl-ethyl)-amide

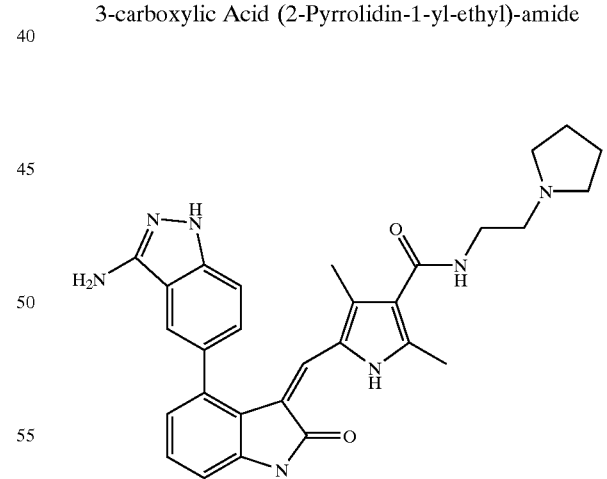

$^1$H NMR (400 MHz, DMSO-d$_6$) δ 13.46 (s, 1H, NH), 11.51 (s, 1H, NH), 11.0 (s, 1H, NH), 7.73 (s, 1H), 7.41 (br s, 1H, NH), 7.35 (d, 1H), 7.14–7.22 (m, 2H), 6.89 (d, 1H), 6.82 (d, 1H), 6.76 (s, 1H), 5.37 br s, 2H, NH$_2$), 2.99 (m, 2H), 2.54 (m, 2H), 2.44 (m, 2H), 2.35 (s, 3H, CH$_3$), 1.7 (m, 4H), 1.62 (m, 2H), 1.4 (s, 3H, CH$_3$). MS m/z 508.5 [M−1].

Example 280

3-{3-[1-[3-Methyl-4-(morpholine-4-carbonyl)-1H-pyrrol-2-yl]-meth-(Z)-ylidene]-2-oxo-2,3-dihydro-1H-indol-4-yl}-benzoic Acid

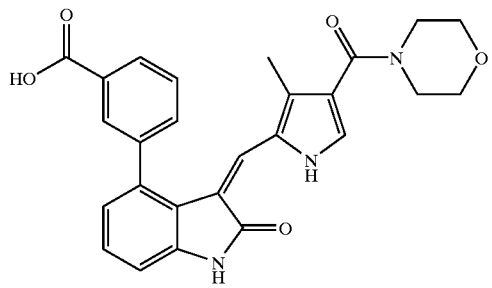

$^1$H NMR (400 MHz, DMSO-d$_6$) δ 13.51 (s, 1H, NH), 11.14 (s, 1H, NH), 8.05 (m, 1H), 7.95 (s, 1H), 7.7 (m, 2H), 7.40 (d, 1H), 7.22 (t, 1H), 6.94 (d, 1H), 6.79 (s, 1H), 3.51 (m, 4H), 3.43 (m, 4H), 1.55 (s, 3H, CH$_3$). MS m/z 458.4 [M$^+$+1].

Example 281

5-[4-(3-Fluoro-phenyl)-2-oxo-1,2-dihydro-indol-(3Z)-ylidenemethyl]-2,4-dimethyl-1H-pyrrole-3-carboxylic Acid (2-Hydroxy-3-pyrrolidin-1-yl-propyl)-amide

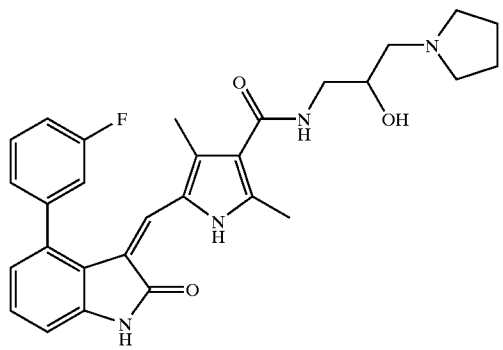

$^1$H NMR (400 MHz, DMSO-d$_6$) δ 13.46 (s, 1H, NH), 11.06 (s, 1H, NH), 7.58 (m, 1H), 7.46 (m, 1H), 7.25–7.35 (m, 3H), 7.18 (t, 1H), 6.93 (d, 1H), 6.78 (d, 1H), 6.77 (s, 1H), 3.68 (m, 1H), 3.36 (m, 2H), 3.28 (dd, 1H), 3.1 (dd, 1H), 2.52 (m, 4H), 2.37 (s, 3H, CH$_3$), 1.71 (s, 3H, CH$_3$), 1.66 (m, 4H). MS m/z 503.4 [M$^+$+1].

Example 282

3-[1-[4-(3-Diethylamino-pyrrolidine-1-carbonyl)-3,5-dimethyl-1H-pyrrol-2-yl]-meth-(Z)-ylidene]-4-(3-fluoro-phenyl)-1,3-dihydro-indol-2-one

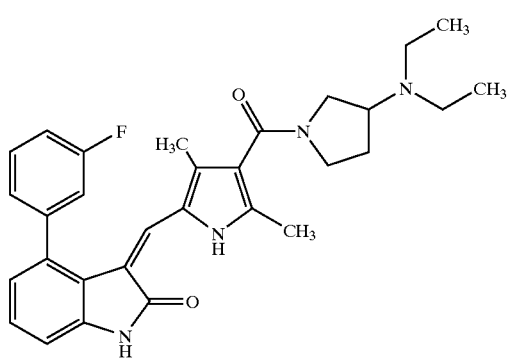

MS m/z 499 [M−1].

Example 283

3-[1-[3-(3-Diethylamino-pyrrolidine-1-carbonyl)-5-methyl-1H-pyrrol-2-yl]-meth-(Z)-ylidene]-4-(3-fluoro-phenyl)-1,3-dihydro-indol-2-one

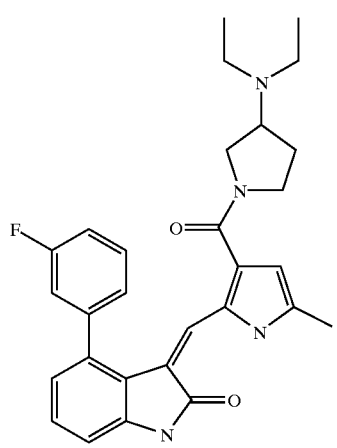

MS m/z 485 [M−1].

Example 284

3-[1-{4-[2-(3-Diethylamino-pyrrolidin-1-yl)-2-oxo-ethyl]-3,5-dimethyl-1H-pyrrol-2-yl}-meth-(Z)-ylidene]-4-(3-fluoro-phenyl)-1,3-dihydro-indol-2-one

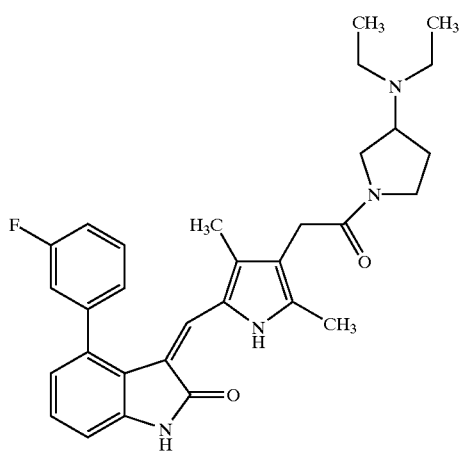

MS m/z 513 [M−1].

Example 285

3-[1-{3-[2-(3-Diethylamino-pyrrolidin-1-yl)-2-oxo-ethyl]-5-methyl-1H-pyrrol-2-yl}-meth-(Z)-ylidene]-4-(3-fluoro-phenyl)-1,3-dihydro-indol-2-one

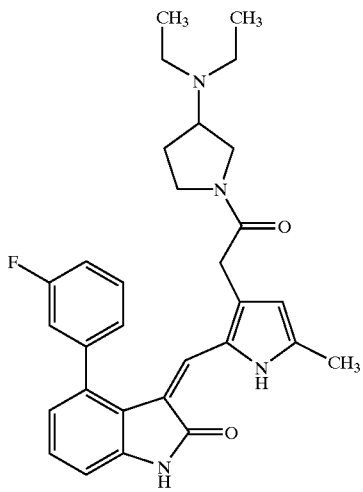

MS m/z 499 [M−1].

Example 286

5-[4-(2,4-Difluoro-phenyl)-2-oxo-1,2-dihydro-indol-(3Z)-ylidenemethyl]-2,4-dimethyl-1H-pyrrole-3-carboxylic Acid (2-Pyrrolidin-1-yl-ethyl)-amide

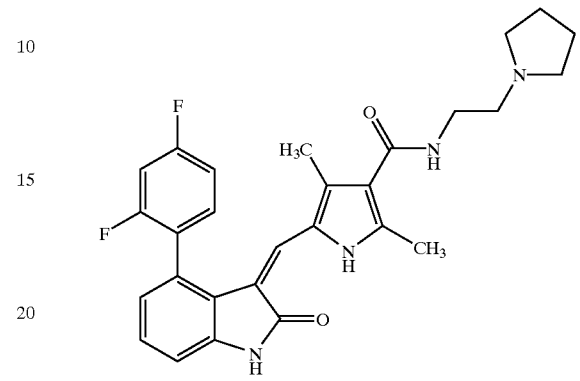

$^1$H NMR (400 MHz, DMSO-$d_6$) δ 13.46 (s, NH, 1H), 11.09 (s, NH, 1H), 7.49 (m, 3H), 7.30 (m, 1H), 7.20 (t, J=7.8 Hz, 1H), 6.96 (d, J=7.8 Hz, 1H), 6.81 (dd, J=0.8 Hz, J=7.8 Hz, 1H), 6.59 (s, 1H), 3.27 (m, 2H), 2.48 (m, 6H), 2.36 (s, 3H), 1.74 (s, 3H), 1.64 (m, 4H). MS m/z 489 [M−1].

Example 287

2-[4-(2,4-Difluoro-phenyl)-2-oxo-1,2-dihydro-indol-(3Z)-ylidenemethyl]-5-methyl-1H-pyrrole-3-carboxylic Acid (3-Pyrrolidin-1-yl-propyl)-amide

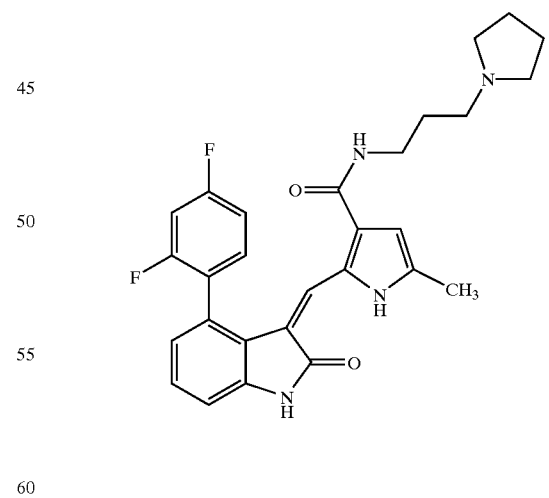

$^1$H NMR (400 MHz, DMSO-$d_6$) δ 13.79 (s, NH, 1H), 11.18 (s, NH, 1H), 7.93 (m, 1H), 7.88 (m, 1H), 7.37 (m, 1H), 7.21 (m, 2H), 7.13 (m, 1H), 6.95 (d, J=6.6 Hz, 1H), 6.77 (d, J=7.8 Hz, 1H), 6.37 (m, 1H), 3.10 (m, 2H), 2.39 (m, 6H), 2.30 (s, 3H), 1.67 (m, 4H), 1.59 (m, 2H). MS m/z 489 [M−1].

Example 288

4-(2,4-Difluoro-phenyl)-3-[1-[3,5-dimethyl-4-(4-methyl-piperazine-1-carbonyl)-1H-pyrrol-2-yl]-meth-(Z)-ylidene]-1,3-dihydro-indol-2-one

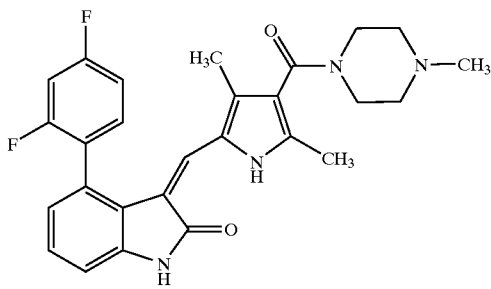

¹H NMR (400 MHz, DMSO-d$_6$) δ 13.45 (s, NH, 1H), 11.09 (s, NH, 1H), 7.50 (m, 2H), 7.29 (m, 1H), 7.20 (t, J=7.6 Hz, 1H), 6.96 (dd, J=0.8 Hz, J=7.8 Hz, 1H), 6.81 (dd, J=0.8 Hz, J=7.4 Hz, 1H), 6.57 (s, 1H), 3.28 (m, 4H), 2.27 (m, 4H), 2.23 (s, 3H), 2.16 (s, 3H), 1.62 (s, 3H). MS m/z 475 [M−1].

Example 289

4-(2,4-Difluoro-phenyl)-3-[1-[5-methyl-3-(4-pyrrolidin-1-yl-piperidine-1-carbonyl)-1H-pyrrol-2-yl]-meth-(Z)-ylidene]-1,3-dihydro-indol-2-one

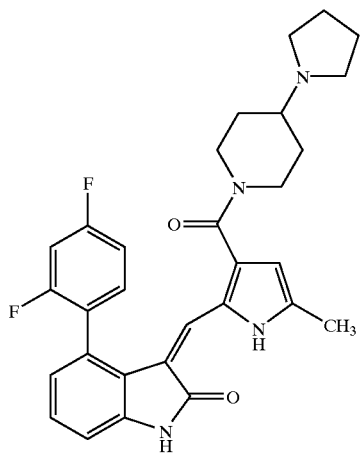

¹H NMR (400 MHz, DMSO-d$_6$) δ 13.63 (s, NH, 1H), 11.14 (s, NH, 1H), 7.40 (m, 1H), 7.29 (m, 1H), 7.20 (t, J=7.8 Hz, 1H), 7.16 (m, 1H), 6.95 (dd, J=0.8 Hz, J=7.8 Hz, 1H), 6.82 (s, 1H), 6.76 (dd, J=0.8 Hz, J=7.4 Hz, 1H), 6.08 (d, J=2.3 Hz, 1H), 4.09 (m, 1H), 3.58 (m, 1H), 2.87 (m, 2H), 2.45 (m, 4H), 2.31 (s, 3H), 2.19 (m, 1H), 1.82 (m, 1H), 1.66 (m, 5H), 1.21 (m, 2H). MS m/z 515 [M−1].

Example 290

4-(3-Chloro-phenyl)-3-[1-[4-((R)-3-hydroxy-pyrrolidine-1-carbonyl)-3-methyl-1H-pyrrol-2-yl]-meth-(Z)-ylidene]-1,3-dihydro-indol-2-one

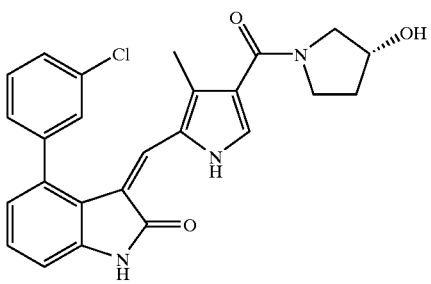

¹H NMR (400 MHz, DMSO-d$_6$) δ 13.50 (s, NH, 1H), 11.14 (s, NH, 1H), 7.59 (m, 4H), 7.42 (m, 1H), 7.21 (t, J=7.8 Hz, 1H), 6.93 (dd, J=0.8 Hz, J=7.8 Hz, 1H), 6.85 (s, 1H), 6.81 (dd, J=0.8 Hz, J=7.8 Hz, 1H), 4.92 (m, 1H), 4.24 (m, 1H), 3.58 (m, 1H), 3.50 (m, 2H), 3.29 (m, 1H), 1.85 (m, 1H), 1.77 (m, 1H), 1.74 (s, 3H). MS m/z 446 [M−1].

Example 291

4-(3-Chloro-phenyl)-3-[1-[3-((R)-3-hydroxy-pyrrolidine-1-carbonyl)-5-methyl-1H-pyrrol-2-yl]-meth-(Z)-ylidene]-1,3-dihydro-indol-2-one

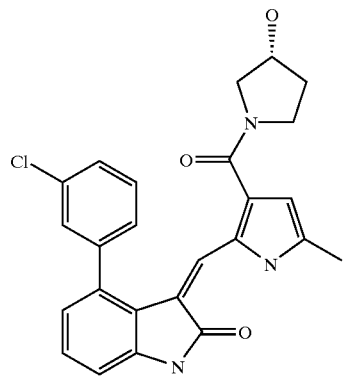

¹H NMR (400 MHz, DMSO-d$_6$) (2 conformational isomer) δ 13.65 (s, NH, 1H), 11.08 (br s, NH, 1H), 7.44 (m, 2H), 7.38 (m, 1H), 7.32 (m, 1H), 7.19 (m, 2H), 6.91 (d, J=7.8 Hz, 1H), 6.75 (dd, J=0.8 Hz, J=7.4 Hz, 1H), 6.20 (m, 1H), 4.82 (m, 1H), 4.31 (m, 0.5H), 4.13 (m, 0.5H), 3.30 (m, 4H), 2.31 (s, 3H), 1.82 (m, 2H). MS m/z 446 [M−1].

Example 292

4-(2-Fluoro-phenyl)-3-[1-[4-((R)-3-hydroxy-pyrrolidine-1-carbonyl)-3-methyl-1H-pyrrol-2-yl]-meth-(Z)-ylidene]-1,3-dihydro-indol-2-one

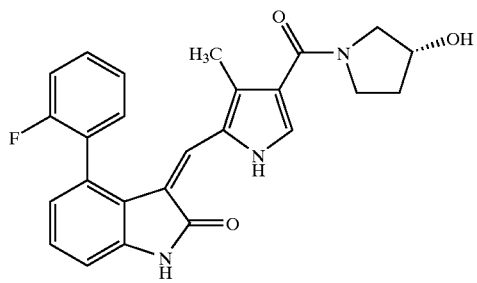

$^1$H NMR (400 MHz, DMSO-d$_6$) δ 13.52 (s, NH, 1H), 11.08 (br s, NH, 1H), 7.56 (m, 2H), 7.43 (m, 3H), 7.23 (t, J=7.8 Hz, 1H), 6.95 (d, J=7.8 Hz, 1H), 6.84 (d, J=7.8 Hz, 1H), 6.71 (s, 1H), 4.92 (m, 1H), 4.22 (m, 1H), 3.58 (m, 1H), 3.94 (m, 1H), 3.28 (m, 2H), 1.86 (m, 1H), 1.72 (m, 1H), 1.68 (s, 3H). MS m/z 430 [M−1].

Example 293

4-(3-Fluoro-phenyl)-3-[1-[4-((R)-3-hydroxy-pyrrolidine-1-carbonyl)-3,5-dimethyl-1H-pyrrol-2-yl]-meth-(Z)-ylidene]-1,3-dihydro-indol-[2-one

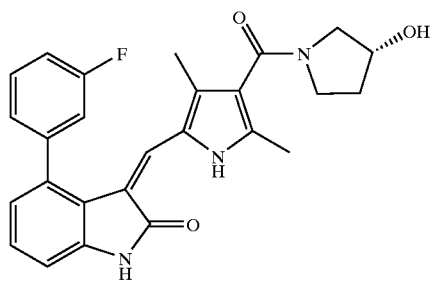

$^1$H NMR (400 MHz, DMSO-d$_6$) (2 conformational isomer) δ 13.39 (s, NH, 1H), 11.04 (s, NH, 1H), 7.58 (m, 1H), 7.29 (m, 3H), 7.18 (t, J=7.8 Hz, 1H), 6.93 (dd, J=1.2 Hz, J=7.8 Hz, 1H), 6.79 (dd, J=0.8 Hz, J=7.8 Hz, 1H), 6.75 (s, 1H), 4.95 (m, 0.5H), 4.85 (m, 0.5H), 4.29 (m, 0.5H), 4.15 (m, 0.5H), 3.45 (m, 1H), 3.25 (m, 3H), 2.22 (s, 3H), 1.81 (m, 2H), 1.59 (s, 3H). MS m/z 444 [M−1].

Example 294

4-(3-Fluoro-phenyl)-3-[1-{4-[2-((R)-3-hydroxy-pyrrolidin-1-yl)-2-oxo-ethyl]-3,5-dimethyl-1H-pyrrol-2-yl}-meth-(Z)-ylidene]-1,3-dihydro-indol-2-one

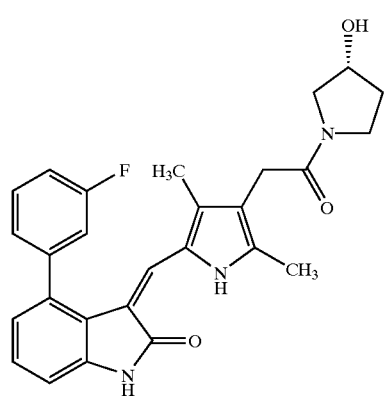

$^1$H NMR (400 MHz, DMSO-d$_6$) (2 conformational isomer) δ 13.29 (s, NH, 1H), 10.92 (s, NH, 1H), 7.57 (m, 1H), 7.28 (m, 3H), 7.12 (t, J=7.4 Hz, 1H), 6.92 (dd, J=0.8 Hz, J=7.8 Hz, 1H), 6.76 (dd, J=0.8 Hz, J=7.6 Hz, 1H), 6.74 (s, 1H), 4.99 (d, J=3.5 Hz, 0.5H), 4.88 (d, J=3.5 Hz, 0.5H), 4.29 (m, 0.5H), 4.21 (m, 0.5H), 3.54 (m, 1H), 3.37 (m, 1H), 3.25 (m, 2H), 2.20 (s, 3H), 1.82 (m, 2H), 1.52 (s, 3H). MS m/z 458 [M−1].

Example 295

4-(2,6-Difluoro-phenyl)-3-[1-[3-methyl-4-(4-methyl-piperazine-1-carbonyl)-1H-pyrrol-2-yl]-meth-(Z)-ylidene]-1,3-dihydro-indol-2-one

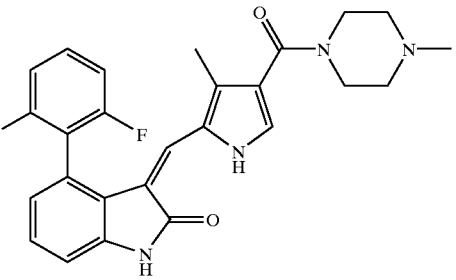

$^1$H NMR (400 MHz, DMSO-d$_6$) δ 13.49 (s, NH, 1H), 10.19 (s, NH, 1H), 7.64 (m, 1H), 7.40 (d, J=3.1 Hz, 1H), 7.35 (m, 2H), 7.26 (t, J=7.8 Hz, 1H), 6.99 (dd, J=0.8 Hz, J=7.8 Hz, 1H), 6.89 (d, J=7.0 Hz, 1H), 6.29 (s, 1H), 3.44 (m, 4H), 2.23 (m, 4H), 2.15 (s, 3H), 1.62 (s, 3H). MS m/z 461 [M−1].

Example 296

4-(2,6-Difluoro-phenyl)-3-[1-[3,5-dimethyl-4-(4-methyl-piperazine-1-carbonyl)-1H-pyrrol-2-yl]-meth-(Z)-ylidene]-1,3-dihydro-indol-2-one

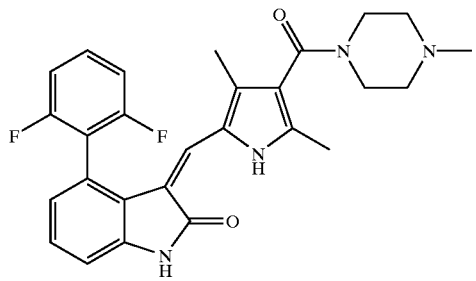

MS m/z 475 [M−1].

Example 297

4-(3-Chloro-phenyl)-3-[1-[5-methyl-3-(4-methyl-piperazine-1-carbonyl)-1H-pyrrol-2-yl]-meth-(Z)-ylidene]-1,3-dihydro-indol-2-one

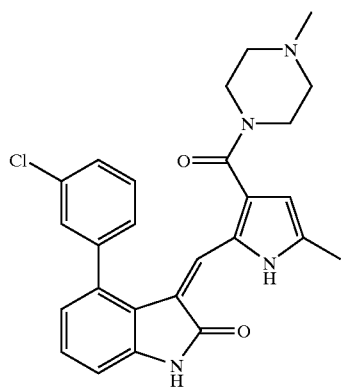

$^1$H NMR (400 MHz, DMSO-$d_6$) δ 13.63 (s, NH, 1H), 11.09 (br s, NH, 1H), 7.44 (m, 2H), 7.37 (s, 1H), 7.32 (m, 1H), 7.18 (t, J=7.8 Hz, 1H), 6.94 (s, 1H), 6.91 (d, J=7.8 Hz, 1H), 6.75 (d, J=7.4 Hz, 1H), 6.06 (d, J=2.0 Hz, 1H), 3.33 (m, 2H), 3.22 (m, 2H), 2.30 (s, 3H), 2.24 (m, 2H), 2.16 (s, 3H), 2.11 (m, 2H).

MS m/z 459 [M−1].

Example 298

4-(3-Fluoro-phenyl)-3-[1-[5-methyl-3-(4-methyl-piperazine-1-carbonyl)-1H-pyrrol-2-yl]-meth-(Z)-ylidene]-1,3-dihydro-indol-2-one

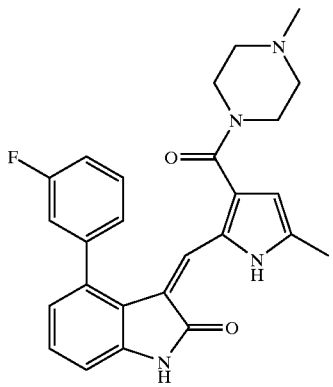

$^1$H NMR (400 MHz, DMSO-$d_6$) δ 13.61 (s, NH, 1H), 11.12 (s, NH, 1H), 7.46 (m, 1H), 7.19 (m, 4H), 6.94 (s, 1H), 6.91 (dd, J=1.2 Hz, J=7.8 Hz, 1H), 6.75 (dd, J=1.2 Hz, J=7.8 Hz, 1H), 6.05 (d, J=2.3 Hz, 1H), 3.21 (m, 4H), 2.32 (s, 3H), 2.25 (m, 2H), 2.17 (s, 3H), 2.12 (m, 2H). MS m/z 445 [M$^+$+1].

Example 299

5-[4-(2,6-Difluoro-phenyl)-2-oxo-1,2-dihydro-indol-(3Z)-ylidenemethyl]-2,4-dimethyl-1H-pyrrole-3-carboxylic Acid (2-Pyrrolidin-1-yl-ethyl)-amide

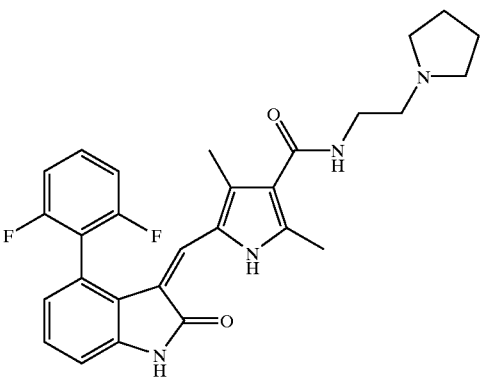

$^1$H NMR (400 MHz, DMSO-$d_6$) δ 13.44 (s, NH, 1H), 10.12 (s, NH, 1H), 7.63 (m, 1H), 7.50 (m, 1H), 7.34 (m, 2H), 7.22 (t, J=7.8 Hz, 1H), 6.97 (dd, J=0.8 Hz, J=7.8 Hz, 1H), 6.87 (d, J=7.8 Hz, 1H), 6.59 (s, 1H), 3.28 (m, 2H), 2.52 (m, 6H), 2.37 (s, 3H), 1.68 (s, 3H), 1.65 (m, 4H). MS m/z 489 [M−1].

Example 300

2-[4-(2,6-Difluoro-phenyl)-2-oxo-1,2-dihydro-indol-(3Z)-ylidenemethyl]-5-methyl-1H-pyrrole-3-carboxylic Acid (3-Pyrrolidin-1-yl-propyl)-amide

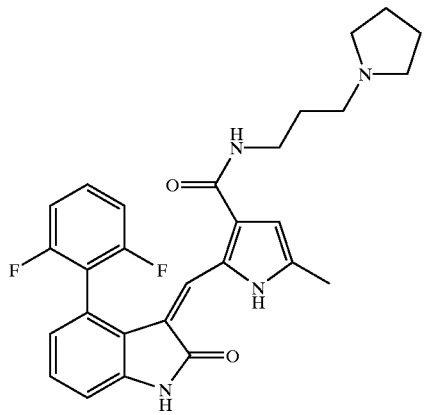

$^1$H NMR (400 MHz, DMSO-d$_6$) δ 13.79 (s, NH, 1H), 11.17 (br s, NH, 1H), 7.91 (m, 1H), 7.85 (s, 1H), 7.48 (m, 1H), 7.22 (t, J=7.4 Hz, 1H), 7.14 (m, 2H), 6.97 (d, J=7.8 Hz, 1H), 6.80 (d, J=7.8 Hz, 1H), 6.35 (m, 1H), 3.61 (m, 2H), 2.41 (m, 6H), 2.30 (s, 3H), 1.68 (m, 4H), 1.58 (m, 2H). MS m/z 489 [M$^-$–1].

Example 301

4-(2,6-Difluoro-phenyl)-3-[1-[3,5-dimethyl-4-(4-pyrrolidin-1-yl-piperidine-1-carbonyl)-1H-pyrrol-2-yl]-meth-(Z)-ylidene]-1,3-dihydro-indol-2-one

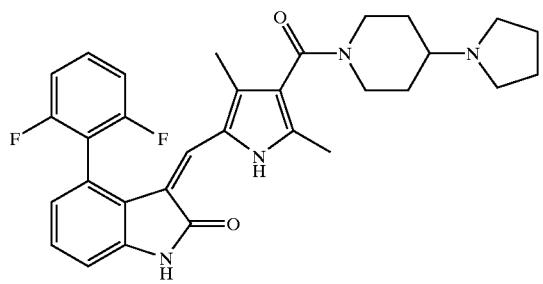

MS m/z 529 [M–1].

Example 302

2-[4-(2-Fluoro-phenyl)-2-oxo-1,2-dihydro-indol-(3Z)-ylidenemethyl]-5-methyl-1H-pyrrole-3-carboxylic Acid [2-(4-Acetyl-piperazin-1-yl)-ethyl]-amide

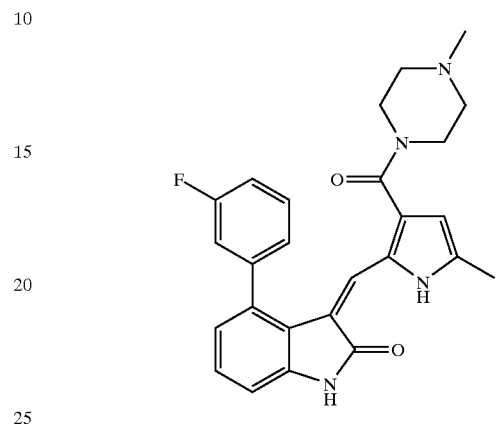

$^1$H NMR (400 MHz, DMSO-d$_6$) δ 13.80 (s, NH, 1H), 11.13 (s, NH, 1H), 7.84 (s, 1H), 7.75 (m, 1H), 7.43 (m, 1H), 7.34 (m, 1H), 7.25 (m, 2H), 7.20 (t, J=7.8 Hz, 1H), 6.94 (d, J=6.6 Hz, 1H), 6.77 (d, J=7.8 Hz, 1H), 6.35 (s, 1H), 3.42 (m, 4H), 3.15 (m, 2H), 2.39 (m, 6H), 2.29 (s, 3H), 1.98 (s, 3H). MS m/z 514 [M–1].

Example 303

2-[4-(3-Fluoro-phenyl)-2-oxo-1,2-dihydro-indol-(3Z)-ylidenemethyl]-5-methyl-1H-pyrrole-3-carboxylic Acid [2-(4-Acetyl-piperazin-1-yl)-ethyl]-amide

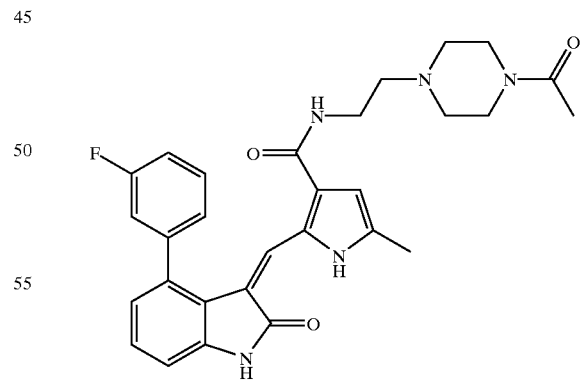

$^1$H NMR (400 MHz, DMSO-d$_6$) δ 13.80 (s, NH, 1H), 11.08 (s, NH, 1H), 7.99 (s, 1H), 7.75 (m, 1H), 7.43 (m, 1H), 7.17 (m, 4H), 6.91 (d, J=6.6 Hz, 1H), 6.75 (d, J=6.6 Hz, 1H), 6.35 (s, 1H), 3.42 (m, 4H), 3.15 (m, 2H), 2.39 (m, 6H), 2.29 (s, 3H), 1.98 (s, 3H). MS m/z 514 [M–1].

Example 304

5-[4-(2-Fluoro-phenyl)-2-oxo-1,2-dihydro-indol-(3Z)-ylidenemethyl]-4-methyl-1H-pyrrole-3-carboxylic Acid [2-(4-Acetyl-piperazin-1-yl)-ethyl]-amide

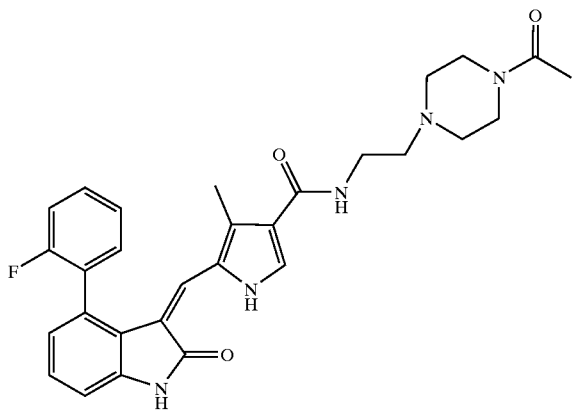

$^1$H NMR (400 MHz, DMSO-d$_6$) δ 13.53 (s, NH, 1H), 11.17 (s, NH, 1H), 8.28 (br m, 1H), 7.83 (br s, 1H), 7.58 (m, 1H), 7.46 (m, 2H), 7.40 (t, J=7.8 Hz, 1H), 7.23 (t, J=7.8 Hz, 1H), 6.96 (dd, J=0.8 Hz, J=7.4 Hz, 1H), 6.83 (d, J=7.8 Hz, 1H), 6.72 (s, 1H), 4.38 (m, 1H), 3.96 (m, 1H), 3.53 (m, 5H), 3.20 (m, 2H), 2.98 (m, 3H), 2.01 (s, 3H), 1.80 (s, 3H).

MS m/z 514 [M−1].

Example 305

5-[4-(2-Fluoro-phenyl)-2-oxo-1,2-dihydro-indol-(3Z)-ylidenemethyl]-4-methyl-1H-pyrrole-3-carboxylic Acid (2-Piperidin-1-yl-ethyl)-amide

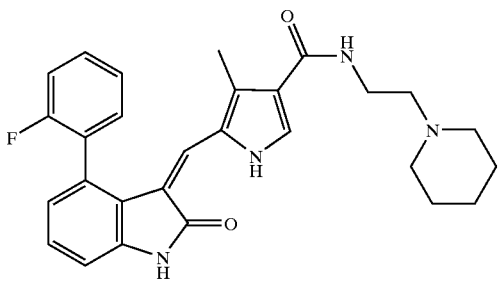

$^1$H NMR (400 MHz, DMSO-d$_6$) δ 13.47 (s, NH, 1H), 11.11 (br s, NH, 1H), 7.71 (m, 1H), 7.66 (d, J=3.5 Hz, 1H), 7.56 (m, 1H), 7.44 (m, 3H), 7.22 (t, J=7.4 Hz, 1H), 6.95 (d, J=7.8 Hz, 1H), 6.83 (d, J=7.8 Hz, 1H), 6.71 (s, 1H), 3.23 (m, 2H), 2.32 (m, 6H), 1.75 (s, 3H), 1.45 (m, 4H), 1.34 (m, 2H). MS m/z 471 [M−1].

Example 306

2-[4-(3-Chloro-phenyl)-2-oxo-1,2-dihydro-indol-(3Z)-ylidenemethyl]-5-methyl-1H-pyrrole-3-carboxylic Acid (2-Piperidin-1-yl-ethyl)-amide

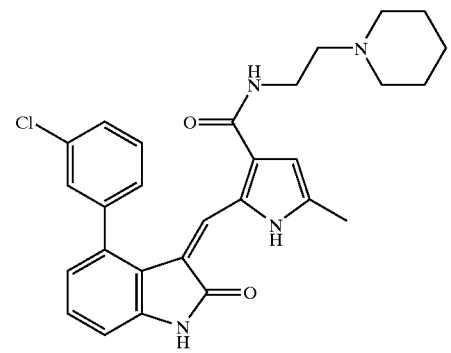

$^1$H NMR (400 MHz, DMSO-d$_6$) δ 13.69 (s, NH, 1H), 11.11 (s, NH, 1H), 7.99 (s, 1H), 7.70 (m, 1H), 7.43 (m, 1H), 7.37 (m, 2H), 7.30 (d, J=7.4 Hz, 1H), 7.18 (t, J=7.8 Hz, 1H), 6.91 (d, J=7.8 Hz, 1H), 6.75 (d, J=7.8 Hz, 1H), 6.36 (s, 1H), 3.15 (m, 2H), 2.38 (m, 4H), 2.31 (m, 2H), 2.29 (s, 3H), 1.50 (m, 4H), 1.38 (m, 2H). MS m/z 487 [M−1].

Example 307

5-[4-(3-Chloro-phenyl)-2-oxo-1,2-dihydro-indol-(3Z)-ylidenemethyl]-4-methyl-1H-pyrrole-3-carboxylic Acid (2-Piperidin-1-yl-ethyl)-amide

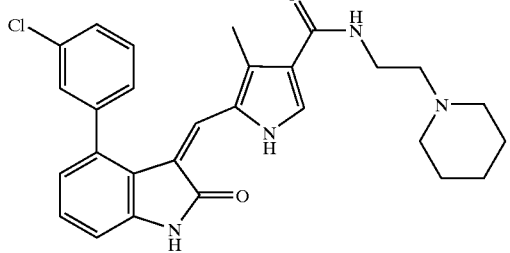

$^1$H NMR (400 MHz, DMSO-d$_6$) δ 13.46 (s, NH, 1H), 11.12 (s, NH, 1H), 7.75 (m, 1H), 7.67 (d, J=3.5 Hz, 1H), 7.57 (m, 2H), 7.52 (s, 1H), 7.40 (m, 1H), 7.21 (t, J=7.4 Hz, 1H), 6.92 (d, J=7.0 Hz, 1H), 6.85 (s, 1H), 6.80 (d, J=7.8 Hz, 1H), 3.25 (m, 2H), 2.41 (m, 6H), 1.84 (s, 3H), 1.48 (m, 4H), 1.36 (m, 2H). MS m/z 487 [M−1].

Example 308

2-[4-(3-Chloro-phenyl)-2-oxo-1,2-dihydro-indol-(3Z)-ylidenemethyl]-5-methyl-1H-pyrrole-3-carboxylic Acid (2-Hydroxy-3-pyrrolidin-1-yl-propyl)-amide

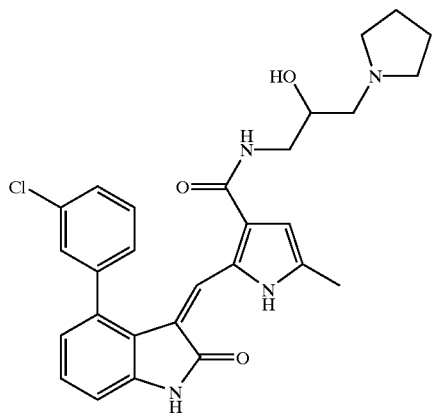

$^1$H NMR (400 MHz, DMSO-d$_6$) δ 13.82 (s, NH, 1H), 11.18 (s, NH, 1H), 8.02 (s, 1H), 7.84 (m, 1H), 7.40 (m, 3H), 7.31 (m, 1H), 7.19 (t, 1H), 6.91 (d, 1H), 6.76 (d, 1H), 6.40 (s, 1H), 4.68 (m, 1H), 3.64 (m, 1H), 3.29 (m, 1H), 2.84 (m, 1H), 2.45 (m, 4H), 2.34 (m, 2H), 2.30 (s, 3H), 1.69 (m, 4H). MS m/z 503 [M−1].

Example 309

2-[4-(3-Fluoro-phenyl)-2-oxo-1,2-dihydro-indol-(3Z)-ylidenemethyl]-5-methyl-1H-pyrrole-3-carboxylic Acid (2-Hydroxy-3-pyrrolidin-1-yl-propyl)-amide

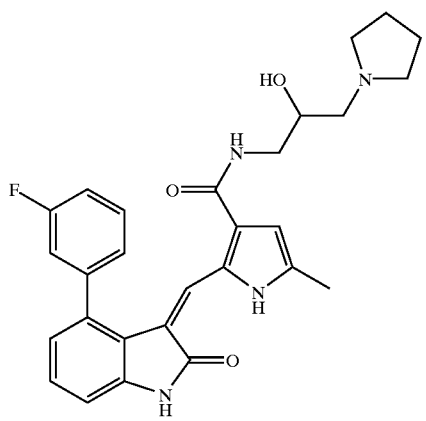

$^1$H NMR (400 MHz, DMSO-d$_6$) δ 13.84 (s, NH, 1H), 11.10 (br s, NH, 1H), 8.01 (s, 1H), 7.85 (m, 1H), 7.42 (m, 1H), 7.15 (m, 4H), 6.91 (d, J=7.8 Hz, 1H), 6.75 (d, J=7.8 Hz, 1H), 6.39 (s, 1H), 4.69 (m, 1H), 3.62 (m, 1H), 3.26 (m, 1H), 2.92 (m, 1H), 2.46 (m, 4H), 2.32 (m, 2H), 2.29 (s, 3H), 1.68 (m, 4H). MS m/z 487 [M−1].

Example 310

5-[4-(3-Chloro-phenyl)-2-oxo-1,2-dihydro-indol-(3Z)-ylidenemethyl]4-methyl-1H-pyrrole-3-carboxylic Acid (2-Hydroxy-3-pyrrolidin-1-yl-propyl)-amide

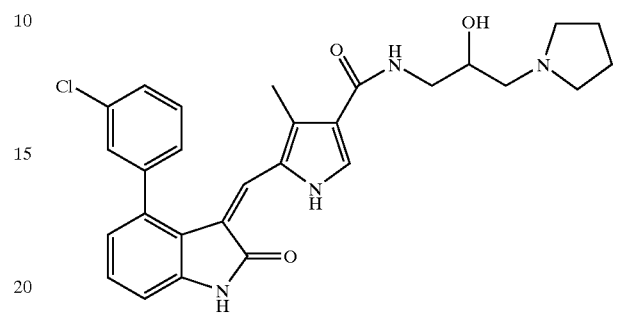

$^1$H NMR (400 MHz, DMSO-d$_6$) δ 13.46 (s, NH, 1H), 11.12 (s, NH, 1H), 7.82 (m, 1H), 7.71 (d, J=3.1 Hz, 1H), 7.58 (m, 2H), 7.52 (s, 1H), 7.41 (m, 1H), 7.21 (t, J=7.8 Hz, 1H), 6.92 (dd, J=0.8 Hz, J=7.8 Hz, 1H), 6.85 (s, 1H), 6.80 (dd, J=0.8 Hz, J=7.4 Hz, 1H), 4.73 (m, 1H), 3.66 (m, 1H), 3.28 (m, 2H), 3.03 (m, 1H), 2.44 (m, 4H), 2.32 (m, 1H), 1.82 (s, 3H), 1.62 (m, 4H). MS m/z 503 [M−1].

Example 311

5-[4-(2-Fluoro-phenyl)-2-oxo-1,2-dihydro-indol-(3Z)-ylidenemethyl]-4-methyl-1H-pyrrole-3-carboxylic Acid (2-Hydroxy-3-pyrrolidin-1-yl-propyl)-amide

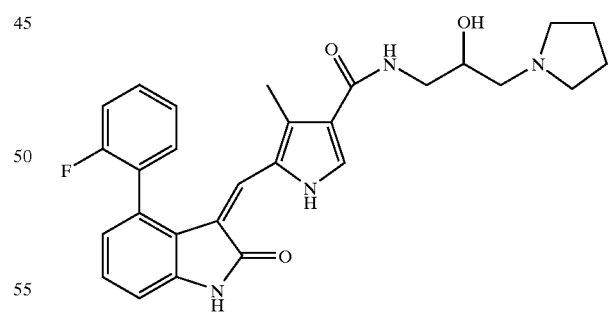

$^1$H NMR (400 MHz, DMSO-d$_6$) δ 13.47 (s, NH, 1H), 11.13 (s, NH, 1H), 7.81 (m, 1H), 7.70 (d, J=3.1 Hz, 1H), 7.57 (m, 1H), 7.42 (m, 3H), 7.21 (t, J=7.8 Hz, 1H), 6.95 (dd, J=1.2 Hz, J=7.8 Hz, 1H), 6.83 (dd, J=0.8 Hz, J=7.4 Hz, 1H), 6.71 (s, 1H), 4.72 (m, 1H), 3.65 (m, 1H), 3.29 (m, 2H), 3.03 (m, 1H), 2.44 (m, 4H), 2.32 (m, 1H), 1.79 (s, 3H), 1.63 (m, 4H). MS m/z 487 [M−1].

Example 312

5-[4-(3-Chloro-phenyl)-2-oxo-1,2-dihydro-indol-(3Z)-ylidenemethyl]-2,4-dimethyl-1H-pyrrole-3-carboxylic Acid (2-Hydroxy-3-pyrrolidin-1-yl-propyl)-amide

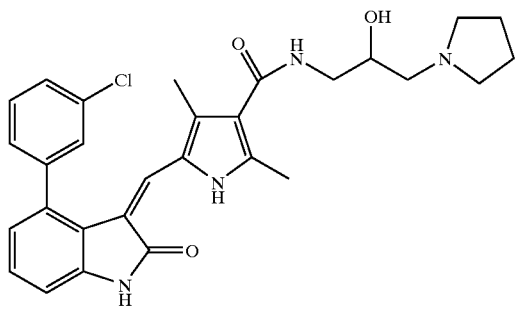

$^1$H NMR (400 MHz, DMSO-d$_6$) δ 13.47 (s, NH, 1H), 11.06 (s, NH, 1H), 7.56 (m, 2H), 7.51 (s, 1H), 7.46 (m, 1H), 7.39 (m, 1H), 7.18 (t, J=7.8 Hz, 1H), 6.92 (d, J=7.8 Hz, 1H), 6.78 (d, J=7.8 Hz, 1H), 6.76 (s, 1H), 4.72 (m, 1H), 3.68 (m, 1H), 3.28 (m, 1H), 3.11 (m, 1H), 2.36 (m, 5H), 1.74 (s, 3H), 1.65 (m, 5H). MS m/z 517 [M−1].

Example 313

4-(3-Chloro-phenyl)-3-[1-[4-((S)-3-hydroxy-pyrrolidine-1-carbonyl)-3,5-dimethyl-1H-pyrrol-2-yl]-meth-(Z)-ylidene]-1,3-dihydro-indol-2-one

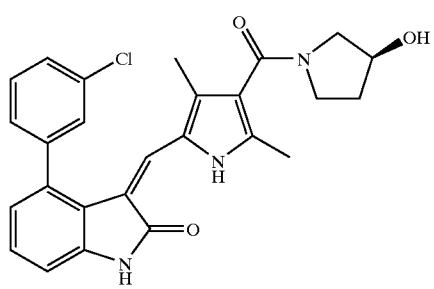

$^1$H NMR (400 MHz, DMSO-d$_6$) δ 13.38 (s, NH, 1H), 11.04 (s, NH, 1H), 7.56 (m, 2H), 7.52 (m, 1H), 7.39 (m, 1H), 7.17 (t, J=7.4 Hz, 1H), 6.92 (d, J=7.8 Hz, 1H), 6.78 (d, J=7.0 Hz, 1H), 6.74 (s, 1H), 4.89 (m, 1H), 4.21 (m, 1H), 3.45 (m, 2H), 3.25 (m, 1H), 3.04 (m, 1H), 2.22 (s, 3H), 1.80 (m, 2H), 1.60 (s, 3H). MS m/z 460 [M−1].

Example 314

4-(3-Chloro-phenyl)-3-[1-[4-((S)-3-hydroxy-pyrrolidine-1-carbonyl)-3-methyl-1H-pyrrol-2-yl]-meth-(Z)-ylidene]-1,3-dihydro-indol-2-one

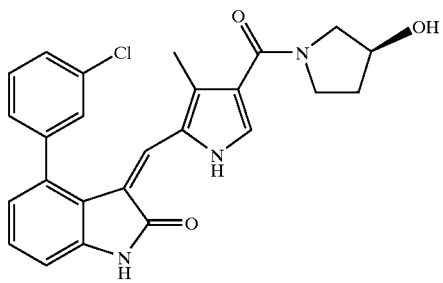

$^1$H NMR (400 MHz, DMSO-d$_6$) δ 13.49 (s, NH, 1H), 11.13 (s, NH, 1H), 7.56 (m, 4H), 7.41 (m, 1H), 7.17 (t, J=7.8 Hz, 1H), 6.92 (dd, J=0.8 Hz, J=7.8 Hz, 1H), 6.85 (s, 1H), 6.80 (dd, J=0.8 Hz, J=7.4 Hz, 1H), 6.74 (s, 1H), 4.91 (m, 1H), 4.24 (m, 1H), 3.58 (m, 1H), 3.46 (m, 2H), 3.28 (m, 1H), 1.86 (m, 1H), 1.78 (m, 1H), 1.74 (s, 3H). MS m/z 446 [M−1].

Example 315

4-(3-Chloro-phenyl)-3-[1-[3-((S)-3-hydroxy-pyrrolidine-1-carbonyl)-5-methyl-1H-pyrrol-2-yl]-meth-(Z)-ylidene]-1,3-dihydro-indol-2-one

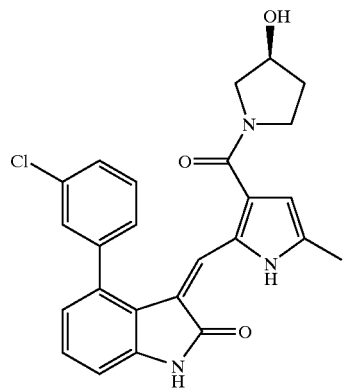

$^1$H NMR (400 MHz, DMSO-d$_6$) δ 13.64 (s, NH, 1H), 11.12 (s, NH, 1H), 7.44 (m, 2H), 7.38 (m, 1H), 7.32 (m, 1H), 7.19 (m, 2H), 6.91 (d, J=7.8 Hz, 1H), 6.75 (d, J=7.0 Hz, 1H), 6.18 (m, 1H), 4.91 (m, 1H), 4.22 (m, 1H), 3.40 (m, 2H), 3.21 (m, 2H), 2.30 (s, 3H), 1.81 (m, 2H). MS m/z 446 [M−1].

Example 316

4-(2-Fluoro-phenyl)-3-[1-[4-((S)-3-hydroxy-pyrrolidine-1-carbonyl)-3-methyl-1H-pyrrol-2-yl]-meth-(Z)-ylidene]-1,3-dihydro-indol-2-one

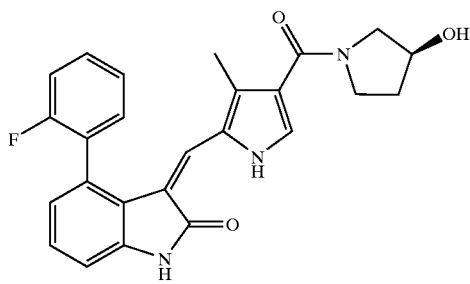

¹H NMR (400 MHz, DMSO-d₆) δ 13.50 (s, NH, 1H), 11.15 (s, NH, 1H), 7.56 (m, 1H), 7.43 (m, 3H), 7.23 (t, J=7.8 Hz, 1H), 6.95 (dd, J=0.8 Hz, J=7.8 Hz, 1H), 6.83 (dd, J=0.8 Hz, J=7.8 Hz, 1H), 6.71 (s, 1H), 4.92 (m, 1H), 4.22 (m, 1H), 3.58 (m, 1H), 3.45 (m, 2H), 3.28 (m, 1H), 1.85 (m, 1H), 1.75 (m, 1H), 1.69 (s, 3H). MS m/z 430 [M−1].

Example 317

4-(3-Fluoro-phenyl)-3-[1-[4-((S)-3-hydroxy-pyrrolidine-1-carbonyl)-3,5-dimethyl-1H-pyrrol-2-yl]-meth-(Z)-ylidene]-1,3-dihydro-indol-2-one

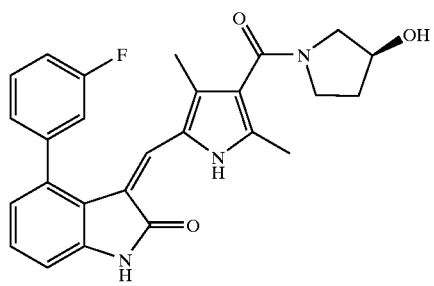

¹H NMR (400 MHz, DMSO-d₆) δ 13.38 (s, NH, 1H), 11.04 (s, NH, 1H), 7.57 (m, 1H), 7.31 (m, 3H), 7.17 (t, J=7.8 Hz, 1H), 6.92 (d, J=7.8 Hz, 1H), 6.78 (d, J=7.8 Hz, 1H), 6.75 (s, 1H), 4.90 (m, 1H), 4.20 (m, 1H), 3.47 (m, 2H), 3.24 (m, 1H), 3.04 (m, 2H), 2.21 (s, 3H), 1.80 (m, 2H), 1.58 (s, 3H). MS m/z 444 [M−1].

Example 318

4-(3-Fluoro-phenyl)-3-[1-{4-[2-((S)-3-hydroxy-pyrrolidin-1-yl)-2-oxo-ethyl]-3,5-dimethyl-1H-pyrrol-2-yl}-meth-(Z)-ylidene]-1,3-dihydro-indol-2-one

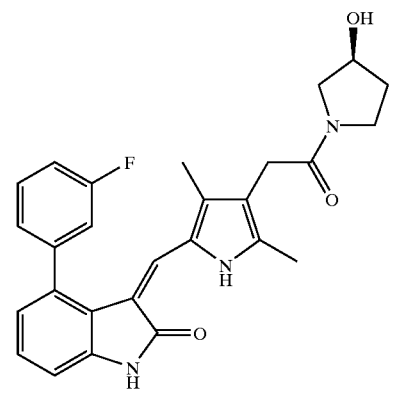

¹H NMR (400 MHz, DMSO-d₆) δ 13.29 (s, NH, 1H), 10.92 (s, NH, 1H), 7.57 (m, 1H), 7.28 (m, 3H), 7.13 (t, J=7.4 Hz, 1H), 6.91 (d, J=7.0 Hz, 1H), 6.76 (m, 2H), 4.92 (m, 1H), 4.22 (m, 1H), 3.54 (m, 2H), 3.28 (s, 2H), 3.22 (m, 2H), 2.19 (s, 3H), 1.81 (m, 2H), 1.52 (s, 3H). MS m/z 458 [M−1].

Example 319

4-(3-Fluoro-phenyl)-3-[1-[4-(4-hydroxy-piperidin-1-ylmethyl)-3,5-dimethyl-1H-pyrrol-2-yl]-meth-(Z)-ylidene]-1,3-dihydro-indol-2-one

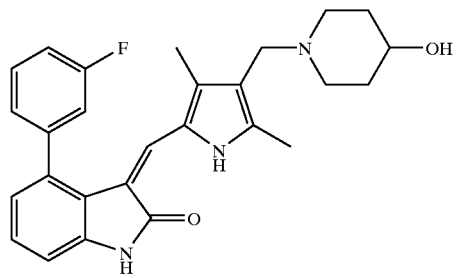

¹H NMR (400 MHz, DMSO-d₆) δ 13.28 (s, NH, 1H), 10.94 (s, NH, 1H), 7.57 (m, 1H), 7.28 (m, 3H), 7.13 (t, 1H), 6.91 (dd, 1H), 6.76 (m, 2H), 4.48 (d, 1H), 3.38 (m, 1H), 3.11 (s, 2H), 2.55 (m, 2H), 2.22 (s, 3H), 1.89 (m, 2H), 1.62 (m, 2H), 1.60 (s, 3H), 1.28 (m, 2H). MS m/z 444 [M−1].

Example 320

3-[1-(3,5-Dimethyl-4-morpholin-4-ylmethyl-1H-pyrrol-2-yl)-meth-(Z)-ylidene]-4-(3-fluoro-phenyl)-1,3-dihydro-indol-2-one

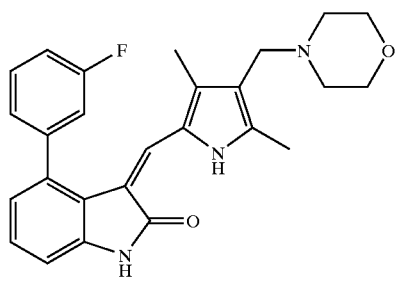

$^1$H NMR (400 MHz, DMSO-d$_6$) δ 13.28 (s, NH, 1H), 10.96 (s, NH, 1H), 7.57 (m, 1H), 7.28 (m, 3H), 7.13 (t, J=7.4 Hz, 1H), 6.90 (dd, J=0.8 Hz, J=7.4 Hz, 1H), 6.76 (m, 2H), 3.47 (m, 4H), 3.16 (s, 2H), 2.25 (s, 3H), 2.22 (m, 4H), 1.62 (s, 3H). MS m/z 430 [M−1].

Example 321

2-[4-(3-Fluoro-phenyl)-2-oxo-1,2-dihydro-indol-(3Z)-ylidenemethyl]-]-4,5,6,7-tetrahydro-1H-indole-3-carboxylic Acid

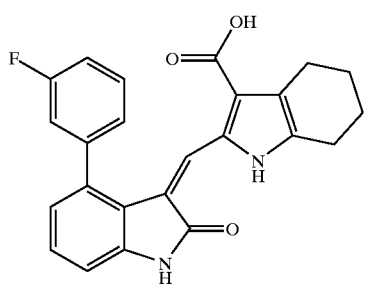

$^1$H NMR (400 MHz, DMSO-d$_6$) δ 11.17 (s, NH, 1H), 8.05 (s, 1H), 7.44 (m, 1H), 7.20 (m, 4H), 6.92 (dd, J=0.8 Hz, J=7.8 Hz, 1H), 6.75 (dd, J=0.8 Hz, J=7.4 Hz, 1H), 2.62 (m, 4H), 1.68 (m, 4H). MS m/z 401 [M−1].

Example 322

2-[4-(3-Fluoro-phenyl)-2-oxo-1,2-dihydro-indol-(3Z)-ylidenemethyl]-4,5,6,7-tetrahydro-1H-indole-3-carboxylic Acid (3-Pyrrolidin-1-yl-propyl)-amide

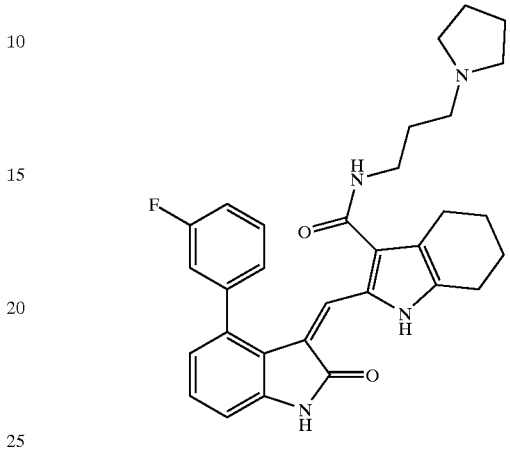

$^1$H NMR (400 MHz, DMSO-d$_6$) δ 13.53 (s, NH, 1H), 11.06 (s, NH, 1H), 7.52 (m, 1H), 7.42 (m, 1H), 7.36 (s, 1H), 7.17 (m, 4H), 6.90 (d, J=7.4 Hz, 1H), 6.75 (d, J=7.4 Hz, 1H), 3.27 (m, 2H), 3.04 (m, 2H), 2.64 (m, 2H), 2.39 (m, 6H), 1.64 (m, 10H). MS m/z 511 [M−1].

Example 323

4-(3-Fluoro-phenyl)-3-1-[3-(3-hydroxy-pyrrolidine-1-carbonyl)-4,5,6,7-tetrahydro-1H-indol-2-yl]-meth-(Z)-ylidene]-1,3-dihydro-indol-2-one

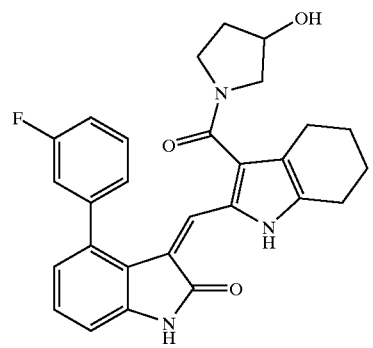

$^1$H NMR (400 MHz, DMSO-d$_6$) δ 13.44 (s, NH, 1H), 11.07 (s, NH, 1H), 7.46 (m, 1H), 7.25 (m, 1H), 7.17 (m, 3H), 6.90 (d, J=7.8 Hz, 1H), 6.78 (m, 1H), 6.73 (dd, J=0.8 Hz, J=7.8 Hz, 1H), 4.88 (m, 1H), 4.20 (m, 1H), 3.35 (m, 2H), 3.18 (m, 1H), 2.86 (m, 1H), 2.65 (m, 2H), 2.28 (m, 2H), 1.70 (m, 6H). MS m/z 470 [M−1].

Example 324

4-(2-Fluoro-phenyl)-3-[1-{3-[(S)-2-(4-hydroxy-piperidin-1-ylmethyl)-pyrrolidine-1-carbonyl]-5-methyl-1H-pyrrol-2-yl}-meth-(Z)-ylidene]-1,3-dihydro-indol-2-one

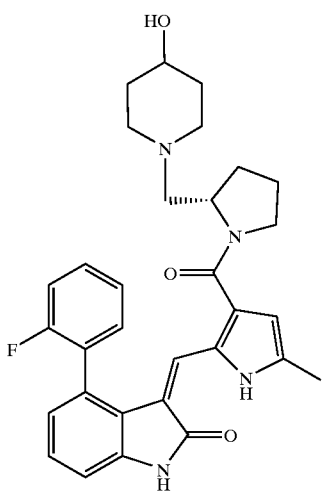

MS m/z 527 [M−1].

Example 325

4-(2-Fluoro-phenyl)-3-[1-{3-[(S)-2-((R)-3-hydroxy-pyrrolidin-1-ylmethyl)-pyrrolidine-1-carbonyl]-5-methyl-1H-pyrrol-2-yl}-meth-(Z)-ylidene]-1,3-dihydro-indol-2-one

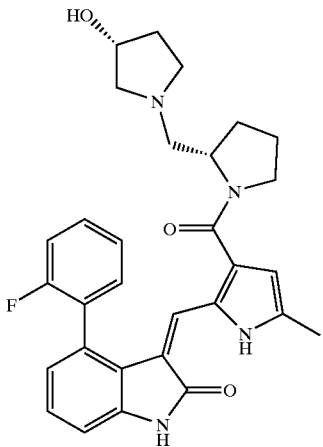

MS m/z 513 [M−1].

Example 326

4-(3-Fluoro-phenyl)-3-[1-{4-[(S)-2-((R)-3-hydroxy-pyrrolidin-1-ylmethyl)-pyrrolidine-1-carbonyl]-3,5-dimethyl-1H-pyrrol-2-yl}-meth-(Z)-ylidene]-1,3-dihydro-indol-2-one

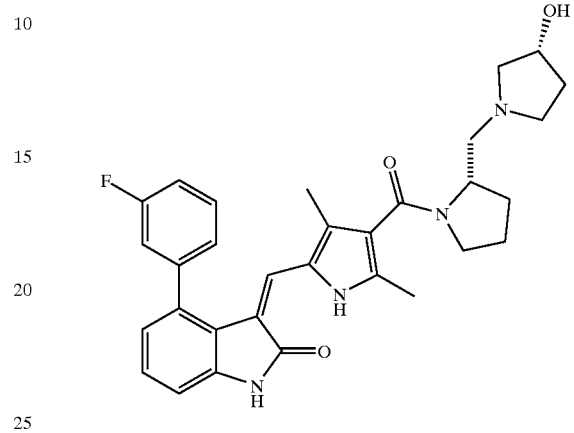

$^1$H NMR (400 MHz, DMSO-$d_6$) δ 13.31 (s, NH, 1H), 10.62 (s, NH, 1H), 7.56 (m, 1H), 7.24 (m, 3H), 7.16 (t, J=7.8 Hz, 1H), 6.94 (d, J=7.8 Hz, 1H), 6.81 (s, 1H), 6.78 (d, J=6.8 Hz, 1H), 4.15 (m, 2H), 4.05 (m, 1H), 2.88 (m, 4H), 2.76 (m, 1H), 2.58 (m, 2H), 2.38 (m, 2H), 2.24 (s, 3H), 1.88 (m, 4H), 1.72 (m, 1H), 1.64 (s, 3H), 1.53 (m, 1H). MS m/z 527 [M−1].

Example 327

4-(3-Fluoro-phenyl)-3-[1-{3-[(S)-2-((R)-3-hydroxy-pyrrolidin-1-ylmethyl)-pyrrolidine-1-carbonyl]-5-methyl-1H-pyrrol-2-yl}-meth-(Z)-ylidene]-1,3-dihydro-indol-2-one

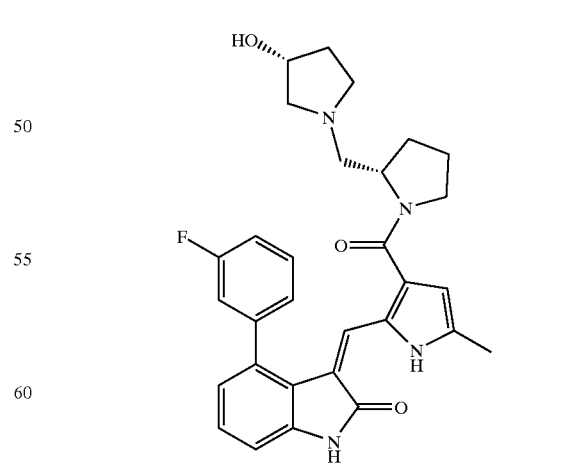

MS m/z 513 [M⁻−1].

Example 328

2-[4-(3-Fluoro-phenyl)-2-oxo-1,2-dihydro-indol-(3Z)-ylidenemethyl]-5-methyl-1H-pyrrole-3-carboxylic Acid {2-[4-(2-Hydroxy-acetyl)-piperazin-1-yl]-ethyl}-amide

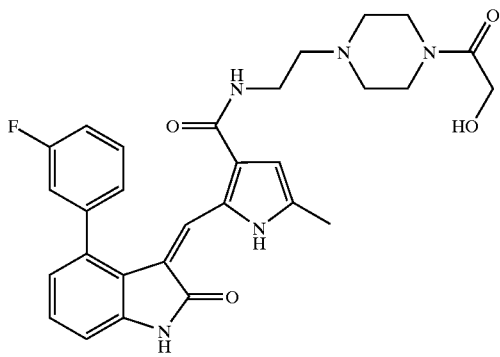

$^1$H NMR (400 MHz, DMSO-d$_6$) δ 13.79 (s, NH, 1H), 11.12 (s, NH, 1H), 7.99 (s, 1H), 7.76 (m, 1H), 7.45 (m, 1H), 7.16 (m, 4H), 6.91 (d, 1H), 6.75 (d, 1H), 6.36 (s, 1H), 4.52 (t, 1H), 4.07 (d, 2H), 3.46 (m, 2H), 3.36 (m, 2H), 3.16 (m, 2H), 2.39 (m, 6H), 2.29 (s, 3H). MS m/z 530 [M−1].

Example 329

4-(2,6-Difluoro-phenyl)-3-[1-[4-(3-piperidin-1-yl-propionyl)-1,4,5,6,7,8-hexahydro-pyrrolo[3,2-b]azepin-2-yl]-meth-(Z)-ylidene]-1,3-dihydro-indol-2-one

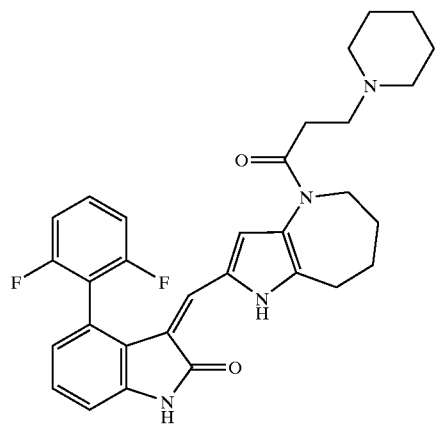

4-(3-Piperidin-1-yl-propionyl)-1,4,5,6,7,8-hexahydro-pyrrolo[3,2-b]azepine-2-carbaldehyde (80 mg, 0.26 mmol) was condensed with 4-(2,6-difluoro-phenyl)-1,3-dihydro-indol-2-one (61 mg, 0.25 mmol) and piperidine (1 drop) in ethanol (3 mL) at rt for over the weekend. The precipitate was filtered, washed with ethanol and dried to give 80 mg of the titled compound as a yellow solid.

$^1$H NMR (400 MHz, DMSO-d$_6$) δ 13.46 (s, 1H, NH), 11.14 (s, 1H, NH), 7.62 (m, 1H), 7.25 (m, 1H), 6.99 (d, 1H), 6.87 (d, 1H), 6.37 (s, 1H), 6.21 (s, 1H), 3.47 (m, 2H), 2.72 (m, 2H), 2.38 (m, 2H), 2.3 (m, 2H), 2.13 (m, 4H), 1.68 (m, 2H), 1.60 (m, 2H), 1.37 (m, 4H), 1.31 (m, 2H). MS m/z 531.2 [M$^+$+1].

Example 330

5-[4-(3-Fluoro-phenyl)-2-oxo-1,2-dihydro-indol-(3Z)-ylidenemethyl]-4-(3-methanesulfonyl-propyl)-2-methyl-1H-pyrrole-3-carboxylic Acid

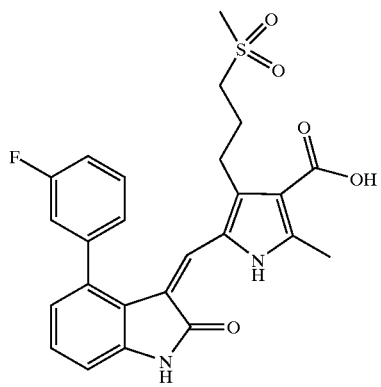

$^1$H NMR (400 MHz, DMSO-d$_6$) δ 13.79 (s, NH, 1H), 12.22 (s, 1H), 11.17 (s, NH, 1H), 7.60 (m, 1H), 7.40 (m, 1H), 7.31 (m, 2H), 7.21 (t, J=7.8 Hz, 1H), 6.94 (d, J=7.0 Hz, 1H), 6.79 (d, J=7.4 Hz, 1H), 6.77 (s, 1H), 2.92 (s, 3H), 2.69 (m, 2H), 2.48 (s, 3H), 2.32 (m, 2H), 1.61 (m, 2H). MS m/z 481 [M−1].

Example 331

5-[4-(4-Chloro-phenyl)-2-oxo-1,2-dihydro-indol-(3Z)-ylidenemethyl]-4-(3-methanesulfonyl-propyl)-2-methyl-1H-pyrrole-3-carboxylic Acid

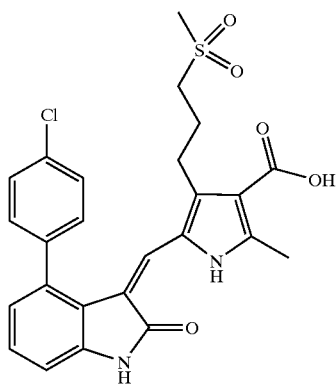

$^1$H NMR (400 MHz, DMSO-d$_6$) δ 13.80 (s, NH, 1H), 12.22 (s, 1H), 11.17 (s, NH, 1H), 7.62 (m, 2H), 7.48 (m, 2H), 7.21 (t, J=7.8 Hz, 1H), 6.94 (d, J=7.8 Hz, 1H), 6.77 (d, J=7.8 Hz, 1H), 6.75 (s, 1H), 2.94 (s, 3H), 2.73 (m, 2H), 2.47 (s, 3H), 2.34 (m, 2H), 1.63 (m, 2H). MS m/z 497 [M$^-$−1].

Example 332

4-(3-Fluoro-phenyl)-3-[1-[4-((R)-3-hydroxy-pyrrolidine-1-carbonyl)-3-(3-methanesulfonyl-propyl)-5-methyl-1H-pyrrol-2-yl]-meth-(Z)-ylidene]-1,3-dihydro-indol-2-one

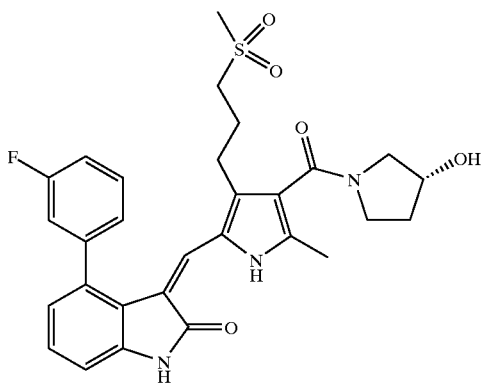

$^1$H NMR (400 MHz, DMSO-d$_6$) δ 13.47 (s, NH, 1H), 11.10 (s, NH, 1H), 7.59 (m, 1H), 7.38 (m, 1H), 7.29 (m, 2H), 7.19 (t, J=7.8 Hz, 1H), 6.92 (d, J=7.4 Hz, 1H), 6.78 (d, J=7.8 Hz, 1H), 6.71 (d, J=0.8 Hz, 1H), 4.92 (m, 1H), 4.22 (m, 1H), 3.48 (m, 2H), 3.21 (m, 2H), 2.89 (s, 3H), 2.71 (m, 2H), 2.24 (s, 3H), 2.08 (m, 2H), 1.82 (m, 2H), 1.52 (m, 2H). MS m/z 550 [M−1].

Example 333

4-(3-Fluoro-phenyl)-3-[1-[3-(3-methanesulfonyl-propyl)-5-methyl-4-(4-methyl-piperazine-1-carbonyl)-1H-pyrrol-2-yl]-meth-(Z)-ylidene]-1,3-dihydro-indol-2-one

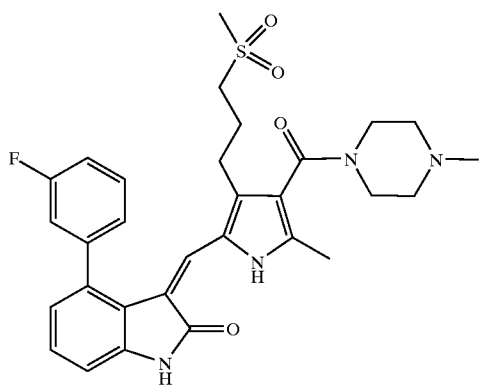

$^1$H NMR (400 MHz, DMSO-d$_6$) δ 13.52 (s, NH, 1H), 11.10 (s, NH, 1H), 7.60 (m, 1H), 7.40 (m, 1H), 7.31 (m, 2H), 7.19 (t, J=7.8 Hz, 1H), 6.93 (d, J=7.4 Hz, 1H), 6.78 (dd, J=0.8 Hz, J=7.8 Hz, 1H), 6.72 (s, 1H), 3.31 (m, 4H), 2.92 (s, 3H), 2.78 (m, 2H), 2.30 (m, 4H), 2.20 (s, 3H), 2.18 (s, 3H), 2.05 (m, 2H), 1.51 (m, 2H). MS m/z 563 [M−1].

Example 334

4-(4-Chloro-phenyl)-3-[1-[3-(3-methanesulfonyl-propyl)-5-methyl-4-(4-methyl-piperazine-1-carbonyl)-1H-pyrrol-2-yl]-meth-(Z)-ylidene]-1,3-dihydro-indol-2-one

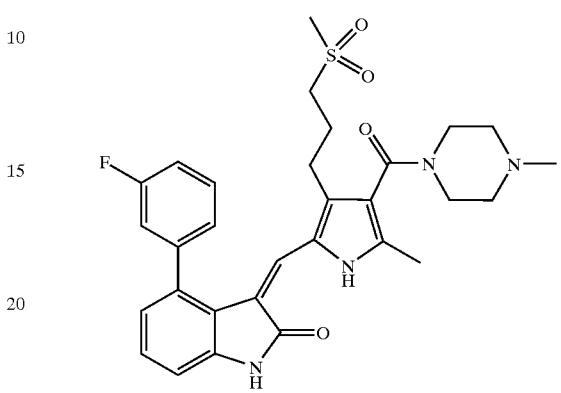

$^1$H NMR (400 MHz, DMSO-d$_6$) δ 13.53 (s, NH, 1H), 11.10 (s, NH, 1H), 7.62 (m, 2H), 7.44 (m, 2H), 7.19 (t, J=7.8 Hz, 1H), 6.93 (d, J=7.8 Hz, 1H), 6.77 (dd, J=0.8 Hz, J=7.4 Hz, 1H), 6.71 (s, 1H), 3.34 (m, 4H), 2.92 (s, 3H), 2.78 (m, 2H), 2.28 (m, 4H), 2.21 (s, 3H), 2.15 (s, 3H), 2.10 (m, 2H), 1.55 (m, 2H). MS m/z 581 [M$^+$+1].

Example 335

3-[1-[3-((cis)-3,5-Dimethyl-piperazine-1-carbonyl)-5-methyl-1H-pyrrol-2-yl-meth-(Z)-ylidene]-4-[3-(2-hydroxy-ethoxy)-phenyl]-1,3-dihydro-indol-2-one

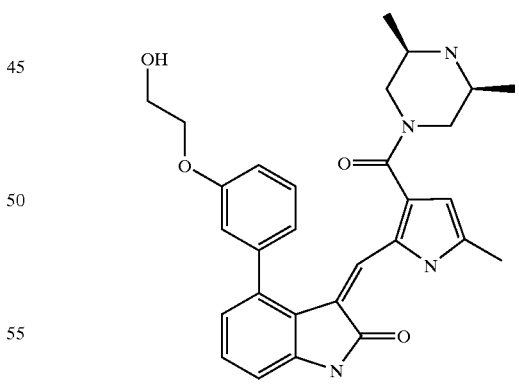

$^1$H NMR (400 MHz, DMSO-d$_6$) δ 13.63 (s, NH, 1H), 11.09 (s, NH, 1H), 7.30 (m, 1H), 7.16 (t, J=7.8 Hz, 1H), 6.98 (s, 1H), 6.90 (m, 4H), 6.73 (dd, J=0.8 Hz, J=7.8 Hz, 1H), 6.03 (d, J=2.0 Hz, 1H), 4.13 (m, 1H), 3.99 (m, 2H), 3.70 (m, 2H), 3.38 (m, 1H), 3.06 (m, 1H), 2.44 (m, 2H), 2.30 (s, 3H), 2.18 (m, 2H), 1.81 (m, 1H), 1.04 (m, 3H), 0.81 (m, 3H). MS m/z 499 [M−1].

Example 336

3-[1-[3,5-Dimethyl-4-(4-methyl-piperazine-1-carbonyl)-1H-pyrrol-2-yl]-meth-(Z)-ylidene]-4-[3-(2-hydroxy-ethoxy)phenyl]-1,3-dihydro-indol-2-one

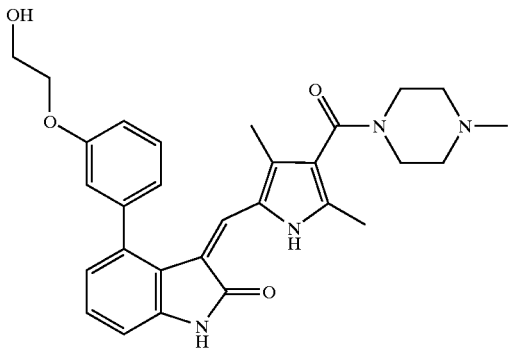

$^1$H NMR (400 MHz, DMSO-d$_6$) δ 13.44 (s, NH, 1H), 11.01 (s, NH, 1H), 7.43 (t, J=8.2 Hz, 1H), 7.16 (t, J=7.8 Hz, 1H), 7.03 (m, 1H), 6.95 (m, 2H), 6.89 (dd, J=1.2 Hz, J=7.8 Hz, 1H), 6.86 (s, 1H), 6.78 (dd, J=0.8 Hz, J=7.4 Hz, 1H), 4.84 (t, J=5.5 Hz, 1H), 3.98 (t, J=5.1 Hz, 2H), 3.67 (m, 2H), 3.41 (m, 4H), 2.28 (m, 4H), 2.21 (s, 3H), 2.15 (s, 3H), 1.57 (s, 3H). MS m/z 499 [M−1].

Example 337

4-[3-(2-Hydroxy-ethoxy)-phenyl]-3-[1-[3-methyl-4-(4-methyl-piperazine-1-carbonyl)-1H-pyrrol-2-yl]-meth-(Z)-ylidene]-1,3-dihydro-indol-2-one

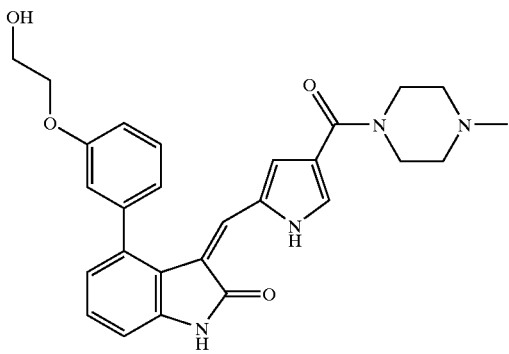

$^1$H NMR (400 MHz, DMSO-d$_6$) δ 13.44 (s, NH, 1H), 11.04 (s, NH, 1H), 7.40 (t, J=8.2 Hz, 1H), 7.31 (d, J=3.1 Hz, 1H), 7.14 (t, J=7.8 Hz, 1H), 7.00 (m, 1H), 6.91 (m, 2H), 6.87 (s, 1H), 6.85 (d, J=7.4 Hz, 1H), 6.74 (d, J=7.8 Hz, 1H), 4.79 (t, J=5.5 Hz, 1H), 3.94 (t, J=5.1 Hz, 2H), 3.63 (m, 2H), 3.38 (m, 4H), 2.19 (m, 4H), 2.10 (s, 3H), 1.59 (s, 3H). MS m/z 485 [M−1].

Example 338

5-[4-[3-(2-Hydroxy-ethoxy)-phenyl]-2-oxo-1,2-dihydro-indol-(3Z)-ylidenemethyl]-2,4-dimethyl-1H-pyrrole-3-carboxylic Acid (2-Pyrrolidin-1-yl-ethyl)-amide

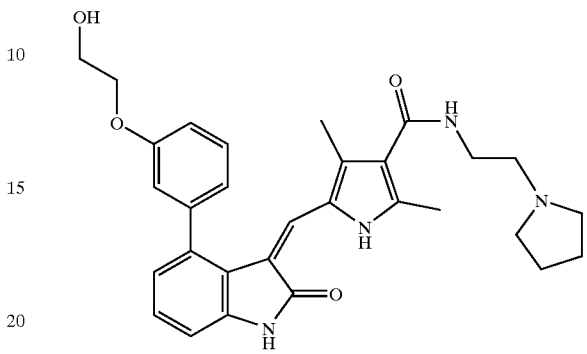

4-[3-(2-Hydroxy-ethoxy)-phenyl]-1,3-dihydro-indol-2-one (0.25 mg) was condensed with 5-formyl-2,4-dimethyl-1H-pyrrole-3-carboxylic acid (2-pyrrolidin-1-yl-ethyl)-amide (0.25 mmol) and pyrrolidine (2 drops) in ethanol (2 mL) at rt for overnight to give 76.4 mg (60%) of the titled compound as a yellow solid.

$^1$H NMR (400 MHz, DMSO-d$_6$) δ 13.42 (s, NH, 1H), 10.97 (s, 1H, NH), 7.38 (m, 2H), 7.11 (t, 1H), 6.99 (m, 1H), 6.85 (dd, 1H), 6.82 (s, 1H), 6.73 (dd, 1H), 4.81 (m, 1H), 3.94 (t, 2H), 3.63 (m, 2H), 3.22 (m, 4H), 2.45 (m, 4H), 2.31 (s, 3H, CH$_3$), 1.65 (s, 3H, CH$_3$), 1.61 (m, 4H). MS m/z 515.6 [M$^+$+1].

Example 339

3-[1-[3,5-Dimethyl-4-(4-pyrrolidin-1-yl-piperidine-1-carbonyl)-1H-pyrrol-2-yl]-meth-(Z)-ylidene]-4-[3-(2-hydroxy-ethoxy)-phenyl]-1,3-dihydro-indol-2-one

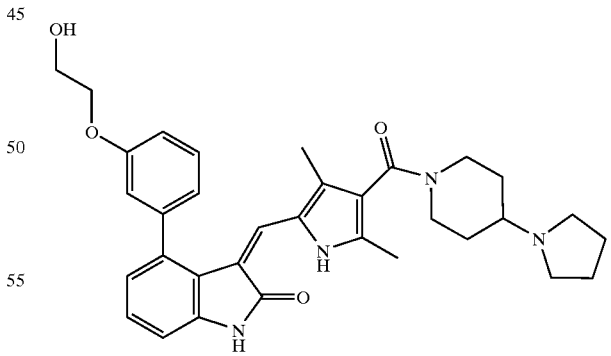

$^1$H NMR (400 MHz, DMSO-d$_6$) δ 13.42 (s, NH, 1H), 11.02 (br s, NH, 1H), 7.43 (t, J=7.8 Hz, 1H), 7.16 (t, J=7.8 Hz, 1H), 7.03 (m, 1H), 6.95 (m, 2H), 6.89 (d, J=7.8 Hz, 1H), 6.85 (s, 1H), 6.78 (d, J=7.4 Hz, 1H), 4.83 (m, 1H), 3.97 (m, 2H), 3.67 (m, 2H), 3.18 (m, 1H), 2.93 (m, 2H), 2.43 (m, 4H), 2.21 (s, 3H), 2.14 (m, 1H), 1.75 (m, 2H), 1.63 (m, 6H), 1.56 (s, 3H), 1.21 (m, 1H). MS m/z 553 [M−1].

Example 340

4-[3-(2-Hydroxy-ethoxy)-phenyl]-3-[1-[5-methyl-3-(4-pyrrolidin-1-yl-piperidine-1-carbonyl)-1H-pyrrol-2-yl]-meth-(Z)-ylidene]-1,3-dihydro-indol-2-one

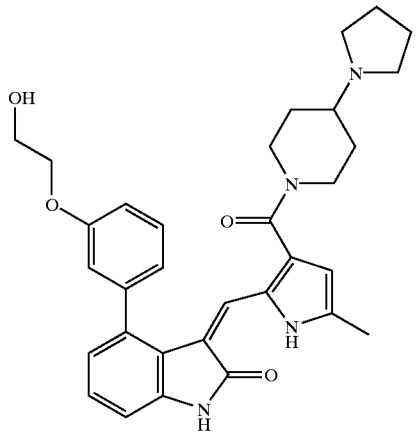

$^1$H NMR (400 MHz, DMSO-d$_6$) δ 13.60 (s, NH, 1H), 11.08 (s, NH, 1H), 7.30 (t, J=7.8 Hz, 1H), 7.16 (t, J=7.8 Hz, 1H), 6.95 (m, 2H), 6.87 (m, 3H), 6.73 (d, J=7.4 Hz, 1H), 6.03 (d, J=2.3 Hz, 1H), 4.86 (m, 1H), 4.02 (m, 1H), 3.97 (m, 2H), 3.68 (m, 2H), 3.45 (m, 1H), 2.75 (m, 2H), 2.46 (m, 4H), 2.29 (s, 3H), 2.13 (m, 1H), 1.79 (m, 1H), 1.66 (m, 6H), 1.15 (m, 1H). MS m/z 539 [M−1].

Example 341

4-[3-(2-Hydroxy-ethoxy)-phenyl]-3-[1-[4-((R)-3-hydroxy-pyrrolidine-1-carbonyl)-3,5-dimethyl-1H-pyrrol-2-yl]-meth-(Z)-ylidene]-1,3-dihydro-indol-2-one

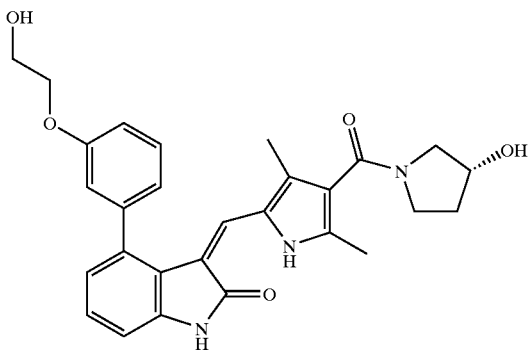

$^1$H NMR (400 MHz, DMSO-d$_6$) δ 13.38 (s, NH, 1H), 11.00 (s, NH, 1H), 7.43 (t, J=8.2 Hz, 1H), 7.15 (t, J=7.4 Hz, 1H), 7.02 (m, 1H), 6.95 (m, 2H), 6.89 (dd, J=0.8 Hz, J=7.8 Hz, 1H), 6.85 (s, 1H), 6.77 (dd, J=0.8 Hz, J=7.8 Hz, 1H), 4.91 (m, 1H), 4.84 (m, 1H), 4.21 (m, 1H), 3.98 (t, J=5.1 Hz, 2H), 3.67 (m, 2H), 3.44 (m, 1H), 3.24 (m, 2H), 3.05 (m, 1H), 2.22 (s, 3H), 1.80 (m, 2H), 1.58 (s, 3H). MS m/z 486 [M−1].

Example 342

5-[4-(4-Chloro-phenyl)-2-oxo-1,2-dihydro-indol-(3Z)-ylidenemethyl]-2,4-dimethyl-1H-pyrrole-3-carboxylic Acid

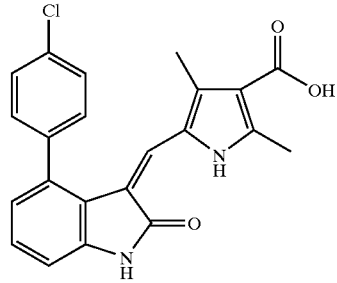

$^1$H NMR (400 MHz, DMSO-d$_6$) δ 13.57 (s, NH, 1H), 12.05 (s, 1H), 11.05 (s, NH, 1H), 7.55 (m, 2H), 7.38 (m, 2H), 7.15 (t, J=7.8 Hz, 1H), 6.88 (dd, J=0.8 Hz, J=7.8 Hz, 1H), 6.73 (dd, J=0.8 Hz, J=7.4 Hz, 1H), 6.65 (s, 1H), 2.42 (s, 3H), 1.75 (s, 3H). MS m/z 391 [M−1].

Example 343

2-[4-(4-Chloro-phenyl)-2-oxo-1,2-dihydro-indol-(3Z)-ylidenemethyl]-5-methyl-1H-pyrrole-3-carboxylic Acid

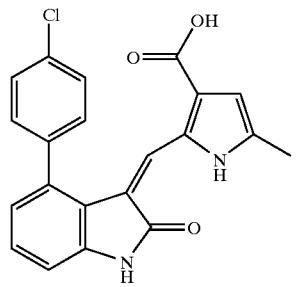

MS m/z 377 [M−1].

Example 344

3-[1-[3,5-Dimethyl-4-(4-morpholin-4-yl-piperidine-1-carbonyl)-1H-pyrrol-2-yl]-meth-(Z)-ylidene]-4-(3-fluoro-phenyl)-1,3-dihydro-indol-2-one

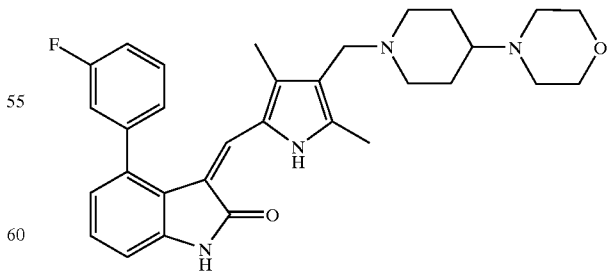

To a stirred mixture of 4-amino-1-benzylpiperidine (1.53 mL, 7.5 mmol), K$_2$CO$_3$ (2.28 g, 16.5 mmol) and DMF (15 mL) heated at 50° C. was added dropwise over 60 min bis(2-bromoethyl)ether (0.96 mL, 7.65 mmol). After stirring for 6 hours at 80° C., the solvent was removed by blowing with a stream of nitrogen over 2 hours. The residue was purified on a silica gel column to give 1.7 g (87%) of 4-(1-benzyl-piperidin-4-yl)-morpholine as a waxy solid.

$^1$H NMR (400 MHz, DMSO-d$_6$) δ 7.31 (m, 4H), 7.26 (m, 1H), 3.72 (t, 4H), 3.49 (s, 2H), 2.94 (br d, 2H), 2.54 (t, 4H), 2.19 (tt, 1H), 1.96 (td, 2H), 1.78 (br d, 2H), 1.55 (m, 2H).

4-(1-benzyl-piperidin-4-yl)-morpholine (1.56 g, 6.0 mmol) was hydrogenated using Pd(OH)$_2$ (20% on carbon, 390 mg, 25 wt %), 1.7 M HCl (10.6 mL) in methanol (50 mL) at 50° C. for 10 hours. The resulted amine dihydrochloride off-white solid was subjected to free-basing using excess basic resin to give 932 mg (91%) of 4-piperidin-4-yl-morpholine as waxy crystalline solid.

$^1$H NMR (400 MHz, DMSO-d$_6$) δ 3.53 (br s, 4H), 3.30 (br s, 1H), 2.92 (br d, 1H), 2.41 (s, 4H), 2.35 (m, 2H), 2.12 (br t, 1H), 1.65 (br d, 2H), 1.18 (br q, 2H). MS m/z 171 [M$^+$+1].

5-[4-(3-Fluoro-phenyl)-2-oxo-1,2-dihydro-indol-(3Z)-ylidenemethyl]-2,4-dimethyl-1H-pyrrole-3-carboxylic acid (1 eq.) and BOP (1.25 eq.) were suspended in DMF (5 mL) at rt and TEA (2.4 eq.) was added. After 15 mina, to the homogenous reaction mixture was added 4-piperidin-4-yl-morpholine (1.25 eq.) all at once. After stirring for 2 days, the reaction was added to a mixture of chloroform-isopropanol (5:1) and 5% aq. LiCl. The organic layer was separated, washed with 5% aq. LiCl (2×), 1M aq. NaOH (3×), brine, dried and concentrated. The residue was purified to give the titled compound.

$^1$H NMR (400 MHz, DMSO-d$_6$) δ 13.42 (s, 1H, NH), 11.04 (s, 1H, NH), 7.57 (q, J=7.4 Hz, 1H), 7.29 (m, 3H), 7.18 (t, J=7.6 Hz, 1H), 6.93 (d, J=7.8 Hz, 1H), 6.79 (d, J=7.4 Hz, 1H), 6.75 (s, 1H), 3.53 (m, 5H), 2.85 (m, 2H), 2.41 (m, 5H), 2.31 (m, 1H), 2.22 (m, 4H), 1.75 (m, 2H), 1.57 (m, 4H). MS m/z 529.2 [M$^+$+1].

Example 345

4-(3,4-Dimethoxy-phenyl)-3-[1-[3-methyl-4-(4-methyl-piperazine-1-carbonyl)-1H-pyrrol-2-yl]-meth-(Z)-ylidene]-1,3-dihydro-indol-2-one

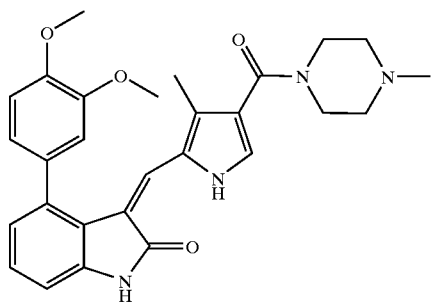

$^1$H NMR (400 MHz, DMSO-d$_6$) δ 13.47 (s, NH, 1H), 11.06 (s, NH, 1H), 7.35 (d, J=3.1 Hz, 1H), 7.17 (t, J=7.8 Hz, 1H), 7.10 (d, J=8.2 Hz, 1H), 6.99 (d, J=2.0 Hz, 1H), 6.92 (m, 2H), 6.88 (d, J=7.0 Hz, 1H), 6.81 (d, J=7.8 Hz, 1H), 3.79 (s, 3H), 3.71 (s, 3H), 3.43 (m, 4H), 2.25 (m, 4H), 2.15 (s, 3H), 1.64 (s, 3H). MS m/z 485 [M−1].

Example 346

4-(3,4-Dimethoxy-phenyl)-3-1-[3-((cis)-3,5-dimethyl-piperazine-1-carbonyl)-5-methyl-1H-pyrrol-2-yl]-meth-(Z)-ylidene]-1,3-dihydro-indol-2-one

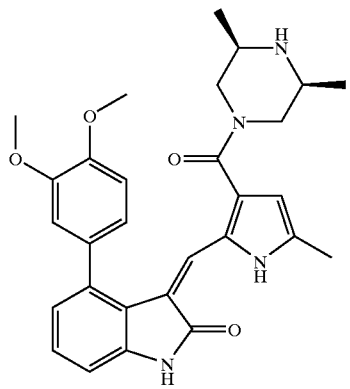

$^1$H NMR (400 MHz, DMSO-d$_6$) δ 13.61 (s, NH, 1H), 11.06 (s, NH, 1H), 7.14 (m, 2H), 6.98 (m, 1H), 6.87 (m, 3H), 6.73 (dd, J=0.8 Hz, J=7.4 Hz, 1H), 6.03 (s, 1H), 4.05 (m, 1H), 3.82 (s, 3H), 3.65 (s, 3H), 3.32 (m, 1H), 2.41 (m, 2H), 2.31 (s, 3H), 2.19 (m, 2H), 1.92 (br m, 1H), 0.99 (m, 3H), 0.79 (m, 3H). MS m/z 499 [M−1].

Example 347

5-[4-(3,4-Dimethoxy-phenyl)-2-oxo-1,2-dihydro-indol-(3Z)-ylidenemethyl]-2,4-dimethyl-1H-pyrrole-3-carboxylic Acid (2-Pyrrolidin-1-yl-ethyl)-amide

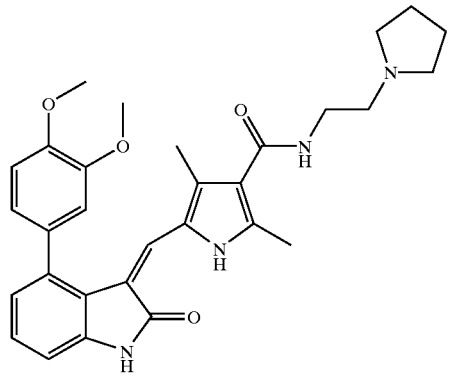

$^1$H NMR (400 MHz, DMSO-d$_6$) δ 13.46 (s, NH, 1H), 10.98 (s, NH, 1H), 7.42 (t, 1H), 7.14 (t, 1H), 7.11 (d, 1H), 6.98 (d, 1H), 6.91 (m, 2H), 6.86 (s, 1H), 6.79 (dd, 1H), 3.80 (s, 3H), 3.70 (s, 3H), 3.28 (m, 4H), 2.45 (m, 4H), 2.35 (s, 3H), 1.71 (s, 3H), 1.64 (m, 4H). MS m/z 513 [M−1].

Example 348

2-[4-(3,4-Dimethoxy-phenyl)-2-oxo-1,2-dihydro-indol-(3Z)-ylidenemethyl]-5-methyl-1H-pyrrole-3-carboxylic Acid (3-Pyrrolidin-1-yl-propyl)-amide

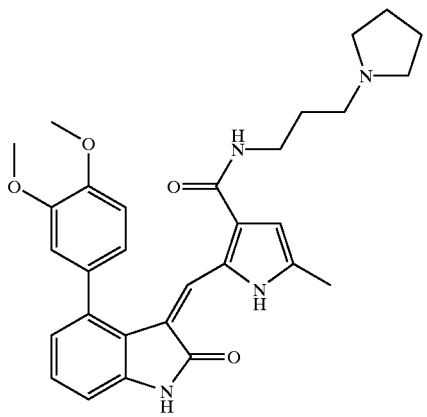

$^1$H NMR (400 MHz, DMSO-d$_6$) δ 13.87 (s, NH, 1H), 11.06 (s, NH, 1H), 8.10 (s, 1H), 7.85 (m, 1H), 7.6 (m, 1H), 7.15 (t, J=7.4 Hz, 1H), 6.99 (d, J=7.8 Hz, 1H), 6.89 (s, 1H), 6.86 (d, J=8.2 Hz, 1H), 6.77 (d, J=7.8 Hz, 1H), 6.33 (s, 1H), 3.81 (s, 3H), 3.61 (s, 3H), 3.05 (m, 2H), 2.54 (m, 2H), 2.28 (s, 3H), 1.72 (m, 6H), 1.60 (m, 1H), 1.24 (m, 2H), 0.82 (m, 1H). MS m/z 513 [M−1].

Example 349

4-(3,4-Dimethoxy-phenyl)-3-[1-[5-methyl-3-(4-pyrrolidin-1-yl-piperidine-1-carbonyl)-1H-pyrrol-2-yl]-meth-(Z)-ylidene]-1,3-dihydro-indol-2-one

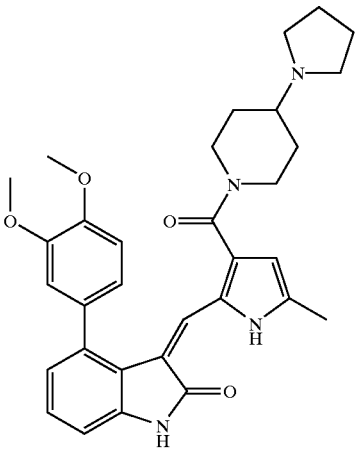

$^1$H NMR (400 MHz, DMSO-d$_6$) δ 13.61 (s, NH, 1H), 11.06 (s, NH, 1H), 7.14 (t, J=7.8 Hz, 1H), 7.10 (br s, 1H), 6.97 (d, J=8.2 Hz, 1H), 6.87 (m, 3H), 6.73 (dd, J=0.8 Hz, J=7.8 Hz, 1H), 6.04 (d, J=2.0 Hz, 1H), 3.99 (m, 1H), 3.81 (s, 3H), 3.68 (s, 3H), 3.43 (m, 1H), 2.68 (m, 2H), 2.44 (m, 4H), 2.30 (s, 3H), 2.09 (m, 1H), 1.74 (m, 2H), 1.65 (m, 5H), 1.17 (m, 1H). MS m/z 539 [M−1].

Example 350

4-(3,4-Dimethoxy-phenyl)-3-[1-[4-((R)-3-hydroxy-pyrrolidine-1-carbonyl)-3,5-dimethyl-1H-pyrrol-2-yl]-meth-(Z)-ylidene]-1,3-dihydro-indol-2-one

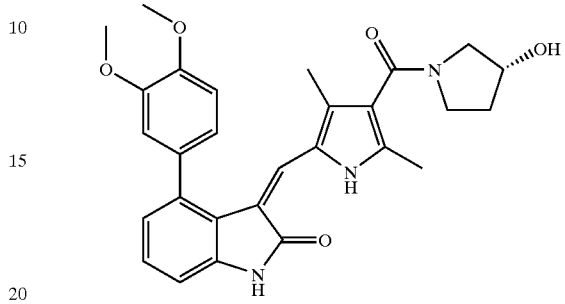

$^1$H NMR (400 MHz, DMSO-d$_6$) δ 13.37 (s, NH, 1H), 10.97 (s, NH, 1H), 7.14 (t, J=7.8 Hz, 1H), 7.09 (d, J=8.2 Hz, 1H), 6.97 (d, J=2.0 Hz, 1H), 6.91 (dd, J=2.0 Hz, J=7.8 Hz, 1H), 6.88 (d, J=6.6 Hz, 1H), 6.94 (s, 1H), 6.79 (d, J=6.6 Hz, 1H), 4.90 (m, 1H), 4.21 (m, 1H), 3.79 (s, 3H), 3.71 (s, 3H), 3.48 (m, 2H), 3.25 (m, 2H), 2.21 (s, 3H), 1.81 (m, 2H), 1.59 (s, 3H). MS m/z 486 [M−1].

Example 351

2,4-Dimethyl-5-[4-(3-methylcarbamoyl-phenyl)-2-oxo-1,2-dihydro-indol-(3Z)-ylidenemethyl]-1H-pyrrole-3-carboxylic Acid (2-Pyrrolidin-1-yl-ethyl)-amide

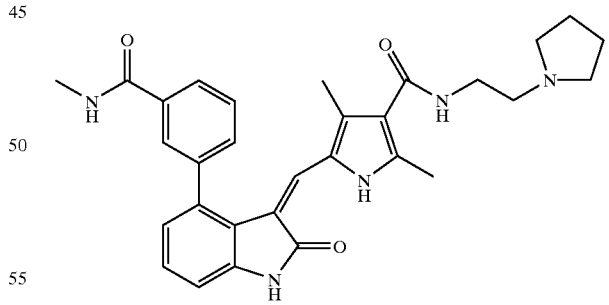

$^1$H NMR (400 MHz, DMSO-d$_6$) δ 13.46 (s, NH, 1H), 11.06 (s, NH, 1H), 8.52 (m, 1H), 7.95 (m, 1H), 7.90 (s, 1H), 7.62 (t, J=7.8 Hz, 1H), 7.56 (m, 1H), 7.43 (t, J=5.5 Hz, 1H), 7.19 (t, J=7.8 Hz, 1H), 6.93 (dd, J=0.8 Hz, J=7.8 Hz, 1H), 6.80 (dd, J=0.8 Hz, J=7.4 Hz, 1H), 6.72 (s, 1H), 3.24 (m, 2H), 2.75 (d, J=4.7 Hz, 3H), 2.42 (m, 4H), 2.35 (s, 3H), 1.64 (m, 4H), 1.58 (s, 3H). MS m/z 510 [M−1].

Example 352

5-[4-(4-Chloro-phenyl)-2-oxo-1,2-dihydro-indol-(3Z)-ylidenemethyl]-2,4-dimethyl-1H-pyrrole-3-carboxylic Acid [2-(1,1-Dioxo-1λ-thiomorpholin-4-yl)-ethyl]-amide

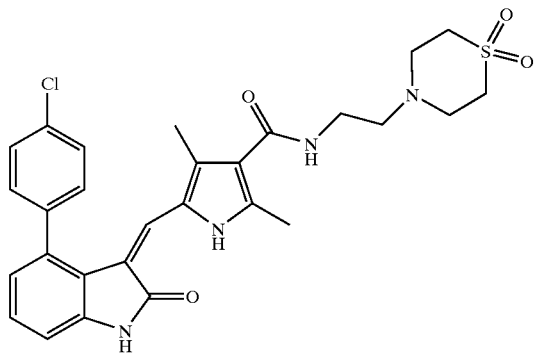

$^1$H NMR (400 MHz, DMSO-d$_6$) δ 13.39 (s, NH, 1H), 10.99 (s, NH, 1H), 7.55 (m, 2H), 7.38 (m, 3H), 7.13 (t, J=7.8 Hz, 1H), 6.88 (dd, J=0.8 Hz, J=7.8 Hz, 1H), 6.74 (dd, J=1.2 Hz, J=7.8 Hz, 1H), 6.60 (s, 1H), 3.22 (m, 2H), 3.00 (m, 4H), 2.87 (m, 4H), 2.54 (t, J=6.3 Hz, 2H), 2.32 (s, 3H), 1.68 (s, 3H). MS m/z 552 [M−1].

Example 353

5-[4-(2-Fluoro-phenyl)-2-oxo-1,2-dihydro-indol-(3Z)-ylidenemethyl]-4-methyl-1H-pyrrole-3-carboxylic Acid [2-(1,1-Dioxo-1λ-thiomorpholin-4-yl)-ethyl]-amide

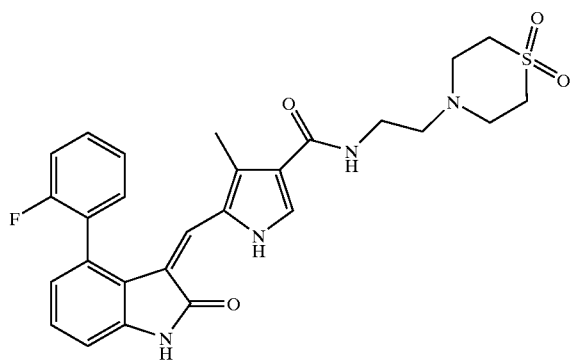

$^1$H NMR (400 MHz, DMSO-d$_6$) δ 13.48 (s, NH, 1H), 11.13 (s, NH, 1H), 7.76 (m, 1H), 7.68 (d, J=3.1 Hz, 1H), 7.58 (m, 1H), 7.43 (m, 3H), 7.23 (t, J=7.8 Hz, 1H), 6.96 (d, J=7.8 Hz, 1H), 6.83 (d, J=7.4 Hz, 1H), 6.72 (s, 1H), 3.24 (m, 2H), 3.04 (m, 4H), 2.91 (m, 4H), 2.57 (t, J=6.6 Hz, 2H), 1.78 (s, 3H). MS m/z 551 [M−1].

Example 354

5-[4-(2,6-Difluoro-phenyl)-2-oxo-1,2-dihydro-indol-(3Z)-ylidenemethyl]-4-methyl-1H-pyrrole-3-carboxylic Acid [2-(1,1-Dioxo-1λ-thiomorpholin-4-yl)-ethyl]-amide

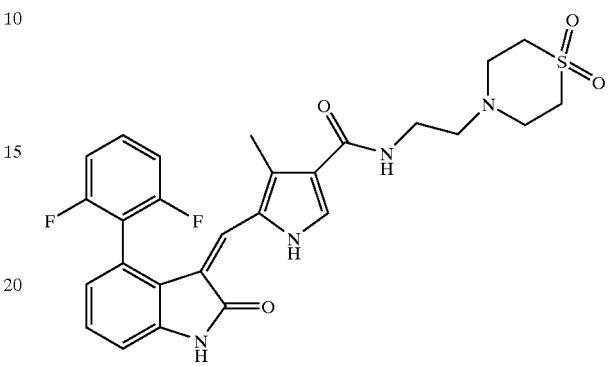

$^1$H NMR (400 MHz, DMSO-d$_6$) δ 13.48 (s, NH, 1H), 11.18 (s, NH, 1H), 7.79 (t, 1H), 7.70 (d, 1H), 7.65 (m, 1H), 7.35 (m, 2H), 7.26 (t, 1H), 6.99 (d, 1H), 6.89 (d, 1H), 6.67 (s, 1H), 3.25 (m, 2H), 3.04 (m, 4H), 2.91 (m, 4H), 2.58 (t, 2H), 1.82 (s, 3H). MS m/z 539 [M−1].

Example 355

5-[4-(2,6-Difluoro-phenyl)-2-oxo-1,2-dihydro-indol-(3Z)-ylidenemethyl]-2,4-dimethyl-1H-pyrrole-3-carboxylic Acid [2-(1,1-Dioxo-1λ-thiomorpholin-4-yl)-ethyl]-amide

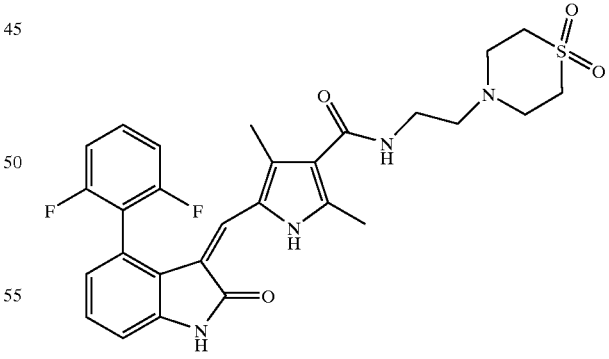

$^1$H NMR (400 MHz, DMSO-d$_6$) δ 13.54 (s, NH, 1H), 11.00 (br s, NH, 1H), 7.63 (m, 1H), 7.47 (t, J=5.5 Hz, 1H), 7.33 (m, 2H), 7.22 (t, J=7.8 Hz, 1H), 6.99 (d, J=7.8 Hz, 1H), 6.86 (d, J=7.8 Hz, 1H), 6.39 (s, 1H), 3.27 (m, 2H), 3.05 (m, 4H), 2.91 (m, 4H), 2.58 (t, J=6.3 Hz, 2H), 2.38 (s, 3H), 1.71 (s, 3H). MS m/z 553 [M−1].

Example 356

2-[4-(2,6-Difluoro-phenyl)-2-oxo-1,2-dihydro-indol-(3Z)-ylidenemethyl]-5-methyl-1H-pyrrole-3-carboxylic Acid [2-(1,1-Dioxo-1λ-thiomorpholin-4-yl)-ethyl]-amide

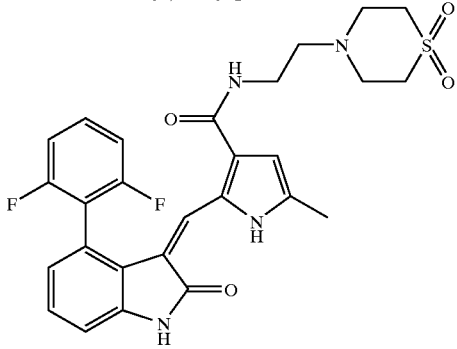

$^1$H NMR (400 MHz, DMSO-d$_6$) δ 13.80 (s, NH, 1H), 11.19 (s, NH, 1H), 7.91 (m, 1H), 7.81 (m, 1H), 7.51 (m, 1H), 7.20 (m, 3H), 6.98 (m, 1H), 6.82 (m, 1H), 6.40 (m, 1H), 3.18 (m, 2H), 3.12 (m, 4H), 2.95 (m, 4H), 2.55 (m, 2H), 2.31 (s, 3H). MS m/z 539 [M−1].

Example 357

5-[4-(2,6-Difluoro-phenyl)-2-oxo-1,2-dihydro-indol-(3Z)-ylidenemethyl]-2,4-dimethyl-1H-pyrrole-3-carboxylic Acid

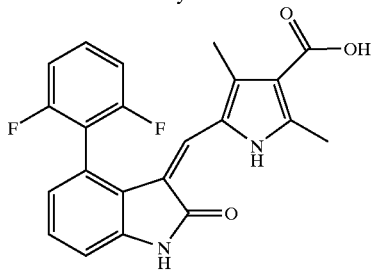

$^1$H NMR (400 MHz, DMSO-d$_6$) δ 13.69 (s, NH, 1H), 12.12 (s, 1H), 11.18 (s, NH, 1H), 7.64 (m, 1H), 7.34 (m, 2H), 7.24 (t, J=7.8 Hz, 1H), 7.00 (d, J=7.8 Hz, 1H), 6.89 (d, J=7.8 Hz, 1H), 6.64 (s, 1H), 3.32 (s, 3H), 1.79 (s, 3H). MS m/z 393 [M−1].

Example 358

2-[4-(2,6-Difluoro-phenyl)-2-oxo-1,2-dihydro-indol-(3Z)-ylidenemethyl]-5-methyl-1H-pyrrole-3-carboxylic Acid

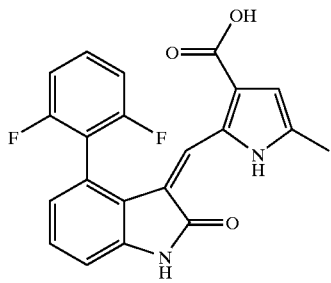

$^1$H NMR (400 MHz, DMSO-d$_6$) δ 12.10 (s, 1H), 11.13 (s, NH, 1H), 7.83 (s, 1H), 7.51 (m, 1H), 7.26 (t, J=7.8 Hz, 1H), 7.19 (m, 2H), 7.00 (dd, J=0.8 Hz, J=7.4 Hz, 1H), 6.82 (d, J=7.8 Hz, 1H), 6.40 (d, J=2.3 Hz, 1H), 2.30 (s, 3H). MS m/z 379 [M−1].

Example 359

5-[4-(2,6-Difluoro-phenyl)-2-oxo-1,2-dihydro-indol-(3Z)-ylidenemethyl]-4-methyl-1H-pyrrole-3-carboxylic Acid

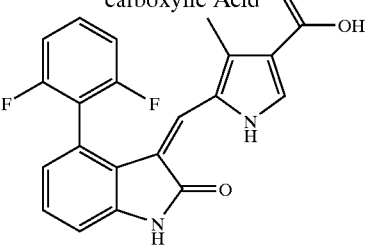

$^1$H NMR (400 MHz, DMSO-d$_6$) δ 13.58 (s, NH, 1H), 11.22 (s, NH, 1H), 7.75 (d, J=3.1 Hz, 1H), 7.64 (m, 1H), 7.34 (m, 2H), 7.27 (t, J=7.8 Hz, 1H), 7.00 (d, J=7.0 Hz, 1H), 6.90 (d, J=7.8 Hz, 1H), 6.66 (s, 1H), 1.82 (s, 3H). MS m/z 379 [M−1].

Example 360

3-[1-(4-{(S)-2-[(Cyclopropylmethyl-amino)-methyl]-pyrrolidine-1-carbonyl}-3,5-dimethyl-1H-pyrrol-2-yl)-meth-(Z)-ylidene]-4-(3-fluoro-phenyl)-1,3-dihydro-indol-2-one

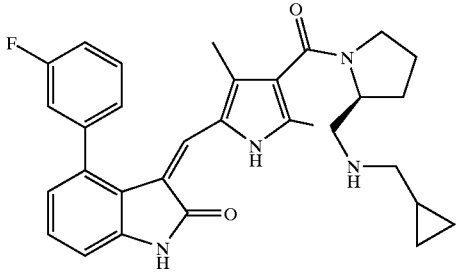

To a solution of 5-[4-(3-fluoro-phenyl)-2-oxo-1,2-dihydro-indol-(3Z)-ylidenemethyl]-2,4-dimethyl-1H-pyrrole-3-carboxylic acid (70 mg, 0.185 mmol), EDC (70 mg, 0.37 mmol), HOBt (26 mg, 0.19 mmol) in DMF (4 mL) was added TEA (0.08 mL) and cyclopropylmethyl-(S)-1-pyrrolidin-2-ylmethyl-amine (0.05 mL, 0.37 mmol). The mixture was stirred at rt for 20 hours. The reaction was diluted with DCM, washed with water, NaHCO$_3$, dried and concentrated. The residue was purified on a silica gel column to give the titled compound.

$^1$H NMR (400 MHz, CD$_2$Cl$_2$) δ 12.9 (br s, 1H, NH), 8.6 (br s, 1H), 7.06 (m, 1H), 6.89 (m, 4H), 6.6 (m, 1H), 6.45 (m, 2H), 4.07 (m, 1H), 2.9 (m, 3H), 2.6 (m, 2H), 2.4 (m, 1H), 2.0 (m, 1H), 1.92 (s, 3H, CH$_3$), 1.3 (m, 2H), 1.26 (s, 3H, CH$_3$), 0.84 (m, 2H), 0.3 (m, 1H), 0.08 (m, 2H). MS m/z 513.6 [M$^+$+1].

Example 361

3-[1-(3-{(S)-2-[(Cyclopropylmethyl-amino)-methyl]-pyrrolidine-1-carbonyl}-5-methyl-1H-pyrrol-2-yl)-meth-(Z)-ylidene]-4-(3-fluoro-phenyl)-1,3-dihydro-indol-2-one

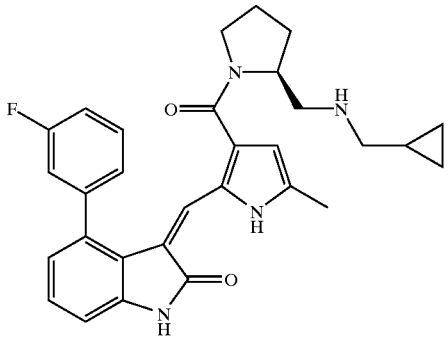

To a solution of 2-[4-(3-fluoro-phenyl)-2-oxo-1,2-dihydro-indol-(3Z)-ylidenemethyl]-5-methyl-1H-pyrrole-3-carboxylic acid (80 mg, 0.22 mmol), EDC (80 mg), HOBt (30 mg) in DMF (4 mL) was added TEA (0.08 mL) and cyclopropylmethyl-(S)-1-pyrrolidin-2-ylmethyl-amine (0.05 mL). The mixture was stirred at rt for 20 hours. The reaction was diluted with DCM, washed with water, NaHCO$_3$, dried and concentrated. The residue was purified on a silica gel column to give the titled compound.
MS m/z 499.6 [M$^+$+1].

Example 362

4-(2,6-Difluoro-phenyl)-3-[1-[4-((S)-pyrrolidine-2-carbonyl)-1,4,5,6,7,8-hexahydropyrrolo[3,2-b]azepin-2-yl]-meth-(Z)-ylidene]-1,3-dihydro-indol-2-one

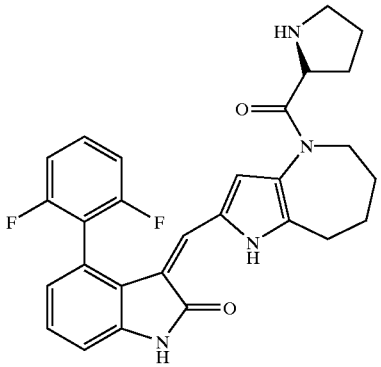

(S)-2-(2-Formyl-5,6,7,8-tetrahydro-1H-pyrrolo[3,2-b]azepine-4-carbonyl)-pyrroline-1-carboxylic acid tert-butyl ester (0.2 mmol) was condensed with 4-(2,6-difluoro-phenyl)-1,3-dihydro-indol-2-one (0.2 mmol) and piperidine (2 drops) in ethanol (2 mL) to give 20 mg of the titled compound as a yellow solid.
$^1$H NMR (400 MHz, DMSO-d$_6$) δ 13.52 (br s, 1H, NH), 11.16 (s, 1H, NH), 7.62 (m, 1H), 7.27 (m, 4H), 6.99 (d, 1H), 6.88 (d, 1H), 6.37 (s, 1H), 6.19 (s, 1H), 4.52 (s, 1H), 3.55 (m, 2H), 3.37 (m, 2H), 2.88 (m, 1H), 2.70 (m, 1H), 1.90 (m, 2H), 1.62–1.76 (m, 6H). MS m/z 487.4 [M−1].

Example 363

2-[4-(3,5-Difluoro-phenyl)-2-oxo-1,2-dihydro-indol-(3Z)-ylidenemethyl]-5-methyl-1H-pyrrole-3-carboxylic Acid (2-Hydroxy-3-pyrrolidin-1-yl-propyl)-amide

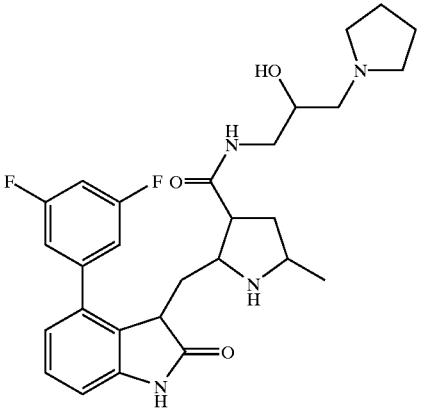

4-(3,5-Difluoro-phenyl)-1,3-dihydro-indol-2-one (73.5 mg, 0.3 mmol) was condensed with 2-formyl-5-methyl-1H-pyrrole-3-carboxylic acid (2-hydroxy-3-pyrrolidin-1-yl-propyl)-amide (excess) and piperidine in ethanol to give 40 mg of the titled compound as a yellow solid.
$^1$H NMR (400 MHz, DMSO-d$_6$) δ 13.87 (s, NH, 1H), 11.20 (s, 1H, NH), 8.10 (m, s, 2H), 7.29 (m, 1H), 7.21 (t, 1H), 7.05 (m, 2H), 6.94 (dd, 1H), 6.78 (dd, 1H), 6.54 (d, 1H), 5.83 (d, 1H), 3.94 (m, 1H), 3.75 (m, 2H), 3.15 (m, 3H), 3.05 (m, 4H), 2.31 (s, 3H, CH$_3$), 1.98 (m, 2H), 1.88 (m, 2H). MS m/z 507.2 [M$^+$+1].

Example 364

2-[4-(2,4-Difluoro-phenyl)-2-oxo-1,2-dihydro-indol-(3Z)-ylidenemethyl]-5-methyl-1H-pyrrole-3-carboxylic Acid (2-Hydroxy-3-pyrrolidin-1-yl-propyl)-amide

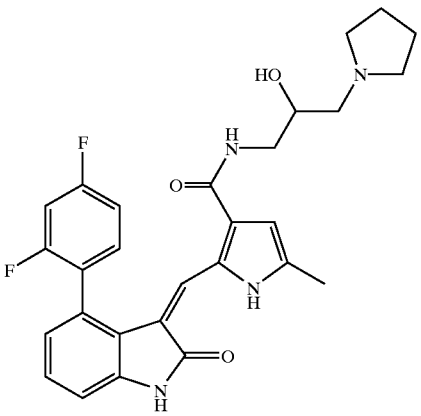

4-(2,4-Difluoro-phenyl)-1,3-dihydro-indol-2-one (73.5 mg, 0.3 mmol) was condensed with 2-formyl-5-methyl-1H-pyrrole-3-carboxylic acid (2-hydroxy-3-pyrrolidin-1-yl-propyl)-amide (excess) and piperidine in ethanol to give 75 mg (60%) of the titled compound as a yellow solid.
$^1$H NMR (400 MHz, DMSO-d$_6$) δ 13.86 (br s, NH, 1H), 11.17 (s, 1H, NH), 7.95 (m, 1H), 7.91 (m, 1H), 7.38 (m, 1H), 7.21 (m, 1H), 7.15 (m, t, 2H), 6.95 (dd, 1H), 6.77 (dd, 1H), 6.46 (m, 1H), 3.77 (m, 1H), 3.25 (m, 2H), 3.03 (m, 1H), 2.6–2.9 (m, 5H), 2.3 (s, 3H, CH₃), 1.79 (m, 4H). MS m/z 507.4 [M⁺+1].

Example 365

2-[4-(3-Chloro-4-fluoro-phenyl)-2-oxo-1,2-dihydro-indol-(3Z)-ylidenemethyl]-5-methyl-1H-pyrrole-3-carboxylic Acid (2-Hydroxy-3-pyrrolidin-1-yl-propyl)-amide

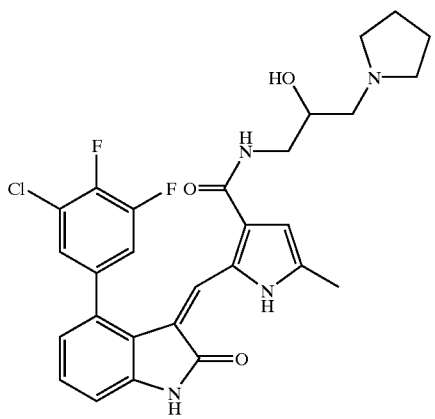

4-(3-Chloro-4-fluoro-phenyl)-1,3-dihydro-indol-2-one (78.3 mg, 0.3 mmol) was condensed with 2-formyl-5-methyl-1H-pyrrole-3-carboxylic acid (2-hydroxy-3-pyrrolid-1-yl-propyl)-amide (excess) and piperidine in ethanol to give 75 mg (60%) of the titled compound as a yellow solid.

¹H NMR (400 MHz, DMSO-d₆) δ 13.82 (s, NH, 1H), 11.16 (s, 1H, NH), 7.99 (s, 1H), 7.96 (m, 1H), 7.51 (dd, 1H), 7.42 (t, 1H), 7.31 (m, 1H), 7.20 (t, 1H), 6.93 (d, 1H), 6.78 (d, 1H), 6.47 (d, 1H), 3.82 (m, 1H), 3.27 (m, 2H), 2.7–3.05 (m, 6H), 2.30 (s, 3H, CH₃), 1.83 (m, 4H). MS m/z 523.4 [M⁺+1].

Example 366

2-[4-(4-Chloro-phenyl)-2-oxo-1,2-dihydro-indol-(3Z)-ylidenemethyl]-5-methyl-1H-pyrrole-3-carboxylic Acid (2-Hydroxy-3-pyrrolidin-1-yl-propyl)-amide

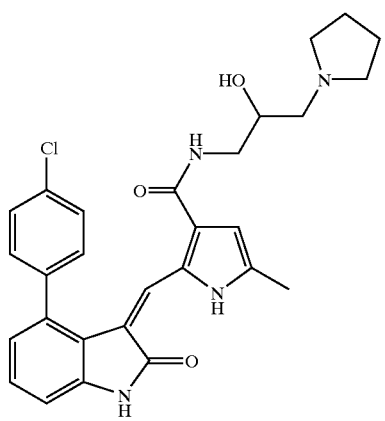

Yellow solid.

¹H NMR (400 MHz, DMSO-d₆) δ 13.80 (br s, NH, 1H), 11.10 (s, 1H, NH), 7.93 (s, 1H), 7.86 (m, 1H), 7.39 (d, 2H), 7.29 (d, 2H), 7.14 (t, 1H), 6.86 (d, 1H), 6.70 (d, 1H), 6.40 (d, 1H), 3.78 (m, 1H), 3.22 (m, 3H), 3.02 (m, 1H), 2.7–2.9 (m, 4H), 2.25 (s, 3H, CH₃), 1.79 (m, 4H). MS m/z 505.4 [M⁺+1].

Example 367

2-[4-(2,3-Difluoro-phenyl)-2-oxo-1,2-dihydro-indol-(3Z)-ylidenemethyl]-5-methyl-1H-pyrrole-3-carboxylic Acid (2-Hydroxy-3-pyrrolidin-1-yl-propyl)-methyl-amide

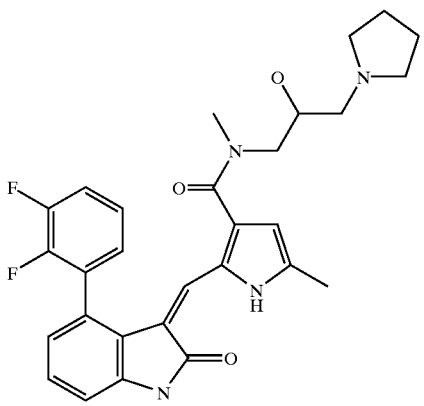

2-[4-(2,3-Difluoro-phenyl)-2-oxo-1,2-dihydro-indol-(3Z)-ylidenemethyl]-5-methyl-1H-pyrrole-3-carboxylic acid (115 mg, 0.3 mmol) was coupled with 1-methylamino-3-pyrrolidin-1-yl-propan-2-ol (3 eq.), EDC (2 eq.), HOBt (1 eq.) in DMF (1.5 mL) to give 108 mg of the titled compound as a yellow solid. MS 521.2 [M⁺+1].

Example 368

4-(3-Fluoro-phenyl)-3-[1-[4-((R)-3-hydroxy-pyrrolidin-1-ylmethyl)-3,5-dimethyl-1H-pyrrol-2-yl]-meth-(Z)-ylidene]-1,3-dihydro-indol-2-one

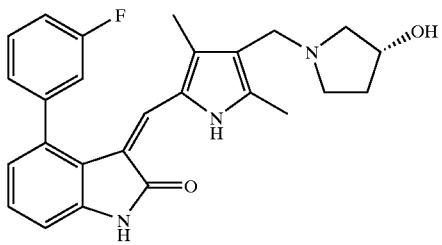

¹H NMR (400 MHz, DMSO-d₆) δ 13.30 (s, NH, 1H), 10.92 (s, NH, 1H), 7.57 (m, 1H), 7.29 (m, 3H), 7.14 (t, 1H), 6.91 (d, 1H), 6.76 (m, 2H), 4.17 (m, 1H), 2.45 (m, 2H), 2.29 (s, 3H), 2.21 (m, 2H), 1.95 (m, 1H), 1.62 (s, 3H), 1.58 (m, 2H), 1.28 (m, 1H), 0.82 (m, 1H). MS m/z 430 [M⁻−1].

Example 369

4-(2-Fluoro-phenyl)-3-[1-[4-(3-hydroxy-piperidin-1-ylmethyl)-3,5-dimethyl-1H-pyrrol-2-yl]-meth-(Z)-ylidene]-1,3-dihydro-indol-2-one

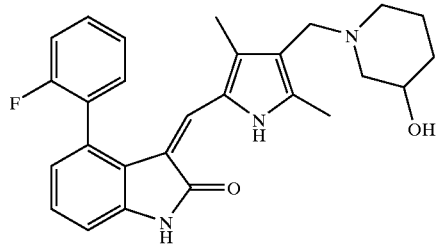

$^1$H NMR (400 MHz, DMSO-d$_6$) δ 13.27 (s, NH, 1H), 10.90 (s, NH, 1H), 7.49 (m, 1H), 7.35 (m, 3H), 7.11 (t, J=7.8 Hz, 1H), 6.88 (d, J=7.8 Hz, 1H), 6.74 (d, J=8.2 Hz, 1H), 6.56 (s, 1H), 4.45 (m, 1H), 3.10 (m, 2H), 2.19 (s, 3H), 2.11 (m, 2H), 1.68 (m, 2H), 1.50 (s, 3H), 1.41 (m, 2H), 1.25 (m, 2H), 0.95 (m, 1H). MS m/z 444 [M−1].

Example 370

2-[4-(3-Fluoro-phenyl)-2-oxo-1,2-dihydro-indol-(3Z)-ylidenemethyl]-5-methyl-1H-pyrrole-3-carboxylic acid (2-Piperidin-1-yl-ethyl)-amide

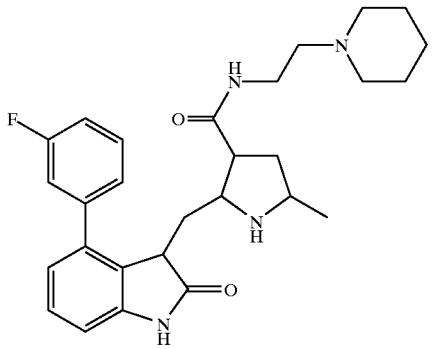

2-[4-(3-Fluoro-phenyl)-2-oxo-1,2-dihydro-indol-(3Z)-ylidenemethyl]-5-methyl-1H-pyrrole-3-carboxylic acid (90.5 mg) was coupled with 2-piperidin-1-yl-ethylamine (48 mg, 1.5 eq.), HOBt (1 eq.), EDC (1.5 eq.) and TEA (3 drops) in THF (2 mL), DMF (0.3 mL) at rt for overnight to give 82 mg (70%) of the titled compound as a yellow solid.

$^1$H NMR (400 MHz, DMSO-d$_6$) δ 13.80 (br s, NH, 1H), 11.12 (s, 1H, NH), 7.99 (s, 1H), 7.70 (t, 1H), 7.45 (m, 1H), 7.17 (m, 4H), 6.91 (dd, 1H), 6.76 (dd, 1H), 6.35 (d, 1H), 3.13 (m, 2H), 2.37 (m, 4H), 2.29 (m, s, 5H), 1.50 (m, 4H), 1.39 (m, 2H). MS m/z 473.6 [M$^+$+1].

Example 371

2-[4-(3-Fluoro-phenyl)-2-oxo-1,2-dihydro-indol-(3Z)-ylidenemethyl]-5-methyl-1H-pyrrole-3-carboxylic Acid [2-(3-Acetylamino-pyrrolidin-1-yl)-ethyl]-amide

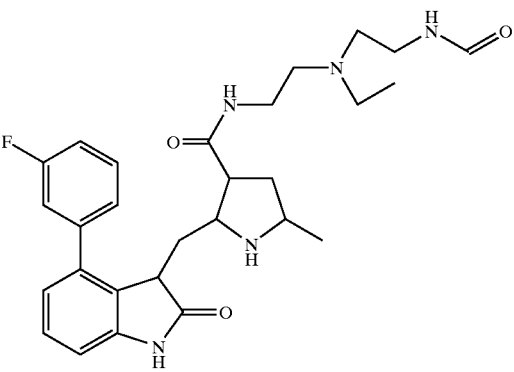

2-[4-(3-Fluoro-phenyl)-2-oxo-1,2-dihydro-indol-(3Z)-ylidenemethyl]-5-methyl-1H-pyrrole-3-carboxylic acid (90.5 mg) was coupled with N-[1-(2-amino-ethyl)-pyrrolidin-3-yl]-acetamide (58.5 mg, 1.5 eq.), HOBt (1 eq.), EDC (1.5 eq.) and TEA (3 drops) in THF (2 mL), DMF (0.3 mL) at rt for overnight to give 97 mg (78%) of the titled compound as a yellow solid.

$^1$H NMR (400 MHz, DMSO-d$_6$) δ 13.80 (s, NH, 1H), 11.12 (s, 1H, NH), 7.99 (s, 1H), 7.98 (m, 1H), 7.77 (t, 1H), 7.45 (m, 1H), 7.17 (m, 4H), 6.91 (dd, 1H), 6.74 (dd, 1H), 6.35 (d, 1H), 4.14 (m, 1H), 3.12 (m, 2H), 2.6–2.72 (m, 2H), 2.42 (m, 3H), 2.33 (m, 1H), 2.29 (s, 3H, CH$_3$), 2.05 (m, 1H), 1.76 (s, 1H, CH$_3$), 1.53 (m, 1H). MS m/z 516.4 [M$^+$+1].

Example 372

2-[4-(3-Fluoro-phenyl)-2-oxo-1,2-dihydro-indol-(3Z)-ylidenemethyl]-5-methyl-1H-pyrrole-3-carboxylic Acid (1-Methyl-piperidin-4-ylmethyl)-amide

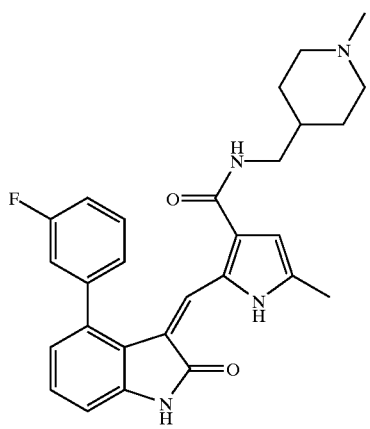

2-[4-(3-Fluoro-phenyl)-2-oxo-1,2-dihydro-indol-(3Z)-ylidenemethyl]-5-methyl-1H-pyrrole-3-carboxylic acid (90.5 mg) was coupled with C-(1-methyl-piperidin-4-yl)-methylamine (1.5 eq.), HOBt (1 eq.), EDC (1.5 eq.) and TEA (3 drops) in THF (2 mL), DMF (0.3 mL) at rt for overnight to give 65 mg (55%) of the titled compound as a yellow solid.

$^1$H NMR (400 MHz, DMSO-d$_6$) δ 13.80 (br s, NH, 1H), 11.11 (s, 1H, NH), 8.00 (s, 1H), 7.81 (t, 1H), 7.42 (m, 1H), 7.16 (m, 4H), 6.91 (dd, 1H), 6.75 (dd, 1H), 6.39 (d, 1H), 2.90 (t, 2H), 2.72 (m, 2H), 2.29 (s, 3H, CH$_3$), 2.13 (s, 3H, CH$_3$), 1.79 (m, 2H), 1.54 (m, 2H), 1.38 (m, 1H), 1.12 (m, 2H). MS m/z 473.6 [M$^+$+1].

Example 373

2-[4-(3-Fluoro-phenyl)-2-oxo-1,2-dihydro-indol-(3Z)-ylidenemethyl]-5-methyl-1H-pyrrole-3-carboxylic Acid [2-(4-Hydroxy-piperidin-1-yl)-ethyl]-amide

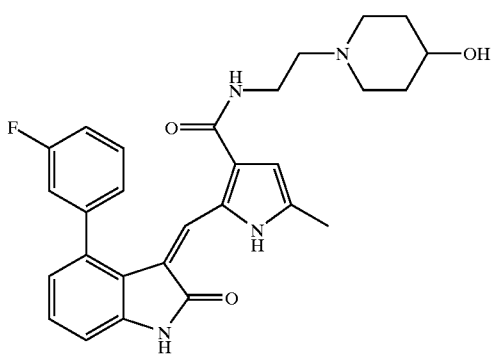

2-[4-(3-Fluoro-phenyl)-2-oxo-1,2-dihydro-indol-(3Z)-ylidenemethyl]-5-1H-pyrrole-3-carboxylic acid (90.5 mg) was coupled with 1-(2-amino-ethyl)-piperidin-4-ol (54 mg, 1.5 eq.), HOBt (1 eq.), EDC (1.5 eq.) and TEA (3 drops) in THF (2 mL), DMF (0.3 mL) at rt for overnight to give 69.8 mg (57%) of the titled compound as a yellow solid.

$^1$H NMR (400 MHz, DMSO-d$_6$) δ 13.80 (br s, NH, 1H), 11.12 (s, 1H, NH), 7.99 (s, 1H), 7.71 (t, 1H), 7.43 (m, 1H), 6.91 (d, 1H), 6.76 (d, 1H), 6.35 (d, 1H), 4.53 (d, 1H), 3.43 (m, 1H), 3.12 (m, 2H), 2.71 (m, 2H), 2.30 (m, 2H), 2.29 (s, 3H, CH$_3$), 2.05 (m, 2H), 1.69 (m, 2H), 1.38 (m, 2H). MS m/z 489.4 [M$^+$+1].

Example 374

2-[4-(3-Fluoro-phenyl)-2-oxo-1,2-dihydro-indol-(3Z)-ylidenemethyl]-5-methyl-1H-pyrrole-3-carboxylic Acid [3-(1,1-Dioxo-1λ6-thiomorpholin-4-yl)-2-hydroxy-propyl]-amide

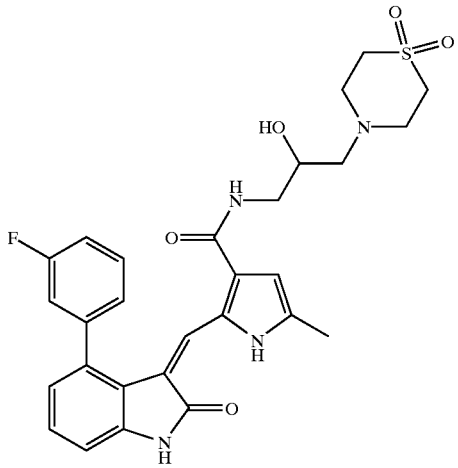

2-[4-(3-Fluoro-phenyl)-2-oxo-1,2-dihydro-indol-(3Z)-ylidenemethyl]-5-1H-pyrrole-3-carboxylic acid (108 mg, 0.3 mmol) was coupled with 1-amino-3(1,1-dioxo-1λ$^6$-thiomorpholin-4-yl)-propan-2-ol (1.8 mmol), HOBt (1 eq.), EDC (1.5 eq.) and TEA (3 drops) in THF (1 mL), acetonitrile (1 mL) at rt for overnight to give 107 mg (65%) of the titled compound as a yellow solid.

$^1$H NMR (400 MHz, DMSO-d$_6$) δ 13.84 (br s, NH, 1H), 11.13 (s, 1H, NH), 8.00 (s, 1H), 7.79 (t, 1H), 7.44 (m, 1H), 7.17 (m, 4H), 6.91 (dd, 1H), 6.76 (dd, 1H), 6.42 (d, 1H), 4.76 (d, 1H), 3.67 (m, 1H), 3.17 (m, 1H), 3.06 (m, 4H), 2.96 (m, 6H), 2.29 (s, 3H, CH$_3$). MS m/z 551.2 [M−1].

Example 375

5-[4-(4-Chloro-phenyl)-2-oxo-1,2-dihydro-indol-(3Z)-ylidenemethyl]-2,4-dimethyl-1H-pyrrole-3-carboxylic Acid [3-(1,1-Dioxo-16-thiomorpholin-4-yl)-2-hydroxy-propyl]-amide

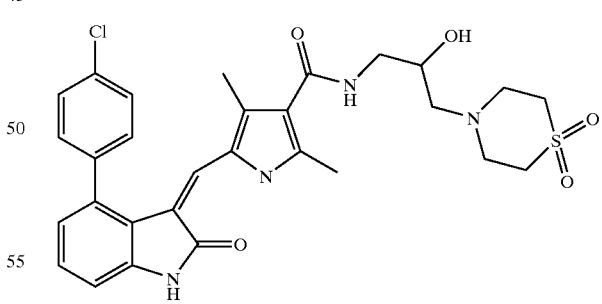

5-[4-(4-Chloro-phenyl)-2-oxo-1,2-dihydro-indol-(3Z)-ylidenemethyl]-2,4-dimethyl-1H-pyrrole-3-carboxylic acid (112 mg, 0.3 mmol) was coupled with 1-amino-3-(1,1-dioxo-1λ$^6$-thiomorpholin-4-yl)-propan-2-ol (1.8 mmol), HOBt (1 eq.), EDC (1.5 eq.) and TEA (3 drops) in THF (1 mL), acetonitrile (1 mL) at rt for overnight to give 96.2 mg (55%) of the titled compound.

$^1$H NMR (400 MHz, DMSO-d$_6$) δ 13.49 (s, NH, 1H), 11.10 (br s, 1H, NH), 7.59 (d, 1H), 7.44 (m, 1H), 7.17 (t,

1H), 6.91 (d, 1H), 6.77 (d, 1H), 6.65 (s, 1H), 4.8 (m, 1H), 3.71 (m, 1H), 3.35 (m, 1H), 3.12 (m, 1H), 3.05 (m, 4H), 2.94 (m, 4H), 2.5 (m, 1H), 2.43 (m, 1H), 2.37 (s, 3H, CH$_3$), 1.72 (s, 3H, CH$_3$). MS m/z 581.2 [M−1].

Example 376

5-[4-(2,6-Difluoro-phenyl)-2-oxo-1,2-dihydro-indol-(3Z)-ylidenemethyl]4-methyl-1H-pyrrole-3-carboxylic Acid [3-(1,1-Dioxo-1λ$^6$-thiomorpholin-4-yl)-2-hydroxy-propyl]-amide

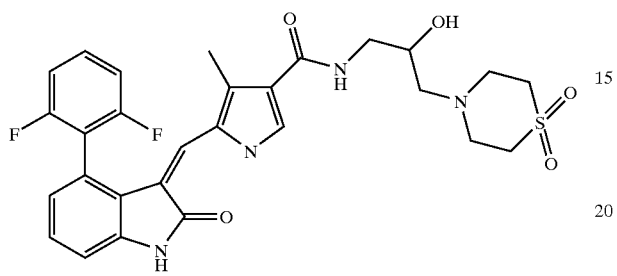

5-[4-(2,6-Difluoro-phenyl)-2-oxo-1,2-dihydro-indol-(3Z)-ylidenemethyl]-4-methyl-1H-pyrrole-3-carboxylic acid (114 mg, 0.3 mmol) was coupled with 1-amino-3-(1,1-dioxo-1λ$^6$-thiomorpholin-4-yl)-propan-2-ol (1.8 mmol), HOBt (1 eq.), EDC (1.5 eq.) and TEA (3 drops) in THF (1 mL), acetonitrile (1 mL) at rt for overnight to give 102 mg (60%) of the titled compound.

$^1$H NMR (400 MHz, DMSO-d$_6$) δ 13.52 (s, NH, 1H), 11.20 (br s, 1H, NH), 7.81 (d, 1H), 7.74 (d, 1H), 7.65 (m, 1H), 7.34 (m, 2H), 7.25 (t, 1H), 6.99 (dd, 1H), 6.88 (d, 1H), 6.66 (s, 1H), 4.83 (d, 1H), 6.66 (s, 1H), 4.83 (m, 1H), 3.70 (m, 1H), 3.35 (m, 1H), 3.08 (m, 1H), 3.04 (m, 4H), 2.93 (m, 4H), 2.50 (m, 1H), 2.40 (m, 1H), 1.81 (s, 3H, CH$_3$). MS m/z 569.2 [M−1].

Example 377

4-(2,6-Difluoro-phenyl)-3-[1-[3-methyl-4-((S)-3-pyrrolidin-1-ylmethyl-piperidine-1-carbonyl)-1H-pyrrol-2-yl]-meth-(Z)-ylidene]-1,3-dihydro-indol-2-one

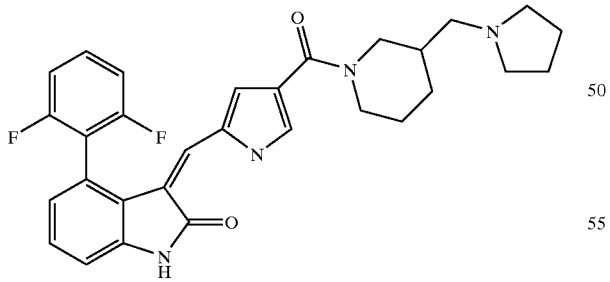

5-[4-(2,6-Difluoro-phenyl)-2-oxo-1,2-dihydro-indol-(3Z)-ylidenemethyl]-4-methyl-1H-pyrrole-3-carboxylic acid (114 mg, 0.3 mmol) was coupled with (R)-3-pyrrolidin-1-ylmethyl-piperidine (99 mg, 2 eq.), HOBt (1 eq.), EDC (1.5 eq.) and TEA (3 drops) in THF (1 mL) and aceonitrile (1 mL) at rt for overnight to give 111.3 mg (70%) of the titled compound as a yellow solid.

MS m/z 531 [M$^+$+1].

Example 378

4-(4-Chloro-phenyl)-3-[1-[3,5-dimethyl-4-((S)-3-pyrrolidin-1-ylmethyl-piperidine-1-carbonyl)-1H-pyrrol-2-yl]-meth-(Z)-ylidene]-1,3-dihydro-indol-2-one

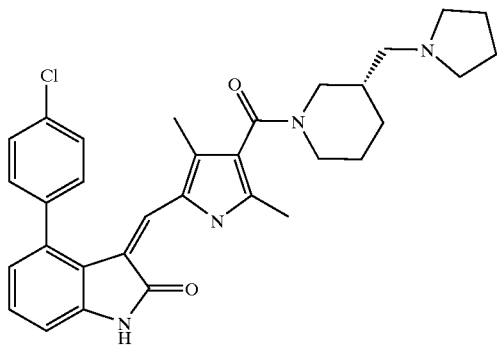

5-[4-(4-Chloro-phenyl)-2-oxo-1,2-dihydro-indol-(3Z)-ylidenemethyl]-2,4-dimethyl-1H-pyrrole-3-carboxylic acid (112 mg, 0.3 mmol) was coupled with (R)-3-pyrrolidin-1-ylmethyl-piperidine (99 mg, 2 eq.), HOBt (1 eq.), EDC (1.5 eq.) and TEA (3 drops) in THF (1 mL) and acetonitrile (1 mL) at rt for overnight to give 89.5 mg (55%) of the titled compound as a yellow solid.

MS m/z 543 [M$^+$+1].

Example 379

4-(3-Fluoro-phenyl)-3-[1-[5-methyl-3-(4-pyrrolidin-1-ylmethyl-piperidine-1-carbonyl)-1H-pyrrol-2-yl]-meth-(Z)-ylidene]-1,3-dihydro-indol-2-one

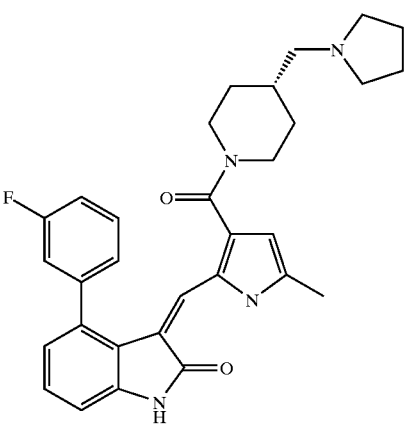

2-[4-(3-Fluoro-phenyl)-2-oxo-1,2-dihydro-indol-(3Z)-ylidenemethyl]-5-methyl-1H-pyrrole-3-carboxylic acid (108 mg, 0.3 mmol) was coupled with (R)-3-pyrrolidin-1-ylmethyl-piperidine (99 mg, 2 eq.), HOBt (1 eq.), EDC (1.5 eq.) and TEA (3 drops) in THF (1 mL), acetonitrile (1 mL) at rt for overnight to give 107 mg (70%) of the titled compound as a yellow solid.

MS 513.2 [M$^+$+1].

Example 380

3-[1-[3,5-Dimethyl-4-(1-methyl-1,2,3,6-tetrahydro-pyridin-4-yl)-1H-pyrrol-2-yl]-meth-(Z)-ylidene]4-(3-fluoro-phenyl)-1,3-dihydro-indol-2-one

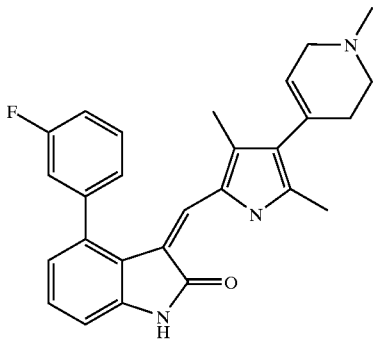

$^1$H NMR (400 MHz, DMSO-d$_6$) δ 13.4 (s, 1H, NH), 10.95 (s, 1H, NH), 7.56 (m, 1H), 7.28 (m, 3H), 7.14 (t, 1H), 6.91 (dd, 1H), 6.77 (dd, 1H), 6.76 (s, 1H), 5.40 (m, 1H), 2.95 (m, 2H), 2.50 (m, 2H), 2.25 (s, 3H, CH$_3$), 2.21 (s, 3H, CH$_3$), 2.17 (m, 2H), 1.55 (s, 3H, CH$_3$). MS m/z 428.2 [M$^+$+1].

Example 381

2-[4-(3-Fluoro-phenyl)-2-oxo-1,2-dihydro-indol-(3Z)-ylidenemethyl]-5-methyl-1H-pyrrole-3-carboxylic Acid [2-(2,2,2-Trifluoro-ethylamino)-ethyl]-amide

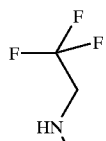

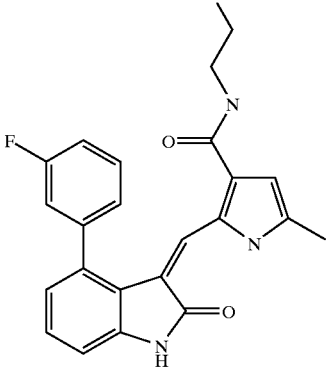

A mixture of 2-[4-(3-fluoro-phenyl)-2-oxo-1,2-dihydro-indol-(3Z)-ylidenemethyl]-5-methyl-1H-pyrrole-3-carboxylic acid (53 mg, 0.15 mmol), HOBt (28 mg), EDC (36 mg), TEA (0.042 mL) and N$^1$-(2,2,2-trifluoro-ethyl)-ethane-1,2-diamine (0.036 mL) in DMF (1 mL) was stirred at rt for 48 hours. The solvent was removed and diluted with sat. NaHCO$_3$. It was then extracted with DCM, dried and concentrated. The residue was purified on a silica gel column to give 52 mg (71%) of the titled compound.

$^1$H NMR (400 MHz, DMSO-d$_6$) δ 13.8 (s, 1H, NH), 11.14 (s, 1H, NH), 7.98 (s, 1H), 7.8 (t, 1H), 7.45 (m, 1H), 7.19 (m, 4H), 6.93 (d, 1H), 6.78 (d, 1H), 6.38 (d, 1H), 3.26 (m, 2H), 3.12 (m, 2H), 2.67 (t, 2H), 2.31 (s, 3H, CH$_3$). MS m/z 487.4 [M$^+$+1].

Example 382

3-[1-[4-(1-Acetyl-piperidine-4-carbonyl)-1,4,5,6,7,8-hexahydro-pyrrolo[3,2-b]azepin-2-yl]-meth-(Z)-ylidene]-4-(3-fluoro-phenyl)-1,3-dihydro-indol-2-one

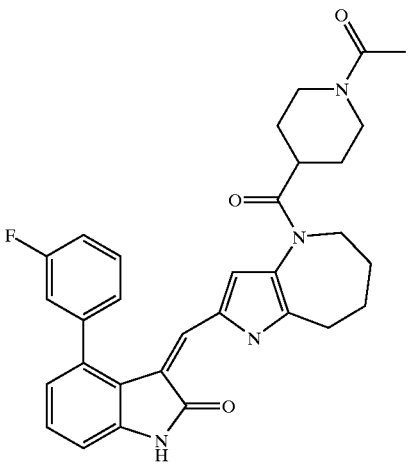

4-(1-Acetyl-piperidine-4-carbonyl)-1,4,5,6,7,8-hexahydro-pyrrolo[3,2-b]azepine-2-carbaldehyde (56 mg) was condensed with 4-(3-fluoro-phenyl)-1,3-dihydro-indol-2-one (40 mg) and piperidine (2 drops) in ethanol (1 mL) at rt for overnight. The solvent was concentrated and the residue was purified on a silica gel column to give 50 mg of the title compound as a yellow solid.

$^1$H NMR (400 MHz, CD$_2$Cl$_2$) δ 13.47 (s, 1H, NH), 9.16 (br s, 1H, NH), 7.48 (m, 1H), 7.2–7.3 (m, 4H), 6.97 (d, 1H), 6.88 (d, 1H), 6.76 (s, 1H), 6.09 (s, 1H), 4.50 (d, 1H), 3.77 (d, 1H), 2.91 (m, 2H), 2.78 (m, 2H), 2.4 (m, 1H), 2.04 (s, 3H, CH$_3$), 1.94 (m, 1H), 1.82 (m, 3H), 1.70 (m, 3H), 1.57 (m, 3H). MS m/z 527.4 [M$^+$+1].

Example 383

(R)-1-{2-[4-(3-Fluoro-phenyl)-2-oxo-1,2-dihydro-indol-(3Z)-ylidenemethyl]-5-methyl-1H-pyrrole-3-carbonyl}-piperidine-3-carboxylic Acid Cyclopropylamide Chiral

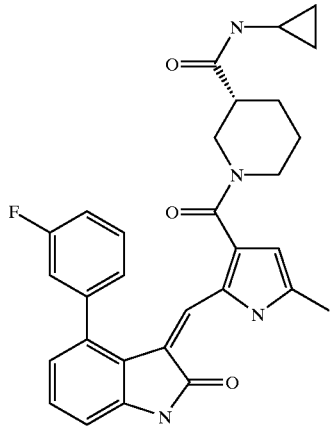

2-[4-(3-Fluoro-phenyl)-2-oxo-1,2-dihydro-indol-(3Z)-ylidenemethyl]-5-methyl-1H-pyrrole-3-carboxylic acid (108 mg, 0.3 mmol) was coupled with (R)-piperidine-3-carboxylic acid cyclopropylamide (69.3 mg, 1.5 eq.), HOBt (40.5 mg, 1 eq.), EDC (86 mg, 1.5 eq.) and TEA (0.06 mL) in DMF (1 mL) to give 57 mg (37%) of the titled compound.

MS m/z 513.4 [M$^+$+1].

Example 384

4-(3-Fluoro-phenyl)-3-[1-[4-methyl-3-(4-methyl-piperazine-1-carbonyl)-1H-pyrrol-2-yl]-meth-(Z)-ylidene]-1,3-dihydro-indol-2-one

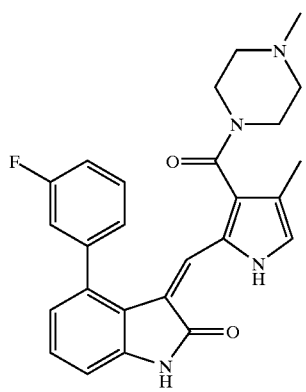

MS m/z 443.4 [M−1].

Example 385

2-[4-(3-Fluoro-phenyl)-2-oxo-1,2-dihydro-indol-(3Z)-ylidenemethyl]4-methyl-1H-pyrrole-3-carboxylic Acid (3-Pyrrolidin-1-yl-propyl)-amide

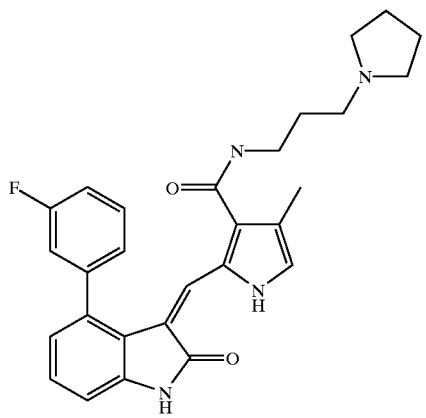

$^1$H NMR (400 MHz, DMSO-d$_6$) δ 13.50 (s, 1H, NH), 11.10 (s, 1H, NH), 7.63 (m, 2H), 7.4 (m, 1H), 7.22 (s, 1H), 7.14 (m, 3H), 7.01 (d, 1H), 6.86 (dd, 1H), 6.71 (dd, 1H), 2.97 (m, 2H), 1.98 (s, 3H, CH$_3$), 1.59 (m, 4H), 1.50 (m, 2H), 1.2 (m, 3H), 0.78 (m, 3H). MS m/z 473.1 [M$^+$+1].

Example 386

3-[1-[3,5-Dimethyl-4-(1-methyl-piperidin-4-yl)-1H-pyrrol-2-yl]-meth-(Z)-ylidene]4-(3-fluoro-phenyl)-1,3-dihydro-indol-2-one

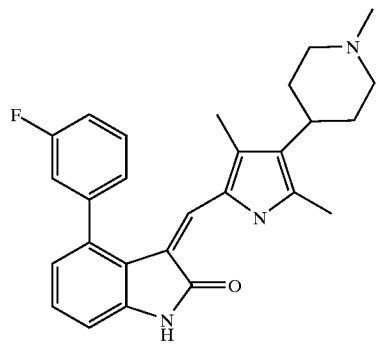

$^1$H NMR (400 MHz, DMSO-d$_6$) δ 13.32 (s, 1H, NH), 10.9 (s, 1H, NH), 7.56 (m, 1H), 7.27 (m, 3H), 7.12 (m, 1H), 6.90 (dd, 1H), 6.75 (m, 2H), 2.78 (m, 2H), 2.34 (m, 1H), 2.27 (s, 3H, CH$_3$), 2.14 (s, 3H, CH$_3$), 1.86 (m, 2H), 1.74 (m, 2H), 1.59 (s, 3H, CH$_3$), 1.44 (m, 2H). MS m/z 430.2 [M$^+$+1].

Example 387

3-[1-[3,5-Dimethyl-4-(1-methyl-piperidin-4-yl)-1H-pyrrol-2-yl]-meth-(Z)-ylidene]-4-(4-fluoro-phenyl)-1,3-dihydro-indol-2-one

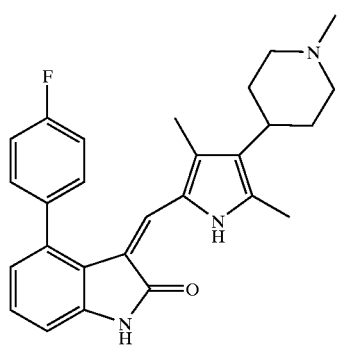

$^1$H NMR (400 MHz, DMSO-d$_6$) δ 13.31 (s, 1H, NH), 10.89 (s, 1H, NH), 7.43 (m, 1H), 7.35 (m, 1H), 7.11 (t, 1H), 6.89 (dd, 1H), 6.73 (dd, 1H), 6.68 (s, 1H), 2.78 (m, 2H), 2.34 (m, 1H), 2.34 (m, 1H), 2.27 (s, 3H, CH$_3$), 2.13 (s, 3H, CH$_3$), 1.85 (m, 2H), 1.76 (m, 2H), 1.60 (s, 3H CH$_3$), 1.43 (m, 2H). MS m/z 428.6 [M−1].

Example 388

4-(2,3-Difluoro-phenyl)-3-[1-[3,5-dimethyl-4-(1-methyl-piperidin-4-yl)-1H-pyrrol-2-yl]-meth-(Z)-ylidene]-1,3-dihydro-indol-2-one

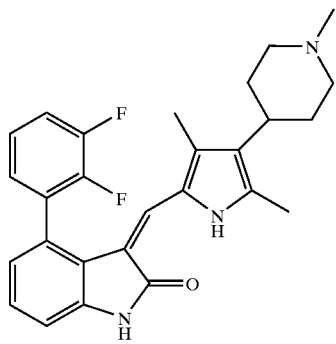

$^1$H NMR (400 MHz, DMSO-d$_6$) δ 13.35 (s, 1H, NH), 10.96 (s, 1H, NH), 7.58 (m, 1H), 7.39 (m, 1H), 7.28 (m, 1H), 7.16 (t, 1H), 6.95 (dd, 1H), 6.81 (dd, 1H), 6.62 (s, 1H), 2.78 (m, 2H), 2.35 (m, 1H), 2.28 (s, 3H, CH$_3$), 2.14 (s, 3H, CH$_3$), 1.86 (m, 2H), 1.75 (m, 2H), 1.61 (s, 3H, CH$_3$), 1.45 (m, 2H). MS m/z 446.6 [M−1].

Example 389

4-(3,5-Difluoro-phenyl)-3-[1-[3,5-dimethyl-4-(1-methyl-piperidin-4-yl)-1H-pyrrol-2-yl]-meth-(Z)-ylidene]-1,3-dihydro-indol-2-one

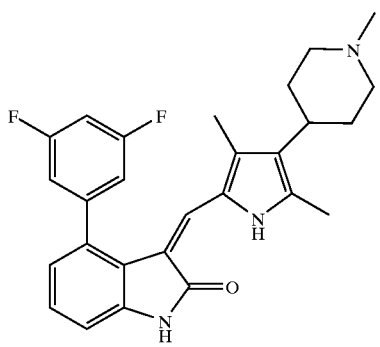

$^1$H NMR (400 MHz, DMSO-d$_6$) δ 13.35 (s, 1H, NH), 10.93 (s, 1H, NH), 7.37 (m, 1H), 7.2 (m, 2H), 7.13 (t, 1H), 6.92 (dd, 1H), 6.79 (s, 1H), 6.77 (dd, 1H), 2.78 (m, 2H), 2.36 (m, 1H), 2.28 (s, 3H, CH$_3$), 2.14 (s, 3H, CH$_3$), 1.86 (m, 2H), 1.77 (m, 2H), 1.67 (s, 3H, CH$_3$), 1.45 (m, 2H). MS m/z 446.5 [M−1].

Example 390

4-(2,6-Difluoro-phenyl)-3-[1-[3,5-dimethyl-4-(1-methyl-piperidin-4-yl)-1H-pyrrol-2-yl]-meth-(Z)-ylidene]-1,3-dihydro-indol-2-one

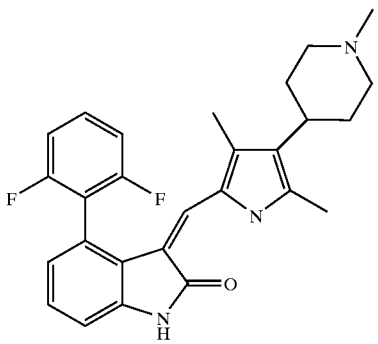

$^1$H NMR (400 MHz, DMSO-d$_6$) δ 13.36 (s, 1H, NH), 10.96 (s, 1H, NH), 7.61 (m, 1H), 7.32 (m, 2H), 7.17 (t, 1H), 6.96 (dd, 1H), 6.83 (dd, 1H), 6.56 (s, 1H), 2.78 (m, 2H), 2.34 (m, 1H), 2.28 (s, 3H, CH$_3$), 2.14 (s, 3H, CH$_3$), 1.86 (m, 2H) 1.75 (m, 2H), 1.58 (s, 3H, CH$_3$), 1.45 (m, 2H). MS m/z 446.5 [M−1].

Example 391

4-(3,4-Dimethoxy-phenyl)-3-[1-[3,5-dimethyl-4-(1-methyl-piperidin-4-yl)-1H-pyrrol-2-yl]-meth-(Z)-ylidene]-1,3-dihydro-indol-2-one

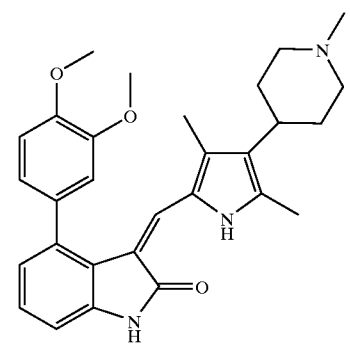

$^1$H NMR (400 MHz, DMSO-d$_6$) δ 13.29 (s, 1H, NH), 10.84 (s, 1H, NH), 7.09 (m, 2H), 6.96 (d, 1H), 6.89 (dd, 1H), 6.86 (d, 1H), 6.84 (s, 1H), 6.76 (d, 1H), 3.80 (s, 3H, CH$_3$), 3.71 (s, 3H, CH$_3$), 2.86 (m, 2H), 2.40 (m, 1H), 2.27 (s, 3H, CH$_3$), 2.22 (m, 2H), 1.78 (m, 2H), 1.61 (s, 3H, CH$_3$), 1.47 (m, 2H). MS m/z 472.4 [M$^+$+1].

Example 392

5-[4-(2,3-Difluoro-phenyl)-2-oxo-1,2-dihydro-indol-(3Z)-ylidenemethyl]-2,4-dimethyl-1H-pyrrole-3-carboxylic Acid

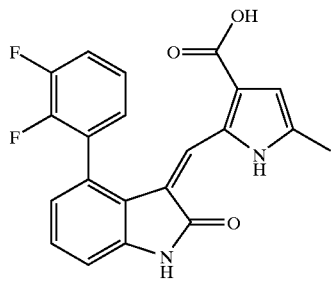

$^1$H NMR (400 MHz, DMSO-d$_6$) δ 12.13 (s, 1H, OH), 11.28 (s, 1H, NH), 7.88 (m, 1H), 7.44 (m, 1H), 7.18–7.32 (m, 3H), 6.98 (dd, 1H), 6.80 (dd, 1H), 6.40 (d, 1H), 2.30 (s, 3H, CH$_3$). MS m/z 379.4 [M−1].

Example 393

4-(2,4-Difluoro-phenyl)-3-[1-[3,5-dimethyl-4-(1-methyl-piperidin-4-yl)-1H-pyrrol-2-yl]-meth-(Z)-ylidene]-1,3-dihydro-indol-2-one

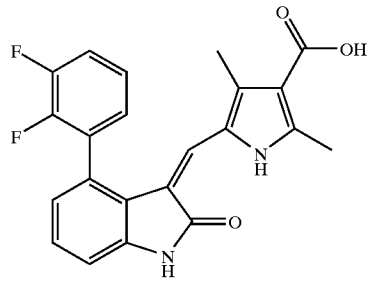

$^1$H NMR (400 MHz, DMSO-d$_6$) δ 13.67 (s, 1H, NH), 12.12 (br s, 1H, COOH), 11.17 (s, 1H, NH), 7.61 (m, 1H), 7.41 (m, 1H), 7.30 (m, 1H), 7.24 (t, 1H), 6.99 (dd, 1H), 6.87 (dd, 1H), 6.70 (s, 1H), 1.82 (s, 3H, CH$_3$). MS m/z 393.2 [M−1].

Example 394

4-(2,4-Difluoro-phenyl)-3-[1-[3,5-dimethyl-4-(1-methyl-piperidin-4-yl)-1H-pyrrol-2-yl]-meth-(Z)-ylidene]-1,3-dihydro-indol-2-one

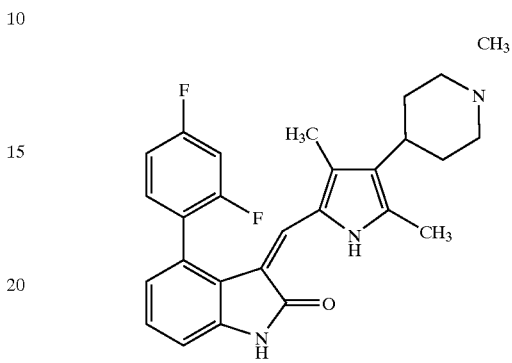

$^1$H NMR (400 MHz, DMSO-d$_6$) δ 13.33 (s, 1H, NH), 10.93 (s, 1H, NH), 7.45 (m, 2H), 7.28 (m, 1H), 7.14 (t, 1H), 6.93 (dd, 1H), 6.77 (dd, 1H), 6.56 (s, 1H), 2.79 (m, 2H), 2.35 (m, 1H), 2.28 (s, 3H, CH$_3$), 2.14 (s, 3H, CH$_3$), 1.86 (m, 2H), 1.77 (m, 2H), 1.64 (s, 3H, CH$_3$), 1.45 (m, 2H). MS m/z 448.1 [M$^+$+1].

Example 395

4-(2,3-Difluoro-phenyl)-3-[1-[3,5-dimethyl-4-(4-methyl-piperazine-1-carbonyl)-1H-pyrrol-2-yl]-meth-(Z)-ylidene]-1,3-dihydro-indol-2-one

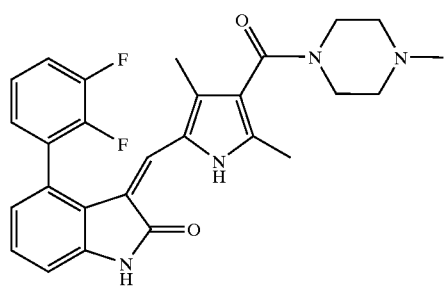

Yellow solid.

$^1$H NMR (400 MHz, DMSO-d$_6$) δ 13.45 (s, 1H, NH), 11.12 (s, 1H, NH), 7.6 (m, 1H), 7.41 (m, 1H), 7.29 (m, 1H), 7.22 (t, 1H), 6.98 (dd, 1H), 6.85 (dd, 1H), 6.62 (d, 1H), 3.32 (m, 4H), 2.23 (s, m, 7H), 2.14 (s, 3H, CH$_3$), 1.59 (s, 3H, CH$_3$). MS m/z 475.4 [M−1].

Example 396

4-(2,3-Difluoro-phenyl)-3-[1-[3,5-dimethyl-4-(4-pyrrolidin-1-yl-piperidine-1-carbonyl)-1H-pyrrol-2-yl]-meth-(Z)-ylidene]-1,3-dihydro-indol-2-one

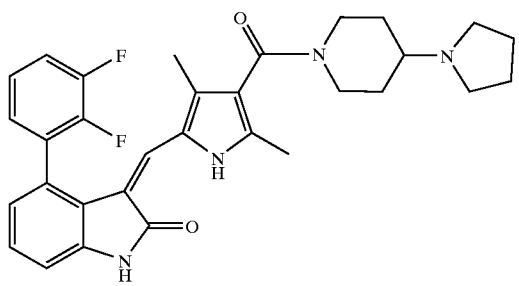

Yellow solid.

$^1$H NMR (400 MHz, DMSO-d$_6$) δ 13.43 (br s, 1H, NH), 11.11 (s, 1h, NH), 7.59 (m, 1H), 7.40 (m, 1h), 7.29 (m, 1H), 6.98 (dd, 1H), 6.85 (dd, 1H), 6.62 (s, 1H), 3.32 (m, 2H), 2.94 (m, 2H), 2.43 (m, 4H), 2.22 (s, 3H, CH$_3$), 2.14 (m, 1H), 1.77 (m, 2H), 1.63 (m, 4H), 1.58 (s, 3H), 1.22 (m, 2H). MS m/z 529.5 [M−1].

Example 397

4-(2,3-Difluoro-phenyl)-3-[1-[3,5-dimethyl-4-((S)-2-pyrrolidin-1-ylmethyl-pyrrolidine-1-carbonyl)-1H-pyrrol-2-yl]-meth-(Z)-ylidene]-1,3-dihydro-indol-2-one

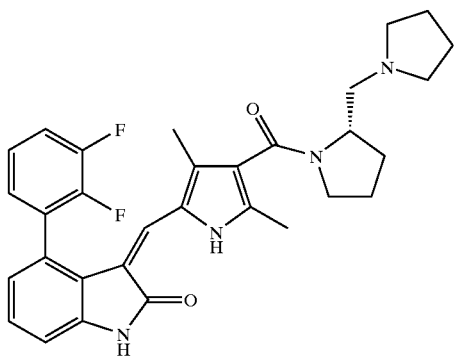

Yellow solid.

$^1$H NMR (400 MHz, DMSO-d$_6$) δ 13.4 (br s, 1H, NH), 11.10 (s, 1H, NH), 7.59 (m, 1H), 7.40 (m, 1H), 7.29 (m, 1H), 7.21 (t, 1H), 6.97 (dd, 1H), 6.85 (dd, 1H), 6.61 (s, 1H), 4.22 (m, 1H), 3.12 (m, 2H, 2.45 (m, 4H), 2.23 (s, 3H, CH$_3$), 2.1 (m, 2H), 1.85 (m, 4H), 1.65 (m, 2H, 1.6 (s, 3H, CH$_3$), 1.45 (m, 2H). MS m/z 529.5 [M−1].

Example 398

4-(2,3-Difluoro-phenyl)-3-[1-[3-((cis)-3,5-dimethyl-piperazine-1-carbonyl)-5-methyl-1H-pyrrol-2-yl]-meth-(Z)-ylidene]-1,3-dihydro-indol-2-one

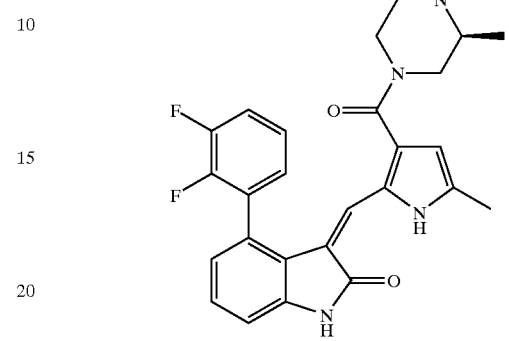

Orange solid.

$^1$H NMR (400 MHz, DMSO-d$_6$) δ 13.59 (s, 1H, NH), 11.16 (s, 1H, NH), 7.44 (m, 1H), 7.14–7.3 (m, 3H), 6.97 (dd, 1H), 6.86 (s, 1H), 6.79 (dd, 1H), 6.06 (d, 1H), 4.15 (m, 1H), 3.47 (m, 1H), 3.32 (m, under water peak), 2.45 (m, under DMSO peak), 2.31 (s, 3H, CH$_3$), 2.05 (m, 1H), 1.03 (s, 3H, CH$_3$), 0.8 (s, 3H, CH$_3$). MS m/z 475.4 [M−1].

Example 399

2-[4-(2,3-Difluoro-phenyl)-2-oxo-1,2-dihydro-indol-(3Z)-ylidenemethyl]-5methyl-1H-pyrrole-3-carboxylic Acid (3-Pyrrolidin-1-yl-propyl)-amide

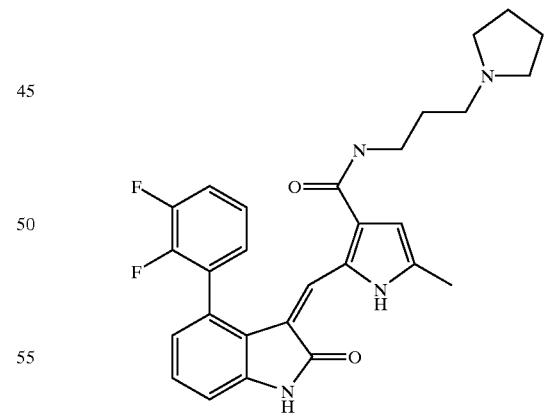

Orange solid.

$^1$H NMR (400 MHz, DMSO-d$_6$) δ 13.8 (s, 1H, NH), 11.2 (s, 1H, NH), 7.9 (m, 2H), 7.28 (m, 1H), 7.26 (m, 1H), 7.22 (t, 1H), 7.14 (m, 1H), 6.97 (dd, 1H), 6.79 (dd, 1H), 6.38 (d, 1H), 3.09 (m, 2H), 2.41 (m, 6H), 2.3 (s, 3H, CH$_3$), 1.68 (m, 4H), 1.58 (m, 2H). MS m/z 489.4 [M−1].

Example 400

2-[4-(3-Fluoro-phenyl)-2-oxo-1,2-dibydro-indol-(3Z)-ylidenemethyl]-5-iodo-4-methyl-1H-pyrrole-3-carboxylic Acid (3-Pyrrolidin-1-yl-propyl)-amide

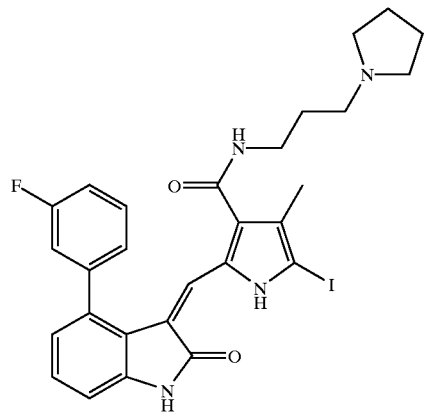

Earthy yellow solid.

$^1$H NMR (400 MHz, DMSO-$d_6$) δ 11.24 (s, 1H, NH), 7.8 (t, 1H), 7.44 (m, 1H), 7.2 (m, 4H), 7.1 (s, 1H), 6.93 (dd, 1H), 6.78 (dd, 1H), 3.02 (m, 2H), 2.40 (m, 6H), 1.96 (s, 3H, CH$_3$), 1.63 (m, 4H), 1.52 (m, 2H). MS m/z 597.3 [M–1].

Example 401

2-[4-(3-Fluoro-phenyl)-2-oxo-1,2-dihydro-indol-(3Z)-ylidenemethyl]-5-methyl-1H-pyrrole-3-carboxylic Acid [(S)-2-Hydroxy-3-(3-methyl-2,5-dioxo-imidazolidin-1-yl)-propyl]-amide

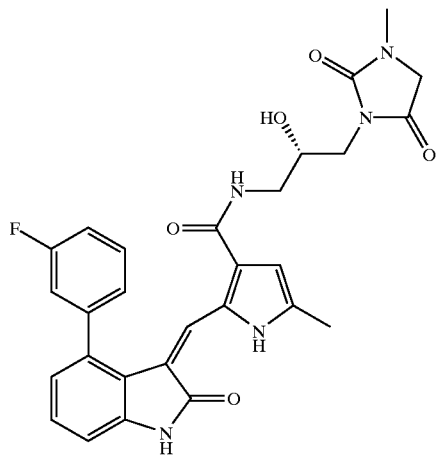

Orange solid.

$^1$H NMR (400 MHz, DMSO-$d_6$) δ 13.84 (s, 1H, NH), 11.13 (s, 1H, NH), 8.0 (s, 1H), 7.82 (t, 1H), 7.42 (m, 1H), 7.15 (m, 4H), 6.91 (d, 1H), 6.76 (d, 1H), 6.42 (d, 1H), 4.98 (d, 1H), 3.96 (s, 2H), 3.76 (m, 2H), 3.25 (m, 1H), 3.15 (m, 1H), 2.95 (m, 1H), 2.86 (s, 3H, CH$_3$), 2.3 (s, 3H, CH$_3$). MS m/z 532.4 [M$^+$+1].

Example 402

2-[4-(3-Fluoro-phenyl)-2-oxo-1,2-dihydro-indol-(3Z)-ylidenemethyl]-5-methyl-1H-pyrrole-3-carboxylic Acid [(R)-2-Hydroxy-3-(3-methyl-2,5-dioxo-imidazolidin-1-yl)-propyl]-amide

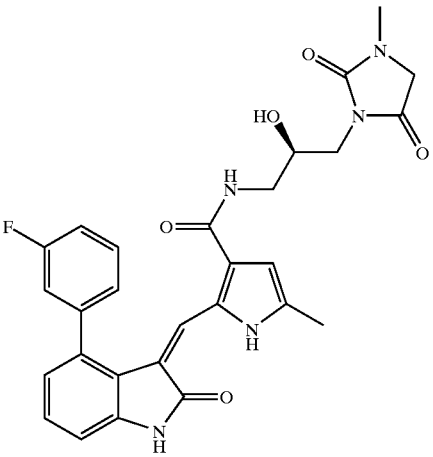

$^1$H NMR (400 MHz, DMSO-$d_6$) δ 13.82 (s, 1H, NH), 11.13 (s, 1H, NH), 8.0 (s, 1H), 7.83 (t, 1H), 7.42 (m, 1H), 7.15 (m, 4H), 6.91 (d, 1H), 6.76 (d, 1H), 6.43 (d, 1H), 4.98 (d, 1H), 3.96 (s, 2H), 3.76 (m, 2H), 3.25 (m, 1H), 3.15 (m, 1H), 2.95 (m, 1H), 2.86 (s, 3H, CH$_3$), 2.30 (s, 3H, CH$_3$).

Example 403

4-(3-Fluoro-phenyl)-3-[1-[5-methyl-3-(3-morpholin-4-yl-azetidine-1-carbonyl)-1H-pyrrol-2-yl]-meth-(Z)-ylidene]-1,3-dihydro-indol-2-one

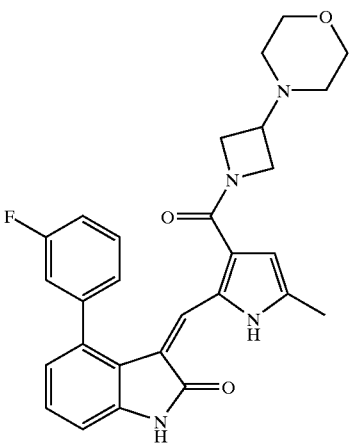

Yellow solid.

$^1$H NMR (400 MHz, DMSO-$d_6$) δ 13.68 (s, 1H, NH), 11.14 (s, 1H, NH), 7.51 (s, 1H), 7.48 (m, 1H), 7.2 (m, 4H), 6.92 (dd, 1H), 6.77 (dd, 1H), 6.2 (d, 1H), 3.92 (m, 1H), 3.78 (m, 2H), 3.67 (m, 1H), 3.57 (m, 4H), 3.0 (m, 1H), 2.29 (s, 3H, CH$_3$), 2.25 (m, 4H).

Example 404

3-[1-{3-[3-((2R,6S)-2,6-Dimethyl-morpholin-4-yl)-azetidine-1-carbonyl]-5-methyl-1H-pyrrol-2-yl}-meth-(Z)-ylidene]4-(3-fluoro-phenyl)-1,3-dihydro-indol-2-one

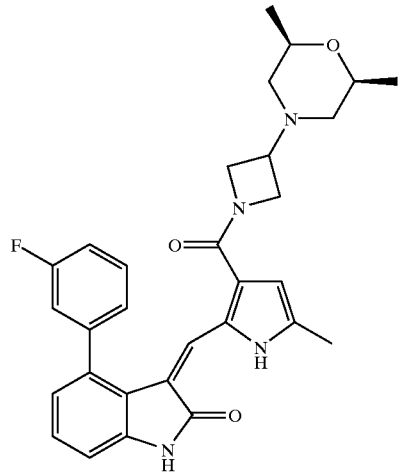

Yellow solid.

$^1$H NMR (400 MHz, DMSO-d$_6$) δ 13.78 (s, 1H, NH), 11.14 (s, 1H, NH), 7.52 (s, 1H), 7.48 (m, 4H), 7.25 (m, 4H), 6.92 (dd, 1H), 6.77 (dd, 1H), 6.2 (d, 1H), 3.8 (m, 1H), 3.78 (m, 2H), 3.67 (m, 1H), 3.55 (m, 2H), 2.96 (m, 1H), 2.74 (m, 1H), 2.60 (m, 1H), 2.3 (s, 3H, CH$_3$), 1.45 (m, 2H), 1.05 (d, 3H, CH$_3$), 0.99 (d, 3H, CH$_3$).

Example 405

4-(3-Fluoro-phenyl)-3-[1-{3-[(S)-2-((S)-3-fluoro-pyrrolidin-1-ylmethyl)-pyrrolidine-1-carbonyl]-5-methyl-1H-pyrrol-2-yl}-meth-(Z)-ylidene]-1,3-dihydro-indol-2-one

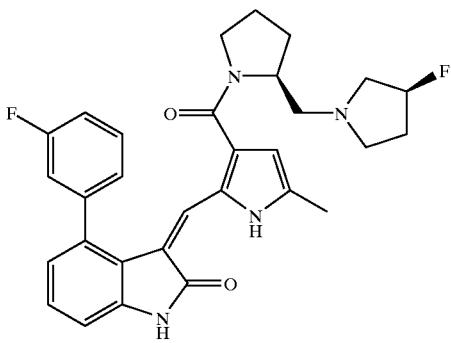

To a solution of 2-[4-(3-fluoro-phenyl)-2-oxo-1,2-dihydro-indol-(3Z)-ylidenemethyl]-5-methyl-1H-pyrrole-3-carboxylic acid (100 mg, 0.28 mmol), EDC (115 mg, 0.3 mmol), HOBt (40 mg, 0.3 mmol) in DMF (4 mL) was added TEA (0.14 mL) and (S)-3-fluoro-1-(S)-1-pyrrolidin-2-ylmethyl-pyrrolidine (100 mg, 0.58 mmol). The mixture was stirred at rt for 20 hours, The reaction was diluted with DCM, washed with water, NaHCO$_3$, dried and concentrated. The residue was purified on a silica gel column to give the titled compound.

MS m/z 517.4 [M$^+$+1].

Example 406

4-(3-Fluoro-phenyl)-3-[1-{3-[(R)-2-((S)-3-fluoro-pyrrolidin-1-ylmethyl)-pyrrolidine-1-carbonyl]-5-methyl-1H-pyrrol-2-yl}-meth-(Z)-ylidene]-1,3-dihydro-indol-2-one

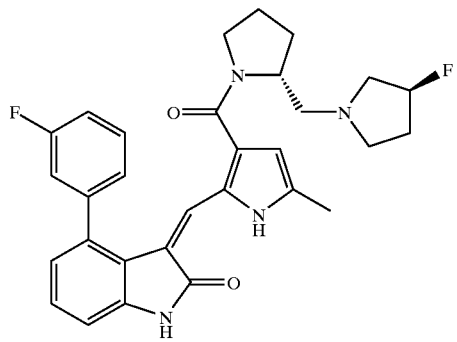

To a solution of 2-[4-(3-fluoro-phenyl)-2-oxo-1,2-dihydro-indol-(3Z)-ylidenemethyl]-5-methyl-1H-pyrrole-3-carboxylic acid (100 mg, 0.28 mmol), EDC (120 mg, 0.63 mmol), HOBt (40 mg, 0.3 mmol) in DMF (4 mL) was added TEA (0.15 mL) and (S)-3-fluoro-1-(R)-1-pyrrolidin-2-ylmethyl-pyrrolidine (95 mg, 0.55 mmol). The mixture was stirred at rt for 20 hours. The reaction was diluted with DCM, washed with water, NaHCO$_3$, dried and concentrated. The residue was purified on a silica gel column to give the titled compound.

MS m/z 517.4 [M$^+$+1].

Example 407

3-[1-[3-(4-Cyclopropylamino-piperidine-1-carbonyl)-5-methyl-1H-pyrrol-2-yl]-meth-(Z)-ylidene]-4-(3-fluoro-phenyl)-1,3-dihydro-indol-2-one

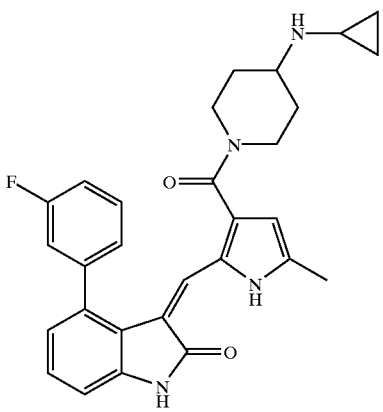

To a solution of 2-[4-(3-fluoro-phenyl)-2-oxo-1,2-dihydro-indol-(3Z)-ylidenemethyl]-5-methyl-1H-pyrrole-3-carboxylic acid (105 mg, 0.29 mmol), EDC (120 mg, 0.58 mmol), HOBt (40 mg, 0.3 mmol) in DMF (4 mL) was added TEA 90.15 mL) and cyclopropyl-piperidin-4-yl-amine. The mixture was stirred at rt for 20 hours. The reaction was diluted with DCM, washed with water, NaHCO$_3$, dried and concentrated. The residue was purified on a silica gel column to give the titled compound.

¹H NMR (400 MHz, CDCl₃) δ 13.32 (s, 1H, NH), 8.35 (s, 1H), 7.46 (m, 1H), 7.23 (m, 1H), 7.12 (m, 3H), 7.02 (br s, 1H, NH), 6.83 (dd, 1H), 6.79 (dd, 1H), 5.99 (d, 1H), 4.44 (m, 1H), 3.66 (m, 1H), 2.81 (m, 1H), 2.34 (s, 3H, CH₃), 2.15 (m, 1H), 2.0 (m, 1H), 1.80 (m, 1H), 1.69 (m, 2H), 1.28 (m, 1H), 1.1 (m, 1H), 0.47 (m, 2H), 0.34 (m, 2H). MS m/z 485.2 [M⁺+1].

Example 408

3-[1-[3-((2R,4R)-2-Cyclopropylaminomethyl-4-hydroxy-pyrrolidine-1-carbonyl)-5-methyl-1H-pyrrol-2-yl]-meth-(Z)-ylidene]-4-(3-fluoro-phenyl)-1,3-dihydro-indol-2-one

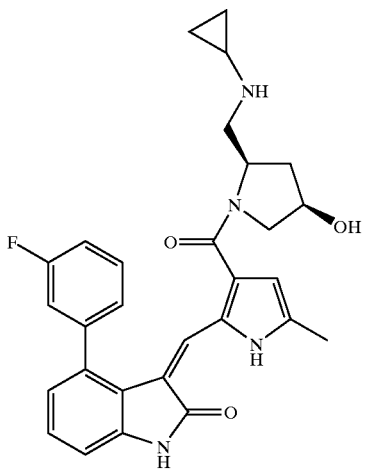

To a solution of cis-4-hydroxy-D-proline (6.5 g, 0.05 mol) in 10% TEA/MeOH (80 mL) was added di-tert-butyl dicarbonate (21.6 g, 2 eq.). After refluxing for 45 mins, the reaction was allowed to cool to rt and the solvent was removed under reduced pressure. The residue was adjusted to pH 3–4 and extracted with ethyl acetate. The combined organic layer was dried and concentrated to give 8 g of (2R,4R)-4-hydroxy-pyrrolidine-1,2-dicarboxylic acid 1-tert-butyl ester as a white semi-solid.

¹H NMR (400 MHz, DMSO-d₆) δ 4.13 (m, 1H), 4.01 (m, 1H), 3.41 (m, 1H), 3.12 (m, 1H), 2.25 (m, 1H), 1.76 (m, 1H), 1.31 and 1.37 (2s, 9H, Boc).

Cyclopropylamine was coupled with (2R,4R)-4-hydroxy-pyrrolidine-1,2-dicarboxylic acid 1-tert-butyl ester (8 g), EDC, HOBt, TEA in DMF to give 5 g of (2R,4R)-2-cyclopropylcarbamoyl-4-hydroxy-pyrrolidine-1-carboxylic acid tert-butyl ester as a white semi-solid.

¹H NMR (400 MHz, DMSO-d₆) δ 4.06 (m, 1H), 3.97 (m, 1H), 3.42 (m, 1H), 3.15 (m, 1H), 2.62 (m, 1H), 2.23 (m, 1H), 1.64 (m, 1H), 1.33 (Boc), 0.61 (m, 2H), 0.42 (m, 2H).

(2R,4R)-2-Cyclopropylcarbamoyl-4-hydroxy-pyrrolidine-1-carboxylic acid tert-butyl ester (5 g) was deprotected using 50 mL of 30% TFA in DCM at rt for 2 hours to give 3 g of (2R,4R)-4-hydroxy-pyrrolidine-2-carboxylic acid cyclopropylamide as a light yellow oil.

¹H NMR (400 MHz, DMSO-d₆) δ 4.32 (m, 1H), 4.1 (m, 1H), 3.2 (m, 2H), 2.67 (m, 1H), 2.35 (m, 1H), 1.85 (m, 1H), 0.67 (m, 2H), 0.45 (m, 2H).

(2R,4R)-4-Hydroxy-pyrrolidine-2-carboxylic acid cyclopropylamide (3 g) was reduced using LAH (2 g) in THF (150 mL) to give 1 g of (3R,5R)-5-cyclopropylaminomethyl-pyrrolidin-3-ol.

To a mixture of 2-[4-(3-fluoro-phenyl)-2-oxo-1,2-dihydro-indol-(3Z)-ylidenemethyl]-5-methyl-1H-pyrrole-3-carboxylic acid (100 mg, 0.28 mmol), EDC (64 mg, 1.2 eq.), HOBt (45 mg, 1.2 eq.) in DMF (3 mL) was added TEA (0.098 mL) and (3R,5R)-5-cyclopropylaminomethyl-pyrrolidin-3-ol. The mixture was stirred at rt for overnight. After the usual work up, 65 mg of the titled compound was obtained as a yellow solid.

¹H NMR (400 MHz, DMSO-d₆) δ 10.95 (s, 1H, NH), 7.46 (m, 1H), 7.19 (m, 5H), 6.94 (d, 1H), 6.76 (d, 1H), 6.16 (s, 1H), 4.1 (m, 2H), 4.0 (m, 1H), 3.48 (m, 1H), 3.16 (m, 1H), 2.80 (m, 1H), 2.55 (d, 1H), 2.33 (s, 3H, CH₃), 2.15 (m, 2H), 1.72 (m, 1H), 0.34 (m, 2H), 0.2 (m, 2H). MS m/z 501.4 [M⁺+1].

Example 409

2-[4-(2,3-Difluoro-phenyl)-2-oxo-1,2-dihydro-indol-(3Z)-ylidenemethyl]-5-methyl-1H-pyrrole-3-carboxylic Acid (3-Cyclopropylamino-2-hydroxy-propyl)-amide

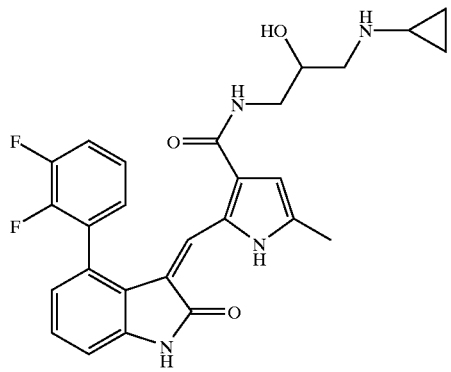

Red solid. MS m/z 491.3 [M−1].

Example 410

2-[4-(2,3-Difluoro-phenyl)-2-oxo-1,2-dihydro-indol-(3Z)-ylidenemethyl]-5-methyl-1H-pyrrole-3-carboxylic Acid (2-Hydroxy-3-pyrrolidin-1-yl-propyl)-amide

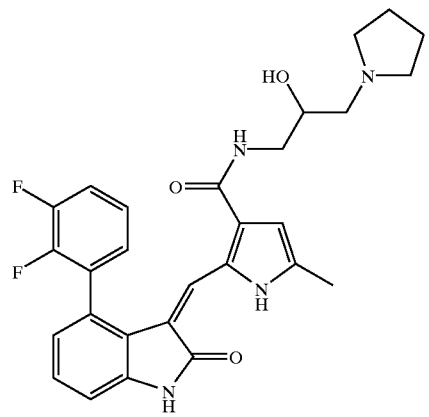

Red solid.

¹H NMR (400 MHz, DMSO-d₆) δ 13.82 (s, 1H, NH), 11.20 (s, 1H, NH), 8.0 (dd, 2H), 7.69 (m, 1H), 7.65 (m, 1H), 7.44 (m, 1H), 7.27 (m, 1H), 7.23 (t, 1H), 7.14 (m, 1H), 6.98 (dd, 1H), 6.80 (dd, 1H), 6.47 (m, 1H), 3.77 (m, 1h), 3.20 (m, 1H), 3.05 (m, 1H), 2.31 (s, 3H, CH₃), 1.82 (m, 4H), 1.63 (m, 2H), 1.1 (m, 1H), 0.8 (m, 4H). MS m/z 505.4 [M−1].

Example 411

4-(2,3-Difluoro-phenyl)-3-[1-{3-[(S)-2-((R)-3-hydroxy-pyrrolidin-1-ylmethyl)-pyrrolidine-1-carbonyl]-5-methyl-1H-pyrrol-2-yl}-meth-(Z)-ylidene]-1,3-dihydro-indol-2-one

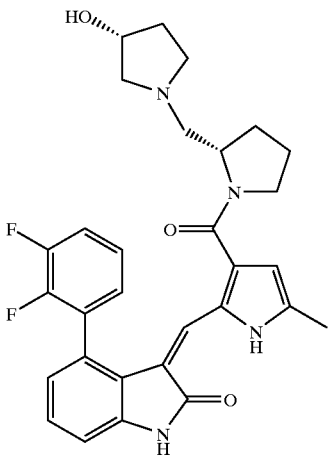

Yellow solid.

MS m/z 531.5 [M−1].

Example 412

4-(2,3-Difluoro-phenyl)-3-[1-{3-[(S)-2-((S)-3-fluoro-pyrrolidin-1-ylmethyl)-pyrrolidine-1-carbonyl]-5-methyl-1H-pyrrol-2-yl}-meth-(Z)-ylidene]-1,3-dihydro-indol-2-one

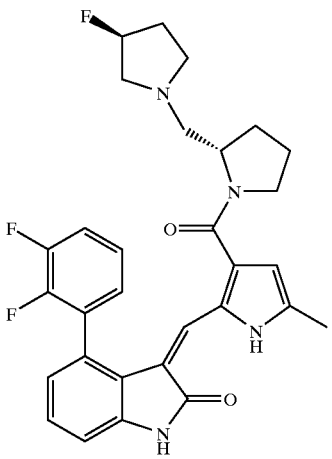

Yellow solid.

MS m/z 533.5 [M−1].

Example 413

3-[1-[3-((S)-3-Cyclopropylaminomethyl-piperidine-1-carbonyl)-5-methyl-1H-pyrrol-2-yl]-meth-(Z)-ylidene]-4-(3-fluoro-phenyl)-1,3-dihydro-indol-2-one

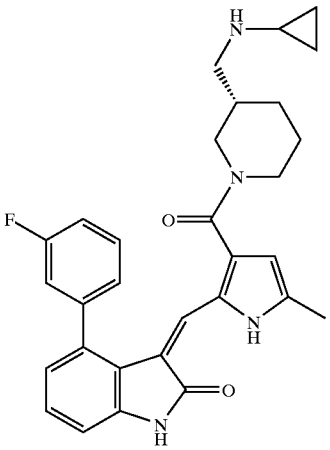

Yellow solid.

MS m/z 497.6 [M−1].

Example 414

4-(4-Chloro-phenyl)-3-[1-[3-((S)-3-cyclopropylaminomethyl-piperidine-1-carbonyl)-5-methyl-1H-pyrrol-2-yl]-meth-(Z)-ylidene]-1,3-dihydro-indol-2-one

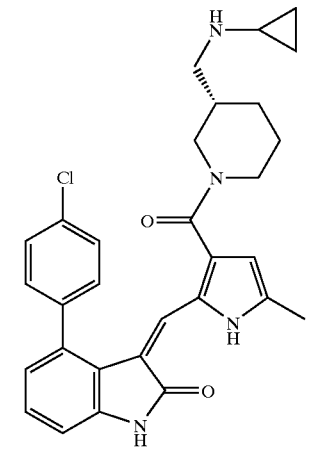

Yellow solid.

MS m/z 513.6 [M−1].

Example 415

2-[4-(3-Fluoro-phenyl)-2-oxo-1,2-dihydro-indol-(3Z)-ylidenemethyl]-5-methyl-1H-pyrrole-3-carboxylic Acid (2-Hydroxy-3-pyrrolidin-1-yl-propyl)-methyl-amide

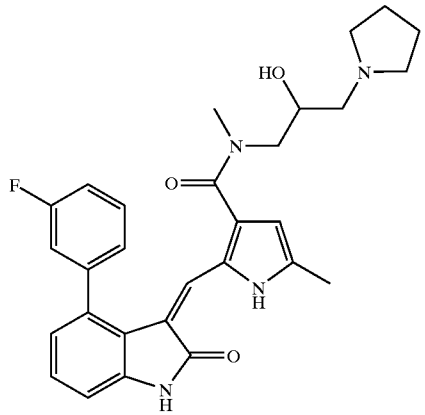

Yellow solid.

$^1$H NMR (400 MHz, DMSO-d$_6$) δ 13.56 (s, 1H, NH), 11.01 (br s, 1H, NH), 7.46 (m, 1H), 7.24 (m, 1H), 7.17 (m, 3H), 6.91 (m, 1H), 6.85 (s, 1H), 6.74 (d, 1H), 6.09 (s, 1H), 4.70 (m, 1H), 3.55 (m, 1H), 2.93 (m, 1H), 2.83 (s, 3H, CH$_3$), 2.25 (m, 4H), 2.12 (m, 4H), 1.70 (m, 2H), 1.51 (m, 3H). MS m/z 503.4 [M$^+$+1].

Example 416

2-[4-(3-Fluoro-phenyl)-2-oxo-1,2-dihydro-indol-(3Z)-ylidenemethyl]-5-methyl-1H-pyrrole-3-carboxylic Acid (3-Cyclopropylamino-2-hydroxy-propyl)-amide

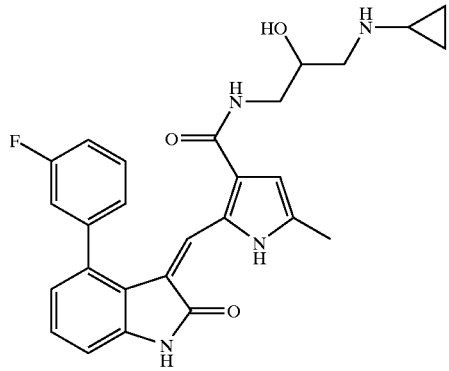

Yellow solid.

$^1$H NMR (400 MHz, DMSO-d$_6$) δ 13.85 (s, 1H, NH), 11.14 (s, 1H, NH), 8.0 (s, 1H), 7.83 (t, 1H), 7.44 (m, 1H), 7.18 (m, 4H), 6.93 (dd, 1H), 6.78 (dd, 1H), 6.42 (d, 1H), 3.61 (m, 1H), 3.14 (m, 2H), 3.02 (m, 2H), 2.5–2.62 (m, 3H), 2.31 (s, 3H, CH$_3$), 2.13 (m, 2H). MS m/z 475.2 [M$^+$+1].

Example 417

4-(3-Fluoro-phenyl)-3-[1-[4-(2-pyrrolidin-1-yl-ethyl)-4,5,6,7-tetrahydro-1H-indol-2-yl]-meth-(Z)-ylidene]-1,3-dihydro-indol-2-one

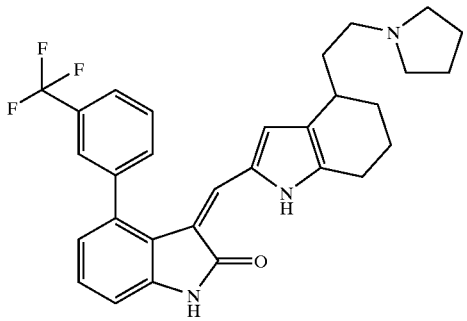

4-(2-Pyrrolidin-1-yl-ethyl)-4,5,6,7-tetrahydro-1H-indole-2-carbaldehyde (0.2 was condensed with 4-(3-fluoro-phenyl)-1,3-dihydro-indol-2-one (0.2 mmol) and piperidine (2 drops) in ethanol at rt for overnight. The solvent was removed and the residue was purified on a silica gel column to give 25 mg of the titled compound as a yellow solid.

$^1$H NMR (400 MHz, CD$_3$OD) δ 7.52 (m, 1H), 7.14–7.24 (m, 4H), 6.94 (d, 1H), 6.8 (d, 1H), 6.74 (s, 1H), 6.07 (s, 1H), 3.22 (m, 4H), 3.12 (m, 2H), 2.70 (m, 3H), 2.01 (m, 6H), 1.95 (m, 1H), 1.75 (m, 2H), 1.42 (m, 1H). MS m/z 456 [M$^+$+1].

Biological Evaluation

It will be appreciated that, in any given series of compounds, a range of biological activities will be observed. In its presently preferred aspects, this invention relates to novel 4-aryl substituted indolinones capable of modulating, regulating and/or inhibiting protein kinase activity. The following assays may be employed to select those compounds demonstrating the optimal degree of the desired activity.

I. Assay Procedures

The following in vitro assays may be used to determine the level of activity and effect of the different compounds of the present invention on one or more of the PKs. Similar assays can be designed along the same lines for any PK using techniques well known in the art.

Several of the assays described herein are performed in an ELISA (Enzyme-Linked Immunosorbent Sandwich Assay) format (Voller, et al., 1980, "Enzyme-Linked Immunosorbent Assay," Manual of Clinical Immunology, 2d ed., Rose and Friedman, Am. Soc. Of Microbiology, Washington, D.C., pp. 359–371). The general procedure is as follows: a compound is introduced to cells expressing the test kinase, either naturally or recombinantly, for a selected period of time after which, if the test kinase is a receptor, a ligand known to activate the receptor is added. The cells are lysed and the lysate is transferred to the wells of an ELISA plate previously coated with a specific antibody recognizing the substrate of the enzymatic phosphorylation reaction. Non-substrate components of the cell lysate are washed away and the amount of phosphorylation on the substrate is detected with an antibody specifically recognizing phosphotyrosine compared with control cells that were not contacted with a test compound.

The presently preferred protocols for conducting the ELISA experiments for specific PKs is provided below.

However, adaptation of these protocols for determining the activity of compounds against other RTKs, as well as for CTKs and STKs, is well within the scope of knowledge of those skilled in the art. Other assays described herein measure the amount of DNA made in response to activation of a test kinase, which is a general measure of a proliferative response. The general procedure for this assay is as follows: a compound is introduced to cells expressing the test kinase, either naturally or recombinantly, for a selected period of time after which, if the test kinase is a receptor, a ligand known to activate the receptor is added. After incubation at least overnight, a DNA labeling reagent such as 5-bromodeoxyuridine (BrdU) or $H^3$-thymidine is added. The amount of labeled DNA is detected with either an anti-BrdU antibody or by measuring radioactivity and is compared to control cells not contacted with a test compound.

GST-FLK-1 BIOASSAY

This assay analyzes the tyrosine kinase activity of GST-Flk1 on poly(glu-tyr) peptides.

Materials and Reagents:
1. Corning 96-well ELISA plates (Corning Catalog No. 25805-96).
2. poly(glu-tyr) 4:1, lyophilizate (Sigma Catalog No. P0275), 1 mg/ml in sterile PBS.
3. PBS Buffer: for 1 L, mix 0.2 g $KH_2PO_4$, 1.15 g $Na_2HPO_4$, 0.2 g KCl and 8 g NaCl in approx. 900 ml $dH_2O$. When all reagents have dissolved, adjust the pH to 7.2 with HCl. Bring total volume to 1 L with $dH_2O$.
4. PBST Buffer: to 1 L of PBS Buffer, add 1.0 ml Tween-20.
5. TBB—Blocking Buffer: for 1 L, mix 1.21 g TRIS, 8.77 g NaCl, 1 ml TWEEN-20 in approximately 900 ml $dH_2O$. Adjust pH to 7.2 with HCl. Add 10 g BSA, stir to dissolve. Bring total volume to 1 L with $dH_2O$. Filter to remove particulate matter.
6. 1% BSA in PBS: add 10 g BSA to approx. 990 ml PBS buffer, stir to dissolve. Adjust total volume to 1 L with PBS buffer, filter to remove particulate matter.
7. 50 mM Hepes pH 7.5.
8. GST-Flk1cd purified from sf9 recombinant baculovirus transfomnation (SUGEN, Inc.).
9. 4% DMSO in $dH_2O$.
10. 10 mM ATP in $dH_2O$.
11. 40 mM $MnCl_2$
12. Kinase Dilution Buffer (KDB): mix 10 ml Hepes (pH 7.5), 1 ml 5M NaCl, 40 µL 100 mM sodium orthovanadate and 0.4 ml of 5% BSA in $dH_2O$ with 88.56 ml $dH_2O$.
13. NUNC 96-well V bottom polypropylene plates, Applied Scientific Catalog #AS-72092
14. EDTA: mix 14.12 g ethylenediaminetetraacetic acid (EDTA) with approx. 70 ml $dH_2O$. Add 10 N NaOH until EDTA dissolves. Adjust pH to 8.0. Adjust total volume to 100 ml with $dH_2O$.
15. 1° and 2° Antibody Dilution Buffer: mix 10 ml of 5% BSA in PBS buffer with 89.5 ml TBST.
16. Anti-phosphotyrosine rabbit polyclonal antisera (SUGEN, Inc.)
17. Goat anti-rabbit HRP conjugate.
18. ABST solution: To approx. 900 ml $dH_2O$ add 19.21 g citric acid and 35.49 g $Na_2HPO_4$. Adjust pH to 4.0 with phosphoric acid. Add 2,2'-Azinobis(3-ethyl-benzthiazoline-6-sulfonic acid (ABTS, Sigma, Cat. No. A-1888, hold for approx. ½ hour, filter.
19. 30% Hydrogen Peroxide.
20. $ABST/H_2O_2$: add 3 µl of $H_2O_2$ to 15 ml of ABST solution.
21. 0.2 M HCl.

Procedure:
1. Coat Corning 96-well ELISA plates with 2 µg of polyEY in 100 µl PBS/well, hold at room temperature for 2 hours or at 40° C. overnight. Cover plates to prevent evaporation.
2. Remove unbound liquid from wells by inverting plate. Wash once with TBST. Pat the plate on a paper towel to remove excess liquid.
3. Add 100 µl of 1% BSA in PBS to each well. Incubate, with shaking, for 1 hr. at room temperature.
4. Repeat step 2.
5. Soak wells with 50 mM HEPES (pH7.5, 150 µl/well).
6. Dilute test compound with $dH_2O$/4% DMSO to 4 times the desired final assay concentration in 96-well polypropylene plates.
7. Add 25 µl diluted test compound to each well of ELISA plate. In control wells, place 25 µl of $dH_2O$/4% DMSO.
8. Dilute GST-Flk1 0.005 µg (5 ng)/well in KDB.
9. Add 50 µl of diluted enzyme to each well.
10. Add 25 µl 0.5 M EDTA to negative control wells.
11. Add 25 µl of 40 mM $MnCl_2$ with 4×ATP (2 µM) to all wells (100 µl final volume, 0.5 µM ATP final concentration in each well).
12. Incubate, with shaking, for 15 minutes at room temperature.
13. Stop reaction by adding 25 µl of 500 mM EDTA to each well.
14. Wash 3× with TBST and pat plate on paper towel to remove excess liquid.
15. Add 100 µl per well anti-phosphotyrosine antisera, 1:10,000 dilution in antibody dilution buffer. Incubate, with shaking, for 90 min. at room temperature.
16. Wash as in step 14.
17. Add 100 µl/well of goat anti-rabbit HRP conjugate (1:6,000 in antibody dilution buffer). Incubate, with shaking, for 90 minutes are room temperature.
18. Wash as in Step 14.
19. Add 100 µl room temperature $ABST/H_2O_2$ solution to each well.
20. Incubate, with shaking for 15 to 30 minutes at room temperature.
21. If necessary, stop reaction by adding 100 µl of 0.2 M HCl to each well.
22. Read results on Dynatech MR7000 ELISA reader with test filter at 410 nM and reference filter at 630 nM.

PYK2 BIOASSAY

This assay is used to measure the in vitro kinase activity of HA epitope-tagged full length pyk2 (FL.pyk2-HA) in an ELISA assay.

Materials and Reagents:
1. Corning 96-well ELISA plates.
2. 12CA5 monoclonal anti-HA antibody (SUGEN, Inc.)
3. PBS (Dulbecco's Phosphate-Buffered Saline (Gibco Catalog #450-1300EB)
4. TBST Buffer: for 1 L, mix 8.766 g NaCl, 6.057 g TRIS and 1 ml of 0.1% Triton X-100 in approx. 900 ml $dH_2O$. Adjust pH to 7.2, bring volume to 1 L.

5. Blocking Buffer: for 1 L, mix 100 g 10% BSA, 12.1 g 100 mM TRIS, 58.44 g 1M NaCl and 10 mL of 1% TWEEN-20.
6. FL.pyk2-HA from sf cell lysates (SUGEN, Inc.).
7. 4% DMSO in MilliQue $H_2O$.
8. 10 mM ATP in $dH_2O$.
9. 1M $MnCl_2$.
10. 1M $MgCl_2$.
11. 1M Dithiothreitol (DTT).
12. 10×Kinase buffer phosphorylation: mix 5.0 ml 1M Hepes (pH 7.5), 0.2 ml 1M $MnCl_2$, 1.0 ml 1 M $MgCl_2$, 1.0 ml 10% Triton X-100 in 2.8 ml $dH_2O$. Just prior to use, add 0.1 ml 1M DTT.
13. NUNC 96-well V bottom polypropylene plates.
14. 500 mM EDTA in $dH_2O$.
15. Antibody dilution buffer: for 100 mL, 1 mL 5% BSA/PBS and 1 mL 10% Tween-20 in 88 mL TBS.
16. HRP-conjugated anti-Ptyr (PY99, Santa Cruz Biotech Cat. No. SC-7020).
17. ABTS, Moss, Cat. No. ABST-2000.
18. 10% SDS.

Procedure:
1. Coat Corning 96 well ELISA plates with 0.5 μg per well 12CA5 anti-HA antibody in 100 μl PBS. Store overnight at 4° C.
2. Remove unbound HA antibody from wells by inverting plate. Wash plate with $dH_2O$. Pat the plate on a paper towel to remove excess liquid.
3. Add 150 μl Blocking Buffer to each well. Incubate, with shaking, for 30 min at room temperature.
4. Wash plate 4× with TBS-T.
5. Dilute lysate in PBS (1.5 μg lysate/100 μl PBS).
6. Add 100 μl of diluted lysate to each well. Shake at room temperature for 1 hr.
7. Wash as in step 4.
8. Add 50 μl of 2×kinase Buffer to ELISA plate containing captured pyk2-HA.
9. Add 25 μL of 400 μM test compound in 4% DMSO to each well. For control wells use 4% DMSO alone.
10. Add 25 μL of 0.5 M EDTA to negative control wells.
11. Add 25 μl of 20 μM ATP to all wells. Incubate, with shaking, for 10 minutes.
12. Stop reaction by adding 25 μl 500 mM EDTA (pH 8.0) to all wells.
13. Wash as in step 4.
14. Add 100 μL HRP conjugated anti-Ptyr diluted 1:6000 in Antibody Dilution Buffer to each well. Incubate, with shaking, for 1 hr. at room temperature.
15. Wash plate 3× with TBST and 1× with PBS.
16. Add 100 μL of ABST solution to each well.
17. If necessary, stop the development reaction by adding 20 μL 10% SDS to each well.
18. Read plate on ELISA reader with test filter at 410 nM and reference filter at 630 nM.

FGFR1 BIOASSAY

This assay is used to measure the in vitro kinase activity of FGF1-R in an ELISA assay.

Materials and Reagents:
1. Costar 96-well ELISA plates (Corning Catalog #3369).
2. Poly(Glu-Tyr) (Sigma Catalog #P0275).
3. PBS (Gibco Catalog #450-1300EB)
4. 50 mM Hepes Buffer Solution.
5. Blocking Buffer (5% BSA/PBS).
6. Purified GST-FGFR1 (SUGEN, Inc.)
7. Kinase Dilution Buffer. Mix 500 μl 1M Hepes (GIBCO), 20 μl 5% BSA/PBS, 10 μl 100 mM sodium orthovanadate and 50 μl 5M NaCl.
8. 10 mM ATP
9. ATP/$MnCl_2$ phosphorylation mix: mix 20 μL ATP, 400 μL 1M $MnCl_2$ and 9.56 ml $dH_2O$.
10. NUNC 96-well V bottom polypropylene plates (Applied Scientific Catalog #AS-72092).
11. 0.5M EDTA.
12. 0.05% TBST Add 500 μL TWEEN to 1 liter TBS.
13. Rabbit polyclonal anti-phosphotyrosine serum (SUGEN, Inc.).
14. Goat anti-rabbit IgG peroxidase conjugate (Biosource, Catalog #ALI0404).
15. ABTS Solution.
16. ABTSJ$H_2O_2$ solution.

Procedure:
1. Coat Costar 96 well ELISA plates with 1 μg per well Poly(Glu-Tyr) in 100 μl PBS. Store overnight at 4° C.
2. Wash coated plates once with PBS.
3. Add 150 μL of 5%BSA/PBS Blocking Buffer to each well. Incubate, with shaking, for 1 hr at room temperature.
4. Wash plate 2× with PBS, then once with 50 mM Hepes. Pat plates on a paper towel to remove excess liquid and bubbles.
5. Add 25 μL of 0.4 mM test compound in 4% DMSO or 4% DMSO alone (controls) to plate.
6. Dilute purified GST-FGFR1 in Kinase Dilution Buffer (5 ng kinase/50 μl KDB/well).
7. Add 50 μL of diluted kinase to each well.
8. Start kinase reaction by adding 25 μl/well of freshly prepared ATP/Mn++ (0.4 ml 1M $MnCl_2$, 40 μL 10 mM ATP, 9.56 ml $dH_2O$), freshly prepared).
9. Stop reaction with 25 μL of 0.5M EDTA.
10. Wash plate 4× with fresh TBST.
11. Make up Antibody Dilution Buffer: For 50 ml, mix 5 ml of 5% BSA, 250 μl of 5% milk and 50 μl of 100 mM sodium vanadate, bring to final volume with 0.05% TBST.
12. Add 100 μl per well of anti-phosphotyrosine (1:10000 dilution in ADB). Incubate, with shaking for 1 hr. at room temperature.
13. Wash as in step 10.
14. Add 100 μl per well of Biosource Goat anti-rabbit IgG peroxidase conjugate (1:6000 dilution in ADB). Incubate, with shaking for 1 hr at room temperature.
15. Wash as in step 10 and then with PBS to remove bubbles and excess TWEEN.
16. Add 100 μl of ABTS/$H_2O_2$ solution to each well.
17. Incubate, with shaking, for 10 to 20 minutes. Remove any bubbles.
18. Read assay on Dynatech MR7000 ELISA reader: test filter at 410 nM, reference filter at 630 nM.

PDGFR BIOASSAY

This assay is used to the in vitro kinase activity of PDGFR in an ELISA assay.

Materials and Reagents:
1. Corning 96-well ELISA plates
2. 28D4C10 monoclonal anti-PDGFR antibody (SUGEN, Inc.).
3. PBS.
4. TBST Buffer.
5. Blocking Buffer (same as for EGFR bioassay).
6. PDGFR-β expressing NIH 3T3 cell lysate (SUGEN, Inc.).
7. TBS Buffer.
8. TBS+10% DMSO.
9. ATP.
10. $MnCl_2$
11. Kinase buffer phosphorylation mix: for 10 ml, mix 250 µl 1M TRIS, 200 µl 5M NaCl, 100 µl 1M $MnCl_2$ and 5011 100 mM Triton X-100 in enough $dH_2O$ to make 10 ml.
12. NUNC 96-well V bottom polypropylene plates.
13. EDTA.
14. Rabbit polyclonal anti-phosphotyrosine serum (SUGEN, Inc.).
15. Goat anti-rabbit IgG peroxidase conjugate (Biosource Cat. No. ALI0404).
16. ABTS.
17. Hydrogen peroxide, 30% solution.
18. $ABTS/H_2O_2$.
19. 0.2 M HCl.

Procedure:
1. Coat Corning 96 well ELISA plates with 0.5 g 28D4C 10 in 100 µl PBS per well, hold overnight at 4° C.
2. Remove unbound 28D4C10 from wells by inverting plate to remove liquid. Wash 1× with $dH_2O$. Pat the plate on a paper towel to remove excess liquid.
3. Add 150 µl of Blocking Buffer to each well. Incubate for 30 min. at room temperature with shaking.
4. Wash plate 3× with deionized water, then once with TBST. Pat plate on a paper towel to remove excess liquid and bubbles.
5. Dilute lysate in HNTG (10 µg lysate/100 µl HNTG).
6. Add 100 µl of diluted lysate to each well. Shake at room temperature for 60 min.
7. Wash plates as described in Step 4.
8. Add 80 µl working kinase buffer mix to ELISA plate containing captured PDGFR.
9. Dilute test compound 1:10 in TBS in 96-well polypropylene plates.
10. Add 10 µl diluted test compound to -ELISA plate. To control wells, add 10 µl TBS+10% DMSO. Incubate with shaking for 30 minutes at room temperature.
11. Add 10 µl ATP directly to all wells except negative control well (final well volume should be approximately 100 µl with 20 µM ATP in each well.) Incubate 30 minutes with shaking.
12. Stop reaction by adding 10 µl of EDTA solution to each well.
13. Wash 4× with deionized water, twice with TBST.
14. Add 100 µl anti-phosphotyrosine (1:3000 dilution in TBST) per well.

Incubate with shaking for 30–45 min. at room temperature.
15. Wash as in Step 4.
16. Add 100 µl Biosource Goat anti-rabbit IgG peroxidase conjugate (1:2000 dilution in TBST) to each well. Incubate with shaking for 30 min. at room temperature.
17. Wash as in Step 4.
18. Add 100 µl of $ABTS/H_2O_2$ solution to each well.
19. Incubate 10 to 30 minutes with shaking. Remove any bubbles.
20. If necessary stop reaction with the addition of 100 µl 0.2 M HCl per well.
21. Read assay on Dynatech MR7000 ELISA reader with test filter at 410 nM and reference filter at 630 nM.

CELLULAR HER-2 KINASE ASSAY

This assay is used to measure HER-2 kinase activity in whole cells in an ELISA format.

Materials and Reagents:
1. DMEM (GIBCO Catalog #11965-092).
2. Fetal Bovine Serum (FBS, GIBCO Catalog #16000-044), heat inactivated in a water bath for 30 min. at 56° C.
3. Trypsin (GIBCO Catalog #25200-056).
4. L-Glutamine (GIBCO Catalog #25030-081).
5. HEPES (GIBCO Catalog #15630-080).
6. Growth Media: Mix 500 ml DMEM, 55 ml heat inactivated FBS, 10 ml HEPES and 5.5 ml L-Glutamine.
7. Starve Media: Mix 500 ml DMEM, 2.5 ml heat inactivated FBS, 10 ml HEPES and 5.5 ml L-Glutamine.
8. PBS.
9. Flat Bottom 96-well Tissue Culture Micro Titer Plates (Corning Catalog #25860).
10. 15 cm Tissue Culture Dishes (Corning Catalog #08757148).
11. Corning 96-well ELISA Plates.
12. NUNC 96-well V bottom polypropylene plates.
13. Costar Transfer Cartridges for the Transtar 96 (Costar Catalog #7610).
14. SUMO 1: monoclonal anti-EGFR antibody (SUGEN, Inc.).
15. TBST Buffer.
16. Blocking Buffer: 5% Carnation Instant Milk® in PBS.
17. EGF Ligand: EGF-201, Shinko American, Japan. Suspend powder in 100 µL of 10 mM HCl. Add 100 µL 10 mM NaOH. Add 800 µL PBS and transfer to an Eppendorf tube, store at −20° C. until ready to use.
18. HNTG Lysis Buffer: For Stock 5×HNTG, mix 23.83 g Hepes, 43.83 g NaCl, 500 ml glycerol and 100 ml Triton X-100 and enough $dH_2O$ to make 1 L of total solution. For 1×HNTG*, mix 2 ml 5×HNTG, 100 µL 0.1M $Na_3VO_4$, 250 µL 0.2M $Na_4P_2O_7$ and 100 µL EDTA.
19. EDTA.
20. $Na_3VO_4$: To make stock solution, mix 1.84 g $Na_3VO_4$ with 90 ml $dH_2O$. Adjust pH to 10. Boil in microwave for one minute (solution becomes clear). Cool to room temperature. Adjust pH to 10. Repeat heating/cooling cycle until pH remains at 10.
21. 200 mM $Na_4P_2O_7$.

22. Rabbit polyclonal antiserum specific for phosphotyrosine (anti-Ptyr antibody, SUGEN, Inc.).
23. Affinity purified antiserum, goat anti-rabbit IgG antibody, peroxidase conjugate (Biosource Cat #ALI0404).
24. ABTS Solution.
25. 30% Hydrogen peroxide solution.
26. ABTS/$H_2O_2$.
27. 0.2 M HCl.

Procedure:

1. Coat Corning 96 well ELISA plates with SUMO1 at 1.0 $\mu$g per well in PBS, 100 $\mu$l final volume/well. Store overnight at 4° C.
2. On day of use, remove coating buffer and wash plate 3 times with d$H_2O$ and once with TBST buffer. All washes in this assay should be done in this manner, unless otherwise specified.
3. Add 100 $\mu$L of Blocking Buffer to each well. Incubate plate, with shaking, for 30 min. at room temperature. Just prior to use, wash plate.
4. Use EGFr/HER-2 chimera/3T3-C7 cell line for this assay.
5. Choose dishes having 80–90% confluence. Collect cells by trypsinization and centrifuge at 1000 rpm at room temperature for 5 min.
6. Resuspend cells in starve medium and count with trypan blue.

Viability above 90% is required. Seed cells in starve medium at a density of 2,500 cells per well, 90 $\mu$L per well, in a 96 well microtiter plate. Incubate seeded cells overnight at 37° under 5% $CO_2$.

7. Start the assay two days after seeding.
8. Test compounds are dissolved in 4% DMSO. Samples are then further diluted directly on plates with starve-DMEM. Typically, this dilution will be 1:10 or greater. All wells are then transferred to the cell plate at a further 1:10 dilution (10 $\mu$l sample and media into 90 $\mu$l of starve media). The final DMSO concentration should be 1% or lower. A standard serial dilution may also be used.
9. Incubate under 5% $CO_2$ at 37° C. for 2 hours.
10. Prepare EGF ligand by diluting stock EGF (16.5 $\mu$M) in warm DMEM to 150 nM.
11. Prepare fresh HNTG* sufficient for 100 $\mu$L per well; place on ice.
12. After 2 hour incubation with test compound, add prepared EGF ligand to cells, 50 $\mu$L per well, for a final concentration of 50 nM. Positive control wells receive the same amount of EGF. Negative controls do not receive EGF. Incubate at 37° C. for 10 min.
13. Remove test compound, EGF, and DMEM. Wash cells once with PBS.
14. Transfer HNTG* to cells, 100 $\mu$L per well. Place on ice for 5 minutes. Meanwhile, remove blocking buffer from ELISA plate and wash.
15. Scrape cells from plate with a micropipettor and homogenize cell material by repeatedly aspirating and dispensing the HNTG* lysis buffer. Transfer lysate to a coated, blocked, washed ELISA plate.
16. Incubate, with shaking, at room temperature for 1 hr.
17. Remove lysate, wash. Transfer freshly diluted anti-Ptyr antibody (1:3000 in TBST) to ELISA plate, 100 $\mu$L per well.
18. Incubate, with shaking, at room temperature, for 30 min.
19. Remove anti-Ptyr antibody, wash. Transfer freshly diluted BIOSOURCE antibody to ELISA plate(1:8000 in TBST, 100 $\mu$L per well).
20. Incubate, with shaking, at room temperature for 30 min.
21. Remove BIOSOURCE antibody, wash. Transfer freshly prepared ABTS/$H_2O_2$ solution to ELISA plate, 100 $\mu$L per well.
22. Incubate, with shaking, for 5–10 minutes. Remove any bubbles.
23. Stop reaction by adding 100 $\mu$L of 0.2M HCl per well.
24. Read assay on Dynatech MR7000 ELISA reader with test filter set at 410 nM and reference filter at 630 nM.

CDK2/CYCLIN A ASSAY

This assay is used to measure the in vitro serine/threonine kinase activity of human cdk2/cyclin A in a Scintillation Proximity Assay (SPA).

Materials and Reagents.

1. Wallac 96-well polyethylene terephthalate (flexi) plates (Wallac Catalog #1450-401).
2. Amersham Redivue [$\gamma^{33}$P] ATP (Amersham catalog #AH 9968).
3. Amersham streptavidin coated polyvinyltoluene SPA beads (Amersham catalog #RPNQ0007). The beads should be reconstituted in PBS without magnesium or calcium, at 20 mg/ml.
4. Activated cdk2/cyclin A enzyme complex purified from Sf9 cells (SUGEN, Inc.).
5. Biotinylated peptide substrate (Debtide). Peptide biotin-X-PKTPKKAKKL is dissolved in d$H_2O$ at a concentration of 5 mg/ml.
6. 20% DMSO in d$H_2O$.
7. Kinase buffer: for 10 ml, mix 9.1 ml d$H_2O$, 0.5 ml TRIS(pH 7.4), 0.2 ml 1M $MgCl_2$, 0.2 ml 10% NP40 and 0.02 ml 1M DTT, added fresh just prior to use.
8. 10 mM ATP in d$H_2O$.
9. 1M Tris, pH adjusted to 7.4 with HCl.
10. 1M $MgCl_2$.
11. 1M DTT.
12. PBS (Gibco Catalog #14190-144).
13. 0.5M EDTA.
14. Stop solution: For 10 ml, mix 9.25 ml PBS, 0.05 ml 10 mM ATP, 0.1 ml 0.5 M EDTA, 0.1 ml 10% Triton X-100 and 1.5 ml of 50 mg/ml SPA beads.

Procedure:

1. Prepare solutions of test compounds at 4× the desired final concentration in 5% DMSO. Add 10 $\mu$L to each well. For positive and negative controls, use 10 $\mu$L 20% DMSO alone in wells.
2. Dilute the peptide substrate (deb-tide) 1:250 with d$H_2O$ to give a final concentration of 0.02 mg/ml.
3. Mix 24 $\mu$L 0.1 mM ATP with 24 $\mu$Ci 733P ATP and enough d$H_2O$ to make 600 $\mu$L.
4. Mix diluted peptide and ATP solutions 1:1 (600 $\mu$L+600 $\mu$L per plate). Add 10 $\mu$L of this solution to each well.
5. Dilute 5 $\mu$L of cdk2/cyclin A solution into 2.1 ml 2×kinase buffer (per plate). Add 20 $\mu$L enzyme per well. For negative controls, add 20 $\mu$L 2×kinase buffer without enzyme.

6. Mix briefly on a plate shaker; incubate for 60 minutes.
7. Add 200 µL stop solution per well.
8. Let stand at least 10 min.
9. Spin plate at approx. 2300 rpm for 10–15 min.
10. Count plate on Trilux reader.

MET TRANSPHOSPHORYLATION ASSAY

This assay is used to measure phosphotyrosine levels on a poly(glutamic acid:tyrosine, 4:1) substrate as a means for identifying agonists/antagonists of met transphosphorylation of the substrate.

Materials and Reagents:
1. Corning 96-well ELISA plates, Corning Catalog #25805-96.
2. Poly(glu-tyr), 4:1, Sigma, Cat. No; P 0275.
3. PBS, Gibco Catalog #450-1300EB
4. 50 mM HEPES
5. Blocking Buffer: Dissolve 25 g Bovine Serum Albumin, Sigma Cat. No A-7888, in 500 ml PBS, filter through a 4 sum filter.
6. Purified GST fusion protein containing the Met kinase domain, SUGEN, Inc.
7. TBST Buffer.
8. 10% aqueous (MilliQue $H_2O$) DMSO.
9. 10 mM aqueous ($dH_2O$) Adenosine-5'-triphosphate, Sigma Cat. No. A-5394.
10. 2×Kinase Dilution Buffer: for 100 ml, mix 10 mL 1M HEPES at pH 7.5 with 0.4 mL 5% BSA/PBS, 0.2 mL 0.1 M sodium orthovanadate and 1 mL 5M sodium chloride in 88.4 mL $dH_2O$.
11. 4×ATP Reaction Mixture: for 10 mL, mix 0.4 mL 1 M manganese chloride and 0.02 mL 0.1 M ATP in 9.56 mL $dH_2O$.
12. 4×Negative Controls Mixture: for 10 mL, mix 0.4 mL 1 M manganese chloride in 9.6 mL $dH_2O$.
13. NUNC 96-well V bottom polypropylene plates, Applied Scientific Catalog #S-72092
14. 500 mM EDTA.
15. Antibody Dilution Buffer: for 100 mL, mix 10 mL 5% BSA/PBS, 0.5 mL 5% Carnation® Instant Milk in PBS and 0.1 mL 0.1 M sodium orthovanadate in 88.4 mL TBST.
16. Rabbit polyclonal antophosphotyrosine antibody, SUGEN, Inc.
17. Goat anti-rabbit horseradish peroxidase conjugated antibody, Biosource, Inc.
18. ABTS Solution: for 1 L, mix 19.21 g citric acid, 35.49 g $Na_2HPO_4$ and 500 mg ABTS with sufficient $dH_2O$ to make 1 L.
19. ABTS/$H_2O_2$: mix 15 mL ABST solution with 2µL $H_2O_2$ five minutes before use.
20. 0.2 M HCl Procedure:
1. Coat ELISA plates with 2 µg Poly(Glu-Tyr) in 100 µL PBS, hold overnight at 4° C.
2. Block plate with 150 µL of 5% BSA/PBS for 60 min.
3. Wash plate twice with PBS then once with 50 mM Hepes buffer pH 7.4.
4. Add 50 µl of the diluted kinase to all wells. (Purified kinase is diluted with Kinase Dilution Buffer. Final concentration should be 10 ng/well.)
5. Add 25 µL of the test compound (in 4% DMSO) or DMSO alone (4% in $dH_2O$) for controls to plate.
6. Incubate the kinase/compound mixture for 15 minutes.
7. Add 25 µL of 40 mM $MnCl_2$ to the negative control wells.
8. Add 25 µL ATP/$MnCl_2$ mixture to the all other wells (except the negative controls). Incubate for 5 min.
9. Add 25 µL 500 mM EDTA to stop reaction.
10. Wash plate 3× with TBST.
11. Add 100 µL rabbit polyclonal anti-Ptyr diluted 1:10,000 in Antibody Dilution Buffer to each well. Incubate, with shaking, at room temperature for one hour.
12. Wash plate 3× with TBST.
13. Dilute Biosource HRP conjugated anti-rabbit antibody 1:6,000 in Antibody Dilution buffer. Add 100 µL per well and incubate at room temperature, with shaking, for one hour.
14. Wash plate 1× with PBS.
15. Add 100 µl of ABTS/$H_2O_2$ solution to each well.
16. If necessary, stop the development reaction with the addition of 100 µl of 0.2M HCl per well.
17. Read plate on Dynatech MR7000 ELISA reader with the test filter at 410 nM and the reference filter at 630 nM.

IGF-1 Transphosphorylation Assay

This assay is used to measure the phosphotyrosine level in poly(glutamic acid:tyrosine, 4:1) for the identification of agonists/antagonists of gst-IGF-1 transphosphorylation of a substrate.

Materials and Reagents:
1. Corning 96-well ELISA plates.
2. Poly(Glu-Tyr), 4: 1, Sigma Cat. No. P 0275.
3. PBS, Gibco Catalog #450-1300EB.
4. 50 mM HEPES
5. TBB Blocking Buffer: for 1 L, mix 100 g BSA, 12.1 gTRIS (pH 7.5), 58.44 g sodium chloride and 10 mL 1%TWEEN-20.
6. Purified GST fusion protein containing the IGF-1 kinase domain (SUGEN, Inc.)
7. TBST Buffer: for 1 L, mix 6.057 g Tris, 8.766 g sodium chloride and 0.5 ml TWEEN-20 with enough $dH_2O$ to make 1 liter.
8. 4% DMSO in Milli-Q $H_2O$.
9. 10 mM ATP in $dH_2O$.
10. 2×Kinase Dilution Buffer: for 100 mL, mix 10 mL 1 M HEPES (pH 7.5), 0.4 mL 5% BSA in $dH_2O$, 0.2 mL 0.1 M sodium orthovanadate and 1 mL 5 M sodium chloride with enough $dH_2O$ to make 100 mL.
11. 4×ATP Reaction Mixture: for 10 mL, mix 0.4 mL 1 M $MnCl_2$ and 0.008 mL 0.01 M ATP and 9.56 mL $dH_2O$.
12. 4×Negative Controls Mixture: mix 0.4 mL 1 M $MnCl_2$ in 9.60 mL $dH_2O$.
13. NUNC 96-well V bottom polypropylene plates.
14. 500 mM EDTA in $dH_2O$.
15. Antibody Dilution Buffer: for 100 mL, mix 10 mL 5% BSA in PBS, 0.5 mL 5% Carnation Instant Non-fat Milk in PBS and 0.1 mL 0.1 M sodium orthovanadate in 88.4 mL TBST.
16. Rabbit Polyclonal antiphosphotyrosine antibody, SUGEN, Inc.

17. Goat anti-rabbit HRP conjugated antibody, Biosource.
18. ABTS Solution.
20. ABTS/$H_2O_2$: mix 15 mL ABTS with 2 µL $H_2O_2$ 5 minutes before using.
21. 0.2 M HCl in $dH_2O$.

Procedure:
1. Coat ELISA plate with 2.0 µg/well Poly(Glu, Tyr), 4:1 (Sigma P0275) in 100 µl PBS. Store plate overnight at 4° C.
2. Wash plate once with PBS.
3. Add 100 µl of TBB Blocking Buffer to each well. Incubate plate for 1 hour with shaking at room temperature.
4. Wash plate once with PBS, then twice with 50 mM Hepes buffer pH 7.5.
5. Add 25 µL of test compound in 4% DMSO (obtained by diluting a stock solution of 10 mM test compound in 100% DMSO with $dH_2O$) to plate.
6. Add 10.0 ng of gst-IGF-1 kinase in 50 µl Kinase Dilution Buffer to all wells.
7. Start kinase reaction by adding 25 µl 4×ATP Reaction Mixture to all test wells and positive control wells. Add 25 µl 4×Negative Controls Mixture to all negative control wells. Incubates for 10 minutes, with shaking, at room temperature.
8. Add 25 µl 0.5M EDTA (pH 8.0) to all wells.
9. Wash plate 4× with TBST Buffer.
10. Add rabbit polyclonal anti-phosphotyrosine antisera at a dilution of 1:10,000 in 100 µl Antibody Dilution Buffer to all wells. Incubate, with shaking, at room temperature for 1 hour.
11. Wash plate as in step 9.
12. Add 100 µL Biosource anti-rabbit HRP at a dilution of 1:10,000 in Antibody dilution buffer to all wells. Incubate, with shaking, at room temperature for 1 hour.
13. Wash plate as in step 9, follow with one wash with PBS to remove bubbles and excess Tween-20.
14. Develop by adding 100 µl/well ABTS/$H_2O_2$ to each well
15. After about 5 minutes, read on ELISA reader with test filter at 410 nm and referenced filter at 630 nm.

BrdU INCORPORATION ASSAYS

The following assays use cells engineered to express a selected receptor and then evaluate the effect of a compound of interest on the activity of ligand-induced DNA synthesis by determining BrdU incorporation into the DNA.

The following materials, reagents and procedure are general to each of the following BrdU incorporation assays. Variances in specific assays are noted.

General Materials and Reagents:
1. The appropriate ligand.
2. The appropriate engineered cells.
3. BrdU Labeling Reagent: 10 mM, in PBS, pH7.4 (Roche Molecular Biochemicals, Indianapolis, Ind.).
4. FixDenat: fixation solution (Roche Molecular Biochemicals, Indianapolis, Ind.).
5. Anti-BrdU-POD: mouse monoclonal antibody conjugated with peroxidase (Chemicon, Temecula, Calif.).
6. TMB Substrate Solution: tetramethylbenzidine (TMB, ready to use, Roche Molecular Biochemicals, Indianapolis, Ind.).
7. PBS Washing Solution: 1×PBS, pH 7.4.
8. Albumin, Bovine (BSA), fraction V powder (Sigma Chemical Co., USA).

General Procedure:
1. Cells are seeded at 8000 cells/well in 10% CS, 2 mM Gln in DMEM, in a 96 well plate. Cells are incubated overnight at 37° C. in 5% $CO_2$.
2. After 24 hours, the cells are washed with PBS, and then are serum-starved in serum free medium (0%CS DMEM with 0.1% BSA) for 24 hours.
3. On day 3, the appropriate ligand and the test compound are added to the cells simultaneously. The negative control wells receive serum free DMEM with 0.1% BSA only; the positive control cells receive the ligand but no test compound. Test compounds are prepared in serum free DMEM with ligand in a 96 well plate, and serially diluted for 7 test concentrations.
4. After 18 hours of ligand activation, diluted BrdU labeling reagent (1:100 in DMEM, 0.1% BSA) is added and the cells are incubated with BrdU (final concentration is 10 µM) for 1.5 hours.
5. After incubation with labeling reagent, the medium is removed by decanting and tapping the inverted plate on a paper towel. FixDenat solution is added (50 µl/well) and the plates are incubated at room temperature for 45 minutes on a plate shaker.
6. The FixDenat solution is removed by decanting and tapping the inverted plate on a paper towel. Milk is added (5% dehydrated milk in PBS, 200 µl/well) as a blocking solution and the plate is incubated for 30 minutes at room temperature on a plate shaker.
7. The blocking solution is removed by decanting and the wells are washed once with PBS. Anti-BrdU-POD solution is added (1:200 dilution in PBS, 1% BSA, 50 µl/well) and the plate is incubated for 90 minutes at room temperature on a plate shaker.
8. The antibody conjugate is removed by decanting and rinsing the wells 5 times with PBS, and the plate is dried by inverting and tapping on a paper towel.
9. TMB substrate solution is added (100 µl/well) and incubated for 20 minutes at room temperature on a plate shaker until color development is sufficient for photometric detection.
10. The absorbance of the samples are measured at 410 nm (in "dual wavelength" mode with a filter reading at 490 nm, as a reference wavelength) on a Dynatech ELISA plate reader.

EGF-Induced BrdU Incorporation Assay

Materials and Reagents:
1. Mouse EGF, 201 (Toyobo Co., Ltd., Japan).
2. 3T3/EGFRc7.

Remaining Materials and Reagents and Procedure, as above.

EGF-Induced Her-2-driven BrdU Incorporation Assay

Materials and Reagents:
1. Mouse EGF, 201 (Toyobo Co., Ltd., Japan).
2. 3T3/EGFr/Her2/EGFr (EGFr with a Her-2 kinase domain).

Remaining Materials and Reagents and Procedure, as above.

EGF-Induced Her-4-driven BrdU Incorporation Assay

Materials and Reagents:
1. Mouse EGF, 201 (Toyobo Co., Ltd., Japan).
2. 3T3/EGFr/Her4/EGFr (EGFr with a Her-4 kinase domain).

Remaining Materials and Reagents and Procedure, as above.

PDGF-Induced BrdU Incorporation Assay
Materials and Reagents:
1. Human PDGF B/B (Boehringer Mannheim, Germany).
2. 3T3/EGFRc7.

Remaining Materials and Reagents and Procedure, as above.

FGF-Induced BrdU Incorporation Assay
Materials and Reagents:
1. Human FGF2/bFGF (Gibco BRL, USA).
2. 3T3c7/EGFr Remaining Materials and Reagents and Procedure, as above.

IGF1-Induced BrdU Incorporation Assay
Materials and Reagents:
1. Human, recombinant (G511, Promega Corp., USA)
2. 3T3/IGF1r.

Remaining Materials and Reagents and Procedure, as above.

Insulin-induced BrdU Incorporation Assay
Materials and Reagents:
1. Insulin, crystalline, bovine, Zinc (13007, Gibco BRL, USA).
2. 3T3/H25.

Remaining Materials and Reagents and Procedure, as above.

HGF-induced BrdU Incorporation Assay
Materials and Reagents:
1. Recombinant human HGF (Cat. No. 249-HG, R&D Systems, Inc. USA).
2. BxPC-3 cells (ATCC CRL-1687).

Remaining Materials and Reagents, as above.
Procedure:
1. Cells are seeded at 9000 cells/well in RPMI 10% FBS in a 96 well plate. Cells are incubated overnight at 37° C. in 5% $CO_2$.
2. After 24 hours, the cells are washed with PBS, and then are serum starved in 100 $\mu$l serum-free medium (RPMI with 0.1% BSA) for 24 hours.
3. On day 3, 25 $\mu$l containing ligand (prepared at 1 $\mu$g/ml in RPMI with 0.1% BSA; final HGF conc. is 200 ng/ml) and test compounds are added to the cells. The negative control wells receive 25 $\mu$l serum-free RPMI with 0.1% BSA only; the positive control cells receive the ligand (HGF) but no test compound. Test compounds are prepared at 5 times their final concentration in serum-free RPMI with ligand in a 96 well plate, and serially diluted to give 7 test concentrations. Typically, the highest final concentration of test compound is 100 $\mu$M, and 1:3 dilutions are used (i.e. final test compound concentration range is 0.137–100 $\mu$M).
4. After 18 hours of ligand activation, 12.5 $\mu$l of diluted BrdU labeling reagent (1:100 in RPMI, 0.1% BSA) is added to each well and the cells are incubated with BrdU (final concentration is 10 $\mu$M) for 1 hour.
5. Same as General Procedure.
6. Same as General Procedure.
7. The blocking solution is removed by decanting and the wells are washed once with PBS. Anti-BrdU-POD solution (1:100 dilution in PBS, 1% BSA) is added (100 $\mu$l/well) and the plate is incubated for 90 minutes at room temperature on a plate shaker.
8. Same as General Procedure.
9. Same as General Procedure.
10. Same as General Procedure.

Exponential BrdU Incorporation Assay

This assay is used to measure the proliferation (DNA synthesis) of exponentially growing A431 cells. The assay will screen for compounds that inhibit cell cycle progression.

Materials and Reagents:

Healthy growing A431 cells. The remainder of the Materials and Reagents are the same as listed above in the general protocol section.

Procedure:
1. A431 cells are seeded at 8000 cells/well in 10% FBS, 2 mM Gln in DMEM, on a 96-well plate. Cells are incubated overnight at 37° C. in 5% $CO_2$.
2. On day 2, test compounds are serially diluted to 7 test concentrations in the same growth medium on a 96-well plate and then are added to the cells on a 96-well tissue culture plate.
3. After 20–24 hours of incubation, diluted BrdU labeling reagent (1:100 in DMEM, 0.1% BSA) is added and the cells are incubated with BrdU (final concentration is 10 $\mu$M) for 2 hours.

Steps 5–10 of the General Procedure are used to complete the assay.

Src Transphosphorylation Assay

This assay is used to screen for inhibitors of the tyrosine kinase Src.

Materials and Reagents:
1. Coating buffer: PBS containing sodium azide (0.2 mg/ml).
2. 1% w/v BSA in PBS.
3. Wash buffer: PBS containing 0.05% v/v Tween 20 (PBS-TWEEN)
4. 500 mM HEPES pH7.4.
5. ATP (40 [M]+$MgCl_2$ (80 mM) in distilled water.
6. $MgCl_2$ (80 mM) in distilled water (for no ATP blanks).
7. Test compounds, 10 mM in DMSO.
8. Assay Buffer: 100 mM HEPES, pH 7.4, containing 2 mM DTT, 0.2 mM sodium orthovanadate and 0.2 mgs/ml BSA.
9. Partially purified recombinant human Src (UBI (14-117)
10. Anti-phosphotyrosine (SUGEN rabbit polyclonal anti-PY).
11. HRP-linked goat anti-rabbit Ig (Biosource International #6430)
12. HRP substrate ABTS or Pierce Peroxidase substrate.
13. Corning ELISA plates.

Procedure:
1. Coat plates with 100 $\mu$l of 20 $\mu$g/ml poly(Glu-Tyr) (Sigma Cat. No.P0275) containing 0.01% sodium azide. Hold overnight at 4° C.
2. Block with 1% BSA at 100 $\mu$l/well for one hour at room temperature.
3. Plate test compounds (10 mM in DMSO) at 2 ul/well on a Costar plate ready for dilution with $dH_2O$ and plating to reaction plates.

4. Dilute Src kinase 1:10,000 in Reaction Buffer, for 5 plates prepare 25 ml as follows: 2.5 mls 1M HEPES pH7.4 (stored sterile at 4° C.), 21.85 ml distilled water, 0.1 ml 5% BSA, 0.5 ml 10 mM sodium orthovanadate (stored sterile at 4° C.), 50 μl 1.0M DTT (stored frozen at 20° C.), and 2.5 μl Src Kinase (stored frozen at −80° C.).

5. Add 48 μl of distilled water to the 2 ∥l of each compound in the dilution plate then add 25 μl/well of this to the reaction plate.

6. Add 50 μl of HRP to each reaction buffer well and then 25 μl ATP-MgCl$_2$/well (MgCl$_2$ only to no ATP blanks). Incubate at room temperature for 15 minutes on plate shaker. Stop reaction by adding 25 μl of 0.5M EDTA to each well.

7. Wash 4× with PBS-TWEEN.

8. Add 100 μl anti-phosphotyrosine (1:10,000 of anti-pTyr serum or 1:3,000 of 10% glycerol diluted PA-affinity purified antibody) in PBS-TWEEN containing 0.5% BSA, 0.025% Non-fat milk powder and 100 μM sodium orthovanadate. Incubate with continuous shaking at room temperature for one hour.

9. Wash plates 4× with PBS-TWEEN.

10. Add 100 μl HPP-linked Ig (1:5,000) in PBS-TWEEN containing 0.5% BSA, 0.025% Non-fat milk powder, 100 μM sodium orthovanadate. Incubate with shaking at room temperature for one hour.

11. Wash plates 4× with PBS-TWEEN and then once with PBS.

12. Develop plate using ABTS or other peroxidase substrate.

Cell Cycle Analysis

A431 cells in standard growth medium are exposed to a desired concentration of a test compound for 20–24 hours at 37° C. The cells are then collected, suspended in PBS, fixed with 70% ice-cold methanol and stained with propidium iodide. The DNA content is then measured using a FACScan flow cytometer. Cell cycle phase distribution can then be estimated using CellFIT software (Becton-Dickinson).

HUV-EC-C Assay

This assay is used to measure a compound's activity against PDGF-R, FGF-R, VEGF, aFGF or Flk-1/KDR, all of which are naturally expressed by HUV-EC cells.

DAY 0

1. Wash and trypsinize HUV-EC-C cells (human umbilical vein endothelial cells, (American Type Culture Collection, catalogue no. 1730 CRL). Wash with Dulbecco's phosphate-buffered saline (D-PBS, obtained from Gibco BRL, catalogue no. 14190-029) 2 times at about 1 ml/10 cm$^2$ of tissue culture flask. Trypsinize with 0.05% trypsin-EDTA in non-enzymatic cell dissociation solution (Sigma Chemical Company, catalogue no. C-1544). The 0.05% trypsin is made by diluting 0.25% trypsin/1 mM EDTA (Gibco, catalogue no. 25200-049) in the cell dissociation solution. Trypsinize with about 1 ml/25–30 cm$^2$ of tissue culture flask for about 5 minutes at 37° C. After cells have detached from the flask, add an equal volume of assay medium and transfer to a 50 ml sterile centrifuge tube (Fisher Scientific, catalogue no. 05-539-6).

2. Wash the cells with about 35 ml assay medium in the 50 ml sterile centrifuge tube by adding the assay medium, centrifuge for 10 minutes at approximately 200×g, aspirate the supernatant, and resuspend with 35 ml D-PBS. Repeat the wash two more times with D-PBS, resuspend the cells in about 1 ml assay medium/15 cm$^2$ of tissue culture flask. Assay medium consists of F12K medium (Gibco BRL, catalogue no. 21127-014) and 0.5% heat-inactivated fetal bovine serum. Count the cells with a Coulter Counter® (Coulter Electronics, Inc.) and add assay medium to the cells to obtain a concentration of 0.8–1.0×10$^5$ cells/ml.

3. Add cells to 96-well flat-bottom plates at 100 μl/well or 0.8–1.0×10$^4$ cells/well, incubate ~24 h at 37° C., 5% CO$_2$.

DAY 1

1. Make up two-fold test compound titrations in separate 96-well plates, generally 50 μM on down to 0 μM. Use the same assay medium as mentioned in day 0, step 2 above. Titrations are made by adding 90 μl/well of test compound at 200 μM (4× the final well concentration) to the top well of a particular plate column. Since the stock test compound is usually 20 mM in DMSO, the 200 μM drug concentration contains 2% DMSO.

A diluent made up to 2% DMSO in assay medium (F12K+0.5% fetal bovine serum) is used as diluent for the test compound titrations in order to dilute the test compound but keep the DMSO concentration constant. Add this diluent to the remaining wells in the column at 60 μl/well. Take 60 μl from the 120 μl of 200 μM test compound dilution in the top well of the column and mix with the 60 μl in the second well of the column. Take 60 μl from this well and mix with the 60 μl in the third well of the column, and so on until two-fold titrations are completed. When the next-to-the-last well is mixed, take 60 μl of the 120 μl in this well and discard it. Leave the last well with 60 μl of DMSO/media diluent as a non-test compound-containing control. Make 9 columns of titrated test compound, enough for triplicate wells each for: (1) VEGF (obtained from Pepro Tech Inc., catalogue no. 100-200, (2) endothelial cell growth factor (ECGF) (also known as acidic fibroblast growth factor, or aFGF) (obtained from Boehringer Mannheim Biochemica, catalogue no. 1439 600), or, (3) human PDGF B/B (1276-956, Boehringer Mannheim, Germany) and assay media control. ECGF comes as a preparation with sodium heparin.

2. Transfer 50 μl/well of the test compound dilutions to the 96-well assay plates containing the 0.8–1.0×10$^4$ cells/ 100 μl/well of the HUV-EC-C cells from day 0 and incubate ~2 h at 37° C., 5% CO$_2$.

3. In triplicate, add 50 μl/well of 80 μg/ml VEGF, 20 ng/ml ECGF, or media control to each test compound condition. As with the test compounds, the growth factor concentrations are 4× the desired final concentration. Use the assay media from day 0 step 2 to make the concentrations of growth factors. Incubate approximately 24 hours at 37° C., 5% CO$_2$. Each well will have 50 μl test compound dilution, 50 μl growth factor or media, and 100 μl cells, which calculates to 200 pl/well total. Thus the 4×concentrations of test compound and growth factors become 1×once everything has been added to the wells.

DAY 2

1. Add $^3$H-thymidine (Amersham, catalogue no. TRK-686) at 1 μCi/well (10 μl/well of 100 μCi/ml solution made up in RPMI media+10% heat-inactivated fetal bovine serum) and incubate ~24 h at 37° C., 5% CO$_2$. RPMI is obtained from Gibco BRL, catalogue no. 11875-051.

DAY 3

1. Freeze plates overnight at −20° C.

DAY 4

Thaw plates and harvest with a 96-well plate harvester (Tomtec Harvester 96®) onto filter mats (Wallac, catalogue no. 1205-401), read counts on a Wallac Betaplate® liquid scintillation counter.

In Vivo Animal Models
XENOGRAFT ANIMAL MODELS

The ability of human tumors to grow as xenografts in athymic mice (e.g., Balb/c, nu/nu) provides a useful in vivo model for studying the biological response to therapies for human tumors. Since the first successful xenotransplantation of human tumors into athymic mice, (Rygaard and Povlsen, 1969, Acta Pathol. Microbial. Scand. 77:758–760), many different human tumor cell lines (e.g., mammary, lung, genitourinary, gastrointestinal, head and neck, glioblastoma, bone, and malignant melanomas) have been transplanted and successfully grown in nude mice. The following assays may be used to determine the level of activity, specificity and effect of the different compounds of the present invention. Three general types of assays are useful for evaluating compounds: cellular/catalytic, cellular/biological and in vivo. The object of the cellular/catalytic assays is to determine the effect of a compound on the ability of a TK to phosphorylate tyrosines on a known substrate in a cell. The object of the cellular/biological assays is to determine the effect of a compound on the biological response stimulated by a TK in a cell. The object of the in vivo assays is to determine the effect of a compound in an animal model of a particular disorder such as cancer.

Suitable cell lines for subcutaneous xenograft experiments include C6 cells (glioma, ATCC #CCL 107), A375 cells (melanonia, ATCC #CRL 1619), A431 cells (epidennoid carcinoma, ATCC #CRL 1555), Calu 6 cells (lung, ATCC #HTB 56), PC3 cells (prostate, ATCC #CRL 1435), SKOV3TP5 cells, S114 (NIH3T3 fibroblast cell line genetically engineered for cMet and HGF expressions from NCI), U-87MG (human malignant glioma, ATCC HTB 14) and NIH 3T3 fibroblasts genetically engineered to overexpress EGFR, PDGFR, IGF-1R or any other test kinase. The following protocol can be used to perform xenograft experiments:

Female athymic mice (BALB/c, nu/nu) are obtained from Simonsen Laboratories (Gilroy, Calif.). All animals are maintained under clean-room conditions in Micro-isolator cages with Alpha-dri bedding. They receive sterile rodent chow and water ad libitum.

Cell lines are grown in appropriate medium (for example, MEM, DMEM, Ham's F10, or Ham's F12 plus 5%–10% fetal bovine serum (FBS) and 2 mM glutamine (GLN)). All cell culture media, glutamine, and fetal bovine serum are purchased from Gibco Life Technologies (Grand Island, N.Y.) unless otherwise specified. All cells are grown in a humid atmosphere of 90–95% air and 5–10% $CO_2$ at 37° C. All cell lines are routinely subcultured twice a week and are negative for mycoplasma as determined by the Mycotect method (Gibco).

Cells are harvested at or near confluency with 0.05% Trypsin-EDTA and pelleted at 450×g for 10 min. Pellets are resuspended in sterile PBS or media (without FBS) to a particular concentration and the cells are implanted into the hindflank of the mice (8–10 mice per group, 2–10×$10^6$ cells/animal). Tumor growth is measured over 3 to 6 weeks using venier calipers. Tumor volumes are calculated as a product of length×width×height unless otherwise indicated. P values are calculated using the Students t-test. Test compounds in 50–100 $\mu$L excipient (DMSO, or VPD:D5W) can be delivered by IP injection at different concentrations generally starting at day one after implantation.

TUMOR INVASION MODEL

The following tumor invasion model has been developed and may be used for the evaluation of therapeutic value and efficacy of the compounds identified to selectively inhibit KDR/FLK-1 receptor.

Procedure 8 week old nude mice (female) (Simonsen Inc.) are used as experimental animals. Implantation of tumor cells can be performed in a laminar flow hood. For anesthesia, Xylazine/Ketamine Cocktail (100 mg/kg ketamine and 5 mg/kg Xylazine) are administered intraperitoneally. A midline incision is done to expose the abdominal cavity (approximately 1.5 cm in length) to inject $10^7$ tumor cells in a volume of 100 $\mu$l medium. The cells are injected either into the duodenal lobe of the pancreas or under the serosa of the colon. The peritoneum and muscles are closed with a 6-0 silk continuous suture and the skin is closed by using wound clips. Animals are observed daily.

Analysis

After 2–6 weeks, depending on gross observations of the animals, the mice are sacrificed, and the local tumor metastases to various organs (lung, liver, brain, stomach, spleen, heart, muscle) are excised and analyzed (measurement of tumor size, grade of invasion, immunochemistry, in situ hybridization determination, etc.).

Additional Assays

Additional assays which may be used to evaluate the compounds of this invention include, without limitation, a bio-flk-1 assay, an EGF receptor-HER2 chimeric receptor assay in whole cells, a bio-src assay, a bio-lck assay and an assay measuring the phosphorylation function of raf. The protocols for each of these assays may be found in U.S. application Ser. No. 09/099,842, which is incorporated by reference, including any drawings, herein. Additionally, U.S. Pat. No. 5,792,783, filed Jun. 5, 1996 and U.S. application Ser. No. 09/322,297, filed May 28, 1999 are incorporated by reference as if fully set forth herein.

The present invention is not to be limited in scope by the exemplified aspects which are intended as illustrations of single aspects of the invention, and any clones, DNA or amino acid sequences which are functionally equivalent are within the scope of the invention. Indeed, various modifications of the invention in addition to those described herein will become apparent to those skilled in the art from the foregoing description and accompanying drawings. Such modifications are intended to fall within the scope of the appended claims.

All references cited herein are hereby incorporated by reference in their entirety.

TABLE 2

Kinase Inhibition of Selected Compounds

| Example | FGFR1 $IC_{50}(\mu M)$ | FLK-1 $IC_{50}(\mu M)$ | EGFR $IC_{50}(\mu M)$ | PDGFR $IC_{50}(\mu M)$ | MET $IC_{50}(\mu M)$ | FGFR3 $IC_{50}(\mu M)$ | SRC $IC_{50}(\mu M)$ | P38 $IC_{50}(\mu M)$ |
|---|---|---|---|---|---|---|---|---|
| 3 | 0.031 | 0.009 | >20 | 0.44 | 0.078 | | 1.02 | >10 |
| 4 | 0.74 | 0.074 | >20 | 14.60 | 0.70 | | >20 | >10 |
| 6 | 0.057 | 0.021 | 16.19 | 2.95 | 0.073 | | 4.93 | >10 |

TABLE 2-continued

Kinase Inhibition of Selected Compounds

| Example | FGFR1 IC$_{50}$(μM) | FLK-1 IC$_{50}$(μM) | EGFR IC$_{50}$(μM) | PDGFR IC$_{50}$(μM) | MET IC$_{50}$(μM) | FGFR3 IC$_{50}$(μM) | SRC IC$_{50}$(μM) | P38 IC$_{50}$(μM) |
|---|---|---|---|---|---|---|---|---|
| 10 | 1.54 | 0.18 | >20 | 11.93 | 0.23 | | 1.82 | >10 |
| 13 | <0.0091 | 0.013 | 13.12 | 2.32 | 0.10 | 0.021 | 1.05 | >10 |
| 15 | 2.07 | 0.032 | >20 | 10.13 | 0.37 | 0.072 | 2.27 | 4.9 |
| 18 | 1.19 | 0.42 | 9.33 | 10.36 | 0.27 | 0.35 | 7.81 | 9.5 |
| 20 | 1.15 | 0.23 | >20 | 3.39 | 0.52 | 1.29 | 10.38 | >10 |
| 22 | 0.057 | 0.016 | 15.92 | 1.64 | 0.14 | 0.074 | 1.58 | 13.1 |
| 25 | 0.56 | 0.18 | >20 | 11.68 | 0.11 | 0.34 | 9.86 | >10 |
| 27 | 0.63 | 0.17 | >20 | >20 | 0.15 | 0.61 | 13.87 | >10 |
| 29 | 0.029 | 0.041 | 12.88 | 0.69 | 0.065 | 0.32 | 1.25 | >10 |
| 32 | 0.35 | 0.051 | >20 | 11.63 | 0.12 | 1.77 | 5.37 | >10 |
| 34 | 0.50 | 1.06 | >20 | >20 | 0.13 | 0.94 | 7.26 | >10 |
| 35 | 0.22 | 0.092 | >20 | 1.59 | 0.34 | 1.99 | 9.72 | >10 |
| 38 | 0.080 | 0.029 | 16.35 | 2.19 | 0.11 | 0.046 | 1.25 | >10 |
| 40 | 0.19 | 0.041 | >20 | 11.08 | 0.27 | 0.38 | 6.57 | >10 |
| 41 | 0.56 | 0.079 | >20 | 3.84 | 0.32 | 0.79 | 5.42 | >10 |
| 46 | 0.022 | 0.009 | >20 | 4.19 | 0.12 | 0.009 | 0.66 | >10 |
| 48 | 0.60 | 0.012 | >20 | 8.39 | 1.06 | 0.19 | 3.80 | >10 |
| 52 | 0.035 | 0.005 | >20 | 1.54 | 0.092 | <0.0091 | 0.54 | >10 |
| 53 | 1.15 | 0.021 | >20 | >20 | 0.29 | 0.68 | 13.49 | >10 |
| 57 | 0.26 | 0.029 | >20 | >20 | 0.42 | 0.087 | 4.74 | >10 |
| 58 | 0.25 | 0.054 | >20 | 16.06 | 0.073 | 0.22 | 4.81 | >10 |
| 60 | 0.15 | 0.018 | 7.01 | 2.37 | 0.25 | 0.55 | 2.01 | 7.9 |
| 61 | 0.021 | 0.006 | >20 | 9.12 | 0.11 | <0.0091 | 1.72 | 6.3 |
| 63 | 0.24 | 0.043 | 14.98 | 2.18 | 0.043 | 0.094 | 1.14 | |
| 93 | 0.083 | <0.0091 | >20 | 3.76 | 0.08 | | >20 | |
| 99 | 0.61 | 0.17 | >20 | >20 | 0.18 | | >20 | |
| 104 | 0.3 | 0.066 | >20 | 18.97 | 0.58 | | 7.09 | |
| 119 | 0.24 | 0.18 | >20 | 9.87 | 0.059 | | 8.61 | |
| 140 | 0.52 | 0.075 | >20 | >20 | 0.68 | | 4.31 | |

Table 2 shows data of kinase inhibition of selected compounds. The Example numbers of Table 2 correspond to the Example numbers in Table 1 of the specification.

Scatter Assay

Materials and Reagents:
1. HGF: recombinant human HGF, Cat. No. 249-HG, R&D Systems, Inc., USA. HGF is dissolved in PBS with 0.1% BSA at a stock concentration of 50 mg/ml.

Procedure:
1. cell lineL MDCK clone #2.
2. MDCK cell were plated in 96-well plate in MEM with 10% FBS at low density of 25 cells/well and grown to small colonies of 10–15 cells.
3. Cells were then treated with HGF (50 ng/Ml) in the presence of various concentrations of compounds diluted in MEM with 0.5% FBS.
4. After overnight incubation, cells were fixed and stained with 0.2% crystal violet in 10% buffer Formalin.
5. Plates were allowed to air dry.
6. Photographs were taken of individual colonies.

Met Phosphorylation—Cellular Assay

Materials and Reagents:
1. Falcon 10 cm culture dishes.
2. A549 lung carcinoma cells.
3. F12K growth medium (with 2% FBS+2 mM glutamine.
4. F12K assay medium (with 0.1% BSA).
5. Fisher cell scrapers.
6. Lysis buffer (HNTG, 1 mM sodium orthovanidate, 1 mM PMSF and 2 mM sodium fluoride).
7. 1.5 ml Eppendorf tubes.
8. Eppendorf microcentrifuge.
9. BCA assay reagents A and B (#23223 and 23224, Pierce).
10. Sample tube rotator.
11. Gel blot container rotator.
12. 5×sample buffer.
13. Novex pre-cast tris-glycine 8% acrylamide gels.
14. Bio-Rad electrophoresis chamber.
15. SDS-PAGE buffer.
16. TBS (pH 7.6)+0.1% Triton X-100 (TBST), with and without 5% milk.
17. Western blot transfer buffer.
18. Osmonics nitrocellulose paper.
19. Bio-Rad Transblot paper.
20. Gel transfer apparatus.
21. Anti-phosphotyrosine (mouse monoclonal).
22. Bio-Rad Kaleidoscope Prestained Standards (161-0324).
23. Anti-h-met (C-28) rabbit polyclonal, conjugated and non-conjugated with agarose (#sc-161 AC and sc-161, Santa Cruz Biotechnology, Inc.).
24. Donkey and anti-rabbit Ig-HRP (NA 934, Amersham).
25. Sheet anti-mouselg-HRP (NA 931, Amersham).
26. SuperSignal West Pico Chemiluminescent Substrate (#34080, Pierce).
27. Saran Wrap.
28. Kodak BioMax exposure cassette.
29. Fuji X-ray film.
30. Kodak film developer.

Procedure:
1. Plate cells in 10 cm dishes with growth medium with 2% FBS+2 mM glutamine. Grow to near confluency.

2. Serum starve cells overnight in assay medium with 0.1% BSA.

3. Add drug to the plates, one dose per plate, usually in a 2-flod titration. Add asay medium (with the same DMSO concentration as the drugs) for no drug.

4. Incubate plates 4–5 hours with the drug, then add HG, 50 ng/ml for 10 minutes.

5. Wash plates once with PBS, add 400 µl lysis buffer, and scrape off the cells. Collect in 1.5 ml Eppendorf tubes.

6. After about 10–20 minutes in the lysis buffer, centrifuge lysates in a microcentrifuger at full speed (14,000 g) and collect the supernatants in a separate Eppendorf tube.

7. Determine protein concentration with the BCA assay reagents.

8. Adjust sample concentration to 0.5 mg protein in 0.4 ml using lysis buffer.

9. Add 15 µl anti-h-met AC for immunoprecipitation, rotate samples for 2 hours at 4° C.

10. Wash samples 3 times with lysis buffer and resuspend in 35 µl 5×sample buffer.

11. Boil sample at 100° C. for 10 minutes and microcentrifuge at highest setting for 30 minutes to pellet the agarose beads.

12. Load 15 µl each to 2 gels, one for anti-phosphorylation and the other for anti-h-met. Also load 10 µl of prestained standards, one lane per gel.

13. Run gel around 100–125 V, then transfer gel to nitrocellulose either overnight at 70 mAmps or 1 hour at 500 mAmps.

14. Block membranes on rotator for 1 hour in TBS+0.1% Triton X-100 (TBST)+5% PBS. All steps from this point are at room temperature unless otherwise unless otherwise noted.

15. Add 0.8 µg/ml antiphosphotyrosine and 0.25 µg/ml anti-h-met on rotator either for 2 hours or overnight.

16. Wash membranes 3 times 5 minutes each in TBST on rotator.

17. Add HRP-conjugated antibodies )sheep anti-mouse for the antiphosphotyroeins; donkey anti-rabbit for the nati-h-met) at 1:5000 for approximately 45 minutes on rotator.

18. Wash membranes 3 times for 5 minutes each in TBST on rotator.

19. Add the 2 reagents in the SuperSignal kit together in equal volumes (3 ml+3 ml for each blot), rotate for 1–2 minutes.

20. Wrap blots in Saran Wrap and tape securely inside the exposure cassette.

21. In the darkroom with only the safety light on, place a sheet of film inside the cassette. After an allotted time, remove film and place in the developer machine for automatic processing. Experiment with the exposure time to get proper exposure.

What is claimed is:
1. A compound of the formula I:

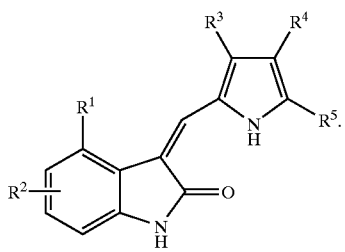

wherein:

$R^1$ is aryl, optionally substituted by one or more substituent selected from the group consisting of halogen, —$OR^6$, —$COR^6$, —$COOR^6$, $OCOR^6$, —$CONR^6R^7$, —$R^6NCOR^7$, —$NR^6R^7$, —CN, —$NO_2$, —$CX_3$, —$SR^6$, $SOR^6$, —$SO_2R^6$, —$SO_2OR^6$, —$SO_2NR^6R^7$, —$R^6NSO_2R^7$, perfluoroalkyl, lower alkyl, lower alkyl further substituted by one or more of $R^2$, lower alkenyl, lower alkenyl further substituted by one or more of $R^2$, lower alkynyl, lower alkynyl further substituted by one or more of $R^2$, cycloalkyl, cycloalkyl further substituted by one or more of $R^2$, a heterocyclic ring, a heterocyclic ring further substituted by one or more of $R^2$, aryl and aryl further substituted by one or more of $R^2$;

$R^2$ is selected from the group consisting of hydrogen, halogen, —$OR^6$, —$CONR^6R^7$, —$R^6NCOR^7$, —$NR^6R^7$, —$CX_3$, —$SR^6$, $SOR^6$, —$SO_2OR^6$, —$SO_2NR^6R^7$, lower alkyl and aryl;

$R^3$ is selected from the group consisting of hydrogen, halogen, —$OR^6$, —$COR^6$, —$OCOR^6$, —$CONR^6R^7$, —$NR^6R^7$, —CN, —$NO_2$, and lower alkyl; wherein said lower alkyl is further substituted by —$CONR^6R^7$, $NR^6R^7$, —$SO_2R^6$, —$R^6NSO_2R$, or $SO_2NR^6R^7$;

$R^4$ is selected from the group consisting of hydrogen, halogen, —$OR^6$, —$COR^6$, —$OCOR^6$, —$CONR^6R^7$, —$NR^6R^7$, —CN, —$NO_2$, and lower alkyl, wherein said lower alkyl is further substituted by —$CONR^6R^7$, $NR^6R^7$, —$SO_2R^6$, —$R^6NSO_2R$, or $SO_2NR^6R^7$;

$R^5$ is selected from the group consisting of hydrogen, halogen, —$OR^6$, —$COR^6$, —$OCOR^6$, —$CONR^6R^7$, —$NR^6R^7$, —CN, —$NO_2$, and lower alkyl;

provided that no more than one of $R^3$, $R^4$, or $R^5$ is hydrogen;

$R^6$ and $R^7$ are independently selected from the group consisting of hydrogen, —$CX_3$, perfluoroalkyl, lower alkyl, lower alkenyl, lower alkynyl, cycloalkyl, a heterocyclic ring and aryl;

wherein lower alkyl, lower alkenyl, lower alkynyl, cycloalkyl, the heteocyclic ring or aryl may be further substituted by one or more of (i) —$NR^{12}R^{13}$, (ii) hydroxy, (iii) halo, (iv) a heterocyclic ring, (v) lower alkyl, (vi) —C(O)—$NR^{12}R^{13}$, (vii) —$OR^{12}$, (viii) —$SO_2R^{12}R^{13}$, or (ix) —$COR^6$;

wherein said heterocyclic ring (iv) may be further substituted by one or more of lower alkyl, —$COR^{12}$, —$NR^{12}COR^{13}$, halogen, —$OR^{12}$, $CX_3$, —$C(O)NR^{12}R^{13}$, —$SO_2R^{12}R^{13}$, or —$SO_2NR^{12}R^{13}$, or $R^6$ and $R^7$ may be linked together to form a 4, 5- or 6-membered ring, optionally containing a hetero atom selected from the group consisting of N, O, S and $SO_2$, which may be further substituted by $-CONR^{12}R^{13}$, lower alkyl, hydroxy, $-(CH_2)_n-NR^{12}R^{13}$, $-(CH_2)_n$-heterocycle, $-(CH_2)_n-C(O)-NR^{12}R^{13}$, $-(CH_2)_n SO_2R^{12}R^{13}$, or $-(CH_2)_nNSO_2R^{12}R^{13}$, wherein said heterocycle may be further substituted by halo, lower alkyl, $-COR^{12}$, hydroxy, $-C(O)-NR^{12}R^{13}$, $-OR^{12}$, $-SO_2R^{12}R^{13}$, or $-SO_2NR^{12}R^{13}$;

X is fluorine, chlorine, bromine or iodine;

$R^{12}$ is selected from the group consisting of hydrogen, $-CX_3$, perfluoroalkyl, lower alkyl, lower alkenyl, lower alkynyl, $-(CH_2)_n$-cycloalkyl, $-(CH_2)_n$-heterocycle, and aryl;

$R^{13}$ is selected from the group consisting of hydrogen, $-CX_3$, perfluoroalkyl, lower alkyl, lower alkenyl, lower alkynyl, $-(CH_2)_n$-cycloalkyl, $-(CH_2)_n$-heterocycle, and aryl;

or $R^{12}$ and $R^{13}$ may be linked together to form a 4-, 5- or 6-membered ring optionally containing one or more hetero atoms selected from the group consisting of O, N, S, SO and $SO_2$, which may contain 1 or 2 double bonds;

or a pharmaceutically acceptable salt thereof.

2. A compound selected from the group consisting of:

2-methyl-4-[3-(4-methyl-piperazin-1-yl-propyl]-5-(2-oxo-4-phenyl-1,2-dihydro-indol-3-ylidenemethyl)-1H-pyrrole-3-carboxylic acid ester, 3-[3,5-dimethyl-4-(4-methyl-piperazine-1-carbonyl)-1H-pyrrol-2-ylmethylene]-4-phenyl-1,3-dihydro-indol-2-one, 2,4-dimethyl-5-(2-oxo-4-phenyl-1,2-dihydro-indol-3-ylidenemethyl)-1H-pyrrole-3-carboxylic acid (2-diethylamino-ethyl)-amide, 3-[3,5-dimethyl-4-(4-methyl-piperazine-1-carbonyl)-1H-pyrrol-2-ylmethylene]-4-(4-fluoro-phenyl)-1,3-dihydro-indol-2-one, 5-[4-(4-fluoro-phenyl)-2-oxo-1,2-dihydro-indol-3-ylidenemethyl]-2,4-dimethyl-1H-pyrrole-3-carboxylic acid (2-diethylamino-ethyl)-amide, 5-[4-(4-fluoro-phenyl)-2-oxo-1,2-dihydro-indol-3-ylidenemethyl]-2,4-dimethyl-1H-pyrrole-3-carboxylic acid (2-pyrrolidin-1-yl-ethyl)-amide, 5-[4-(4-fluoro-phenyl)-2-oxo-1,2-dihydro-indol-3-ylidenemethyl]-2,4-dimethyl-1H-pyrrole-3-carboxylic acid (2-[1,2,3]triazol-1-yl-ethyl)-amide, 4-(4-fluoro-phenyl)-3-[5-methyl-3-(4-methyl-piperazine-1-carbonyl)-1H-pyrrol-2-ylmethylene]-1,3-dihydroindol-2-one, 2-[4-(4-fluoro-phenyl)-2-oxo-1,2-dihydro-indol-3-ylidenemethyl]-5-methyl-1H-pyrrole-3-carboxylic acid (2-[1,2,3]triazol-1-yl-ethyl)-amide, 3-[3-(3-dimethylamino-pyrrolidine-1-carbonyl)-5-methyl-1H-pyrrol-2-ylmethylene]-4-(4-fluoro-phenyl)-1,3-dihydro-indol-2-one, 3-[3-((R)-3-dimethylamino-pyrrolidine-1-carbonyl)-5-methyl-1H-pyrrol-2-ylmethylene]-4-(4-fluoro-phenyl)-1,3-dihydro-indol-2-one, 3-[3-((S)-3-dimethylamino-pyrrolidine-1-carbonyl)-5-methyl-1H-pyrrol-2-ylmethylene]-4-(4-fluoro-phenyl)-1,3-dihydro-indol-2-one, 3-[3,5-dimethyl-4-(4-methyl-piperazine-1-carbonyl)-1H-pyrrol-2-ylmethylene]-4-(3-fluoro-phenyl)-1,3-dihydro-indol-2-one, 5-[4-(3-fluoro-phenyl)-2-oxo-1,2-dihydro-indol-3-ylidenemethyl]-2,4-dimethyl-1H-pyrrole-3-carboxylic acid (2-diethylamino-ethyl)-amide, 5-[4-(3-fluoro-phenyl)-2-oxo-1,2-dihydro-indol-3-ylidenemethyl]-2,4-dimethyl-1H-pyrrole-3-carboxylic acid (2-pyrrolidin-1-yl-ethyl)-amide, 5-[4-(3-fluoro-phenyl)-2-oxo-1,2-dihydro-indol-3-ylidenemethyl]-2,4-dimethyl-1H-pyrrole-3-carboxylic acid (2-[1,2,3]triazol-1-yl-ethyl)-amide, 3-[3-(3-dimethylamino-pyrrolidine-1-carbonyl)-5-methyl-1H-pyrrol-2-ylmethylene]-4-(3-fluoro-phenyl)-1,3-dihydro-indol-2-one, 3-[3-((R)-3-dimethylamino-pyrrolidine-1-carbonyl)-5-methyl-1H-pyrrol-2-ylmethylene]-4-(3-fluoro-phenyl)-1,3-dihydro-indol-2-one, 3-[3-((S)-3-dimethylamino-pyrrolidine-1-carbonyl)-5-methyl-1H-pyrrol-2-ylmethylene]-4-(3-fluoro-phenyl)-1,3-dihydro-indol-2-one, 5-[4-(3-fluoro-phenyl)-2-oxo-1,2-dihydro-indol-3-ylidenemethyl]-2-methyl-4-[3-(4-methyl-piperazin-1-yl)-propyl]-1H-pyrrole-3-carboxylic acid ethyl ester, 3-[3-(cis-3,5-dimethyl-piperazine-1-carbonyl)-5-methyl-1H-pyrrol-2-ylmethylene]-4-(3-fluoro-phenyl)-1,3-dihydro-indol-2-one, 3-[3-(trans-3,5-dimethyl-piperazine-1-carbonyl)-5-methyl-1H-pyrrol-2-ylmethylene]-4-(3-fluoro-phenyl)-1,3-dihydro-indol-2-one, 4-(4-chloro-phenyl)-3-[3,5-dimethyl-4-(4-methyl-piperazine-1-carbonyl)-1H-pyrrol-2-ylmethylene]-1,3-dihydro-indol-2-one, 5-[4-(4-chloro-phenyl)-2-oxo-1,2-dihydro-indol-3-ylidenemethyl]-2,4-dimethyl-1H-pyrrole-3-carboxylic acid (2-diethylamino-ethyl)-amide, 5-[4-(4-chloro-phenyl)-2-oxo-1,2-dihydro-indol-3-ylidenemethyl]-2,4-dimethyl-1H-pyrrole-3-carboxylic acid (2-pyrrolidin-1-yl-ethyl)-amide, 5-[4-(4-chloro-phenyl)-2-oxo-1,2-dihydro-indol-3-ylidenemethyl]-2,4-dimethyl-1H-pyrrole-3-carboxylic acid (2-[1,2,3]triazol-1-yl-ethyl)-amide, 4-(4-chloro-phenyl)-3-[3-(3-dimethylamino-pyrrolidine-1-carbonyl)-5-methyl-1H-pyrrol-2-ylmethylene]-1,3-dihydro-indol-2-one, 4-(4-chloro-phenyl)-3-[3-(3-dimethylamino-pyrrolidine-1-carbonyl)-5-methyl-1H-pyrrol-2-ylmethylene]-1,3-dihydro-indol-2-one, 5-[4-(4-chloro-phenyl)-2-oxo-1,2-dihydro-indol-3-ylidenemethyl]-2-methyl-4-[3-(4-methyl-piperazin-1-yl)-propyl]-1H-pyrrole-3-carboxylic acid ethyl ester, 4-(4-chloro-phenyl)-3-[3-(cis-3,5-dimethyl-piperazine-1-carbonyl)-5-methyl-1H-pyrrol-2-ylmethylene]-1,3-dihydro-indol-2-one, 4-(4-chloro-phenyl)-3-[3-(trans-3,5-dimethyl-piperazine-1-carbonyl)-5-methyl-1H-pyrrol-2-ylmethylene]-1,3-dihydro-indol-2-one, 4-(3-chloro-phenyl)-3-[3,5-dimethyl-4-(4-methyl-piperazine-1-carbonyl)-1H-pyrrol-2-ylmethylene]-1,3-dihydro-indol-2-one, 5-[4-(3-chloro-phenyl)-2-oxo-1,2-dihydro-indol-3-ylidenemethyl]-2,4-dimethyl-1H-pyrrole-3-carboxylic acid (2-diethylamino-ethyl)-amide, 5-[4-(3-chloro-phenyl)-2-oxo-1,2-dihydro-indol-3-ylidenemethyl]-2,4-dimethyl-1H-pyrrole-3-carboxylic acid (2-pyrrolidin-1-yl-ethyl)-amide, 5-[4-(3-chloro-phenyl)-2-oxo-1,2-dihydro-indol-3-ylidenemethyl]-2,4-dimethyl-1H-pyrrole-3-carboxylic acid (2-[1,2,3]triazol-1-yl-ethyl)-amide, 4-(3-chloro-phenyl)-3-[3-(3-dimethylamino-pyrrolidine-1-carbonyl)-5-methyl-1H-pyrrol-2-ylmethylene]-1,3-dihydro-indol-2-one, 4-(3-chloro-phenyl)-3-[3-((R)-3-dimethylamino-pyrrolidine-1-carbonyl)-5-methyl-1H-pyrrol-2-ylmethylene]-1,3-dihydro-indol-2-one, 4-(3-chloro-phenyl)-3-[3-((S)-3-dimethylamino-pyrrolidine-1-carbonyl)-5-methyl-1H-pyrrol-2-ylmethylene]-1,3-dihydro-indol-2-one, 2-[4-(3-chloro-phenyl)-2-oxo-1,2-dihydro-indol-3-ylidenemethyl]-5-methyl-1H-pyrrole-3-carboxylic acid (2-[1,2,3]triazol-1-yl-ethyl)-amide, 4-(3-chloro-phenyl)-3-[3-(cis-3,5-dimethyl-piperazine-1-carbonyl)-5-methyl-1H-pyrrol-2-ylmethylene]-1,3-dihydro-indol-2-one, 4-(3-chloro-phenyl)-3-[3-(trans-3,5-dimethyl-piperazine-1-carbonyl)-5-methyl-1H-pyrrol-2-ylmethylene]-1,3-dihydro-indol-2-one, 3-[3,5-dimethyl-4-(4-methyl-piperazine-1-carbonyl)-1H-pyrrol-2-ylmethylene]-4-(4-methoxy-phenyl)-1,3-dihydro-indol-2-one, 5-[4-(4-methoxy-phenyl)-2-oxo-1,2-dihydro-indol-3-ylidenemethyl]-2,4-dimethyl-1H-pyrrole-3-carboxylic acid (2-diethylamino-ethyl)-amide, 5-[4-(4-methoxy-phenyl)-2-oxo-1,2-dihydro-indol-3-ylidenemethyl]-2,4-dimethyl-1H-pyrrole-3-carboxylic acid (2-pyrrolidin-1-yl-ethyl)-amide, 5-[4-(4-methoxy-phenyl)-2-oxo-1,2-dihydro-indol-3-ylidenemethyl]-2,4-dimethyl-1H-pyrrole-3-carboxylic acid (2-[1,2,3]triazol-1-yl-ethyl)-amide, 3-[4-(cis-3,5-dimethyl-piperazine-1-carbonyl)-3,5-dimethyl-1H-pyrrol-2-ylmethylene]-4-(4-methoxy-phenyl)-1,3-dihydro-indol-2-one, 3-[4-(trans-3,5-dimethyl-piperazine-1-carbonyl)-3,5-dimethyl-1H-pyrrol-2-ylmethylene]-4-(4-methoxy-phenyl)-1,3-dihydro-indol-2-one, 2-[4-(4-methoxy-phenyl)-2-oxo-1,2-dihydro-indol-3-ylidenemethyl]-5-methyl-1H-pyrrole-3-carboxylic acid (2-pyrrolidin-1-yl-ethyl)-amide, 2-[4-(4-methoxy-phenyl)-2-oxo-1,2-dihydro-indol-3-ylidenemethyl]-5-methyl-1H-pyrrole-3-carboxylic acid (2-[1,2,3]triazol-1-yl-ethyl)-amide, 3-[3-(3-dimethylamino-pyrrolidine-1-carbonyl)-5-methyl-1H-pyrrol-2-ylmethylene]-4-(4-methoxy-phenyl)-1,3-dihydro-indol-2-one, 3-[3-((R)-3-dimethylamino-pyrrolidine-1-carbonyl)-5-methyl-1H-pyrrol-2-ylmethylene]-4-(4-methoxy-phenyl)-1,3-dihydro-indol-2-one, 3-[3-((S)-3-dimethylamino-pyrrolidine-1-carbonyl)-5-methyl-1H-pyrrol-2-ylmethylene]-4-(4-methoxy-phenyl)-1,3-dihydro-indol-2-one, 3-[3,5-dimethyl-4-(4-methyl-piperazine-1-carbonyl)-1H-pyrrol-2-ylmethylene]-4-(3-methoxy-phenyl)-1,3-dihydro-indol-2-one, 5-[4-(3-methoxy-phenyl)-2-oxo-1,2-dihydro-indol-3-ylidenemethyl]-2,4-dimethyl-1H-pyrrole-3-carboxylic acid (2-diethylamino-ethyl)-amide, 5-[4-(3-methoxy-phenyl)-2-oxo-1,2-dihydro-indol-3-ylidenemethyl]-2,4-dimethyl-1H-pyrrole-3-carboxylic acid (2-pyrrolidin-1-yl-ethyl)-amide, 5-[4-(3-methoxy-phenyl)-2-oxo-1,2-dihydro-indol-3-ylidenemethyl]-2,4-dimethyl-1H-pyrrole-3-carboxylic acid (2-[1,2,3]triazol-1-yl-ethyl)-amide, 3-[4-(cis-3,5-dimethyl-piperazine-1-carbonyl)-3,5-dimethyl-1H-pyrrol-2-ylmethylene]-4-(3-methoxy-phenyl)-1,3-dihydro-indol-2-one, 3-[4-(trans-3,5-dimethyl-piperazine-1-carbonyl)-3,5-dimethyl-1H-pyrrol-2-ylmethylene]-4-(3-methoxy-phenyl)-1,3-dihydro-indol-2-one, 2-[4-(3-methoxy-phenyl)-2-oxo-1,2-dihydro-indol-3-ylidenemethyl]-5-methyl-1H-pyrrole-3-carboxylic acid (2-pyrrolidin-1-yl-ethyl)-amide, 2-[4-(3-methoxy-phenyl)-2-oxo-1,2-dihydro-indol-3-ylidenemethyl]-5-methyl-1H-pyrrole-3-carboxylic acid (2-[1,2,3]triazol-1-yl-ethyl)-amide, 5-[4-(3-methoxy-phenyl)-2-oxo-1,2-dihydro-indol-3-ylidenemethyl]-2,4-dimethyl-1H-pyrrole-3-carboxylic acid (2-diisopropylamino-ethyl)-amide, 4-(4-bromo-phenyl)-3-[3,5-dimethyl-4-(4-methyl-piperazine-1-carbonyl)-1H-pyrrol-2-ylmethylene]-1,3-dihydro-indol-2-one, 5-[4-(4-bromo-phenyl)-2-oxo-1,2-dihydro-indol-3-ylidenemethyl]-2,4-dimethyl-1H-pyrrole-3-carboxylic acid (2-diethylamino-ethyl)-amide, 5-[4-(4-bromo-phenyl)-2-oxo-1,2-dihydro-indol-3-ylidenemethyl]-2,4-dimethyl-1H-pyrrole-3-carboxylic acid (2-pyrrolidin-1-yl-ethyl)-amide, 5-[4-(4-bromo-phenyl)-2-oxo-1,2-dihydro-indol-3-ylidenemethyl]-2,4-dimethyl-1H-pyrrole-3-carboxylic acid (2-[1,2,3]triazol-1-yl-ethyl)-amide, 4-(4-bromo-phenyl)-3-[4-(cis-3,5-dimethyl-piperazine-1-carbonyl)-3,5-dimethyl-1H-pyrrol-2-ylmethylene]-1,3-dihydro-indol-2-one, 4-(4-bromo-phenyl)-3-[4-(trans-3,5-dimethyl-piperazine-1-carbonyl)-3,5-dimethyl-1H-pyrrol-2-ylmethylene]-1,3-dihydro-indol-2-one, 2-[4-(4-bromo-phenyl)-2-oxo-1,2-dihydro-indol-3-ylidenemethyl]-5-methyl-1H-pyrrole-3-carboxylic acid (2-pyrrolidin-1-yl-ethyl)-amide, 2-[4-(4-bromo-phenyl)-2-oxo-1,2-dihydro-indol-3-ylidenemethyl]-5-methyl-1H-pyrrole-3-carboxylic acid (2-[1,2,3]triazol-1-yl-ethyl)-amide, 5-[4-(4-bromo-phenyl)-2-oxo-1,2-dihydro-indol-3-ylidenemethyl]-2,4-dimethyl-1H-pyrrole-3-carboxylic acid (2-diisopropylamino-ethyl)-amide, 5-[4-(4-bromo-phenyl)-2-oxo-1,2-dihydro-indol-3-ylidenemethyl]-4-methyl-1H-pyrrole-3-carboxylic acid (2-diethylamino-ethyl)-amide, 4-(3-Bromo-phenyl)-3-[3,5-dimethyl-4-(4-methyl-piperazine-1-carbonyl)-1H-pyrrol-2-ylmethylene]-1,3-dihydro-indol-2-one, 5-[4-(3-bromo-phenyl)-2-oxo-1,2-dihydro-indol-3-ylidenemethyl]-2,4-dimethyl-1H-pyrrole-3-carboxylic acid (2-diethylamino-ethyl)-amide, 5-[4-(3-bromo-phenyl)-2-oxo-1,2-dihydro-indol-3-ylidenemethyl]-2,4-dimethyl-1H-pyrrole-3-carboxylic acid (2-pyrrolidin-1-yl-ethyl)-amide, 5-[4-(3-bromo-phenyl)-2-oxo-1,2-dihydro-indol-3-ylidenemethyl]-2,4-dimethyl-1H-pyrrole-3-carboxylic acid (2-[1,2,3]triazol-1-yl-ethyl)-amide, 3-[4-(cis-3,5-dimethyl-piperazine-1-carbonyl)-3,5-dimethyl-1H-pyrrol-2-ylmethylene]-4-(3-bromo-phenyl)-1,3-dihydro-indol-2-one, 3-[4-(trans-3,5-dimethyl-piperazine-1-carbonyl)-3,5-dimethyl-1H-pyrrol-2-ylmethylene]-4-(3-bromo-phenyl)-1,3-dihydro-indol-2-one, 2-[4-(3-bromo-phenyl)-2-oxo-1,2-dihydro-indol-3-ylidenemethyl]-5-methyl-1H-pyrrole-3-carboxylic acid (2-pyrrolidin-1-yl-ethyl)-amide, 2-[4-(3-bromo-phenyl)-2-oxo-1,2-dihydro-indol-3-ylidenemethyl]-5-methyl-1H-pyrrole-3-carboxylic acid (2-[1,2,3]triazol-1-yl-ethyl)-amide, 5-[4-(3-bromo-phenyl)-2-oxo-1,2-dihydro-indol-3-ylidenemethyl]-2,4-dimethyl-1H-pyrrole-3-carboxylic acid (2-diisopropylamino-ethyl)-amide, 5-[4-(4-fluoro-phenyl)-2-oxo-1,2-dihydro-indol-3-ylidenemethyl]-4-methyl-1H-pyrrole-2-carboxylic acid (2-diethylamino-ethyl)-amide, 5-[4-(3-fluoro-phenyl)-2-oxo-1,2-dihydro-indol-3-ylidenemethyl]-4-methyl-1H-pyrrole-2-carboxylic acid (2-diethylamino-ethyl)-amide, 5-[4-(4-chloro-phenyl)-2-oxo-1,2-dihydro-indol-3-ylidenemethyl]-4-methyl-1H-pyrrole-2-carboxylic acid (2-diethylamino-ethyl)-amide, 5-[4-(3-chloro-phenyl)-2-oxo-1,2-dihydro-indol-3-ylidenemethyl]-4-methyl-1H-pyrrole-2-carboxylic acid (2-diethylamino-ethyl)-amide, 5-[4-(4-bromo-phenyl)-2-oxo-1,2-dihydro-indol-3-ylidenemethyl]-4-methyl-1H-pyrrole-2-carboxylic acid (2-diethylamino-ethyl)-amide, 5-[4-(3-bromo-phenyl)-2-oxo-1,2-dihydro-indol-3-ylidenemethyl]-4-methyl-1H-pyrrole-2-carboxylic acid (2-diethylamino-ethyl)-amide, 5-[4-(4-methoxy-phenyl)-2-oxo-1,2-dihydro-indol-3-ylidenemethyl]-4-methyl-1H-pyrrole-2-carboxylic acid (2-diethylamino-ethyl)-amide, 5-[4-(3-methoxy-phenyl)-2-oxo-1,2-dihydro-indol-3-ylidenemethyl]-4-methyl-1H-pyrrole-2-carboxylic acid (2-diethylamino-ethyl)-amide, 3-(3,5-dimethyl-1H-pyrrol-2-ylmethylene)-4-(4-fluoro-phenyl)-1,3-dihydro-indol-2-one, 3-(3,5-dimethyl-1H-pyrrol-2-ylmethylene)-4-(3-fluoro-phenyl)-1,3-dihydro-indol-2-one, 3-(3,5-dimethyl-1H-pyrrol-2-ylmethylene)-4-(4-chloro-phenyl)-1,3-dihydro-indol-2-one, 3-(3,5-dimethyl-1H-pyrrol-2-ylmethylene)-4-(3-chloro-phenyl)-1,3-dihydro-indol-2-one, 3-(3,5-dimethyl-1H-pyrrol-2-ylmethylene)-4-(4-bromo-phenyl)-1,3-dihydro-indol-2-one, 3-(3,5-dimethyl-1H-pyrrol-2-ylmethylene)-4-(3-bromo-phenyl)-1,3-dihydro-indol-2-one, 3-(3,5-dimethyl-1H-pyrrol-2-ylmethylene)-4-(4-methoxy-phenyl)-1,3-dihydro-indol-2-one, 3-(3,5-dimethyl-1H-pyrrol-2-ylmethylene)-4-(3-methoxy-phenyl)-1,3-dihydro-indol-2-one, 5-[4-(4-Fluoro-phenyl)-2-oxo-1,2-dihydro-indol-3-ylidenemethyl]-4-methyl-1H-pyrrole-3-carboxylic acid (2-diethylamino-ethyl)-amide, 5-[4-(3-Fluoro-phenyl)-2-oxo-1,2-dihydro-indol-3-ylidenemethyl]-4-methyl-1H-pyrrole-3-carboxylic acid (2-diethylamino-ethyl)-amide, 5-[4-(4-Chloro-phenyl)-2-oxo-1,2-dihydro-indol-3-ylidenemethyl]-4-methyl-1H-pyrrole-3-carboxylic acid (2-diethylamino-ethyl)-amide, 5-[4-(3-Chloro-phenyl)-2-oxo-1,2-dihydro-indol-3-ylidenemethyl]-4-methyl-1H-pyrrole-3-carboxylic acid (2-diethylamino-ethyl)-amide, 5-[4-(3-Bromo-phenyl)-2-oxo-1,2-dihydro-indol-3-ylidenemethyl]-4-methyl-1H-pyrrole-3-carboxylic acid (2-diethylamino-ethyl)-amide, 5-[4-(4-Methoxy-phenyl)-2-oxo-1,2-dihydro-indol-3-ylidenemethyl]-4-methyl-1H-pyrrole-3-carboxylic acid (2-diethylamino-ethyl)-amide, 5-[4-(3-Methoxy-phenyl)-2-oxo-1,2-dihydro-indol-3-ylidenemethyl]-4-methyl-1H-pyrrole-3-carboxylic acid (2-diethylamino-ethyl)-amide, 3-[3,5-Dimethyl-4-(4-methyl-[piperazine-1-carbonyl)-1H-pyrrol-2-ylmethylene]-4-(2-fluoro-phenyl)-1,3-dihydro-indol-2-one, 5-[4-(2-Fluoro-phenyl)-2-oxo-1,2-dihydro-indol-3-ylidenemethyl]-2,4-dimethyl-1H-pyrrole-3-carboxylic acid (2-diethylamino-ethyl)-amide, 5-[4-(2-Fluoro-phenyl)-2-oxo-1,2-dihydro-indol-3-ylidenemethyl]-2,4-dimethyl-1H-pyrrole-3-carboxylic acid (2-pyrrolidin-1-yl-ethyl)-amide, 5-[4-(2-Fluoro-phenyl)-2-oxo-1,2-dihydro-indol-3-ylidenemethyl]-2,4-dimethyl-1H-pyrrole-3-carboxylic acid (2-[1,2,3]triazol-1-yl-ethyl)-amide, 2-[4-(2-Fluoro-phenyl)-2-oxo-1,2-dihydro-indol-3-ylidenemethyl]-5-methyl-1H-pyrrole-3-carboxylic acid (2-diethylamino-ethyl)-amide, 2-[4-(2-Fluoro-phenyl)-2-oxo-1,2-dihydro-indol-3-ylidenemethyl]-5-methyl-1H-pyrrole-3-carboxylic acid (2-pyrrolidin-1-yl-ethyl)-amide, 2-[4-(2-Fluoro-phenyl)-2-oxo-1,2-dihydro-indol-3-ylidenemethyl]-5-methyl-1H-pyrrole-3-carboxylic acid (2-[1,2,3]triazol-1-yl-ethyl)-amide, 3-[3-(cis-3,5-dimethyl-piperazine-carbonyl)-5-methyl-1H-pyrrol-2-ylmethylene]-4-(2-fluoro-phenyl)-1,3-dihydro-indol-2-one, 3-[3-(trans-3,5-dimethyl-piperazine-carbonyl)-5-methyl-1H-pyrrol-2-ylmethylene]-4-(2-fluoro-phenyl)-1,3-dihydro-indol-2-one, 5-[4-(4-Fluoro-phenyl)-2-oxo-1,2-dihydro-indol-3-ylidenemethyl]-2,4-dimethyl-1H-pyrrole-3-carboxylic acid (3-diethylamino-propyl)-amide, 2-[4-(4-Fluoro-phenyl)-2-oxo-1,2-dihydro-indol-3-ylidenemethyl]-5-methyl-1H-pyrrole-3-carboxylic acid (3-pyrrolidin-1-yl-propyl)-amide, 5-[4-(3-Fluoro-phenyl)-2-oxo-1,2-dihydro-indol-3-ylidenemethyl]-2,4-dimethyl-1H-pyrrole-3-carboxylic acid (3-diethylamino-propyl)-amide, 3-[3,5-Dimethyl-4-(4-methyl-piperazine-1-carbonyl)-1H-pyrrol-2-ylmethylene]-4-(3-trifluoromethyl-phenyl)-1,3-dihydro-indol-2-one, 2,4-Dimethyl-5-[2-oxo-4-(3-trifluoromethyl-phenyl)-1,2-dihydro-indol-3-ylidenemethyl]-1H-pyrrole-3-carboxylic acid (2-diethylamino-ethyl)-amide, 2,4-Dimethyl-5-[2-oxo-4-(3-trifluoromethyl-phenyl)-1,2-dihydro-indol-3-ylidenemethyl]-1H-pyrrole-3-carboxylic acid (2-pyrrolidin-1-yl-ethyl)-amide, 2,4-Dimethyl-5-[2-oxo-4-(3-trifluoromethyl-phenyl)-1,2-dihydro-indol-3-ylidenemethyl]-1H-pyrrole-3-carboxylic acid (2-[1,2,3]triazol-1-yl-ethyl)-amide, 5-methyl-2-[2-oxo-4-(3-trifluoromethyl-phenyl)-1,2-dihydro-indol-3-ylidenemethyl]-1H-pyrrole-3-carboxylic acid (2-diethylamino-ethyl)-amide, 5-methyl-2-[2-oxo-4-(3-trifluoromethyl-phenyl)-1,2-dihydro-indol-3-ylidenemethyl]-1H-pyrrole-3-carboxylic acid (2-pyrrolidin-1-yl-ethyl)-amide, 5-methyl-2-[2-oxo-4-(3-trifluoromethyl-phenyl)-1,2-dihydro-indol-3-ylidenemethyl]-1H-pyrrole-3-carboxylic acid (2-[1,2,3]triazol-1-yl-ethyl)-amide, 3-{3-[cis-3,5-dimethyl-piperazine-1-carbonyl]-5-methyl-1H-pyrrol-2-ylmethylene}-4-(2-trifluoromethyl-phenyl)-1,3-dihydro-indol-2-one, 2,4-Dimethyl-5-[2-oxo-4-(3-trifluoromethyl-phenyl)-1,2-dihydro-indol-3-ylidenemethyl]-1H-pyrrole-3-carboxylic acid (3-diethylamino-propyl)-amide, 5-methyl-2-[2-oxo-4-(3-trifluoromethyl-phenyl)-1,2-dihydro-indol-3-ylidenemethyl]-1H-pyrrole-3-carboxylic acid (3-pyrrolidin-1-yl-propyl)-amide, 3-[3-methyl-4-(4-methyl-piperazine-1-carbonyl)-1H-pyrrol-2-ylmethylene]-4-(3-trifluoromethyl-phenyl)-1,3-dihydro-indol-2-one, 3-{3-Methyl-4-[cis-3,5-dimethyl-piperazine-1-carbonyl]-1H-pyrrol-2-ylmethylene}-4-(3-trifluoromethyl-phenyl)-1,3-dihydro-indol-2-one, 4-(3-chloro-4-fluoro-phenyl)-3-[3,5-dimethyl-4-(4-methyl-piperazine-1-carbonyl)-1H-pyrrol-2-ylmethylene]-1,3-dihydro-indol-2-one, 5-[4-(3-chloro-4-fluoro-phenyl)-2-oxo-1,2-dihydro-indol-3-ylidenemethyl]-2,4-dimethyl-1H-pyrrole-3-carboxylic acid (2-diethylamino-ethyl)-amide, 5-[4-(3-chloro-4-fluoro-phenyl)-2-oxo-1,2-dihydro-indol-3-ylidenemethyl]-2,4-dimethyl-1H-pyrrole-3-carboxylic acid (2-[1,2,3]triazol-1-yl-ethyl)-amide, 2-[4-(3-chloro-4-fluoro-phenyl)-2-oxo-1,2-dihydro-indol-3-ylidenemethyl]-5-methyl-1H-pyrrole-3-carboxylic acid (2-pyrrolidin-1-yl-ethyl)-amide, 2-[4-(3-chloro-4-fluoro-phenyl)-2-oxo-1,2-dihydro-indol-3-ylidenemethyl]-5-methyl-1H-pyrrole-3-carboxylic acid (2-[1,2,3]triazol-1-yl-ethyl)-amide, 2-[4-(3-chloro-4-fluoro-phenyl)-2-oxo-1,2-dihydro-indol-3-ylidenemethyl]-5-methyl-1H-pyrrole-3-carboxylic acid (3-pyrrolidin-1-yl-propyl)-amide, 4-(4-chloro-phenyl)-3-{3,5-dimethyl-4-[3-(4-methyl-piperazin-1-yl)-3-oxo-propyl]-1H-pyrrol-2-ylmethylene}-1,3-dihydro-indol-2-one, 4-(2-fluoro-phenyl)-3-[3-methyl-4-(4-methyl-piperazine-1-carbonyl)-1H-pyrrol-2-ylmethylene]-1,3-dihydro-indol-2-one, 4-(4-fluoro-phenyl)-3-[3-methyl-4-(4-methyl-piperazine-1-carbonyl)-1H-pyrrol-2-ylmethylene]-1,3-dihydro-indol-2-one, 4-(4-chloro-phenyl)-3-[3-methyl-4-(4-methyl-piperazine-1-carbonyl)-1H-pyrrol-2-ylmethylene]-1,3-dihydro-indol-2-one, 4-(4-bromo-phenyl)-3-[3-methyl-4-(4-methyl-piperazine-1-carbonyl)-1H-pyrrol-2-ylmethylene]-1,3-dihydro-indol-2-one, 4-(3-bromo-phenyl)-3-[3-methyl-4-(4-methyl-piperazine-1-carbonyl)-1H-pyrrol-2-ylmethylene]-1,3-dihydro-indol-2-one, 4-(4-methoxy-phenyl)-3-[3-methyl-4-(4-methyl-piperazine-1-carbonyl)-1H-pyrrol-2-ylmethylene]-1,3-dihydro-indol-2-one, 4-(3-methoxy-phenyl)-3-[3-methyl-4-(4-methyl-piperazine-1-carbonyl)-1H-pyrrol-2-ylmethylene]-1,3-dihydro-indol-2-one, 3-[3-methyl-4-(4-methyl-piperazine-1-carbonyl)-1H-pyrrol-2-ylmethylene]-4-phenyl-1,3-dihydro-indol-2-one, 3-{4-[cis-3,5-dimethyl-piperazine-1-carbonyl]-3-methyl-1H-pyrrol-2-ylmethylene}-4-(4-fluoro-phenyl)-1,3-dihydro-indol-2-one, 4-(4-Chloro-phenyl)-3-{4-[cis-3,5-dimethyl-piperazine-1-carbonyl]-3-methyl-1H-pyrrol-2-ylmethylene]-1,3-dihydro-indol-2-one, 4-(4-Bromo-phenyl)-3-{4-[cis-3,5-dimethyl-piperazine-1-carbonyl]-3-methyl-1H-pyrrol-2-ylmethylene]-1,3-dihydro-indol-2-one, 3-{4-[cis-3,5-dimethyl-piperazine-1-carbonyl]-3-methyl-1H-pyrrol-2-ylmethylene}-4-(4-methoxy-phenyl)-1,3-dihydro-indol-2-one, 3-{4-[cis-3,5-dimethyl-piperazine-1-carbonyl]-3-methyl-1H-pyrrol-2-ylmethylene}-4-(3-methoxy-phenyl)-1,3-dihydro-indol-2-one, 3-{4-[cis-3,5-dimethyl-piperazine-1-carbonyl]-3-methyl-1H-pyrrol-2-ylmethylene}-4-phenyl-1,3-dihydro-indol-2-one, 4-(4-chloro-phenyl)-3-{4-{3-[cis-3,5-dimethyl-piperazin-1-yl]-3-oxo-propyl}-3,5-dimethyl-1H-pyrrol-2-ylmethylene}-1,3-dihydro-indol-2-one, 3-{4-{3-[cis-3,5-Dimethyl-piperazin-1-yl]-3-oxo-propyl}-3,5-dimethyl-1H-pyrrol-2-ylmethylene}-4-(4-fluoro-phenyl)-1,3-dihydro-indol-2-one, 3-[3,5-Dimethyl-4-(4-methyl-piperazine-1-carbonyl)-1H-pyrrol-2-ylmethylene]-4-(4-trifluoromethoxy-phenyl)-1,3-dihydro-indol-2-one, 2,4-Dimethyl-5-[2-oxo-4-(4-trifluoromethoxy-phenyl)-1,2-dihydro-indol-3-ylidenemethyl]-1H-pyrrole-3-carboxylic acid (2-diethylamino-ethyl)-amide, 2,4-Dimethyl-5-[2-oxo-4-(4-trifluoromethoxy-phenyl)-1,2-dihydro-indol-3-ylidenemethyl]-1H-pyrrole-3-carboxylic acid (2-[1,2,3]triazol-1-yl-ethyl)-amide, 5-methyl-2-[2-oxo-4-(4-trifluoromethoxy-phenyl)-1,2-dihydro-indol-3-ylidenemethyl]-1H-pyrrole-3-carboxylic acid (2-pyrrolidin-1-yl-ethyl)-amide, 5-methyl-2-[2-oxo-4-(4-trifluoromethoxy-phenyl)-1,2-dihydro-indol-3-ylidenemethyl]-1H-pyrrole-3-carboxylic acid (2-[1,2,3]triazol-1-yl-ethyl)-amide, 5-methyl-2-[2-oxo-4-(4-trifluoromethoxy-phenyl)-1,2-dihydro-indol-3-ylidenemethyl]-1H-pyrrole-3-carboxylic acid (3-pyrrolidin-1-yl-propyl)-amide, 3-[3-(trans-3,5-Dimethyl-piperazine-1-carbonyl)-5-methyl-1H-pyrrol-2-ylmethylene]-4-(3-fluoro-phenyl)-1,3-dihydro-indol-2-one, 4-(4-Chloro-phenyl)-3-[3-(trans-3,5-dimethyl-piperazine-1-carbonyl)-5-methyl-1H-pyrrol-2-ylmethylene]-1,3-dihydro-indol-2-one, 4-(3-Chloro-phenyl)-3-[3-(trans-3,5-dimethyl-piperazine-1-carbonyl)-5-methyl-1H-pyrrol-2-ylmethylene]-1,3-dihydro-indol-2-one, 3-[4-(trans-3,5-Dimethyl-piperazine-1-carbonyl)-3,5-dimethyl-1H-pyrrol-2-ylmethylene]-4-(4-methoxy-phenyl)-1,3-dihydro-indol-2-one, 3-[4-(trans-3,5-Dimethyl-piperazine-1-carbonyl)-3,5-dimethyl-1H-pyrrol-2-ylmethylene]-4-(3-methoxy-phenyl)-1,3-dihydro-indol-2-one, 4-(4-Bromo-phenyl)-3-[4-[trans-3,5-dimethyl-piperazine-1-carbonyl)-3,5-dimethyl-1H-pyrrol-2-ylmethylene]-1,3-dihydro-indol-2-one, 3-[4-(trans-3,5-Dimethyl-piperazine-1-carbonyl)-3,5-dimethyl-1H-pyrrol-2-ylmethylene]-4-(3-bromo-phenyl)-1,3-dihydro-indol-2-one, 3-{3-[trans-3,5-dimethyl-piperazine-1-carbonyl]-5-methyl-1H-pyrrol-2-ylmethylene}-4-(2-fluoro-phenyl)-1,3-dihydro-indol-2-one, 3-{3-[trans-3,5-dimethyl-piperazine-1-carbonyl]-5-methyl-1H-pyrrol-2-ylmethylene}-4-(2-trifluoromethyl-phenyl)-1,3-dihydro-indol-2-one, 3-{3-Methyl-4-[trans-3,5-dimethyl-piperazine-1-carbonyl]-1H-pyrrol-2-ylmethylene}-4-(3-trifluoromethyl-phenyl)-1,3-dihydro-indol-2-one, 3-{4-[trans-3,5-dimethyl-piperazine-1-carbonyl]-3-methyl-1H-pyrrol-2-ylmethylene}-4-(4-fluoro-phenyl)-1,3-dihydro-indol-2-one, 4-(4-Chloro-phenyl)-3-{4-[trans-3,5-dimethyl-piperazine-1-carbonyl]-3-methyl-1H-pyrrol-2-ylmethylene]-1,3-dihydro-indol-2-one, 4-(4-Bromo-phenyl)-3-{4-[trans-3,5-dimethyl-piperazine-1-carbonyl]-3-methyl-1H-pyrrol-2-ylmethylene]-1,3-dihydro-indol-2-one, 3-{4-[trans-3,5-dimethyl-piperazine-1-carbonyl]-3-methyl-1H-pyrrol-2-ylmethylene}-4-(4-methoxy-phenyl)-1,3-dihydro-indol-2-one, 3-{4-[trans-3,5-dimethyl-piperazine-1-carbonyl]-3-methyl-1H-pyrrol-2-ylmethylene}-4-(3-methoxy-phenyl)-1,3-dihydro-indol-2-one, 3-{4-[trans-3,5-dimethyl-piperazine-1-carbonyl]-3-methyl-1H-pyrrol-2-ylmethylene}-4-phenyl-1,3-dihydro-indol-2-one, 4-(4-chloro-phenyl)-3-{4-{3-[trans-3,5-dimethyl-piperazin-1-yl]-3-oxo-propyl}-3,5-dimethyl-1H-pyrrol-2-ylmethylene}-1,3-dihydro-indol-2-one, 3-{4-{3-[trans-3,5-Dimethyl-piperazin-1-yl]-3-oxo-propyl}-3,5-dimethyl-1H-pyrrol-2-ylmethylene}-4-(4-fluoro-phenyl)-1,3-dihydro-indol-2-one, 2-Methyl-4-[3-(4-methyl-piperazin-1-yl)-propyl]-5-(2-oxo-4-phenyl-1,2-dihydro-indol-3-ylidenemethyl)-1H-pyrrole-3-carboxylic acid ethyl ester, 3-[3,5-Dimethyl-4-(4-methyl-piperazine-1-carbonyl)-1H-pyrrol-2-ylmethylene]-4-phenyl-1,3-dihydro-indol-2-one, 2,4-Dimethyl-5-(2-oxo-4-phenyl-1,2-dihydro-indol-3-ylidenemethyl)-1H-pyrrole-3-carboxylic acid (2-diethylamino-ethyl)-amide, 3-[3,5-Dimethyl-4-(4-methyl-piperazine-1-carbonyl)-1H-pyrrol-2-ylmethylene]-4-(4-fluoro-phenyl)-1,3-dihydro-indol-2-one, 5-[4-(4-Fluoro-phenyl)-2-oxo-1,2-dihydro-indol-3-ylidenemethyl]-2,4-dimethyl-1H-pyrrole-3-carboxylic acid (2-diethylamino-ethyl)-amide, 5-[4-(4-Fluoro-phenyl)-2-oxo-1,2-dihydro-indol-3-ylidenemethyl]-2,4-dimethyl-1H-pyrrole-3-carboxylic acid (2-pyrrolidin-1-yl-ethyl)-amide, 5-[4-(4-Fluoro-phenyl)-2-oxo-1,2-dihydro-indol-3-ylidenemethyl]-2,4-dimethyl-1H-pyrrole-3-carboxylic acid (2-[1,2,3]triazol-1-yl-ethyl)-amide, 4-(4-Fluoro-phenyl)-3-[5-methyl-3-(4-methyl piperazine-1-carbonyl)-1H-pyrrol-2-ylmethylene]-1,3-dihydro-indol-2-one, 2-[4-(4-Fluoro-phenyl)-2-oxo-1,2-dihydro-indol-3-ylidenemethyl]-5-methyl-1H-pyrrole-3-carboxylic acid (2-[1,2,3]triazol-1-yl-ethyl) amide, 3-[3-((S)-3-Dimethylamino-pyrrolidine-1-carbonyl)-5-methyl-1H-pyrrol-2-yhnethylene]-4-(4-fluoro-phenyl)-1,3-dihydro indol-2-one, 3-[3-((R)-3-Dimethylamino-pyrrolidine-1-carbonyl)-5-methyl-1H-pyrrol-2-ylmethylene]-4-(4-fluoro-phenyl)-1,3-dihydro indol-2-one, 3-[3,5-Dimethyl-4-(4-methyl-piperazine-1-carbonyl)-1H-pyrrol-2-ylmethylene]-4-(3-fluoro-phenyl)-1,3-dihydro-indol-2-one, 5-[4-(3-Fluoro-phenyl)-2-oxo-1,2-dihydro-indol-3-ylidenemethyl]-2,4-dimethyl-1H-pyrrole-3-carboxylic acid (2-diethylamino-ethyl)-amide, 5-[4-(3-Fluoro-phenyl)-2-oxo-1,2-dihydro-indol-3-ylidenemethyl]-2,4-dimethyl-1H-pyrrole-3-carboxylic acid (2-pyrrolidin-1-yl-ethyl)-amide, 5-[4-(3-Fluoro-phenyl)-2-oxo-1,2-dihydro-indol-3-ylidenemethyl]-2,4-dimethyl-1H-pyrrole-3-carboxylic acid (2-[1,2,3]triazol-1-yl-ethyl)-amide, 3-[3-((S)-3-Dimethylamino-pyrrolidine-1-carbonyl)-5-methyl-1H-pyrrol-2-ylmethylene]-4-(3-fluoro-phenyl)-1,3-dihydro indol-2-one, 3-[3-((R)-3-Dimethylamino-pyrrolidine-1-carbonyl)-5-methyl-1H-pyrrol-2-ylmethylene]-4-(3-fluoro-phenyl)-1,3-dihydro indol-2-one, 5-[4-(3-Fluoro-phenyl)-2-oxo-1,2-dihydro-indol-3-ylidenemethyl]-2-methyl-4-[methyl-piperazin-1-yl)-propyl]-1H-pyrrole-3-carboxylic acid ethyl ester, 3-[3-(cis-3,5-Dimethyl-piperazine-1-carbonyl)-5-methyl-1H-pyrrol-2-ylmethylene]-4-(3-fluoro-phenyl)-1,3-dihydro indol-2-one, 4-(4-Chloro-phenyl)-3-[3,5-dimethyl-4-(4-methyl-piperazine-1-carbonyl)-1H-pyrrol-2-ylmethylene]-1,3-dihydro-indol-2-one, 5-[4-(4-Chloro-phenyl)-2-oxo-1,2-dihydro-indol-3-ylidenemethyl]-2,4-dimethyl-1H-pyrrole-3-carboxylic acid (2-diethylamino-ethyl)-amide, 5-[4-(4-Chloro-phenyl)-2-oxo-1,2-dihydro-indol-3-ylidenemethyl]-2,4-dimethyl-1H-pyrrole-3-carboxylic acid (2-pyrrolidin-1-yl-ethyl)-amide, 5-[4-(4-Chloro-phenyl)-2-oxo-1,2-dihydro-indol-3-ylidenemethyl]-2,4-dimethyl-1H-pyrrole-3-carboxylic acid (2-[1,2,3]triazol-1-yl-ethyl)-amide, 4-(4-Chloro-phenyl)-3-[3-((S)-3-dimethylamino-pyrrolidine-1-carbonyl)-5-methyl-1H-pyrrol-2-ylmethylene]-1,3-dihydro-indol-2-one, 4-(4-Chloro-phenyl)-3-[3-((R)-3-dimethylamino-pyrrolidme-1-carbonyl)-5-methyl-1H-pyrrol-2-ylmethylene]-1,3-dihydro-indol-2-one, 5-[4-(4-Chloro-phenyl)-2-oxo-1,2-dihydro-indol-3-ylidenemethyl]-2-methyl-4-[3-(4-methyl-piperazin-1-yl)-propyl]-1H-pyrrole-3-carboxylic acid ethyl ester, 4-(4-Chloro-phenyl)-3-[3-(cis-3,5-dimethyl-piperazine-1-carbonyl)-5-methyl-1H-pyrrol-2 ylmethylene]-1,3-dihydro-indol-2-one, 4-(3-Chloro-phenyl)-3-[3,5-dimethyl-4-(4-methyl-piperazine-1-carbonyl)-1H-pyrrol-2-ylmethylene]-1,3-dihydro-indol-2-one, 5-[4-(3-Chloro-phenyl)-2-oxo-1,2-dihydro-indol-3-ylidenemethyl]-2,4-dimethyl-1H-pyrrole-3-carboxylic acid (2-diethylamino-ethyl)-amide, 5-[4-(3-Chloro-phenyl)-2-oxo-1,2-dihydro-indol-3-ylidenemethyl]-2,4-dimethyl-1H-pyrrole-3-carboxylic acid (2-pyrrolidin-1-yl-ethyl)-amide, 5-[4-(3-Chloro-phenyl)-2-oxo-1,2-dihydro-indol-3-ylidenemethyl]-2,4-dimethyl-1H-pyrrole-3-carboxylic acid (2-[1,2,3]triazol-1-yl-ethyl)-amide, 4-(3-Chloro-phenyl)-3-[3-((S)-3-dimethylamino-pyrrolidine-1-carbonyl)-5-methyl-1H-pyrrol-2-ylmethylene]-1,3-dihydro-indol-2-one, 4-(3-Chloro-phenyl)-3-[3-((R)-3-dimethylamino-pyrrolidine-1-carbonyl)-5-methyl-1H-pyrrol-2-ylmethylene]-1,3-dihydro-indol-2-one, 2-[4-(3-Chloro-phenyl)-2-oxo-1,2-dihydro-indol-3-ylidenemethyl]-5-methyl-1H-pyrrole-3-carboxylic acid (2-[1,2,3]triazol-1-yl-ethyl)-amide, 4-(3-Chloro-phenyl)-3-[3-(cis-3,5-dimethyl-piperazine-1-carbonyl)-5-methyl-1H-pyrrol-2 ylmethylene]-1,3-dihydro-indol-2-one, 3-[3,5-Dimethyl-4-(4-methyl-piperazine-1-carbonyl)-1H-pyrrol-2-ylmethylene]-4-(4-methoxy-phenyl)-1,3-dihydro-indol-2-one, 5-[4-(4-Methoxy-phenyl)-2-oxo-1,2-dihydro-indol-3-ylidenemethy]-2,4-dimethyl-1H-pyrrole-3-carboxylic acid (2-diethylamino-ethyl)-amide, 5-[4-(4-Methoxy-phenyl)-2-oxo-1,2-dihydro-indol-3-ylidenemethyl]-2,4-dimethyl-1H-pyrrole-3-carboxylic acid (2-pyrrolidin-1-yl-ethyl)-amide, 5-[4-(4-Methoxy-phenyl)-2-oxo-1,2-dihydro-indol-3-ylidenemethyl]-2,4-dimethyl-1H-pyrrole-3-carboxylic acid (2-[1,2,3]triazol-1-yl-ethyl)-amide, 3-[4-(cis-3,5-Dimethyl-piperazine-1-carbonyl)-3,5-dimethyl-1H-pyrrol-2-ylmethylene]-4-(4-methoxy-phenyl)-1,3-dihydro-indol-2-one, 2-[4-(4-Methoxy-phenyl)-2-oxo-1,2-dihydro-indol-3-ylidenemethyl]-5-methyl-1H-pyrrole-3-carboxylic acid (2-pyrrolidin-1-yl-ethyl)-amide, 2-[4-(4-Methoxy-phenyl)-2-oxo-1,2-dihydro-indol-3-ylidenemethyl]-5-methyl-1H-pyrrole-3-carboxylic acid (2-[1,2,3]triazol-1-yl-ethyl)-amide, 3-[3-((S)-3-Dimethylamino-pyrrolidine-1-carbonyl)-5-methyl-1H-pyrrol-2-ylmethylene]-4-(4-methoxy-phenyl)-1,3-dihydro-indol-2-one, 3-[3-((R)-3-Dimethylamino-pyrrolidine-1-carbonyl)-5-methyl-1H-pyrrol-2-ylmethylene]-4-(4-methoxy-phenyl)-1,3-dihydro-indol-2-one, 3-[3,5-Dimethyl-4-(4-methyl-piperazine-1-carbonyl)-1H-pyrrol-2-ylmethylene]-4-(3-methoxy-phenyl)-1,3-dihydro-indol-2-one, 5-[4-(3-Methoxy-phenyl)-2-oxo-1,2-dihydro-indol-3-ylidenemethyl]-2,4-dimethyl-1H-pyrrole-3-carboxylic acid (2-diethylamino-ethyl)-amide, 5-[4-(3-Methoxy-phenyl)-2-oxo-1,2-dihydro-indol-3-ylidenemethyl]-2,4-dimethyl-1H-pyrrole-3-carboxylic acid (2-pyrrolidin-1-yl-ethyl)-amide, 5-[4-(3-Methoxy-phenyl)-2-oxo-1,2-dihydro-indol-3-ylidenemethyl]-2,4-dimethyl-1H-pyrrole-3-carboxylic acid (2-[1,2,3]triazol-1-yl-ethyl)-amide, 3-[4-(cis-3,5-Dimethyl-piperazine-1-carbonyl)-3,5-dimethyl-1H-pyrrol-2-yl methylene]-4-(3-methoxy-phenyl)-1,3-dihydro-indol-2-one, 2-[4-(3-Methoxy-phenyl)-2-oxo-1,2-dihydro-indol-3-ylidenemethyl]-5-methyl-1H-pyrrole-3-carboxylic acid (2-pyrrolidin-1-yl-ethyl)-amide, 2-[4-(3-Methoxy-phenyl)-2-oxo-1,2-dihydro-indol-3-ylidenemethyl]-5-methyl-1H-pyrrole-3-carboxylic acid (2-[1,2,3]triazol-1-yl-ethyl)-amide, 5-[4-(3-Methoxy-phenyl)-2-oxo-1,2-dihydro-indol-3-ylidenemethyl]-2,4-dimethyl-1H-pyrrole-3-carboxylic acid (2-diisopropylamino-ethyl)-amide, 4-(4-Bromo-phenyl)-3-[3,5-dimethyl-4-(4-methyl-piperazine-1-carbonyl)-1H-pyrrol-2-ylmethylene]-1,3-dihydro-indo 1-2-one, 5-[4-(4-Bromo-phenyl)-2-oxo-1,2-dihydro-indol-3-ylidenemethyl]-2,4-dimethyl-1H-pyrrole-3-carboxylic acid (2-diethylamino-ethyl)-amide, 5-[4-(4-Bromo-phenyl)-2-oxo-1,2-dihydro-indol-3-ylidenemethyl]-2,4-dimethyl-1H-pyrrole-3-carboxylic acid (2-pyrrolidin-1-yl-ethyl)-amide, 5-[4-(4-Bromo-phenyl)-2-oxo-1,2-dihydro-indol-3-ylidenemethyl]-2,4-dimethyl-1H-pyrrole-3-carboxylic acid (2-[1,2,3]triazol-1-yl-ethyl)-amide, 4-(4-Bromo-phenyl)-3-[4-[cis-3,5-dimethyl-piperazine-1-carbonyl)-3,5-dimethyl-1H-pyrrol-2-ylmethylene]-1,3-dihydro-indol-2-one, 2-[4-(4-Bromo-phenyl)-2-oxo-1,2-dihydro-indol-3-ylidenemethyl]-5-methyl-1H-pyrrole-3-carboxylic acid (2-pyrrolidin-1-yl-ethyl)-amide, 2-[4-(4-Bromo-phenyl)-2-oxo-1,2-dihydro-indol-3-ylidenemethyl]-5-methyl-1H-pyrrole-3-carboxylic acid (2-E1,2,3]triazol-1-yl-ethyl)-amide, 5-[4-(4-Bromo-phenyl)-2-oxo-1,2-dihydro-indol-3-ylidenemethyl]-2,4-dimethyl-1H-pyrrole-3-carboxylic acid (2-diisopropylamino-ethyl)-amide, 5-[4-(4-Bromo-phenyl)-2-oxo-1,2-dihydro-indol-3-ylidenemethyl]-4-methyl-1H-pyrrole-3-carboxylic acid (2-diethylamino-ethyl)-amide, 3-[3,5-Dimethyl-4-(4-methyl-piperazine-1-carbonyl)-1H-pyrrol-2-ylmethylene]-4-(3-bromo-phenyl)-1,3-dihydro-indol-2-one, 5-[4-(3-Bromo-phenyl)-2-oxo-1,2-dihydro-indol-3-ylidenemethyl]-2,4-dimethyl-1H-pyrrole-3-carboxylic acid (2-diethylamino-ethyl)-amide, 5-[4-(3-Bromo-phenyl)-2-oxo-1,2-dihydro-indol-3-ylidenemethyl]-2,4-dimethyl-1H-pyrrole-3-carboxylic acid (2-pyrrolidin-1-yl-ethyl)-amide, 5-[4-(3-Bromo-phenyl)-2-oxo-1,2-dihydro-indol-3-ylidenemethyl]-2,4-dimethyl-1H-pyrrole-3-carboxylic acid (2-[1,2,3]triazol-1-yl-ethyl)-amide, 3-[4-(cis-3,5-Dimethyl-piperazine-1-carbonyl)-3,5-dimethyl-1H-pyrrol-2-ylmethylene]-4-(3-bromo-phenyl)-1,3-dihydro-indol-2-one, 2-[4-(3-Bromo-phenyl)-2-oxo-1,2-dihydro-indol-3-ylidenemethyl]-5-methyl-1H-pyrrole-3-carboxylic acid (2-pyrrolidin-1-yl-ethyl)-amide, 2-[4-(3-Bromo-phenyl)-2-oxo-1,2-dihydro-indol-3-ylidenemethyl]-5-methyl-1H-pyrrole-3-carboxylic acid (2-[1,2,3)triazol-1-yl-ethyl)-amide, 5-[4-(3-Bromo-phenyl)-2-oxo-1,2-dihydro-indol-3-ylidenemethyl]-2,4-dimethyl-1H-pyrrole-3-carboxylic acid (2-diisopropylamino-ethyl)-amide, 5-[4-(4-Fluoro-phenyl)-2-oxo-1,2-dihydro-indol-3-ylidenemethyl]-4-methyl-1H-pyrrole-2-carboxylic acid (2-diethylamino-ethyl)-amide, 5-[4-(3-Fluoro-phenyl)-2-oxo-1,2-dihydro-indol-3-ylidenemethyl]-4-methyl-1H-pyrrole-2-carboxylic acid (2-diethylamino-ethyl)-amide, 5-[4-(4-Chloro-phenyl)-2-oxo-1,2-dihydro-indol-3-ylidenemethyl]-4-methyl-1H-pyrrole-2-carboxylic acid (2-diethylamino-ethyl)-amide, 5-[4-(3-Chloro-phenyl)-2-oxo-1,2-dihydro-indol-3-ylidenemethyl]-4-methyl-1H-pyrrole-2-carboxylic acid (2-diethylamino-ethyl)-amide, 5-[4-(4-Bromo-phenyl)-2-oxo-1,2-dihydro-indol-3-ylidenemethyl]-4-methyl-1H-pyrrole-2-carboxylic acid (2-diethylamino-ethyl)-amide, 5-[4-(3-Bromo-phenyl)-2-oxo-1,2-dihydro-indol-3-ylidenemethyl]-4-methyl-1H-pyrrole-2-carboxylic acid (2-diethylamino-ethyl)-amide, 5-[4-(4-Methoxy-phenyl)-2-oxo-1,2-dihydro-indol-3-ylidenemethyl]-4-methyl-1H-pyrrole-2-carboxylic acid (2-diethylamino-ethyl)-amide, 5-[4-(3-Methoxy-phenyl)-2-oxo-1,2-dihydro-indol-3-ylidenemethyl]-4-methyl-1H-pyrrole-2-carboxylic acid (2-diethylamino-ethyl)-amide, 3-(3,5-Dimethyl-1H-pyrrol-2-ylmethylene)-4 (4-fluoro-phenyl)-1,3-dihydro-indol-2-one, 3-(3,5-Dimethyl-1H-pyrrol-2-ylmethylene)-4 (3-fluoro-phenyl)-1,3-dihydro-indol-2-one, 3-(3,5-Dimethyl-1H-pyrrol-2-ylmethylene)-4 (4-chloro-phenyl)-1,3-dihydro-indol-2-one, 3-(3,5-Dimethyl-1H-pyrrol-2-ylmethylene)-4 (3-chloro-phenyl)-1,3-dihydro-indol-2-one, 3-(3,5-Dimethyl-1H-pyrrol-2-ylmethylene)-4 (4-bromo-phenyl)-1,3-dihydro-indol-2-one, 3-(3,5-Dimethyl-1H-pyrrol-2-ylmethylene)-4 (3-bromo-phenyl)-1,3-dihydro-indol-2-one, 3-(3,5-Dimethyl-1H-pyrrol-2-ylmethylene)-4 (4-methoxy-phenyl)-1,3-dihyoro-indol-2-one, 3-(3,5-Dimethyl-1H-pyrrol-2-ylmethylene)-4 (3-methoxy-phenyl)-1,3-dihydro-indol-2-one, 5-[4-(4-Fluoro-phenyl)-2-oxo-1,2-dihydro-indol-3-ylidenemethyl]-4-methyl-1H-pyrrole-3-carboxylic acid (2-diethylamino-ethyl)-amide, 5-[4-(3-Fluoro-phenyl)-2-oxo-1,2-dihydro-indol-3-ylidenemethyl]-4-methyl-1H-pyrrole-3-carboxylic acid (2-diethylamino-ethyl)-amide, 5-[4-(4-Chloro-phenyl)-2-oxo-1,2-dihydro-indol-3-ylidenemethyl]-4-methyl-1H-pyrrole-3-carboxylic acid (2-diethylamino-ethyl)-amide, 5-[4-(3-Chloro-phenyl)-2-oxo-1,2-dihydro-indol-3-ylidenemethyl]-4-methyl-1H-pyrrole-3-carboxylic acid (2-diethylamino-ethyl)-amide, 5-[4-(3-bromo-phenyl)-2-oxo-1,2-dihydro-indol-3-ylidenemethyl]-4-methyl-1H-pyrrole-3-carboxylic acid (2-diethylamino-ethyl)-amide, 5-[4-(4-Methoxy-phenyl)-2-oxo-1,2-dihydro-indol-3-ylidenemethyl]-4-methyl-1H-pyrrole-3-carboxylic acid (2-diethylamino-ethyl)-amide, 5-[4-(3-Methoxy-phenyl)-2-oxo-1,2-dihydro indol-3-ylidenemethyl]-4-methyl-1H-pyrrole-3-carboxylic acid (2-diethylamino-ethyl)-amide, 3-[3,5-Dimethyl-4-(4-methyl-piperazine-1-carbonyl)-1H-pyrrol-2-ylmethylene]-4-(2-fluoro-phenyl)-1,3-dihydro-indol-2-one, 5-[4-(2-Fluoro-phenyl)-2-oxo-1,2-dihydro-indol-3-ylidenemethyl]-2,4-dimethyl-1H-pyrrole-3-carboxylic acid (2-diethylamino-ethyl)-amide, 5-[4-(2-Fluoro-phenyl)-2-oxo-1,2-dihydro-indol-3-ylidenemethyl]-2,4-dimethyl-1H-pyrrole-3-carboxylic acid (2-pyrrolidin-1-yl-ethyl)-amide, 5-[4-(2-Fluoro-phenyl)-2-oxo-1,2-dihydro-indol-3-ylidenemethyl]-2,4-dimethyl-1H-pyrrole-3-carboxylic acid (2-[1,2,3]triazol-1-yl-ethyl)-amide, 2-[4-(2-fluoro-phenyl)-2-oxo-1,2-dihydro-indol-3-ylidenemethyl]-5-methyl-1H-pyrrole-3-carboxylic acid (2-diethylamino-ethyl)-amide, 2-[4-(2-fluoro-phenyl)-2-oxo-1,2-dihydro-indol-3-ylidenemethyl]-5-methyl-1H-pyrrole-3-carboxylic acid (2-pyrrolidin-1-yl-ethyl)-amide, 2-[4-(2-fluoro-phenyl)-2-oxo-1,2-dihydro-indol-3-ylidenemethyl]-5-methyl-1H-pyrrole-3-carboxylic acid (2-[1,2,3]triazol-1-yl-ethyl) amide, 3-[3-(cis-3,5-dimethyl-piperazine-1-carbonyl)-5-methyl-1H-pyrrol-2-ylmethylene]-4-(2-fluoro-phenyl)-1,3-dihydro indol-2-one, 5-[4-(4-Fluoro-phenyl)-2-oxo-1,2-dihydro-indol-3-ylidenemethyl]-2,4-dimethyl-1H-pyrrole-3-carboxylic acid (3-diethylamino-propyl)-amide, 2-[4-(4-fluoro-phenyl)-2-oxo-1,2-dihydro-indol-3-ylidenemethyl]-5-methyl-1H-pyrrole-3-carboxylic acid (3-pyrrolidin-1-yl-propyl)-amide, 5-[4-(3-Fluoro-phenyl)-2-oxo-1,2-dihydro-indol-3-ylidenemethyl]-2,4-dimethyl-1H-pyrrole-3-carboxylic acid (3-diethylamino-propyl)-amide, 3-[3,5-Dimethyl-4-(4-methyl-piperazine-1-carbonyl)-1H-pyrrol-2-ylmethylene]-4-(3-trifluoromethyl-phenyl)-1,3-dihydro-indol-2-one, 2,4-Dimethyl-5-[2-oxo-4-(3-trifluoromethyl-phenyl)-1,2-dihydro-indol-3-ylidenemethyl]-1H-pyn-ole-3-carboxylic acid (2-diethylamino-ethyl)-amide, 2,4-Dimethyl-5-[2-oxo-4-(3-trifluoromethyl-phenyl)-1,2-dihydro-indol-3-ylidenemethyl]-1H-pyrrole-3-carboxylic acid (2-pyrrolidin-1-yl-ethyl)-amide, 2,4-Dimethyl-5-[2-oxo-4-(3-trifluoromethyl-phenyl)-1,2-dihydro-indol-3-ylidenemethyl]-1H-pyrrole-3-carboxylic acid (2-[1,2,3]triazol-1-yl-ethyl)-amide, 5-methyl-2-[2-oxo-4-(3-trifluoromethyl-phenyl)-1,2-dihydro-indol-3-ylidenemethyl]-1H-pyrrole-3-carboxylic acid (2-diethylamino-ethyl)-amide, 5-methyl-2-[2-oxo-4-(3-trifluoromethyl-phenyl)-1,2-dihydro-indol-3-ylidenemethyl]-1H-pyrrole-3-carboxylic acid (2-pyrrolidin-1-yl-ethyl)-amide, 5-methyl-2-[2-oxo-4-(3-trifluoromethyl-phenyl)-1,2-dihydro-indol-3-ylidenemethyl]-1H-pyrrole-3-carboxylic acid (2-[1,2,3]triazol-1-yl-ethyl)-amide, 3-[3-(cis-3,5-dimethyl-piperazine-1-carbonyl)-5-methyl-1H-pyrrol-2-ylmethylene]-4-(2-trifluoromethyl-phenyl)-1,3-dihydro-indol-2-one 2,4-Dimethyl-~-[2-oxo-4-(3-trifluoromethyl-phenyl)-1,2-dihydro-indol-3-ylidenemethyl]-1H-pyrrole-3-carboxylic acid (3-diethylamino-propyl)-amide, 2,4-Dimethyl-5-[2-oxo-4-(3-trifluoromethyl-phenyl)-1,2dihydro-indol-3-ylidenemethyl]-1H-pyrrole-3-carboxylic acid (3-diethylamino-propyl)-amide, 5-methyl-2-[2-oxo-4-(3-trifluoromethyl-phenyl)-1,2-dihydro-indol-3-ylidenemethyl]-1H-pyrrole-3-carboxylic acid (3-pyrrolidin-1-yl-propyl)-amide, 3-[3-methyl-4-(4-methyl-piperazine-1-carbonyl)-1H-pyrrol-2-ylmethylene]-4 (3-trifluorometbyl-phenyl)-1, 3-dihydro indol-2-one, 3-[3-Methyl-4-(cis-3,5-dimethyl-piperazine-1-carbonyl)-1H-pyrrol-2-ylmethylene]-4-(3-trifluoromethyl-phenyl)-1,3-dihydro-indol-2-one, 4-(3-chloro-4-fluoro-phenyl)-3-[3,5-dimethyl-4-(4-methyl-piperazine-1-carbonyl)-1H-pyrrol-2-ylmethylene]-1,3-dihydro-indol-2-one, 5-[4-(3-chloro-4-fluoro-phenyl)-2-oxo-1,2-dihydro-indol-3-ylidenemethyl]-2,4-dimethyl-1H-pyrrole-3-carboxylicacid (2-diethylamino-ethyl)-amide, 5-[4-(3-chloro-4-fluoro-phenyl)-2-oxo-1,2-dihydro-indol-3-ylidenemethyl]-2,4-dimethyl-1H-pyrrole-3-carboxylicacid (2-[1,2,3]triazol-1-yl-ethyl)-amide, 2-[4-(3-chloro-4-fluoro-phenyl)-2-oxo-1,2-dihydro-indol-3-ylidenemethyl]-5-methyl-1H-pyrrole-3-carboxylic acid (2-pyrrolidin-1-yl-ethyl)-amide, 2-[4-(3-chloro-4-fluoro-phenyl)-2-oxo-1,2-dihydro-indol-3-ylidenemethyl]-5-methyl-1H pyrrole-3-carboxylic acid (2-[1,2,3]triazol-1-yl-ethyl)-amide, 2-[4-(3-chloro-4-fluoro-phenyl)-2-oxo-1,2-dihydro-indol-3-ylidenemethyl]-5-methyl-1H pyrrole-3-carboxylic acid (3-pyrrolidin-1-yl-propyl)-amide, 4-(4-chloro-phenyl)-3-[3,5-dimethyl-4-[3-(4-methyl-piperazin-1-yl)-3-oxo-propyl]-1H-pyrrol-2-ylmethylene]-1,3-dihydro-indol-2-one, 4-(2-fluoro-phenyl)-3-[3-methyl-4-(4-methyl-piperazine-1-carbonyl)-1H-pyrrol-2-ylmethylene]-1,3-dihydro-indol-2-one, 4-(4-fluoro-phenyl)-3-[3-methyl-4-(4-methyl-piperazine-1-carbonyl)-1H-pyrrol-2-ylmethylene]-1,3-dihydro-indol-2-one, 4-(4-chloro-phenyl)-3-[3-methyl-4-(4-methyl-piperazine-1-carbonyl)-1H-pyrrol-2-ylmethylene]-1,3-dihydro-indol-2-one, 4-(4-bromo-phenyl)-3-[3-methyl-4-(4-methyl-piperazine-1-carbonyl)-1H-pyrrol-2-ylmethylene]-1,3-dihydro-indol-2-one, 4-(3-bromo-phenyl)-3-[3-methyl-4-(4-methyl-piperazine-1-carbonyl)-1H-pyrrol-2-ylmethylene]-1,3-dihydro-indol-2-one, 4-(4-methoxy-phenyl)-3-[3-methyl-4-(4-methyl-piperazine-1-carbonyl)-1H-pyrrol-2-ylmethylene]-1,3-dihydro-indol-2-one, 4-(3-methoxy-phenyl)-3-[3-methyl-4-(4-methyl-piperazine-4-carbonyl)-1H-pyrrol-2-ylmethylene]-1,3-dihydro-indol-2-one, 3-[3-methyl-4-(4-methyl-piperazine-1-carbonyl)-1H-pyrrol-2-ylmethylene]-4-phenyl-1,3-dihydro-indol-2-one, 3-[4-(cis-3,5-dimethyl-piperazine-1-carbonyl)-3-methyl-1H-pyrrol-2-ylmethylene]-4-(4-fluoro-phenyl)-1,3-dihydro indol-2-one, 4-(4-Chloro-phenyl)-3-[4-[cis-3,5-dimethyl-piperazine-4-1-carbonyl]-3-methyl-1H-pyrrol-2 ylmethylene]-1,3-dihydro-indol-2-one, 4-(4-Bromo-phenyl)-3-[4-(cis-3,5-dimethyl-piperazine-1-carbonyl)-3-methyl-1H-pyrrol-2 ylmethylene]-1,3-dihydro-indol-2-one, 3-[4-(cis-3,5-dimethyl-piperazine-1-carbonyl)-3-methyl-1H-pyrrol-2-ylmethylene-4-(4-methoxy-phenyl)-1,3-dihydro-indol-2-one, 3-[4-(cis-3,5-dimethyl-piperazine-1-carbonyl)-3-methyl-1H-pyrrol-2-ylmethylene]-4-(3-methoxy-phenyl)-1,3-dihydro-indol-2-one, 3-[4-(cis-3,5-dimethyl-piperazine-1-carbonyl)-3-methyl-1H-pyrrol-2-ylmethylene]-4-phenyl-1,3-dihydro-indol-2-one, 4-(4-chloro-phenyl)-3-[4-[3-(cis-3,5-dimethyl-piperazin-1-yl)-3-oxo-propyl]-3,5-dimethyl-1H-pyrrol-2-ylmethylene]-1,3-dihydro-indol-2-one, 3-[4-[3-(cis-3,5-Dimethyl-piperazin-1-yl)-3-oxo-propyl]-3,5-dimethyl-1H-pyrrol-2-ylmethylene]-4-(4-fluoro-phenyl)-1,3-dihydro-indol-2-one, 3-[3,5-Dimethyl-4-(4-methyl-piperazine-1-carbonyl)-1H-pyrrol-2-ylmethylene]-4-(4-trifluoromethoxy-phenyl)-1,3-dihydro-indol-2one, 2,4-Dimethyl-5-[2-oxo-4-(4-trifluoromethoxyphenyl)-1,2-dihydro-indol-3-ylidenemethyl]-1H-pyrrole-3-carboxylic acid (2-diethylamino-ethyl)-amide, 2,4-Dimethyl-5-[2-oxo-4-(4-trifluoromethoxy phenyl)-1,2-dihydro-indol-3-ylidenemethyl]-1H-pyrrole-3-carboxylic acid (2-[1,2,3]triazol 1-yl-ethyl)-amide, 5-methyl-2-[2-oxo-4-(4-trifluoromethoxy-phenyl)-1,2-dihydro-indol-3-ylidenemethyl]-1H-pyrrole-3-carboxylic acid (2-pyrrolidin-1-yl-ethyl)-amide, 5-methyl-2-[2-oxo-4-(4-trifluoromethoxy-phenyl)-1,2-dihydro-indol-3-ylidenemethyl]-1H-pyrrole-3-carboxylic acid (2-[1,2,3]triazol 1-yl-ethyl)-amide, 5-methyl-2-[2-oxo-4-(4-trifluoromethoxy-phenyl)-1,2-dihydro-indol-3-ylidenemethyl]-1H-pyrrole-3-carboxylic acid (3-pyrrolidin-1-yl-propyl)-amide, 3-[3-(trans-3,5-Dimethyl-piperazine-1-carbonyl)-5-methyl-1H-pyrrol-2-ylmethylene]-4-(3-fluoro-phenyl)-1,3-dihydro indol-2-one, 4-(4-Chloro-phenyl)-3-[3-(trans-3,5-dimethyl piperazine-1-carbonyl)-5-methyl-1H-pyrrol-2 ylmethylene]-1,3-dihydro-indol-2-one, 4-(3-Chloro-phenyl)-3-[3-(trans-3,5-dimethyl piperazine-1-carbonyl)-5-methyl-1H-pyrrol-2 ylmethylene]-1,3-dihydro-indol-2-one, 3-[4-(trans-3,5-Dimethyl-piperazine-1-carbonyl)-3,5-dimethyl-1H-pyrrol-2-ylmethylene]-4-(4-methoxy-phenyl)-1,3-dihydro-indol-2-one, 3-[4-(trans-3,5-Dimethyl-piperazine-1-carbonyl)-3,5-dimethyl-1H-pyrrol-2-ylmethylene]-4-(3-methoxy-phenyl)-1,3-dihydro-indol-2-one, 4-(4-Bromo-phenyl)-3-[4-[trans-3,5-dimethyl piperazine-1-carbonyl)-3,5-dimethyl-1H-pyrrol-2-ylmethylene]-1,3-dihydro-indol-2-one, 3-[4-(trans-3,5-Dimethyl-piperazine-1-carbonyl)-3,5-dimethyl-1H-pyrrol-2-ylmethylene]-4-(3-bromo-phenyl)-1,3-dihydro-indol-2-one, 3-[3-[trans-3,5-dimethyl-piperazine-1-carbonyl]-5-methyl-1H-pyrrol-2-ylmethylene]-4-(2-fluoro-phenyl)-1,3-dihydro-indol-2-one, 3-[3-[trans-3,5-dimethyl-piperazine-1-carbonyl]-5-methyl-1H-pyrrol-2-ylmethylene]-4-(2-trifluoromethyl-phenyl)-1,3-dihydro-indol-2-one, 3-[3-Methyl-4-[trans-3,5-dimethyl-piperazine-1-carbonyl]-1H-pyrrol-2-ylmethylene]-4-(3-trifluoromethyl-phenyl)-1,3-dihydro-indo 1-2-one, 3-[4-[trans-3,5-dimethyl-piperazine-1-carbonyl]-3-methyl-1N-pyrrol-2-ylmethylene]-4-(4-fluoro-phenyl)-1,3-dihydro-indol-2-one, 4-(4-Chloro-phenyl)-3-[4-[trans-3,5-dimethyl-piperazine-1-carbonyl]-3-methyl-1H-pyrrol-2-ylmethylene]-1,3-dihydro-indol-2-one, 4-(4-Bromo-phenyl)-3-[4-[trans-3,5-dimethyl-piperazine-1-carbonyl]-3-methyl-1H-pyrrol-2-ylmethylene]-1,3-dihydro-indol-2-one, 3-[4-[trans-3,5-dimethyl-piperazine-1-carbonyl]-3-methyl-1H-pyrrol-2-ylmethylene]-4-(4-methoxy-phenyl)-1,3-dihydro-indol-2-one, 3-[4-[trans-3,5-dimethyl-piperazine-1-carbonyl]-3-methyl-1H-pyrrol-2-ylmethylene]-4-(3-methoxy-phenyl)-1,3-dihydro-indol-2-one, 3-{4-[trans-3,5-dimethyl-piperazine-1-carbonyl]-3-methyl-1H-pyrrol-2-ylmethylene]-4-phenyl-1,3-dihydro-indol-2-one, 4-(4-chloro-phenyl)-3-(4-[3-[trans-3,5-dimethyl-piperazin-1-yl]-3-oxo-propyl]-3,5-dimethyl-1H-pyrrol-2-ylmethylene]-1,3-dihydro-indol-2-one; and 3-(4-[3-[trans-3,5-Dimethyl-piperazin-1-yl]-3-oxo-propyl]-3,5-dimethyl-1H-pyrrol-2-ylmethylene]-4-(4-fluoro-phenyl)-1,3-dihydro-indol-2-one.

3. A method of modulating the catalytic activity of a protein kinase comprising contacting said protein kinase with a compound of claim 1, or a pharmaceutically acceptable salt thereof.

4. The method of claim 3, wherein said protein kinase is selected from the group consisting of a receptor tyrosine kinase, a non-receptor tyrosine kinase and a serine-threonine kinase.

5. The method of claim 4, wherein said receptor tyrosine kinase whose catalytic activity is modulated by a compound of this invention is selected from the group consisting of EGF, HER2, HER3, HER4, IR, IGF-IR, IRR, PDGFRα, PDGFRβ, CSFIR, C-Kit, C-fms, Flk-1R, Flk4, KDR/Flk-1, Flt-1, FGFR-1R, FGFR-2R, FGFR-3R, FGFR-4R, DDR-1, DDR-2 and Met.

6. The method of claim 4, wherein said cellular tyrosine kinase whose catalytic activity is modulated by a compound of this invention is selected from the group consisting of Src, Frk, Btk, Csk, Abl, ZAP70, Fes/Fps, Fak, Jak, Ack, Yes, Fyn, Lyn, Lck, BIk, Hck, Fgr, Aur 2 and Yrk.

7. The method of claim 4, wherein said serine-threonine protein kinase whose catalytic activity is modulated by a compound of this invention is selected from the group consisting of CDK2, Raf, NEK and BUB 1.

8. A method for treating a protein kinase related disorder comprising administering to an organism in need thereof a therapeutically effective amount of a compound of claim 1, or pharmaceutically acceptable salt thereof.

9. The method of claim 8, wherein said protein kinase related disorder is selected from the group consisting of a receptor tyrosine kinase related disorder, a non-receptor tyrosine kinase disorder and a serine-threonine kinase related disorder.

10. The method of claim 8, wherein said protein kinase related disorder is selected from the group consisting of a MET kinase related disorder, FLK kinase related disorder, a FGFR kinase related disorder, SRC kinase related disorder, a DDR kinase related disorder, and a PDGFR kinase related disorder.

11. The method of claim 8, wherein said protein kinase related disorder is a cancer.

12. The method of claim 11, wherein said cancer is selected from the group consisting of squamous cell carcinoma, astrocytoma, Kaposi's sarcoma, glioblastoma, lung cancer, bladder cancer, head and neck cancer, melanoma, ovarian cancer, prostate cancer, breast cancer, small-cell lung cancer, glioma, colorectal cancer, genitourinary cancer and gastrointestinal cancer.

13. The method of claim 8, wherein said protein kinase related disorder is selected from the group consisting of diabetes, an autoimmune disorder, a hyperproliferation disorder, restenosis, fibrosis, psoriasis, von Heppel-Lindau disease, osteoarthritis, rheumatoid arthritis, angiogenesis, an inflammatory disorder, an immunological disorder and a cardiovascular disorder.

14. The method of claim 8, wherein said organism is a human.

15. A pharmaceutical composition comprising a compound of claim 1 or a pharmaceutically acceptable salt thereof.

16. The pharmaceutical composition of claim 15, which further comprises a phamaceutically acceptable carrier or excipient.

17. The pharmaceutical composition of claim 15, which further comprises other therapeutic agents.

18. The pharmaceutical composition of claim 17, wherein the other therapeutic agent is selected from the group consisting of an alkylating agent, an antimetabolic chemotherapeutic agent, a natural product based chemotherapeutic agent, mitoxantrone or paclitaxel.

19. A compound of formula II:

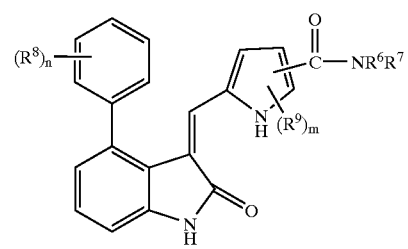

III wherein each $R^8$ is independently halogen, —$OR^6$, —$COR^6$, —$COOR^6$, $OCOR^6$, —$CONR^6R^7$, —$R^6NCOR^7$, —$NR^6R^7$, —CN, —$NO_2$, —$CX_3$, —$SR^6$, $SOR^6$, —$SO_2R^6$, —$SO_2OR^6$, —$SO_2NR^6R^7$, —$R^6NSO_2R^7$, perfluoroalkyl, lower alkyl, lower alkyl further substituted by one or more of $R^2$, lower alkenyl, lower alkenyl further substituted by one or more of $R^2$, lower alkynyl, lower alkynyl further substituted by one or more of $R^2$, cycloalkyl, cycloalkyl further substituted by one or more of $R^2$, a heterocylic ring, a heterocylic ring further substituted by one or more of $R^2$, aryl and aryl further substituted by one or more of $R^2$;

$R^2$ is selected from the group consisting of hydrogen, halogen, —$OR^6$, —$COR^6$, —$COOR^6$, $OCOR^6$, —$CONR^6R^7$, —$R^{12}NCOR^{13}$, —$NR^6R^7$, —$R^6NC(O)R^7$, —CN, —$NO_2$, —$CX_3$, —$SR^6$, $SOR^6$, —$SO_2R^6$, —$SO_2OR^6$, —$SO_2NR^6R^7$, —$R^6NSO_2R^7$, perfluoroalkyl, lower alkyl, lower alkenyl, lower alkynyl, cycloalkyl, a heterocyclic ring and aryl;

$R^6$ and $R^7$ are independently selected from the group consisting of hydrogen, —$CX_3$, perfluoroalkyl, lower alkyl, lower alkenyl, lower alkynyl, cycloalkyl, a heterocyclic ring and aryl;

wherein lower alkyl, lower alkenyl, lower alkynyl, cycloalkyl, the heteocyclic ring or aryl may be further substituted by one or more of (i) —$NR^{12}R^{13}$, (ii) hydroxy, (iii) halo, (iv) a heterocyclic ring, (v) lower alkyl, (vi) —$C(O)$—$NR^{12}R^{13}$, (vii) —$OR^{12}$, (viii) —$SO_2R^{12}R^{13}$, or (ix) —$COR^6$;

wherein said heterocyclic ring (iv) may be further substituted by one or more of lower alkyl, —$COR^{12}$, —$NR^{12}COR^{13}$, halogen, —$OR^{12}$, $CX_3$, —$C(O)NR^{12}R^{13}$, —$SO_2R^{12}R^{13}$, or —$SO_2NR^{12}R^{13}$, or $R^6$ and $R^7$ may be linked together to form a 4, 5- or 6-membered ring, optionally containing a hetero atom selected from the group consisting of N, O, S and $SO_2$, which may be further substituted by —$CONR^{12}R^{13}$, lower alkyl, hydroxy, —$(CH_2)_n$—$NR^{12}R^{13}$, —$(CH_2)_n$-heterocycle, —$(CH_2)_n$—$C(O)$—$NR^{12}R^{13}$, —$(CH_2)_n$$SO_2R^{12}R^{13}$, or —$(CH_2)_nNSO_2R^{12}R^{13}$, wherein said heterocycle may be further substituted by halo, lower alkyl, —$COR^{12}$, hydroxy, —$C(O)$—$NR^{12}R^{13}$, —$OR^{12}$, —$SO_2R^{12}R^{13}$, or —$SO_2NR^{12}R^{13}$;

X is fluorine, chlorine, bromine or iodine;

$R^{12}$ is selected from the group consisting of hydrogen, —$CX_3$, perfluoroalkyl, lower alkyl, lower alkenyl, lower alkynyl, —$(CH_2)_n$-cycloalkyl, —$(CH_2)_n$-heterocycle, and aryl;

$R^{13}$ is selected from the group consisting of hydrogen, —$CX_3$, perfluoroalkyl, lower alkyl, lower alkenyl, lower alkynyl, —$(CH_2)_n$-cycloalkyl, —$(CH_2)_n$-heterocycle, and aryl;

or $R^{12}$ and $R^{13}$ may be linked together to form a 4-, 5- or 6-membered ring optionally containing one or more hetero atoms selected from the group consisting of O, N, S, SO and $SO_2$, which may contain 1 or 2 double bonds and may be further substituted by halogen, —$OR^6$, —$COR^6$, —$COOR^6$, $OCOR^6$, —$CONR^6R^7$, —$R^{12}NCOR^{13}$, —$NR^6R^7$, —$R^6NC(O)R^7$, —CN, —$NO_2$, —$CX_3$, —$SR^6$, $SOR^6$, —$SO_2R^6$, —$SO_2OR^6$, —$SO_2NR^6R^7$, —$R^6NSO_2R^7$, perfluoroalkyl, lower alkyl, lower alkenyl, lower alkynyl, cycloalkyl, a heterocyclic ring and aryl;

$R^9$ is selected from the group consisting of halogen, —$CX_3$, lower alkyl, cycloalkyl, a heterocyclic ring and aryl, each of which may be further substituted by halogen, —$OR^6$, —$COOR^6$, —$OCOR^6$, —$CONR^6R^7$, —$R^6NCOR^7$, —$NR^6R^7$, —$CX_3$, —$SR^6$, $SOR^6$, $SO_2R^6$, —$SO_2OR^6$, $SO_2NR^6R^7$, or —$R^6NSO_2R^7$; and m is 1 or 2, or a pharmaceutically acceptable salt thereof.

20. A compound of claim 19 wherein $R^8$ is hydrogen, halogen, lower alkyl or lower alkyl substituted with $R^2$;

$R^2$ is hydroxy or hydrogen;

n is 0–2;

$R^9$ is lower alkyl;

m is 1 or 2;

$R^6$ and $R^7$ independently are lower alkyl which may be substituted with hydrogen, hydroxy or $NR^{12}R^{13}$;

$R^6$ and $R^7$ can form a 5 or 6 membered ring with one or more hetero atoms selected from N, O which is further substituted with lower alkyl or —$(CH_2)_nNR^{12}R^{13}$;

$R^{12}$ and $R^{13}$ independently are hydrogen, lower alkyl, —C(O)-lower alkyl, or —$(CH_2)_n$-cycloalkyl;

or $R^{12}$ and $R^{13}$ can form a 5 or 6 membered ring having one or more hetero atoms selected from the group consisting of O and N and having 1 or 2 double bonds wherein the ring is further substituted with hydroxy, —C(O)-lower alkyl or —$NR^6C(O)$-lower alkyl.

* * * * *